US011459551B1

(12) United States Patent
Joyce et al.

(10) Patent No.: US 11,459,551 B1
(45) Date of Patent: Oct. 4, 2022

(54) COMPOSITIONS, SYSTEMS, AND METHODS FOR GENOME EDITING

(71) Applicant: Inari Agriculture Technology, Inc., Cambridge, MA (US)

(72) Inventors: Adam Patrick Joyce, Stow, MA (US); Michael Andreas Kock, Rheinfelden (DE); Hannah Pham, Somerville, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 479 days.

(21) Appl. No.: 16/557,566

(22) Filed: Aug. 30, 2019

Related U.S. Application Data

(60) Provisional application No. 62/725,910, filed on Aug. 31, 2018.

(51) Int. Cl.
*C12N 9/22* (2006.01)
*C12N 15/11* (2006.01)

(52) U.S. Cl.
CPC ................ *C12N 9/22* (2013.01); *C12N 15/11* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,790,490 | B2 | 10/2017 | Zhang et al. |
| 9,896,696 | B2 | 2/2018 | Begemann et al. |
| 2015/0059010 | A1 | 2/2015 | Cigan et al. |
| 2015/0082478 | A1 | 3/2015 | Cigan et al. |
| 2015/0344912 | A1 | 12/2015 | Kim et al. |
| 2016/0138008 | A1 | 5/2016 | Doudna et al. |

FOREIGN PATENT DOCUMENTS

| | | | |
|---|---|---|---|
| WO | 2016166340 | A1 | 10/2016 |

OTHER PUBLICATIONS

Sternberg et al. (DNA interrogation by the CRISPR RNA-guided endonuclease Cas9, Nature. Mar. 6, 2014; 507(7490): 62-67) (Year: 2014).*
Begemann et al., "Characterization and Validation of a Novel Group of Type V, Class 2 Nucleases for in vivo Genome Editing", bioRxiv, 2017, pp. 1-9, https://doi.org/10.1101/192799.
Burstein et al., "New CRISPR-Cas Systems from Uncultivated Microbes", published as Nature, 2017, pp. 237-241, vol. 542, No. 7640 doi:10.1038/nature21059.
Cong et al., "Multiplex Genome Engineering Using CRISPR/Cas Systems", Science, 2013, pp. 819-823, vol. 339, No. 6121.
Di Tomasso et al., "The ARiBo Tag: A Reliable Tool for Affinity Purification of RNAs under Native Conditions", Nucleic Acids Research, 2011, pp. 1-10, vol. 39, No. 3, e18.
Hendel et al., "Chemically Modified Guide RNAs Enhance CRISPR-Cas Genome Editing in Human Primary Cells", published as Nature Biotechnology, 2015, pp. 985-989, vol. 33, No. 9.
Kieft et al., "A General Method for Rapid and Nondenaturing Purification of RNAs", RNA, 2004, pp. 988-995, vol. 10.
Lee et al., "RNA-protein Analysis Using a Conditional CRISPR Nuclease", Proceedings of the National Academy of Sciences USA, Apr. 2013, pp. 5416-5421 , vol. 110, No. 14.
Leppek et al., "An Optimized Streptavidin-Binding RNA Aptamer for Purification of Ribonucleoprotein Complexes Identifies Novel ARE-Binding Proteins", Nucleic Acids Research, 2014, pp. 1-15, vol. 42, No. 2.
Park et al., "Extension of the crRNA Enhances Cpf1 Gene Editing in vitro and in vivo", Nature Communications, 2018, pp. 1-12, doi: 10.1038/s41467-018-05641-3.
Parrott et al., "RNA Aptamers for the MS2 Bacteriophage Coat Protein and the Wild-Type RNA Operator have Similar Solution Behaviour", Nucleic Acids Research, 2000, pp. 489-497, vol. 28, No. 2.
Ran et al., "Genome Engineering Using the CRISPR-Cas9 System", Nature Protocols, 2013, pp. 2281-2308, vol. 8, No. 11.
Shmakov et al., "Discovery and Functional Characterization of Diverse Class 2 CRISPR-Cas Systems", Molecular Cell, 2015, pp. 385-397, vol. 60.
Srisawat et al., "RNA Affinity Tags for Purification of RNAs and Ribonucleoprotein Complexes", Methods, Feb. 2002, pp. 156-161, vol. 26, No. 2.
Zetsche et al., "Cpf1 is a Single RNA-Guided Endonuclease of a Class 2 CRISPR-Cas System", Cell, 2015, pp. 759-771, vol. 163.

* cited by examiner

*Primary Examiner* — Suzanne M Noakes
*Assistant Examiner* — Jae W Lee
(74) *Attorney, Agent, or Firm* — McKee, Voorhees & Sease, PLC

(57) ABSTRACT

This disclosure provides compositions that include a polynucleotide including or encoding a Cas12a tracrRNA, and methods for their use in sequence-specific genome editing, especially of eukaryotic genomic sequences. In particular, this disclosure provides Cas12a tracrRNA-containing compositions and methods for their use in Cas12a-mediated editing of a target sequence, wherein the editing efficiency is increased in comparison to controls lacking the Cas12a tracrRNA.

6 Claims, 14 Drawing Sheets

Specification includes a Sequence Listing.

LbCpf1 putative tracr 1 (19/36=52.8% identity)

```
Tracr 1 (84 nt)  5'  ACTTATACTAAATTTTAACTGTATACTTTCCCAAAATACCATAGGCTCTCTGAATCTCTTAACCCAGATTCCAAGGGCTTTTTT  3'
                     |  || ||| | |   || | | || | |   |||
     DR (36 nt)  5'  ATCTACACTTAGTAGAAATTATTTAATCTTTGAAAC  3'  (Reverse Complement)
```

LbCpf1 putative tracr 2 (18/36=50% identity)

```
Tracr 2 (65 nt)  5'  AATTGCAAATCTTTGAAATAATGCAGACTTAAATTTATAAATTCATGGAATAAGGTGATTTTATT  3'
                     |  | ||  |  | ||||| ||  |  |||  |
     DR (36 nt)  5'  ATCTACACTTAGTAGAAATTATTTAATCTTTGAAAC  3'  (Reverse Complement)
```

Figure 3

AsCpf1 putative tracr (18/35=51.4% identity)

```
Tracr 2 (72nt)  5'  CATTGTCTAACCTGCAAACCTCCAACTTACTATTGCTAAGGAGTATATATTTTGTATAAAAGGTCTTTTTTC 3'
                                                         |   |  | |       |  ||||||||||||  |
DR (35 nt)                                          5'  ATCTACAAGAGTAGAAATTAAAAAGGTCTTTTGAC 3'  (Reverse Complement)
```

COMPOSITIONS, SYSTEMS, AND METHODS FOR GENOME EDITING

REFERENCE TO RELATED APPLICATIONS

This application claims benefit of priority to U.S. Provisional Patent Application No. 62/725,910 filed 31 Aug. 2018, which is incorporated herein by reference in its entirety.

INCORPORATION OF SEQUENCE LISTINGS

A sequence listing containing the file named "10015US2_ST25.txt" which is 527142 bytes (measured in MS-Windows®), comprises 203 biological sequences, and was created on 29 Aug. 2019, is electronically filed herewith via the USPTO's EFS system, and is herein incorporated by reference in its entirety.

A replacement sequence listing containing the file named "10015US2.1_ST25.txt" which is 529407 bytes (measured in MS-Windows®), which comprises 203 biological sequences, which was created on 30 Sep. 2019, and which does not go beyond the disclosure of the originally filed sequence listing file named "10015US1_ST25.txt," is herein incorporated by reference in its entirety.

FIELD

Aspects of this disclosure relate to biotechnology, in particular compositions and methods for genome editing.

BACKGROUND

Recent advances in genome editing technologies have provided opportunities for precise modification of the genome in many types of organisms, including plants and animals. For example, technologies based on genome editing proteins, such as zinc finger nucleases, TALENs, and CRISPR systems are advancing rapidly and it is now possible to target genetic changes to specific DNA sequences in the genome.

CRISPR technology for editing the genes of eukaryotes is disclosed in U.S. Patent Application Publications 2016/0138008A1 (now U.S. Pat. No. 10,227,11) and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 (Cas12a) endonucleases and corresponding guide RNAs and PAM sites are disclosed in U.S. Pat. No. 9,790,490 and U.S. patent application Ser. No. 15/566,528 (national phase of PCT Application PCT/EP2016/058442, published as WO 2016/166340), now published as U.S. Patent Application Publication 2018/0282713. Other CRISPR nucleases useful for editing genomes include C2c1 and C2c3 (see Shmakov et al. (2015) *Mol. Cell,* 60:385-397) and CasX and CasY (see Burstein et al. (2016) *Nature*, doi:10.1038/nature21059). Plant RNA promoters for expressing CRISPR guide RNA and plant codon-optimized CRISPR Cas9 endonuclease are disclosed in U.S. patent application Ser. No. 15/120,110, published as U.S. Patent Application Publication 2017/0166912, national phase application claiming priority to International Patent Application PCT/US2015/018104 (published as WO 2015/131101 and claiming priority to U.S. Provisional Patent Application 61/945,700). Methods of using CRISPR technology for genome editing in plants are disclosed in in U.S. Patent Application Publications U.S. 2015/0082478A1 and U.S. 2015/0059010A1 and in International Patent Application PCT/US2015/038767 A1 (published as WO 2016/007347, claiming priority to U.S. Provisional Patent Application 62/023,246, with U.S. National Phase application U.S. Ser. No. 15/325,116, now published as U.S. Patent Application Publication 2017/0306349).

U.S. Pat. No. 9,790,490 and Zetsche et al. (2015) *Cell,* 163:759-771 teach that a tracrRNA is not required for nuclease cleavage activity of Cpf1 (Cas12a) effector protein complexes and suggest deletion of such sequences from engineered genome editing systems. This disclosure demonstrates that the presence of the tracrRNA as such has a beneficial effect on Cas12a editing efficiency and that the tracrRNA can be usefully employed in genome editing.

SUMMARY

Disclosed herein are polynucleotides, DNA expression systems, compositions, and methods of use thereof, useful for genome editing.

In one aspect, the invention provides a method of tethering a functional RNA molecule to a Cas12a crRNA, the method including hybridizing (a) a functional RNA molecule including a Cas12a tracrRNA and a functional RNA moiety; and (b) a Cas12a crRNA that includes a 3' extension capable of hybridizing with a segment of the functional RNA molecule; thereby tethering the functional RNA molecule to the Cas12a crRNA. In embodiments, the functional RNA molecule is transcribed from a DNA molecule that encodes the Cas12a tracrRNA and the functional RNA moiety; in embodiments, DNA encoding the functional RNA moiety is inserted or integrated at a native (naturally occurring) or artificial (engineered) restriction endonuclease cleavage site that is located in or adjacent to (typically within the 3' region of) the DNA encoding the Cas12a tracrRNA. In embodiments, the crRNA 3' extension includes nucleotides that when base-paired form about one helical turn, or at least 10 contiguous nucleotides. In embodiments, the Cas12a tracrRNA further includes a 5' extension. The functional RNA moiety is characterized by one or more functions. Embodiments of the RNA moiety include RNA sequences for annealing to one or more polynucleotides, RNA sequences that provide structures for binding to other molecules (including proteins or small molecule ligands) or that are catalytically active, or RNA sequences that serve as directly or indirectly detectable labels. In many embodiments of the method, the Cas12a crRNA is complexed with, or is capable of complexing with, a Cas12a nuclease to form a Cas12a ribonucleoprotein complex containing the functional RNA molecule; thus, in embodiments, the method further includes the step of associating or complexing a Cas12a nuclease with a Cas12a crRNA that has (e.g., in a preceding or simultaneous step), or will have (e.g., in a subsequent step) the functional RNA molecule tethered to it. In embodiments, the Cas12a nuclease is one having a naturally occurring sequence (e.g., a native sequence of a Cas12a nuclease such as, but not limited to, LbCas12a, AsCas12a, and FnCas12a); in other embodiments, the Cas12a nuclease includes a modification, such as an amino acid sequence modification or a chemical modification.

In a related aspect, the invention provides a modified Cas12a ribonucleoprotein complex including: (a) a Cas12a nuclease; (b) a functional RNA molecule including a Cas12a tracrRNA and a functional RNA moiety; and (c) a Cas12a crRNA that includes a 3' extension capable of hybridizing with a segment of the functional RNA molecule. In embodiments, the Cas12a nuclease is one having a naturally occurring sequence (e.g., a native sequence of a Cas12a nuclease such as, but not limited to, LbCas12a, AsCas12a, and FnCas12a); in other embodiments, the Cas12a nuclease includes a modification, such as an amino acid sequence modification or a chemical modification. In a preferred embodiment the expression and/or presence of the Cas12a tracrRNA enhances the genome editing capability of the Cas12a nuclease.

In another aspect, the invention provides a method of inserting a nucleotide sequence encoded by a donor polynucleotide at a specific locus in a target DNA, the method including: (a) annealing a donor polynucleotide to the modified Cas12a ribonucleoprotein complex of claim 12, wherein the functional RNA moiety includes an RNA sequence for annealing to the donor polynucleotide, and wherein the Cas12a crRNA includes a spacer sequence that corresponds to a specific target locus in a target DNA, thus forming a donor:RNP complex; and (b) contacting the target DNA with the donor:RNP complex; whereby the nucleotide sequence encoded by the donor polynucleotide is inserted at the specific target locus in the target DNA. In embodiments, the donor polynucleotide includes single-stranded DNA, optionally including chemical modifications. In embodiments, the donor polynucleotide includes double-stranded DNA, optionally including chemical modifications. In embodiments, the donor polynucleotide encodes coding sequence, non-coding sequence (e.g., a non-coding sequence or regulatory element that modifies expression of a target gene located at or near the target locus), or both coding and non-coding sequence. In embodiments, the target DNA is genomic DNA, e.g., genomic DNA or nuclear DNA of a eukaryote. In embodiments, the target DNA is mitochondrial or plastid DNA.

In another aspect, the invention provides a DNA expression system including (a) DNA sequence for a first promoter; and (b) operably linked and heterologous to the first promoter a DNA encoding a first RNA molecule including a Cas12a tracrRNA and including a restriction endonuclease cleavage site (native or engineered) that is suitable for insertion of a sequence coding for a functional RNA moiety. In embodiments, the DNA expression system further includes: (c) optionally, a DNA sequence for a second promoter; (d) operably linked and heterologous to the first promoter or the second promoter, a DNA encoding a Cas12a crRNA that includes a 3' extension capable of hybridizing with a segment of the first RNA molecule; and (e) optionally, a terminator; in embodiments, the first promoter and the DNA encoding the first RNA molecule, and the DNA encoding a Cas12a crRNA that includes a 3' extension are contained in a single construct, and in other embodiments, the first promoter and the DNA encoding the first RNA molecule are contained in a first construct, and the second promoter and the DNA encoding a Cas12a crRNA that includes a 3' extension are contained in a second construct. Where the DNA expression system is provided in a first construct and a second construct, these can be provided in a single vector or in separate vectors. In some embodiments wherein the DNA expression system includes DNA encoding a Cas12a crRNA, the first promoter drives expression of both the DNA encoding the first RNA molecule and the DNA encoding the Cas12a crRNA. In some embodiments, the Cas12a tracrRNA further includes a 5' extension. In many embodiments of the DNA expression system, the Cas12a crRNA is capable of complexing with a Cas12a nuclease to form a Cas12a ribonucleoprotein complex. In a preferred embodiment the expression and/or presence of the Cas12a tracrRNA enhances the genome editing capability of the Cas12a nuclease.

In another aspect, the invention provides a DNA expression system including: (a) DNA sequence for a first promoter; and (b) operably linked and heterologous to the first promoter, a DNA encoding a functional RNA molecule including a Cas12a tracrRNA and a functional RNA moiety. The functional RNA moiety is characterized by one or more functions. Embodiments of the RNA moiety include RNA sequences for annealing to one or more polynucleotides, RNA sequences that provide structures for binding to other molecules (including proteins or small molecule ligands) or that are catalytically active, or RNA sequences that serve as directly or indirectly detectable labels. In embodiments, the DNA expression system further includes: (c) optionally, a DNA sequence for a second promoter; (d) operably linked and heterologous to the first promoter or the second promoter, a DNA encoding a Cas12a crRNA that includes a 3' extension capable of hybridizing with a segment of the functional RNA molecule; and (e) optionally, a terminator. In embodiments wherein the DNA expression system includes the DNA encoding the Cas12a crRNA, the DNA expression system can be provided in a single construct (e.g., where the first promoter drives expression of both the DNA encoding the functional RNA molecule and the DNA encoding the Cas12a crRNA). In embodiments wherein the DNA expression system includes the second promoter, the second promoter can be operably linked to the DNA encoding the crRNA (e.g., in a second construct). In embodiments where the DNA expression system is provided in two constructs, these can be in a single vector or in separate vectors. In embodiments, the Cas12a tracrRNA further includes a 5' extension. In many embodiments of the DNA expression system, the Cas12a crRNA is capable of complexing with, a Cas12a nuclease to form a Cas12a ribonucleoprotein complex containing the functional RNA molecule. In embodiments, the Cas12a nuclease is one having a naturally occurring sequence (e.g., a native sequence of a Cas12a nuclease such as, but not limited to, LbCas12a, AsCas12a, and FnCas12a); in other embodiments, the Cas12a nuclease includes a modification, such as an amino acid sequence modification or a chemical modification. In a preferred embodiment the expression and/or presence of the Cas12a tracrRNA enhances the genome editing capability of the Cas12a nuclease.

In another aspect, the invention provides an engineered system including: (a) a Cas12a nuclease; and (b) at least one engineered Cas12a crRNA, or a polynucleotide encoding the engineered Cas12a crRNA, wherein the engineered Cas12a crRNA includes (i) at least one direct repeat sequence or fragment thereof that is capable of associating with the Cas12a nuclease, and (ii) a spacer sequence that is designed to hybridize with a target sequence in a eukaryotic cell, wherein the at least one direct repeat sequence or fragment thereof is adjacent to and 5' to the spacer sequence; and (c) a Cas12a tracrRNA including a nucleotide sequence that has at least 50% complementarity with, the nucleotide sequence of the at least one direct repeat of the engineered Cas12a crRNA. In another aspect, the invention further provides an engineered system including: (a) a Cas12a nuclease; and (b) at least one engineered Cas12a crRNA, or a polynucleotide encoding the engineered Cas12a crRNA, wherein the engineered Cas12a crRNA includes (i) at least one direct repeat sequence or fragment thereof that is capable of associating with the Cas12a nuclease, and (ii) a spacer sequence that is designed to hybridize with a target sequence in a eukaryotic cell, wherein the at least one direct repeat sequence or fragment thereof is adjacent to and 5' to the spacer sequence; and (c) a Cas12a tracrRNA including a naturally occurring putative Cas12a tracrRNA sequence that is identified from the same genomic region as the Cas12a nuclease by at least the following steps: (i) identifying in the genomic region flanking the DNA encoding the Cas12a nuclease at least one nucleotide sequence that includes a CRISPR array including direct repeats, and (ii) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat. In yet another aspect, the invention provides an engineered system including: (a) one or more nucleotide sequences encoding a Cas12a nuclease; and (b) one or more nucleotide sequences encoding at least one engineered Cas12a crRNA that is designed to form a complex with the Cas12a nuclease and that includes a spacer sequence designed to hybridize with a target sequence in a eukaryotic cell; and (c) one or more nucleotide sequences encoding at least one Cas12a tracrRNA. In yet another aspect, the invention provides an engineered system including: (a) a Cas12a nuclease, or one or more nucleotide sequences encoding the Cas12a nuclease; and (b) at least one engineered Cas12a crRNA designed to form a complex with the Cas12a nuclease and including a spacer sequence designed to hybridize with a target sequence in a eukaryotic cell, or one or more nucleotide sequences encoding the at least one engineered Cas12a crRNA polynucleotide; and (c) at least one tracrRNA, or one or more nucleotide sequences encoding the at least one Cas12a tracrRNA. In embodiments of these engineered systems, the engineered Cas12a crRNA, or the polynucleotide (such as a pre-processed Cas12a crRNA precursor transcript) encoding the engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In embodiments of these engineered systems, the engineered Cas12a crRNA further includes a 3' extension adjacent to the spacer sequence. In embodiments of these engineered systems, the eukaryotic cell is a non-human animal cell (e.g., a cell of an animal selected from the group consisting of invertebrates, vertebrates, insects, arthropods, mollusks, fish, reptiles, amphibians, birds, mammals, primates, and non-human primates), a human cell, a plant cell, or a fungal cell. In embodiments of these engineered systems, the eukaryotic cell is in vitro, ex vivo, or in vivo.

In another aspect, the invention provides an engineered system including one or more vectors including: (a) a first regulatory element (such as a promoter) that is heterologous to and operably linked to one or more nucleotide sequences encoding a Cas12a nuclease; and (b) a second regulatory element (such as a promoter) that is heterologous to and operably linked to one or more nucleotide sequences encoding at least one engineered Cas12a crRNA that is designed to form a complex with the Cas12a nuclease and that includes a spacer sequence designed to hybridize with a target sequence in a eukaryotic cell; and (c) a third regulatory element (such as a promoter) that is heterologous to and operably linked to one or more nucleotide sequences encoding at least one Cas12a tracrRNA; wherein components (a) and (b) and (c) are located on the same vector or on different vectors of the system. In embodiments each of the regulatory elements includes one or more expression elements (such as a promoter, an enhancer, or an intron) that is functional in a eukaryotic cell.

In another aspect, the invention provides an engineered system including one or more vectors including: (a) a first expression cassette including at least a first promoter that is heterologous to and operably linked to one or more nucleotide sequences encoding a Cas12a nuclease and—optionally—a first transcription terminator sequence; and (b) a second expression cassette including at least a second promoter that is heterologous to operably linked to one or more nucleotide sequences encoding at least one engineered Cas12a crRNA that is designed to form a complex with the Cas12a nuclease and that includes a spacer sequence designed to hybridize with a target sequence in a eukaryotic cell and—optionally—a second transcription terminator sequence; and (c) a third expression cassette including at least a third promoter that is heterologous to operably linked to one or more nucleotide sequences encoding at least one Cas12a tracrRNA and—optionally—a third transcription terminator sequence, wherein components (a) and (b) and (c) are located on the same vector or on different vectors of the system. In embodiments each of the promoters and each of the transcription terminator sequences is functional in a eukaryotic cell. In embodiments, each of the promoters is heterologous to the nucleotide sequence of which the promoter drives expression.

Further aspects of the invention are related to the engineered systems disclosed and claimed herein. These aspects include compositions (e.g., a delivery particle or a delivery liquid) that include one or more of the engineered systems. Embodiments of the compositions include those wherein the Cas12a tracrRNA is present in a molar excess, relative to the amount of Cas12a nuclease. Specific embodiments of the compositions include those wherein the Cas12a tracrRNA is present in a molar amount that is at least 10-fold greater than the molar amount of the Cas12a nuclease. Additional aspects of the invention include a method of modifying a locus of interest having a target sequence of a eukaryotic cell including delivering one or more of the engineered systems to the locus of interest, wherein the spacer sequence hybridizes with the target sequence, whereby modification of the locus of interest occurs. In embodiments of the method, the locus of interest is within a eukaryotic cell. In embodiments of the method, the eukaryotic cell is a non-human animal cell (e.g., a cell of an animal selected from the group consisting of invertebrates, vertebrates, insects, arthropods, mollusks, fish, reptiles, amphibians, birds, mammals, primates, and non-human primates), a human cell, a plant cell, or a fungal cell. In embodiments of the method, the eukaryotic cell is in vitro, ex vivo, or in vivo. In embodiments of the method, the modification of the locus of interest is an insertion of at least one nucleotide, a deletion of at least one nucleotide, a change of at least one nucleotide (such as creation of a point mutation in the locus), non-homologous end-joining (NHEJ), or homology-dependent repair (HDR).

In another aspect, the invention provides a method of editing a genetic locus with a Cas12a nuclease, including contacting DNA that includes the genetic locus with: (a) a Cas12a nuclease; and (b) an engineered Cas12a crRNA that includes a spacer sequence that is designed to hybridize with a target sequence in the genetic locus; and (c) a Cas12a tracrRNA, thereby editing the genetic locus; wherein the efficiency of editing of the genetic locus is increased compared to a control method in which the DNA that includes the genetic locus is contacted with the Cas12a nuclease and the Cas12a crRNA, but not the Cas12a tracrRNA. In embodiments, the efficiency of editing is assessed by quantifying the amount of Cas12a nuclease required to obtain a given percentage of edited target sequences (or percentage of cells containing the edited target sequences); efficiency is increased where a given editing efficiency is achieved using a lower amount of Cas12a nuclease. In embodiments of the method, the Cas12a tracrRNA is provided in a molar excess, relative to the Cas12a nuclease. In embodiments of the method, the Cas12a tracrRNA is provided in a molar amount that is at least 10-fold greater than the molar amount of the Cas12a nuclease.

In a related aspect, the invention further provides a composition for modifying a genetic locus in a eukaryotic cell, including: (a) a eukaryotic cell containing a genetic locus to be modified; and (b) a Cas12a nuclease, or a polynucleotide encoding the Cas12a nuclease; and (c) an engineered Cas12a crRNA that includes a spacer sequence corresponding to a specific sequence in the genetic locus, or a polynucleotide encoding the Cas12a crRNA; and (d) a Cas12a tracrRNA, or a polynucleotide encoding the Cas12a tracrRNA, wherein the Cas12a tracrRNA is provided in molar excess relative to the Cas12a nuclease. In embodiments of the composition, the Cas12a tracrRNA is identified from the same genomic region as the Cas12a nuclease by at least the following steps: (a) identifying in the genomic region flanking the DNA encoding the Cas12a nuclease at least one nucleotide sequence that includes a CRISPR array including direct repeats; (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat. In embodiments of the composition, the Cas12a tracrRNA is present in a molar excess, relative to the Cas12a nuclease. In embodiments of the composition, the Cas12a tracrRNA is present in a molar amount that is at least 10-fold greater than the molar amount of the Cas12a nuclease.

The DNA expression systems, engineered systems, compositions, and methods disclosed herein can be employed with Cas12a nucleases or modified variants thereof. In embodiments, the Cas12a nuclease is any one of the Cas12a ("Cpf1") nucleases disclosed in U.S. Pat. No. 9,790,490 or in U.S. patent application Ser. No. 15/566,528 (national phase entry of International Application No. PCT/EP2016/058442, published as WO2016166340), or in U.S. Pat. No. 9,896,696 which are specifically incorporated herein by reference. In embodiments, the Cas12a nuclease is a Cas12a ("Cpf1") nuclease identified from *Francisella novicida* U112 (FnCas12a or "FnCpf1"), from *Acidaminococcus* sp. BV3L6 (AsCas12a or "AsCpf1"), or from Lachnospiraceae bacterium ND2006 (LbCas12a or "LbCpf1"), or is an orthologue thereof, such as an orthologue having at least 50% sequence identity to FnCas12a ("FnCpf1"); see, e.g., the FnCpf1 nuclease contained in the FnCpf1 locus having SEQ ID NO:211 in U.S. Pat. No. 9,790,490, incorporated herein by reference. In embodiments, a Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease includes orthologues of LbCas12a, AsCas12a, or FnCas12a. In embodiments, the Cas12a nuclease is a deactivated Cas12a nuclease, a tagged or labelled Cas12a nuclease, or a Cas12a fusion; examples are described elsewhere in this disclosure. The systems and compositions including a tracrRNA and methods of use thereof that are disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

Related aspects of the invention include eukaryotes and eukaryotic cells containing a genomic modification obtained by use of the polynucleotides, compositions, engineered systems, and methods of use thereof disclosed herein. Embodiments include non-human animals and non-human animal cells, non-human animal stem cells, human cells, human stem cells, and human somatic (non-gametic) cells; isolated tissue (e.g., nervous tissue, epithelial tissue, liver, spleen, pancreas, muscle tissue, bone, connective tissue, endocrine system tissues, and tumours) or cells (e.g., blood cells, erythrocytes, leukocytes, lymphocytes, liver cells, bone cells, immune cells, T cells, B cells, dendritic cells, and tumour cells) or cell organelles (e.g., mitochondria or chloroplasts, either isolated or contained within the eukaryotic cell, tissue, or organism) obtained from a non-human animal or from a human; engineered hybridoma cells; fungi, fungal cells, plants, plant tissue, plant cells, and seeds having such a genomic modification, e.g., a genomic modification including a heterologous nucleotide sequence encoded by a donor polynucleotide and integrated into a specific locus in the genome, wherein the donor polynucleotide is provided in a donor:RNP complex that includes the donor polynucleotide ("donor") annealed to a modified Cas12a ribonucleoprotein ("RNP") that includes: (a) a Cas12a nuclease; (b) a functional RNA molecule including a Cas12a tracrRNA and a functional RNA moiety, wherein the functional RNA moiety includes an RNA sequence for annealing to the donor polynucleotide and optionally an RNA sequence for annealing to the crRNA 3' extension; and (c) a Cas12a crRNA that includes a 3' extension capable of hybridizing with a segment of the functional RNA molecule. Additional aspects of the invention include progeny plants or progeny seeds obtained from a plant, plant cell, plant tissue, or seed having a genomic modification obtained by use of the polynucleotides, compositions, and methods of use disclosed herein. Also encompassed by the invention are raw plant materials, processed plant products, and commodity plant products obtained from a plant, plant cell, plant tissue, or seed (or from progeny plants or seeds thereof) having a genomic modification obtained by use of the polynucleotides, compositions, and methods of use disclosed herein.

BRIEF DESCRIPTION OF THE DRAWINGS

FIG. 3 illustrates the alignments of the reverse complement of the LbCpf1 direct repeat (DR) sequence, ATCTACACTTAGTAGAAATTATTTAATCTTTGAAAC (SEQ ID NO:5), with the LbCpf1 tracrRNA 1 ("putative tracrRNA 1") (SEQ ID NO:2) (top, showing 52.8% identity between the two sequences) and the LbCpf1 tracrRNA 2 ("putative tracrRNA 2") (SEQ ID NO:4) (bottom, showing 50.0% identity between the two sequences), as described in detail in Example 1.

FIG. 6 illustrates the alignment of the reverse complement of the AsCpf1 direct repeat (DR) sequence, ATCTACAAGAGTAGAAATTAAAAAGGTCTTTTGAC (SEQ ID NO:8) with the AsCpf1 tracrRNA ("putative tracrRNA") (SEQ ID NO:7), showing 51.4% identity between the two sequences as described in detail in Example 1.

FIG. 9B (right) schematically depicts an alternative design wherein the DNA expression system includes (a) DNA sequence for a first promoter; (b) operably linked and heterologous to the first promoter, a DNA encoding a first RNA molecule including a Cas12a tracrRNA or putative tracrRNA and including a restriction endonuclease cleavage site that is suitable for insertion of a sequence coding for a functional RNA moiety; and (c) operably linked and heterologous to the first promoter, a DNA encoding a Cas12a crRNA including multiple guide RNAs (Cas12a crRNAs), and including a 3' extension capable of hybridizing with a segment of the first RNA molecule, as described in detail in Example 3.

FIG. 9C (right) further schematically depicts an expression construct for expressing a guide RNA (Cas12a crRNA), as described in detail in Example 3.

FIG. 10 (bottom) schematically depicts a second DNA expression system, described in detail in Example 3, and similar to that shown in FIG. 10 (top), except that the guide RNA includes multiple guide RNAs, and includes a 3' extension capable of hybridizing with a segment of the first RNA molecule; the 3'-most direct repeat is optional.

DETAILED DESCRIPTION OF THE INVENTION

Figure 1:
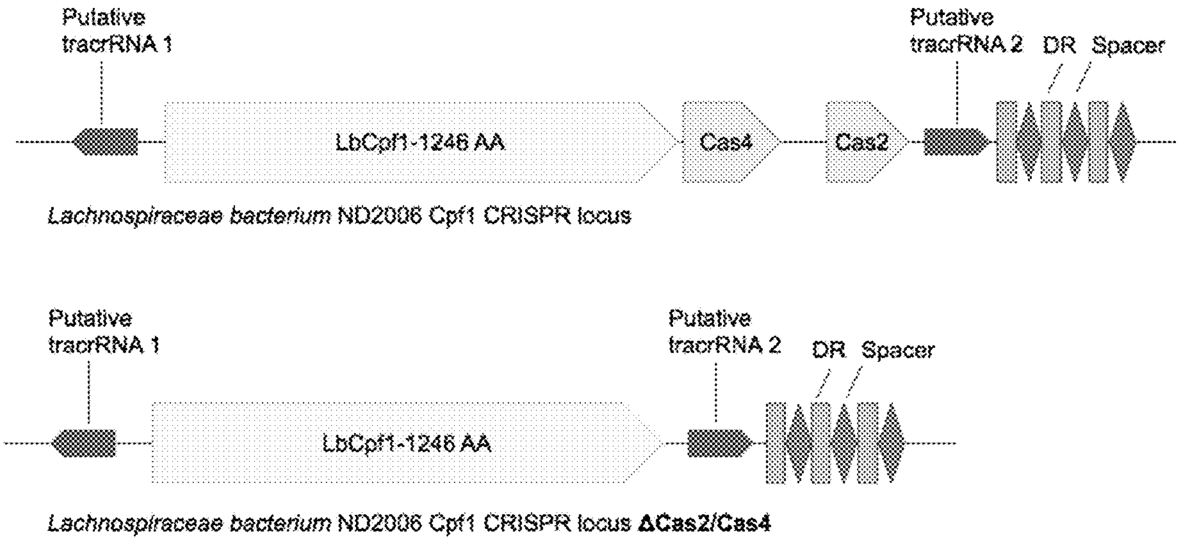
FIG. 1 illustrates schematics of the Lachnospiraceae bacterium ND2006 Cas12a ("LbCpf1") CRISPR locus and Cas12a tracrRNA ("putative tracrRNA") location as described in detail in Example 1. The schematics are shown with (upper figure) and without (lower figure) the Cas4 and Cas2 components of the locus. The direct repeats ("DR") are indicated by upright rectangles and the spacer sequences indicated by diamonds.

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art. Where a term is provided in the singular, the inventors also contemplate aspects of the invention described by the plural of that term. As used herein, the terms "comprise," comprises, "comprising," "include," "includes," and "including" can be interchanged and are to be construed as at least having the features to which they refer while not excluding any additional unspecified features. The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

By "polynucleotide" is meant a nucleic acid molecule containing multiple nucleotides and refers to "oligonucleotides" (defined here as a polynucleotide molecule of between 2-25 nucleotides in length) and polynucleotides of 26 or more nucleotides. Polynucleotides are generally described as single- or double-stranded. Where a polynucleotide contains double-stranded regions formed by intra- or intermolecular hybridization, the length of each double-stranded region is conveniently described in terms of the number of base pairs. Aspects of this invention include the use of polynucleotides or compositions containing polynucleotides; embodiments include one or more oligonucleotides or polynucleotides or a mixture of both, including single- or double-stranded RNA or single- or double-stranded DNA or double-stranded DNA/RNA hybrids or chemically modified analogues or a mixture thereof. In various embodiments, a polynucleotide includes a combination of ribonucleotides and deoxyribonucleotides (e.g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides), or includes non-canonical nucleotides such as inosine, thiouridine, or pseudouridine. In embodiments, the polynucleotide includes chemically modified nucleotides (see, e.g., Verma and Eckstein (1998) *Annu. Rev. Biochem.,* 67:99-134); for example, the naturally occurring phosphodiester backbone of an oligonucleotide or polynucleotide can be partially or completely modified with phosphorothioate, phosphorodithioate, or methylphosphonate internucleotide linkage modifications; modified nucleoside bases or modified sugars can be used in oligonucleotide or polynucleotide synthesis; and oligonucleotides or polynucleotides can be labelled with a fluorescent moiety (e.g., fluorescein or rhodamine or a fluorescence resonance energy transfer or FRET pair of chromophore labels) or other label (e.g., biotin or an isotope). Modified nucleic acids, particularly modified RNAs, are disclosed in U.S. Pat. No. 9,464,124, incorporated by reference in its entirety herein.

"CRISPR (Clustered Regularly Interspaced Short Palindromic Repeats)/Cas (CRISPR-associated) systems," or CRISPR systems, are adaptive defense systems originally discovered in bacteria and archaea. CRISPR systems use RNA-guided nucleases termed CRISPR-associated or "Cas" endonucleases (e.g., Cas9 or Cas12a ("Cpf1")) to cleave foreign DNA. In atypical CRISPR/Cas system, a Cas endonuclease is directed to a target nucleotide sequence (e.g., a site in the genome that is to be sequence-edited) by sequence-specific, non-coding "guide RNAs" that target single- or double-stranded DNA sequences. In microbial hosts, CRISPR loci encode both Cas endonucleases and "CRISPR arrays" of the non-coding RNA elements that determine the specificity of the CRISPR-mediated nucleic acid cleavage.

Two classes (1 and 2) of CRISPR systems have been identified across a wide range of bacterial hosts. The well characterized class 2 CRISPR systems use a single Cas endonuclease (rather than multiple Cas proteins). One class 2 CRISPR system includes a type II Cas endonuclease such as Cas9, a CRISPR RNA ("crRNA"), and a trans-activating crRNA ("tracrRNA"). A "trans-activating crRNA" or "tracrRNA" is a trans-encoded small RNA that is partially homologous to repeats within a CRISPR array. At least in the case of Cas9 type CRISPR systems, both a tracrRNA and a crRNA are required for the CRISPR array to be processed and for the nuclease to cleave the target DNA sequence. In contrast, Cas12a type CRISPR systems have been reported to function without a tracrRNA, with the Cas12a CRISPR arrays processed into mature crRNAs without the requirement of a tracrRNA; see Zetsche et al. (2015) *Cell,* 163: 759-771 and U.S. Pat. No. 9,790,490. The Cas9 crRNA contains a "spacer sequence", typically an RNA sequence of about 20 nucleotides (in various embodiments this is 20, 21, 22, 23, 24, 25, or up to about 30 contiguous nucleotides in length) that corresponds to (e.g., is identical or nearly identical to, or alternatively is complementary or nearly complementary to) a target DNA sequence of about equivalent length. The Cas9 crRNA also contains a region that binds to the Cas9 tracrRNA to form a partially double-stranded structure which is cleaved by RNase III, resulting in a crRNA:tracrRNA hybrid or duplex. The crRNA: tracrRNA hybrid then directs the Cas9 endonuclease to recognize and cleave the target DNA sequence; in some examples, a tracrRNA and crRNA (e.g., a crRNA including a spacer sequence) can be included in a chimeric nucleic acid referred to as a "single guide RNA" (sgRNA).

The Cas12a ("Cpf1") CRISPR system includes the type V endonuclease Cas12a (also known as "Cpf1"). Cas12a nucleases are characterized as having only a RuvC nuclease domain, in contrast to Cas9 nucleases which have both RuvC and HNH nuclease domains. Cas12a nucleases are generally smaller proteins than Cas9 nucleases, and can function with a smaller guide RNA (e.g., a crRNA having at least one spacer flanked by direct repeats), which are practical advantages in that the nuclease and guide RNAs are more economical to produce and potentially more easily delivered to a cell. Examples of Cas12a nucleases include AsCas12a or "AsCpf1" (from *Acidaminococcus* sp.) and LbCas12a or "LbCpf1" (from Lachnospiraceae bacteria). In contrast to Cas9 type CRISPR systems, Cas12a-associated ("Cpf1"-associated) CRISPR arrays have been reported to be processed into mature crRNAs without the requirement of a tracrRNA, i.e., the naturally occurring Cas12a (Cpf1) CRISPR system was reported to require only the Cas12a (Cpf1) nuclease and a Cas12a crRNA to cleave the target DNA sequence; see Zetsche et al. (2015) *Cell,* 163:759-771; U.S. Pat. No. 9,790,490.

The term "tracrRNA" sequence or analogous terms includes any polynucleotide sequence that has sufficient complementarity with a crRNA sequence to hybridize. Embodiments of tracrRNA sequences useful in the compositions, engineered systems, and methods provided by this disclosure include those described as a "putative transactivating crRNA" or "putative tracrRNA" in U.S. Pat. No. 9,490,490 (e.g., in FIGS. 46, 48-51, and 54 of U.S. Pat. No. 9,490,490, and SEQ IDS NO: 28, 31, 34, 40, 43, 44, 47, and 50 of U.S. Pat. No. 9,490,490) and its priority documents, all of which are incorporated by reference herein. Embodiments of methods of identifying orthologues of CRISPR-Cas system enzymes may involve identifying tracrRNA sequences in genomes of interest.

The term "Cas12a tracrRNA" as used herein means a naturally occurring Cas12a tracrRNA or an engineered derivative thereof. In a preferred embodiment, the term "Cas12a tracrRNA" refers to a naturally occurring Cas12a tracrRNA has a nucleotide sequence that includes or comprises: (a) a nucleotide sequence or region of about 60 to about 100 contiguous nucleotides that has more than 50% identity to the direct repeat (DR) or tracr mate sequence in the Cas12a crRNA, preferably also has (b) secondary structure, and preferably also has (c) a transcriptional terminator. In some embodiments, a naturally occurring Cas12a tracrRNA has a nucleotide sequence that includes or comprises: (a) a nucleotide sequence or region of about 60 to about 100 contiguous nucleotides that has more than 50% identity to the direct repeat (DR) or tracr mate sequence in the Cas12a crRNA, and preferably also has (b) secondary structure, but is not associated with a transcriptional terminator. In some embodiments, the Cas12a tracrRNA is physically associated with the corresponding Cas12a crRNA and/or with the corresponding Cas12a nuclease. In other embodiments, the Cas12a tracrRNA is not physically associated with the corresponding Cas12a crRNA and/or with the corresponding Cas12a nuclease.

A naturally occurring tracrRNA sequence can be identified from a genome as DNA sequence encoding a RNA molecule (a "putative tracrRNA") that is predicted to be or putatively transcribed (or that may be determined to be transcribed, e.g., by RNA analysis) from a CRISPR genomic region, specifically from a locus that flanks the DNA encoding the CRISPR nuclease and that includes a predicted transcriptional terminator in the direction of transcription; is about 60 to about 100 nucleotides in length, e.g., 60-80 nucleotides, 60-85 nucleotides, 60-90 nucleotides, or 65-95 nucleotides; and is not a direct repeat in the CRISPR array, but rather has a nucleotide sequence of sufficient complementarity with a crRNA sequence to hybridize, e.g., of at least 50% identity to or at least 50% complementarity to the direct repeat in a CRISPR array. Steps for identifying tracrRNA sequences have been described, e.g., in U.S. Pat. No. 9,790,490, incorporated here by reference: "Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith." RNA sequencing can be used to further characterize such sequences identified as potential or putative tracrRNAs.

In embodiments, an engineered Cas12a tracrRNA is used in place of or as a substitute for a naturally occurring tracrRNA or putative tracrRNA identified from a genome. In embodiments, an engineered Cas12a tracrRNA is designed based on guidelines similar to those employed for identifying a naturally occurring tracrRNA or putative tracrRNA identified from a genome. In embodiments, an engineered Cas12a tracrRNA is designed to have a sequence of about 60 to about 100 ribonucleotides and to have at least 50% complementarity to the sequence of the direct repeat of the Cas12a crRNA with which the engineered Cas12a tracrRNA is meant to be used. Engineered Cas12a tracrRNAs can be expressed with any of the systems described in this disclosure, e.g., in an expression construct using any of the promoters, terminator, or other expression elements described herein.

The genomic DNA sequence targeted for editing or modification must generally be adjacent to a "protospacer adjacent motif" ("PAM") that is specific for a given Cas endonuclease; however, PAM sequences are short and relatively non-specific, appearing throughout a given genome. CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). Some endonucleases, e.g., Cas9 endonucleases, are associated with G-rich PAM sites, e.g., 5'-NGG, and perform blunt-end cleaving of the target DNA at a location three nucleotides upstream from (5' from) the PAM site. Cas12a (Cpf1) CRISPR systems cleave the target DNA adjacent to a short T-rich PAM sequence, e.g., 5'-TTN, in contrast to the G-rich PAM sequences identified for Cas9 systems. Examples of Cas12a PAM sequences include those for the naturally occurring *Acidaminococcus* sp. BV3L6 Cpf1 (AsCpf1) and Lachnospiraceae bacterium ND2006 Cpf1 (LbCpf1) TTTV, where V can be A, C, or G. In some instances, Cas12a can also recognize a 5'-CTA PAM motif Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Various methods (including in silico and/or wet lab methods) for identification of the appropriate PAM sequence are known in the art and are routine, and any convenient method can be used. A PAM sequence can be identified using a PAM depletion assay. Cas12a cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e.g., Zetsche et al. (2015) *Cell,* 163:759-771.

For the purposes of gene editing, CRISPR arrays can be designed to contain one or multiple guide RNAs designed to target a DNA sequence for editing, where the guide RNA includes at least one spacer sequence that corresponds to a specific locus of about equivalent length in the target DNA; see, for example, Cong et al. (2013) *Science,* 339:819-823; Ran et al. (2013) *Nature Protocols,* 8:2281-2308. As used herein "guide RNA" or "gRNA" refers to a nucleic acid that comprises or includes a nucleotide sequence (sometimes referred to a "spacer sequence") that corresponds to (e.g., is identical or nearly identical to, or alternatively is complementary or nearly complementary to) a target DNA sequence (e.g., a contiguous nucleotide sequence that is to be modified) in a genome; the guide RNA functions in part to direct the CRISPR nuclease to a specific location on the genome. In embodiments, a gRNA is a CRISPR RNA ("crRNA"), such as the engineered Cas12a crRNAs described in this disclosure. For nucleases (such as a Cas9 nuclease) that require a combination of a trans-activating crRNA ("tracrRNA") and a crRNA for the nuclease to cleave the target nucleotide sequence, the gRNA can be a tracrRNA:crRNA hybrid or duplex, or can be provided as a single guide RNA (sgRNA). At least 16 or 17 nucleotides of gRNA sequence corresponding to a target DNA sequence are required by Cas9 for DNA cleavage to occur; for Cas12a (Cpf1) at least 16 nucleotides of gRNA sequence corresponding to a target DNA sequence are needed to achieve detectable DNA cleavage and at least 18 nucleotides of gRNA sequence corresponding to a target DNA sequence were reported necessary for efficient DNA cleavage in vitro; see Zetsche et al. (2015) *Cell,* 163:759-771. Cas12a (Cpf1) endonuclease and corresponding guide RNAs and PAM sites are disclosed in U.S. Pat. No. 9,790,490, which is incorporated herein by reference in its entirety and particularly for its disclosure of DNA encoding Cas12a (Cpf1) endonucleases and guide RNAs and PAM sites. In practice, guide RNA sequences are generally designed to contain a spacer sequence of between 17-24 contiguous nucleotides (frequently 19, 20, or 21 nucleotides) with exact complementarity (e.g., perfect base-pairing) to the targeted gene or nucleic acid sequence; guide RNAs having spacers with less than 100% complementarity to the target sequence can be used (e.g., a gRNA with a spacer having a length of 20 nucleotides and between 1-4 mismatches to the target sequence), but this can increase the potential for off-target effects. The design of effective guide RNAs for use in plant genome editing is disclosed in U.S. Patent Application Publication 2015/0082478 A1, the entire specification of which is incorporated herein by reference. Chemically modified sgRNAs have been demonstrated to be effective in Cas9 genome editing; see, for example, Hendel et al. (2015) *Nature Biotechnol.,* 33:985-991.

CRISPR-type genome editing has value in various aspects of agriculture research and development. CRISPR elements, e.g., CRISPR endonucleases and CRISPR single-guide RNAs, are useful in effecting genome editing without remnants of the CRISPR elements or selective genetic markers occurring in progeny. Alternatively, genome-inserted CRISPR elements are useful in plant lines adapted for multiplex genetic screening and breeding. For instance, a plant species can be created to express one or more of a CRISPR endonuclease such as a Cas12a-type endonuclease or combinations with unique PAM recognition sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for trait introgression. Multiple endonucleases can be provided in expression cassettes with the appropriate promoters to allow multiple genome editing in a spatially or temporally separated fashion in either in chromosome DNA or episome DNA.

CRISPR technology for editing the genes of eukaryotes is disclosed in U.S. Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cas12a (Cpf1) endonuclease and corresponding guide RNAs and PAM sites are disclosed in U.S. Pat. No. 9,790,490 and U.S. patent application Ser. No. 15/566,528 (national phase of PCT Application PCT/EP2016/058442, published as WO 2016/166340). Plant RNA promoters for expressing CRISPR guide RNA and plant codon-optimized CRISPR Cas9 endonuclease are disclosed in U.S. patent application Ser. No. 15/120,110, published as U.S. Patent Application Publication 2017/0166912, national phase application claiming priority to International Patent Application PCT/US2015/018104 (published as WO 2015/131101 and claiming priority to U.S. Provisional Patent Application 61/945,700). Methods of using CRISPR technology for genome editing in plants are disclosed in in U.S. Patent Application Publications U.S. 2015/0082478A1 and U.S. 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety.

Endonucleases such as Cas9 and Cas12a (Cpf1) can be provided to a cell in different forms. In an embodiment, an endonuclease is provided as a ribonucleoprotein (RNP) complex, e.g., a preassembled RNP that includes the endonuclease complexed with a polynucleotide including the gRNA or encoding a gRNA, or a preassembled RNP that includes a polynucleotide that encodes the endonuclease (and optionally encodes the gRNA, or is provided with a separate polynucleotide including the gRNA or encoding a gRNA), complexed with a protein. In embodiments, the endonuclease is a fusion protein, i.e., wherein the endonuclease is covalently bound through a peptide bond to a cell-penetrating peptide, a nuclear localization signal peptide, a chloroplast transit peptide, or a mitochondrial targeting peptide; such fusion proteins are conveniently encoded in a single nucleotide sequence, optionally including codons for linking amino acids. In embodiments, the endonuclease or a polynucleotide that encodes the endonuclease is provided as a complex with a cell-penetrating peptide or other transfecting agent. In embodiments, the endonuclease or a polynucleotide that encodes the endonuclease is complexed with, or covalently or non-covalently bound to, a further element, e.g., a carrier molecule, an antibody, an antigen, a viral movement protein, a polymer, a detectable label (e.g., a moiety detectable by fluorescence, radioactivity, or enzymatic or immunochemical reaction), a quantum dot, or a particulate or nanoparticulate. In embodiments, the endonuclease or a polynucleotide that encodes the endonuclease is provided in a solution, or is provided in a liposome, micelle, emulsion, reverse emulsion, suspension, or other mixed-phase composition. Similarly, editing complexes such as those disclosed herein (or compositions including such editing complexes) can be provided in combination with further elements (e.g., a carrier molecule, an antibody, an antigen, a viral movement protein, a polymer, a detectable label, a quantum dot, or a particulate or nanoparticulate) or provided in a suitable form (e.g., in a solution, liposome, micelle, emulsion, reverse emulsion, suspension, or other mixed-phase composition).

By "integration of heterologous sequence" is meant integration or insertion of one or more nucleotides, resulting in a sequence (including the inserted nucleotide(s) as well as at least some adjacent nucleotides of the genomic sequence flanking the site of insertion at a double-strand break effected by a CRISPR endonuclease) that is heterologous (e.g., would not otherwise or does not normally occur at the site of insertion). The term "heterologous" is also used to refer to a given sequence in relationship to another, e.g., the sequence of a donor DNA is heterologous to the sequence at the site of the double-strand break wherein the donor DNA is integrated. The term "heterologous" is also used to refer to components of a synthetic polynucleotide construct, where the components do not naturally occur together; for example, an expression cassette or construct can include a promoter to drive expression of a downstream sequence, where the promoter is heterologous to that downstream sequence. As used herein, the terms "heterologous promoter", "heterologous terminator", "heterologous coding sequence", and the like refer to discrete genetic sequences such as promoters and other expression-related genetic elements (e.g., promoters, enhancers, introns, terminators, silencers, and insulators), that are not normally associated with a particular nucleic acid in nature. For example, a "promoter that is heterologous to a coding region" is a promoter that is not normally associated with the coding region in nature.

By "capable of specifically binding to" is meant an agent that binds substantially or preferentially only to a defined target (such as an oligonucleotide or polynucleotide to a specific nucleic acid). In some examples, an oligonucleotide or polynucleotide capable of specifically binding to a target nucleic acid is complementary to the target nucleic acid. However, exact complementarity is not required for specific binding. The term "capable of hybridizing" refers to the ability of two polynucleotides to hybridize or "anneal", i.e., to form Watson-Crick base pairs; one of skill in the art would understand that the ability to hybridize requires a sufficient degree of complementarity between the two polynucleotides under given conditions (e.g., temperature) and that the degree of complementarity can be estimated using algorithms in the art.

By "complementary" is meant sequences with at least sufficient complementarity to permit enough base-paring for two nucleic acids to hybridize (for example, for a tether to hybridize with or bind to a gRNA or donor DNA), which in some examples may be under typical physiological conditions for the cell. In some examples, the oligonucleotide or polynucleotide is at least 80% complementary to the target, for example, at least 85%, 90%, 95%, 96%, 97%, 98%, 99%, or 100% complementary to the target.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available at ncbi[dot]nlm[dot]nih[dot]gov/BLAST. See, e.g., Altschul et al. (1990) *Mol. Biol.,* 215:403-410. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.,* 70: 173-187 (1997). Also, the GAP program using the Needleman and Wunsch alignment method can be utilized to align sequences. See *Mol. Biol.,* 48: 443-453 (1970).

The term "operably linked" refers to a juxtaposition wherein the components so described are in a relationship permitting them to function in their intended manner. For instance, a promoter is operably linked to a coding sequence if the promoter affects its transcription or expression.

By "native" is meant naturally occurring in a genome, such as a prokaryotic or eukaryotic genome. A "native" restriction endonuclease cleavage site means a restriction endonuclease cleavage site that is found in a naturally existing genome, such as a restriction endonuclease cleavage site that is naturally found within genomic DNA encoding the tracrRNA, in contrast to an artificial or engineered restriction endonuclease cleavage site that is created through recombinant nucleic acid technology.

By "engineered" is meant artificial, synthetic, or not occurring in nature. For example, a polynucleotide that includes two DNA sequences that are heterologous to each other can be engineered or synthesized by recombinant nucleic acid techniques.

By a "complex" is meant two or more associated components, such as two or more associated nucleic acids and/or proteins. A complex may include two or more covalently linked nucleic acids and/or proteins, two or more non-covalently linked nucleic acids and/or proteins, or a combination thereof. In an example, a complex includes a nuclease (such as a Cas12a nuclease) and an appropriate crRNA; such a complex can optionally include one or more polynucleotides, such as the tracrRNA molecules described herein, donor polynucleotides, and functional RNA moieties. In some examples, a complex includes a gRNA (such as a crRNA) and a donor polynucleotide (or a template for production of a donor polynucleotide), which may be covalently or non-covalently linked. In other examples, a complex includes a nuclease and a donor DNA, which may be covalently linked. In further example, a complex includes one or more CRISPR nuclease polypeptides, a gRNA, and a donor DNA (or a template for production of donor DNA).

By "covalently linked" is meant that two elements (such as a gRNA and a tether or a gRNA and a donor DNA) are joined by a covalent bond, for example, an internucleotide linkage such as a phosphodiester bond, a phosphorothioate bond, a phosphothioate bond, or a peptide bond.

By "non-covalently linked" is meant that two elements (such as two discrete polynucleotides, or a polypeptide and a polynucleotide) interact non-covalently, for example by hydrogen bonding, such as Watson-Crick base pairing. Other non-covalent interactions include non-Watson-Crick pairing, electrostatic interactions, van der Waals forces, π-effects, and hydrophobic effects.

By "in vivo" is meant that the systems, compositions, and methods of this disclosure are applied to or within a living organism, such as a living intact non-human animal, a living human, or a living plant or seed. By "in vitro" is meant that the systems, compositions, and methods of this disclosure are applied to cells or tissue maintained alive independently of an intact multicellular organism, such as a living intact non-human animal, a living intact human, or a living intact plant or seed; examples of in vitro embodiments include those where the systems, compositions, and methods of this disclosure are applied to stable or transient animal or plant cell lines in culture and tissue samples in culture. In vitro embodiments further include prokaryotic cell cultures. By "ex vivo" is meant occurring in cells, tissue, or organs (e.g., blood, blood cells, T cells, liver cells or tissue, skin, bone, muscle, eggs or ovules, sperm, pollen, etc.) removed from a living non-human animal, human, or plant and at least temporarily maintained alive in culture. Ex vivo cells or tissues may be returned to a living intact multicellular organism, such as the living non-human animal, human, or plant from which the cells or tissue were originally removed. In an embodiment, the systems, compositions, and methods of this disclosure are applied to human T-cells for the purpose of generating chimeric antigen receptor T cells ("CAR-T cells"), which may be delivered to a human as atherapeutic; see, e.g., Liu et al., *Frontiers Immunol.,* 10:456, available at doi: 10.3389/fimmu.2019.00456. Ex vivo cells or tissues may be grown into differentiated tissue or even differentiated organs, or undifferentiated tissue or callus. Ex vivo plant cells or plant tissues may be grown into intact plants.

Method of Tethering a Functional RNA Molecule to a Cas12a crRNA or a Cas12a Ribonucleoprotein An aspect of this invention provides a method of tethering a functional RNA molecule to a Cas12a crRNA, optionally to a Cas12a ribonucleoprotein including a Cas12a nuclease and a Cas12a crRNA. In embodiments, the method includes the step of hybridizing (a) a functional RNA molecule including a Cas12a tracrRNA and a functional RNA moiety; and (b) a Cas12a crRNA that includes a 3' extension capable of hybridizing with a segment of the functional RNA molecule; thereby tethering the functional RNA molecule to the Cas12a crRNA. In embodiments, the method includes the step of hybridizing (a) a functional RNA molecule including a Cas12a tracrRNA and a functional RNA moiety; and (b) a naturally occurring Cas12a crRNA that optionally includes a 3' extension capable of hybridizing with a segment of the functional RNA molecule; thereby tethering the functional RNA molecule to the Cas12a crRNA. In embodiments, the method includes the step of hybridizing (a) a functional RNA molecule including a Cas12a tracrRNA and a functional RNA moiety; and (b) an engineered Cas12a crRNA that optionally includes a 3' extension capable of hybridizing with a segment of the functional RNA molecule; thereby tethering the functional RNA molecule to the Cas12a crRNA.

Embodiments of a "Cas12a tracrRNA" include an RNA molecule having the nucleotide sequence of a naturally occurring tracrRNA identified from a native Cas12a locus. For example, a naturally occurring Cas12a tracrRNA can be identified from a genome using the techniques described by Zetsche et al. (2015) *Cell,* 163:759-771, and in U.S. Pat. No. 9,790,490. A naturally occurring Cas12a tracrRNA can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably but not necessarily includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the transcribed tracrRNA has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments, the transcribed tracrRNA has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments, the Cas12a tracrRNA has a sequence that is selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring tracrRNA identified from a native Cas12a locus. Examples include RNA molecules that include the nucleotide sequence of a tracrRNA (or putative tracrRNA) identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label.

In embodiments of the method, the functional RNA molecule is provided by transcription of a DNA molecule including DNA encoding the Cas12a tracrRNA and DNA encoding the functional RNA moiety, wherein the DNA encoding the functional RNA moiety is inserted at a restriction endonuclease cleavage site in or adjacent to the DNA encoding the Cas12a tracrRNA. In embodiments, the restriction endonuclease cleavage site is located within the 3' region of the DNA encoding the Cas12a tracrRNA, or within a short distance (e.g., within about 40, about 30, about 20, or about 10 nucleotides) of the 3' end of the Cas12a tracrRNA. In embodiments, the restriction endonuclease cleavage site occurs natively in the Cas12a tracrRNA, that is to say, occurs in a naturally occurring DNA sequence that encodes a predicted or putative Cas12a tracrRNA. In other embodiments, the restriction endonuclease cleavage site is artificial or engineered; a non-limiting example includes a naturally occurring DNA sequence that encodes a predicted or putative Cas12a tracrRNA and further includes at least one nucleotide that is artificially added, deleted, or substituted to provide an engineered restriction endonuclease cleavage site located in or adjacent to the sequence encoding the tracrRNA.

In embodiments of the method, the crRNA 3' extension includes nucleotides that when base-paired form about one helical turn. In embodiments, the crRNA 3' extension includes at least 10 contiguous nucleotides. In embodiments, the crRNA 3' extension increases hybridization of the Cas12a crRNA to the Cas12a tracrRNA. In some embodiments, the Cas12a tracrRNA further includes a 5' extension, such as the 5' extensions disclosed by Park et al. (2018) *Nature Communications*, doi: 10.1038/s41467-018-05641-3.

The functional RNA molecule includes a Cas12a tracrRNA and at least one functional RNA moiety. In embodiments, the functional RNA moiety is a nucleotide sequence inserted at a restriction endonuclease cleavage site in or adjacent to the DNA encoding the Cas12a tracrRNA. Non-limiting embodiments of functional RNA moieties include: (a) an RNA sequence for annealing to a donor polynucleotide (e.g., a single- or double-stranded DNA containing a nucleotide template for HDR-mediated editing, or a single- or double-stranded polynucleotide including a nucleotide sequence to be integrated by an NHEJ mechanism at a double-stranded break effected, for example, by the Cas12a nuclease); (b) an RNA sequence for annealing to the crRNA 3' extension; (c) a terminator sequence; (d) an RNA aptamer; (e) a ribozyme or catalytically active RNA; (f) a detectable label, such as a fluorescent tag; (g) a bar-coding sequence, or short nucleotide sequence useful for marking and identifying DNA that contains the bar-coding sequence; and (h) an RNA sequence forming at least partially double-stranded RNA. In an embodiment, the functional RNA moiety includes RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). In embodiments, the functional RNA moiety is a terminator, e.g., a terminator functional in eukaryotic cells, such as a U6 poly-T terminator, an SV40 terminator, an hGH terminator, a BGH terminator, an rbGlob terminator, a synthetic terminator functional in a eukaryotic cell, a 3' element from an *Agrobacterium* sp. gene, a 3' element from a non-human animal gene, a 3' element from a human gene, and a 3' element from a plant gene, wherein the 3' element terminate transcription of an RNA transcript located immediately 5' to the 3' element. Non-limiting examples of RNA aptamers include an MS2 aptamer (see Parrott et al. (2000) *Nucleic Acids Res.,* 28(2):489-497), an ARiBo tag (see Di Tomasso et al. (2011) *Nucleic Acids Res.,* 39(3):e18; doi: 10.1093/nar/gkq1084), a streptavidin-binding aptamer (see Leppek and Stoecklin (2014) *Nucleic Acids Res.,* 452(2): e13; doi: 10.1093/nar/gkt956), a Csy4 aptamer (see Lee et al. (2013) *Proc. Natl. Acad. Sci. USA,* 110(14):5416-5421; doi: 10.1073/pnas.1302807110, and a Sephadex aptamer (see Srisawat and Engelke (2002) *Methods,* 26(2):156-161; doi: 10.1016/S1046-2023(02)00018-X. Many aptamers are useful for affinity purification and tagging; for example, a two-element affinity tag useful for preparing large quantities of RNA includes a variant of the hepatitis delta virus (H6V) ribozyme that is activated by imidazole and a hairpin loop from a thermostable SRP RNA that forms a high-affinity and kinetically stable complex with the *Thermotoga maritima* Ffh-M domain protein (see Keift and Batey (2004) *RNA,* 10(6): 988-995; doi: 10.1261/rna.7040604).

In embodiments, the method includes the step of hybridizing in vitro (a) a functional RNA molecule including a Cas12a tracrRNA and a functional RNA moiety; and (b) a Cas12a crRNA that includes a 3' extension capable of hybridizing with a segment of the functional RNA molecule. In embodiments, the method includes the step of hybridizing in vitro (a) a functional RNA molecule including a Cas12a tracrRNA and a functional RNA moiety; and (b) a naturally occurring or an engineered Cas12a crRNA that optionally includes a 3' extension capable of hybridizing with a segment of the functional RNA molecule. In some embodiments, a heating (melting) step and a cooling step are employed during the hybridization. In some embodiments, the hybridization is carried out at room temperature, without additional heating or cooling steps.

In many embodiments of the method, the Cas12a crRNA is complexed with, or is capable of complexing with, a Cas12a nuclease to form a Cas12a ribonucleoprotein complex containing the functional RNA molecule. Complexing of the Cas12a crRNA with the Cas12a nuclease can occur prior to, concurrently with, or after hybridization of the functional RNA molecule with the Cas12a crRNA. In embodiments, the method includes the step of hybridizing (a) a functional RNA molecule including a Cas12a tracrRNA and a functional RNA moiety; and (b) a naturally occurring Cas12a crRNA that optionally includes a 3' extension capable of hybridizing with a segment of the functional RNA molecule; following this hybridization, the Cas12a nuclease is added to form the Cas12a ribonucleoprotein. In embodiments, the method includes the step of hybridizing (a) a functional RNA molecule including a Cas12a tracrRNA and a functional RNA moiety; and (b) an engineered Cas12a crRNA that optionally includes a 3' extension capable of hybridizing with a segment of the functional RNA molecule; following this hybridization, the Cas12a nuclease is added to form the Cas12a ribonucleoprotein. A related aspect of the invention is therefore a modified Cas12a ribonucleoprotein complex including (a) a Cas12a nuclease; (b) a functional RNA molecule including a Cas12a tracrRNA and a functional RNA moiety; and (c) a naturally occurring or an engineered Cas12a crRNA that optionally includes a 3' extension capable of hybridizing with a segment of the functional RNA molecule.

In embodiments of the method wherein the Cas12a crRNA is complexed with, or is capable of complexing with, a Cas12a nuclease, or in embodiments of the modified Cas12a ribonucleoprotein complex thus formed, the Cas12a nuclease is any one of the Cas12a ("Cpf1") nucleases disclosed in U.S. Pat. No. 9,790,490 or in U.S. patent application Ser. No. 15/566,528 (national phase entry of International Application No. PCT/EP2016/058442, published as WO2016166340), or in U.S. Pat. No. 9,896,696 which are specifically incorporated herein by reference. In specific embodiments, the Cas12a nuclease is a Cas12a ("Cpf1") nuclease identified from *Francisella novicida* U112 (FnCas12a or "FnCpf1"), from *Acidaminococcus* sp. BV3L6 (AsCas12a or "AsCpf1"), or from Lachnospiraceae bacterium ND2006 (LbCas12a or "LbCpf1"), or is an orthologue thereof, such as an orthologue having at least 50% sequence identity to FnCas12a ("FnCpf1"); see, e.g., the FnCpf1 nuclease contained in the FnCpf1 locus having SEQ ID NO:211 in U.S. Pat. No. 9,790,490, incorporated herein by reference. In embodiments, a Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease includes orthologues of LbCas12a, AsCas12a, or FnCas12a. In embodiments, the Cas12a nuclease is deactivated. In embodiments, the Cas12a nuclease includes at least one modification selected from the group consisting of: (a) a localization or signal peptide (e.g., a nuclear localization signal (NLS), a chloroplast or plastid transit peptide (CTP), or a mitochondrial targeting peptide (MTP)); (b) a detectable label (e.g., a fluorescent dye); (c) a cell-penetrating peptide; (d) an endosomal escape peptide; and (e) an affinity tag. In embodiments, the Cas12a nuclease includes at least one modification selected from a fluorescent protein (e.g., green fluorescent protein (GFP), YFP, RFP, CFP, mCherry, tdTomato, mScarlett), a histidine tag (e.g., a 6×His tag), a hemagglutinin (HA) tag, a FLAG tag, a Myc tag, horseradish peroxidase (HRP), alkaline phosphatase (AP), beta-galactosidase (GAL), glucose-6-phosphate dehydrogenase, beta-N-acetylglucosaminidase, beta-glucuronidase, invertase, xanthine oxidase (XO), firefly luciferase (LUC), and glucose oxidase (GO). The systems and compositions including a tracrRNA and methods of use thereof that are disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

A Method of Integrating a Sequence Encoded by a Donor Polynucleotide at a Specific Locus Another aspect of the invention provides a method of integrating or inserting a nucleotide sequence encoded by a donor polynucleotide at a specific locus in a target DNA, wherein the method includes the steps of: (1) annealing a donor polynucleotide to a modified Cas12a ribonucleoprotein complex, wherein the modified Cas12a ribonucleoprotein complex includes: (a) a Cas12a nuclease; (b) a functional RNA molecule including a Cas12a tracrRNA and a functional RNA moiety; and (c) a Cas12a crRNA that includes a 3' extension capable of hybridizing with a segment of the functional RNA molecule; wherein the functional RNA moiety includes an RNA sequence for annealing to the donor polynucleotide; and wherein the Cas12a crRNA includes a spacer sequence that corresponds to a specific target locus in a target DNA, thus forming a donor:RNP complex; and (2) contacting the target DNA with the donor:RNP complex; whereby the nucleotide sequence encoded by the donor polynucleotide is integrated or inserted at the specific target locus in the target DNA.

In embodiments, the Cas12a nuclease that forms part of the modified Cas12a ribonucleoprotein complex is any one of the Cas12a ("Cpf1") nucleases disclosed in U.S. Pat. No. 9,790,490 or in U.S. patent application Ser. No. 15/566,528 (national phase entry of International Application No. PCT/EP2016/058442, published as WO2016166340), or in U.S. Pat. No. 9,896,696 which are specifically incorporated herein by reference. In specific embodiments, the Cas12a nuclease is a Cas12a ("Cpf1") nuclease identified from *Francisella novicida* U112 (FnCas12a or "FnCpf1"), from *Acidaminococcus* sp. BV3L6 (AsCas12a or "AsCpf1"), or from Lachnospiraceae bacterium ND2006 (LbCas12a or "LbCpf1"), or is an orthologue thereof, such as an orthologue having at least 50% sequence identity to FnCas12a ("FnCpf1"); see, e.g., the FnCpf1 nuclease contained in the FnCpf1 locus having SEQ ID NO:211 in U.S. Pat. No. 9,790,490, incorporated herein by reference. In embodiments, a Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization or signal peptide (e.g., a nuclear localization signal (NLS), a chloroplast or plastid transit peptide (CTP), or a mitochondrial targeting peptide (MTP)); (b) a detectable label (e.g., a fluorescent dye); (c) a cell-penetrating peptide; (d) an endosomal escape peptide; and (e) an affinity tag. The methods including the use of a tracrRNA as disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

Embodiments of a "Cas12a tracrRNA" include an RNA molecule having the nucleotide sequence of a naturally occurring tracrRNA identified from a native Cas12a locus. For example, a naturally occurring Cas12a tracrRNA can be identified from a genome using the techniques described by Zetsche et al. (2015) *Cell,* 163:759-771, and in U.S. Pat. No. 9,790,490. A naturally occurring Cas12a tracrRNA can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably but not necessarily includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the transcribed tracrRNA has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments, the transcribed tracrRNA has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments, the Cas12a tracrRNA has a sequence that is selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring tracrRNA identified from a native Cas12a locus. Examples include RNA molecules that include the nucleotide sequence of a tracrRNA (or putative tracrRNA) identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label.

In embodiments, the functional RNA moiety includes an RNA sequence for annealing to the donor polynucleotide. The RNA sequence for annealing to the donor polynucleotide has a length and degree of sequence identity that in combination are sufficient to allow hybridization of the functional RNA moiety and the donor polynucleotide at physiological conditions. For convenience and economy, in some embodiments, the RNA sequence for annealing to the donor polynucleotide is short, about 10 nucleotides in length, and has exact (100%) sequence complementarity to a segment of the donor polynucleotide of equivalent length. In other embodiments, the RNA sequence for annealing to the donor polynucleotide is greater than 10 nucleotides in length, and has at least 50%, at least 60%, at least 70%, at least 80%, at least 90%, or at least 95% sequence complementarity to a segment of the donor polynucleotide of equivalent length.

In embodiments, the donor polynucleotide includes single-stranded DNA, optionally including chemical modifications. In other embodiments, the donor polynucleotide includes double-stranded DNA, optionally including chemical modifications. In some embodiments, the donor polynucleotide includes both DNA and RNA, for example as a duplex formed by a DNA strand and an RNA strand. In embodiments, the donor polynucleotide is designed to include a template for genome editing via homology-dependent repair (HDR); the template generally includes a "core sequence" that is to replace a sequence of the genome of about the same size, as well as "homology arms" that flank the core sequence on either side and have a sequence complementary to the genomic regions flanking the genomic sequence to be replaced or edited. In other embodiments, the donor polynucleotide does not include homology arms or does not include a core sequence and homology arms, for example in embodiments where the donor polynucleotide is used to make a deletion.

In general, a donor polynucleotide including a template encoding a nucleotide change over a region of less than about 50 nucleotides is conveniently provided in the form of single-stranded DNA; larger donor templates (e.g., more than 100 nucleotides) are often conveniently provided as double-stranded DNAs. Thus in some embodiments, the donor polynucleotide is about 25 nucleotides, 50 nucleotides, 60 nucleotides, 70 nucleotides 80 nucleotides, 90 nucleotides, 100 nucleotides, 200 nucleotides, 300 nucleotides, 400 nucleotides, 500 nucleotides, 600 nucleotides, 700 nucleotides, 800 nucleotides, 900 nucleotides, 1000 nucleotides, 1200 nucleotides, 1500 nucleotides, 1800 nucleotides, 2000 nucleotides, 2500 nucleotides, 3000 nucleotides, 5000 nucleotides, 10,000 nucleotides, or more (such as about 25-200 nucleotides, 50-300 nucleotides, 100-500 nucleotides, 200-800 nucleotides, 700-2000 nucleotides, 1000-2500 nucleotides, 2000-5000 nucleotides, 4000-8000 nucleotides, or 6000-10,000 nucleotides).

The target DNA or target sequence (i.e., the DNA to be edited) is in many embodiments genomic DNA or chromosomal DNA of a eukaryotic cell or eukaryotic organism. In embodiments, the target DNA is mitochondrial DNA or plastid DNA. In embodiments, the target DNA includes recombinant DNA, for example, a transgene stably integrated in the genome of a eukaryote, such as of a plant. Target sequences and eukaryotic cells are described in detail below under the section headed "Related Disclosure".

DNA Expression Systems (I)

Another aspect of the invention provides a DNA expression system including: (a) DNA sequence for a first promoter; and (b) operably linked and heterologous to the first promoter, a DNA sequence encoding a first RNA molecule including a Cas12a tracrRNA and including a restriction endonuclease cleavage site that is suitable for insertion of a sequence coding for a functional RNA moiety.

The first promoter is heterologous to the DNA encoding a first RNA molecule including a Cas12a tracrRNA and including a restriction endonuclease cleavage site. The first promoter is selected for operability in the context (in vitro or in vivo) in which the DNA expression system is to be used. Thus, in certain embodiments, the first promoter is a promoter that functions in prokaryotic cells, such as in bacterial cells. In preferred embodiments, the first promoter is a promoter that functions in eukaryotic cells, such as in non-human animal (e.g., mammalian, human) or human or plant or fungal cells; in embodiments, the first promoter is one identified from a eukaryotic genome, such as a non-human animal or human or plant or fungal genome. In embodiments, the first promoter is a promoter selected from the group consisting of pol III promoters, pol II promoters, and pol I promoters. In embodiments, the first promoter is a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, and an EF1a promoter. For use in plants, useful promoters include constitutive, conditional, inducible, and temporally or spatially specific promoters (e.g., a tissue specific promoter, a developmentally regulated promoter, or a cell cycle regulated promoter). In embodiments, the promoter is a pol II promoter. In embodiments, the promoter is a constitutive promoter that drives DNA expression in plant cells; in embodiments, the promoter drives DNA expression in the nucleus or in an organelle such as a chloroplast or mitochondrion. Examples of constitutive promoters include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and an opaline synthase (NOS) and octapine synthase (OCS) promoter from *Agrobacterium tumefaciens*. In embodiments, the promoter is a promoter from figwort mosaic virus (FMV), a RUBISCO promoter, or a pyruvate phosphate dikinase (PDK) promoter, which is active in the chloroplasts of mesophyll cells. Other contemplated promoters include cell-specific or tissue-specific or developmentally regulated promoters, for example, a promoter that limits the expression of the DNA expression system to germline or reproductive cells (e.g., promoters of genes encoding DNA ligases, recombinases, replicases, or other genes specifically expressed in germline or reproductive cells). In embodiments, the first promoter is a plant U6 spliceosomal RNA promoter, which can be native to the genome of the plant cell or from a different species, e.g., a U6 promoter from maize, tomato, or soybean such as those disclosed in U.S. patent application Ser. No. 15/120,110, published as U.S. Patent Application Publication 2017/0166912, national phase application claiming priority to PCT/US2015/018104 (published as WO 2015/131101 and claiming priority to U.S. Provisional Patent Application 61/945,700), or a homologue thereof, in an example, such a promoter is operably linked to DNA sequence encoding a first RNA molecule including a Cas12a tracrRNA and including a restriction endonuclease cleavage site that is suitable for insertion of a sequence coding for a functional RNA moiety, followed by a suitable 3' element such as a U6 poly-T terminator. In another embodiment, the first promoter is a plant U3, 7SL (signal recognition particle RNA), U2, or U5 promoter, or chimerics thereof, e.g., as described in U.S. patent application Ser. No. 15/120,110, published as U.S. Patent Application Publication 2017/0166912, national phase application claiming priority to PCT/US2015/018104 (published as WO 2015/131101 and claiming priority to U.S. Provisional Patent Application 61/945,700). All of the patent publications referenced in this paragraph are incorporated herein by reference in their entirety. Additional non-limiting embodiments of promoters functional in plants are provided in Example 5.

Embodiments of a "Cas12a tracrRNA" include an RNA molecule having the nucleotide sequence of a naturally occurring tracrRNA identified from a native Cas12a locus. For example, a naturally occurring Cas12a tracrRNA can be identified from a genome using the techniques described by Zetsche et al. (2015) *Cell,* 163:759-771, and in U.S. Pat. No. 9,790,490. A naturally occurring Cas12a tracrRNA can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the transcribed tracrRNA has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments, the transcribed tracrRNA has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments, the Cas12a tracrRNA has a sequence that is selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring tracrRNA identified from a native Cas12a locus. Examples include RNA molecules that include the nucleotide sequence of a tracrRNA (or putative tracrRNA) identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label. In embodiments of the DNA expression system, the Cas12a tracrRNA further includes a 5' extension, such as the 5' extensions disclosed by Park et al. (2018) *Nature Communications*, doi: 10.1038/s41467-018-05641-3.

In one application, the DNA expression system is useful for expression of an RNA molecule that includes a Cas12a tracrRNA and a functional RNA moiety. Thus, the DNA expression system includes a DNA sequence that encodes a first RNA molecule including a Cas12a tracrRNA, and that includes a restriction endonuclease cleavage site that is suitable for insertion of a sequence coding for an RNA moiety. In embodiments, the restriction endonuclease cleavage site is located in or adjacent to the DNA encoding the Cas12a tracrRNA. In embodiments, the restriction endonuclease cleavage site is located within the DNA encoding the Cas12a tracrRNA. In preferred embodiments, the restriction endonuclease cleavage site is located within the 3' region of the DNA encoding the Cas12a tracrRNA, or within a short distance (e.g., within about 40, about 30, about 20, or about 10 nucleotides) of the 3' end of the Cas12a tracrRNA. In many embodiments, the restriction endonuclease recognizes and binds to the DNA at the same location at which the endonuclease cuts the DNA. In some embodiments, the restriction endonuclease cleavage site (that is, where the restriction endonuclease cuts) can be at a location on the DNA at a short distance from where the restriction endonuclease recognizes and binds to the DNA. In embodiments, the restriction endonuclease cleavage site occurs natively in the Cas12a tracrRNA, that is to say, occurs in a naturally occurring DNA sequence that encodes a predicted or putative Cas12a tracrRNA. In other embodiments, the restriction endonuclease cleavage site is artificial or engineered; in a non-limiting example includes a naturally occurring DNA sequence that encodes a predicted or putative Cas12a tracrRNA and further includes at least one nucleotide that is artificially added, deleted, or substituted to provide an engineered restriction endonuclease cleavage site located in or adjacent to the sequence encoding the tracrRNA. In embodiments, the DNA expression system further includes a terminator located 3' to the DNA sequence encoding the tracrRNA.

In embodiments, the DNA expression system further includes: (a) optionally, a DNA sequence for a second promoter; (b) operably linked and heterologous to the first promoter or the second promoter, a DNA encoding a Cas12a crRNA that includes a 3' extension capable of hybridizing with a segment of the first RNA molecule (wherein the segment can be within or part of the tracrRNA that is part of the first RNA molecule); and (c) optionally, a terminator. The optional second promoter is selected for operability in the context (in vitro or in vivo) in which the DNA expression system is to be used. Thus, in certain embodiments, the second promoter is a promoter that functions in prokaryotic cells, such as in bacterial cells. In preferred embodiments, the second promoter is a promoter that functions in eukaryotic cells, such as in non-human animal (e.g., mammalian, human) or human or plant or fungal cells; in embodiments, the first promoter is one identified from a eukaryotic genome, such as a non-human animal or human or plant or fungal genome. In embodiments, the second promoter is a promoter such as those described as suitable for the first promoter. In embodiments, the first promoter and the second promoter, if present, are different promoters. In embodiments, the first promoter and the DNA encoding the first RNA molecule, and the DNA encoding a Cas12a crRNA that includes a 3' extension are contained in a single construct. In some embodiments where the DNA expression system includes the second promoter, the first promoter and the DNA encoding the first RNA molecule are contained in a first construct, and the second promoter and the DNA encoding a Cas12a crRNA that includes a 3' extension are contained in a second construct; in such embodiments, the first construct and the second construct can be provided (a) in a single vector, or (b) in separate vectors. In other embodiments, the first promoter drives expression of both the DNA encoding the first RNA molecule and the DNA encoding the Cas12a crRNA.

In embodiments where the DNA expression system further includes a terminator located 3' to the DNA sequence encoding the tracrRNA, the terminator is functional in the cell wherein the DNA expression system is to be used. By "terminator" is meant a DNA segment near the 3' end of an expression cassette that acts as a signal to terminate transcription and directs polyadenylation of the resultant mRNA. Such a 3' element is also sometimes referred to as a "3'-untranslated region" or "3'-UTR" or a "polyadenylation signal". Non-limiting embodiments of terminators functional in eukaryotic cells include a U6 poly-T terminator, an SV40 terminator, an hGH terminator, a BGH terminator, an rbGlob terminator, a synthetic terminator functional in a eukaryotic cell, a 3' element from an *Agrobacterium* sp. gene, a 3' element from a non-human animal gene, a 3' element from a human gene, and a 3' element from a plant gene, wherein the 3' element terminate transcription of an RNA transcript located immediately 5' to the 3' element. Useful 3' elements include: *Agrobacterium tumefaciens* nos 3', tml 3', tmr 3', tins 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in U.S. Patent Application Publication 2002/0192813 A1, incorporated herein by reference. Cas12a tracrRNAs (such as putative Cas12a tracrRNAs identified as described herein) may have associated endogenous pol III terminators which can be used in the DNA expression systems disclosed herein. In embodiments, the DNA expression system includes a heterologous promoter operably linked to a DNA sequence that encodes a first RNA molecule that includes a Cas12a tracrRNA and that includes a restriction endonuclease cleavage site that is suitable for insertion of a sequence coding for an RNA moiety, and further includes an endogenous pol III terminator (e.g., the terminator naturally associated with a putative Cas12a tracrRNA), or a heterologous terminator. In preferred embodiments of the various DNA expression systems disclosed herein, the terminator is functional in a eukaryotic cell, such as a plant cell; in embodiments, the terminator is one identified from eukaryotic genomic sequence, such as a plant genomic sequence. In embodiments, the terminator has a sequence selected from the group consisting of SEQ ID NOs:72-100.

In embodiments of the DNA expression system, the Cas12a crRNA is capable of complexing with a Cas12a nuclease to form a Cas12a ribonucleoprotein complex or system. In embodiments, the Cas12a nuclease is any one of the Cas12a ("Cpf1") nucleases disclosed in U.S. Pat. No. 9,790,490 or in U.S. patent application Ser. No. 15/566,528 (national phase entry of International Application No. PCT/EP2016/058442, published as WO2016166340), or in U.S. Pat. No. 9,896,696 which are specifically incorporated herein by reference. In specific embodiments, the Cas12a nuclease is a Cas12a ("Cpf1") nuclease identified from *Francisella novicida* U112 (FnCas12a or "FnCpf1"), from *Acidaminococcus* sp. BV3L6 (AsCas12a or "AsCpf1"), or from Lachnospiraceae bacterium ND2006 (LbCas12a or "LbCpf1"), or is an orthologue thereof, such as an orthologue having at least 50% sequence identity to FnCas12a ("FnCpf1"); see, e.g., the FnCpf1 nuclease contained in the FnCpf1 locus having SEQ ID NO:211 in U.S. Pat. No. 9,790,490, incorporated herein by reference. In embodiments, a Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. In embodiments of the DNA expression system, the first promoter has a DNA sequence selected from the group consisting of SEQ ID NOs:16-71 and the Cas12a tracrRNA has a nucleotide sequence including a sequence selected from the group consisting of SEQ ID NOs:1, 3, 6, 139-146, and 149-169. In embodiments of the DNA expression system, the first promoter has a DNA sequence selected from the group consisting of SEQ ID NOs:16-71, the Cas12a tracrRNA has a nucleotide sequence including a sequence selected from the group consisting of SEQ ID NOs:1, 3, 6, 139-146, and 149-169, and the optional first terminator has a sequence selected from the group consisting of SEQ ID NOs:72-100. The systems including a tracrRNA as disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

DNA Expression Systems (II)

Another aspect of the invention provides a DNA expression system including: (a) DNA sequence for a first promoter; and (b) operably linked and heterologous to the first promoter, a DNA sequence encoding a functional RNA molecule including a Cas12a tracrRNA and a functional RNA moiety. In embodiments, the DNA expression system includes (a) DNA sequence for a first promoter; and (b) operably linked and heterologous to the first promoter, a DNA sequence encoding a functional RNA molecule including a Cas12a tracrRNA and a functional RNA moiety, and (c) a terminator 3' to and operably linked to the DNA encoding a functional RNA molecule. In embodiments, the DNA expression system further includes: (a) optionally, a DNA sequence for a second promoter; (b) operably linked and heterologous to the first promoter or the second promoter, a DNA encoding a Cas12a crRNA that includes a 3' extension capable of hybridizing with a segment of the functional RNA molecule; and (c) optionally, a terminator.

The first promoter is heterologous to the DNA sequence encoding a functional RNA molecule including a Cas12a tracrRNA and a functional RNA moiety. Where the DNA expression system further includes a DNA encoding a Cas12a crRNA that includes a 3' extension capable of hybridizing with a segment of the functional RNA molecule, the first promoter is also heterologous to this DNA. The optional second promoter is heterologous to the DNA encoding a Cas12a crRNA that includes a 3' extension capable of hybridizing with a segment of the functional RNA molecule. Each promoter is selected for operability in the context (in vitro or in vivo) in which the DNA expression system is to be used. Thus, in embodiments, the first promoter (and the optional second promoter) is a promoter that functions in prokaryotic cells, such as in bacterial cells. In preferred embodiments, the first promoter is a promoter that functions in eukaryotic cells, such as in non-human animal (e.g., mammalian, human) or human or plant or fungal cells; in embodiments, the first promoter is one identified from a eukaryotic genome, such as a non-human animal or human or plant or fungal genome. In embodiments, the first promoter is a promoter selected from the group consisting of pol III promoters, pol II promoters, and pol I promoters. In embodiments, the first promoter is a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, and an EF1a promoter. In embodiments, the first promoter (and the optional second promoter) is a promoter that functions in eukaryotic cells, such as in plant cells. For use in plants, useful promoters include constitutive, conditional, inducible, and temporally or spatially specific promoters (e.g., a tissue specific promoter, a developmentally regulated promoter, or a cell cycle regulated promoter). In embodiments, the promoter is a pol II promoter. In embodiments, the promoter is a constitutive promoter that drives DNA expression in plant cells; in embodiments, the promoter drives DNA expression in the nucleus or in an organelle such as a chloroplast or mitochondrion. Examples of constitutive promoters include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and an opaline synthase (NOS) and octapine synthase (OCS) promoter from *Agrobacterium tumefaciens*. In embodiments, the promoter is a promoter from figwort mosaic virus (FMV), a RUBISCO promoter, or a pyruvate phosphate dikinase (PDK) promoter, which is active in the chloroplasts of mesophyll cells. Other contemplated promoters include cell-specific or tissue-specific or developmentally regulated promoters, for example, a promoter that limits the expression of the DNA expression system to germline or reproductive cells (e.g., promoters of genes encoding DNA ligases, recombinases, replicases, or other genes specifically expressed in germline or reproductive cells). In embodiments, the first promoter is a plant U6 spliceosomal RNA promoter, which can be native to the genome of the plant cell or from a different species, e.g., a U6 promoter from maize, tomato, or soybean such as those disclosed in U.S. patent application Ser. No. 15/120,110, published as U.S. Patent Application Publication 2017/0166912, national phase application claiming priority to PCT/US2015/018104 (published as WO 2015/131101 and claiming priority to U.S. Provisional Patent Application 61/945,700), or a homologue thereof, in an example, such a promoter is operably linked to DNA sequence encoding a functional RNA molecule including a Cas12a tracrRNA and a functional RNA moiety, followed by a suitable 3' element such as a U6 poly-T terminator. In another embodiment, the first promoter is a plant U3, 7SL (signal recognition particle RNA), U2, or U5 promoter, or chimerics thereof, e.g., as described in U.S. patent application Ser. No. 15/120,110, published as U.S. Patent Application Publication 2017/0166912, national phase application claiming priority to PCT/US2015/018104 (published as WO 2015/131101 and claiming priority to U.S. Provisional Patent Application 61/945,700). All of the patent publications referenced in this paragraph are incorporated herein by reference in their entirety.

Embodiments of a "Cas12a tracrRNA" include an RNA molecule having the nucleotide sequence of a naturally occurring tracrRNA identified from a native Cas12a locus. For example, a naturally occurring Cas12a tracrRNA can be identified from a genome using the techniques described by Zetsche et al. (2015) *Cell,* 163:759-771, and in U.S. Pat. No. 9,790,490. A naturally occurring Cas12a tracrRNA can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the transcribed tracrRNA has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments, the transcribed tracrRNA has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments, the Cas12a tracrRNA has a sequence that is selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring tracrRNA identified from a native Cas12a locus. Examples include RNA molecules that include the nucleotide sequence of a tracrRNA (or putative tracrRNA) identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label. In embodiments of the DNA expression system, the Cas12a tracrRNA further includes a 5' extension, such as the 5' extensions disclosed by Park et al. (2018) *Nature Communications*, doi: 10.1038/s41467-018-05641-3.

In embodiments where the DNA expression system further includes a terminator located 3' to and operably linked to the DNA encoding a functional RNA molecule, the terminator is functional in the cell wherein the DNA expression system is to be used. By "terminator" is meant a DNA segment near the 3' end of an expression cassette that acts as a signal to terminate transcription and directs polyadenylation of the resultant mRNA. Such a 3' element is also sometimes referred to as a "3'-untranslated region" or "3'-UTR" or a "polyadenylation signal". Non-limiting embodiments of terminators functional in eukaryotic cells include a U6 poly-T terminator, an SV40 terminator, an hGH terminator, a BGH terminator, an rbGlob terminator, a synthetic terminator functional in a eukaryotic cell, a 3' element from an *Agrobacterium* sp. gene, a 3' element from a non-human animal gene, a 3' element from a human gene, and a 3' element from a plant gene, wherein the 3' element terminate transcription of an RNA transcript located immediately 5' to the 3' element. Useful 3' elements include: *Agrobacterium tumefaciens* nos 3', tml 3', tmr 3', tins 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in U.S. Patent Application Publication 2002/0192813 A1, incorporated herein by reference. Cas12a tracrRNAs (such as putative Cas12a tracrRNAs identified as described herein) may have associated endogenous pol III terminators which can be used in the DNA expression systems disclosed herein. In embodiments, the DNA expression system includes: (a) DNA sequence for a first promoter; (b) operably linked and heterologous to the first promoter, a DNA sequence encoding a functional RNA molecule including a Cas12a tracrRNA and a functional RNA moiety; and (c) an endogenous pol III terminator (e.g., the terminator naturally associated with a putative Cas12a tracrRNA), or a heterologous terminator. In preferred embodiments of the various DNA expression systems disclosed herein, the terminator is functional in a eukaryotic cell, such as a plant cell; in embodiments, the terminator is one identified from eukaryotic genomic sequence, such as a plant genomic sequence.

In embodiments of the DNA expression system, the first promoter and the DNA encoding the functional RNA molecule, and the DNA encoding a Cas12a crRNA that includes a 3' extension are contained in a single construct. In embodiments of the DNA expression system that include the optional second promoter, the first promoter and the DNA encoding the functional RNA molecule are contained in a first construct, and the second promoter and the DNA encoding a Cas12a crRNA that includes a 3' extension are contained in a second construct; in such embodiments, the first construct and the second construct can be provided (a) in a single vector, or (b) in separate vectors. In embodiments, the first promoter drives expression of both the DNA encoding the functional RNA molecule and the DNA encoding the Cas12a crRNA.

The DNA expression system is useful for expressing a functional RNA molecule including a Cas12a tracrRNA and a functional RNA moiety. Non-limiting embodiments of functional RNA moieties include: (a) an RNA sequence for annealing to a donor polynucleotide (e.g., a single- or double-stranded DNA containing a nucleotide template for HDR-mediated editing, or a single- or double-stranded polynucleotide including a nucleotide sequence to be integrated by an NHEJ mechanism at a double-stranded break effected, for example, by the Cas12a nuclease); (b) an RNA sequence for annealing to the crRNA 3' extension; (c) a terminator sequence; (d) an RNA aptamer; (e) a ribozyme or catalytically active RNA; (f) a detectable label, such as a fluorescent tag; (g) a bar-coding sequence, or short nucleotide sequence useful for marking and identifying DNA that contains the bar-coding sequence; and (h) an RNA sequence forming at least partially double-stranded RNA. In an embodiment, the functional RNA moiety includes RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). Non-limiting examples of RNA aptamers include an MS2 aptamer (see Parrott et al. (2000) *Nucleic Acids Res.*, 28(2):489-497), an ARiBo tag (see Di Tomasso et al. (2011) *Nucleic Acids Res.*, 39(3):e18; doi: 10.1093/nar/gkq1084), a streptavidin-binding aptamer (see Leppek and Stoecklin (2014) *Nucleic Acids Res.*, 452(2):e13; doi: 10.1093/nar/gkt956), a Csy4 aptamer (see Lee et al. (2013) *Proc. Natl. Acad. Sci. USA,* 110(14):5416-5421; doi: 10.1073/pnas.1302807110, and a Sephadex aptamer (see Srisawat and Engelke (2002) *Methods,* 26(2):156-161; doi: 10.1016/S1046-2023(02)00018-X. Many aptamers are useful for affinity purification and tagging; for example, a two-element affinity tag useful for preparing large quantities of RNA includes a variant of the hepatitis delta virus (H6V) ribozyme that is activated by imidazole and a hairpin loop from a thermostable SRP RNA that forms a high-affinity and kinetically stable complex with the *Thermotoga maritima* Ffh-M domain protein (see Keift and Batey (2004) *RNA,* 10(6): 988-995; doi: 10.1261/rna.7040604).

In embodiments of the DNA expression system, the Cas12a crRNA is capable of complexing with a Cas12a nuclease to form a Cas12a ribonucleoprotein complex containing the functional RNA molecule including a Cas12a tracrRNA and a functional RNA moiety. In embodiments, the Cas12a nuclease is any one of the Cas12a ("Cpf1") nucleases disclosed in U.S. Pat. No. 9,790,490 or in U.S. patent application Ser. No. 15/566,528 (national phase entry of International Application No. PCT/EP2016/058442, published as WO2016166340), or in U.S. Pat. No. 9,896,696 which are specifically incorporated herein by reference. In specific embodiments, the Cas12a nuclease is a Cas12a ("Cpf1") nuclease identified from *Francisella novicida* U112 (FnCas12a or "FnCpf1"), from *Acidaminococcus* sp. BV3L6 (AsCas12a or "AsCpf1"), or from Lachnospiraceae bacterium ND2006 (LbCas12a or "LbCpf1"), or is an orthologue thereof, such as an orthologue having at least 50% sequence identity to FnCas12a ("FnCpf1"); see, e.g., the FnCpf1 nuclease contained in the FnCpf1 locus having SEQ ID NO:211 in U.S. Pat. No. 9,790,490, specifically incorporated herein by reference. In embodiments, a Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020*, Candidatus Methanoplasma termitum, Eubacterium eligens, Moraxella bovoculi* 237*, Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide;

and (e) an affinity tag. In embodiments of the DNA expression system, the first promoter has a DNA sequence selected from the group consisting of SEQ ID NOs:16-71 and the Cas12a tracrRNA has a nucleotide sequence including a sequence selected from the group consisting of SEQ ID NOs:1, 3, 6, 139-146, and 149-169. In embodiments of the DNA expression system, the first promoter has a DNA sequence selected from the group consisting of SEQ ID NOs:16-71, the Cas12a tracrRNA has a nucleotide sequence including a sequence selected from the group consisting of SEQ ID NOs:1, 3, 6, 139-146, and 149-169, and the optional first terminator has a sequence selected from the group consisting of SEQ ID NOs:72-100. The systems including a tracrRNA as disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

Engineered Systems

Another aspect of the invention provides a first engineered system including: (a) a Cas12a nuclease; and (b) at least one engineered Cas12a crRNA, or a polynucleotide encoding the engineered Cas12a crRNA, wherein the engineered Cas12a crRNA includes (i) at least one direct repeat sequence or fragment thereof that is capable of associating with the Cas12a nuclease, and (ii) a spacer sequence that is designed to hybridize with a target sequence in a eukaryotic cell, wherein the at least one direct repeat sequence or fragment thereof is adjacent to and 5' to the spacer sequence; and (c) a Cas12a tracrRNA including a nucleotide sequence that has at least 50% complementarity with, the nucleotide sequence of the at least one direct repeat of the engineered Cas12a crRNA.

In another aspect, the invention provides a second engineered system including: (a) a Cas12a nuclease; and (b) at least one engineered Cas12a crRNA, or a polynucleotide encoding the engineered Cas12a crRNA, wherein the engineered Cas12a crRNA includes (i) at least one direct repeat sequence or fragment thereof that is capable of associating with the Cas12a nuclease, and (ii) a spacer sequence that is designed to hybridize with a target sequence in a eukaryotic cell, wherein the at least one direct repeat sequence or fragment thereof is adjacent to and 5' to the spacer sequence; and (c) a Cas12a tracrRNA including a naturally occurring putative Cas12a tracrRNA sequence that is identified from the same genomic region as the Cas12a nuclease by at least the following steps: (i) identifying in the genomic region flanking the DNA encoding the Cas12a nuclease at least one nucleotide sequence that includes a CRISPR array including direct repeats, and (ii) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat.

In embodiments of the first or second engineered systems, the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The systems including a tracrRNA as disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of the first or second engineered systems, the Cas12a tracrRNA includes a nucleotide sequence that has at least 50% complementarity with, the nucleotide sequence of the at least one direct repeat of the engineered Cas12a crRNA; such a Cas12a tracrRNA can include a naturally occurring putative Cas12a tracrRNA sequence identified from a native Cas12a locus. For example, a naturally occurring putative Cas12a tracrRNA sequence can be identified from a genome using the techniques described by Zetsche et al. (2015) *Cell,* 163:759-771, and in U.S. Pat. No. 9,790,490. A naturally occurring putative Cas12a tracrRNA sequence can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the naturally occurring putative Cas12a tracrRNA sequence has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments, the naturally occurring putative Cas12a tracrRNA sequence has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments of the first or second engineered systems, the Cas12a tracrRNA has a nucleotide sequence including a sequence selected from the group consisting of SEQ ID NOs:1, 3, 6, 139-146, and 149-169. An alternative embodiment of a “Cas12a tracrRNA” includes an RNA molecule having or including a nucleotide sequence based on the nucleotide sequence of a naturally occurring putative Cas12a tracrRNA sequence identified from a native Cas12a locus. Examples include RNA molecules that include the nucleotide sequence of a naturally occurring putative Cas12a tracrRNA sequence identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label. In embodiments of the first or second engineered systems, the Cas12a tracrRNA further includes a 5' extension, such as the 5' extensions disclosed by Park et al. (2018) *Nature Communications*, doi: 10.1038/s41467-018-05641-3.

In embodiments of the first or second engineered systems, the engineered Cas12a crRNA includes a spacer sequence that is designed to hybridize with a target sequence in a eukaryotic cell. Target sequences and eukaryotic cells are described in detail below under the section headed “Related Disclosure”. In embodiments of the first or second engineered systems, the “polynucleotide encoding the engineered Cas12a crRNA” is a naturally occurring polynucleotide, e.g., a pre-processed transcript that includes at least the Cas12a crRNA and often includes additional nucleotides that are removed during processing. In embodiments of the first or second engineered systems, the “polynucleotide encoding the engineered Cas12a crRNA” is an engineered or recombinant polynucleotide. In embodiments of the first or second engineered systems, the engineered Cas12a crRNA, or the polynucleotide encoding the engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In some embodiments of the first or second engineered systems wherein the engineered Cas12a crRNA further includes at least one direct repeat sequence or fragment thereof capable of associating with the Cas12a nuclease, wherein the at least one direct repeat sequence or fragment thereof is adjacent to and 3' to the spacer sequence, the Cas12a tracrRNA has a nucleotide sequence that has at least about 50% or preferably greater than 50% complementarity to the at least one direct repeat sequence or fragment adjacent to and 3' to the spacer sequence.

In embodiments of the first or second engineered systems, the engineered Cas12a crRNA, or the polynucleotide encoding the engineered Cas12a crRNA, further includes: (a) at least one direct repeat sequence or fragment thereof capable of associating with the Cas12a nuclease, wherein the at least one direct repeat sequence or fragment thereof is adjacent to and 3' to the spacer sequence; and (b) a 3' extension adjacent to the spacer sequence. In embodiments of the first or second engineered systems, the 3' extension includes nucleotides that when base-paired form about one helical turn. In embodiments of the first or second engineered systems, the 3' extension includes at least 10 contiguous nucleotides. In embodiments of the first or second engineered systems wherein the engineered Cas12a crRNA further includes a 3' extension adjacent to the spacer sequence, the Cas12a tracrRNA includes a nucleotide sequence having sufficient complementarity (e.g., about 50% or greater than 50%) to the engineered Cas12a crRNA’s 3' extension to allow hybridization between the tracrRNA and the engineered Cas12a crRNA. In embodiments, the polynucleotide encoding the engineered Cas12a crRNA is a pre-processed Cas12a crRNA precursor transcript that includes, in 5' to 3' direction, a first direct repeat or fragment thereof, the spacer, and a 3' extension; in some embodiments, the 3' extension includes a second direct repeat or fragment thereof, and/or includes at least 10 contiguous nucleotides, and/or includes nucleotides that when base-paired form about one helical turn; in some embodiments, such a pre-processed Cas12a crRNA precursor transcript is processed (e.g., in vivo or in vitro), resulting in a processed Cas12a crRNA that has had the 3' extension nucleotides excised.

In another aspect, the invention provides a third engineered system including: (a) one or more nucleotide sequences encoding a Cas12a nuclease; and (b) one or more nucleotide sequences encoding at least one engineered Cas12a crRNA that is designed to form a complex with the Cas12a nuclease and that includes a spacer sequence designed to hybridize with a target sequence in a eukaryotic cell; and (c) one or more nucleotide sequences encoding at least one Cas12a tracrRNA.

In another aspect, the invention provides a fourth engineered system including: (a) a Cas12a nuclease, or one or more DNA or RNA nucleotide sequences encoding the Cas12a nuclease; and (b) at least one engineered Cas12a crRNA designed to form a complex with the Cas12a nuclease and including a spacer sequence designed to hybridize with a target sequence in a eukaryotic cell, or one or more DNA or RNA nucleotide sequences encoding the at least one engineered Cas12a crRNA polynucleotide; and (c) at least one tracrRNA, or one or more DNA or RNA nucleotide sequences encoding the at least one Cas12a tracrRNA.

In embodiments of the third or fourth engineered systems, the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The systems including a tracrRNA as disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of the third or fourth engineered systems, the engineered Cas12a crRNA includes a spacer sequence that is designed to hybridize with a target sequence in a eukaryotic cell. Target sequences and eukaryotic cells are described in detail below under the section headed "Related Disclosure". In embodiments of the third or fourth engineered systems, the "polynucleotide encoding the engineered Cas12a crRNA" is a naturally occurring polynucleotide, e.g., a pre-processed transcript that includes at least the Cas12a crRNA and often includes additional nucleotides that are removed during processing. In embodiments of the third or fourth engineered systems, the "polynucleotide encoding the engineered Cas12a crRNA" is an engineered or recombinant polynucleotide. In embodiments of the third or fourth engineered systems, the at least one engineered Cas12a crRNA, or a polynucleotide encoding the at least one engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In embodiments of the third or fourth engineered systems, the engineered Cas12a crRNA, or a polynucleotide encoding the engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In embodiments of the third or fourth engineered systems where the engineered Cas12a crRNA further includes at least one direct repeat sequence or fragment thereof capable of associating with the Cas12a nuclease, wherein the at least one direct repeat sequence or fragment thereof is adjacent to and 3' to the spacer sequence, the Cas12a tracrRNA has a nucleotide sequence that has at least about 50% or preferably greater than 50% complementarity to the at least one direct repeat sequence or fragment adjacent to and 3' to the spacer sequence. In embodiments of the third or fourth engineered systems, the engineered Cas12a crRNA further includes a 3' extension adjacent to the spacer sequence; in some embodiments, the 3' extension includes nucleotides that when base-paired form about one helical turn; in some embodiments, the 3' extension includes at least 10 contiguous nucleotides. In embodiments of the third or fourth engineered systems where the engineered Cas12a crRNA further includes a 3' extension adjacent to the spacer sequence, the Cas12a tracrRNA has a nucleotide sequence having sufficient complementarity (e.g., about 50% or greater than 50%) to the engineered Cas12a crRNA's 3' extension to allow hybridization between the Cas12a tracrRNA and the engineered Cas12a crRNA.

In embodiments of the third or fourth engineered systems, the at least one tracrRNA, or the one or more nucleotide sequences encoding the at least one Cas12a tracrRNA, includes a nucleotide sequence that has at least 50% complementarity with, the nucleotide sequence of the at least one direct repeat of the engineered Cas12a crRNA. In embodiments of the third or fourth engineered systems, the at least one tracrRNA, or the one or more nucleotide sequences encoding the at least one Cas12a tracrRNA, includes a nucleotide sequence of a naturally occurring putative Cas12a tracrRNA sequence identified from a native Cas12a locus, such as a nucleotide sequence of a naturally occurring putative Cas12a tracrRNA sequence identified from a genome using the techniques described by Zetsche et al. (2015) *Cell,* 163:759-771, and in U.S. Pat. No. 9,790,490. A naturally occurring putative Cas12a tracrRNA sequence can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the naturally occurring putative Cas12a tracrRNA sequence has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments of the third or fourth engineered systems, the at least one tracrRNA, or the one or more nucleotide sequences encoding the at least one Cas12a tracrRNA, has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments of the third or fourth engineered systems, the at least one tracrRNA, or the one or more nucleotide sequences encoding the at least one Cas12a tracrRNA, has a nucleotide sequence including a sequence selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring putative Cas12a tracrRNA sequence identified from a native Cas12a locus. Examples include RNA molecules that include the nucleotide sequence of a naturally occurring putative Cas12a tracrRNA sequence identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label. In embodiments of the third or fourth engineered systems, the at least one tracrRNA, or the one or more nucleotide sequences encoding the at least one Cas12a tracrRNA, further includes a 5' extension, such as the 5' extensions disclosed by Park et al. (2018) *Nature Communications*, doi: 10.1038/s41467-018-05641-3.

In another aspect, the invention provides a fifth engineered system including one or more vectors including: (a) a first regulatory element that is heterologous to and operably linked to one or more nucleotide sequences encoding a Cas12a nuclease; and (b) a second regulatory element that is heterologous to and operably linked to one or more nucleotide sequences encoding at least one engineered Cas12a crRNA that is designed to form a complex with the Cas12a nuclease and that includes a spacer sequence designed to hybridize with a target sequence in a eukaryotic cell; and (c) a third regulatory element that is heterologous to and operably linked to one or more nucleotide sequences encoding at least one Cas12a tracrRNA; wherein components (a) and (b) and (c) are located on the same vector or on different vectors of the system.

In embodiments of the fifth engineered system, the first regulatory element, the second regulatory element, and the third regulatory element each include a promoter that is functional in the eukaryotic cell. Each promoter is selected for operability in the context (in vitro or in vivo) in which the DNA expression system is to be used. Thus, in embodiments, the first regulatory element, the second regulatory element, and the third regulatory element each include a promoter that functions in prokaryotic cells, such as in bacterial cells. In preferred embodiments, the first regulatory element, the second regulatory element, and the third regulatory element each include a promoter that functions in eukaryotic cells, such as in non-human animal (e.g., mammalian, human) or human or plant or fungal cells; in embodiments, the first regulatory element, the second regulatory element, and the third regulatory element each include a promoter identified from a eukaryotic genome, such as a non-human animal or human or plant or fungal genome. In embodiments of the fifth engineered system, any one or more of the regulatory elements also includes other elements that regulate expression, such as, but not limited to, enhancers and introns, examples of which are provided in Table 3. In embodiments of the fifth engineered system, the first regulatory element, the second regulatory element, and the third regulatory element each include a promoter selected from the group consisting of pol III promoters, pol II promoters, and pol I promoters. In embodiments of the fifth engineered system, the first regulatory element, the second regulatory element, and the third regulatory element each include a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, and an EF1a promoter. In embodiments, the first regulatory element, the second regulatory element, and the third regulatory element each include a promoter selected from the group consisting of pol III promoters, pol II promoters, and pol I promoters. In embodiments, the first regulatory element, the second regulatory element, and the third regulatory element each include a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, an EF1a promoter. In embodiments, the first regulatory element, the second regulatory element, and the third regulatory element each include a promoter that functions in eukaryotic cells, such as in plant cells. For use in plants, useful promoters include constitutive, conditional, inducible, and temporally or spatially specific promoters (e.g., a tissue specific promoter, a developmentally regulated promoter, or a cell cycle regulated promoter). In embodiments, the promoter is a pol II promoter. In embodiments, the promoter is a constitutive promoter that drives DNA expression in plant cells; in embodiments, the promoter drives DNA expression in the nucleus or in an organelle such as a chloroplast or mitochondrion. Examples of constitutive promoters include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and an opaline synthase (NOS) and octapine synthase (OCS) promoter from *Agrobacterium tumefaciens*. In embodiments, the promoter is a promoter from figwort mosaic virus (FMV), a RUBISCO promoter, or a pyruvate phosphate dikinase (PDK) promoter, which is active in the chloroplasts of mesophyll cells. Other contemplated promoters include cell-specific or tissue-specific or developmentally regulated promoters, for example, a promoter that limits the expression of the DNA expression system to germline or reproductive cells (e.g., promoters of genes encoding DNA ligases, recombinases, replicases, or other genes specifically expressed in germline or reproductive cells). In embodiments, the first regulatory element, the second regulatory element, and/or the third regulatory element includes a plant U6 spliceosomal RNA promoter, which can be native to the genome of the plant cell or from a different species, e.g., a U6 promoter from maize, tomato, or soybean such as those disclosed in U.S. patent application Ser. No. 15/120,110, published as U.S. Patent Application Publication 2017/0166912, national phase application claiming priority to PCT/US2015/018104 (published as WO 2015/131101 and claiming priority to U.S. Provisional Patent Application 61/945,700), or a homologue thereof; in an embodiment of the fifth engineered system, such a promoter is operably linked to DNA sequence encoding one or more nucleotide sequences encoding at least one Cas12a tracrRNA, followed by a suitable 3' element such as a U6 poly-T terminator. In another embodiment, the first promoter is a plant U3, 7SL (signal recognition particle RNA), U2, or U5 promoter, or chimerics thereof, e.g., as described in U.S. patent application Ser. No. 15/120,110, published as U.S. Patent Application Publication 2017/0166912, national phase application claiming priority to PCT/US2015/018104 (published as WO 2015/131101 and claiming priority to U.S. Provisional Patent Application 61/945,700). All of the patent publications referenced in this paragraph are incorporated herein by reference in their entirety. In embodiments of the fifth engineered system, the eukaryotic cell is a plant cell, and wherein the third regulatory element includes a promoter having a nucleotide sequence selected from the group consisting of SEQ ID NOs:16-71. In embodiments of the fifth engineered system, the at least one Cas12a tracrRNA is at least one Cas12a tracrRNA having a nucleotide sequence including a sequence selected from the group consisting of SEQ ID NOs:1, 3, 6, 139-146, and 149-169. In specific embodiments of the fifth engineered system, the eukaryotic cell is a plant cell, the third regulatory element includes a promoter having a nucleotide sequence selected from the group consisting of SEQ ID NOs:16-71, and the at least one Cas12a tracrRNA is at least one Cas12a tracrRNA having a nucleotide sequence including a sequence selected from the group consisting of SEQ ID NOs:1, 3, 6, 139-146, and 149-169.

In embodiments of the fifth engineered system, the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The systems including a tracrRNA as disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of the fifth engineered system, the at least one engineered Cas12a crRNA includes a spacer sequence designed to hybridize with a target sequence in a eukaryotic cell. Target sequences and eukaryotic cells are described in detail below under the section headed "Related Disclosure". In embodiments of the fifth engineered system, the at least one engineered Cas12a crRNA, or the one or more nucleotide sequences encoding the at least one engineered Cas12a crRNA, further includes at least one direct repeat sequence or fragment thereof that is capable of associating with the Cas12a nuclease and is adjacent to and 5' to the spacer sequence. In embodiments of the fifth engineered system, the engineered Cas12a crRNA, or a polynucleotide encoding the engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In embodiments of the fifth engineered system where the engineered Cas12a crRNA further includes at least one direct repeat sequence or fragment thereof capable of associating with the Cas12a nuclease, wherein the at least one direct repeat sequence or fragment thereof is adjacent to and 3' to the spacer sequence, the Cas12a tracrRNA has a nucleotide sequence that has at least about 50% or preferably greater than 50% complementarity to the at least one direct repeat sequence or fragment adjacent to and 3' to the spacer sequence. In embodiments of the fifth engineered system, the engineered Cas12a crRNA further includes a 3' extension adjacent to the spacer sequence; in some embodiments, the 3' extension includes nucleotides that when base-paired form about one helical turn; in some embodiments, the 3' extension includes at least 10 contiguous nucleotides. In embodiments of the fifth engineered system where the engineered Cas12a crRNA further includes a 3' extension adjacent to the spacer sequence, the Cas12a tracrRNA has a nucleotide sequence having sufficient complementarity (e.g., about 50% or greater than 50%) to the engineered Cas12a crRNA's 3' extension to allow hybridization between the Cas12a tracrRNA and the engineered Cas12a crRNA.

In embodiments of the fifth engineered system, the at least one tracrRNA, or the one or more nucleotide sequences encoding at least one Cas12a tracrRNA, includes a nucleotide sequence that has at least 50% complementarity with, the nucleotide sequence of a direct repeat sequence or fragment thereof that is capable of associating with the Cas12a nuclease and is adjacent to and 5' to the spacer sequence of the engineered Cas12a crRNA. In embodiments of the fifth engineered system, the at least one tracrRNA, or the one or more nucleotide sequences encoding the at least one Cas12a tracrRNA, includes a nucleotide sequence of a naturally occurring putative Cas12a tracrRNA sequence identified from a native Cas12a locus, such as a nucleotide sequence of a naturally occurring putative Cas12a tracrRNA sequence identified from a genome using the techniques described by Zetsche et al. (2015) *Cell,* 163:759-771, and in U.S. Pat. No. 9,790,490. A naturally occurring putative Cas12a tracrRNA sequence can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the naturally occurring putative Cas12a tracrRNA sequence has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments of the fifth engineered system, the at least one tracrRNA, or the one or more nucleotide sequences encoding the at least one Cas12a tracrRNA, has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments of the fifth engineered system, the at least one tracrRNA, or the one or more nucleotide sequences encoding the at least one Cas12a tracrRNA, has a nucleotide sequence including a sequence selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring putative Cas12a tracrRNA sequence identified from a native Cas12a locus. Examples include RNA molecules that include the nucleotide sequence of a naturally occurring putative Cas12a tracrRNA sequence identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label. In embodiments of the fifth engineered system, the at least one tracrRNA, or the one or more nucleotide sequences encoding the at least one Cas12a tracrRNA, further includes a 5' extension, such as the 5' extensions disclosed by Park et al. (2018) *Nature Communications*, doi: 10.1038/s41467-018-05641-3.

Another aspect of the invention provides a sixth engineered system including one or more vectors including: (a) a first expression cassette including at least a first promoter that is heterologous to and operably linked to one or more nucleotide sequences encoding a Cas12a nuclease and—optionally—a first transcription terminator sequence; and (b) a second expression cassette including at least a second promoter that is heterologous to operably linked to one or more nucleotide sequences encoding at least one engineered Cas12a crRNA that is designed to form a complex with the Cas12a nuclease and that includes a spacer sequence designed to hybridize with a target sequence in a eukaryotic cell and—optionally—a second transcription terminator sequence; and (c) a third expression cassette including at least a third promoter that is heterologous to operably linked to one or more nucleotide sequences encoding at least one Cas12a tracrRNA and—optionally—a third transcription terminator sequence, wherein components (a) and (b) and (c) are located on the same vector or on different vectors of the system.

In embodiments of the sixth engineered system, the first promoter, the second promoter, and the third promoter are each a promoter that is functional in the eukaryotic cell, and wherein the first transcription terminator, the second transcription terminator, and the third transcription terminator are each a transcription terminator that is functional in the eukaryotic cell. In embodiments, the first promoter, the second promoter, and the third promoter are each a promoter selected from the group consisting of pol III promoters, pol II promoters, and pol I promoters. In embodiments of the sixth engineered system, the first promoter, the second promoter, and the third promoter are each a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, an EF1a promoter. In embodiments of the sixth engineered system, the first promoter, the second promoter, and the third promoter are each a promoter with a nucleotide sequence selected from the group consisting of SEQ ID NOs:16-71. In embodiments of the sixth engineered system, the first transcription terminator, the second transcription terminator, and the third transcription terminator are each selected from the group consisting of a U6 poly-T terminator, an SV40 terminator, an hGH terminator, a BGH terminator, an rbGlob terminator, a synthetic terminator functional in a eukaryotic cell, a 3' element from an *Agrobacterium* sp. gene, a 3' element from a non-human animal gene, a 3' element from a human gene, and a 3' element from a plant gene, wherein the 3' element terminate transcription of an RNA transcript located immediately 5' to the 3' element. In embodiments of the sixth engineered system, the first transcription terminator, the second transcription terminator, and the third transcription terminator are each a transcription terminator having a sequence selected from the group consisting of SEQ ID NOs:72-100.

In embodiments of the sixth engineered system, the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The systems including a tracrRNA as disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of the sixth engineered system, the at least one tracrRNA, or the one or more nucleotide sequences encoding at least one Cas12a tracrRNA, includes a nucleotide sequence that has at least 50% complementarity with, the nucleotide sequence of a direct repeat sequence or fragment thereof that is capable of associating with the Cas12a nuclease and is adjacent to and 5' to the spacer sequence of the engineered Cas12a crRNA. In embodiments of the sixth engineered system, the at least one tracrRNA, or the one or more nucleotide sequences encoding the at least one Cas12a tracrRNA, includes a nucleotide sequence of a naturally occurring putative Cas12a tracrRNA sequence identified from a native Cas12a locus, such as a nucleotide sequence of a naturally occurring putative Cas12a tracrRNA sequence identified from a genome using the techniques described by Zetsche et al. (2015) *Cell,* 163:759-771, and in U.S. Pat. No. 9,790,490. A naturally occurring putative Cas12a tracrRNA sequence can be identified from a genome as DNA sequence encoding a RNA molecule that: is predicted to be or putatively transcribed (or that may be determined to be transcribed, e.g., by RNA analysis) from a Cas12a CRISPR genomic region, specifically from a locus that flanks the DNA encoding the Cas12a CRISPR nuclease; that preferably includes a predicted transcriptional terminator in the direction of transcription; that is about 60 to about 100 nucleotides in length, e.g., 60-80 nucleotides, 60-85 nucleotides, 60-90 nucleotides, or 65-95 nucleotides; and that is not a direct repeat in the Cas12a CRISPR array, but rather has a nucleotide sequence that permits the transcribed tracrRNA to hybridize to the crRNA (i.e., the naturally occurring putative Cas12a tracrRNA sequence has sufficient complementarity to a crRNA sequence to hybridize to the crRNA). In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4. In embodiments of the sixth engineered system, the at least one tracrRNA, or the one or more nucleotide sequences encoding the at least one Cas12a tracrRNA, has a nucleotide sequence having at least 50% identity (e.g., at least 50%, at least 51%, at least 52%, at least 53%, at least 54%, at least 55%, at least 56%, at least 57%, at least 58%, at least 59%, or at least 60% sequence identity) to the sequence of the direct repeat. In embodiments of the sixth engineered system, the at least one tracrRNA, or the one or more nucleotide sequences encoding the at least one Cas12a tracrRNA, has a nucleotide sequence including a sequence selected from the group consisting of SEQ ID NOs:1, 3, 6, 139-146, and 149-169. An alternative embodiment of a "Cas12a tracrRNA" includes an RNA molecule having or including a nucleotide sequence based on the nucleotide sequence of a naturally occurring putative Cas12a tracrRNA sequence identified from a native Cas12a locus. Examples include RNA molecules that include the nucleotide sequence of a naturally occurring putative Cas12a tracrRNA sequence identified from a native Cas12a locus but that further include one or more modifications such as (a) additional nucleotides, e.g., an extension at the 3' terminus, (b) insertion, deletion, or substitution of one or more nucleotides within the naturally occurring tracrRNA sequence, preferably maintaining the secondary structure of the tracrRNA, and (c) chemical modifications, e.g., addition of a detectable label. In embodiments of the sixth engineered system, the at least one tracrRNA, or the one or more nucleotide sequences encoding the at least one Cas12a tracrRNA, further includes a 5' extension, such as the 5' extensions disclosed by Park et al. (2018) *Nature Communications*, doi: 10.1038/s41467-018-05641-3.

In embodiments of the sixth engineered system, the at least one engineered Cas12a crRNA includes a spacer sequence designed to hybridize with a target sequence in a eukaryotic cell. Target sequences and eukaryotic cells are described in detail below under the section headed "Related Disclosure". In embodiments, the eukaryotic cell is a non-human animal cell, a human cell, a plant cell, or a fungal cell. In embodiments of the sixth engineered system, the eukaryotic cell is in vitro, ex vivo, or in vivo.

Disclosure Related to the Engineered Systems

The disclosure of this section is related to embodiments of the first, second, third, fourth, fifth, and sixth engineered systems.

In embodiments of any one of the first, second, third, fourth, fifth, and sixth engineered systems, the Cas12a nuclease is: (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The systems including a tracrRNA as disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of any one of the first, second, third, fourth, fifth, and sixth engineered systems, the at least one Cas12a tracrRNA has a nucleotide sequence selected from SEQ ID NOs:1, 3, 6, 139-146, and 149-169. In embodiments of any one of the first, second, third, fourth, fifth, and sixth engineered systems, the genomic sequence encoding the Cas12a nuclease and the genomic sequence encoding the Cas12a tracrRNA occur naturally within the same region in a genome; in embodiments, the genomic sequence encoding the Cas12a tracrRNA is located preferably within about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 kilobases of the DNA segment(s) encoding the Cas12a nuclease. In embodiments of any one of the first, second, third, fourth, fifth, and sixth engineered systems, the target sequence is located 3' of a Protospacer Adjacent Motif (PAM) and the PAM sequence is TTN, where N is A/C/G or T and the Cas12a nuclease is FnCpf1, or the PAM sequence is TTTV, where V is A/C or G and the Cas12a nuclease is PaCpf1p, LbCpf1 or AsCpf1.

In embodiments of any one of the first, second, fourth, fifth, and sixth engineered systems, the Cas12a tracrRNA is a putative Cas12a tracrRNA that is identified from the same genomic region as the Cas12a nuclease by at least the following steps: (a) identifying in the genomic region flanking the DNA encoding the Cas12a nuclease at least one nucleotide sequence that includes a CRISPR array including direct repeats; (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat. In embodiments, the genomic sequence encoding the Cas12a tracrRNA is located preferably within about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 kilobases of the DNA segment(s) encoding the Cas12a nuclease. In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4.

In embodiments of any one of the first, second, fourth, fifth, and sixth engineered systems, the Cas12a tracrRNA is provided: (a) as DNA encoding a first RNA molecule including the Cas12a tracrRNA and including a restriction endonuclease cleavage site that is suitable for insertion of a sequence coding for a functional RNA moiety; or (b) as a functional RNA molecule including the Cas12a tracrRNA and a functional RNA moiety, or as a polynucleotide encoding the functional RNA molecule; or (c) by a DNA expression system including: (i) DNA sequence for a first promoter; and (ii) operably linked and heterologous to the first promoter, a DNA sequence encoding a first RNA molecule including a Cas12a tracrRNA and including a restriction endonuclease cleavage site that is suitable for insertion of a sequence coding for a functional RNA moiety; or (d) by a DNA expression system including: (a) DNA sequence for a first promoter; and (b) operably linked and heterologous to the first promoter, a DNA sequence encoding a functional RNA molecule including a Cas12a tracrRNA and a functional RNA moiety. In embodiments, the DNA expression system includes (a) DNA sequence for a first promoter; and (b) operably linked and heterologous to the first promoter, a DNA sequence encoding a functional RNA molecule including a Cas12a tracrRNA and a functional RNA moiety, and (c) a terminator 3' to and operably linked to the DNA encoding a functional RNA molecule.

In embodiments of any one of the first, second, third, fourth, fifth, and sixth engineered systems, the Cas12a tracrRNA is provided as DNA encoding a first RNA molecule including the Cas12a tracrRNA and including a restriction endonuclease cleavage site that is suitable for insertion of a sequence coding for a functional RNA moiety, and wherein the functional RNA moiety is at least one selected from the group consisting of: (a) a nucleotide sequence for annealing to a donor polynucleotide; (b) a nucleotide sequence for annealing to the crRNA 3' extension; (c) a terminator sequence; (d) an RNA aptamer; (e) an enzymatically active RNA sequence; (f) a detectable label; and (g) an RNA sequence forming at least partially double-stranded RNA. In embodiments of any one of the first, second, fourth, fifth, and sixth engineered systems, the Cas12a tracrRNA is provided as DNA encoding a first RNA molecule including the Cas12a tracrRNA and including a restriction endonuclease cleavage site that is suitable for insertion of a sequence coding for a functional RNA moiety, wherein the functional RNA moiety includes RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). In embodiments of any one of the first, second, fourth, fifth, and sixth engineered systems, the Cas12a tracrRNA is provided as DNA encoding a first RNA molecule including the Cas12a tracrRNA and including a restriction endonuclease cleavage site that is suitable for insertion of a sequence coding for a functional RNA moiety, wherein the functional RNA moiety includes an RNA sequence for annealing to a donor polynucleotide, and wherein the composition further includes the donor polynucleotide.

In embodiments of any one of the first, second, third fourth, fifth, and sixth engineered systems, the Cas12a tracrRNA is provided as a functional RNA molecule including the Cas12a tracrRNA and a functional RNA moiety, or as a polynucleotide encoding the functional RNA molecule, and wherein the functional RNA moiety is at least one selected from the group consisting of: (a) a nucleotide sequence for annealing to a donor polynucleotide; (b) a nucleotide sequence for annealing to the crRNA 3' extension; (c) a terminator sequence; (d) an RNA aptamer; (e) an enzymatically active RNA sequence; (f) a detectable label; and (g) an RNA sequence forming at least partially double-stranded RNA. In embodiments of any one of the first, second, third, fourth, fifth, and sixth engineered systems, the Cas12a tracrRNA is provided as a functional RNA molecule including the Cas12a tracrRNA and a functional RNA moiety, or as a polynucleotide encoding the functional RNA molecule, and wherein the functional RNA moiety includes RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). In embodiments of any one of the first, second, third, fourth, fifth, and sixth engineered systems, the Cas12a tracrRNA is provided as a functional RNA molecule including the Cas12a tracrRNA and a functional RNA moiety, or as a polynucleotide encoding the functional RNA molecule, and wherein the functional RNA moiety includes RNA forming at least partially double-stranded RNA capable of silencing a gene that is involved in one or more small RNA-mediated silencing pathways, e.g., RDR6, SDE3, RDR2, WEX, SGS3, DCL2-4, UPF1, UPF3, HEN1, NRPD1A, NRPD2, DRD1, HDA6, AGO1, and MOP1.

In embodiments of any one of the first, second, third, fourth, fifth, and sixth engineered systems, the Cas12a tracrRNA is provided as a functional RNA molecule including the Cas12a tracrRNA and a functional RNA moiety, or as a polynucleotide encoding the functional RNA molecule, wherein the functional RNA moiety includes an RNA sequence for annealing to a donor polynucleotide, and wherein the system further includes the donor polynucleotide. In embodiments, the donor polynucleotide is single-stranded DNA, or is blunt-ended double-stranded DNA, or is double-stranded DNA with an overhang at least at one terminus, or is an at least partially double-stranded DNA/RNA hybrid. In embodiments of any one of the first, second, third, fourth, fifth, and sixth engineered systems, the Cas12a tracrRNA is provided in a molar excess, relative to the amount of Cas12a nuclease. In embodiments of any one of the first, second, third, fourth, fifth, and sixth engineered systems, the Cas12a tracrRNA is provided in a molar amount that is at least 10-fold greater than the molar amount of the Cas12a nuclease.

A related aspect of the invention includes a delivery particle including the engineered system any one of the first, second, third, fourth, fifth, and sixth engineered systems. In embodiments of the delivery particle, the Cas12a nuclease is complexed with the engineered Cas12a crRNA polynucleotide, e.g., to form a Cas12a ribonucleoprotein. In embodiments of the delivery particle, the Cas12a tracrRNA is present in a molar excess, relative to the amount of Cas12a nuclease (or Cas12a ribonucleoprotein). In embodiments of the delivery particle, the Cas12a tracrRNA is present in a molar amount that is at least 10-fold greater than the molar amount of the Cas12a nuclease (or Cas12a ribonucleoprotein). In embodiments of the delivery particle, the Cas12a nuclease is first complexed with the engineered Cas12a crRNA polynucleotide, e.g., to form a Cas12a ribonucleoprotein, followed by provision, without an annealing step, of the Cas12a tracrRNA in a molar amount that is at least 10-fold greater than the molar amount of the Cas12a nuclease (or Cas12a ribonucleoprotein).

A related aspect of the invention includes a delivery liquid including the engineered system any one of the first, second, third, fourth, fifth, and sixth engineered systems. In embodiments of the delivery liquid, the Cas12a nuclease is complexed with the engineered Cas12a crRNA polynucleotide, e.g., to form a Cas12a ribonucleoprotein. In embodiments of the delivery liquid, the Cas12a tracrRNA is present in a molar excess, relative to the amount of Cas12a nuclease (or Cas12a ribonucleoprotein). In embodiments of the delivery liquid, wherein the Cas12a tracrRNA is present in a molar amount that is at least 10-fold greater than the molar amount of the Cas12a nuclease (or Cas12a ribonucleoprotein). In embodiments of the delivery liquid, the Cas12a nuclease is first complexed with the engineered Cas12a crRNA polynucleotide, e.g., to form a Cas12a ribonucleoprotein, followed by provision, without an annealing step, of the Cas12a tracrRNA in a molar amount that is at least 10-fold greater than the molar amount of the Cas12a nuclease (or Cas12a ribonucleoprotein).

Yet another aspect of the invention includes a method of modifying or editing a target sequence in a locus of interest of a eukaryotic cell including delivering the engineered system according to any one of the first, second, third, fourth, fifth, and sixth engineered systems to the locus of interest, wherein the spacer sequence hybridizes with the target sequence, whereby modification or editing of the locus of interest occurs. Target sequences and eukaryotic cells are described in detail below under the section headed "Related Disclosure". The locus of interest is any specific locus in a DNA molecule, chromosome, or genome obtained from or located within a eukaryotic cell, a eukaryotic tissue, or a eukaryotic organism; in embodiments, the DNA molecule, chromosome, or genome is in vitro, ex vivo, or in vivo. In embodiments of the method, the eukaryotic cell includes a cell of a cell line or a cell of a multicellular organism, and the locus of interest includes a locus of interest in the genome of the eukaryotic cell. In embodiments of the method, the locus of interest is DNA encoding a gene of interest, and can include coding sequence, non-coding sequence, or both coding and non-coding sequence, and can include an intact functional gene (e.g., including untranscribed regions located 3' or 5' to DNA regions encoding a polypeptide, introns, and regulatory elements such as promoters, enhancers, polyadenylation signals, and terminators). In embodiments of the method, the target sequence is a segment of the locus of interest; in embodiments, the target sequence includes about 20 to about 30 contiguous nucleotides and has near perfect or perfect sequence complementarity to the nucleotide sequence of the spacer of the Cas12a crRNA. In embodiments of the method, the eukaryotic cell is a non-human animal cell, a human cell, a plant cell, or a fungal cell. In embodiments of the method, the eukaryotic cell is in vitro, ex vivo, or in vivo. In embodiments of the method, the locus of interest is within a eukaryotic cell, a eukaryotic tissue, or a eukaryotic organism; in embodiments, the locus of interest is within the genome of a non-human animal, a human, a plant, or a fungus, or within the genome of a eukaryotic organelle such as a mitochondrion or a plastid (e.g., a chloroplast). In embodiments of the method, the eukaryotic cell includes a non-human animal or human stem cell or a non-human animal or human stem cell line. In embodiments of the method, the locus of interest is within a eukaryotic DNA molecule in vitro or in a recombinant DNA molecule or recombinant vector.

In embodiments of the method, the eukaryotic cell includes a plant cell, and the modification of the locus of interest is correlated with a modified trait in a plant including cells containing the modification of the locus of interest. In embodiments of the method, the eukaryotic cell includes a plant cell, the modification of the locus of interest is correlated with a modified trait in a plant including cells containing the modification of the locus of interest, and the method further includes obtaining, growing, or regenerating a plant from the plant cell, wherein the plant includes cells containing the modification of the locus of interest, and wherein the plant exhibits the modified trait effected by the modification of the locus of interest. In embodiments of the method, the eukaryotic cell includes a plant cell, and the method further includes identifying a trait of interest in a plant obtained, grown, or regenerated from the plant cell, wherein the trait of interest is effected by the modification of the locus of interest. In embodiments of the method, the eukaryotic cell includes a plant cell, the method further includes identifying a trait of interest in a plant obtained, grown, or regenerated from the plant cell, wherein the trait of interest is effected by the modification of the locus of interest, and the method further includes (a) introducing a nucleotide sequence including the locus of interest into a plant cell, a plant cell line, or a plant germplasm, and generating from the plant cell, the plant cell line, or the plant germplasm a plant including cells containing the nucleotide sequence including the locus of interest; or (b) introducing the modified locus of interest into a plant cell, a plant cell line, or a plant germplasm, and generating from the plant cell, the plant cell line, or the plant germplasm a plant including cells containing the modified locus of interest; or (c) modifying expression of the locus of interest in a plant cell, a plant cell line, or a plant germplasm, and generating from the plant cell, the plant cell line, or the plant germplasm a plant including cells containing the locus of interest having modified expression; or (d) deleting the locus of interest or an endogenous nucleotide sequence including the locus of interest in a plant cell, and generating from the plant cell, the plant cell line, or the plant germplasm a plant including cells in which the locus of interest or the endogenous nucleotide sequence including the locus of interest has been deleted.

In embodiments of the method, the eukaryotic cell includes a non-human animal cell (e.g. a somatic cell or gamete of a non-human animal, in vivo, in vitro, or ex vivo), and the modification of the locus of interest is correlated with a modified trait or characteristic in a non-human animal including cells containing the modification of the locus of interest. In embodiments of the method, the eukaryotic cell includes a non-human animal cell, the modification of the locus of interest is correlated with a modified trait or characteristic in a non-human animal or in a non-human animal cell line including cells containing the modification of the locus of interest, and the method further includes obtaining, growing, regenerating, or breeding a non-human animal or a non-human animal cell line from the non-human animal cell, wherein the non-human animal or a non-human animal cell line includes cells containing the modification of the locus of interest, and wherein the non-human animal or a non-human animal cell line exhibits the modified trait or characteristic effected by the modification of the locus of interest. In embodiments of the method, the eukaryotic cell includes a non-human animal cell, and the method further includes identifying a trait or characteristic of interest in a non-human animal or a non-human animal cell line obtained, grown, regenerated, or bred from the non-human animal cell, wherein the trait or characteristic of interest is effected by the modification of the locus of interest. In embodiments of the method, the eukaryotic cell includes a non-human animal cell, the method further includes identifying a trait or characteristic of interest in a non-human animal or a non-human animal cell line obtained, grown, regenerated, or bred from the non-human animal cell, wherein the trait or characteristic of interest is effected by the modification of the locus of interest, and the method further includes (a) introducing a nucleotide sequence including the locus of interest into a non-human animal cell, a non-human animal cell line, or a non-human animal, and obtaining, growing, regenerating, or breeding from the non-human animal cell, the non-human animal cell line, or the non-human animal a non-human animal or a non-human animal cell line including cells containing the nucleotide sequence including the locus of interest; or (b) introducing the modified locus of interest into a non-human animal cell, a non-human animal cell line, or a non-human animal, and obtaining, growing, regenerating, or breeding from the non-human animal cell, the non-human animal cell line, or the non-human animal a non-human animal or a non-human animal cell line including cells containing the modified locus of interest; or (c) modifying expression of the locus of interest in a non-human animal cell, a non-human animal cell line, or a non-human animal, and obtaining, growing, regenerating, or breeding from the non-human animal cell, the non-human animal cell line, or the non-human animal a non-human animal or a non-human animal cell line including cells containing the locus of interest having modified expression; or (d) deleting the locus of interest or an endogenous nucleotide sequence including the locus of interest in a non-human animal cell, a non-human animal cell line, or a non-human animal, and obtaining, growing, regenerating, or breeding from the non-human animal cell, the non-human animal cell line, or the non-human animal a non-human animal or a non-human animal cell line including cells in which the locus of interest or the endogenous nucleotide sequence including the locus of interest has been deleted.

In embodiments of the method, the engineered system or a component thereof is delivered via delivery particles, delivery vesicles, delivery liquids, or one or more viral or bacterial vectors. In embodiments of the method, the engineered system or a component thereof is delivered via delivery particles such as delivery nanoparticles or delivery microparticles including at least one material or reagent selected from the group consisting of a lipid, a sugar, a metal, or a protein. In embodiments of the method, the system or a component thereof is delivered via delivery exosomes or liposomes. In embodiments of the method, the engineered system or a component thereof is delivered via at least one viral vector selected from the group consisting of adenoviruses, lentiviruses, adeno-associated viruses, retroviruses, geminiviruses, begomoviruses, tobamoviruses, potex viruses, comoviruses, wheat streak mosaic virus, barley stripe mosaic virus, bean yellow dwarf virus, bean pod mottle virus, cabbage leaf curl virus, beet curly top virus, tobacco yellow dwarf virus, tobacco rattle virus, potato virus X, and cowpea mosaic virus. In embodiments of the method, the engineered system or a component thereof is delivered via at least one bacterial vector capable of transforming a plant cell and selected from the group consisting of *Agrobacterium* sp., *Rhizobium* sp., *Sinorhizobium* (Ensifer) sp., *Mesorhizobium* sp., *Bradyrhizobium* sp., *Azobacter* sp., and *Phyllobacterium* sp. Additional information on delivery particles, delivery vesicles, delivery liquids, viral or bacterial vectors, and reagents and methods for their use is found in the section below headed "Delivery Methods and Delivery Agents".

In embodiments of the method, the Cas12a nuclease is: (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag.

In embodiments of the method, the Cas12a tracrRNA has a nucleotide sequence including a sequence selected from the group consisting of SEQ ID NOs:1, 3, 6, 139-146, and 149-169. In embodiments of the method, the tracrRNA is a putative Cas12a tracrRNA that is identified from the same genomic region as the Cas12a nuclease by at least the following steps: (a) identifying in the genomic region flanking the DNA encoding the Cas12a nuclease at least one nucleotide sequence that includes a CRISPR array including direct repeats; (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat. In embodiments of the method, the Cas12a tracrRNA locus is directly adjacent to the DNA encoding the Cas12a nuclease. In embodiments of the method, there is additional genomic sequence, such as DNA sequence encoding other Cas nucleases, located between the Cas12a tracrRNA locus and the DNA encoding the Cas12a nuclease; see, e.g., FIGS. 1 and 4.

Methods of Editing a Genetic Locus with a Cas12a Nuclease with Increased Efficiency A further aspect of the invention includes a method of editing a genetic locus with a Cas12a nuclease, including contacting DNA that includes the genetic locus with: (a) a Cas12a nuclease; and (b) an engineered Cas12a crRNA that includes a spacer sequence that is designed to hybridize with a target sequence in the genetic locus; and (c) a Cas12a tracrRNA, thereby editing the genetic locus; wherein the efficiency of editing of the genetic locus is increased compared to a control method in which the DNA that includes the genetic locus is contacted with the Cas12a nuclease and the Cas12a crRNA, but not the Cas12a tracrRNA. The method enables editing a genetic locus or target sequence with a Cas12a nuclease with increased efficiency, in comparison to methods previously reported that employ a Cas12a nuclease and a Cas12a crRNA (or "guide RNA") but do not include a Cas12a tracrRNA. Efficiency of editing is increased, e.g., when the percentage of cells containing the expected edit at the genetic locus is increased compared to that seen in a control, or when a given level of editing is obtained using a lower amount of Cas12a nuclease, compared to a control. A related aspect is a method of increasing the efficiency of editing a genetic locus by a Cas12a ribonucleoprotein that includes a Cas12a nuclease and a Cas12a crRNA, by providing together with the Cas12a ribonucleoprotein a Cas12a tracrRNA that is capable of hybridizing to the Cas12a crRNA (e.g., a Cas12a tracrRNA of between about 60 to about 100 nucleotides in length that has at least 50% complementarity to the sequence of the Cas12a crRNA), whereby the efficiency of the editing of the genetic locus is increased, compared to that obtained in a control method where the Cas12a ribonucleoprotein is provided without the Cas12a tracrRNA; in embodiments of the method, the Cas12a tracrRNA is provided in molar excess of the Cas12a ribonucleoprotein.

In embodiments of the methods, the Cas12a nuclease and the engineered Cas12a crRNA are provided as a ribonucleoprotein complex. In embodiments, the Cas12a nuclease is provided as a polynucleotide encoding the Cas12a nuclease. In embodiments, the Cas12a nuclease is: (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The methods including use of a tracrRNA as disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of the methods, the Cas12a tracrRNA is provided: (a) as DNA encoding a first RNA molecule including the Cas12a tracrRNA and including a restriction endonuclease cleavage site that is suitable for insertion of a sequence coding for a functional RNA moiety; or (b) as a functional RNA molecule including the Cas12a tracrRNA and a functional RNA moiety, or as a polynucleotide encoding the functional RNA molecule; or (c) by a DNA expression system comprising (i) DNA sequence for a first promoter; and (ii) operably linked and heterologous to the first promoter, DNA encoding a first RNA molecule comprising a Cas12a tracrRNA and comprising a restriction endonuclease cleavage site that is suitable for insertion of a sequence coding for a functional RNA moiety; and (iii) optionally, a terminator 3' to and operably linked to the DNA encoding the first RNA molecule; or (d) by a DNA expression system comprising: (i) DNA sequence for a first promoter; and (ii) operably linked and heterologous to the first promoter, a DNA encoding a functional RNA molecule comprising a Cas12a tracrRNA and a functional RNA moiety; and (iii) optionally, a terminator 3' to and operably linked to the DNA encoding a functional RNA molecule. In embodiments of the methods, the Cas12a tracrRNA is provided as a synthetic Cas12a tracrRNA, e.g., a Cas12a tracrRNA synthesized in vitro from an expression construct including a heterologous promoter operably linked to DNA encoding the Cas12a tracrRNA and optionally including an operably linked terminator. In embodiments of the methods, the Cas12a tracrRNA is provided as a Cas12a tracrRNA obtained from a naturally occurring source, e.g., isolated from a Cas12a tracrRNA that naturally occurs in genomic DNA, or amplified from a Cas12a tracrRNA that naturally occurs in genomic DNA.

In embodiments of the methods, the Cas12a tracrRNA is a putative tracrRNA. In embodiments, the putative Cas12a tracrRNA is identified from the same genomic region as the Cas12a nuclease by at least the following steps: (a) identifying in the genomic region flanking the DNA encoding the Cas12a nuclease at least one nucleotide sequence that includes a CRISPR array including direct repeats; (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat. In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4.

In embodiments of the methods, the Cas12a tracrRNA is provided in a molar excess, relative to the Cas12a nuclease. In embodiments, the Cas12a tracrRNA is provided in a molar amount that is at least 10-fold (e.g., at least 10-fold, 15-fold, 20-fold, 30-fold, 50-fold, 90-fold, 100-fold, 150-fold, or 200-fold) greater than the molar amount of the Cas12a nuclease. In embodiments, the Cas12a tracrRNA is added in a molar excess (relative to the Cas12a nuclease) to a composition containing the Cas12a ribonucleoprotein including the Cas12a nuclease and the Cas12a crRNA. In embodiments, the Cas12a tracrRNA has a nucleotide sequence comprising a sequence selected from the group consisting of SEQ ID NOs:1, 3, 6, 139-146, and 149-169.

In embodiments of the methods, the engineered Cas12a crRNA includes a spacer sequence that is designed to hybridize with a target sequence in the genetic locus. In embodiments, the target sequence is a segment of a genetic locus or a gene of interest. In embodiments, the target sequence includes about 20 to about 30 contiguous nucleotides and has near perfect or perfect sequence complementarity to the nucleotide sequence of the spacer of the Cas12a crRNA. In embodiments, the engineered Cas12a crRNA, or a polynucleotide encoding the engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In embodiments, the engineered Cas12a crRNA further includes a 3' extension adjacent to the spacer sequence. In embodiments, the 3' extension includes nucleotides that when base-paired form about one helical turn. In embodiments, the 3' extension includes at least 10 contiguous nucleotides. In embodiments, the Cas12a tracrRNA has a nucleotide sequence having sufficient complementarity to the engineered Cas12a crRNA's 3' extension to allow hybridization between the tracrRNA and the engineered Cas12a crRNA.

In embodiments of the methods, the editing of the genetic locus is effecting an indel in the genetic locus. In embodiments, the editing of the genetic locus is effecting non-homologous end joining (NHEJ) in the genetic locus. In embodiments, the editing of the genetic locus is effecting homology-dependent repair (HDR) in the genetic locus; in such embodiments, the method can further comprise providing a donor polynucleotide encoding a sequence to be integrated at a double-stranded break that is effected by the method in the genetic locus; examples of suitable donor polynucleotides are described above under the heading "A Method of Integrating a Sequence Encoded by a Donor Polynucleotide at a Specific Locus".

In embodiments of the methods, the DNA that includes the genetic locus is genomic DNA. In embodiments, the genetic locus is genomic DNA of a eukaryotic nucleus, or mitochondrial DNA, or plastid DNA. In embodiments, the DNA that includes the genetic locus is in a eukaryotic DNA molecule in vitro. In embodiments, the DNA that includes the genetic locus is in a eukaryotic cell; in embodiments, the eukaryotic cell is an isolated eukaryotic cell, or a eukaryotic cell in culture, or a eukaryotic cell located in a tissue or organ of a eukaryotic organism. In embodiments, the eukaryotic cell is a cell of a non-human animal, an invertebrate, a vertebrate, a mollusk, an arthropod, an insect, a fish, a reptile, an amphibian, a bird, a mammal, a primate, a non-human primate, a human, a plant, or a fungus. In embodiments, the eukaryotic cell includes a cell of a cell line or a cell of a multicellular organism, and wherein the genetic locus to be modified includes a locus of interest in the genome of the eukaryotic cell. In embodiments, the eukaryotic cell is in vitro, ex vivo, or in vivo. In embodiments, the eukaryotic cell includes a non-human animal or human stem cell or a non-human animal or human stem cell line. Target sequences and eukaryotic cells are described in detail below under the section headed "Related Disclosure".

Compositions for Modifying a Genetic Locus

Yet another aspect of the invention provides a composition for modifying a genetic locus in a eukaryotic cell, including: (a) a eukaryotic cell containing a genetic locus to be modified; and (b) a Cas12a nuclease, or a polynucleotide encoding the Cas12a nuclease; and (c) an engineered Cas12a crRNA that includes a spacer sequence that is designed to hybridize with a target sequence in the genetic locus, or a polynucleotide encoding the Cas12a crRNA; and (d) a Cas12a tracrRNA, or a polynucleotide encoding the Cas12a tracrRNA, wherein the Cas12a tracrRNA is provided in molar excess relative to the Cas12a nuclease. In embodiments wherein the genetic locus is to be modified by homology-dependent repair, the composition further includes: (e) a donor polynucleotide encoding a sequence to be integrated at a double-stranded break in the genetic locus; examples of suitable donor polynucleotides are described above under the heading "A Method of Integrating a Sequence Encoded by a Donor Polynucleotide at a Specific Locus".

In embodiments of the composition, the Cas12a tracrRNA is identified from the same genomic region as the Cas12a nuclease by at least the following steps: (a) identifying in the genomic region flanking the DNA encoding the Cas12a nuclease at least one nucleotide sequence that includes a CRISPR array including direct repeats; (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat. In embodiments, the Cas12a tracrRNA locus is directly adjacent to the DNA encoding the Cas12a nuclease. In embodiments, there is additional genomic sequence, such as DNA sequence encoding other Cas nucleases, located between the Cas12a tracrRNA locus and the DNA encoding the Cas12a nuclease; see, e.g., FIGS. 1 and 4.

In embodiments of the composition, the Cas12a tracrRNA is present in a molar excess, relative to the Cas12a nuclease. In embodiments, the Cas12a tracrRNA is present in a molar amount that is at least 10-fold (e.g., at least 10-fold, 15-fold, 20-fold, 30-fold, 50-fold, 90-fold, 100-fold, 150-fold, or 200-fold) greater than the molar amount of the Cas12a nuclease.

In embodiments of the composition, the eukaryotic cell is a cell of a non-human animal, an invertebrate, a vertebrate, a mollusk, an arthropod, an insect, a fish, a reptile, an amphibian, a bird, a mammal, a primate, a non-human primate, a human, a plant, or a fungus. In embodiments, the eukaryotic cell includes a cell of a cell line or a cell of a multicellular organism, and wherein the genetic locus to be modified includes a locus of interest in the genome of the eukaryotic cell. In embodiments, the eukaryotic cell is in vitro, ex vivo, or in vivo. In embodiments, the eukaryotic cell includes a non-human animal or human stem cell or a non-human animal or human stem cell line.

In embodiments of the composition, the Cas12a nuclease and the engineered Cas12a crRNA are provided as a ribonucleoprotein complex. In embodiments, the Cas12a nuclease is provided as a polynucleotide encoding the Cas12a nuclease. In embodiments, the Cas12a nuclease is: (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. In embodiments, the Cas12a nuclease is deactivated. In embodiments, the Cas12a nuclease includes at least one modification selected from the group consisting of: (a) a localization signal (e.g., a nuclear localization signal, a mitochondrial localization signal, or a plastid localization signal); (b) a detectable label (e.g., a fluorescent dye); (c) a cell-penetrating peptide; (d) an endosomal escape peptide; and (e) an affinity tag. The compositions including a tracrRNA as disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KIM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO:137) in containing at least one point mutation selected from the group consisting of K382N, Q393K, S925A, E933N, K943F/Q, K972L, K1064G, P670I, N671I, D727A, E939A, and D1053A.

In embodiments of the composition, the engineered Cas12a crRNA includes a spacer sequence that is designed to hybridize with a target sequence in the genetic locus. In embodiments, the target sequence is a segment of a genetic locus or a gene of interest; in embodiments, the target sequence includes about 20 to about 30 contiguous nucleotides and has near perfect or perfect sequence complementarity to the nucleotide sequence of the spacer of the Cas12a crRNA. In embodiments, the engineered Cas12a crRNA, or a polynucleotide encoding the engineered Cas12a crRNA, further includes at least one direct repeat sequence or fragment thereof capable of associating with the Cas12a nuclease, wherein the at least one direct repeat sequence or fragment thereof is adjacent to and 3' to the spacer sequence. In embodiments, the engineered Cas12a crRNA further includes a 3' extension adjacent to the spacer sequence. In embodiments, the 3' extension includes nucleotides that when base-paired form about one helical turn. In embodiments, the 3' extension includes at least 10 contiguous nucleotides. In embodiments, the Cas12a tracrRNA has a nucleotide sequence having sufficient complementarity to the engineered Cas12a crRNA's 3' extension to allow hybridization between the tracrRNA and the engineered Cas12a crRNA.

In embodiments of the composition, the Cas12a tracrRNA is provided: (a) as DNA encoding a first RNA molecule including the Cas12a tracrRNA and including a restriction endonuclease cleavage site that is suitable for insertion of a sequence coding for a functional RNA moiety; or (b) as a functional RNA molecule including the Cas12a tracrRNA and a functional RNA moiety, or as a polynucleotide encoding the functional RNA molecule; or (c) by a DNA expression system comprising (i) DNA sequence for a first promoter; and (ii) operably linked and heterologous to the first promoter, DNA encoding a first RNA molecule comprising a Cas12a tracrRNA and comprising a restriction endonuclease cleavage site that is suitable for insertion of a sequence coding for a functional RNA moiety; and (iii) optionally, a terminator 3' to and operably linked to the DNA encoding the first RNA molecule; or (d) by a DNA expression system comprising: (i) DNA sequence for a first promoter; and (ii) operably linked and heterologous to the first promoter, a DNA encoding a functional RNA molecule comprising a Cas12a tracrRNA and a functional RNA moiety; and (iii) optionally, a terminator 3' to and operably linked to the DNA encoding a functional RNA molecule.

In embodiments of the composition, the Cas12a tracrRNA is provided as DNA encoding a first RNA molecule including the Cas12a tracrRNA and including a restriction endonuclease cleavage site that is suitable for insertion of a sequence coding for a functional RNA moiety, and wherein the functional RNA moiety is at least one selected from the group consisting of: (a) a nucleotide sequence for annealing to a donor polynucleotide; (b) a nucleotide sequence for annealing to the crRNA 3' extension; (c) a terminator sequence; (d) an RNA aptamer; (e) an enzymatically active RNA sequence; (f) a detectable label; and (g) an RNA sequence forming at least partially double-stranded RNA. In embodiments of the composition, the Cas12a tracrRNA is provided as DNA encoding a first RNA molecule including the Cas12a tracrRNA and including a restriction endonuclease cleavage site that is suitable for insertion of a sequence coding for a functional RNA moiety, wherein the functional RNA moiety includes RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). In embodiments of the composition, the Cas12a tracrRNA is provided as DNA encoding a first RNA molecule including the Cas12a tracrRNA and including a restriction endonuclease cleavage site that is suitable for insertion of a sequence coding for a functional RNA moiety, wherein the functional RNA moiety includes an RNA sequence for annealing to a donor polynucleotide, and wherein the composition further includes the donor polynucleotide. In embodiments of the composition, the Cas12a tracrRNA is provided as a functional RNA molecule including the Cas12a tracrRNA and a functional RNA moiety, or as a polynucleotide encoding the functional RNA molecule, and wherein the functional RNA moiety is at least one selected from the group consisting of: (a) a nucleotide sequence for annealing to a donor polynucleotide; (b) a nucleotide sequence for annealing to the crRNA 3' extension; (c) a terminator sequence; (d) an RNA aptamer; (e) an enzymatically active RNA sequence; (f) a detectable label; and (g) an RNA sequence forming at least partially double-stranded RNA. In embodiments of the composition, the Cas12a tracrRNA is provided as a functional RNA molecule including the Cas12a tracrRNA and a functional RNA moiety, or as a polynucleotide encoding the functional RNA molecule, and wherein the functional RNA moiety includes RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). In embodiments of the composition, the Cas12a tracrRNA is provided as a functional RNA molecule including the Cas12a tracrRNA and a functional RNA moiety, or as a polynucleotide encoding the functional RNA molecule, wherein the functional RNA moiety includes an RNA sequence for annealing to a donor polynucleotide, and wherein the composition further includes the donor polynucleotide.

In embodiments of the composition, the genetic locus in a eukaryotic cell to be modified is genomic DNA. In embodiments, the genetic locus is in genomic DNA of a eukaryotic nucleus, or mitochondrial DNA, or plastid DNA. In embodiments, the genetic locus is in a eukaryotic DNA molecule in vitro. In embodiments, the genetic locus is in a eukaryotic cell; in embodiments, the eukaryotic cell is an isolated eukaryotic cell, or a eukaryotic cell in culture, or a eukaryotic cell located in a tissue or organ of a eukaryotic organism. In embodiments, the eukaryotic cell is a cell of a non-human animal, an invertebrate, a vertebrate, a mollusk, an arthropod, an insect, a fish, a reptile, an amphibian, a bird, a mammal, a primate, a non-human primate, a human, a plant, or a fungus. In embodiments, the eukaryotic cell includes a cell of a cell line or a cell of a multicellular organism, and wherein the genetic locus to be modified includes a locus of interest in the genome of the eukaryotic cell. In embodiments, the eukaryotic cell is in vitro, ex vivo, or in vivo. In embodiments, the eukaryotic cell includes a non-human animal or human stem cell or a non-human animal or human stem cell line. Target sequences and eukaryotic cells are described in detail below under the section headed "Related Disclosure".

Related Disclosure

Target Sequences or Target Genes: Embodiments of the polynucleotides, compositions, engineered systems, and methods disclosed herein are useful in editing or effecting a sequence-specific modification of a target DNA sequence or target gene in a DNA molecule, a chromosome, or a genome. In embodiments, the target sequence or target gene includes coding sequence (DNA encoding a polypeptide, such as a structural protein or an enzyme), non-coding sequence, or both coding and non-coding sequence. In embodiments, the target sequence or target gene is a gene of a pest or pathogen of a non-human animal, a human, or a plant; important target genes include genes of invertebrate pests (e.g., arthropods, nematodes, and mollusks) of plants, and invertebrate parasites of animals. In embodiments, the target sequence or target gene includes regulatory sequence or translatable (coding) sequence for genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). In embodiments, the target gene is an endogenous gene of a eukaryotic cell; in other embodiments, the target gene is an exogenous gene (e.g., a transgene) in a eukaryotic cell. In embodiments, the target sequence or target gene is a gene that is involved in one or more small RNA-mediated (sRNA-mediated) silencing pathways, i.e., a gene involved in RNA-mediated sequence-specific inhibition of gene expression wherein silencing may occur at transcription, post-transcription, or translation, and wherein the sRNA-mediated silencing pathways can be classified by the biosynthesis, biogenesis, and recognition of types of regulatory sRNAs, e.g., short interfering RNAs (siRNAs), microRNAs (miRNAs), and phased sRNAs; possible target sequences include DNA encoding a regulatory RNA (e.g., DNA encoding a pre-miRNA or miRNA precursor, or DNA encoding a recognition site for a mature miRNA or an siRNA) and DNA encoding any of the participating sRNA silencing pathway proteins (e.g., RDR6, SDE3, RDR2, WEX, SGS3, DCL2-4, UPF1, UPF3, HEN1, NRPD1A, NRPD2, DRD1, HDA6, AGO1, and MOP1); see, e.g., U.S. Pat. No. 9,222,100, incorporated herein by reference. Examples of non-coding sequences include DNA encoding long non-coding RNAs (lncRNAs), DNA encoding microRNAs (miRNAs), DNA encoding tRNAs or ribosomal RNAs (rRNAs), DNA encoding untranscribed regions that are located 5' to or 3' to DNA encoding a polypeptide, and DNA encoding regulatory elements (e.g., promoters, enhancers, introns, terminators, silencers, insulators). In embodiments, the target DNA is genomic DNA, e.g., genomic DNA or nuclear DNA of a eukaryote. In embodiments, the target DNA is mitochondrial or plastid DNA, e.g., mitochondrial DNA of a non-human animal, an animal, or a plant, or plastid DNA of a plant or eukaryotic alga.

Eukaryotic Cells and Eukaryotic Species of Interest: Embodiments of the polynucleotides, compositions, engineered systems, and methods disclosed herein are useful in genome editing of eukaryotes, cells of eukaryotes, and DNA obtained from eukaryotes. In embodiments, the polynucleotides, compositions, engineered systems, and methods disclosed herein are useful in genome editing of non-human animals and non-human animal cells, non-human animal stem cells, human cells, human stem cells, and human somatic (non-gametic) cells; isolated tissue (e.g., nervous tissue, epithelial tissue, liver, spleen, pancreas, muscle tissue, bone, connective tissue, endocrine system tissues, and tumours) or cells (e.g., blood cells, erythrocytes, leukocytes, lymphocytes, liver cells, bone cells, immune cells, T cells, B cells, dendritic cells, and tumour cells) or cell organelles (e.g., mitochondria or chloroplasts, either isolated or contained within the eukaryotic cell, tissue, or organism) obtained from a non-human animal or from a human; engineered hybridoma cells; fungi, fungal cells, plants, plant tissue, plant cells, and seeds. In embodiments, the polynucleotides, compositions, engineered systems, and methods disclosed herein are useful in genome editing of a non-human animal cell (e.g., a cell of an animal selected from the group consisting of invertebrates, vertebrates, insects, arthropods, mollusks, fish, reptiles, amphibians, birds, mammals, primates, and non-human primates), a human cell, a plant cell, or a fungal cell. In embodiments, the eukaryotic cell, tissue, or cell organelle is obtained from an economically or agriculturally important animal species, such as, but not limited to, bees, fruit flies, shrimp, oysters, clams, mussels, salmon, trout, carp, tilapia, catfish, barramundi, striped bass, pigeons, chickens, turkeys, ducks, geese, goats, sheep, cattle, water buffalo, horses, pigs, dogs, cats, rabbits, mice, and rats. In embodiments, the eukaryotic cell is in vitro, ex vivo, or in vivo. In embodiments, the eukaryotic cell is a non-human animal stem cell or a non-human animal gametic cell, from which a non-animal tissue or even an intact animal can be developed. In embodiments, the polynucleotides, compositions, engineered systems, and methods disclosed herein are useful in editing of eukaryotic DNA (e.g., genomic DNA) in vitro. In embodiments, the polynucleotides encoding the Cas12a nuclease and Cas12a nuclease variants described herein are codon-optimized, in whole or in part, for the eukaryotic species wherein the Cas12a editing system is to be employed. In an embodiment, a codon-optimized polynucleotide encoding a Cas12a nuclease contains one or more codons selected for having a high frequency for specifying a given amino acid in the eukaryotic species in which the codon-optimized polynucleotide is to be introduced or expressed. Codon usage or bias is known in the art for various eukaryotes; see, e.g., Quax et al. (2015) Molecular Cell, 59:149-161. See also U.S. Pat. No. 6,015,891, incorporated herein by reference.

In embodiments, the polynucleotides, compositions, engineered systems, and methods disclosed herein are useful in genome editing of plants, plant tissue (including callus), plant cells, or plant protoplasts obtained from any monocot or dicot plant species of interest, for example, row crop plants, fruit-producing plants and trees, vegetables, trees, and ornamental plants including ornamental flowers, shrubs, trees, groundcovers, and turf grasses. Examples of plants, plant tissue, plant cells, or plant protoplasts that are useful in such genome editing include whole plant, intact nodal bud, shoot apex or shoot apical meristem, root apex or root apical meristem, lateral meristem, intercalary meristem, seedling, whole seed, halved seed or other seed fragment, zygotic embryo, somatic embryo, ovule, pollen, microspore, anther, hypocotyl, cotyledon, leaf, petiole, stem, tuber, root, callus, or plant cell or plant protoplast cultures. Plants or plant tissues or cells can be haploid, inducibly haploid, haploid-inducing, diploid, or polyploid. Plant species of interest include, but are not limited to, alfalfa (*Medicago sativa*), almonds (*Prunus dulcis*), apples (*Malus* x *domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other capsicum peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), eucalyptus (*Eucalyptus* spp.), flax (*Linum usitatissumum* L.), geraniums (*Pelargonium* spp.), grapefruit (*Citrus* x *paradisi*), grapes (*Vitus* spp.) including wine grapes (*Vitus vinifera*), guava (*Psidium guajava*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (Ellis quineensis), olive (*Olea europaea*), onion (*Allium cepa*), orange (*Citrus sinensis*), *papaya* (*Carica papaya*), peaches and nectarines (*Prunus persica*), pear (*Pyrus* spp.), pea (Pisa *sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria* x *ananassa*), sugar beet (*Beta vulgaris*), sugarcanes (*Saccharum* spp.), sunflower (*Helianthus annuus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), or yams (*Discorea* spp.).

Nuclease Fusions and Complexes: In embodiments, the Cas12a nuclease is a fusion protein, e.g., wherein the Cas12a nuclease is covalently bound through a peptide bond to a cell-penetrating peptide, a nuclear localization signal peptide, a chloroplast transit peptide, or a mitochondrial targeting peptide; such fusion proteins are conveniently encoded in a single nucleotide sequence, optionally including codons for linking amino acids. In embodiments, the Cas12a nuclease is a fusion protein, wherein the Cas12a nuclease is covalently bound to another polypeptide via a linker polypeptide, for example, via a glycine polymer $(G)_n$, a glycine-serine polymer, a glycine-alanine polymer, and an alanine-serine polymer. In embodiments, the Cas12a nuclease is chemically conjugated to another polypeptide, e.g., via a non-peptide covalent bond. In embodiments, the Cas12a nuclease is associated with another polypeptide via a non-covalent bond. In embodiments, the Cas12a nuclease is a fusion protein, wherein the Cas12a nuclease is covalently bound to a protein (or a domain from a protein) that inhibits transcription (e.g., a protein that represses transcription, recruits transcription inhibitor proteins, modifies a target DNA through a process such as methylation, recruits a DNA modifier, modulates histones associated with a target DNA, recruits a histone modifier such as those that modify acetylation and/or methylation of histones, or similar functions). Examples of proteins (or fragments thereof) that can be used in decrease transcription include but are not limited to: transcriptional repressors such as the Kruppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZl, and the like; histone lysine demethylases such as JMJD2A/JHDM3A, JMJD2B, JMJD2C/GASC1, JMJD2D, JARID1A/RBP2, JARIDlB/PLU-1, JARID1C/SMCX, JARIDlD/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as Hhal DNA m5c-methyltransferase (M.Hhal), DNA methyltransferase 1 (DNMT1), DNA methyltransferase 3a (DNMT3a), DNA methyltransferase 3b (DNMT3b), MET1, DRM3 (plants), ZMET2, CMT1, CMT2 (plants), and the like; and periphery recruitment elements such as Lamin A, Lamin B, and the like. In embodiments, the Cas12a nuclease is a fusion protein, wherein the Cas12a nuclease is covalently bound to a protein (or a domain from a protein) that increases transcription (e.g., a protein that activates transcription, recruits transcription activator proteins, modifies a target DNA through a process such as demethylation, recruits a DNA modifier, modulates histones associated with a target DNA, recruits a histone modifier such as those that modify acetylation and/or methylation of histones, or similar functions). Examples of proteins (or fragments thereof) that can be used in increase transcription include but are not limited to: transcriptional activators such as VP16, VP64, VP48, VP160, $p^{65}$ subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like. In embodiments, the Cas12a nuclease is a fusion protein, wherein the Cas12a nuclease is covalently bound to a heterologous polypeptide that has enzymatic activity that modifies a target nucleic acid (e.g., ssRNA, dsRNA, ssDNA, dsDNA), for example, nuclease activity such as that provided by a restriction enzyme (e.g., Fokl nuclease), methyltransferase activity such as that provided by a methyltransferase (e.g., Hhal DNA m5c-methyltransferase, M.Hhal), DNA methyltransferase 1 (DNMT1), DNA methyltransferase 3a (DNMT3a), DNA methyltransferase 3b (DNMT3b), MET1, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS 1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity). In embodiments, the Cas12a nuclease is a fusion protein, wherein the Cas12a nuclease is covalently bound to a heterologous polypeptide that has enzymatic activity that modifies a polypeptide (e.g., a histone) associated with a target nucleic acid (e.g., ssRNA, dsRNA, ssDNA, dsDNA), for example, methyltransferase activity such as that provided by a histone methyltransferase (HMT) (e.g., suppressor of variegation 3-9 homolog 1 (SUV39H1, also known as KMTIA), euchromatic histone lysine methyltransferase 2 (G9A, also known as KMT1C and EHMT2), SUV39H2, ESET/SETDB 1, and the like, SET1A, SET1B, MLL1 to 5, ASH1, SYMD2, NSD1, DOT1L, Pr-SET7/8, SUV4-20H1, EZH2, RIZl), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARIDlB/PLU-1, JARID1C/SMCX, JARIDlD/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HB01/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity. In embodiments, the Cas12a nuclease is a fusion protein, wherein the Cas12a nuclease is covalently bound to a dihydrofolate reductase (DHFR) destabilization domain (e.g., to generate a chemically controllable chimeric Cas12a nuclease).

In embodiments, the Cas12a nuclease or a polynucleotide that encodes the Cas12a nuclease or a ribonucleoprotein including the Cas12a nuclease is provided as a complex with a cell-penetrating peptide or other transfecting agent. In embodiments, the Cas12a nuclease or a polynucleotide that encodes the Cas12a nuclease or a ribonucleoprotein including the Cas12a nuclease is complexed with, or covalently or non-covalently bound to, a further element, e.g., a carrier molecule, an antibody, an antigen, a viral movement protein, a polymer, a detectable label (e.g., a moiety detectable by fluorescence, radioactivity, or enzymatic or immunochemical reaction), a quantum dot, or a particulate or nanoparticulate.

In some cases, the fusion partner can modulate transcription (e.g., inhibit transcription, increase transcription) of a target DNA. For example, in some cases the fusion partner Vectors: In certain embodiments, a vector or an expression cassette contained in a vector includes additional components, e.g., a polynucleotide encoding a drug resistance or herbicide gene or a polynucleotide encoding a detectable marker such as green fluorescent protein (GFP) or beta-glucuronidase (gus) to allow convenient screening or selection of cells expressing the vector. In embodiments, the vector or expression cassette includes additional elements for improving delivery to a plant cell or plant protoplast or for directing or modifying expression of one or more genome-editing system elements, for example, fusing a sequence encoding a cell-penetrating peptide, localization signal, transit, or targeting peptide to the Cas12a nuclease, or adding a nucleotide sequence to stabilize a guide RNA; such fusion proteins (and the polypeptides encoding such fusion proteins) or combination polypeptides, as well as expression cassettes and vectors for their expression in a cell, are specifically claimed. In embodiments, a Cas12a nuclease is fused to a localization signal, transit, or targeting peptide, e.g., a nuclear localization signal (NLS), a chloroplast transit peptide (CTP), or a mitochondrial targeting peptide (MTP); in a vector or an expression cassette, the nucleotide sequence encoding any of these can be located either 5' and/or 3' to the DNA encoding the nuclease. CRISPR nuclease fusion proteins containing nuclear localization signals and codon-optimized for expression in maize are disclosed in U.S. patent application Ser. No. 15/120,110, published as U.S. Patent Application Publication 2017/0166912, national phase application claiming priority to PCT/US2015/018104 (published as WO/2015/131101 and claiming priority to U.S. Provisional Patent Application 61/945,700), incorporated herein by reference. In another example, a chloroplast-targeting RNA is appended to the 5' end of an mRNA encoding an endonuclease to drive the accumulation of the mRNA in chloroplasts; see Gomez, et al. (2010) *Plant Signal Behav.*, 5: 1517-1519. In an embodiment, a Cas12a nuclease is fused to a nuclear localization signal (NLS), such as the NLS from SV40. In an embodiment, a Cas12a nuclease is fused to a cell-penetrating peptide (CPP), such as octa-arginine or nona-arginine or a homoarginine 12-mer oligopeptide, or a CPP disclosed in the database of cell-penetrating peptides CPPsite 2.0, publicly available at crdd [dot]osdd[dot]net/raghava/cppsite/. In an embodiment, a Cas12a nuclease is fused to a chloroplast transit peptide (CTP) sequence. In embodiments, a CTP sequence is obtained from any nuclear gene that encodes a protein that targets a chloroplast, and the isolated or synthesized CTP DNA is appended to the 5' end of the DNA that encodes a Cas12a nuclease targeted for use in a chloroplast. Chloroplast transit peptides and their use are described in U.S. Pat. Nos. 5,188,642, 5,728,925, and 8,420,888, all of which are incorporated herein by reference in their entirety. Specifically, the CTP nucleotide sequences provided with the sequence identifier (SEQ ID) numbers 12-15 and 17-22 of U.S. Pat. No. 8,420,888 are incorporated herein by reference. In an embodiment, a Cas12a nuclease is fused to a mitochondrial targeting peptide (MTP), such as a plant MTP sequence; see, e.g., Jores et al. (2016) *Nature Communications,* 7:12036-12051.

Plasmids designed for use in plants and encoding CRISPR genome editing elements (CRISPR nucleases and guide RNAs) are publicly available from plasmid repositories such as Addgene (Cambridge, Mass.; also see "addgene[dot] com") or can be designed using publicly disclosed sequences, e.g., sequences of CRISPR nucleases. In embodiments, such plasmids are used to co-express both Cas12a nuclease mRNA and guide RNA(s) (Cas12a crRNA(s)); in other embodiments, Cas12a nuclease mRNA and guide RNA (Cas12a crRNA) are encoded on separate plasmids. In embodiments, the plasmids are *Agrobacterium* TI plasmids. Materials and methods for preparing expression cassettes and vectors for CRISPR endonuclease and guide RNA for stably integrated and/or transient plant transformation are disclosed in U.S. patent application Ser. No. 15/120,110, published as U.S. Patent Application Publication 2017/0166912, national phase application claiming priority to PCT/US2015/018104 (published as WO/2015/131101 and claiming priority to U.S. Provisional Patent Application 61/945,700), U.S. Patent Application Publication 2015/0082478 A1, and PCT/US2015/038767 (published as WO/2016/007347 and claiming priority to U.S. Provisional Patent Application 62/023,246), all of which are incorporated herein by reference in their entirety. In embodiments, such expression cassettes are isolated linear fragments, or are part of a larger construct that includes bacterial replication elements and selectable markers; such embodiments are useful, e.g., for particle bombardment or nanoparticle delivery or protoplast transformation. In embodiments, the expression cassette is adjacent to or located between T-DNA borders or contained within a binary vector, e.g., for *Agrobacterium*-mediated transformation. In embodiments, a plasmid encoding a Cas12a nuclease is delivered to a cell (such as a plant cell or a plant protoplast) for stable integration of the Cas12a nuclease into the genome of the cell, or alternatively for transient expression of the Cas12a nuclease. In embodiments, plasmids encoding a Cas12a nuclease are delivered to a plant cell or a plant protoplast to achieve stable or transient expression of the Cas12a nuclease, and one or multiple guide RNAs (Cas12a crRNAs) (such as a library of individual guide RNAs or multiple pooled guide RNAs) or plasmids encoding the guide RNAs are delivered to the plant cell or plant protoplast individually or in combinations, thus providing libraries or arrays of plant cells or plant protoplasts (or of plant callus or whole plants derived therefrom), in which a variety of genome edits are provided by the different guide RNAs (Cas12a crRNAs).

In embodiments, the polynucleotides, ribonucleoproteins, DNA expression systems, and engineered systems are delivered to a eukaryotic cell using a viral vector. Viral vectors especially useful in animal cells include viral vectors based on vaccinia virus; poliovirus; adenovirus (see, e.g., Li et al., Invest Opthalmol Vis Sci 35:2543 2549, 1994; Borras et al, Gene Ther 6:515 524, 1999; Li and Davidson, PNAS 92:7700 7704, 1995; Sakamoto et al., H Gene Ther 5: 1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90: 10613-10617); SV40; herpes simplex virus; human immunodeficiency virus (see, e.g., Miyoshi et al., PNAS 94: 10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector. Viral vectors especially useful in plant cells include geminiviruses, begomoviruses, tobamoviruses, potex viruses, comoviruses, wheat streak mosaic virus, barley stripe mosaic virus, bean yellow dwarf virus, bean pod mottle virus, cabbage leaf curl virus, beet curly top virus, tobacco yellow dwarf virus, tobacco rattle virus, potato virus X, and cowpea mosaic virus.

In embodiments, the polynucleotides, ribonucleoproteins, DNA expression systems, and engineered systems are delivered to a plant cell using a bacterial vector. In embodiments of the method, the engineered system or a component thereof is delivered via at least one bacterial vector capable of transforming a plant cell and selected from the group consisting of *Agrobacterium* sp., *Rhizobium* sp., *Sinorhizobium* (Ensifer) sp., *Mesorhizobium* sp., *Bradyrhizobium* sp., *Azobacter* sp., and *Phyllobacterium* sp.

Delivery Methods and Delivery Agents: The polynucleotides, ribonucleoproteins, DNA expression systems, engineered systems, and vectors (collectively referred to here as "genome editing reagents") that are aspects of the invention can be delivered to a eukaryotic cell, such as a plant cell, using various techniques and agents. In embodiments, one or more treatments is employed to deliver genome editing reagents into a plant cell or plant protoplast, e.g., through barriers such as a cell wall or a plasma membrane or nuclear envelope or other lipid bilayer. In an embodiment, genome editing reagents are delivered directly, for example by direct contact of the polynucleotide composition with a plant cell or plant protoplast. A genome editing reagent-containing composition in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a eukaryotic cell, such as a non-human animal cell, a human cell, a fungal cell, or a plant cell or plant protoplast (e.g., through abrasion or puncture or otherwise disruption of the cell wall or cell membrane, by spraying or dipping or soaking or otherwise directly contacting, by microinjection). For example, a eukaryotic cell, such as a non-human animal cell, a human cell, a fungal cell, or a plant cell or plant protoplast is soaked in a liquid genome editing reagent-containing composition, whereby the genome editing reagent is delivered to the plant cell or plant protoplast. In embodiments, the genome editing reagent-containing composition is delivered using negative or positive pressure, for example, using vacuum infiltration or application of hydrodynamic or fluid pressure. In embodiments, the genome editing reagent-containing composition is introduced into a eukaryotic cell, such as a non-human animal cell, a human cell, a fungal cell, or a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in U.S. Published Patent Application 2014/0287509, incorporated by reference in its entirety herein. Other techniques useful for delivering the genome editing reagent-containing composition to a eukaryotic cell, such as a non-human animal cell, a human cell, a fungal cell, or a plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In embodiments, the genome editing reagent-containing composition is provided to a plant cell or plant protoplast by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the gRNA; see, e.g., Broothaerts et al. (2005) *Nature,* 433:629-633. Any of these techniques or a combination thereof are alternatively employed on the plant part or tissue or intact plant (or seed) from which a plant cell or plant protoplast is optionally subsequently obtained or isolated; in embodiments, the genome editing reagent-containing composition is delivered in a separate step after the plant cell or plant protoplast has been obtained or isolated.

In embodiments, a treatment employed in delivery of a genome editing reagent to a eukaryotic cell, such as a non-human animal cell, a human cell, a fungal cell, or a plant cell or plant protoplast is carried out under a specific thermal regime, which can involve one or more appropriate temperatures, e.g., chilling or cold stress (exposure to temperatures below that at which normal growth of the eukaryotic cell occurs), or heating or heat stress (exposure to temperatures above that at which normal growth of the eukaryotic cell occurs), or treating at a combination of different temperatures. In embodiments, a specific thermal regime is carried out on the eukaryotic cell, such as a non-human animal cell, a human cell, a fungal cell, or plant cell or plant protoplast, in one or more steps separate from the genome editing reagent delivery. In embodiments, a specific thermal regime is carried out on a plant cell or plant protoplast, or on a plant or plant part from which a plant cell or plant protoplast is subsequently obtained or isolated, in one or more steps separate from the genome editing reagent delivery.

A Cas12a nuclease or a polynucleotide that encodes the Cas12a nuclease or a ribonucleoprotein including the Cas12a nuclease can be provided to a cell (e.g., a plant cell) by any suitable technique. In embodiments, the Cas12a nuclease or a polynucleotide that encodes the Cas12a nuclease or a ribonucleoprotein including the Cas12a nuclease is provided in a solution, or is provided in a liposome, micelle, emulsion, reverse emulsion, suspension, or other mixed-phase composition. In embodiments, the Cas12a nuclease or a polynucleotide that encodes the Cas12a nuclease or a ribonucleoprotein including the Cas12a nuclease is provided by directly contacting a plant cell or plant protoplast with the Cas12a nuclease or a polynucleotide that encodes the Cas12a nuclease or a ribonucleoprotein including the Cas12a nuclease. In embodiments, the Cas12a nuclease or a polynucleotide that encodes the Cas12a nuclease or a ribonucleoprotein including the Cas12a nuclease is provided by transporting the Cas12a nuclease or a polynucleotide that encodes the Cas12a nuclease or a ribonucleoprotein including the Cas12a nuclease into a plant cell or plant protoplast using a chemical, enzymatic, or physical agent. In embodiments, the Cas12a nuclease is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of a plant cell or plant protoplast with a polynucleotide encoding the Cas12a nuclease; see, e.g., Broothaerts et al. (2005) *Nature,* 433:629-633. In an embodiment, the Cas12a nuclease is provided by transcription in a plant cell or plant protoplast of a DNA that encodes the Cas12a nuclease and is stably integrated in the genome of the plant cell or plant protoplast or that is provided to the plant cell or plant protoplast in the form of a plasmid or expression vector (e.g., a viral vector) that encodes the Cas12a nuclease. In embodiments, the Cas12a nuclease is provided to the plant cell or plant protoplast as a polynucleotide that encodes the Cas12a nuclease, e.g., in the form of an mRNA encoding the nuclease.

In embodiments, a whole plant or plant part or seed, or an isolated plant cell or plant protoplast, or the plant or plant part from which a plant cell or plant protoplast is obtained or isolated, is treated with one or more delivery agents which can include at least one chemical, enzymatic, or physical agent, or a combination thereof. In embodiments, a genome editing reagent-containing composition further includes one or more one chemical, enzymatic, or physical agent for delivery. Treatment with the chemical, enzymatic or physical agent can be carried out simultaneously with the genome editing reagent delivery, or in one or more separate steps that precede or follow the genome editing reagent delivery. In embodiments, a chemical, enzymatic, or physical agent, or a combination of these, is associated or complexed with a genome editing reagent composition; examples of such associations or complexes include those involving non-covalent interactions (e.g., ionic or electrostatic interactions, hydrophobic or hydrophilic interactions, formation of liposomes, micelles, or other heterogeneous composition) and covalent interactions (e.g., peptide bonds, bonds formed using cross-linking agents). In non-limiting examples, a genome editing reagent is provided as a liposomal complex with a cationic lipid, or as a complex with a carbon nanotube, or as a fusion protein between the nuclease and a cell-penetrating peptide. Examples of agents useful for delivering a genome editing reagent include the various cationic liposomes and polymer nanoparticles reviewed by Zhang et al. (2007) *J Controlled Release,* 123:1-10, and the cross-linked multilamellar liposomes described in U.S. Patent Application Publication 2014/0356414 A1, incorporated by reference in its entirety herein.

In embodiments, the chemical agent is at least one selected from the group consisting of:

(a) solvents (e.g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);

(b) fluorocarbons (e.g., perfluorodecalin, perfluoromethyldecalin);

(c) glycols or polyols (e.g., propylene glycol, polyethylene glycol);

(d) surfactants, including cationic surfactants, anionic surfactants, non-ionic surfactants, and amphiphilic surfactants, e.g., alkyl or aryl sulfates, phosphates, sulfonates, or carboxylates; primary, secondary, or tertiary amines; quaternary ammonium salts; sultaines, betaines; cationic lipids; phospholipids; tallowamine; bile acids such as cholic acid; long chain alcohols; organosilicone surfactants including nonionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents;

(g) peptides, proteins, or enzymes (e.g., cellulase, pectolyase, maceroenzyme, pectinase), including cell-penetrating or pore-forming peptides (e.g., (BO100)2K8, Genscript; poly-lysine, poly-arginine, or poly-homoarginine peptides; gamma zein, see U.S. Patent Application publication 2011/0247100, incorporated herein by reference in its entirety; transcription activator of human immunodeficiency virus type 1 ("HIV-1 Tat") and other Tat proteins, see, e.g., www[dot]lifetein[dot]com/Cell_Penetrating_Peptides[dot]html and Jarver (2012) *Mol. Therapy-Nucleic Acids,* 1:e27, 1-17); octa-arginine or nona-arginine; poly-homoarginine (see Unnamalai et al. (2004) *FEBSLetters,* 566:307-310); see also the database of cell-penetrating peptides CPPsite 2.0 publicly available at crdd[dot]osdd[dot]net/raghava/cppsite/

(h) RNase inhibitors;

(i) cationic branched or linear polymers such as chitosan, poly-lysine, DEAE-dextran, polyvinylpyrrolidone ("PVP"), or polyethylenimine ("PEI", e.g., PEI, branched, MW 25,000, CAS #9002-98-6; PEI, linear, MW 5000, CAS #9002-98-6; PEI linear, MW 2500, CAS #9002-98-6);

(j) dendrimers (see, e.g., U.S. Patent Application Publication 2011/0093982, incorporated herein by reference in its entirety);

(k) counter-ions, amines or polyamines (e.g., spermine, spermidine, putrescine), osmolytes, buffers, and salts (e.g., calcium phosphate, ammonium phosphate);

(l) polynucleotides (e.g., non-specific double-stranded DNA, salmon sperm DNA);

(m) transfection agents (e.g., Lipofectin®, Lipofectamine®, and Oligofectamine®, and Invivofectamine® (all from Thermo Fisher Scientific, Waltham, Mass.), PepFect (see Ezzat et al. (2011) *Nucleic Acids Res.,* 39:5284-5298), TransIt® transfection reagents (Mirus Bio, LLC, Madison, Wis.), and poly-lysine, poly-homoarginine, and poly-arginine molecules including octa-arginine and nona-arginine as described in Lu et al. (2010) *J. Agric. Food Chem.,* 58:2288-2294);

(n) antibiotics, including non-specific DNA double-strand-break-inducing agents (e.g., phleomycin, bleomycin, talisomycin); and (o) antioxidants (e.g., glutathione, dithiothreitol, ascorbate).

In embodiments, the chemical agent is provided simultaneously with the genome editing reagent. In embodiments, the genome editing reagent is covalently or non-covalently linked or complexed with one or more chemical agent; for example, a polynucleotide genome editing reagent can be covalently linked to a peptide or protein (e.g., a cell-penetrating peptide or a pore-forming peptide) or non-covalently complexed with cationic lipids, polycations (e.g., polyamines), or cationic polymers (e.g., PEI). In embodiments, the genome editing reagent is complexed with one or more chemical agents to form, e.g., a solution, liposome, micelle, emulsion, reverse emulsion, suspension, colloid, or gel.

In embodiments, the physical agent is at least one selected from the group consisting of particles or nanoparticles (e.g., particles or nanoparticles made of materials such as carbon, silicon, silicon carbide, gold, tungsten, polymers, or ceramics) in various size ranges and shapes, magnetic particles or nanoparticles (e.g., silenceMag Magnetotransfection™ agent, OZ Biosciences, San Diego, Calif.), abrasive or scarifying agents, needles or microneedles, matrices, and grids. In embodiments, particulates and nanoparticulates are useful in delivery of the polynucleotide composition or the nuclease or both. Useful particulates and nanoparticles include those made of metals (e.g., gold, silver, tungsten, iron, cerium), ceramics (e.g., aluminum oxide, silicon carbide, silicon nitride, tungsten carbide), polymers (e.g., polystyrene, polydiacetylene, and poly(3,4-ethylenedioxythiophene) hydrate), semiconductors (e.g., quantum dots), silicon (e.g., silicon carbide), carbon (e.g., graphite, graphene, graphene oxide, or carbon nanosheets, nanocomplexes, or nanotubes), and composites (e.g., polyvinylcarbazole/graphene, polystyrene/graphene, platinum/graphene, palladium/graphene nanocomposites). In embodiments, such particulates and nanoparticulates are further covalently or non-covalently functionalized, or further include modifiers or cross-linked materials such as polymers (e.g., linear or branched polyethylenimine, poly-lysine), polynucleotides (e.g., DNA or RNA), polysaccharides, lipids, polyglycols (e.g., polyethylene glycol, thiolated polyethylene glycol), polypeptides or proteins, and detectable labels (e.g., a fluorophore, an antigen, an antibody, or a quantum dot). In various embodiments, such particulates and nanoparticles are neutral, or carry a positive charge, or carry a negative charge. Embodiments of compositions including particulates include those formulated, e.g., as liquids, colloids, dispersions, suspensions, aerosols, gels, and solids. Embodiments include nanoparticles affixed to a surface or support, e.g., an array of carbon nanotubes vertically aligned on a silicon or copper wafer substrate. Embodiments include polynucleotide compositions including particulates (e.g., gold or tungsten or magnetic particles) delivered by a Biolistic-type technique or with magnetic force. The size of the particles used in Biolistics is generally in the "microparticle" range, for example, gold microcarriers in the 0.6, 1.0, and 1.6 micrometer size ranges (see, e.g., instruction manual for the Helios® Gene Gun System, Bio-Rad, Hercules, Calif.; Randolph-Anderson et al. (2015) "Sub-micron gold particles are superior to larger particles for efficient Biolistic® transformation of organelles and some cell types", Bio-Rad US/EG Bulletin 2015), but successful Biolistics delivery using larger (40 nanometer) nanoparticles has been reported in cultured animal cells; see O'Brian and Lummis (2011) *BMC Biotechnol.*, 11:66-71. Other embodiments of useful particulates are nanoparticles, which are generally in the nanometer (nm) size range or less than 1 micrometer, e.g., with a diameter of less than about 1 nm, less than about 3 nm, less than about 5 nm, less than about 10 nm, less than about 20 nm, less than about 40 nm, less than about 60 nm, less than about 80 nm, and less than about 100 nm. Specific, non-limiting embodiments of nanoparticles commercially available (all from Sigma-Aldrich Corp., St. Louis, Mo.) include gold nanoparticles with diameters of 5, 10, or 15 nm; silver nanoparticles with particle sizes of 10, 20, 40, 60, or 100 nm; palladium "nanopowder" of less than 25 nm particle size; single-, double-, and multi-walled carbon nanotubes, e.g., with diameters of 0.7-1.1, 1.3-2.3, 0.7-0.9, or 0.7-1.3 nm, or with nanotube bundle dimensions of 2-10 nm by 1-5 micrometers, 6-9 nm by 5 micrometers, 7-15 nm by 0.5-10 micrometers, 7-12 nm by 0.5-10 micrometers, 110-170 nm by 5-9 micrometers, 6-13 nm by 2.5-20 micrometers. Embodiments include genome editing reagent-containing compositions including materials such as gold, silicon, cerium, or carbon, e.g., gold or gold-coated nanoparticles, silicon carbide whiskers, carborundum, porous silica nanoparticles, gelatin/silica nanoparticles, nanoceria or cerium oxide nanoparticles (CNPs), carbon nanotubes (CNTs) such as single-, double-, or multi-walled carbon nanotubes and their chemically functionalized versions (e.g., carbon nanotubes functionalized with amide, amino, carboxylic acid, sulfonic acid, or polyethylene glycol moieties), and graphene or graphene oxide or graphene complexes; see, for example, Wong et al. (2016) *Nano Lett.*, 16:1161-1172; Giraldo et al. (2014) *Nature Materials*, 13:400-409; Shen et al. (2012) *Theranostics*, 2:283-294; Kim et al. (2011) *Bioconjugate Chem.*, 22:2558-2567; Wang et al. (2010) *J. Am. Chem. Soc. Comm.*, 132:9274-9276; Zhao et al. (2016) *Nanoscale Res. Lett.*, 11:195-203; and Choi et al. (2016) *J. Controlled Release*, 235:222-235. See also, for example, the various types of particles and nanoparticles, their preparation, and methods for their use, e.g., in delivering polynucleotides and polypeptides to cells, disclosed in U.S. Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety.

In embodiments, a genome editing reagent is delivered to plant cells or plant protoplasts prepared or obtained from a plant, plant part, or plant tissue that has been treated with the polynucleotide compositions (and optionally the nuclease). In embodiments, one or more one chemical, enzymatic, or physical agent, separately or in combination with the genome editing reagent, is provided/applied at a location in the plant or plant part other than the plant location, part, or tissue from which the plant cell or plant protoplast is obtained or isolated. In embodiments, the genome editing reagent is applied to adjacent or distal cells or tissues and is transported (e.g., through the vascular system or by cell-to-cell movement) to the meristem from which plant cells or plant protoplasts are subsequently isolated. In embodiments, a genome editing reagent-containing composition is applied by soaking a seed or seed fragment or zygotic or somatic embryo in the genome editing reagent-containing composition, whereby the genome editing reagent is delivered to the seed or seed fragment or zygotic or somatic embryo from which plant cells or plant protoplasts are subsequently isolated. In embodiments, a flower bud or shoot tip is contacted with a genome editing reagent-containing composition, whereby the genome editing reagent is delivered to cells in the flower bud or shoot tip from which plant cells or plant protoplasts are subsequently isolated. In embodiments, a genome editing reagent-containing composition is applied to the surface of a plant or of a part of a plant (e.g., a leaf surface), whereby the genome editing reagent is delivered to tissues of the plant from which plant cells or plant protoplasts are subsequently isolated. In embodiments a whole plant or plant tissue is subjected to particle- or nanoparticle-mediated delivery (e.g., Biolistics or carbon nanotube or nanoparticle delivery) of a genome editing reagent-containing composition, whereby the genome editing reagent is delivered to cells or tissues from which plant cells or plant protoplasts are subsequently isolated.

EXAMPLES

Example 1

This example illustrates techniques for identifying trans-activating CRISPR (tracrRNA) sequences that are useful in compositions and methods of the invention. More specifically, this example provides examples of Cas12a tracrRNA sequences identified from Lachnospiraceae bacterium ND2006 ("Lb") and *Acidaminococcus* sp. BV3L6 ("As").

Steps for identifying tracrRNA sequences have been described, e.g., in U.S. Pat. No. 9,790,490, incorporated here by reference: "Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith." RNA sequencing can be used to further characterize such sequences identified as potential or putative tracrRNAs.

Similar techniques are used to identify putative tracrRNA sequences for Cas12a (Cpf1) nucleases from Lachnospiraceae bacterium ND2006 ("Lb") and *Acidaminococcus* sp. BV3L6 ("As"). The techniques employed include: identifying sequences that are located in the CRISPR region flanking the DNA encoding the CRISPR nuclease and that have a nucleotide sequence that permits the transcribed tracrRNA to hybridize to the crRNA (i.e., the transcribed tracrRNA has sufficient complementarity to a crRNA sequence to hybridize to the crRNA), and searching for the presence of a predicted transcriptional terminator in direction of transcription. Sequences having at least 50% sequence identity to the direct repeat in a corresponding CRISPR array are identified as potential tracrRNA sequences; sequences having slightly less than 50% sequence identity to the direct repeat are also evaluated. In this non-limiting example, putative tracrRNA sequences are identified having lengths of between 65 to 84 nucleotides and between 50.0% to 52.8% sequence identity to the direct repeat.

Figure 2:
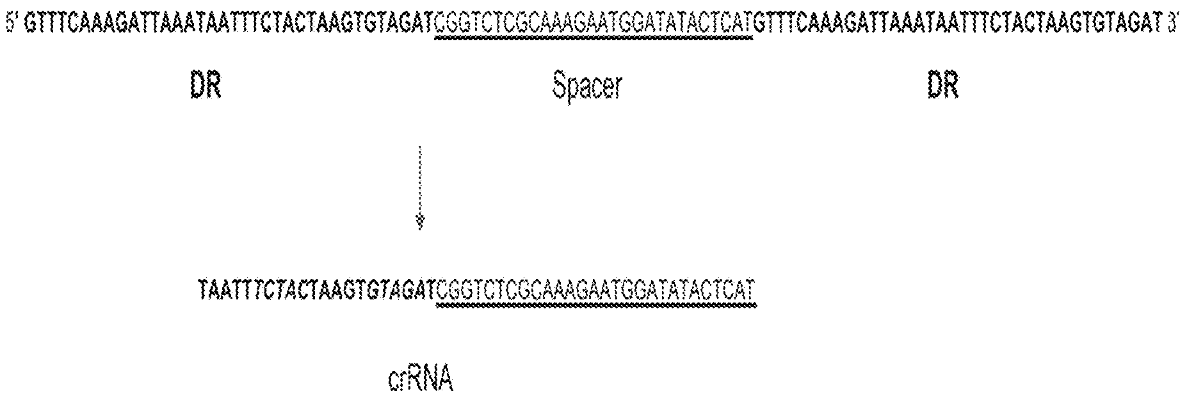
FIG. 2 illustrates a segment of the LbCpf1 CRISPR locus as described in detail in Example 1, showing the arrangement in a CRISPR array of the LbCpf1 direct repeats ("DR", in bold font) (SEQ ID NO:173) flanking a spacer sequence ("spacer", in underlined font) (SEQ ID NO:175), and illustrating the predicted crRNA (SEQ ID NO:176) processing from this CRISPR array. The DR, spacer, and predicted crRNA sequences are provided as DNA equivalents.

FIG. 1 illustrates schematics of the Lachnospiraceae bacterium ND2006 Cas12a ("LbCpf1") CRISPR locus and putative tracrRNA location; the schematics are shown with (upper figure) and without (lower figure) the Cas4 and Cas2 components of the locus. FIG. 2 illustrates a segment of the LbCpf1 CRISPR locus, showing the arrangement in a CRISPR array of the LbCpf1 direct repeats ("DR", in bold font) flanking a spacer sequence ("spacer", in underlined font), and illustrating the predicted crRNA processing from this CRISPR array. The following are identified as putative tracrRNA sequences: LbCpf1 putative tracrRNA 1 (84 nucleotides) having the RNA sequence of SEQ ID NO:1 encoded by the DNA sequence of SEQ ID NO:2, and LbCpf1 putative tracrRNA 2 (65 nucleotides) having the RNA sequence of SEQ ID NO:3 encoded by the DNA sequence of SEQ ID NO:4. FIG. 3 illustrates the alignments of the reverse complement of the LbCpf1 direct repeat (DR) sequence, SEQ ID NO:5, with the LbCpf1 putative tracrRNA 1 (SEQ ID NO:2) (top, showing 52.8% identity between the two sequences) and the LbCpf1 putative tracrRNA 2 (SEQ ID NO:4) (bottom, showing 50.0% identity between the two sequences).

Figure 4:
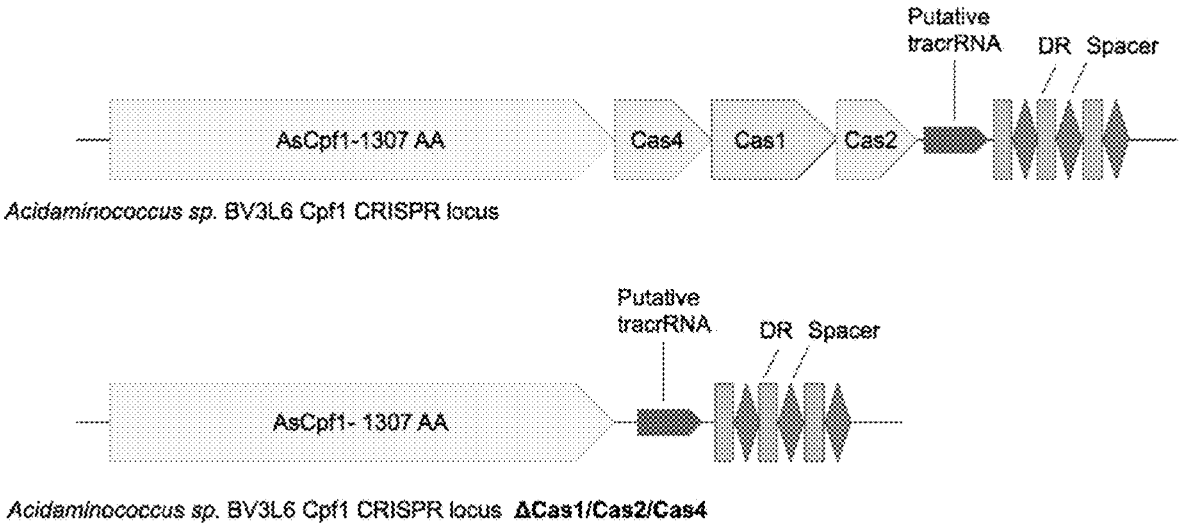
FIG. 4 illustrates schematics of the *Acidaminococcus* sp. BV3L6 ("As") Cas12a ("AsCpf1") CRISPR locus and tracrRNA ("putative tracrRNA") location as described in detail in Example 1. The schematics are shown with (upper figure) and without (lower figure) the Cas 1, Cas2, and Cas4 components of the locus. The direct repeats ("DR") are indicated by upright rectangles and the spacer sequences are indicated by diamonds.
Figure 5:
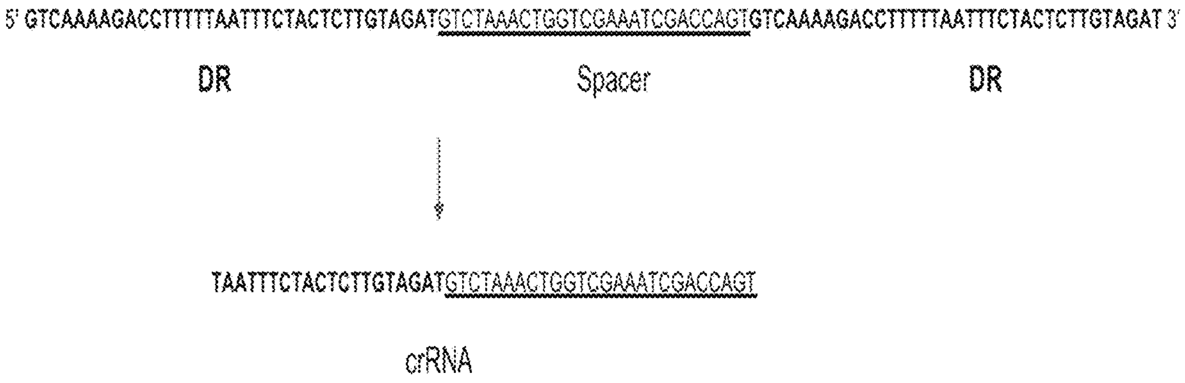
FIG. 5 illustrates a segment of the AsCpf1 CRISPR locus as described in detail in Example 1, showing the arrangement in a CRISPR array of the AsCpf1 direct repeats ("DR", in bold font) (SEQ ID NO:176) flanking a spacer sequence ("spacer", in underlined font) (SEQ ID NO:177), and illustrating the predicted crRNA (SEQ ID NO:178) processing from this CRISPR array. The DR, spacer, and predicted crRNA sequences are provided as DNA equivalents.

FIG. 4 illustrates schematics of the *Acidaminococcus* sp. BV3L6 ("As") Cas12a ("AsCpf1") CRISPR locus and putative tracrRNA location; the schematics are shown with (upper figure) and without (lower figure) the Cas 1, Cas2, and Cas4 components of the locus. FIG. 5 illustrates a segment of the AsCpf1 CRISPR locus, showing the arrangement in a CRISPR array of the AsCpf1 direct repeats ("DR", in bold font) flanking a spacer sequence ("spacer", in underlined font), and illustrating the predicted crRNA processing from this CRISPR array. A putative AsCpf1 tracrRNA (72 nucleotides) is identified as having the RNA sequence of SEQ ID NO:6 encoded by the DNA sequence of SEQ ID NO:7. FIG. 6 illustrates the alignment of the reverse complement of the AsCpf1 direct repeat (DR) sequence, SEQ ID NO:8, with the AsCpf1 putative tracrRNA (SEQ ID NO:7), showing 51.4% identity between the two sequences.

Example 2

This example describes identification of restriction endonuclease recognition and cleavage sites in and adjacent to Cas12a tracrRNA sequences. It is understood that the recognition site to which restriction endonuclease binds may also be where cleavage occurs, or may be a short distance from where cleavage occurs.

Figure 7:
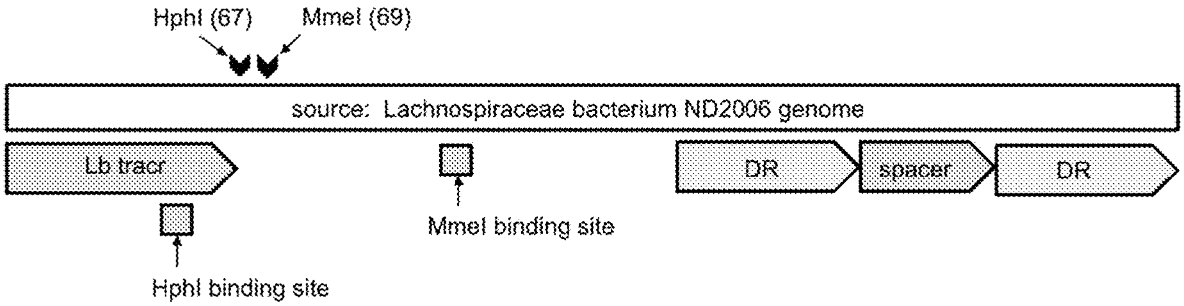
FIG. 7 schematically illustrates the position (not to scale) of some of the restriction endonuclease sites within the Lb Cas12a locus as described in detail in Example 2. Endonuclease recognition and binding sites are indicated by squares; the endonuclease cleavage sites are indicated by arrowheads. "DR" indicates a direct repeat.

Recognition and cleavage sites for commercially available restriction endonucleases are identified in the Lachnospiraceae bacterium ND2006 ("Lb") and *Acidaminococcus* sp. BV3L6 ("As") Cas112a loci, specifically in the region of the putative tracrRNA sequences described in Example 1. Table 1 lists restriction endonuclease sites located in or adjacent to (3 to) the DNA encoding the LbCpf1 putative tracrRNA 2 (65 nucleotides) (see Example 1); FIG. 7 schematically illustrates the position (not to scale) of some of the restriction endonuclease sites within the Lb Cas112a locus.

TABLE 1

| Restriction endonuclease name | Recognition pattern for endonuclease binding | Recognition pattern SEQ ID NO: | Endonuclease cleavage location, relative to the 5' terminus of the Lb tracrRNA 2 sequence |
|---|---|---|---|
| HphI | GGTGA(8/7) | 183 | 67 |
| AsuHPI | GGTGA(8/7) | 184 | 67 |
| MmeI | TCCRAC(20/18) | 185 | 69 |

Figure 8:
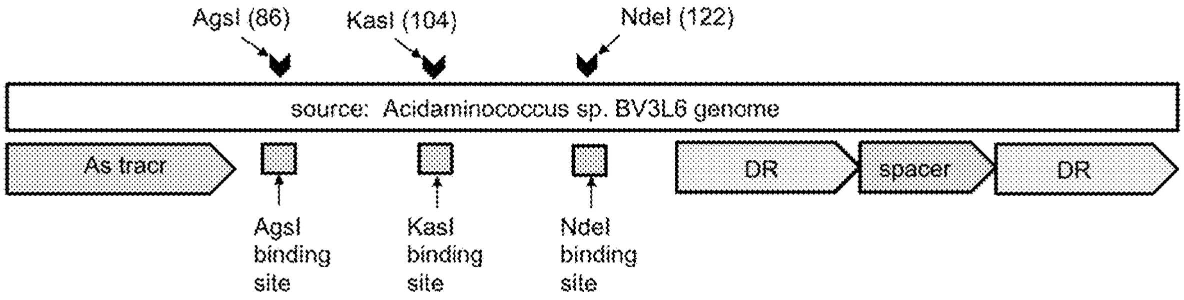
FIG. 8 schematically illustrates the position (not to scale) of some of the restriction endonuclease sites within the As Cas12a locus as described in detail in Example 2. Endonuclease recognition and binding sites are indicated by squares; the endonuclease cleavage sites are indicated by arrowheads. "DR" indicates a direct repeat.

Table 2 lists restriction endonuclease sites located in or adjacent to (3' to) the DNA encoding the AsCpf1 putative tracrRNA (72 nucleotides) (see Example 1); FIG. 8 schematically illustrates the position (not to scale) of some of the restriction endonuclease sites within the As Cas112a locus.

TABLE 2

| Restriction endonuclease name | Recognition pattern for endonuclease binding | Recognition pattern SEQ ID NO: | Endonuclease cleavage location, relative to the 5' terminus of the As tracrRNA sequence |
|---|---|---|---|
| AgsI | TTS^AA | 186 | 86 |
| MwoI, BstMWI, HpyF10VI | GCNNNNN^NNGC | 187 | 113 |
| Hin6I, HinP1I, HspAI | G^CGC | 188 | 105 |
| HhaI, AspLEI, BstHHI, CfoI | GCG^C | 189 | 107 |
| GlaI | GC^GC | 190 | 106 |
| AcyI, BsaHI, BssNI, BstACI, Hin1I, Hsp92I | GR^CGYC | 191 | 105 |
| HaeII, BfoI, BstH2I | RGCGC^Y | 192 | 108 |
| NlaIV, BmiI, BspLI, PspN4I | GGN^NCC | 193 | 106 |
| KasI, SspDI | G^GCGCC | 194 | 104 |
| NarI, Mly113I | GG^CGCC | 195 | 105 |
| PluTI | GGCGC^C | 196 | 108 |
| DinI, EgeI, EheI, SfoI | GGC^GCC | 197 | 106 |
| AccB1I, BanI, BshNI, BspT107I | G^GYRCC | 198 | 104 |
| EcoT22I, Mph1103I, NsiI, Zsp2I | ATGCA^T | 199 | 118 |
| BsmI, Mva1269I, PctI | GAATGC(1/−1) | 200 | 116 |
| Ms1I, RseI, SmiMI | CAYNN^NNRTG | 201 | 121 |
| TspDTI | ATGAA(11/9) | 202 | 109 |
| NdeI, FauNDI | CA^TATG | 203 | 122 |

Example 3

This example illustrates non-limiting embodiments of the polynucleotides and ribonucleoproteins useful in carrying out methods of the invention.

Figure 9:
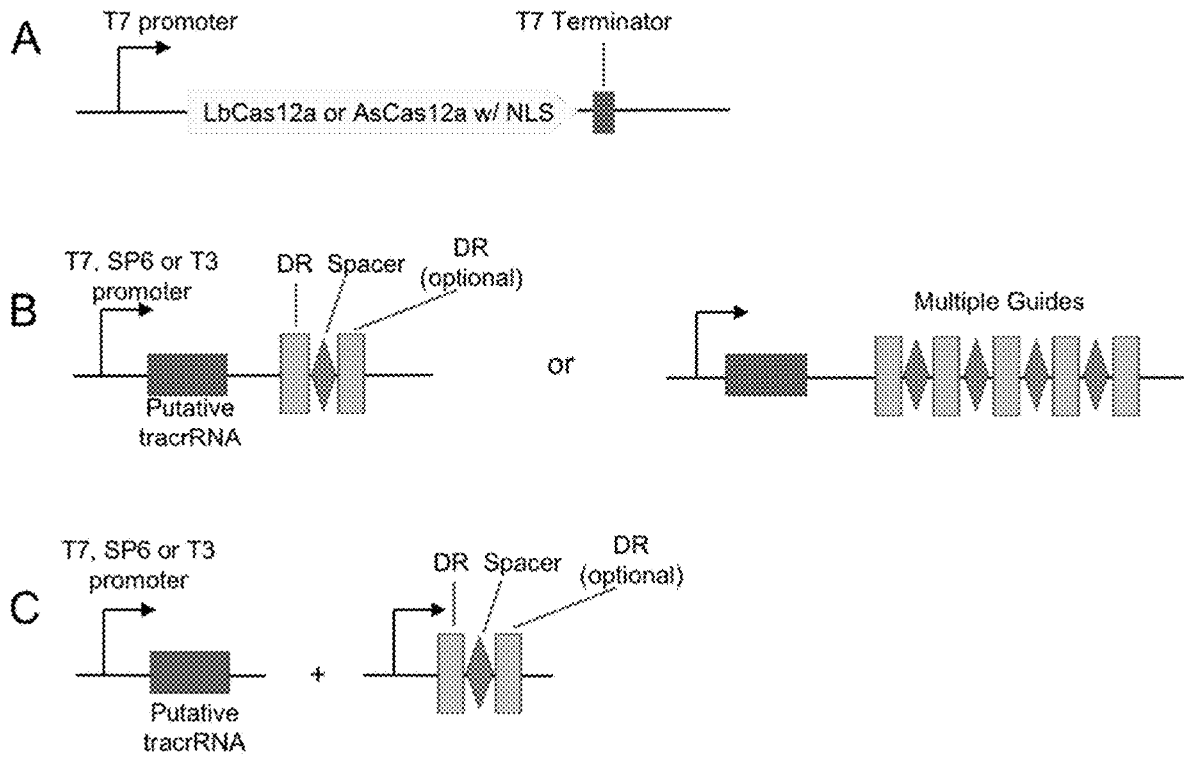
FIG. 9A schematically depicts an expression cassette for expressing a Cas12a nuclease, including a promoter, coding sequence for the Cas12a nuclease, and a terminator, as described in detail in Example 3.
FIG. 9B (left) schematically depicts a DNA expression system including: (a) DNA sequence for a first promoter; (b) operably linked and heterologous to the first promoter, a DNA encoding a first RNA molecule including a Cas12a tracrRNA or putative tracrRNA and including a restriction endonuclease cleavage site that is suitable for insertion of a sequence coding for a functional RNA moiety; and (c) operably linked and heterologous to the first promoter, a DNA encoding a Cas12a crRNA that includes a 3' extension capable of hybridizing with a segment of the first RNA molecule, as described in detail in Example 3.
FIG. 9C (left) schematically depicts a non-limiting example of a DNA expression system including: (a) DNA sequence for a first promoter; and (b) operably linked and heterologous to the first promoter, a DNA sequence encoding a first RNA molecule including a Cas12a tracrRNA or putative tracrRNA and including a restriction endonuclease cleavage site that is suitable for insertion of a sequence coding for a functional RNA moiety, as described in detail in Example 3.

FIG. 9A schematically depicts an expression cassette for expressing a Cas12a nuclease, including a promoter, coding sequence for the Cas12a nuclease, and a terminator. This non-limiting example illustrates a typical bacterial expression vector, wherein the promoter is a T7 promoter, the Cas12a nuclease is a fusion protein including LbCas12a or AsCas12a and at least one copy of a nuclear localization signal (NLS). This T7 expression system can be expressed and purified from *E. coli*. This or similar expression cassettes are useful, e.g., for expressing a Cas12a nuclease, with one or multiple copies of nuclear localization signal (NLS) for nuclear targeting located at the nuclease's N-terminus or C-terminus or both. The Cas12a nuclease may then be supplied as a protein and assembled with a guide RNA to form a ribonucleoprotein in vitro before delivery into cells.

FIG. 9B (left) schematically depicts a DNA expression system including: (a) DNA sequence for a first promoter; (b) operably linked and heterologous to the first promoter, a DNA sequence encoding a first RNA molecule including a Cas12a tracrRNA (here labelled "putative tracrRNA") and including a restriction endonuclease cleavage site (not specifically indicated) that is suitable for insertion of a sequence coding for a functional RNA moiety; and (c) operably linked and heterologous to the first promoter (and to the optional second promoter, if present), a DNA encoding a Cas12a crRNA (which includes a direct repeat, "DR" and a spacer sequence) that includes a 3' extension capable of hybridizing with a segment of the first RNA molecule. FIG. 9B (right) schematically depicts an alternative design wherein the DNA expression system includes a DNA encoding a Cas12a crRNA including multiple guide RNAs (i.e., multiple direct repeats and multiple spacer sequences), and including a 3' extension capable of hybridizing with a segment of the first RNA molecule. Optional elements that can be used in this system include a DNA sequence for a second promoter, which can be positioned between the DNA sequence encoding a first RNA molecule including a Cas12a tracrRNA and the DNA encoding a Cas12a crRNA; and a terminator, which can be positioned 3' to the DNA encoding a Cas12a crRNA. The 3'-most direct repeat is also optional. This or similar expression systems using e.g., a phage polymerase promoter (such as an SP6, T7, or T3 promoter) permit the tracrRNA and a guide RNA (the Cas12a crRNA) to be transcribed in vitro, together.

FIG. 9C (left) schematically depicts a non-limiting example of a DNA expression system including: (a) DNA sequence for a first promoter; and (b) operably linked and heterologous to the first promoter, a DNA sequence encoding a first RNA molecule including a Cas12a tracrRNA (here labelled "putative tracrRNA") and including a restriction endonuclease cleavage site (not specifically indicated) that is suitable for insertion of a sequence coding for a functional RNA moiety. (A similar expression system can also be used for expressing a DNA sequence encoding a functional RNA molecule including a Cas12a tracrRNA and a functional RNA moiety.) FIG. 9C (right) further schematically depicts an expression construct for expressing a guide RNA (here, a Cas12a crRNA including a direct repeat, "DR", and a spacer sequence); the 3'-most direct repeat is optional. These or similar expression systems using e.g., a phage polymerase promoter (such as an SP6, T7, or T3 promoter) permit the tracrRNA and a guide RNA (the Cas12a crRNA) to be transcribed in vitro, separately.

Figure 10:
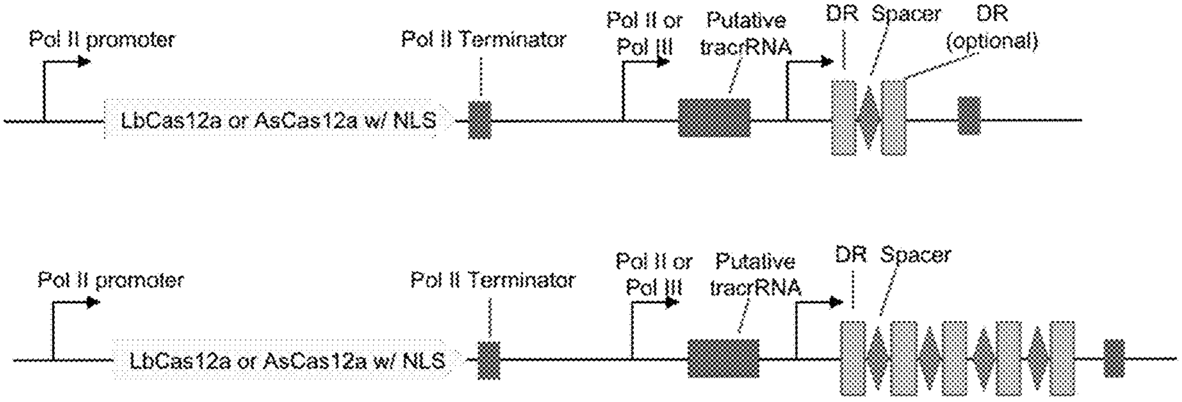
FIG. 10 (top) schematically depicts a DNA expression system, described in detail in Example 3, which includes: (a) DNA sequence for a first promoter; (b) operably linked and heterologous to the first promoter, DNA encoding a Cas12a nuclease; (c) a terminator; (d) a second promoter; (e) operably linked and heterologous to the second promoter, a DNA sequence encoding a functional RNA molecule including a Cas12a tracrRNA or putative tracrRNA and a functional RNA moiety; (f) an optional third promoter; (g) operably linked and heterologous to the second promoter (and to the optional third promoter, if present), a DNA encoding a guide RNA including a Cas12a crRNA that includes a 3' extension capable of hybridizing with a segment of the functional RNA molecule; and (h) a second terminator; the 3'-most direct repeat is optional.

FIG. 10 (top) schematically depicts a DNA expression system including: (a) DNA sequence for a first promoter (here, an RNA polymerase II promoter, such as a maize ubiquitin promoter); (b) operably linked and heterologous to the first promoter, DNA encoding a Cas12a nuclease (here, a fusion protein including LbCas12a or AsCas12a and at least one copy of a nuclear localization signal (NLS)); (c) a pol II terminator; (d) a second promoter (e.g., a pol II or pol III promoter, such as a rice U6 or U3 promoter); (e) operably linked and heterologous to the second promoter, a DNA sequence encoding a functional RNA molecule including a Cas12a tracrRNA (here labelled "putative tracrRNA") and a functional RNA moiety (not specifically indicated); (f) an optional third promoter; (g) operably linked and heterologous to the second promoter (and to the optional third promoter, if present), a DNA encoding a guide RNA including a Cas12a crRNA (which includes a direct repeat, "DR" and a spacer sequence) that includes a 3' extension capable of hybridizing with a segment of the functional RNA molecule; and (h) a second terminator; the 3'-most direct repeat is optional. FIG. 10 (bottom) schematically depicts a second DNA expression system similar to that shown in FIG. 10 (top), except that the guide RNA includes multiple guide RNAs (i.e., multiple direct repeats and multiple spacer sequences), and including a 3' extension capable of hybridizing with a segment of the first RNA molecule; the 3'-most direct repeat is optional. It will be apparent that multiple guide RNAs can alternatively be expressed under the control of multiple promoters. One of skill in the art will appreciate that similar constructs include many of the elements shown in FIG. 10 can be designed for expression of a tracrRNA and a crRNA under either one promoter or two promoters, and that promoters are selected for the type of organism (for example, a dicot plant rather than a monocot plant), tissue, or cell where the encoded nuclease and/or RNAs are to be expressed. Any of these DNA expression systems is conveniently provided on a single plasmid. While FIG. 10 depicts the component expression cassettes orientated in the same direction, it is understood that these can be orientated in opposite directions.

Example 4

This example describes a DNA expression system including: (a) DNA sequence for a first promoter; and (b) operably linked and heterologous to the first promoter, a DNA sequence encoding a functional RNA molecule including a Cas12a tracrRNA and a functional RNA moiety. This example illustrates employing a Cas12a tracrRNA as a scaffold or carrier for a functional RNA moiety (in this case, multiple copies of an aptamer capable of recruiting regulatory proteins as well as RNA for annealing to the crRNA 3' extension), allowing the functional RNA moiety to be incorporated into a Cas12a ribonucleoprotein complex. More specifically, this example illustrates a Cas12a ribonucleoprotein complex including a deactivated Cas12a nuclease, a guide RNA (a Cas12a crRNA having a 3' extension) targeting the promoter region of the maize (*Zea mays*) Lc gene, and a functional RNA molecule provided by integrating multiple copies of an MS2 aptamer as well as sequence for annealing to the crRNA 3' extension into a Cas12a tracr.

Figure 11:
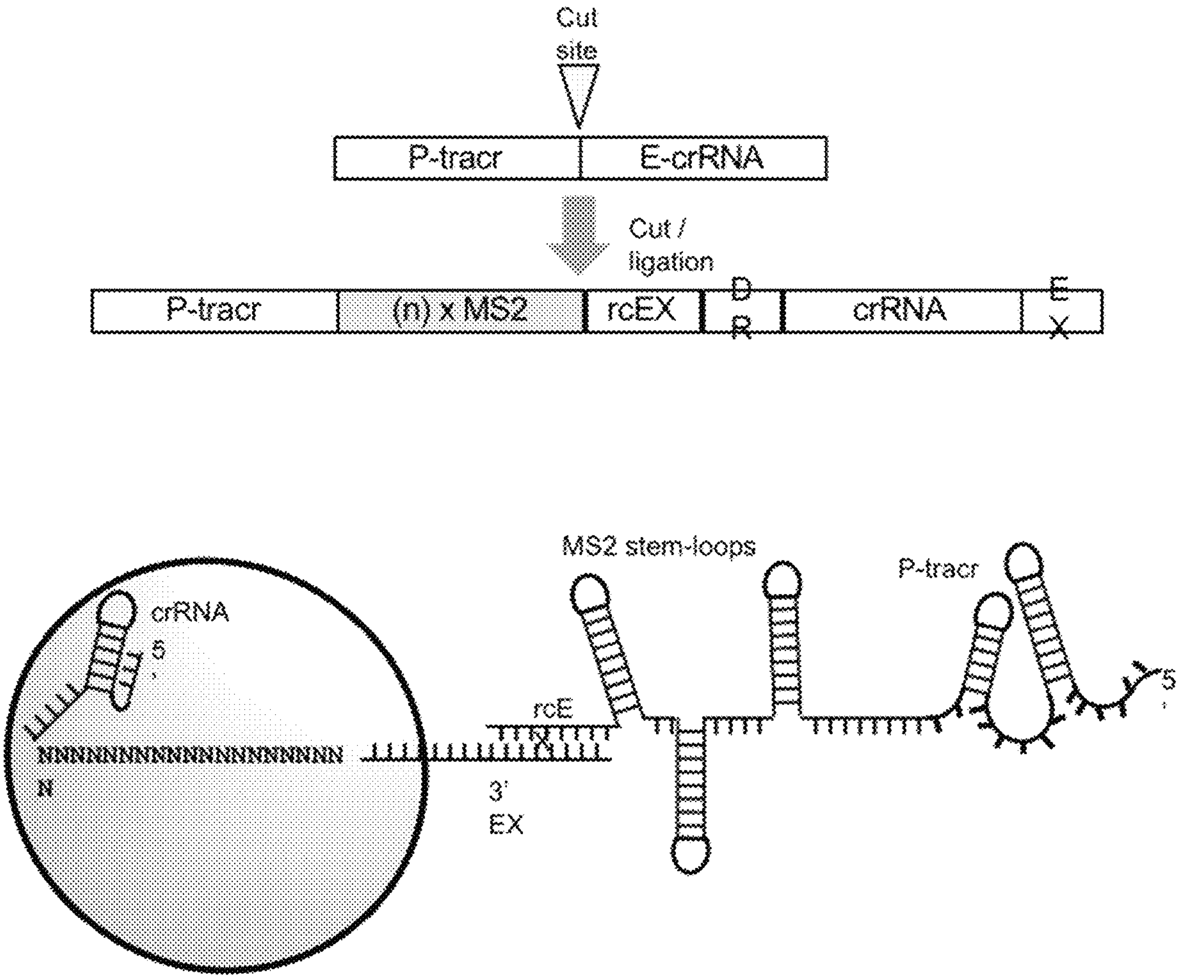
FIG. 11 (top) schematically depicts construction of the DNA encoding the functional RNA molecule by cleavage at an HphI restriction endonuclease cleavage site ("cut site") in or adjacent to a Lb Cas12a tracrRNA ("P-tracr") and before the LbCas12a crRNA with a 3' extension ("E-crRNA"), insertion of DNA encoding multiple copies of an MS2 aptamer ("(n)×MS2") as well as sequence for annealing ("rcEX") to the crRNA 3' extension ("EX"), and ligation to form the DNA encoding the functional RNA molecule, which can be complexed with the Cas12a nuclease to form the ribonucleoprotein depicted in FIG. 11 (bottom).

A ternary system is constructed containing a deactivated Cas12a nuclease, a guide RNA (a Cas12a crRNA having a 3' extension) targeting the promoter region of the maize (*Zea mays*) Lc gene, and a functional RNA molecule provided by integrating multiple copies of an MS2 aptamer and sequence for hybridizing to the crRNA 3' extension into a Cas12a tracr. FIG. 11 (top) schematically depicts construction of the DNA encoding the functional RNA molecule by cleavage at an HphI restriction endonuclease cleavage site (see Example 2 and Table 1) in or adjacent to a tracrRNA identified from the native Lachnospiraceae bacterium ND2006 CRISPR Cas12a locus (see Example 1), insertion of DNA encoding multiple copies of an MS2 aptamer as well as sequence for annealing to the crRNA 3' extension, and ligation to form the DNA encoding the functional RNA molecule, which can be complexed with the Cas12a nuclease to form the ribonucleoprotein depicted in FIG. 11 (bottom). A similar approach is useful for providing functional RNA molecules including a Cas12a tracrRNA and a functional RNA moiety, wherein the functional RNA moiety is one or more RNAs selected from the group consisting of (a) an RNA sequence for annealing to a donor polynucleotide; (b) an RNA sequence for annealing to the crRNA 3' extension; (c) a terminator sequence; (d) an RNA aptamer; (e) a ribozyme; (f) a detectable label; (g) a bar-coding sequence and (h) an RNA sequence forming at least partially double-stranded RNA, for example, RNA forming at least partially double-stranded RNA capable of silencing a gene (e.g., RNA that forms one or more stem-loops where the stem includes double-stranded RNA of at least about 18 base-pairs designed to silence a target gene, or RNA that has the secondary structure of a microRNA precursor and is processed to a mature microRNA designed to silence a target gene). For example, similar approaches are used for providing a functional RNA molecule that includes aptamers engineered to target endogenous proteins, such as transcriptional cofactors.

The DNA encoding the predicted tracrRNA identified from the native Lachnospiraceae bacterium ND2006 CRISPR Cas12a locus has the sequence (SEQ ID NO: 9)

AATTGCAAATCTTTGAAATAATGCAGACTTAAATTTATAAATTCATGGAA

TAAGGTGATTTTATTGTGAAAAAATACTCGTATTTTGTTGGAAAAACATC

TTTTTGTTGTATAATATGATGATATACGG, where the tracrRNA nucleotides are shown in underlined font, the HphI recognition and binding site located within the tracrRNA is shown in bold font, and nucleotides of the native sequence located between the 3' end of the predicted tracrRNA and the 5' end of the CRISPR array are shown in plain font. The DNA encoding the MS2 aptamer stem-loops has the sequence (SEQ ID NO: 10)

GTTTTAGAGCTAGGCCAACATGAGGATCACCCATGTCTGCAGGGCCTAGC

AAGTTAAAATAAGGCTAGTCCGTTATCAACTTGGCCAACATGAGGATCAC

CCATGTCTGCAGGGCCAAGTGGCACCGAGTCGGTGCTTTTT.

The deactivated LbCas12a nuclease is encoded by DNA having the sequence of SEQ ID NO:11, which is a D832A mutant of the wild-type Cas12a nuclease having NCBI reference sequence WP_051666128.1 (see www[dot]ncbi[dot]nlm[dot]nih[dot]gov/protein/WP_051666128.1/). In embodiments, the deactivated LbCas12a nuclease optionally includes additional modifications, for example, one or more copies of a nuclear localization signal (NLS), or an affinity tag for later purification of the nuclease, with, if needed, sequences permitting cleavage and removal of the affinity tag. The DNA encoding the Cas12a crRNA with the 3' extension has the sequence (SEQ ID NO: 12)

GTTTCAAAGATTAAATAATTTCTACTAAGTGTAGAT

TGGACAGAGCTCCAAGTGACCAAAACCGTATATCAT, where the direct repeat is shown in underlined font, the spacer targeting the promoter region of the maize (*Zea mays*) B104 Lc gene is shown in bold font, and the 3' extension is shown in plain font. The DNA targeted for editing is the maize (*Zea mays*) Lc gene, specifically the Zm-Lc promoter region having the sequence (SEQ ID NO: 13)

ATAGAGAGAGAAGAGGGGTCGTGTAGTAGTGCTTAAACTGTACATGAACA

GCAGTAGTGTTACAGAAGCTAAACTCAACCAGAGCTCCACCAAAGACAAA

GAGGGTCTACTTCCATCACCGTCTTGCTCGGTCACTTGGAGCTCTGTCCA

TAAATTAAACCCATCGTGGCATATCTGTAGGCATCTACCCCGTCTTCGTC

GTCCGTTCCTCACTAGCTACCAAGAGGTCGCCATTATTGCCAACATAGAG

TGTACGTGGATGTCTATATATATGCCTACTTGCACCCATATGGCATAGGC

GTTCGATCCCCTTAGCGCGGAGGAGAGCTCCTCCGGTTCTTCTCTACCCT

TCGCATGGAAGTTCTTGCATTGCTTCGTTGCTTCTCTAGTTTCTTCCTTC

TACGTCTTTCCAGCATACGCATGCCCCTCGTCCGCCGGTTCACGAGGCAT

CGTCTGATGATCAGTAGATAATAAGCAATATAATACTGATCTAGAATCGA

GTTGTTGTACTCTTCGCAGATAGGTTCGTTCCTTCACATAGAAGCGAGTA

CAGACTACAGACCACACAGTATCAGCTGGCACGAAACGAAAATGGTTACT

TGCAAATTGCATGCACGAGCTAGAATTATATTCTTCTAATCTTCTTCGTT

GACTTTCTGGCTTCAGCAGGCGCGTGAT, wherein the target sequence that corresponds to the Cas12a crRNA spacer sequence is indicated by bold, underlined font.

The DNA encoding the Lachnospiraceae bacterium ND2006 Cas12a tracrRNA sequence (SEQ ID NO:9) contained within a plasmid vector is cleaved with Hph1 or by another compatible restriction endonuclease (see Table 1, Example 2) and the DNA encoding the MS2 RNA-binding stem-loops (SEQ ID NO:10) is inserted by ligation to provide DNA encoding the functional RNA molecule (FIG. 11, top); alternatively, the DNA encoding the MS2 RNA-binding stem-loops (SEQ ID NO:10) is inserted into the DNA encoding the Cas12a tracrRNA through another molecular cloning method. This functional RNA molecule is transcribed in vitro and purified. A Cas12a crRNA (SEQ ID NO:12) containing a 3' extension of 10 ribonucleotides complementary to the 3' sequence of the Cas12a tracrRNA is similarly transcribed and purified. The two RNA molecules are mixed with deactivated LbCas12a nuclease (SEQ ID NO:11) in 10:1 molar excess in 50 millimolar HEPES buffer (300 millimolar NaCl, 1 millimolar MgCl2) at room temperature for 20 minutes to provide the ternary ribonucleoprotein for use in modifying the Lc promoter. Ternary RNPs are delivered to maize B104 protoplasts using PEG-mediated transformation. An MS2-tagged transcriptional regulator is co-transfected for multi-copy recruitment to the targeted locus, which is predicted to result in a change in expression of the maize Lc gene. An example of a suitable MS2-tagged transcriptional regulator sequence is an MS2-P65-HSF1 fusion of multiple transcriptional activators (P65 and HSF1) having the sequence of SEQ ID NO:14, which includes an MS2 region (nucleotides 1-390), a nuclear localization signal (NLS) (nucleotides 445-465), a PG5 region (nucleotides 481-1023), and an HSF1 region (nucleotides 1047-1419). In an alternative embodiment, the viral protein-derived transcriptional activator, VP64, with the sequence of SEQ ID NO:15, can be similarly tagged with the MS2 sequence and used to activate transcription of the maize Lc gene.

Example 5

This example illustrates non-limiting embodiments of DNA expression systems that include DNA sequence for a first promoter; and, operably linked and heterologous to the first promoter, a DNA sequence encoding either: (1) a first RNA molecule comprising a Cas12a tracrRNA and comprising a restriction endonuclease cleavage site that is suitable for insertion of a sequence coding for a functional RNA moiety, or (2) a functional RNA molecule comprising a Cas12a tracrRNA and a functional RNA moiety.

In an embodiment, the DNA expression system includes: (a) DNA sequence for a first promoter; and, operably linked and heterologous to the first promoter; (b) a DNA sequence encoding a first RNA molecule comprising a Cas12a tracrRNA and comprising a restriction endonuclease cleavage site that is suitable for insertion of a sequence coding for a functional RNA moiety; and (c) optionally, a terminator. In embodiments, the DNA expression system further comprises: (d) optionally, a DNA sequence for a second promoter; (e) operably linked and heterologous to the first promoter or the second promoter, a DNA encoding a Cas12a crRNA that comprises a 3' extension capable of hybridizing with a segment of the first RNA molecule; and (f) optionally, a terminator. In embodiments of such a DNA expression system, the Cas12a crRNA is capable of complexing with a Cas12a nuclease to form a Cas12a ribonucleoprotein complex. The DNA sequence encoding the first promoter and/or the optional second promoter and or the optional terminator(s) is selected according to the biological system of interest (e.g., for expression in a bacterial cell, a yeast cell, an animal cell, or a plant cell). Non-limiting examples of promoters useful in such DNA expression systems include Pol II promoters and Pol III promoters. Non-limiting examples of promoters useful in the DNA expression systems and engineered systems of this disclosure include promoters functional in prokaryotic cells (e.g., useful for in vitro transcription), such as, but not limited to, promoters from T7 bacteriophage (T7), T7 bacteriophage plus lac operators (T7lac), Sp6 bacteriophage (Sp6, used with SP6 RNA polymerase), arabinose metabolic operon (araBAD), *E. coli* tryptophan operator (trp), lac operon (lac), bacteriophage lambda (pL), and a hybrid promoter of lac and trp (Ptac). Non-limiting examples of promoters useful especially in animal cells include promoters from β-actin (ACTB), cytomegalovirus (CMV), elongation factor-1α, (EF1α), phosphoglycerate kinase (PGK1), ubiquitin C (UbC), herpes simplex virus thymidine kinase (HSV-1 TK), early and late simian vacuolating virus 40 (SV40), long terminal repeats (LTRs) from retrovirus, mouse metallothionein-I, *Drosophila* actin 5c, baculovirus polyhedron, yeast transcription elongation factor (TEF1), alcohol dehydrogenase I (ADH1), glyceraldehyde 3-phosphate dehydrogenase (GAPDH), human polymerase III RNA promoter (H1), human U6 small nuclear promoter (U6), an inducible tetracycline response element promoter, and a CAG hybrid (containing a CMV enhancer, chicken beta actin promoter, and rabbit beta-globin splice acceptor); many other promoters useful in animals, including in humans (e.g., for gene therapeutic applications) are available in the art, see, e.g., Zheng and Baum (2008) *Methods Mol. Biol.,* 434:205-219 (available at doi:10.1007/978-1-60327-248-3_13). Non-limiting examples of promoters useful in such DNA expression systems especially in plant cells include a nopaline synthase (Nos) promoter and a ubiquitin promoter; specific examples include a promoter selected from the group consisting of a TaU3 promoter (SEQ ID NO:16), a Nos promoter (SEQ ID NO:17), a ZmUBI1 promoter (SEQ ID NO:18), and a S1UBI10 promoter (SEQ ID NO:19). Further non-limiting examples of promoters especially useful in plant cells include SEQ ID NOs:20-71; see Table 3. Specific embodiments include a DNA expression system wherein the first promoter has a DNA sequence selected from the group consisting of SEQ ID NOs:16-71, and the Cas12a tracrRNA has the sequence of SEQ ID NOs:1, 3, 6, 139-146, and 149-169. Specific embodiments include a DNA expression system having the optional second promoter, wherein the second promoter has a DNA sequence selected from the group consisting of SEQ ID NOs:16-71. In embodiments, the first promoter and optional second promoter have different sequences; in other embodiments, the first promoter and optional second promoter have identical sequences. In embodiments, the Cas12a crRNA is capable of complexing with a Cas12a nuclease to form a Cas12a ribonucleoprotein complex; in embodiments, the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

In embodiments, the DNA expression system includes: (a) DNA sequence for a first promoter wherein the first promoter has a DNA sequence selected from the group consisting of SEQ ID NOs:16-71; and, operably linked and heterologous to the first promoter; (b) a DNA sequence encoding a first RNA molecule comprising a Cas12a tracrRNA, wherein the Cas12a tracrRNA has a sequence that is selected from SEQ ID NOs:1, 3, 6, 139-146, and 149-169, and that comprises a restriction endonuclease cleavage site that is suitable for insertion of a sequence coding for a functional RNA moiety; and (c) optionally, a terminator, preferably a terminator functional in a eukaryotic cell; in embodiments, the DNA expression system further comprises: (d) optionally, a DNA sequence for a second promoter, e.g., a promoter having a DNA sequence selected from the group consisting of SEQ ID NOs:16-71; (e) operably linked and heterologous to the first promoter or the second promoter, a DNA encoding a Cas12a crRNA that comprises a 3' extension capable of hybridizing with a segment of the first RNA molecule and that is capable of complexing with a Cas12a nuclease to form a Cas12a ribonucleoprotein complex, wherein the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A; and (f) optionally, a terminator.

In another embodiment, the DNA expression system includes: (a) DNA sequence for a first promoter; and, operably linked and heterologous to the first promoter, (b) a DNA sequence encoding a functional RNA molecule comprising a Cas12a tracrRNA and a functional RNA moiety. In embodiments, the DNA expression system further comprises: (c) optionally, a DNA sequence for a second promoter; (d) operably linked and heterologous to the first promoter or the second promoter, a DNA encoding a Cas12a crRNA that comprises a 3' extension capable of hybridizing with a segment of the functional RNA molecule; and (e) optionally, a terminator. In embodiments of such a DNA expression system, the Cas12a crRNA is capable of complexing with a Cas12a nuclease to form a Cas12a ribonucleoprotein complex. The DNA sequence encoding the first promoter is selected according to the biological system of interest (e.g., for expression in a bacterial cell, a yeast cell, an animal cell, or a plant cell). Non-limiting examples of promoters useful in such DNA expression systems include a nopaline synthase (Nos) promoter and a ubiquitin promoter; specific examples include a promoter selected from the group consisting of a TaU3 promoter (SEQ ID NO:16), a Nos promoter (SEQ ID NO:17), a ZmUBI1 promoter (SEQ ID NO:18), and a S1UBI10 promoter (SEQ ID NO:19). Specific embodiments include a DNA expression system wherein the first promoter has a DNA sequence selected from the group consisting of SEQ ID NOs:16-71, and the functional RNA molecule includes a Cas12a tracrRNA that has the sequence of SEQ ID NO:3. Specific embodiments include a DNA expression system wherein the Cas12a crRNA is capable of complexing with a Cas12a nuclease to form a Cas12a ribonucleoprotein complex, wherein the first promoter has a DNA sequence selected from the group consisting of SEQ ID NOs:16-71 and wherein the Cas12a nuclease is (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A; in some embodiments of such DNA expression systems, the Cas12a tracrRNA has the sequence of SEQ ID NOs:1, 3, 6, 139-146, and 149-169.

Embodiments of these various DNA expression systems further include additional expression elements, e.g., expression enhancing elements ("enhancers"), 3' untranslated region elements such as terminators or polyadenylation elements, and introns. The DNA sequences encoding the first promoter, optional second promoter, optional terminator, and any other expression element are generally selected according to the biological system of interest (e.g., for expression in a bacterial cell, a yeast cell, an animal cell, or a plant cell). Terminators useful in DNA expression systems and engineered systems of this disclosure include terminators having a sequence selected from the group consisting of SEQ ID NOs:72-100. Other expression elements useful in DNA expression systems and engineered systems of this disclosure include expression elements having a sequence selected from the group consisting of SEQ ID NOs:101-106.

Promoters useful in plant cells include promoters especially suited to monocot plants and promoters especially suited to dicot plants. Non-limiting examples of these various expression elements are provided in Table 3 and are useful for heterologous expression of Cas12a tracrRNAs, such as a tracrRNA having an RNA sequence selected from SEQ ID NOs:1, 3, 6, 139-146, and 149-169 or the Cas12a tracrRNA sequences disclosed in U.S. Pat. No. 9,790,490 (incorporated herein by reference).

TABLE 3

| Designation | Source | Source ID | Application | Type | SEQ ID NO: |
|---|---|---|---|---|---|
| prAtUbi10 | Arabidopsis thaliana | AT4G05320.2 | Pol II promoter | dicot | 20 |
| prGmUBI8 | Glycine max | Glyma10g051100 | Pol II promoter | dicot | 21 |
| prGmUBI1 | Glycine max | Glyma10g251900 | Pol II promoter | dicot | 22 |
| prGmUBI9 | Glycine max | G1yma13g138600 | Pol II promoter | dicot | 23 |
| prGmUBI4 | Glycine max | Glyma13g176100 | Pol II promoter | dicot | 24 |
| prGmUBI7 | Glycine max | Glyma17g042100 | Pol II promoter | dicot | 25 |
| enTCUP2 | tobacco | JX155386.1 | Pol II promoter | dicot | 26 |
| prSlUbi10 | Solanum lycopersicum | LOC101258282 | Pol II promoter | dicot | 27 |
| prWpUbi10 | White pear | LOC103948134 | Pol II promoter | dicot | 28 |
| prBvUbi10 | Sugar beet | LOC104907074 | Pol II promoter | dicot | 29 |
| prRsUbi10 | Radish | LOC108826774 | Pol II promoter | dicot | 30 |
| prIlUbi10 | Japanese morning glory | LOC109190585 | Pol II promoter | dicot | 31 |
| prCuUbi10 | Cucurbita | LOC111802502 | Pol II promoter | dicot | 32 |
| prHaUBI | Helianthus annuus | OTG28215 | Pol II promoter | dicot | 33 |
| prLAT52 | tomato | X15855 | Pol II promoter | dicot | 34 |
| prHaUbi1 | Helianthus annuus | X57005.1 | Pol II promoter | dicot | 35 |
| prPcUbi4 | Parsley | X64345.1 | Pol II promoter | dicot | 36 |
| SlU6-2 | tomato | | Pol III promoter | dicot | 37 |
| MtU6.6 | Medicago truncatula | | Pol III promoter | dicot | 38 |
| GmU6-9.1 | Glycine max | | Pol III promoter | dicot | 39 |
| AtU6 | Arabidopsis thaliana | | Pol III promoter | dicot | 40 |
| GmU6-10 | Glycine max | | Pol III promoter | dicot | 41 |
| TC-AtU6 | Arabidopsis thaliana | | Pol III promoter | dicot | 42 |
| At7SL | Arabidopsis thaliana | | Pol III promoter | dicot | 43 |
| ZmKN1 | Zea mays | AY312169.1 | Pol II promoter | monocot | 44 |
| prOsACT-B | Oryza sativa | CP018159 | Pol II promoter | monocot | 45 |
| prOsACT-A | Oryza sativa | EU155408.1 | Pol II promoter | monocot | 46 |
| PvUBI1 | Panicum virgatum | HM209467.1 | Pol II promoter | monocot | 47 |
| prOsUbi2 | Oryza sativa | LOC_Os02g06640 | Pol II promoter | monocot | 48 |
| prOsUbi1 | Oryza sativa | LOC_Os06g46770 | Pol II promoter | monocot | 49 |
| prAtaUbi1 | Aegilops tauschii | LOC109747268 | Pol II promoter | monocot | 50 |
| prPhUbi1 | Panicum hallii | LOC112888620 | Pol II promoter | monocot | 51 |
| prZmADP1 | Zea mays | LOC542430 | Pol II promoter | monocot | 52 |
| prZmEF1alpha | Zea mays | LOC542581 | Pol II promoter | monocot | 53 |
| prZmADP2 | Zea mays | LOC542584 | Pol II promoter | monocot | 54 |
| prZmUBI1 | Zea mays | S94464 | Pol II promoter | monocot | 55 |
| prLPT2-A | Hordeum vulgare | X69793 | Pol II promoter | monocot | 56 |
| prLPT2-B | Hordeum vulgare | X69793 | Pol II promoter | monocot | 57 |
| prZm1Fluory2 | Zea mays | ZEAMMB73_Zm00001 d049243 | Pol II promoter | monocot | 58 |
| pZMU6-C1_Short | Zea mays | maize | Pol III promoter | monocot | 59 |
| pOsU6.1 | Oryza sativa | rice | Pol III promoter | monocot | 60 |
| pOsU6.2 | Oryza sativa | rice | Pol III promoter | monocot | 61 |
| pOsU6.1_short | Oryza sativa | rice | Pol III promoter | monocot | 62 |
| pOsU6.2_short | Oryza sativa | rice | Pol III promoter | monocot | 63 |
| OsU6 | Oryza sativa | | Pol III promoter | monocot | 64 |
| TaU3 | wheat | | Pol III promoter | monocot | 65 |
| prM24 | Mirabilis mosaic virus | AF454635.1 | Pol II promoter | dicot or monocot | 66 |
| pr35S | Cauliflower mosaic virus | V00140.1 | Pol II promoter | dicot or monocot | 67 |
| prFMV | figwort mosaic virus | X06166.1 | Pol II promoter | dicot or monocot | 68 |
| prFMV 34S-1/2x | figwort mosaic virus | X16673.1 | Pol II promoter | dicot or monocot | 69 |
| prNOS | Agrobacterium | | Pol II promoter | dicot or monocot | 70 |
| prOCS | Agrobacterium | | Pol II promoter | dicot or monocot | 71 |
| tAtUbi10 | Arabidopsis thaliana | AT4G05320.2 | Pol II terminator | dicot | 72 |
| tAtADH thaliana | Arabidopsis | AY536888 | Pol II terminator | dicot | 73 |

TABLE 3-continued

| Designation | Source | Source ID | Application | Type | SEQ ID NO: |
|---|---|---|---|---|---|
| tNtExt | Nicotiana tabacum | D13951 | Pol II terminator | dicot | 74 |
| tHSP 18.2 | Arabidopsis thaliana | GeneID:836093 | Pol II terminator | dicot | 75 |
| tGmUbil | Glycine max | Glyma10g251900 | Pol II terminator | dicot | 76 |
| tSlUbi10 | Solanum lycopersicum | LOC101258282 | Pol II terminator | dicot | 77 |
| tWpUbi10 | White pear | LOC103948134 | Pol II terminator | dicot | 78 |
| tBvUbi10 | Sugar beet | LOC104907074 | Pol II terminator | dicot | 79 |
| tRsUbi10 | Radish | LOC108826774 | Pol II terminator | dicot | 80 |
| tIlUbi10 | Japanese morning glory | LOC109190585 | Pol II terminator | dicot | 81 |
| tCuUbi10 | Cucurbita | LOC111802502 | Pol II terminator | dicot | 82 |
| tHaUBI | Helianthus annuus | OTG28215 | Pol II terminator | dicot | 83 |
| tpea E9 | Pisum sativum | X00806 | Pol II terminator | dicot | 84 |
| tpea 3A | Pisum sativum | X04333.1 | Pol II terminator | dicot | 85 |
| tHaUbi1 | Helianthus annuus | X57005.1 | Pol II terminator | dicot | 86 |
| tZmKN1 | Zea mays | AY312169.1 | Pol II terminator | monocot | 87 |
| tOsAct1 | Oryza sativa | CP018159 | Pol II terminator | monocot | 88 |
| tOsUbi2 | Oryza sativa | LOC_Os02g06640 | Pol II terminator | monocot | 89 |
| tOsUbi1 | Oryza sativa | LOC_Os06g46770 | Pol II terminator | monocot | 90 |
| tAtaUbil | Aegilops tauschii | LOC109747268 | Pol II terminator | monocot | 91 |
| tPhUbil | Panicum hallii | LOC112888620 | Pol II terminator | monocot | 92 |
| tZmADP1 | Zea mays | LOC542430 | Pol II terminator | monocot | 93 |
| tZmEF1alpha | Zea mays | LOC542581 | Pol II terminator | monocot | 94 |
| tZmADP2 | Zea mays | LOC542584 | Pol II terminator | monocot | 95 |
| tZmUbi1 | Zea mays | S94464 | Pol II terminator | monocot | 96 |
| tLPT2 | Hordeum vulgare | X69793 | Pol II terminator | monocot | 97 |
| tZmFluory2 | Zea mays | ZEAMMB73_Zm00001 d049243 | Pol II terminator | monocot | 98 |
| t35S | Cauliflower mosaic virus | V00140.1 | Pol II terminator | dicot or monocot | 99 |
| tNOS | Agrobacterium | | Pol II terminator | dicot or monocot | 100 |
| TMV translational enhancer | tobacco mosaic virus | | enhancer | dicot | 101 |
| FMV 34S double enhancer | figwort mosaic virus | | enhancer | dicot or monocot | 102 |
| FMV34S/CaM V35S enhancer | figwort and cauliflower mosaic virus/synthetic | | enhancer | dicot or monocot | 103 |
| iGmIDH1 | Glycine max | Gene ID: 606295 | intron | dicot | 104 |
| iZmPEPC | Zea mays | LOC542372 | intron | monocot | 105 |
| MALAT1 | mouse | | 3' end (triple helix) | dicot or monocot | 106 |

Example 6

This example illustrates non-limiting embodiments of Cas2a nucleases and their corresponding tracrRNA sequences. Table 4 provides the protein sequences of several Cas2a nucleases and the RNA sequence of each nuclease's associated tracrRNA. Table 4 further identifies for each tracrRNA one or more native restriction endonuclease cleavage sites that are suitable, e.g., for insertion of a sequence coding for a functional RNA moiety.

TABLE 4

| Species | Protein Accession Number | Protein SEQ ID NO: | tracrRNA SEQ ID NO: | Restriction sites within DNA between tracrRNA and CRISPR array | Restriction sites within DNA encoding the tracrRNA | Putative PAM |
|---|---|---|---|---|---|---|
| Uncultured *Clostridium* sp. isolate 2789STDY5608795 | SCH45297.1 | 107 | 139 | SgeI, HpyCH4III, MfeI, SspI | DraI | 5' TTTV |
| Uncultured bacterium (gcode 4) | EKE28449.1 | 108 | 140 | AvrII | HphI, HpyAV, | 5' TTTV |

TABLE 4-continued

| Species | Protein Accession Number | Protein SEQ ID NO: | tracrRNA SEQ ID NO: | Restriction sites within DNA between tracrRNA and CRISPR array | Restriction sites within DNA encoding the tracrRNA | Putative PAM |
|---|---|---|---|---|---|---|
| ACD_3C00058, whole genome shotgun sequence | | | | | | |
| *Thiomicrospira* sp. XS5 ZB100000 | WP_068647 445.1 | 109 | 141 | AjuI, BceAI, HpyCH4III | BseMII, BspHI | 5' TTTV |
| *Flavobacterium bmnchiophilum* FL-15 | WP_014085 038.1 | 110 | 142 | BtsI, TspRI, FspEI | HindIII, DraI | 5' TTTV |
| *Moraxella bovoculi* strain 57922 | AKG14689.1 | 111 | 143 | BslI | DraI, ApoI | 5' TTV |
| *Candidatus Roizmanbacteria* bacterium GW2011_GWA2_37_7 US54_C0016 | KKQ38174.1 | 112 | 144 | DdeI, HgaI, Hpy188I, DrdI, | BbsI, MboII | 5' TTTV |
| *Pseudobutyrivibrio xylanivorans* | SCZ76797.1 | 113 | 145 | TspRI, FspEI | TspDTI, SmoI, BsuI, BpuEI | 5' TTTV |
| *Prevotella bryantii* B14 | SER03894.1 | 114 | 146 | TatI, SeaI | EcoRV, PsiI, | 5' TTTV |
| *Smithella* sp. SCADC | KFO67988.1 | 115 | 147 | PspGI, BstNI, | HhaI | 5' TTTV |
| *Smithella* sp. SCADC | KFO67988.1 | 115 | 148 | EcoRII | CfoI | 5' TTTV |
| Bacteroidetes bacterium GWF2_33_38 | OFY19591.1 | 116 | 149 | CviQI | DraI | 5' TTTV |
| *Candidatus Peribacteria* bacterium RIFCSPLOWO2 | OGJ66851.1 | 117 | 150 | AlwNI, EarI, AcuI | EcoRV, NdeI | 5' TTTV |
| *Nitrospinae* bacterium RIFCSPLOWO2 | OGW03971. 1 | 118 | 151 | BstAPI, BsmAI | HaeII | 5' TTTV |
| *Candidatus Ryanbacteria* bacterium RIFCSPHIGHO2 | OGZ45678.1 | 119 | 152 | BccI, MmeI, Hpy188I | FauI, HpyAV, BseNI | 5' TTTV |
| *Candidatus Wildermuthbacteria* bacterium RIFCSPHIGHO2 | OHA63117.1 | 120 | 153 | MmeI, BglII, Hpy188I | PsiI, Eco57I, | 5' TTTV |
| *Firmicutes* bacterium CAG_194_44_15 | OLA30477.1 | 121 | 154 | BsgI | MaeII | 5' TTTV |
| *Candidatus Gottesmanbacteria* bacterium CG1_02_37_22 | OIO15737.1 | 122 | 155 | FauI, BbvI | PsiI, SspI, BfrI | 5' TTTV |
| *Candidatus Gracilibacteria* bacterium CG1_02_38_174 | OIO75780.1 | 123 | 156 | BaeI | BseMII, BbsI | 5' TTTV |
| *Butyrivibrio fibrisolvens* MD2001 | WP_027216 152.1 | 124 | 157 | BceAI | PsiI, HphI | 5' TTTV |
| *Sneathia amnii* strain SN35 | WP_084710 347.1 | 125 | 158 | BccI, BspPI | SspI, DraI | 5' TTTV |
| *Coprococcus eutactus* strain 2789STDY5608843 | WP_082431 329.1 | 126 | 159 | PsiI, ApaLI | TspDTI, MaeIII | 5' TTTV |
| *Lachnospira pectinoschiza* strain 2789STDY5834886 | WP_055306 762.1 | 127 | 160 | MseI | BccI, SspI, DraI | 5' TTTV |
| Bacteroidetes oral taxon 274 str. F0058 | WP_009217 842.1 | 128 | 161 | BsrGI, AseI, BsrDI | TspDTI, ApoI | 5' TTN |
| *Arcobacter butzleri* L348 isolate CHRB125 | WP_052943 011.1 | 129 | 162 | MseI | SspI, HindIII | 5' TTTV |
| *Bacteroidales* bacterium KA00251 | WP_066040 075.1 | 130 | 163 | BccI, BstXI | EarI | 5' TTTV |
| *Acidaminococcus massiliensis* strain Marseille-P2828 | WP_075579 848.1 | 131 | 164 | BccI, Bpu10I | PleI, MlyI | 5' TTTV |
| *Helcococcus kunzii* | WP_005398 606.1 | 132 | 165 | AfeI | EcoRV, NsiI, BsrDI | 5'-YYN |

TABLE 4-continued

| Species | Protein Accession Number | Protein SEQ ID NO: | tracrRNA SEQ ID NO: | Restriction sites within DNA between tracrRNA and CRISPR array | Restriction sites within DNA encoding the tracrRNA | Putative PAM |
|---|---|---|---|---|---|---|
| *Agathobacter rectalis* strain 2789STDY5834884 | CUO57667.1 | 133 | 166 | ApoI | PsiI | 5'TTN |
| *Acidaminococcus* sp. BV3L6 | WP_021736 722.1 | 134 | 167 | KasI, NdeI | MmeI, Bpu10I, BspMI | 5' TTTV |
| *Lachnospiraceae* bacterium ND2006 | WP_051666 128.1 | 135 | 168 | MmeI, HphI | PsiI, AanI | 5' TTTV |
| *Francisella tularensis* subsp. novicida U112 | ABK90267.1 | 136 | 169 | | DraI | 5' TTTV |
| *Omnitrophica* WOR_2 bacterium GWF2_38_59 | OGX23684.1 | 137 | 170 | ApoI | LweI | 5' TTTV |
| *Candidatus Roizmanbacteria* bacterium GW2011_GWA2_37_7 US54_C0016 | KKQ38176.1 | 138 | 171 | CseI | BbsI | 5' TTTV |

Various DNA expression systems disclosed herein are useful for the expression of these Cas 12a tracrRNA sequences. Embodiments include a DNA expression system including (a) DNA sequence for a first promoter; and (b) operably linked and heterologous to the first promoter a DNA sequence encoding a first RNA molecule including a Cas 12a tracrRNA and including a restriction endonuclease cleavage site (native or engineered) that is suitable for insertion of a sequence coding for a functional RNA moiety. The functional RNA moiety is characterized by one or more functions. Embodiments of the RNA moiety include RNA sequences for annealing to one or more polynucleotides, RNA sequences that provide structures for binding to other molecules (including proteins or small molecule ligands) or that are catalytically active, or RNA sequences that serve as directly or indirectly detectable labels. Thus, non-limiting embodiments include a DNA expression system including (a) DNA sequence for a first promoter; and (b) operably linked and heterologous to the first promoter a DNA sequence encoding a first RNA molecule including a Cas12a tracrRNA and including a restriction endonuclease cleavage site (native or engineered) that is suitable for insertion of a sequence coding for a functional RNA moiety, wherein the Cas112a tracrRNA has an RNA sequence selected from SEQ ID NOs:1, 3, 6, 139-146, and 149-169; in some embodiments, the first promoter includes a DNA sequence selected from SEQ ID NOs:16-71. In other embodiments, the Cas112a tracrRNA is selected from the Cas12a tracrRNA sequences disclosed in U.S. Pat. No. 9,790,490 (incorporated herein by reference).

In other embodiments, the DNA expression system includes: (a) DNA sequence for a first promoter; (b) operably linked and heterologous to the first promoter a DNA sequence encoding a first RNA molecule including a Cas12a tracrRNA and including a restriction endonuclease cleavage site (native or engineered) that is suitable for insertion of a sequence coding for a functional RNA moiety; (c) optionally, a DNA sequence for a second promoter; (d) operably linked and heterologous to the first promoter or the second promoter, a DNA encoding a Cas12a crRNA that includes a 3' extension capable of hybridizing with a segment of the first RNA molecule; and (e) optionally, a terminator. In non-limiting embodiments, the Cas12a tracrRNA has an RNA sequence selected from the group consisting of SEQ ID NOs:1, 3, 6, 139-146, and 149-169; in some embodiments, the first promoter includes a DNA sequence selected from the group consisting of SEQ ID NOs:16-71; in some embodiments, the optional second promoter includes a DNA sequence selected from the group consisting of SEQ ID NOs:16-71; in some embodiments, the optional terminator includes a DNA sequence selected from the group consisting of SEQ ID NOs:72-100. In embodiments, the first promoter and the DNA encoding the first RNA molecule, and the DNA encoding a Cas12a crRNA that includes a 3' extension are contained in a single construct, and in other embodiments, the first promoter and the DNA encoding the first RNA molecule are contained in a first construct, and the second promoter and the DNA encoding a Cas12a crRNA that includes a 3' extension are contained in a second construct. Where the DNA expression system is provided in a first construct and a second construct, these can be provided in a single vector or in separate vectors. In some embodiments wherein the DNA expression system includes DNA encoding a Cas12a crRNA, the first promoter drives expression of both the DNA encoding the first RNA molecule and the DNA encoding the Cas12a crRNA. In some embodiments, the Cas12a tracrRNA further includes a 5' extension. In many embodiments of the DNA expression system, the Cas12a crRNA is capable of complexing with a Cas12a nuclease to form a Cas12a ribonucleoprotein complex.

Further embodiments of this disclosure include a DNA expression system including: (a) DNA sequence for a first promoter; and (b) operably linked and heterologous to the first promoter, a DNA sequence encoding a functional RNA molecule including a Cas12a tracrRNA and a functional RNA moiety. The functional RNA moiety is characterized by one or more functions. Embodiments of the RNA moiety include RNA sequences for annealing to one or more polynucleotides, RNA sequences that provide structures for binding to other molecules (including proteins or small molecule ligands) or that are catalytically active, or RNA sequences that serve as directly or indirectly detectable labels. In embodiments, the DNA expression system further includes: (c) optionally, a DNA sequence for a second promoter; (d) operably linked and heterologous to the first promoter or the second promoter, a DNA encoding a Cas12a crRNA that includes a 3' extension capable of hybridizing with a segment of the functional RNA molecule; and (e) optionally, a terminator. In embodiments, the functional RNA molecule includes a Cas12a tracrRNA having an RNA sequence selected from the group consisting of SEQ ID NOs:1, 3, 6, 139-146, and 149-169; in some embodiments, the first promoter includes a DNA sequence selected from the group consisting of SEQ ID NOs:16-71; in some embodiments, the optional second promoter includes a DNA sequence selected from the group consisting of SEQ ID NOs:16-71; in some embodiments, the optional terminator includes a DNA sequence selected from the group consisting of SEQ ID NOs:72-100. In embodiments wherein the DNA expression system includes the DNA encoding the Cas12a crRNA, the DNA expression system can be provided in a single construct (e.g., where the first promoter drives expression of both the DNA encoding the functional RNA molecule and the DNA encoding the Cas12a crRNA). In embodiments wherein the DNA expression system includes the second promoter, the second promoter can be operably linked to the DNA encoding the crRNA (e.g., in a second construct). In embodiments where the DNA expression system is provided in two constructs, these can be in a single vector or in separate vectors. In embodiments, the Cas12a tracrRNA further includes a 5' extension. In many embodiments of the DNA expression system, the Cas12a crRNA is capable of complexing with a Cas12a nuclease to form a Cas12a ribonucleoprotein complex.

The various embodiments of the DNA expression systems disclosed herein are useful for expression of a Cas12a tracrRNA that is: (1) contained in a first RNA molecule including a Cas12a tracrRNA and including a restriction endonuclease cleavage site (native or engineered) that is suitable for insertion of a sequence coding for a functional RNA moiety, or (2) contained in a functional RNA molecule including a Cas12a tracrRNA and a functional RNA moiety. In embodiments, a Cas12a nuclease is associated or complexed with a Cas12a crRNA that is previously, simultaneously, or subsequently associated with, complexed with, or tethered to the Cas12a tracrRNA that is (1) contained in a first RNA molecule including a Cas12a tracrRNA and including a restriction endonuclease cleavage site (native or engineered) that is suitable for insertion of a sequence coding for a functional RNA moiety, or (2) contained in a functional RNA molecule including a Cas12a tracrRNA and a functional RNA moiety, thus forming a Cas12a ribonucleoprotein complex. In embodiments, the resulting Cas12a ribonucleoprotein complex contains (1) the Cas12a nuclease complexed with the first RNA molecule including a Cas12a tracrRNA and including a restriction endonuclease cleavage site (native or engineered) that is suitable for insertion of a sequence coding for a functional RNA moiety, or (2) the Cas12a nuclease complexed with the functional RNA molecule including a Cas12a tracrRNA and a functional RNA moiety. In embodiments, the Cas12a nuclease is one having a naturally occurring sequence (e.g., a native sequence of a Cas12a nuclease such as, but not limited to, LbCas12a, AsCas12a, FnCas12a, and an ObCsm1); in other embodiments, the Cas12a nuclease includes a modification, such as an amino acid sequence modification (e.g., the point-mutations provided in Table 5) and/or a chemical modification such as (a) a localization or signal peptide (e.g., a nuclear localization signal (NLS), a chloroplast or plastid transit peptide (CTP), or a mitochondrial targeting peptide (MTP)); (b) a detectable label (e.g., a fluorescent dye); (c) a cell-penetrating peptide; (d) an endosomal escape peptide; and (e) an affinity tag. In embodiments, the Cas12a nuclease is one selected from the Cas12a ("Cpf1") nucleases, Cpf1 orthologues, and Cpf1 variants (including the codon-optimized variants) disclosed in U.S. Pat. No. 9,790,490; the Cas12a ("Cpf1") nuclease sequences disclosed in U.S. Patent Application Publication 2018/0282713 (see, e.g., FIG. 3 and Example 5); and Cas12a ("Cpf1") nuclease sequences disclosed in U.S. Pat. No. 9,896,696; all of these cited patents and patent application publications are incorporated herein by reference. In specific embodiments, the Cas12a nuclease is a Cas12a ("Cpf1") nuclease identified from *Francisella novicida* U112 (FnCas12a or "FnCpf1"), from *Acidaminococcus* sp. BV3L6 (AsCas12a or "AsCpf1"), or from Lachnospiraceae bacterium ND2006 (LbCas12a or "LbCpf1"), or is an orthologue thereof, such as an orthologue having at least 50% sequence identity to FnCas12a ("FnCpf1"); see, e.g., the FnCpf1 nuclease contained in the FnCpf1 locus having SEQ ID NO:211 in U.S. Pat. No. 9,790,490, specifically incorporated herein by reference. In other specific embodiments, the Cas12a nuclease is a Cas12a nuclease having Cas12a nuclease activity and having at least 80%, at least 85%, at least 90%, or at least 95% sequence identity with a sequence selected from the group consisting of SEQ ID NOs:11, 107-114, 116-136, and 172. Table 5 provides non-limiting examples of Cas12a nucleases and sequence variants thereof that are useful with the DNA expression systems and engineered systems provided in this disclosure. Most of the point mutations (those not marked with an * or **) provided in Table 5 are designed to increase the efficiency or efficacy of gene editing by the nuclease (in comparison to the unaltered native nuclease). Increased efficiency or efficacy of gene editing includes but is not limited to: altered translation, folding, and/or stability of the Cas12a nuclease or ribonucleoprotein; altered affinity and/or specificity of target binding; altered Cas12a nuclease efficiency on target and/or non-target strands; altered PAM recognition specificity; and altered DNA repair or modification outcomes (e.g., indel rates). The Ca12a nuclease sequence variants include: (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A. The systems and compositions including a tracrRNA and methods of use thereof that are disclosed herein can also be employed with related Cas nucleases, including Csm nucleases, e.g., ObCsm1 (GenBank accession number OGX23684), SmCsm1 (GenBank accession number KFO67988), MiCsm1 (GenBank accession number KKQ38176), or SuCsm1 (GenBank accession number KM12007) (see, e.g., Begemann et al. (2017) bioRxiv, publicly available at dx[dot]doi[dot]org/10[dot]1101/192799), nucleases having a sequence selected from SEQ ID NOs:115, 137, 138, and 137, and variants thereof, such as a variant ObCsm1 that differs from a wild-type ObCsm1 sequence (SEQ ID NO: 137) in containing at least one point mutation selected from the group consisting of K382N, Q393K, S925A, E933N, K943F/Q, K972L, K1064G, P670I, N671I, D727A, E939A, and D1053A.

TABLE 5

| LbCpf1 (WP_051666128) (SEQ ID NO:135) | AsCpf1 (WP_021736722) (SEQ ID NO:134) | FnCpf1 (WP_003034647) (SEQ ID NO:172) | ObCsm1 (OGX23684) (SEQ ID NO: 137) |
|---|---|---|---|
| G309P | L320P | I339P | — |
| Y312F | wt | L342F | — |
| M474I | wt | wt | — |
| D523N | wt | wt | K382N |
| Q531K | wt | Q588K | Q393K |
| C930A | V980A | wt | S925A |
| D937N | Q987N | wt | E933N |
| V954F/Q | T1004F/Q | F1017Q | K943F/Q |
| M975L | wt | wt | K972L |
| A984E | K1035E | K1047E | — |
| I994L | wt | wt | — |
| T1006K | T1057K | wt | wt |
| I1014V | wt | wt | wt |
| V1055N/D | D1107N | N1118D | — |
| L1065F/Y | F1117Y | F1128Y | — |
| Y1180F | wt | wt | wt |
| V1209G | wt | wt | K1064G |
| I1229L | N1291L | wt | — |
| V801I* | wt | L867I* | P670I* |
| Y802I* | wt | wt | N671I* |
| D850A** | D908A** | D917A** | D727A** |
| E943A** | E993A** | E1006A** | E939A** |
| D1198A** | D1263A** | D1255A** | D1053A** |

"wt" = wild type
*mutation expected to increase stabilization of nuclease/crRNA association
**mutation expected to decrease or eliminate endonuclease activity

Example 7

This example illustrates compositions and systems including a Cas12a nuclease, a Cas12a crRNA that comprises a 3' extension, and a Cas12a tracrRNA. More specifically, this illustrates an engineered system including a Cas12a crRNA that includes an artificial 3' ribonucleotide extension including a detectable label (a fluorophore) for in vivo identification of cells containing the Cas12a crRNA. The Cas12a crRNA is synthesized for delivery to plant cells as a ribonucleoprotein complex with a Cas12a nuclease, and (2) cloned into a plant expression vector system for co-expression with Cas12a in vivo.

A ZmLc crRNA was designed with the nucleotide sequence of SEQ ID NO:179 including the direct repeat sequence of SEQ ID NO:180 and the spacer sequence of SEQ ID NO:181 for targeting the promoter of the *Zea mays* Lc gene (GRMZM5G822829); this ZmLc crRNA sequence was modified to contain 11 nucleotides adjacent to and 3' to the spacer region, yielding an engineered 3'-extended ZmLc crRNA. The 3'-extended crRNA sequence is encoded into a dsDNA template downstream of a T7 polymerase binding site and initiator for in vitro transcription using the HiScribe™ T7 High Yield RNA Synthesis Kit (catalogue number E2050S, New England BioLabs, Ipswich, Mass.). Alternatively, the 3'-extended crRNA is chemically synthesized by IDT (Coralville, Iowa), optionally containing chemical modifications or non-natural components. The 3'-extended crRNA is further modified to contain a fluorescent or fluorophore-conjugated nucleotide or nucleotide analog, such as cytidine-5'-phosphate-3'-(6-aminohexyl)phosphate conjugated to Cy5 (NU-1706-CY5, Jena Bioscience, Jena, Germany), at its 3' end using T4 RNA ligase. Alternatively, the 3'-extended crRNA containing one or multiple fluorescent components within or following the polynucleotide extension (e.g., 3' ATTO™ 590 (NHS Ester)) is chemically synthesized by IDT (Coralville, Iowa).

Fluorescent Cas12a ribonucleoprotein complexes (RNPs) are generated with the fluorophore-labelled 3'-extended crRNA, a modified Cas12a nuclease (SEQ ID NO:182), and a Cas12 tracrRNA (SEQ ID NO:3) following the protocols described below in Example 8, incubated with nanoparticles (e.g., 0.6 micrometer gold microcarriers, catalogue number 1652262, BioRad Laboratories, Inc., Hercules, Calif.), and biolistically delivered to meristematic tissue using standard protocols similar to or adapted from Liang et al. (2017) *Nature Communications,* 8:14261, doi: 10.1038/ncomms14261. Meristems are further visualized under a fluorescent microscope several hours following delivery to identify and isolate transformed meristem from non-transformed cells or tissue. Optionally, the transformed meristem is grown into callus or plants.

Example 8

This example illustrates compositions and engineered genome editing systems including a Cas12a nuclease, a Cas12acrRNA, and a Cas12a tracrRNA. In addition to the usefulness of an RNA molecule including a Cas12a tracrRNA for, e.g., tethering a donor polynucleotide to a Cas12a nuclease/crRNA ribonucleoprotein (RNP) complex, it was discovered that addition of a molar excess of tracrRNA to an editing system including a Cas12a nuclease/crRNA RNP unexpectedly resulted in an increase of the overall efficiency of genome editing at a given concentration of RNP.

Protoplasts were prepared from leaves of 2-week old maize (*Zea mays*, variety B104) plants, following a protocol previously described (see Example 1 in U.S. patent application Ser. No. 16/480,992 (filed on 25 Jul. 2019 as the national phase application based on PCT/US2018/015793 filed on 29 Jan. 2018 and published as WO2018/140899), incorporated herein by reference.

Reagents were prepared as follows. The modified Cas12a nuclease employed in this experiment had the amino acid sequence of SEQ ID NO:182; included in this sequence are (a) the native Cas12a nuclease sequence (amino acids positions 19-1246 of SEQ ID NO:182), (b) remains of a linker sequence (amino acid positions 1-7 of SEQ ID NO:182), (c) two linker sequences (amino acid positions 15-18 and 1247-1250 of SEQ ID NO:182), (d) an N-terminus nuclear localization signal (NLS) sequence (amino acid positions 8-14 of SEQ ID NO:182), and (e) a C-terminus linker/NLS (amino acid positions 1247-1259 of SEQ ID NO:182). The Cas12a nuclease (5.85 milligrams/milliliter in aqueous buffer containing 25 millimolar Tris-HCl, 300 millimolar NaCl, 0.1 millimolar EDTA, pH 7.4) was diluted with dilution buffer (25 millimolar Tris-HCl, 300 millimolar NaCl, 0.1 millimolar EDTA, 40% glycerol, pH 7.4) to a final concentration of 1.25 milligrams/milliliter nuclease and 31.5% glycerol. A 30 micromolar solution of Cas12a tracrRNA with the nucleotide sequence of SEQ ID NO:3 was prepared in reaction buffer (40 mM HEPES, 200 mM NaCl, 10 mM MgCl2, and 0.2 mM EDTA, pH 6.5). Additional solutions of 40% polyethylene glycol 4000 (PEG), maize washing solution (0.6 molar mannitol, 4 millimolar MES pH 5.7, and 20 millimolar KCl), and PIM containing 50 millimolar $CaCl_2$ (previously described in Table 25, U.S. patent application Ser. No. 16/480,992, filed on 25 Jul. 2019 as the national phase application based on PCT/US2018/015793 filed on 29 Jan. 2018 and published as WO2018/140899, incorporated herein by reference) were prepared. All solutions were aliquoted into 96-well deep plates and sealed until needed for use in a Biomek $FX^P$ automated liquid handler (Beckman Coulter Life Sciences, Indianapolis, Ind.).

Ribonucleoproteins (RNPs) were prepared with a Cas12a nuclease having the sequence of SEQ ID NO:182 and an ZmLc crRNA with the nucleotide sequence of SEQ ID NO:179 including the direct repeat sequence of SEQ ID NO:180 and the spacer sequence of SEQ ID NO:181 for targeting the promoter of the *Zea mays* Lc gene (GRMZM5G822829). Following a preferred protocol, the ZmLc crRNA was resuspended in reaction buffer to a concentration of 25 micromolar; 1680 microliters of the diluted ZmLc crRNA was mixed with 560 microliters of the Cas12a nuclease solution and incubated 20 minutes at room temperature. To this mixture 1400 microliters of the Cas12a tracrRNA was added and mixed; this "Cas12a nuclease/ZmLc crRNA/tracrRNA editing system" was apportioned in 225 microliter aliquots into 8-strip PCR tubes.

Four mixtures were prepared for use as diluents.

"Diluent 1" (Cas12a nuclease/GmSHAT1-5 crRNA/tracrRNA) was prepared by mixing 420 microliters of 25 micromolar GmSHAT1-5 crRNA (serving as a non-specific Cas12a crRNA, this was designed to target *Glycine max* SHAT1-5, see www[dot]uniprot[dot]org/uniprot/W8E7P1) in reaction buffer (40 mM HEPES, 200 mM NaCl, 10 mM MgCl2, and 0.2 mM EDTA, pH 6.5) and 140 microliters of the Cas12a nuclease solution, incubating for 20 minutes at room temperature, and then adding 350 microliters of the Cas12a tracrRNA solution. This was apportioned in 225 microliter aliquots into 8-strip PCR tubes.

"Diluent 2" (Cas12a nuclease/GmSHAT1-5 crRNA) was prepared by mixing 420 microliters of 25 micromolar GmSHAT5-1 crRNA in reaction buffer (40 mM HEPES, 200 mM NaCl, 10 mM MgCl2, and 0.2 mM EDTA, pH 6.5) and 140 microliters of the Cas12a nuclease solution, incubating for 20 minutes at room temperature, and then adding 350 microliters of the reaction buffer (40 mM HEPES, 200 mM NaCl, 10 mM MgCl2, and 0.2 mM EDTA, pH 6.5). This was apportioned in 225 microliter aliquots into 8-strip PCR tubes.

"Diluent 3" (Cas12a tracr) was prepared by mixing 350 microliters of the Cas12a tracrRNA solution with 560 microliters of reaction buffer (40 mM HEPES, 200 mM NaCl, 10 mM MgCl2, and 0.2 mM EDTA, pH 6.5). This was apportioned in 225 microliter aliquots into 9-strip PCR tubes.

"Diluent 4" consisted of reaction buffer (40 mM HEPES, 200 mM NaCl, 10 mM MgCl2, and 0.2 mM EDTA, pH 6.5) only. This was apportioned in 225 microliter aliquots into 9-strip PCR tubes.

Transfections of the maize protoplasts were carried out in the Biomek $FX^P$ automated liquid handler. A 16-microliter aliquot of the protoplast suspension was added to each well of a U-Bottom 96 well plate pre-coated with 5% Calf Serum with lid removed. A titration series of the Cas12a nuclease/ZmLc crRNA/tracrRNA editing system was made across twelve wells of a master titration plate using the four different diluents; this was stored on the cold block until transfection. The titrations resulted in a dilution series of the Cas12a nuclease/ZmLc crRNA/tracrRNA editing system, as shown in Table 6, which provides the resulting ratios between the additional Cas12a tracrRNA (provided in the diluent) to Cas12a nuclease (provided in the Cas12a nuclease/ZmLc crRNA/tracrRNA editing system).

TABLE 6

| Cas12a nuclease (pmol) | Cas12a tracrRNA (pmol) | Cas12a tracrRNA:Cas12a nuclease ratio |
|---|---|---|
| 0.00 | 193.70 | — |
| 2.13 | 193.70 | 90.81 |
| 4.06 | 193.70 | 47.71 |
| 5.99 | 193.70 | 32.36 |
| 7.88 | 193.70 | 24.59 |
| 9.80 | 193.70 | 19.76 |
| 11.73 | 193.70 | 16.51 |
| 13.66 | 193.70 | 14.18 |
| 15.58 | 193.70 | 12.43 |
| 17.48 | 193.70 | 11.08 |
| 19.40 | 193.70 | 9.98 |
| 21.33 | 193.70 | 9.08 |

Transfections were performed in triplicate. For transfection, 16 microliters of a given titrated dilution was added to each protoplast-containing well, and mixed; 32 microliters of 40% PEG solution are added and mixed, and the plate incubated 5 minutes at room temperature. Sequential additions of maize washing buffer were dispensed across the plate and mixed, and the plate was removed from the automated liquid handler, covered, and centrifuged. The plate was returned to the automated liquid handler for removal of the majority of the supernatant, and the protoplasts resuspended in 120 microliters PIM containing 50 millimolar $CaCl_2$. The plate was covered and incubated at 27 degrees Celsius in the dark for 48 hours before harvesting. Genomic DNA was isolated from the protoplasts, quantified using QuantiFluor (Promega Corporation, Madison, Wis.), and subjected to PCR amplification followed by amplicon sequencing to detect indel edits.

Figure 12:
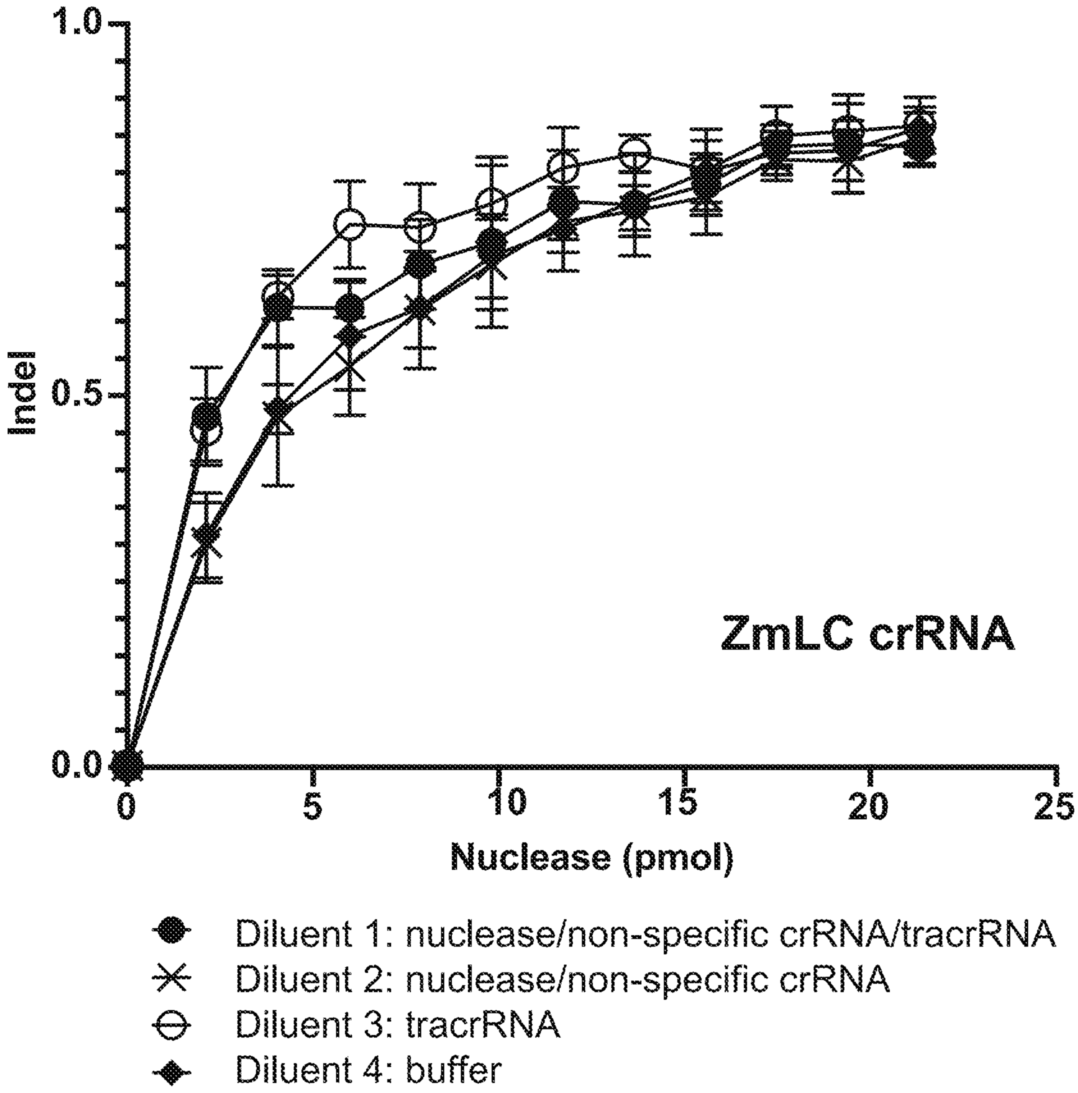
FIG. 12 depicts the results of the experiment described in Example 8 using the GD-30 crRNA. The data are provided as the fraction of edited protoplasts (the number of protoplasts containing an insertion/deletion (indel) at the predicted cleavage site, divided by the total number of protoplasts treated) versus the amount in pmoles of Cas12a nuclease used.

Results, given as the fraction of protoplasts containing an indel at the predicted cleavage site versus the amount of Cas12a nuclease used, are illustrated in FIG. 12. The data indicate that dilutions made with Diluent 2 (Cas12a nuclease/GmSHAT1-5 crRNA in reaction buffer) had no significant effect when compared to the control dilution with Diluent 4 (reaction buffer only). In contrast, dilutions made with Diluent 3 (Cas12a tracrRNA in reaction buffer) markedly increased the editing efficiency at the majority of the nuclease amounts tested; the additional Cas12a tracrRNA appeared to decrease the amount of Cas12a nuclease required to achieve 75% editing to 5.99 pmol, i.e., about a third of the Cas12a nuclease amount needed to achieve the same level of editing efficiency in the control dilution (15.58 pmol). Dilutions made with Diluent 1 (Cas12a nuclease/GmSHAT1-5 crRNA/tracrRNA in reaction buffer) also appeared to slightly increase the editing efficiency of a given amount of Cas12a nuclease; since the difference between Diluent 1 and Diluent 2 was the presence of the Cas12a tracrRNA, it is likely that the increased editing efficiency was due to the Cas12a tracrRNA.

Example 9

This example illustrates compositions and engineered genome editing systems including a Cas12a nuclease, a Cas12acrRNA, and a Cas12a tracrRNA. More specifically, this example illustrates additional experiments that confirmed that addition of a molar excess of tracrRNA to an editing system including a Cas12a nuclease/crRNA RNP unexpectedly resulted in an increase of the overall efficiency of genome editing at a given concentration of RNP.

To further investigate the effects of including a molar excess of Cas12a tracrRNA in a Cas12a nuclease/crRNA/tracrRNA editing system, additional experiments were carried out using different Cas12a crRNAs.

Protoplasts were prepared from etiolated middle leaves of 12-day old maize (*Zea mays*, variety B104) plants, following a protocol previously described (see Example 1 in U.S. patent application Ser. No. 16/480,992 (filed on 25 Jul. 2019 as the national phase application based on PCT/US2018/015793 filed on 29 Jan. 2018 and published as WO2018/140899), incorporated herein by reference.

One experiment tested the effects of various diluents on Cas12a RNPs including a Cas12a nuclease and a "high-performing" Cas12a crRNA, GD-48, which routinely produced indel edits at a frequency between 80-90%. Another experiment tested the effects of various diluents on Cas12a RNPs including a Cas12a nuclease and a "low-performing" Cas12a crRNA, GD-14, which routinely produced indel edits at frequencies below 25%. The nucleotide sequence of both Cas12a crRNAs included, from 5' to 3', a direct repeat sequence (SEQ ID NO:180) and a spacer sequence having perfect complementarity to a specific target sequence in the maize B104 genome.

Experimental procedures were similar to those described in Example 8. The Cas12a nuclease (SEQ ID NO:182) (5.85 milligrams/milliliter in aqueous buffer containing 25 millimolar Tris-HCl, 300 millimolar NaCl, 0.1 millimolar EDTA, pH 7.4) was diluted with dilution buffer (25 millimolar Tris-HCl, 300 millimolar NaCl, 0.1 millimolar EDTA, 40% glycerol, pH 7.4) to a final concentration of 1.25 milligrams/milliliter nuclease and 31.5% glycerol. A 30 micromolar solution of Cas12a tracrRNA (SEQ ID NO:3) was prepared in reaction buffer (40 mM HEPES, 200 mM NaCl, 10 mM MgCl2, and 0.2 mM EDTA, pH 6.5). A 1.25 milligram/milliliter solution of bovine serum albumen (BSA) was prepared in protein storage buffer (25 millimolar Tris-HCl, 300 millimolar NaCl, 0.1 millimolar EDTA, 1 millimolar dithiothreitol, 40% glycerol, pH 7.4). Additional solutions of 40% polyethylene glycol 4000 (PEG), maize washing solution (0.6 molar mannitol, 4 millimolar MES pH 5.7, and 20 millimolar KCl), and PIM containing 50 millimolar $CaCl_2$ (previously described in Table 25, U.S. patent application Ser. No. 16/480,992, filed on 25 Jul. 2019 as the national phase application based on PCT/US2018/015793 filed on 29 Jan. 2018 and published as WO2018/140899, incorporated herein by reference) were prepared. All solutions were aliquoted into 96-well deep plates and sealed until needed for use in a Biomek $FX^P$ automated liquid handler (Beckman Coulter Life Sciences, Indianapolis, Ind.).

Cas12a ribonucleoproteins (RNPs) were prepared with a Cas12a nuclease having the sequence of SEQ ID NO:182 and the "high-performing" Cas12a crRNA, GD-48 as well as the "low-performing" Cas12a crRNA, GD-14. Following a preferred protocol, each Cas12a crRNA was resuspended in reaction buffer to a concentration of 25 micromolar; 1680 microliters of the diluted Cas12a crRNA was mixed with 560 microliters of the Cas12a nuclease solution and incubated 20 minutes at room temperature. To this mixture 1400 microliters of the Cas12a tracrRNA was added and mixed; the resulting "Cas12a nuclease/GD-48 crRNA/tracrRNA editing system" and "Cas12a nuclease/GD-14 crRNA/tracrRNA editing system" were apportioned in 225 microliter aliquots into 8-strip PCR tubes.

Four mixtures were prepared for use as diluents.

"Diluent 1" (Cas12a nuclease/GmSHAT1-5 crRNA/tracrRNA) was prepared by mixing 420 microliters of 25 micromolar GmSHAT1-5 crRNA in reaction buffer (40 mM HEPES, 200 mM NaCl, 10 mM MgCl2, and 0.2 mM EDTA, pH 6.5) and 140 microliters of the Cas12a nuclease solution, incubating for 20 minutes at room temperature, and then adding 350 microliters of the Cas12a tracrRNA solution. This was apportioned in 225 microliter aliquots into 8-strip PCR tubes.

"Diluent 2" (BSA) was prepared by mixing 140 microliters of the BSA stock solution with 770 microliters of reaction buffer (40 mM HEPES, 200 mM NaCl, 10 mM MgCl2, and 0.2 mM EDTA, pH 6.5). This was apportioned in 225 microliter aliquots into 8-strip PCR tubes.

"Diluent 3" (GmSHAT1-5 crRNA/tracrRNA) was prepared by mixing 420 microliters of the GmSHAT1-5 crRNA, 350 microliters of the Cas12a tracrRNA solution, and 140 microliters of reaction buffer (40 mM HEPES, 200 mM NaCl, 10 mM MgCl2, and 0.2 mM EDTA, pH 6.5). This was apportioned in 225 microliter aliquots into 9-strip PCR tubes.

"Diluent 4" consisted of reaction buffer (40 mM HEPES, 200 mM NaCl, 10 mM MgCl2, and 0.2 mM EDTA, pH 6.5) only. This was apportioned in 225 microliter aliquots into 9-strip PCR tubes.

Transfections of the maize protoplasts were carried out in the Biomek $FX^P$ automated liquid handler. A 16-microliter aliquot of the protoplast suspension was added to each well of a U-Bottom 96 well plate pre-coated with 5% Calf Serum with lid removed. A titration series of the Cas12a nuclease/ZmLc crRNA/tracrRNA editing system was made across twelve wells of a master titration plate using the four different diluents; this was stored on the cold block until transfection.

Transfections were performed in triplicate. For transfection, 16 microliters of a given titrated dilution was added to each protoplast-containing well, and mixed; 32 microliters of 40% PEG solution are added and mixed, and the plate incubated 5 minutes at room temperature. Sequential additions of maize washing buffer were dispensed across the plate and mixed, and the plate was removed from the automated liquid handler, covered, and centrifuged. The plate was returned to the automated liquid handler for removal of the majority of the supernatant, and the protoplasts resuspended in 120 microliters PIM containing 50 millimolar $CaCl_2$. The plate was covered and incubated at 27 degrees Celsius in the dark for 36 hours before harvesting. Genomic DNA was isolated from the protoplasts, quantified using QuantiFluor (Promega Corporation, Madison, Wis.), and subjected to PCR amplification followed by amplicon sequencing to detect indel edits.

Figure 13:
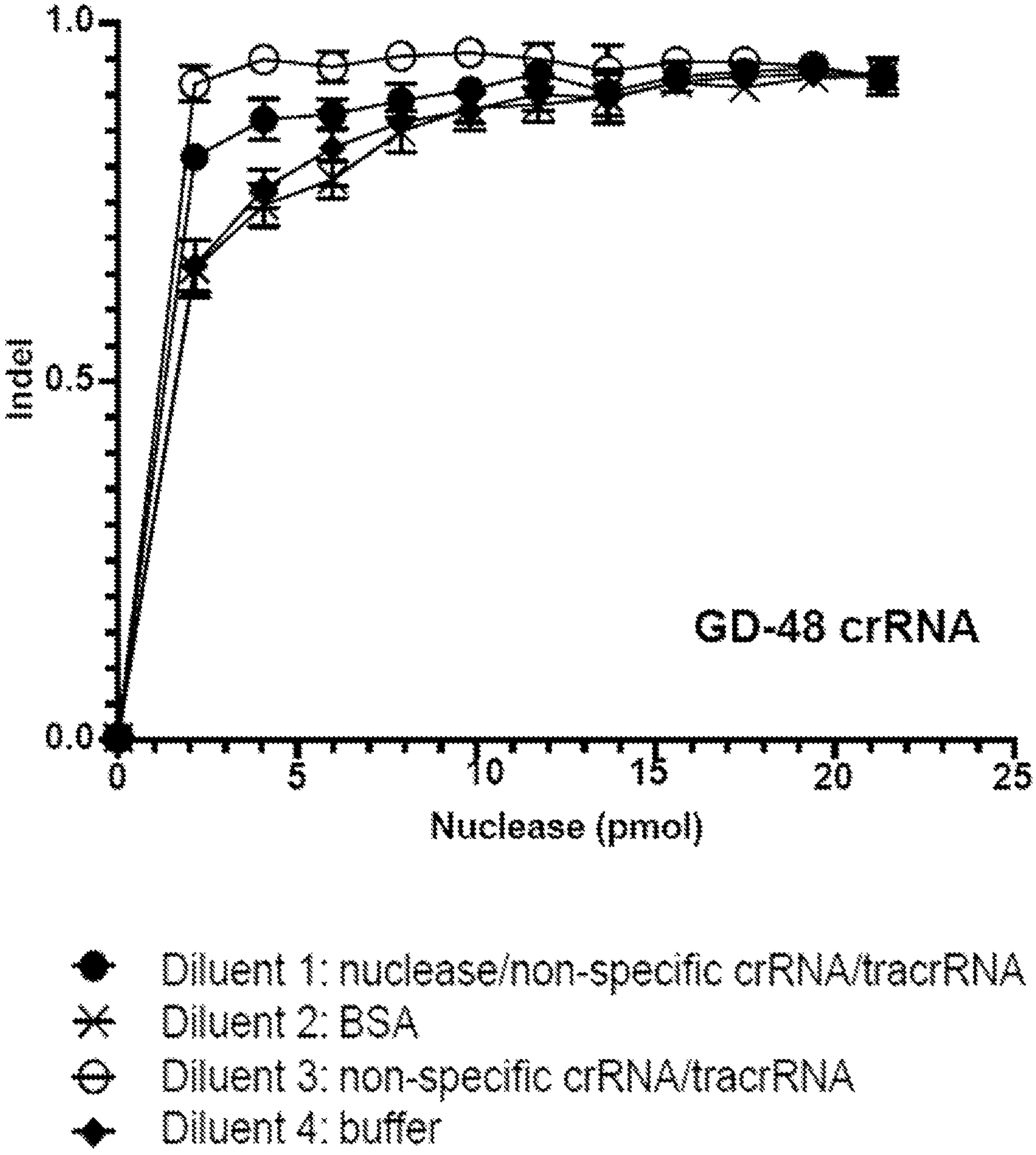
FIG. 13 depicts the results of the experiment using a "high-performing" Cas12a crRNA, GD-48, as described in Example 9. The data are provided as the fraction of edited protoplasts (the number of protoplasts containing an insertion/deletion (indel) at the predicted cleavage site, divided by the total number of protoplasts treated) versus the amount in pmoles of Cas12a nuclease used.
Figure 14:
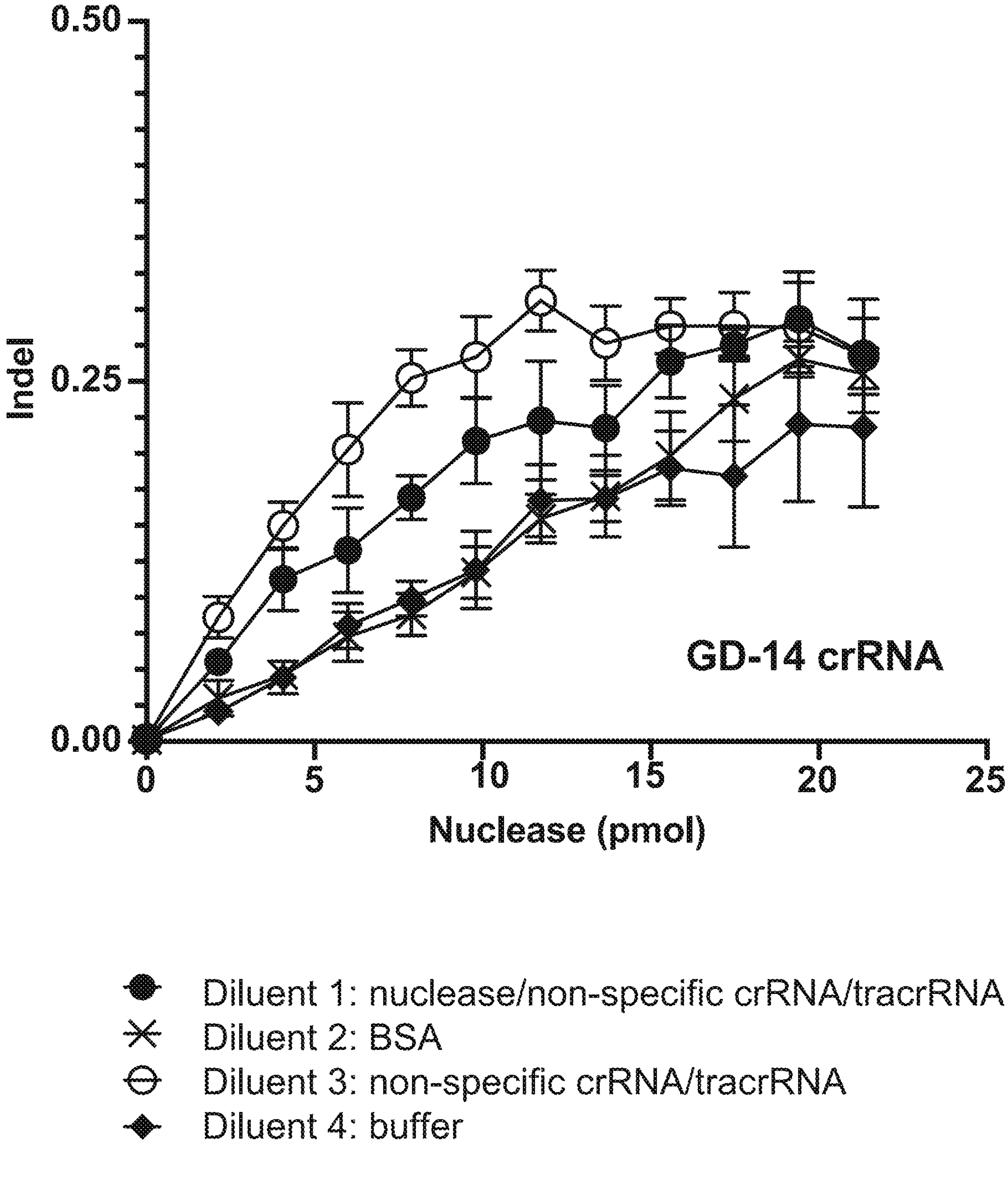
FIG. 14 depicts the results of the experiment using a "low-performing" Cas12a crRNA, GD-14, as described in Example 9. The data are provided as the fraction of edited protoplasts (the number of protoplasts containing an insertion/deletion (indel) at the predicted cleavage site, divided by the total number of protoplasts treated) versus the amount in pmoles of Cas12a nuclease used.

Results, given as the fraction of protoplasts containing an indel at the predicted cleavage site versus the amount of Cas12a nuclease used, are illustrated in FIGS. 13 and 14. The data indicate that dilutions made with Diluent 2 (BSA in reaction buffer) had no significant effect when compared to the control dilution with Diluent 4 (reaction buffer only). In contrast, dilutions made with Diluent 3 (GmSHAT1-5 crRNA/tracrRNA in reaction buffer) markedly increased the editing efficiency at the majority of the Cas12a nuclease amounts tested for both Cas12a crRNAs tested. In the case of the "high-performing" Cas12a crRNA, GD-48, the indel editing frequency reached about maximum (about 90-95%) at much lower Cas12a nuclease concentrations with Diluent 3 than with Diluent 4 (reaction buffer control); use of this Cas12a tracrRNA-containing diluent appeared to decrease the amount of Cas12a nuclease required to achieve about 90% editing to about 2.13 pmol, i.e., about one-seventh the amount of Cas12a nuclease needed to achieve the same level of editing efficiency in the control dilution (15.58 pmol). Dilutions made with Diluent 1 (Cas12a nuclease/GmSHAT1-5 crRNA/tracrRNA in reaction buffer) also appeared to increase the editing efficiency of a given amount of Cas12a nuclease; use of this diluent appeared to decrease the amount of Cas12a nuclease required to achieve about 90% editing to about 11.73 pmol, i.e., about 75% of the amount of Cas12a nuclease needed to achieve the same level of editing efficiency in the control dilution (15.58 pmol).

In the case of the "low-performing" Cas12a crRNA, GD-14, the indel editing frequency reached about maximum (about 30%) at much lower Cas12a nuclease concentrations with Diluent 3 than with Diluent 4 (the reaction buffer control). Furthermore, use of Diluent 3 resulted in a higher maximum indel editing frequency (about 30%), compared to that obtained with Diluent 4 (only about 20%). Thus, use of Diluent 3 increased overall indel editing efficiency by about fifty percent, and reached maximum editing efficiency at a Cas12a nuclease concentration that was estimated to be at least less than half of the Cas12a nuclease concentration needed to reach the maximum editing efficiency observed in the control dilution. Dilutions made with Diluent 1 (Cas12a nuclease/GmSHAT1-5 crRNA/tracrRNA in reaction buffer) also appeared to increase the editing efficiency of a given amount of Cas12a nuclease; the maximum editing efficiency (about 30%) was also greater than that seen with Diluent 4, and this level was reached with about 15.58 pmol of Cas12a nuclease in Diluent 1.

Example 10

Various embodiments of the systems, methods, and compositions provided herein are included in the following non-limiting list of numbered embodiments.

1. A method of tethering a functional RNA molecule to a Cas12a crRNA, the method comprising hybridizing
   (a) a functional RNA molecule comprising a Cas12a tracrRNA and a functional RNA moiety; and
   (b) a Cas12a crRNA that comprises a 3' extension capable of hybridizing with a segment of the functional RNA molecule;
   thereby tethering the functional RNA molecule to the Cas12a crRNA.
2. The method of embodiment 1, wherein the functional RNA molecule is provided by transcription of a DNA molecule comprising DNA encoding the Cas12a tracrRNA and DNA encoding the functional RNA moiety, wherein the DNA encoding the functional RNA moiety is inserted at a restriction endonuclease cleavage site in or adjacent to the DNA encoding the Cas12a tracrRNA.
3. The method of embodiment 2, wherein the restriction endonuclease cleavage site is native.
4. The method of embodiment 2, wherein the restriction endonuclease cleavage site is artificial.
5. The method of embodiment 1, wherein the crRNA 3' extension comprises nucleotides that when base-paired form about one helical turn.
6. The method of embodiment 1, wherein the crRNA 3' extension comprises at least 10 contiguous nucleotides.
7. The method of any one of embodiments 1 to 6, wherein the functional RNA moiety is at least one selected from the group consisting of:
   (a) an RNA sequence for annealing to a donor polynucleotide;
   (b) an RNA sequence for annealing to the crRNA 3' extension;
   (c) a terminator sequence;
   (d) an RNA aptamer;
   (e) a ribozyme;
   (f) a detectable label;
   (g) a bar-coding sequence; and
   (h) an RNA sequence forming at least partially double-stranded RNA.
8. The method of any one of embodiments 1 to 6, wherein the functional RNA moiety comprises RNA forming at least partially double-stranded RNA capable of silencing a gene.
9. The method of any one of embodiments 1 to 8, wherein the Cas12a crRNA is complexed with, or is capable of complexing with, a Cas12a nuclease to form a Cas12a ribonucleoprotein complex containing the functional RNA molecule.
10. The method of embodiment 9, wherein the Cas12a nuclease is:
    (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or
    (b) a Cas12a nuclease selected from the group consisting of LbCas12a, AsCas12a, FnCas12a, and a deactivated Cas12a nuclease; or
    (c) a Cas12a nuclease having at least 80% sequence identity with a sequence selected from the group consisting of SEQ ID NOs:11, 107-114, 116-136, and 172; or
    (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.
11. The method of embodiment 9 or embodiment 10, wherein the Cas12a nuclease comprises at least one modification selected from the group consisting of:
    (a) a localization signal;
    (b) a detectable label;

(c) a cell-penetrating peptide;
(d) an endosomal escape peptide; and
(e) an affinity tag.

12. A modified Cas12a ribonucleoprotein complex comprising (a) a Cas12a nuclease;
(b) a functional RNA molecule comprising a Cas12a tracrRNA and a functional RNA moiety; and
(c) a Cas12a crRNA that comprises a 3' extension capable of hybridizing with a segment of the functional RNA molecule.

13. The modified Cas12a ribonucleoprotein complex of embodiment 12, wherein the Cas12a nuclease is:
(a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or
(b) a Cas12a nuclease selected from the group consisting of LbCas12a, AsCas12a, FnCas12a, and a deactivated Cas12a nuclease; or
(c) a Cas12a nuclease having at least 80% sequence identity with a sequence selected from the group consisting of SEQ ID NOs:11, 107-114, 116-136, and 172; or
(d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

14. The modified Cas12a ribonucleoprotein complex of embodiment 12 or embodiment 13, wherein the Cas12a nuclease comprises at least one modification selected from the group consisting of:
(a) a localization signal;
(b) a detectable label;
(c) a cell-penetrating peptide;
(d) an endosomal escape peptide; and
(e) an affinity tag.

15. A method of integrating a nucleotide sequence encoded by a donor polynucleotide at a specific locus in a target DNA, the method comprising:
(a) annealing a donor polynucleotide to the modified Cas12a ribonucleoprotein complex of embodiment 12, wherein the functional RNA moiety comprises an RNA sequence for annealing to the donor polynucleotide, and wherein the Cas12a crRNA comprises a spacer sequence that corresponds to a specific target locus in a target DNA, thus forming a donor:RNP complex; and
(b) contacting the target DNA with the donor:RNP complex; whereby the nucleotide sequence encoded by the donor polynucleotide is integrated at the specific target locus in the target DNA.

16. The method of embodiment 15, wherein the donor polynucleotide comprises single-stranded DNA, optionally comprising chemical modifications.

17. The method of embodiment 15, wherein the donor polynucleotide comprises double-stranded DNA, optionally comprising chemical modifications.

18. A DNA expression system comprising (a) DNA sequence for a first promoter; and
(b) operably linked and heterologous to the first promoter, DNA encoding a first RNA molecule comprising a Cas12a tracrRNA and comprising a restriction endonuclease cleavage site that is suitable for insertion of a sequence coding for a functional RNA moiety; and
(c) optionally, a terminator 3' to and operably linked to the DNA encoding the first RNA molecule.

19. The DNA expression system of embodiment 18, wherein the restriction endonuclease cleavage site occurs natively in the DNA encoding the Cas12a tracrRNA.

20. The DNA expression system of embodiment 18, wherein the restriction endonuclease cleavage site is artificial.

21. The DNA expression system of embodiment 18, further comprising:
(d) optionally, a DNA sequence for a second promoter;
(e) operably linked and heterologous to the first promoter or the second promoter, DNA encoding a Cas12a crRNA that comprises a 3' extension capable of hybridizing with a segment of the first RNA molecule; and
(f) optionally, a terminator 3' to and operably linked to the DNA encoding the Cas12a crRNA.

22. The DNA expression system of embodiment 21, wherein the first promoter and the DNA encoding the first RNA molecule, and the DNA encoding a Cas12a crRNA that comprises a 3' extension are contained in a single construct.

23. The DNA expression system of embodiment 21, comprising the second promoter, wherein the first promoter and the DNA encoding the first RNA molecule are contained in a first construct, and the second promoter and the DNA encoding a Cas12a crRNA that comprises a 3' extension are contained in a second construct.

24. The DNA expression system of embodiment 23, wherein the first construct and the second construct are provided (a) in a single vector, or (b) in separate vectors.

25. The DNA expression system of embodiment 21, wherein the first promoter drives expression of both the DNA encoding the first RNA molecule and the DNA encoding the Cas12a crRNA that comprises a 3' extension.

26. The DNA expression system of any one of embodiments 21 to 25, wherein the Cas12a tracrRNA further comprises a 5' extension.

27. The DNA expression system of any one of embodiments 21 to 26, wherein the Cas12a crRNA that comprises a 3' extension is capable of complexing with a Cas12a nuclease to form a Cas12a ribonucleoprotein complex.

28. The DNA expression system of embodiment 18, further comprising:

(d) optionally, a DNA sequence for a second promoter;

(e) operably linked and heterologous to the first promoter or the second promoter, DNA encoding a Cas12a crRNA capable of hybridizing with a segment of the first RNA molecule; and (f) optionally, a terminator 3' to and operably linked to the DNA encoding the Cas12a crRNA.

29. The DNA expression system of embodiment 28, wherein the first promoter and the DNA encoding the first RNA molecule, and the DNA encoding a Cas12a crRNA are contained in a single construct.

30. The DNA expression system of embodiment 28, comprising the second promoter, wherein the first promoter and the DNA encoding the first RNA molecule are contained in a first construct, and the second promoter and the DNA encoding a Cas12a crRNA are contained in a second construct.

31. The DNA expression system of embodiment 30, wherein the first construct and the second construct are provided (a) in a single vector, or (b) in separate vectors.

32. The DNA expression system of embodiment 28, wherein the first promoter drives expression of both the DNA encoding the first RNA molecule and the DNA encoding the Cas12a crRNA.

33. The DNA expression system of any one of embodiments 28 to 32, wherein the Cas12a tracrRNA further comprises a 5' extension.

34. The DNA expression system of any one of embodiments 28 to 33, wherein the Cas12a crRNA is capable of complexing with a Cas12a nuclease to form a Cas12a ribonucleoprotein complex.

35. The DNA expression system of embodiment 27 or embodiment 34, wherein the Cas12a nuclease is:

(a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

36. The DNA expression system of any one of embodiments 18 to 35, wherein the first promoter has a DNA sequence selected from the group consisting of SEQ ID NOs:16-71 and wherein the Cas12a tracrRNA has a nucleotide sequence comprising a sequence selected from the group consisting of SEQ ID NOs:1, 3, 6, 139-146, and 149-169.

37. A DNA expression system comprising:

(a) DNA sequence for a first promoter; and (b) operably linked and heterologous to the first promoter, a DNA encoding a functional RNA molecule comprising a Cas12a tracrRNA and a functional RNA moiety; and (c) optionally, a terminator 3' to and operably linked to the DNA encoding a functional RNA molecule.

38. The DNA expression system of embodiment 37, further comprising:

(d) optionally, a DNA sequence for a second promoter;

(e) operably linked and heterologous to the first promoter or the second promoter, a DNA encoding a Cas12a crRNA that comprises a 3' extension capable of hybridizing with a segment of the functional RNA molecule; and (f) optionally, a terminator 3' to and operably linked to the DNA encoding a Cas12 crRNA.

39. The DNA expression system of embodiment 38, wherein the first promoter and the DNA encoding the functional RNA molecule, and the DNA encoding a Cas12a crRNA that comprises a 3' extension are contained in a single construct.

40. The DNA expression system of embodiment 38, comprising the second promoter, wherein the first promoter and the DNA encoding the functional RNA molecule are contained in a first construct, and the second promoter and the DNA encoding a Cas12a crRNA that comprises a 3' extension are contained in a second construct.

41. The DNA expression system of embodiment 40, wherein the first construct and the second construct are provided (a) in a single vector, or (b) in separate vectors.

42. The DNA expression system of embodiment 38, wherein the first promoter drives expression of both the DNA encoding the functional RNA molecule and the DNA encoding the Cas12a crRNA that comprises a 3' extension.

43. The DNA expression system of any one of embodiments 37 to 42, wherein the functional RNA moiety is at least one selected from the group consisting of:

(a) a nucleotide sequence for annealing to a donor polynucleotide;

(b) a nucleotide sequence for annealing to the crRNA 3' extension;

(c) a terminator sequence;

(d) an RNA aptamer;

(e) an enzymatically active RNA sequence;

(f) a detectable label; and (g) an RNA sequence forming at least partially double-stranded RNA.

44. The DNA expression system of any one of embodiments 37 to 42, wherein the functional RNA moiety comprises RNA forming at least partially double-stranded RNA capable of silencing a gene.

45. The DNA expression system of any one of embodiments 38 to 44, wherein the Cas12a tracrRNA further comprises a 5' extension.

46. The DNA expression system of any one of embodiments 38 to 45, wherein the Cas12a crRNA is capable of complexing with a Cas12a nuclease to form a Cas12a ribonucleoprotein complex containing the functional molecule.

47. The DNA expression system of any one of embodiments 37 to 56, wherein the first promoter has a DNA sequence selected from the group consisting of SEQ ID NOs:16-71 and wherein the Cas12a tracrRNA has a nucleotide sequence comprising a sequence selected from the group consisting of SEQ ID NOs:1, 3, 6, 139-146, and 149-169.

48. The DNA expression system of embodiment 46 or 47, wherein the Cas12a nuclease is:

(a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or (b) a Cas12a nuclease selected from the group consisting of LbCas12a, AsCas12a, FnCas12a, and a deactivated Cas12a nuclease; or (c) a Cas12a nuclease having at least 80% sequence identity with a sequence selected from the group consisting of SEQ ID NOs:11, 107-114, 116-136, and 172; or (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

49. An engineered system comprising:

(a) a Cas12a nuclease; and (b) at least one engineered Cas12a crRNA, or a polynucleotide encoding the engineered Cas12a crRNA, wherein the engineered Cas12a crRNA comprises (i) at least one direct repeat sequence or fragment thereof that is capable of associating with the Cas12a nuclease, and (ii) a spacer sequence that is designed to hybridize with a target sequence in a eukaryotic cell, wherein the at least one direct repeat sequence or fragment thereof is adjacent to and 5' to the spacer sequence; and (c) a Cas12a tracrRNA comprising a nucleotide sequence that has at least 50% complementarity with, the nucleotide sequence of the at least one direct repeat of the engineered Cas12a crRNA.

50. An engineered system comprising:

(a) a Cas12a nuclease; and (b) at least one engineered Cas12a crRNA, or a polynucleotide encoding the engineered Cas12a crRNA, wherein the engineered Cas12a crRNA comprises (i) at least one direct repeat sequence or fragment thereof that is capable of associating with the Cas12a nuclease, and (ii) a spacer sequence that is designed to hybridize with a target sequence in a eukaryotic cell, wherein the at least one direct repeat sequence or fragment thereof is adjacent to and 5' to the spacer sequence; and (c) a Cas12a tracrRNA comprising a naturally occurring putative Cas12a tracrRNA sequence that is identified from the same genomic region as the Cas12a nuclease by at least the following steps: (i) identifying in the genomic region flanking the DNA encoding the Cas12a nuclease at least one nucleotide sequence that comprises a CRISPR array including direct repeats, and (ii) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat.

51. The engineered system of embodiment 49 or embodiment 50, wherein the engineered Cas12a crRNA, or the polynucleotide encoding the engineered Cas12a crRNA, further comprises at least one direct repeat sequence or fragment thereof capable of associating with the Cas12a nuclease adjacent to and 3' to the spacer sequence.

52. The engineered system of embodiment 49 or embodiment 50, wherein the engineered Cas12a crRNA further comprises a 3' extension adjacent to the spacer sequence.

53. The engineered system of embodiment 52, wherein the 3' extension comprises nucleotides that when base-paired form about one helical turn.

54. The engineered system of embodiment 52, wherein the 3' extension comprises at least 10 contiguous nucleotides.

55. The engineered system of any one of embodiments 52, 53, and 54, wherein the Cas12a tracrRNA has a nucleotide sequence having sufficient complementarity to the engineered Cas12a crRNA's 3' extension to allow hybridization between the tracrRNA and the engineered Cas12a crRNA.

56. An engineered system comprising:
(a) one or more nucleotide sequences encoding a Cas12a nuclease; and
(b) one or more nucleotide sequences encoding at least one engineered Cas12a crRNA that is designed to form a complex with the Cas12a nuclease and that comprises a spacer sequence designed to hybridize with a target sequence in a eukaryotic cell; and
(c) one or more nucleotide sequences encoding at least one Cas12a tracrRNA.

57. An engineered system comprising:
(a) a Cas12a nuclease, or one or more nucleotide sequences encoding the Cas12a nuclease; and
(b) at least one engineered Cas12a crRNA designed to form a complex with the Cas12a nuclease and comprising a spacer sequence designed to hybridize with a target sequence in a eukaryotic cell, or one or more nucleotide sequences encoding the at least one engineered Cas12a crRNA polynucleotide; and
(c) at least one tracrRNA, or one or more nucleotide sequences encoding the at least one Cas12a tracrRNA.

58. The engineered system of embodiment 56 or embodiment 57, wherein the at least one engineered Cas12a crRNA, or a polynucleotide encoding the at least one engineered Cas12a crRNA, further comprises at least one direct repeat sequence or fragment thereof that is capable of associating with the Cas12a nuclease and is adjacent to and 5' to the spacer sequence.

59. The engineered system of embodiment 56 or embodiment 57, wherein the engineered Cas12a crRNA, or a polynucleotide encoding the engineered Cas12a crRNA, further comprises at least one direct repeat sequence or fragment thereof capable of associating with the Cas12a nuclease adjacent to and 3' to the spacer sequence.

60. The engineered system of embodiment 56 or embodiment 57, wherein the engineered Cas12a crRNA further comprises a 3' extension adjacent to the spacer sequence.

61. The engineered system of embodiment 60, wherein the 3' extension comprises nucleotides that when base-paired form about one helical turn.

62. The engineered system of embodiment 60, wherein the 3' extension comprises at least 10 contiguous nucleotides.

63. The engineered system of any one of embodiments 60, 61, and 62, wherein the Cas12a tracrRNA has a nucleotide sequence having sufficient complementarity to the engineered Cas12a crRNA's 3' extension to allow hybridization between the Cas12a tracrRNA and the engineered Cas12a crRNA.

64. An engineered system comprising one or more vectors comprising:
(a) a first regulatory element that is heterologous to and operably linked to one or more nucleotide sequences encoding a Cas12a nuclease; and
(b) a second regulatory element that is heterologous to and operably linked to one or more nucleotide sequences encoding at least one engineered Cas12a crRNA that is designed to form a complex with the Cas12a nuclease and that comprises a spacer sequence designed to hybridize with a target sequence in a eukaryotic cell; and
(c) a third regulatory element that is heterologous to and operably linked to one or more nucleotide sequences encoding at least one Cas12a tracrRNA;
wherein components (a) and (b) and (c) are located on the same vector or on different vectors of the system.

65. The engineered system of embodiment 64, wherein the first regulatory element, the second regulatory element, and the third regulatory element each comprise a promoter that is functional in the eukaryotic cell.

66. The engineered system of embodiment 65, wherein the first regulatory element, the second regulatory element, and the third regulatory element each comprise a promoter selected from the group consisting of pol III promoters, pol II promoters, and pol I promoters.

67. The engineered system of embodiment 69, wherein the first regulatory element, the second regulatory element, and the third regulatory element each comprise a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, an EF1a promoter.

68. The engineered system of embodiment 64, wherein the eukaryotic cell is a plant cell, and wherein the third regulatory element comprises a promoter having a nucleotide sequence selected from the group consisting of SEQ ID NOs:16-71.

69. The engineered system of any one of embodiments 64-68, wherein the at least one Cas12a tracrRNA is at least one Cas12a tracrRNA having a nucleotide sequence comprising a sequence selected from the group consisting of SEQ ID NOs:1, 3, 6, 139-146, and 149-169.

70. An engineered system comprising one or more vectors comprising:
(a) a first expression cassette comprising at least a first promoter that is heterologous to and operably linked to one or more nucleotide sequences encoding a Cas12a nuclease and—optionally—a first transcription terminator sequence; and
(b) a second expression cassette comprising at least a second promoter that is heterologous to operably linked to one or more nucleotide sequences encoding at least one engineered Cas12a crRNA that is designed to form a complex with the Cas12a nuclease and that comprises a spacer sequence designed to hybridize with a target sequence in a eukaryotic cell and—optionally—a second transcription terminator sequence; and
(c) a third expression cassette comprising at least a third promoter that is heterologous to operably linked to one or more nucleotide sequences encoding at least one Cas12a tracrRNA and—optionally—a third transcription terminator sequence,
wherein components (a) and (b) and (c) are located on the same vector or on different vectors of the system.

71. The engineered system of embodiment 70, wherein the first promoter, the second promoter, and the third promoter are each a promoter that is functional in the eukaryotic cell, and wherein the first transcription terminator, the second transcription terminator, and the third transcription terminator are each a transcription terminator that is functional in the eukaryotic cell.

72. The engineered system of embodiment 70, wherein the first promoter, the second promoter, and the third promoter are each a promoter selected from the group consisting of pol III promoters, pol II promoters, and pol I promoters.

73. The engineered system of embodiment 70, wherein the first promoter, the second promoter, and the third promoter are each a promoter selected from the group consisting of a U6 promoter, an H1 promoter, a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, an EF1a promoter.

74. The engineered system of embodiment 70, wherein the first promoter, the second promoter, and the third promoter are each a promoter with a nucleotide sequence selected from the group consisting of SEQ ID NOs:16-71.

75. The engineered system of embodiment 70, wherein the first transcription terminator, the second transcription terminator, and the third transcription terminator are each selected from the group consisting of a U6 poly-T terminator, an SV40 terminator, an hGH terminator, a BGH terminator, an rbGlob terminator, a synthetic terminator functional in a eukaryotic cell, a 3' element from an *Agrobacterium* sp. gene, a 3' element from a non-human animal gene, a 3' element from a human gene, and a 3' element from a plant gene, wherein the 3' element terminate transcription of an RNA transcript located immediately 5' to the 3' element.

76. The engineered system of embodiment 70, wherein the first transcription terminator, the second transcription terminator, and the third transcription terminator are each a transcription terminator having a sequence selected from SEQ ID NOs:72-100.

77. The engineered system of any one of embodiments 49-76, wherein the eukaryotic cell is a non-human animal cell, a human cell, a plant cell, or a fungal cell.

78. The engineered system of any one of embodiments 49-77, wherein the eukaryotic cell is in vitro, ex vivo, or in vivo.

79. The engineered system of any one of embodiments 49-78, wherein the Cas12a nuclease is:
(a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or
(b) a Cas12a nuclease selected from the group consisting of LbCas12a, AsCas12a, FnCas12a, and a deactivated Cas12a nuclease; or
(c) a Cas12a nuclease having at least 80% sequence identity with a sequence selected from the group consisting of SEQ ID NOs:11, 107-114, 116-136, and 172; or
(d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

80. The engineered system of any one of embodiments 49-79, wherein the Cas12a nuclease comprises one or more of:
(a) a localization signal;
(b) a detectable label;
(c) a cell-penetrating peptide;
(d) an endosomal escape peptide; and
(e) and affinity tag.

81. The engineered system of any one of embodiments 49-80, wherein the at least one Cas12a tracrRNA has a nucleotide sequence selected from SEQ ID NOs:1, 3, 6, 139-146, and 149-169.

82. The engineered system of any one of embodiments 49-81, wherein the genomic sequence encoding the Cas12a nuclease and the genomic sequence encoding the Cas12a tracrRNA occur naturally within the same region in a genome.

83. The engineered system of any one of embodiments 49, 50, 56, 57, 64, and 68, wherein the target sequence is located 3' of a Protospacer Adjacent Motif (PAM) and the PAM sequence is TTN, where N is A/C/G or T and the Cas12a nuclease is FnCpf1, or the PAM sequence is TTTV, where V is A/C or G and the Cas12a nuclease is PaCpf1p, LbCpf1 or AsCpf1.

84. The engineered system of any one of embodiments 49, 56, 57, 64, and 68, wherein the Cas12a tracrRNA is a putative Cas12a tracrRNA that is identified from the same genomic region as the Cas12a nuclease by at least the following steps:
(a) identifying in the genomic region flanking the DNA encoding the Cas12a nuclease at least one nucleotide sequence that comprises a CRISPR array including direct repeats;
(b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat.

85. The engineered system of any one of embodiments 49, 50, 56, 57, 64, and 68, wherein the Cas12a tracrRNA is provided:
(a) as DNA encoding a first RNA molecule comprising the Cas12a tracrRNA and comprising a restriction endonuclease cleavage site that is suitable for insertion of a sequence coding for a functional RNA moiety; or
(b) as a functional RNA molecule comprising the Cas12a tracrRNA and a functional RNA moiety, or as a polynucleotide encoding the functional RNA molecule; or (c) by the DNA expression system of embodiment 18; or (d) by the DNA expression system of embodiment 37.

86. The engineered system of any one of embodiments 49, 50, 56, 57, 64, and 68, wherein the Cas12a tracrRNA is provided as DNA encoding a first RNA molecule comprising the Cas12a tracrRNA and comprising a restriction endonuclease cleavage site that is suitable for insertion of a sequence coding for a functional RNA moiety, and wherein the functional RNA moiety is at least one selected from the group consisting of:

(a) a nucleotide sequence for annealing to a donor polynucleotide;

(b) a nucleotide sequence for annealing to the crRNA 3' extension;

(c) a terminator sequence;

(d) an RNA aptamer;

(e) an enzymatically active RNA sequence;

(f) a detectable label; and (g) an RNA sequence forming at least partially double-stranded RNA.

87. The engineered system of any one of embodiments 49, 50, 56, 57, 64, and 68, wherein the Cas12a tracrRNA is provided as DNA encoding a first RNA molecule comprising the Cas12a tracrRNA and comprising a restriction endonuclease cleavage site that is suitable for insertion of a sequence coding for a functional RNA moiety, wherein the functional RNA moiety comprises RNA forming at least partially double-stranded RNA capable of silencing a gene.

88. The engineered system of any one of embodiments 49, 50, 56, 57, 64, and 68, wherein the Cas12a tracrRNA is provided as DNA encoding a first RNA molecule comprising the Cas12a tracrRNA and comprising a restriction endonuclease cleavage site that is suitable for insertion of a sequence coding for a functional RNA moiety, wherein the functional RNA moiety comprises an RNA sequence for annealing to a donor polynucleotide, and wherein the composition further comprises the donor polynucleotide.

89. The engineered system of any one of embodiments 49, 50, 56, 57, 64, and 68, wherein the Cas12a tracrRNA is provided as a functional RNA molecule comprising the Cas12a tracrRNA and a functional RNA moiety, or as a polynucleotide encoding the functional RNA molecule, and wherein the functional RNA moiety is at least one selected from the group consisting of:

(a) a nucleotide sequence for annealing to a donor polynucleotide;

(b) a nucleotide sequence for annealing to the crRNA 3' extension;

(c) a terminator sequence;

(d) an RNA aptamer;

(e) an enzymatically active RNA sequence;

(f) a detectable label; and (g) an RNA sequence forming at least partially double-stranded RNA.

90. The engineered system of any one of embodiments 49, 50, 56, 57, 64, and 68, wherein the Cas12a tracrRNA is provided as a functional RNA molecule comprising the Cas12a tracrRNA and a functional RNA moiety, or as a polynucleotide encoding the functional RNA molecule, and wherein the functional RNA moiety comprises RNA forming at least partially double-stranded RNA capable of silencing a gene.

91. The engineered system of any one of embodiments 49, 50, 56, 57, 64, and 68, wherein the Cas12a tracrRNA is provided as a functional RNA molecule comprising the Cas12a tracrRNA and a functional RNA moiety, or as a polynucleotide encoding the functional RNA molecule, wherein the functional RNA moiety comprises an RNA sequence for annealing to a donor polynucleotide, and wherein the system further comprises the donor polynucleotide.

92. The engineered system of any one of embodiments 49, 50, 56, 57, 64, and 68, wherein the Cas12a tracrRNA is provided in a molar excess, relative to the amount of Cas12a nuclease.

93. The engineered system of any one of embodiments 49, 50, 56, 57, 64, and 68, wherein the Cas12a tracrRNA is provided in a molar amount that is at least 10-fold greater than the molar amount of the Cas12a nuclease.

94. A delivery particle comprising the engineered system of any one of embodiments 49, 50, 56, 57, 64, and 68.

95. The delivery particle of embodiment 94, wherein the Cas12a nuclease is complexed with the engineered Cas12a crRNA polynucleotide.

96. The delivery particle of embodiment 94, wherein the Cas12a tracrRNA is present in a molar excess, relative to the amount of Cas12a nuclease.

97. The delivery particle of embodiment 94, wherein the Cas12a tracrRNA is present in a molar amount that is at least 10-fold greater than the molar amount of the Cas12a nuclease.

98. A delivery liquid comprising the engineered system of any one of embodiments 49, 50, 56, 57, 64, and 68.

99. The delivery liquid of embodiment 98, wherein the Cas12a nuclease is complexed with the engineered Cas12a crRNA polynucleotide.

100. The delivery liquid of embodiment 98, wherein the Cas12a tracrRNA is present in a molar excess, relative to the amount of Cas12a nuclease.

101. The delivery liquid of embodiment 98, wherein the Cas12a tracrRNA is present in a molar amount that is at least 10-fold greater than the molar amount of the Cas12a nuclease.

102. A method of modifying a target sequence in a locus of interest of a eukaryotic cell comprising delivering the engineered system according to any one of embodiments 49, 50, 56, 57, 64, and 68 to the locus of interest, wherein the spacer sequence hybridizes with the target sequence, whereby modification of the locus of interest occurs.

103. The method of embodiment 102, wherein the locus of interest is within a eukaryotic cell.

104. The method of embodiment 102, wherein the eukaryotic cell is a plant cell.

105. The method of embodiment 102, wherein the eukaryotic cell is a non-human animal cell or a human cell.

106. The method of embodiment 102, wherein the engineered system or a component thereof is delivered via delivery particles, delivery vesicles, delivery liquids, or one or more viral or bacterial vectors.

107. The method of embodiment 102, wherein the engineered system or a component thereof is delivered via delivery particles comprising at least one selected from the group consisting of a lipid, a sugar, a metal, or a protein.

108. The method of embodiment 102, wherein the engineered system or a component thereof is delivered via delivery exosomes or liposomes.

109. The method of embodiment 102, wherein the engineered system or a component thereof is delivered via at least one viral vector selected from the group consisting of adenoviruses, lentiviruses, adeno-associated viruses, retroviruses, geminiviruses, begomoviruses, tobamoviruses, potex viruses, comoviruses, wheat streak mosaic virus, barley stripe mosaic virus, bean yellow dwarf virus, bean pod mottle virus, cabbage leaf curl virus, beet curly top virus, tobacco yellow dwarf virus, tobacco rattle virus, potato virus X, and cowpea mosaic virus.

110. The method of embodiment 102, wherein the system or a component thereof is delivered via at least one bacterial vector capable of transforming a plant cell and selected from the group consisting of *Agrobacterium* sp., *Rhizobium* sp., *Sinorhizobium* (Ensifer) sp., *Mesorhizobium* sp., *Bradyrhizobium* sp., *Azobacter* sp., and *Phyllobacterium* sp.

111. The method of embodiment 102, wherein the Cas12a nuclease is:
- (a) a Cas12a nuclease identified from the genome of a bacterial species selected from the group consisting of *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*; or
- (b) a Cas12a nuclease selected from the group consisting of LbCas12a, AsCas12a, FnCas12a, and a deactivated Cas12a nuclease; or
- (c) a Cas12a nuclease having at least 80% sequence identity with a sequence selected from the group consisting of SEQ ID NOs:11, 107-114, 116-136, and 172; or
- (d) a Cas12a nuclease variant selected from the group consisting of (1) a variant LbCpf1 that differs from a wild-type LbCpf1 sequence (SEQ ID NO:135) in containing at least one point mutation selected from the group consisting of G309P, Y312F, M474I, D523N, Q531K, C930A, D937N, V954F/Q, M975L, A984E, I994L, T1006K, I1014V, V1055N/D, L1065F/Y, Y1180F, V1209G, I1229L, V801I, Y802I, D850A, E943A, and D1198A; (2) a variant AsCpf1 that differs from a wild-type AsCpf1 sequence (SEQ ID NO:134) in containing at least one point mutation selected from the group consisting of L320P, V980A, Q987N, T1004F/Q, K1035E, T1057K, D1107N, F1117Y, N1291L, D908A, E993A, and D1263A; and (3) a variant FnCpf1 that differs from a wild-type FnCpf1 sequence (SEQ ID NO:172) in containing at least one point mutation selected from the group consisting of I339P, L342F, Q588K, F1017Q, K1047E, N1118D, F1128Y, L867I, D917A, E1006A, and D1255A.

112. The method of embodiment 102, wherein the Cas12a nuclease comprises one or more of:
- (a) a localization signal;
- (b) a detectable label;
- (c) a cell-penetrating peptide;
- (d) an endosomal escape peptide; and
- (e) and affinity tag.

113. The method of embodiment 102, wherein the Cas12a tracrRNA has a nucleotide sequence comprising a sequence selected from the group consisting of SEQ ID NOs:1, 3, 6, 139-146, and 149-169.

114. The method of embodiment 102, wherein the tracrRNA is a putative Cas12a tracrRNA that is identified from the same genomic region as the Cas12a nuclease by at least the following steps:
- (a) identifying in the genomic region flanking the DNA encoding the Cas12a nuclease at least one nucleotide sequence that comprises a CRISPR array including direct repeats;
- (b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat.

115. The method of embodiment 102, wherein the eukaryotic cell comprises a cell of a cell line or a cell of a multicellular organism, and wherein the locus of interest comprises a locus of interest in the genome of the eukaryotic cell.

116. The method of embodiment 102, wherein the eukaryotic cell is in vitro, ex vivo, or in vivo.

117. The method of embodiment 102, wherein the eukaryotic cell comprises a non-human animal or human stem cell or a non-human animal or human stem cell line.

118. The method of embodiment 102, wherein the locus of interest is within a eukaryotic DNA molecule in vitro.

119. The method of embodiment 102, wherein the eukaryotic cell comprises a plant cell, and wherein the modification of the locus of interest is correlated with a modified trait in a plant comprising cells containing the modification of the locus of interest.

120. The method of embodiment 119, wherein the method further comprises obtaining, growing, or regenerating a plant from the plant cell, wherein the plant comprises cells containing the modification of the locus of interest, and wherein the plant exhibits the modified trait effected by the modification of the locus of interest.

121. The method of embodiment 102, wherein the eukaryotic cell comprises a plant cell, and the method further comprises identifying a trait of interest in a plant obtained, grown, or regenerated from the plant cell, wherein the trait of interest is effected by the modification of the locus of interest.

122. The method of embodiment 121, further comprising:
- (a) introducing a nucleotide sequence comprising the locus of interest into a plant cell, a plant cell line, or a plant germplasm, and generating from the plant cell, the plant cell line, or the plant germplasm a plant comprising cells containing the nucleotide sequence comprising the locus of interest; or
- (b) introducing the modified locus of interest into a plant cell, a plant cell line, or a plant germplasm, and generating from the plant cell, the plant cell line, or the plant germplasm a plant comprising cells containing the modified locus of interest; or
- (c) modifying expression of the locus of interest in a plant cell, a plant cell line, or a plant germplasm, and generating from the plant cell, the plant cell line, or the plant germplasm a plant comprising cells containing the locus of interest having modified expression; or
- (d) deleting the locus of interest or an endogenous nucleotide sequence comprising the locus of interest in a plant cell, and generating from the plant cell, the plant cell line, or the plant germplasm a plant comprising cells in which the locus of interest or the endogenous nucleotide sequence comprising the locus of interest has been deleted.

123. A method of editing a genetic locus with a Cas12a nuclease, comprising contacting DNA that comprises the genetic locus with:
(a) a Cas12a nuclease; and
(b) an engineered Cas12a crRNA that includes a spacer sequence that is designed to hybridize with a target sequence in the genetic locus; and
(c) a Cas12a tracrRNA, thereby editing the genetic locus;
wherein the efficiency of editing of the genetic locus is increased compared to a control method in which the DNA that comprises the genetic locus is contacted with the Cas12a nuclease and the Cas12a crRNA, but not the Cas12a tracrRNA.

124. The method of embodiment 123, wherein the Cas12a nuclease and the engineered Cas12a crRNA are provided as a ribonucleoprotein complex.

125. The method of embodiment 123, wherein the Cas12a nuclease is provided as a polynucleotide encoding the Cas12a nuclease.

126. The method of embodiment 123, wherein the Cas12a tracrRNA is provided:
(a) as DNA encoding a first RNA molecule comprising the Cas12a tracrRNA and comprising a restriction endonuclease cleavage site that is suitable for insertion of a sequence coding for a functional RNA moiety; or
(b) as a functional RNA molecule comprising the Cas12a tracrRNA and a functional RNA moiety, or as a polynucleotide encoding the functional RNA molecule; or
(c) by the DNA expression system of embodiment 18; or
(d) by the DNA expression system of embodiment 37.

127. The method of embodiment 123, wherein the DNA that comprises the genetic locus is genomic DNA.

128. The method of embodiment 123, wherein the DNA that comprises the genetic locus is in a eukaryotic DNA molecule in vitro.

129. The method of embodiment 123, wherein the DNA that comprises the genetic locus is in a eukaryotic cell.

130. The method of embodiment 129, wherein the eukaryotic cell is a cell of anon-human animal, an invertebrate, a vertebrate, a mollusk, an arthropod, an insect, a fish, a reptile, an amphibian, a bird, a mammal, a primate, a non-human primate, a human, a plant, or a fungus.

131. The method of embodiment 129, wherein the eukaryotic cell comprises a cell of a cell line or a cell of a multicellular organism, and wherein the genetic locus to be modified comprises a locus of interest in the genome of the eukaryotic cell.

132. The method of embodiment 129, wherein the eukaryotic cell is in vitro, ex vivo, or in vivo.

133. The method of embodiment 129, wherein the eukaryotic cell comprises a non-human animal or human stem cell or a non-human animal or human stem cell line.

134. The method of embodiment 123, wherein the Cas12a tracrRNA is a putative tracrRNA.

135. The method of embodiment 134, wherein the putative Cas12a tracrRNA is identified from the same genomic region as the Cas12a nuclease by at least the following steps:
(a) identifying in the genomic region flanking the DNA encoding the Cas12a nuclease at least one nucleotide sequence that comprises a CRISPR array including direct repeats;
(b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat.

136. The method of embodiment 123, wherein the Cas12a tracrRNA is provided in a molar excess, relative to the Cas12a nuclease.

137. The method of embodiment 123, wherein the Cas12a tracrRNA is provided in a molar amount that is at least 10-fold greater than the molar amount of the Cas12a nuclease.

138. The method of embodiment 123, wherein the engineered Cas12a crRNA, or a polynucleotide encoding the engineered Cas12a crRNA, further comprises at least one direct repeat sequence or fragment thereof capable of associating with the Cas12a nuclease adjacent to and 3' to the spacer sequence.

139. The method of embodiment 123, wherein the engineered Cas12a crRNA further comprises a 3' extension adjacent to the spacer sequence.

140. The method of embodiment 123, wherein the 3' extension comprises nucleotides that when base-paired form about one helical turn.

141. The method of embodiment 123, wherein the 3' extension comprises at least 10 contiguous nucleotides.

142. The method of embodiment 123, wherein the Cas12a tracrRNA has a nucleotide sequence having sufficient complementarity to the engineered Cas12a crRNA's 3' extension to allow hybridization between the tracrRNA and the engineered Cas12a crRNA.

143. The method of embodiment 123, wherein the editing of the genetic locus is effecting an indel in the genetic locus.

144. The method of embodiment 123, wherein the editing of the genetic locus is effecting non-homologous end joining (NHEJ) in the genetic locus.

145. The method of embodiment 123, wherein the editing of the genetic locus is effecting homology-dependent repair (HDR) in the genetic locus.

146. A composition for modifying a genetic locus in a eukaryotic cell, comprising:
(a) a eukaryotic cell containing a genetic locus to be modified; and
(b) a Cas12a nuclease, or a polynucleotide encoding the Cas12a nuclease; and
(c) an engineered Cas12a crRNA that includes a spacer sequence corresponding to a specific sequence in the genetic locus, or a polynucleotide encoding the Cas12a crRNA; and
(d) a Cas12a tracrRNA, or a polynucleotide encoding the Cas12a tracrRNA, wherein the Cas12a tracrRNA is provided in molar excess relative to the Cas12a nuclease.

147. The composition of embodiment 146, wherein the Cas12a tracrRNA is identified from the same genomic region as the Cas12a nuclease by at least the following steps:

(a) identifying in the genomic region flanking the DNA encoding the Cas12a nuclease at least one nucleotide sequence that comprises a CRISPR array including direct repeats;

(b) identifying as a putative Cas12a tracrRNA at least one nucleotide sequence in either the sense or antisense direction in the genomic region flanking the DNA encoding the Cas12a nuclease, wherein the putative Cas12a tracrRNA has a nucleotide sequence that has at least 50% complementarity with, the nucleotide sequence of the direct repeat.

148. The composition of embodiment 146, wherein the Cas12a tracrRNA is present in a molar excess, relative to the Cas12a nuclease.

149. The composition of embodiment 146, wherein the Cas12a tracrRNA is present in a molar amount that is at least 10-fold greater than the molar amount of the Cas12a nuclease.

150. The composition of embodiment 146, wherein the eukaryotic cell is a cell of a non-human animal, an invertebrate, a vertebrate, a mollusk, an arthropod, an insect, a fish, a reptile, an amphibian, a bird, a mammal, a primate, a non-human primate, a human, a plant, or a fungus.

151. The composition of embodiment 146, wherein the eukaryotic cell comprises a cell of a cell line or a cell of a multicellular organism, and wherein the genetic locus to be modified comprises a locus of interest in the genome of the eukaryotic cell.

152. The composition of embodiment 146, wherein the eukaryotic cell is in vitro, ex vivo, or in vivo.

153. The composition of embodiment 146, wherein the eukaryotic cell comprises a non-human animal or human stem cell or a non-human animal or human stem cell line.

154. The composition of embodiment 146, wherein the Cas12a tracrRNA is provided:

(a) as DNA encoding a first RNA molecule comprising the Cas12a tracrRNA and comprising a restriction endonuclease cleavage site that is suitable for insertion of a sequence coding for a functional RNA moiety; or (b) as a functional RNA molecule comprising the Cas12a tracrRNA and a functional RNA moiety, or as a polynucleotide encoding the functional RNA molecule; or (c) by the DNA expression system of embodiment 18; or (d) by the DNA expression system of embodiment 37.

155. The composition of embodiment 146, wherein the Cas12a tracrRNA is provided as DNA encoding a first RNA molecule comprising the Cas12a tracrRNA and comprising a restriction endonuclease cleavage site that is suitable for insertion of a sequence coding for a functional RNA moiety, and wherein the functional RNA moiety is at least one selected from the group consisting of:

(a) a nucleotide sequence for annealing to a donor polynucleotide;

(b) a nucleotide sequence for annealing to the crRNA 3' extension;

(c) a terminator sequence;

(d) an RNA aptamer;

(e) an enzymatically active RNA sequence;

(f) a detectable label; and (g) an RNA sequence forming at least partially double-stranded RNA.

156. The composition of embodiment 146, wherein the Cas12a tracrRNA is provided as DNA encoding a first RNA molecule comprising the Cas12a tracrRNA and comprising a restriction endonuclease cleavage site that is suitable for insertion of a sequence coding for a functional RNA moiety, wherein the functional RNA moiety comprises RNA forming at least partially double-stranded RNA capable of silencing a gene.

157. The composition of embodiment 146, wherein the Cas12a tracrRNA is provided as DNA encoding a first RNA molecule comprising the Cas12a tracrRNA and comprising a restriction endonuclease cleavage site that is suitable for insertion of a sequence coding for a functional RNA moiety, wherein the functional RNA moiety comprises an RNA sequence for annealing to a donor polynucleotide, and wherein the composition further comprises the donor polynucleotide.

158. The composition of embodiment 146, wherein the Cas12a tracrRNA is provided as a functional RNA molecule comprising the Cas12a tracrRNA and a functional RNA moiety, or as a polynucleotide encoding the functional RNA molecule, and wherein the functional RNA moiety is at least one selected from the group consisting of:

(a) a nucleotide sequence for annealing to a donor polynucleotide;

(b) a nucleotide sequence for annealing to the crRNA 3' extension;

(c) a terminator sequence;

(d) an RNA aptamer;

(e) an enzymatically active RNA sequence;

(f) a detectable label; and (g) an RNA sequence forming at least partially double-stranded RNA.

159. The composition of embodiment 146, wherein the Cas12a tracrRNA is provided as a functional RNA molecule comprising the Cas12a tracrRNA and a functional RNA moiety, or as a polynucleotide encoding the functional RNA molecule, and wherein the functional RNA moiety comprises RNA forming at least partially double-stranded RNA capable of silencing a gene.

160. The composition of embodiment 146, wherein the Cas12a tracrRNA is provided as a functional RNA molecule comprising the Cas12a tracrRNA and a functional RNA moiety, or as a polynucleotide encoding the functional RNA molecule, wherein the functional RNA moiety comprises an RNA sequence for annealing to a donor polynucleotide, and wherein the composition further comprises the donor polynucleotide.

161. The method of any one of embodiments 102-122, wherein modification of the locus of interest occurs at a greater frequency compared to a control method, wherein a control engineered system identical to the engineered system except for the absence of the Cas12a tracrRNA is delivered to the locus of interest.

162. A method of modifying a target sequence in a locus of interest of a eukaryotic cell comprising delivering the engineered system according to embodiment 92 or 93 to the locus of interest, wherein the spacer sequence hybridizes with the target sequence, whereby modification of the locus of interest occurs at a greater frequency compared to a control method, wherein a control engineered system identical to the engineered system except for the absence of the Cas12a tracrRNA is delivered to the locus of interest.

All cited patents and patent publications referred to in this application are incorporated herein by reference in their entirety. All of the materials and methods disclosed and claimed herein can be made and used without undue experimentation as instructed by the above disclosure and illustrated by the examples. Although the materials and methods of this disclosure have been described in terms of embodiments and illustrative examples, it will be apparent to those of skill in the art that substitutions and variations can be applied to the materials and methods described herein without departing from the concept, spirit, and scope of the invention. For instance, while the particular examples provided illustrate the methods and embodiments described herein using a specific plant, the principles in these examples are applicable to any plant of interest. All such similar substitutes and modifications apparent to those skilled in the art are deemed to be within the spirit, scope, and concept of the invention as encompassed by the embodiments of the inventions recited herein and the specification and appended claims.

What is claimed:

1. A composition for modifying a genetic locus in a eukaryotic cell, comprising:

(a) a eukaryotic cell containing a genetic locus to be modified; and (b) a Cas12a nuclease, or a polynucleotide encoding the Cas12a nuclease; and (c) an engineered Cas12a crRNA that includes a spacer sequence corresponding to a specific sequence in the genetic locus, or a polynucleotide encoding the Cas12a crRNA; and (d) a Cas12a tracrRNA, or a polynucleotide encoding the Cas12a tracrRNA, wherein the Cas12a tracrRNA is present in a molar amount that is at least 10-fold greater than the molar amount of the Cas12a nuclease and the engineered Cas12a crRNA.

2. The composition of claim 1, wherein the Cas12a tracrRNA:

(a) is identified from the same genomic region as the Cas12a nuclease by at least the following steps:

(i) identifying in the genomic region flanking the DNA encoding the Cas12a nuclease at least one nucleotide sequence that comprises a CRISPR array including direct repeats; and (ii) identifying as a putative Cas12a tracrRNA at least one nucleotide sequence in either the sense or anti-sense direction in the genomic region flanking the DNA encoding the Cas12a nuclease, wherein the putative Cas12a tracrRNA has a nucleotide sequence that has at least 50% complementarity with the nucleotide sequence of the direct repeat;

or (b) has a nucleotide sequence comprising a sequence selected from the group consisting of SEQ ID NOs:1, 3, 6, 139-146, and 149-169.

3. The composition of claim 1, wherein the genetic locus in a eukaryotic cell is:

(a) in genomic nuclear DNA of a non-human animal, a human, a plant, or a fungus, or in DNA of a eukaryotic organelle;

(b) in a eukaryotic DNA molecule in vitro;

(c) in a eukaryotic cell, cell line, tissue, callus, or multi-cellular organism.

4. The composition of claim 1, wherein the eukaryotic cell is:

(a) a cell of a non-human animal, a human, a plant, or a fungus; or (b) a cell of a cell line or a cell of a multicellular organism, and wherein the genetic locus to be modified comprises a locus of interest in the genome of the eukaryotic cell; or (c) a eukaryotic cell in vitro, ex vivo, or in vivo.

5. The composition of claim 1, wherein the Cas12a tracrRNA is provided:

(a) as DNA encoding a first RNA molecule comprising the Cas12a tracrRNA and comprising a restriction endonuclease cleavage site that is suitable for insertion of a sequence coding for a functional RNA moiety; or (b) as a functional RNA molecule comprising the Cas12a tracrRNA and a functional RNA moiety, or as a polynucleotide encoding the functional RNA molecule; or (c) by a DNA expression system comprising (i) DNA sequence for a first promoter; and (ii) operably linked and heterologous to the first promoter, DNA encoding a first RNA molecule comprising a Cas12a tracrRNA and comprising a restriction endonuclease cleavage site that is suitable for insertion of a sequence coding for a functional RNA moiety; and (iii) optionally, a terminator 3' to and operably linked to the DNA encoding the first RNA molecule; or (d) by a DNA expression system comprising: (i) DNA sequence for a first promoter; and (ii) operably linked and heterologous to the first promoter, a DNA encoding a functional RNA molecule comprising a Cas12a tracrRNA and a functional RNA moiety; and (iii) optionally, a terminator 3' to and operably linked to the DNA encoding a functional RNA molecule; or (e) as a Cas12a tracrRNA synthesized in vitro; or (f) as a Cas12a tracrRNA obtained from a naturally occurring source.

6. The composition of claim 1, wherein the Cas12a tracrRNA is provided as a functional RNA molecule comprising the Cas12a tracrRNA and a functional RNA moiety, or as a polynucleotide encoding the functional RNA molecule, wherein the functional RNA moiety comprises an RNA sequence for annealing to a donor polynucleotide, and wherein the composition further comprises the donor polynucleotide.

* * * * *

SEQUENCE LISTING

```
<160> NUMBER OF SEQ ID NOS: 203

<210> SEQ ID NO 1
<211> LENGTH: 84
<212> TYPE: RNA
<213> ORGANISM: Unknown
<220> FEATURE:
<223> OTHER INFORMATION: Lachnospiraceae bacterium ND2006

<400> SEQUENCE: 1

acuuauacua aauuuuaacu guauacuuuc ccaaaauacc auaggcucuc ugaaucucuu     60

aacccagauu ccaagggcuu uuuu                                            84


<210> SEQ ID NO 2
<211> LENGTH: 84
<212> TYPE: DNA
<213> ORGANISM: Unknown
<220> FEATURE:
<223> OTHER INFORMATION: Lachnospiraceae bacterium ND2006

<400> SEQUENCE: 2

acttatacta aattttaact gtatactttc ccaaaatacc ataggctctc tgaatctctt     60

aacccagatt ccaagggctt tttt                                            84


<210> SEQ ID NO 3
<211> LENGTH: 65
<212> TYPE: RNA
<213> ORGANISM: Unknown
<220> FEATURE:
<223> OTHER INFORMATION: Lachnospiraceae bacterium ND2006

<400> SEQUENCE: 3

aauugcaaau cuuugaaaua augcagacuu aaauuuauaa auucauggaa uaaggugauu     60

uuauu                                                                 65


<210> SEQ ID NO 4
<211> LENGTH: 65
<212> TYPE: DNA
<213> ORGANISM: Unknown
<220> FEATURE:
<223> OTHER INFORMATION: Lachnospiraceae bacterium ND2006

<400> SEQUENCE: 4

aattgcaaat ctttgaaata atgcagactt aaatttataa attcatggaa taaggtgatt     60

ttatt                                                                 65


<210> SEQ ID NO 5
<211> LENGTH: 36
<212> TYPE: DNA
<213> ORGANISM: Unknown
<220> FEATURE:
```

<223> OTHER INFORMATION: Lachnospiraceae bacterium ND2006

<400> SEQUENCE: 5
atctacactt agtagaaatt atttaatctt tgaaac 36

<210> SEQ ID NO 6
<211> LENGTH: 72
<212> TYPE: RNA
<213> ORGANISM: Unknown
<220> FEATURE:
<223> OTHER INFORMATION: Acidaminococcus sp. BV3L6

<400> SEQUENCE: 6
cauugucuaa ccugcaaacc uccaacuuac uauugcuaag gaguauauau uuuguauaaa 60
aggucuuuuu uc 72

<210> SEQ ID NO 7
<211> LENGTH: 72
<212> TYPE: DNA
<213> ORGANISM: Unknown
<220> FEATURE:
<223> OTHER INFORMATION: Acidaminococcus sp. BV3L6

<400> SEQUENCE: 7
cattgtctaa cctgcaaacc tccaacttac tattgctaag gagtatatat tttgtataaa 60
aggtcttttt tc 72

<210> SEQ ID NO 8
<211> LENGTH: 35
<212> TYPE: DNA
<213> ORGANISM: Unknown
<220> FEATURE:
<223> OTHER INFORMATION: Acidaminococcus sp. BV3L6

<400> SEQUENCE: 8
atctacaaga gtagaaatta aaaaggtctt ttgac 35

<210> SEQ ID NO 9
<211> LENGTH: 128
<212> TYPE: DNA
<213> ORGANISM: Unknown
<220> FEATURE:
<223> OTHER INFORMATION: Lachnospiraceae bacterium ND2006

<400> SEQUENCE: 9
aattgcaaat ctttgaaata atgcagactt aaatttataa attcatggaa taaggtgatt 60
ttattgtgaa aaaatactcg tattttgttg gaaaaacatc tttttgttgt ataatatgat 120
gatatacg 128

<210> SEQ ID NO 10
<211> LENGTH: 141
<212> TYPE: DNA
<213> ORGANISM: Artificial sequence
<220> FEATURE:
<223> OTHER INFORMATION: Synthetic construct

<400> SEQUENCE: 10
gttttagagc taggccaaca tgaggatcac ccatgtctgc agggcctagc aagttaaaat 60
aaggctagtc cgttatcaac ttggccaaca tgaggatcac ccatgtctgc agggccaagt 120
ggcaccgagt cggtgctttt t 141

<210> SEQ ID NO 11
<211> LENGTH: 1246
<212> TYPE: PRT
<213> ORGANISM: Artificial sequence
<220> FEATURE:
<223> OTHER INFORMATION: Synthetic construct

<400> SEQUENCE: 11

```
Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
        115                 120                 125

Gly Asn Glu Gly Tyr Lys Ser Leu Phe Lys Lys Asp Ile Ile Glu Thr
    130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
        195                 200                 205

Glu Lys Val Asp Ala Ile Phe Asp Lys His Glu Val Gln Glu Ile Lys
    210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
                245                 250                 255

Ala Ile Ile Gly Gly Phe Val Thr Glu Ser Gly Glu Lys Ile Lys Gly
            260                 265                 270

Leu Asn Glu Tyr Ile Asn Leu Tyr Asn Gln Lys Thr Lys Gln Lys Leu
        275                 280                 285

Pro Lys Phe Lys Pro Leu Tyr Lys Gln Val Leu Ser Asp Arg Glu Ser
    290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
            340                 345                 350

Gly Ile Phe Val Lys Asn Gly Pro Ala Ile Ser Thr Ile Ser Lys Asp
        355                 360                 365

Ile Phe Gly Glu Trp Asn Val Ile Arg Asp Lys Trp Asn Ala Glu Tyr
```

-continued

```
    370                 375                 380

Asp Asp Ile His Leu Lys Lys Lys Ala Val Val Thr Glu Lys Tyr Glu
385                 390                 395                 400

Asp Asp Arg Arg Lys Ser Phe Lys Lys Ile Gly Ser Phe Ser Leu Glu
                405                 410                 415

Gln Leu Gln Glu Tyr Ala Asp Ala Asp Leu Ser Val Val Glu Lys Leu
            420                 425                 430

Lys Glu Ile Ile Ile Gln Lys Val Asp Glu Ile Tyr Lys Val Tyr Gly
        435                 440                 445

Ser Ser Glu Lys Leu Phe Asp Ala Asp Phe Val Leu Glu Lys Ser Leu
    450                 455                 460

Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Glu Gly Lys
                485                 490                 495

Glu Thr Asn Arg Asp Glu Ser Phe Tyr Gly Asp Phe Val Leu Ala Tyr
            500                 505                 510

Asp Ile Leu Leu Lys Val Asp His Ile Tyr Asp Ala Ile Arg Asn Tyr
        515                 520                 525

Val Thr Gln Lys Pro Tyr Ser Lys Asp Lys Phe Lys Leu Tyr Phe Gln
    530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
            580                 585                 590

Asn Gly Asn Tyr Glu Lys Ile Asn Tyr Lys Leu Leu Pro Gly Pro Asn
        595                 600                 605

Lys Met Leu Pro Lys Val Phe Phe Ser Lys Lys Trp Met Ala Tyr Tyr
    610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
            660                 665                 670

Phe Asn Phe Ser Glu Thr Glu Lys Tyr Lys Asp Ile Ala Gly Phe Tyr
        675                 680                 685

Arg Glu Val Glu Glu Gln Gly Tyr Lys Val Ser Phe Glu Ser Ala Ser
    690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
            740                 745                 750

Gln Ile Arg Leu Ser Gly Gly Ala Glu Leu Phe Met Arg Arg Ala Ser
        755                 760                 765

Leu Lys Lys Glu Glu Leu Val Val His Pro Ala Asn Ser Pro Ile Ala
    770                 775                 780

Asn Lys Asn Pro Asp Asn Pro Lys Lys Thr Thr Thr Leu Ser Tyr Asp
785                 790                 795                 800
```

-continued

```
Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
            820                 825                 830

Glu Val Arg Val Leu Leu Lys His Asp Asp Asn Pro Tyr Val Ile Gly
        835                 840                 845

Ile Ala Arg Gly Glu Arg Asn Leu Leu Tyr Ile Val Val Val Asp Gly
    850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
            900                 905                 910

Asn Ile Lys Glu Leu Lys Ala Gly Tyr Ile Ser Gln Val Val His Lys
        915                 920                 925

Ile Cys Glu Leu Val Glu Lys Tyr Asp Ala Val Ile Ala Leu Glu Asp
    930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
            980                 985                 990

Gln Ile Thr Asn Lys Phe Glu Ser  Phe Lys Ser Met Ser  Thr Gln Asn
        995                 1000                1005

Gly Phe  Ile Phe Tyr Ile Pro  Ala Trp Leu Thr Ser  Lys Ile Asp
    1010                1015                1020

Pro Ser  Thr Gly Phe Val Asn  Leu Leu Lys Thr Lys  Tyr Thr Ser
    1025                1030                1035

Ile Ala  Asp Ser Lys Lys Phe  Ile Ser Ser Phe Asp  Arg Ile Met
    1040                1045                1050

Tyr Val  Pro Glu Glu Asp Leu  Phe Glu Phe Ala Leu  Asp Tyr Lys
    1055                1060                1065

Asn Phe  Ser Arg Thr Asp Ala  Asp Tyr Ile Lys Lys  Trp Lys Leu
    1070                1075                1080

Tyr Ser  Tyr Gly Asn Arg Ile  Arg Ile Phe Arg Asn  Pro Lys Lys
    1085                1090                1095

Asn Asn  Val Phe Asp Trp Glu  Glu Val Cys Leu Thr  Ser Ala Tyr
    1100                1105                1110

Lys Glu  Leu Phe Asn Lys Tyr  Gly Ile Asn Tyr Gln  Gln Gly Asp
    1115                1120                1125

Ile Arg  Ala Leu Leu Cys Glu  Gln Ser Asp Lys Ala  Phe Tyr Ser
    1130                1135                1140

Ser Phe  Met Ala Leu Met Ser  Leu Met Leu Gln Met  Arg Asn Ser
    1145                1150                1155

Ile Thr  Gly Arg Thr Asp Val  Asp Phe Leu Ile Ser  Pro Val Lys
    1160                1165                1170

Asn Ser  Asp Gly Ile Phe Tyr  Asp Ser Arg Asn Tyr  Glu Ala Gln
    1175                1180                1185

Glu Asn  Ala Ile Leu Pro Lys  Asn Ala Asp Ala Asn  Gly Ala Tyr
    1190                1195                1200
```

```
Asn Ile  Ala Arg Lys Val Leu  Trp Ala Ile Gly Gln  Phe Lys Lys
    1205                 1210                 1215

Ala Glu  Asp Glu Lys Leu Asp  Lys Val Lys Ile Ala  Ile Ser Asn
    1220                 1225                 1230

Lys Glu  Trp Leu Glu Tyr Ala  Gln Thr Ser Val Lys  His
    1235                 1240                 1245
```

<210> SEQ ID NO 12
<211> LENGTH: 72
<212> TYPE: DNA
<213> ORGANISM: Artificial sequence
<220> FEATURE:
<223> OTHER INFORMATION: Synthetic construct

<400> SEQUENCE: 12

```
gtttcaaaga ttaaataatt tctactaagt gtagattgga cagagctcca agtgaccaaa     60

accgtatatc at                                                         72
```

<210> SEQ ID NO 13
<211> LENGTH: 678
<212> TYPE: DNA
<213> ORGANISM: Zea mays

<400> SEQUENCE: 13

```
atagagagag aagaggggtc gtgtagtagt gcttaaactg tacatgaaca gcagtagtgt     60

tacagaagct aaactcaacc agagctccac caaagacaaa gagggtctac ttccatcacc    120

gtcttgctcg gtcacttgga gctctgtcca taaattaaac ccatcgtggc atatctgtag    180

gcatctaccc cgtcttcgtc gtccgttcct cactagctac caagaggtcg ccattattgc    240

caacatagag tgtacgtgga tgtctatata tatgcctact tgcacccata tggcataggc    300

gttcgatccc cttagcgcgg aggagagctc ctccggttct tctctaccct tcgcatggaa    360

gttcttgcat tgcttcgttg cttctctagt ttcttccttc tacgtctttc cagcatacgc    420

atgcccctcg tccgccggtt cacgaggcat cgtctgatga tcagtagata ataagcaata    480

taatactgat ctagaatcga gttgttgtac tcttcgcaga taggttcgtt ccttcacata    540

gaagcgagta cagactacag accacacagt atcagctggc acgaaacgaa aatggttact    600

tgcaaattgc atgcacgagc tagaattata ttcttctaat cttcttcgtt gactttctgg    660

cttcagcagg cgcgtgat                                                  678
```

<210> SEQ ID NO 14
<211> LENGTH: 1422
<212> TYPE: DNA
<213> ORGANISM: Artificial sequence
<220> FEATURE:
<223> OTHER INFORMATION: Synthetic construct

<400> SEQUENCE: 14

```
atggcttcaa actttactca gttcgtgctc gtggacaatg gtgggacagg ggatgtgaca     60

gtggctcctt ctaatttcgc taatggggtg gcagagtgga tcagctccaa ctcacggagc    120

caggcctaca aggtgacatg cagcgtcagg cagtctagtg cccagaagag aaagtatacc    180

atcaaggtgg aggtccccaa agtggctacc cagacagtgg gcggagtcga actgcctgtc    240

gccgcttgga ggtcctacct gaacatggag ctcactatcc caattttcgc taccaattct    300

gactgtgaac tcatcgtgaa ggcaatgcag gggctcctca aagacggtaa tcctatccct    360

tccgccatcg ccgctaactc aggtatctac agcgctggag gaggtggaag cggaggagga    420
```

-continued

```
ggaagcggag gaggaggtag cggacctaag aaaaagagga aggtggcggc cgctggatcc    480

ccttcagggc agatcagcaa ccaggccctg gctctggccc ctagctccgc tccagtgctg    540

gcccagacta tggtgccctc tagtgctatg gtgcctctgg cccagccacc tgctccagcc    600

cctgtgctga ccccaggacc accccagtca ctgagcgctc cagtgcccaa gtctacacag    660

gccggcgagg ggactctgag tgaagctctg ctgcacctgc agttcgacgc tgatgaggac    720

ctgggagctc tgctggggaa cagcaccgat cccggagtgt tcacagatct ggcctccgtg    780

gacaactctg agtttcagca gctgctgaat cagggcgtgt ccatgtctca tagtacagcc    840

gaaccaatgc tgatggagta ccccgaagcc attacccggc tggtgaccgg cagccagcgg    900

ccccccgacc ccgctccaac tcccctggga accagcggcc tgcctaatgg gctgtccgga    960

gatgaagact tctcaagcat cgctgatatg gactttagtg ccctgctgtc acagatttcc   1020

tctagtgggc agggaggagg tggaagcggc ttcagcgtgg acaccagtgc cctgctggac   1080

ctgttcagcc cctcggtgac cgtgcccgac atgagcctgc ctgaccttga cagcagcctg   1140

gccagtatcc aagagctcct gtctccccag gagcccccca ggcctcccga ggcagagaac   1200

agcagcccgg attcagggaa gcagctggtg cactacacag cgcagccgct gttcctgctg   1260

gaccccggct ccgtggacac cgggagcaac gacctgccgg tgctgtttga gctgggagag   1320

ggctcctact tctccgaagg ggacggcttc gccgaggacc ccaccatctc cctgctgaca   1380

ggctcggagc ctcccaaagc caaggacccc actgtctcct ga                      1422


<210> SEQ ID NO 15
<211> LENGTH: 138
<212> TYPE: DNA
<213> ORGANISM: Artificial sequence
<220> FEATURE:
<223> OTHER INFORMATION: Synthetic construct

<400> SEQUENCE: 15

atggatgctc ttgacgattt tgacctcgat atgctcgacg ctcttgatga ttttgatctc     60

gacatgctcg atgcacttga tgactttgac cttgacatgc tcgacgcact cgatgacttc    120

gacctcgaca tgctttag                                                  138


<210> SEQ ID NO 16
<211> LENGTH: 400
<212> TYPE: DNA
<213> ORGANISM: Triticum aestivum

<400> SEQUENCE: 16

ggcggcaggg agagttttaa cattgactag cgtgctgata atttgtgaga aataataatt     60

gacaagtaga tactgacatt tgagaagagc ttctgaactg ttattagtaa caaaaatgga    120

aagctgatgc acggaaaaag gaaagaaaaa gccatacttt tttttaggta ggaaaagaaa    180

aagccatacg agactgatgt ctctcagatg ggccgggatc tgtctatcta gcaggcagca    240

gccctaccaa cctcacgggc cagcaattac gagtccttct aaaacgtccc gccgagggcg    300

cgtggccgtg ctgtgcagca gcacgtctaa cattagtccc acctcgccag tttacaggga    360

gcagaaccag cttataagcg gaggcgcggc accaagaagc                          400


<210> SEQ ID NO 17
<211> LENGTH: 299
<212> TYPE: DNA
<213> ORGANISM: Agrobacterium tumefaciens

<400> SEQUENCE: 17
```

gatcatgagc ggagaattaa gggagtcacg ttatgacccc cgccgatgac gcgggacaag 60
ccgttttacg tttggaactg acagaaccgc aacgttgaag gagccactca gccgcgggtt 120
tctggagttt aatgagctaa gcacatacgt cagaaaccat tattgcgcgt tcaaaagtcg 180
cctaaggtca ctatcagcta gcaaatattt cttgtcaaaa atgctccact gacgttccat 240
aaattcccct cggtatccaa ttagagtctc atattcactc tcaatccaaa taatctgca 299

<210> SEQ ID NO 18
<211> LENGTH: 899
<212> TYPE: DNA
<213> ORGANISM: Zea mays

<400> SEQUENCE: 18
tgcagtgcag cgtgacccgg tcgtgcccct ctctagagat aatgagcatt gcatgtctaa 60
gttataaaaa attaccacat atttttttg tcacacttgt ttgaagtgca gtttatctat 120
ctttatacat atatttaaac tttactctac gaataatata atctatagta ctacaataat 180
atcagtgttt tagagaatca tataaatgaa cagttagaca tggtctaaag gacaattgag 240
tattttgaca acaggactct acagttttat ctttttagtg tgcatgtgtt ctcctttttt 300
tttgcaaata gcttcaccta tataatactt catccatttt attagtacat ccatttaggg 360
tttagggtta atggttttta tagactaatt tttttagtac atctatttta ttctatttta 420
gcctctaaat taagaaaact aaaactctat tttagttttt ttatttaata atttagatat 480
aaaatagaat aaaataaagt gactaaaaat taaacaaata ccctttaaga aattaaaaaa 540
actaaggaaa catttttctt gtttcgagta gataatgcca gcctgttaaa cgccgtcgac 600
gagtctaacg gacaccaacc agcgaaccag cagcgtcgcg tcgggccaag cgaagcagac 660
ggcacggcat ctctgtcgct gcctctggac ccctctcgag agttccgctc caccgttgga 720
cttgctccgc tgtcggcatc cagaaattgc gtggcggagc ggcagacgtg agccggcacg 780
gcaggcggcc tcctcctcct ctcacggcac cggcagctac gggggattcc tttcccaccg 840
ctccttcgct ttcccttcct cgcccgccgt aataaataga cacccctcc acaccctct 899

<210> SEQ ID NO 19
<211> LENGTH: 2243
<212> TYPE: DNA
<213> ORGANISM: Solanum lycopersicum

<400> SEQUENCE: 19
atcgtatcca gtgcaccata ttttttggcg attaccactc atattattgt gtttagtaga 60
tattttaggt gcataattga tctcttcttt aaaactaggg gcacttatta ttatacatcc 120
acttgacact tgctttagtt ggctattttt tttattttt attttttgtc aactacccca 180
atttaaattt tatttgatta agatattttt atggacctac tttataatta aaaatatttt 240
ctatttgaaa aggaaggaca aaaatcatac aattttggtc caactactcc tctctttttt 300
tttttggctt tataaaaaag gaaagtgatt agtaataaat aattaaataa tgaaaaaagg 360
aggaaataaa attttcgaat taaaatgtaa aagagaaaaa ggagagggag taatcattgt 420
ttaactttat ctaaagtacc ccaattcgat tttacatgta tatcaaatta tacaaatatt 480
ttattaaaat atagatattg aataatttta ttattcttga acatgtaaat aaaaattatc 540
tattatttca atttttatat aaactattat ttgaaatctc aattatgatt ttttaatatc 600
actttctatc catgataatt tcagcttaaa aagttttgtc aataattaca ttaattttgt 660

```
tgatgaggat gacaagattt cggtcatcaa ttacatatac acaaattgaa atagtaagca    720
acttgatttt ttttctcata atgataatga caaagacacg aaaagacaat tcaatattca    780
cattgattta tttttatatg ataataatta caataataat attcttataa agaaagagat    840
caattttgac tgatccaaaa atttatttat ttttactata ccaacgtcac taattatatc    900
taataatgta aaacaattca atcttactta aatattaatt tgaaataaac tatttttata    960
acgaaattac taaatttatc caataacaaa aaggtcttaa gaagacataa attctttttt   1020
tgtaatgctc aaataaattt gagtaaaaaa gaatgaaatt gagtgatttt tttttaatca   1080
taagaaaata aataattaat ttcaatataa taaaacagta atataatttc ataaatggaa   1140
ttcaatactt acctcttaga tataaaaaat aaatataaaa ataaagtgtt tctaataaac   1200
ccgcaattta aataaaatat ttaatatttt caatcaaatt taaataatta tattaaaata   1260
tcgtagaaaa agagcaatat ataatacaag aaagaagatt taagtacaat tatcaactat   1320
tattatactc taattttgtt atatttaatt tcttacggtt aaggtcatgt tcacgataaa   1380
ctcaaaatac gctgtatgag gacatatttt aaattttaac caataataaa actaagttat   1440
ttttagtata ttttttttgtt taacgtgact taatttttct tttctagagg agcgtgtaag   1500
tgtcaacctc attctcctaa ttttcccaac cacataaaaa aaaaataaag gtagcttttg   1560
cgtgttgatt tggtacacta cacgtcatta ttacacgtgt tttcgtatga ttggttaatc   1620
catgaggcgg tttcctctag agtcggccat accatctata aaataaagct ttctgcagct   1680
catttttttca tcttctatct gatttctatt ataatttctc tgaattgcct tcaaatttct   1740
ctttcaaggt tagaattttt ctctattttt tggtttttgt ttgtttagat tctgagttta   1800
gttaatcagg tgctgttaaa gccctaaatt ttgagttttt ttcggttgtt ttgatggaaa   1860
atacctaaca attgagtttt ttcatgttgt tttgtcggag aatgcctaca attggagttc   1920
ctttcgttgt tttgatgaga aagcccctaa tttgagtgtt tttccgtcga tttgatttta   1980
aaggtttata ttcgagtttt tttcgtcggt ttaatgagaa ggcctaaaat aggagttttt   2040
ctggttgatt tgactaaaaa agccatggaa ttttgtgttt ttgatgtcgc tttggttctc   2100
aaggcctaag atctgagttt ctccggttgt tttgatgaaa aagccctaaa attggagttt   2160
ttatcttgtg ttttaggttg ttttaatcct tataatttga gtttttttcgt tgttctgatt   2220
gttgttttta tgaatttcct gca                                            2243
```

<210> SEQ ID NO 20
<211> LENGTH: 1327
<212> TYPE: DNA
<213> ORGANISM: Arabidopsis thaliana

<400> SEQUENCE: 20

```
gtcgagctgc aggtcaacgg atcaggatat tcttgtttaa gatgttgaac tctatggagg     60
tttgtatgaa ctgatgatct aggaccggat aagttccctt cttcatagcg aacttattca    120
aagaatgttt tgtgtatcat tcttgttaca ttgttattaa tgaaaaaata ttattggtca    180
ttggactgaa cacgagtgtt aaatatggac caggccccaa ataagatcca ttgatatatg    240
aattaaataa caagaataaa tcgagtcacc aaaccacttg cctttttttaa cgagacttgt    300
tcaccaactt gatacaaaag tcattatcct atgcaaatca ataatcatac aaaaatatcc    360
aataacacta aaaaattaaa agaaatggat aatttcacaa tatgttatac gataaagaag    420
ttacttttcc aagaaattca ctgattttat aagcccactt gcattagata aatggcaaaa    480
aaaaacaaaa aggaaaagaa ataaagcacg aagaattcta gaaaatacga aatacgcttc    540
```

aatgcagtgg gacccacggt tcaattattg ccaattttca gctccaccgt atatttaaaa 600
aataaaacga taatgctaaa aaaatataaa tcgtaacgat cgttaaatct caacggctgg 660
atcttatgac gaccgttaga aattgtggtt gtcgacgagt cagtaataaa cggcgtcaaa 720
gtggttgcag ccggcacaca cgagtcgtgt ttatcaactc aaagcacaaa tacttttcct 780
caacctaaaa ataaggcaat tagccaaaaa caactttgcg tgtaaacaac gctcaataca 840
cgtgtcattt tattattagc tattgcttca ccgccttagc tttctcgtga cctagtcgtc 900
ctcgtctttt cttcttcttc ttctataaaa caatacccaa agagctcttc ttcttcacaa 960
ttcagatttc aatttctcaa aatcttaaaa actttctctc aattctctct accgtgatca 1020
aggtaaattt ctgtgttcct tattctctca aaatcttcga ttttgttttc gttcgatccc 1080
aatttcgtat atgttctttg gtttagattc tgttaatctt agatcgaaca cgattttctg 1140
ggtttgatcg ttagatatca tcttaattct cgattagggt ttcatagata tcatccgatt 1200
tgttcaaata atttgagttt tgtcgaataa ttactcttcg atttgtgatt tctatctaga 1260
tctggtgtta gtttctagtt tgtgcgatcg aatttgtcga ttaatctgag tttttctgat 1320
taacagg 1327

<210> SEQ ID NO 21
<211> LENGTH: 872
<212> TYPE: DNA
<213> ORGANISM: Glycine max

<400> SEQUENCE: 21
tccctaatta atgtgatatt gggaaagata cgtatgcaaa gagaatggta attaatgtga 60
gatgaaactg aaaaatgaca aatgagaaat attggaaaaa tcacacgttg aatgaacgtg 120
agtatatgca tgtagaatta gcaggataat gtaattcaaa atggacgaaa aatgtagaat 180
ggagaactta ttcgctttat taataaaaca aaattaattt acgcatgcat tgaggaagac 240
aaaagttaac cgaatccacc ctaattaatg tgatattgag aaagattttt gtttttttggt 300 taatatgata ttggaaaaga tacgttgaaa atataatggt aattaatgtg agaagagact 360
aaaagatgac aaatgagaaa tattggaaaa gtcacgcgtt gaatgaacgg gaatataatg 420
caaaatagac gaaagatgta gaatagagaa cttatttgct ttattaataa aatatgaatt 480
tagttaaatt tgacctaaat tgggccatgt acaaattgta cacaaatata cactaagcat 540
agaaacgaaa atataatata ttatttcgga attttgaaca atattttcca aattttcaat 600
aagcaataac attcaaccac gaattctatt tgtttggtca tgacgtcttt agaggccacg 660
catttgactc ctagaatatt ctggacccac cgtaacaact atccgttact tttcttaatc 720
cctaatcttt caagagttct ggattcttct attcgcccta tataaacaac ccccttttct 780
tcgtgcttca ttcatctcaa tcgcaatctc tcaatcgttt tctacataat acaaacctct 840
ctaatttttg aagctaatta tacccaatct cg 872

<210> SEQ ID NO 22
<211> LENGTH: 1427
<212> TYPE: DNA
<213> ORGANISM: Glycine max

<400> SEQUENCE: 22
aacaattaga tgatacccat tgcccttacg ttttctttaa catcaattat tgtttttgtc 60
aacaagctat cttttagttt tattttattg gtaaaaaata tgtcgccttc aagttgcatc 120

-continued

```
atttaacaca tctcgtcatt agaaaaataa aactcttccc taaacgatta gtagaaaaaa    180

tcattcgata ataaataaga aagaaaaatt agaaaaaaat aacttcattt taaaaaaatc    240

attaaggcta tattttttaa atgactaatt ttatatagac tgtaactaaa agtatacaat    300

ttattatgct atgtatctta aagaattact tataaaaatc tacggaagaa tatcttacaa    360

agtgaaaaac aaatgagaaa gaatttagtg ggatgattat gattttattt gaaaattgaa    420

aaaataatta ttaaagactt tagtggagta agaaagcttt cctattagtc ttttcttatc    480

cataaaaaaa aaaaaaaaaa tctagcgtga cagcttttcc atagatttta ataatgtaaa    540

atactggtag cagccgaccg ttcaggtaat ggacactgtg gtcctaactt gcaacgggtg    600

cgggcccaat ttaataacgc cgtggtaacg gataaagcca agcgtgaagc ggtgaaggta    660

catctctgac tccgtcaaga ttacgaaacc gtcaactacg aaggactccc cgaaatatca    720

tctgtgtcat aaacaccaag tcacaccata catgggcacg cgtcacaata tgattggaga    780

acggttccac cgcatatgct ataaaatgcc cccacacccc tcgaccctaa tcgcacttca    840

attgcaatca aattagttca ttctctttgc gcagttccct acctctcctt tcaaggttcg    900

tagatttctt ctgttttttt ttcttcttct ttattgtttg ttctacatca gcatgatgtt    960

gatttgattg tgttttctat cgtttcatcg attataaatt ttcataatca gaagattcag   1020

cttttattaa tgcaagaacg tccttaattg atgattttat aaccgtaaat taggtctaat   1080

tagagttttt ttcataaaga ttttcagatc cgtttacaac aagccttaat tgttgattct   1140

gtagtcgtag attaaggttt ttttcatgaa ctacttcaga tccgttaaac aacagcctta   1200

tttgttgata cttcactcgt ttttcaagaa attgttcaga tccgttgata aaagccttat   1260

tcgttgattc tgtatggtat ttcaagagat attgctcagg tcctttagca actaccttat   1320

ttgttgattc tgtggccata gattaggatt ttttttcacg aaattgcttc ttgaaattac   1380

gtgatggatt ttgattctga tttatcttgt gattgttgac tctacag                 1427
```

<210> SEQ ID NO 23
<211> LENGTH: 1294
<212> TYPE: DNA
<213> ORGANISM: Glycine max

<400> SEQUENCE: 23

```
tccattattc gggatttagc aaattgtttg tttcttcaat atttgattga atactaattt     60

aaaactaaaa taagagagcg tgacaaatca aaaatatagt gtgttatata atgtttccgt    120

gcaggagatc atataggacc actagttgtt aatcttagtc acaaaacaat acatgtcttg    180

caaagaaaaa atcgtagaca taatctgtta catttttgtt agaaaagttt tgttcagcaa    240

aatgttttca tttaactcga tttgatatgc tgtggttttg gtatttttac acacagtagt    300

ttttttttta attattgtta agcgaattta aaatagttat tattattatt aagaggcttt    360

taaatactga aggtgtaaaa aaaatgcttc aattacttta aaactttaga catcttaatt    420

ttaaccaaaa tatggagcta aaaatgaatc acgaagaaag tatgaaagaa ttcctccatt    480

tttttagcat tttattttgt ctttaaaaat aagaaataaa gtaatatttt aaaaattatt    540

agccagagta aaaaaaattt attaaggctc tttatattta catttttta aatcattaat     600

aatattccta aagtctctta tctatgcaag atttagagtg taatattttt taatttatgt    660

gattaaacaa gtgaagttaa tgaattattg aactcttaaa tactcctaat ttataggtat    720

tgagtgttca aggtgttgaa taatccatta atttcaacca accaaaatat tttgatctaa    780

attttattat tatttgagta gaattcaacc acattcaaag ttgttttctt atgttagagt    840
```

```
aacaactttt tttttttttt tctaaatact cataaatcta atgactcaat tcattcacat    900

gacactttat tttaattatg atgttcaatt tcttagaaaa ttcgaagttt aactttttgg    960

agaccaaatt taaatcaaca tgttattaat tgtatttgac agaaaaaagc ttaaaccaaa   1020

cccattccaa actaaaacat tttaattggt tttggtaatg aatgagttta gttaaagtca   1080

acctaaattt gcaatgtacg cgtttgcgtc gccgtcatta gaggccagaa ttgactccta   1140

gaatattcta gacctaccct aacaactatc cgttactttt cttaatccct aatatttcaa   1200

gagttctaga ttcttctatt cgccctatat aaacaacctc attctcgatt gcttcctaca   1260

ccactaaaat atctctctat tattctcgtt ttca                               1294
```

<210> SEQ ID NO 24
<211> LENGTH: 1176
<212> TYPE: DNA
<213> ORGANISM: Glycine max

<400> SEQUENCE: 24

```
caagcagaac actgagacat agaggaggat tgaagtgcag aaaatatata ttacctctat     60

tctaaaataa gtgtcacatt ttgataaaat aaatcgtttt ttattaaata cactccaatt    120

cttggatttc ttggaattct ccaaaaaaaa aaagagattg tgagatatat taaaaaggtc    180

aataaatctt aaaaaatatt tagttttaaa ataaatttaa aataaattta aaatattgtt    240

agaatgttta tcatcttatt agttggcgac ggataaaaaa atgctattag ttgccgaaaa    300

ggactcataa gccagttgcc ctgtcaacgt gggctcgtgg ttccaattcg tccacgtgtc    360

acaacgtgat tgaaagaggt gcctttgcgt tgctataaaa gcgaagccca caccaaaatc    420

atcatcaatc caaatattta atcctatcct atcgtagcaa agaaagaaag aaagaaaacc    480

ctagcttacc ttttcaactt tcaaggtacc ttctgctcct cttctgtttt cgattaagat    540

ttcggttgtt agggttttat gcttttttttt tttatcgatc atcggacctg tcgagctatt    600

tgaattttga tctggatttt ttttcgtgtc tttgatttta ccgtctatat aattacgcaa    660

cctggtatcc gttttgaaac ttttgttgat tatttggctt tgtttcaaat tatttgttga    720

ttgaaagtga tcctgatgtt atgaggttat atatttaatt tgtcagaact tggggcatgt    780

attgtgtatt gtatacaggt aaaatctcta ttgtttagat ttgttaaagg tattttcctc    840

gtctattttg gatatcaatc tgattgattt atttattgga atcgagttat caaaagcgtt    900

gttgtatttt tgttttgtcc tggctttaat tctgtctatg ttgtatatca ctgcacatgt    960

agttttgtaa cttggttttc cttgttatat tgtttgggag ggtttgatgg actaattttt   1020

caattttttt aagctgtaaa tataatgttg gataattttg ctttcagttc tctgatttgt   1080

attgtctttc cattctctgt tcatgaacat tttaatggtt atgataaaga gttggtgact   1140

gattcattta ttttgttgac tgtattgtat atgtag                             1176
```

<210> SEQ ID NO 25
<211> LENGTH: 1427
<212> TYPE: DNA
<213> ORGANISM: Glycine max

<400> SEQUENCE: 25

```
cataccattg agatccttgt tgagtgtttg agtcctcaat cctcagcaac caatctcaac     60

aaatccacat ggcttacgat tggttccttg cccttgcctt tctccatgga gagaaaaacg    120

tttccatctc gataaaaaag atagaggtaa tacgagagaa ggttaatacg agagacagaa    180
```

```
aatgaaatat ttgaagagat actcattttt attaattgca tggaatgaga agagtggatg    240
gacgatgtat ggaaaatagg tttttctact aatgaagttg acaatatata aatgacagaa    300
ttaaaaaata tattattaat agattagttg gtgacttata aataagatca aatatttctt    360
atagaaggtg atcaatatat aagatcggac ggaatacact ttaaaaaaag attaaaaaaa    420
tattttgtga attcaaaaga attaaaagac aaatttaaat ttaaagtatt aaaaaattat    480
tcataattaa tggattaaaa acatatttaa gaaaaaataa aaattataac aaagagataa    540
atttaggttt taggtggcag aaaagcattt tgtcatcgac gacgttagaa gcaaaatgta    600
gaatcttccg gaccattgta gaaacgtaat ccttatcttg ccgtgcgtgt caatgaccac    660
caccgtacac gtggcaaatc ttaattcgtt cagtttcgga tattttcgtc attgagacat    720
cgcaccaagc tataagtacg acccccttcta cctctaattc atgcatagca attcccaatt    780
cctaattgtt taaacctaat tctcatttct tcatcgttcg attcttctcc tcctaaaggt    840
acggctctgg tttcctctct ctcttgttca ttcttttcgt aatagcaacc ttattagcct    900
tcgtttattg atttttctcc taattacact tcaatttttt cgatttgtgt ttgttacgtc    960
aatctgtata tcttttttgt tgtcgtcgaa tccgaaactt ttcattcgcc tttctgattc   1020
cgtaaatcgt ttgttaagtg caacatcttt ccctgttctt aggtatctga ttgatttctc   1080
tctttctttt tttttttatc agttttgagg aattagggtt cgtgatctga tttgtttctt   1140
taaaatttcc ccggttctta attaggctct gcgatttaat ttcttttatc atatttgaag   1200
aatcatggtt ctttcttggt ttgatttatt gtgcactcag tttctgatat gcaaaatctt   1260
tccctgtttt aattaaggtt tagggtttgc gagttgtcat tttggaaaat agggtttgtg   1320
gtttattgat tgtgtaatcc gtttggttgt aagcagaaac ttctctgttt taaatcattg   1380
tttgtgattt agctctattt tttatggttc tgtttgtgat tgaacag                 1427


<210> SEQ ID NO 26
<211> LENGTH: 502
<212> TYPE: DNA
<213> ORGANISM: Nicotiana tabacum

<400> SEQUENCE: 26

gggatcttct gcaagcatct ctatttcctg aaggtctaac ctcgaagatt taagatttaa     60
ttacgtttat aattacaaaa ttgattctag tatctttaat ttaatgctta tacattatta    120
attaatttag tactttcaat ttgttttcag aaattatttt actatttttt ataaaataaa    180
agggagaaaa tggctattta aatactagcc tattttattt caattttagc ttaaaatcag    240
ccccaattag ccccaatttc aaattcaaat ggtccagccc aattcctaaa taacccaccc    300
ctaacccgcc cggtttcccc ttttgatcca tgcagtcaac gcccagaatt tccctatata    360
attttttaat tcccaaacac ccctaactct atcccatttc tcaccaaccg ccacatagat    420
ctatcctctt atctctcaaa ctctctcgaa ccttccccta accctagcag cctctcatca    480
tcctcacctc aaaacccacc gg                                             502


<210> SEQ ID NO 27
<211> LENGTH: 2243
<212> TYPE: DNA
<213> ORGANISM: Solanum lycopersicum

<400> SEQUENCE: 27

atcgtatcca gtgcaccata ttttttggcg attaccactc atattattgt gtttagtaga     60
tattttaggt gcataattga tctcttcttt aaaactaggg gcacttatta ttatacatcc    120
```

-continued

```
acttgacact tgctttagtt ggctattttt tttatttttt attttttgtc aactacccca    180
atttaaattt tatttgatta agatattttt atggacctac tttataatta aaaatatttt    240
ctatttgaaa aggaaggaca aaaatcatac aattttggtc caactactcc tctctttttt    300
tttttggctt tataaaaaag gaaagtgatt agtaataaat aattaaataa tgaaaaaagg    360
aggaaataaa attttcgaat taaaatgtaa aagagaaaaa ggagagggag taatcattgt    420
ttaactttat ctaaagtacc ccaattcgat tttacatgta tatcaaatta tacaaatatt    480
ttattaaaat atagatattg aataatttta ttattcttga acatgtaaat aaaaattatc    540
tattatttca atttttatat aaactattat ttgaaatctc aattatgatt ttttaatatc    600
actttctatc catgataatt tcagcttaaa aagttttgtc aataattaca ttaattttgt    660
tgatgaggat gacaagattt cggtcatcaa ttacatatac acaaattgaa atagtaagca    720
acttgatttt ttttctcata atgataatga caaagacacg aaaagacaat tcaatattca    780
cattgattta tttttatatg ataataatta caataataat attcttataa agaaagagat    840
caattttgac tgatccaaaa atttatttat ttttactata ccaacgtcac taattatatc    900
taataatgta aaacaattca atcttactta aatattaatt tgaaataaac tatttttata    960
acgaaattac taaatttatc caataacaaa aaggtcttaa gaagacataa attctttttt   1020
tgtaatgctc aaataaattt gagtaaaaaa gaatgaaatt gagtgatttt tttttaatca   1080
taagaaaata aataattaat ttcaatataa taaaacagta atataatttc ataaatggaa   1140
ttcaatactt acctcttaga tataaaaaat aaatataaaa ataaagtgtt tctaataaac   1200
ccgcaattta aataaaatat ttaatatttt caatcaaatt taaataatta tattaaaata   1260
tcgtagaaaa agagcaatat ataatacaag aaagaagatt taagtacaat tatcaactat   1320
tattatactc taattttgtt atatttaatt tcttacggtt aaggtcatgt tcacgataaa   1380
ctcaaaatac gctgtatgag gacatatttt aaattttaac caataataaa actaagttat   1440
ttttagtata tttttttgtt taacgtgact taatttttct tttctagagg agcgtgtaag   1500
tgtcaacctc attctcctaa ttttcccaac cacataaaaa aaaaataaag gtagcttttg   1560
cgtgttgatt tggtacacta cacgtcatta ttacacgtgt tttcgtatga ttggttaatc   1620
catgaggcgg tttcctctag agtcggccat accatctata aaataaagct ttctgcagct   1680
cattttttca tcttctatct gatttctatt ataatttctc tgaattgcct tcaaatttct   1740
ctttcaaggt tagaattttt ctctattttt tggtttttgt ttgtttagat tctgagttta   1800
gttaatcagg tgctgttaaa gccctaaatt ttgagttttt ttcggttgtt ttgatggaaa   1860
atacctaaca attgagtttt ttcatgttgt tttgtcggag aatgcctaca attggagttc   1920
ctttcgttgt tttgatgaga aagcccctaa tttgagtgtt tttccgtcga tttgatttta   1980
aaggtttata ttcgagtttt tttcgtcggt ttaatgagaa ggcctaaaat aggagttttt   2040
ctggttgatt tgactaaaaa agccatggaa ttttgtgttt ttgatgtcgc tttggttctc   2100
aaggcctaag atctgagttt ctccggttgt tttgatgaaa aagccctaaa attggagttt   2160
ttatcttgtg ttttaggttg ttttaatcct tataatttga gttttttcgt tgttctgatt   2220
gttgttttta tgaatttcct gca                                            2243
```

<210> SEQ ID NO 28
<211> LENGTH: 1833
<212> TYPE: DNA
<213> ORGANISM: Pyrus communis

<400> SEQUENCE: 28

```
ttataataac tttaaccgtt tgattaaatt tcaatggtct ggatctccag atttgataga     60
ctggaaggaa tggatccaga gatgatccct ttccttcttt tggcaccacc tcaatggcta    120
atcttgttta atacctaata ctaaattttg ctctgattaa tcgaaggtcc ttgcaataca    180
cgcatacatc atattcaatt gctataaaaa ataaaataca aatttgttta tcttaaattc    240
ttaatcatga tagtatttat attagaaata caatgcaaat gaagtttcaa cacttataaa    300
caacatgaaa tggtgcacaa ccttttaaac taatataaat gaaagttgta actggcgcga    360
aagaagtcga ggagtcagga ttttcaaata attgagtcat gttttcgata aaaaaatttt    420
attagatatt tcgtcgagca cttgttctac atgtcgattt tttacaacat ttcttaaagg    480
cttatgccaa tatatgtcaa taactactat tatatgtaga gtcaaatatg gctatataga    540
atttacagta atattaagaa tggtagaact tgtcatcgga gcatttcgtc aagtatttag    600
tgcgcacaat aggttagatg gcctaatacg aattattggt gattagtgat cgtaataatt    660
cgaagggcaa gtggacagaa aagtataaat actcaaggaa attgttattg gcactccaaa    720
aatctcattt tactctactt ataaatgtat aataagattt ttgaagtact acttctcata    780
ctcaatctcg aagataacgc cgtaagggcc ccgtgaagga ggaagtcatt tgagatcacg    840
gactttgata ttatcaaaga aggggactag ataccaggct ttgccgttta acccgcgcca    900
tcggcacgtc attccatcca cgtgtcgcta aataagtgga cctcctcgtc acgccaacta    960
caattccgtg acgaagtcgc cttctctaac gctataaatc caggcatcag cctctcccct   1020
tcctcacaat tgcgattgtt ttgcttctca acaatctgaa aaatcctcct ctaaatctct   1080
ctcgaagctc cctcagcctt tcaaggtgtg ttcttttttt cttgtttctt gttaatttct   1140
tgtttggttg ctaggaaagt gtaggaaaat tggagattct gtatttgatt tggttgatgt   1200
ttgagattta tgattaatcg gttggatctg ttaaatttag cattgttttg gcttttgatg   1260
ttagggtttt tttatttatt ggatgcgaaa ttagtaactt ggaaagaaaa tttgcgtcga   1320
atcttgtgtt caattttcac gaattagggg ttttgtgtat tttatctaaa tgatcagcat   1380
gtcttttcga attgaaagta aatttctttg tatcaatttt gacaagtagg ttttattctg   1440
tatccgatat cgaaattgag atttgttaat ggtcaattta attttgctat ttatttttat   1500
tccaaaattg agtaatttta gactaaaatt gtgtctttga tctgtgattt aaagctaaag   1560
cagggttttt ttttccttta cctgatttgc tgaaattcaa tttgcaatct tgatcttgaa   1620
ttgatttatt gtatataaat ggctgttaat attttgttta tataaaaatt gggattttct   1680
tgaatttctt tgatttctga tgcattagtt tccaaattag gggttttttt tttttttttt   1740
ttttaatctg attttcttat ctgtaattct taattttaat ctaaagggat ttgttttttt   1800
atgcttaatc ttatggtatt ttggtttctg tag                                1833
```

<210> SEQ ID NO 29
<211> LENGTH: 1631
<212> TYPE: DNA
<213> ORGANISM: Beta vulgaris

<400> SEQUENCE: 29

```
atatgtagcc ctaagggcta tgtatatcat tttcctagat ttattatttg gttgtgcaat     60
ttggtctatt tagataaaat tgagtctatg agacacgggt taagaaatac ttgacataca    120
tttatttagt ttacatatat atacaccaat tacacgcttg gtaactagtc agacaaccca    180
tttactccct ggcccctgcg gtctgtaccc gtttcttttg cacaaagttt caggagaaat    240
```

```
aatgttgtgg gacataaaaa gatagagaaa ctattatttt atattaaagt atgtgattac    300

attccaaaac tagaataaaa agaaatgaat aaactaatta aaaacatctc aaaaaagaat    360

acggataaac taataaagac cgaaactagt actccctccg tcccaaaata tagttcccat    420

tacccatttt ttacggtaat ttatgcaagt agaatctaag agggataaca aagatttttt    480

gtttatttaa ataaatgttg tatggaaaaa gatgatttta ggagagagaa tggagaatga    540

ttggtgggag agcattaatt gtaacatttt ggttgaataa acaaaggaaa aaacaaaatt    600

caagaagcaa ataaatgatg ggacacgatt tttctaggta aattacggaa aaatgtgaaa    660

ctaaatatga aaatgagaac tatatttttg gacacttaaa atggaaatag gaactatatt    720

ttgggacgga gggagtaata aataacgact tggtcgtcta ccgttccaga ccgtcagatt    780

aaaccctcac cataaatctt gtaggtagca cgtactatat aatttcacaa gttcgagaag    840

tcgtgagaat ctccgtctct agttgaaccg cctcaaaagc aaagaaaagt agctttaccc    900

gtgagggcta ggtcaagaca cgtcatacat cacacgtgtc aaacgatgat tggtaaacta    960

gagataattg tcttaattaa gtcggtcaaa caagtcttta aatacagcct attcccttca   1020

ttggtttctc atccttcatt tgaacgtaaa cgatcattca tttttctctc tcctctcttt   1080

caaggtaaat tcctaatttc cttttctctc ttctcagttt tcttcgtaaa ttttcatctc   1140

atttctgtgt aagataacaa gatccaattt agttagtgta agattgattt atctaagaaa   1200

ttcatttgga attttgttct ttttgatttt caatttctca ggattttgtc gacaaaaaat   1260

taatcaaatt ttgtgttttt cagtttcata tagatctttc ttgtgttgtt gaaatacaga   1320

tctgatcatt gttacaattt ctaaaattta ggtttgaaaa ttcgccataa tttctcgtac   1380

ttctgcaatc gattgatttt taattcggaa aaattagtgt taaagatatc gccataattt   1440

atcacaattc tgcaatcgat taaattttcg atctggaaaa atctagggtt aaaatctcgc   1500

cagaatttat cgcaattctc caatcgttta atttctgatt tagtgtattc tagggttaaa   1560

gatctcgtca taaatttttc aaaatttcgt aaattgatgt gatttctgat ccttttcttt   1620

cgattttgta g                                                        1631
```

<210> SEQ ID NO 30
<211> LENGTH: 1441
<212> TYPE: DNA
<213> ORGANISM: Unknown
<220> FEATURE:
<223> OTHER INFORMATION: Raphanus raphanistrum

<400> SEQUENCE: 30

```
taaaagtaca acaacttttt ttttaggaaa caacaactta gctaacatat gtaacaaaat     60

tgcaaactga gctatctatc taatctgaaa ctgctgcact tcttgccact aaactatctc    120

aggaaaccca acttagtctg taagaagaac catcaacgaa caaaactatt cgaagaggct    180

ttcattgact gaataaaccc gatatcttag aaatgggcca agcccaaaaa agtccgtttg    240

atgtgtgata ccgaatccat tgccttcagc ccatttgcca acttgatacc aaaatcatgc    300

aaatatccaa aaccactaaa aaaagaaaaa aacattatgt tatttttcag gaaatttcct    360

ctattaattg tttgaagaaa aaaaaacaat ttgccaactt gataccacaa tcatgcaata    420

tccaaaacga ctaaaaataa aaaacattat gttattttca ggaagattcc ttttttattt    480

ttaaaattca aaattaaaaa ccccacctgc atagaaaaag ggaaaattaa agaaaagaaa    540

agataagagc atcgacatag ggggaccatg ggctcaatta ttggcatttt tttagctcca    600
```

-continued

```
ccgttgatta aaaaaaaaaa gaaagataat aataacaccg atcgtaacga tccgttaaat     660

cacaacgtcg gcttctgtta cggcccgtta gaaactgtgg ttgtcgtgga gttagtaaag     720

aaacggcgtt aaaatagaat gcagccaaca cacgacgggt cgtgggggtt atcaactcaa     780

agcacaaaat atatactttt cctttatacc taaaaaaatc aaaggcgaag gaaagattat     840

cttttccatt aaaaggttgc gtgtaaccaa cgctgaatac acgtcattta acatacgtgt     900

cgaaatccta ttcgctattg cttcaccgcc ataggtttct cgtgaccgag tcctcctcat     960

cctcttgtat aaatcaaacc ctaaacacct cttctccttc acaaatcgaa aaccaattct    1020

tctcaattct caattctcaa ttctcaattc tcaattctct ctctctcgcg aattacgatc    1080

aaggttagat tcgtgtttct tcttctctcg attagctgtt tcgttcgatc gtaattgatt    1140

aagccccgat agatctcgtc gtgattttga ttattagggt tcaattgtta cgattaaggt    1200

ttgattctgg tttcttcttc atcgattagt tgtttcattc aatcgtatat gtattttcga    1260

atttgaatcg gtttgttgag attaaacgat agaactcgtc gtgatttttg atttttccag    1320

atttgtgttg gctacttgat catatatgat ccgtgtttgt atattgtagc gatctctttg    1380

tattgatttc gcaattgatc cgagtcaaaa gagtattgat cttggctttt gtgaattaca    1440

g                                                                    1441
```

<210> SEQ ID NO 31
<211> LENGTH: 1394
<212> TYPE: DNA
<213> ORGANISM: Ipomoea nil

<400> SEQUENCE: 31

```
attagggaaa atagcacttt ttccccctaa gttatatact tatagcattt tttcccccctc     60

aattatttat gtaagtacat tagccccctc aattatttta aaagtggtgg tttttccccc    120

tgatatatta aattgacatt tctaccctta aagtaaacat tttatttttt tacttctcca    180

acaaattatt gtgtatatgt agcaatgacc acggttcggt tcgaactaaa ccgcacacta    240

tagcaatcga attaaaactt ttcggttata attcagatct agaatccaat atttgaattt    300

caatttatta aatttatgaa ccaaaaaaac tggatcatga accgtgaacc ggcgattata    360

gatccggttc gcaattttga accgtcttta ttttaaaatt ttattttatt ttttatttta    420

aaatagtcta aattcaacaa taaatgtaat ttattttttc agttcggaac atgaactggc    480

cattccggtt tgcgatttta ataaactcta aatatcgcat tttgattcta aattgtaatt    540

ggaatatttt ggtttggttg gtatagtatc tgtttggttt gaaccaaatt atagtaataa    600

tttgttggag aagaaaaata aatgaaatat ttattttaag agtaaatatg tccatttaat    660

attttagggg gaaaagaacc acttaaataa ttcaaggaga aaaagtgcta taagtatata    720

actcagggag aaaaagtgtc attttccctt attatatata tatatatata tatatataaa    780

taaaaaaatg aatagtataa aacaaattta taaattttgc cggatcggat aattatgaag    840

cgcgtaggtt ttgaagtcaa aatcggctac ttgccaaatt gcaatttccg aacctaataa    900

tctccaccac gcaaagaaaa tccgacaaat aatgcaagcc gttgcgtgtg gtattgatca    960

atacacgtaa tatccaacac gtgtccctcc ttcataggtc aacaagataa gcactttctt   1020

cgcaaggcgg tcgagacacg cctttataat cttctcctcc ctcgcccttt ctcatccatc   1080

atacgatttc tctattctat ccaaatttct tcctcctcaa aaccttctct caaggtaacc   1140

acagttttct caatcttcct tcctttttgt ttattgttat tattgttaat gttaattgtt   1200

aattttctgt gttattctta ttcgtgattc gtgaattggg gatctggggg ttgtgttctt   1260
```

tgatcttcat aaattgcaat tggttttagg gttttttttt tttttttttt tttttggatt 1320
gaattggtgt taattgagga tgttttatgt ttgtatttga tggttaattt gattttgtat 1380
ttggatatat acag 1394

<210> SEQ ID NO 32
<211> LENGTH: 1438
<212> TYPE: DNA
<213> ORGANISM: Unknown
<220> FEATURE:
<223> OTHER INFORMATION: Cucurbita sp.

<400> SEQUENCE: 32
cttatgtgca acgttacatt tcggttatca tcttagttcc caacaacata actcatgcat 60
caggatgcca ttccatgtct taggacaagt caaccatctt gacttgcttg aacatgtcta 120
tcaagatcaa tctatgtgtc actcatctca ttgtgacatc ctaaacatcc attcatcatg 180
tcattcatac ctatcagggt catccaacac tatttttgat agacccattt caaagaaagt 240
tgtccgagac actcgtccac accgcgacac acatatgtgc cacaagatag cccgcttagg 300
ctacatggcc caggaggaga agagagctaa caccatgcct ctcctataat acattttgag 360
ccatttctaa tctttctgga gtagacgtta ttttgacaag tagtcatatt gtagcattga 420
gcgttgtcgg atatccaatt gacacaaatt ttggtgagtt tcatctttta tataaatgaa 480
cttaactcta gagccgtatc ccgaaaactc atatagaaat tctgacttct aaggttatga 540
cccagggatc tactcgaccc tcttcgagat tgtcttcgac gctcgtggtt ctctccaacc 600
ttcctaattt ttcaatttga ctttaatgta tacccttggt atattagatg atgcatcgtc 660
ctcttttcgt atcataacgc gtattggccc gggaaacata atttaaaagt ctccccaagc 720
ctatctttga gtgtggggtc acagcccatc tagagaaaga agaatagtag attcaactca 780
aagacgcgca aaacgtctag aattttcttg agaaccacta gaacctaact ccgttataac 840
gacgttagtt gttgttttgc gtgctattat tgagtcggct tattgctttg aattttggtc 900
cacagattcc atttctgcct tcgcctgcaa gtaacggcga ttgacagata ataaatgctt 960
acgtggcgga aatgtgtgga taattcatcg cctgccatga cctaattctc cttacaattt 1020
cctataaatt cacccccttcc gccctgggtt tctccgcaat tgaatctctc ttctttcatc 1080
gaccaatcta cagcgaattc ttccaaggta tttttctgct ttcttttctt tttcgctttg 1140
attctgttca tctgtttcga gagttctgga tcggtgttgt ttttttcccc ttttgttgtg 1200
gaaatttttg aatcgtttat tcttctcgga gatctgatgc tttgtggttg gatccgcttg 1260
gatcgtttga agttttatga tatgtattcg gattgtagtg tgttttgtga gagattggct 1320
tgaaacattg ggattttact gattttatcg aagtgaaatt tagaatttag gtttttgact 1380
tgttcgtgtt atcgttttga tagaaattgt cctgattttt gtgtttcctt ctgtatag 1438

<210> SEQ ID NO 33
<211> LENGTH: 2560
<212> TYPE: DNA
<213> ORGANISM: Helianthus annuus

<400> SEQUENCE: 33
tacacttagg ctattactta acgcgggtcg cgagaggcct gtttttcaga tttttaaaat 60
cttttgaaat gattacgaaa tcctggtaat taataacgaa atctttcgta atgatttacc 120
tgacctttcg agtttgaagg ggtaactttg cggtttggcc ctcggttaat tacaactaag 180

```
gacctcgtgt tatttacccg cgttgttaag tccccgatta gtttattaat tactcagaaa    240
gccttcactt tcattattga cgcttttaac ccttctccta cgaattcgat cgtaactttc    300
tcgtttcata acgaaacttc gcgaaattta tatattatat tttagtgagt gtataatacc    360
gttacaaagc cttgggaacg ttaaagggtc actcagaggt ataattaaac atgttgacac    420
ggttaacccc tgtagcttgt aatctctcac tttctttcgt gtttcgcttc tgtacgatct    480
atgatttatt tgtttgaagg ttcaagcatt atttagggtt agtatacagt atatttaccc    540
ttgttgacat ttataaccct cgaatttata tactttcaag gtttgtcaaa attagtcctt    600
tatttaatat taatgccacg tgtaaacaaa tgacacgtgt taacacatca ttggacgcaa    660
aaattcgagg tgttacagta acagatctga acccttgctt gatgctaagt tgttttcttg    720
taggttttat tatttcaatt atcgctttat tgcttcgttc taaacctgat atgtaagcta    780
tgagattatt cttgtttgtc atatacttac atccgtttgt tattgtgatt tattaactgc    840
gtttaagata tgcgcataaa aagttcagtc aacaattaaa accatactac agccgcctgc    900
attattactt ttaagatatg tgtgttattg cttttgcgac cgaaaattat tatcctgttg    960
gtttaatcgg gtcagagata gtcatatcgg tcgggatcga taaacgggtc ggcatcaact   1020
tgggtcgatc ggatccgggt gtgcatgttt gtggttgtag atgttgcagg tggaaagaga   1080
gagaagtgtg ttgaggtggg gtatggcagg attatttata tatttatgaa atgactaaaa   1140
tgcccttgac agacttaaca catatggatg aagttaagtc agttggacca aaatggcaac   1200
gatgaaatat ttttagatcc agatgttaaa aataaaacct ttgaactaaa ctgttaaaat   1260
gacccaaacc atagggacta aaatgacatt taactcttaa aaaaaaatta gaaacaagat   1320
aagggtcacg caatatttta ttccaaaata aaaagaagac gccaaaccta aaaatcagcg   1380
actccattaa aaatcaaaac ccatcaacgg ctcttatctt aactttggtg tttggtcacc   1440
aatactttat acacgtggca cattctccac cgattgttat ctaaccgcac cgtcacgtta   1500
acctttcttt gcgtgcaccc ttagctttat tgttctataa attcaccccc aatttatccc   1560
cttcattcat caaccaattc tcttatcttc ttcaatttct cagatctctt caatcccttc   1620
aaggtatgtt cctttcgatt tgtgtgtttt gtttttgtta atagatctgc tatgtattgt   1680
ttgatctgtt aagttttaga tcgatttgtt tagatttaga tacgctatat cgtttgatcg   1740
gttaggattt tgatcgattt atttaggtct gttatatcgt gtgatctgta agctttttga   1800
ttgatttaga cctaaaattt gatcgtaggt gacttttact atgtatatat tacgtctgat   1860
tgttaggttt tcttttagat ctgtgatatt gtttgatctg taagttttta gattgatcta   1920
gattgaaatt tttaacggta ggtggtttaa tatgcacaat ttaacgtctg attgctagat   1980
tttcgttata gatctgttat attgtctgat ctgttaggtt ttcgatcggt aggtggctaa   2040
atatgtttgt atctgattag atctgatgat tagacaaagg atgatgtgtt ttgatcttga   2100
attcctttcg atttcgcgtt atttataggt ttttgtttca gatcggtgat atatacagtt   2160
ttacgtctga tcattagttt attgttttgg atctgttagt ttattgatcg attaaaacct   2220
acagttgata gtaggtgtct taatatgttt ataattctta gtctgaaccg atttgataag   2280
tacacaacga ttttgaacgg ttaatcgtct agttcttgca gttttgtgga taatgattct   2340
gtttttgta tgatatttga tctgatgatt acataacgtt ttgtggtttt atattatgaa    2400
tttttaacag agattcgtta agatttttca gtcctgtttg ttatgatttt gtttttggtt   2460
gaaattctgt tttattgagg cgtgtttact tgtatttaaa aagttatttt ggtattgtta   2520
ctgatcttct gttcttatgc ttttcaacag tagcaaaacc                         2560
```

<210> SEQ ID NO 34
<211> LENGTH: 601
<212> TYPE: DNA
<213> ORGANISM: Solanum lycopersicum

<400> SEQUENCE: 34
tcgacatact cgactcagaa ggtattgagg aatgatcgat tctgggtcat ttgtgtggtt 60
aatcaccctc caaatcaact aagtcatcct gaaggacaat atcctatttt ttctctcgta 120
ggtttatcat ttaaattact atcgcgtgat aattttgtaa cgtagaaaaa taataccatt 180
aatccaaacg ttatattcat taaaataatt atgatacatt taaaaatatt tcgtgacctc 240
tcaattattg caaattctaa gccatcccaa gttttgaggc taattttttt tactatacta 300
tttttacaac cacaaaaaca taaaaaaataa aaaataaaaa aaataaaccg agtcaattgc 360
tacaatcact tcattattaa ttttaattaa tattatgtgg ttatatatga aactgttaga 420
gaaataatag ctccaccata ttttttctc aatttatttt cactataaaa aggctatttc 480
attataatca aaacaagaca cacacaaaga gaaggagcaa taaaataaaa gtaaacaaca 540
atttgtgtgt ttaaaaaaaa aaaaaaagta cacacaccaa aaaaaaaaat tccaatttaa 600
a 601

<210> SEQ ID NO 35
<211> LENGTH: 2054
<212> TYPE: DNA
<213> ORGANISM: Helianthus annuus

<400> SEQUENCE: 35
taatcaacat cccgctgcaa cgcgcgggta agcataaact cgttcctata caaattacaa 60
ttccaaatca ttcgatgaat caaatgccac ctaagaagat attaatctca taatcaaatt 120
attataccaa atcattgatc tgggctttgt attactcgaa ttaatgctgt tatgttttta 180
ttaaacgtat gggcttgctt gaaccaggct taaggcatga gtgtactttt ttttaaacaa 240
ctaacataat caatttcaag cacttttggg acaccgactg gattaaacgc agtactttga 300
aagtaaccca agtccaccta ctcgtagaca caacagtaaa attactggta aaacctgttg 360
gtttccctga gttttctgtc attgtccact aatgcctcat tcttcaccaa atagaagttg 420
aacctgcata atacaataag gctatgggat atactttcac gccccttaac tacacgtagg 480
catcacatca cgtacttgac cctctttcac ttcacttcac aacaaggaaa ttgtttaacg 540
cccattaaca ccccttaaat taaataaaat acatatatat agcatgttgt gtgtgtgtaa 600
attttgcgat gcttgattct ctccctctct ctcctaatta acttcttaac atataaagct 660
tttaataact cttaacactc ttcaggaacg gtataataaa tgttaacgga taccaactag 720
gattacgtga tacaagcctt cctctctaaa acttaagaaa gtcaccaaaa agaaagtcaa 780
agacggcaac ggcaacccag aagctacgtt ctctttctag attctatgcc ctacctaccg 840
tgtggtgcac aacaacttga cccccatcat tgactctcca ccgtacacgt gtcacgatac 900
catttgttgg tctcctacca cttacgtaac attaatattc catccgtgac cgcctcttct 960
tcatcatcct ataaattcac cttcttatct cttccgcttt cattcgttca tcatcatcac 1020
aattaacaac aatccaaagc aatcttctct catattctta tctcttcctg tttcgcttcg 1080
tctctttcaa ggtatctatc atccttttct ctatatatct cttcttgatt attatgtgtt 1140
gtcagatgtt agatctattt agatttggaa ttgtgtgatt gattatatga tttagaattt 1200

-continued

```
tagatgcatg attgatcttc gtaatcatat gagtaatcgt tttcagcgag acggattgta   1260

gatctggacg attgtaggtt tttacgagtt gttattggat cgtttgatga ttgttgttat   1320

ttgttagttt gatctgttta gatgtaaaat tgtgtgaaca taataacgga gagatgactt   1380

gttgataatc gttctcaacg agacagattc atgttttact ctagatctgg ctaatgtgaa   1440

tttgtgtgtt taattatgtt ttgtatgtat tatatagtga acctatgaag atatggtttg   1500

atgcatgatt attgatatga ataatcctac gagtaatcgt tttttacaag acgacttgtc   1560

tctcactgta gatcatatat gagttgttct tggatcattc gatgactgtt gttgattgat   1620

tcggtttttc tgtgatgata tggtggaact taataatgaa aagatgtttt agatgcatta   1680

ttgatttgat aatcttgagg agtaatcgat tttaacaaga catatacgaa ttaacgaatt   1740

attgcctttt tatttgttag tttgatatga tttaggtata attcgtcctg tttgattcct   1800

ttttctgtaa tgatatgatg aacttaataa cgtagagatg ttttcgatga attttaattt   1860

taatatttgt tagtgtgatt ttgggtagaa ttcgttgtga tttgggtgtt tgacttagtc   1920

actagttcat gtttgatgat cttacttagt acttcataat ttgctttgtt tctcattcca   1980

gcccatctga tttaagttat tgatggtata atttattgct tagggtatta atctgtttgt   2040

attttttaat ccag                                                      2054
```

<210> SEQ ID NO 36
<211> LENGTH: 983
<212> TYPE: DNA
<213> ORGANISM: Petroselinum crispum

<400> SEQUENCE: 36

```
gaattcgaat ccaaaaatta cggatatgaa tataggcata tccgtatccg aattatccgt     60

ttgacagcta gcaacgattg tacaattgct tctttaaaaa aggaagaaag aaagaaagaa    120

aagaatcaac atcagcgtta acaaacggcc ccgttacggc ccaaacggtc atatagagta    180

acggcgttaa gcgttgaaag actcctatcg aaatacgtaa ccgcaaacgt gtcatagtca    240

gatcccctct tccttcaccg cctcaaacac aaaaataatc ttctacagcc tatatataca    300

accccccctt ctatctctcc tttctcacaa ttcatcatct ttctttctct acccccaatt    360

ttaagaaatc ctctcttctc ctcttcattt tcaaggtaaa tctctctctc tctctctctc    420

tctgttattc cttgttttaa ttaggtatgt attattgcta gtttgttaat ctgcttatct    480

tatgtatgcc ttatgtgaat atctttatct tgttcatctc atccgtttag aagctataaa    540

tttgttgatt tgactgtgta tctacacgtg gttatgttta tatctaatca gatatgaatt    600

tcttcatatt gttgcgtttg tgtgtaccaa tccgaaatcg ttgatttttt tcatttaatc    660

gtgtagctaa ttgtacgtat acatatggat ctacgtatca attgttcatc tgtttgtgtt    720

tgtatgtata cagatctgaa aacatcactt ctctcatctg attgtgttgt tacatacata    780

gatatagatc tgttatatca ttttttttat taattgtgta tatatatatg tgcatagatc    840

tggattacat gattgtgatt atttacatga ttttgttatt tacgtatgta tatatgtaga    900

tctggacttt ttggagttgt tgacttgatt gtatttgtgt gtgtatatgt gtgttctgat    960

cttgatatgt tatgtatgtg cag                                            983
```

<210> SEQ ID NO 37
<211> LENGTH: 585
<212> TYPE: DNA
<213> ORGANISM: Solanum lycopersicum

<400> SEQUENCE: 37

```
tgtcttttaa tggataatta ctaattttag cggtactttt tatttattat catttataat     60

aatactatgt taaatatgca acatgtatta gaagtgaatt aagtatgcaa tagatatgta    120

tttaaaaata tattatgctt gtttgataag aagttgatgc attgtattat aagtacgtta    180

gaatgtgcaa taaatatatt atctatcatt agaacttgaa ttataagtga ataatagatt    240

attttttgta atatgaatta aaagtgtatt aaacatgtat taacggtgat caattggtta    300

aaaaaaagtt tattattaaa atgataaatc tttttaattt atagtatatt tatgtaagtt    360

ttcacgttga gtaaatagcg aagaagttgg gcccaaccaa gtaaaataag aaggccgggc    420

cattacaatt aagtcgtcac acaactgggc ttcattgaaa aaagcgcaaa accgattcca    480

ggcccgtgtt agcatgaaga ctcaactcaa ccagagattt ctccctcatc gcttacagaa    540

aaaagctata tgctgtttat attgcgaaat ctaacagtgt agttt                    585
```

<210> SEQ ID NO 38
<211> LENGTH: 352
<212> TYPE: DNA
<213> ORGANISM: Medicago truncatula

<400> SEQUENCE: 38

```
atgcctatct tatatgatca atgaggcatt taattgggtg catatgatgg tgaaaaaagg     60

tgcagctcct ggcttgggaa tgatgactca tgtggaattt ggtcttaaat ttatcacatc    120

cttttgggat gtgatgattg tatcacttgt tcattttgca aagacaaggt gcactgctac    180

aaactttggt ttaatctgaa ataaaacaaa actcactgag aggaagatgc atcccagtag    240

gtgaaagtcg agaaggattt gcatgttact attacacttg ctttttagtc ccacatcgtc    300

tgaaacataa aatatttcag cgtttaaata cttcaagcga accagtaggc tt            352
```

<210> SEQ ID NO 39
<211> LENGTH: 472
<212> TYPE: DNA
<213> ORGANISM: Glycine max

<400> SEQUENCE: 39

```
cccgggttaa gagaattgta agtgtgcttt tatatattta aaattaatat attttgaaat     60

gttaaaatat aaaagaaaat tcaatgtaaa ttaaaaataa ataaatgttt aataaagata    120

aattttaaaa cataaaagaa aatgtctaac aagaggatta agatcctgtg ctcttaaatt    180

tttaggtgtt gaaatcttag ccatacaaaa tatattttat taaaaccaag catgaaaaaa    240

gtcactaaag agctatataa ctcatgcagc tagaaatgaa gtgaagggaa tccagtttgt    300

tctcagtcga aagagtgtct atctttgttc ttttctgcaa ccgagttaag caaaatggga    360

atgcgaggta tcttcctttc gttaggggag caccagatgc atagttagtc ccacattgat    420

gaatataaca agagcttcac agaatatata gcccaggcca cagtaaaagc tt            472
```

<210> SEQ ID NO 40
<211> LENGTH: 445
<212> TYPE: DNA
<213> ORGANISM: Arabidopsis thaliana

<400> SEQUENCE: 40

```
cttcgttgaa caacggaaac tcgacttgcc ttccgcacaa tacatcattt cttcttagct     60

ttttttcttc ttcttcgttc atacagtttt tttttgttta tcagcttaca ttttcttgaa    120

ccgtagcttt cgttttcttc tttttaactt tccattcgga gtttttgtat cttgtttcat    180
```

-continued

```
agtttgtccc aggattagaa tgattaggca tcgaaccttc aagaatttga ttgaataaaa    240

catcttcatt cttaagatat gaagataatc ttcaaaaggc ccctgggaat ctgaaagaag    300

agaagcaggc ccatttatat gggaaagaac aatagtattt cttatatagg cccatttaag    360

ttgaaaacaa tcttcaaaag tcccacatcg cttagataag aaaacgaagc tgagtttata    420

tacagctaga gtcgaagtag tgatt                                          445


<210> SEQ ID NO 41
<211> LENGTH: 306
<212> TYPE: DNA
<213> ORGANISM: Glycine max

<400> SEQUENCE: 41

aaaataaatg gtaaaatgtc aaatcaaaac taggctgcag tatgcagagc agagtcatga     60

tgatactact tactacaccg attcttgtgt gcagaaaaat atgttaaaat aattgaatct    120

ttctctagcc aaatttgaca acaatgtaca ccgttcatat tgagagacga tgcttcttgt    180

ttgctttcgg tggaagctgc atatactcaa cattactcct tcagcgagtt ttccaactga    240

gtcccacatt gcccagacct aacacggtat tcttgtttat aatgaaatgt gccaccacat    300

ggattg                                                               306


<210> SEQ ID NO 42
<211> LENGTH: 445
<212> TYPE: DNA
<213> ORGANISM: Arabidopsis thaliana

<400> SEQUENCE: 42

cttcgttgaa caacggaaac tcgacttgcc ttccgcacaa tacatcattt cttcttagct     60

tttttcttc ttcttcgttc atacagtttt tttttgttta tcagcttaca ttttcttgaa    120

ccgtagcttt cgttttcttc tttttaactt tccattcgga gtttttgtat cttgtttcat    180

agtttgtccc aggattagaa tgattaggca tcgaaccttc aagaatttga ttgaataaaa    240

catcttcatt cttaagatat gaagataatc ttcaaaaggc ccctgggaat ctgaaagaag    300

agaagcaggc ccatttatat gggaaagaac aatagtattt cttatatagg cccatttaag    360

ttgaaaacaa tcttcaaaag tcccacatcg cttagataag aaaacgaagc tgagtttata    420

tacagctaga gtcgaagtag tgatt                                          445


<210> SEQ ID NO 43
<211> LENGTH: 323
<212> TYPE: DNA
<213> ORGANISM: Arabidopsis thaliana

<400> SEQUENCE: 43

ccatggatgt tgttgttacc agaaagtaaa taaatgttca atctctgatg ttctcaagta     60

agtgagtttt attgggaata atattaactt atgttcttct tgcatttgat ttctttgccg    120

ctctcttctt ctatcttaaa tctgtgtata ctatttcact attgggcttt ttattagtct    180

ataatgggac tcaaaataag gctttggccc acatcaaaaa gataagtcac aaatcaaaac    240

taaattcaga gtcttttctc ccacatcggt cactgtactc attttgtgtt tgtttatata    300

ttacacgaac cgatctttgg tac                                            323


<210> SEQ ID NO 44
<211> LENGTH: 1982
<212> TYPE: DNA
<213> ORGANISM: Zea mays
```

<400> SEQUENCE: 44
caattaatgc acgtcggccc agtaactccc gtcggccaga cagggccgac atgcattaat 60
ttgtaatccc cgtcggccag cggtagccga cgggagttac tcggccgatg tgcattaatt 120
ggtaatcccc gtcggccagc cgtagccgac aggaattact aattcccgtc agtgcccgac 180
gagaataagc atatccccaa catctgatgc ccgtcggctt agggtcgacg ggaattaacc 240
atataccgac gagaattagt aatccctatc ggtttagtgc ttattcccgt cggttctgag 300
tcggcgggaa ttaattggat tcttgtagtg atgcactgag tttttactat aattttaaca 360
agtaaaatga ctaacttgga taaaaaaatg tttcgtgggg cgggtacatg gggaacgtgg 420
acggtcctcg tgaactacgg ggattaaatt ttctccattt aaatccccgc ggggactaaa 480
ttagtctcat acccatcccc taatagggga attttccgcg gggaattggg gatcgagtcc 540
ccattgtcat ctctactctg cgcacgtctg gatggtcgcg cctggggccc gaacggttca 600
cgatggcgca gagggtctta tttttcacag cagacctaga tcttgcctct cgggagggat 660
cccgtcgggg aggagagatc ctagggtgtg tcttggtgtc agcaggccac ccaagacgct 720
tctaatcgat gtagaaccga agaaatgcga agatttaagg tagaggaagg ctaaactaga 780
gctactccta atacaaaatg taaaaacgat aagtaaattt gatctgatcg aatgtggggg 840
ttcaatcggc cgtagccctt tatatatata aatgagagat ctgaacccgt tacatgtcgt 900
ttaccgagtt aatctcgtag atttagctaa caaatcccac aagaaaatcg aaatcctaac 960
cgattctaca cacaagcgga ccatccatgc catcaccgcg gatcatccgg cctagcgtcc 1020
cctgcccaaa agtgggctca acaagcctaa atacatataa tttataccac gtgcaacaca 1080
tttattcatc catatcacat gtcatgcaag gcataagcat catgttaact tagttatact 1140
gacatacatt tatgagttga gatgtccagg atgtgagcgc atgagcccat tgtccattca 1200
ggaccaagac aggctactaa gcactttcta cataacttgt atgtgctaac tatagcatgc 1260
ttatatggct ctctccaaag ttcaaagcta gctcaaatct tttgatttaa taaaacttaa 1320
atttgtttga tttcagataa actgataatt tttataaatat ttagagtgag ttgaaaacag 1380
aaactggccg caaatccacc tcaagccttt tgatttgacc taaaaaaaag aagcccccac 1440
aaacaccact ccacactagt gcactgtctc tctccaaagg cagctgcatt ggcctccagc 1500
cttttcccta ctgtgccgcg cgccctccct tctctctaat gatagcatag ggagagaagg 1560
catactccga ggcatccttc tcctttccct ctccttcccc aaacccttttt cctctttccc 1620
tcgccccaag aacttcatct catctccagg cgcccctttt gcgcttgcgc aggagtagct 1680
cacggggaca gtgggcggat agctcgatcg ctgcaccact acttcactgg aggtccgccc 1740
actccctagg caagcaagac tagtagccgc agtctaacaa tagctctcct gcttccggtt 1800
cagctactgc tgctagcgaa gtttggccac atctgatgtc aagagcatgg cgcatgcaca 1860
tactttctgc ttgcttttac atagcatact atagtttatg catgctgctc atgtagacat 1920
gtgcatctgg tgttcggaac tttctcaaac ggccgtgggt gtttgcaggt gggggcaaaa 1980
cc 1982

<210> SEQ ID NO 45
<211> LENGTH: 2051
<212> TYPE: DNA
<213> ORGANISM: Oryza sativa

<400> SEQUENCE: 45

-continued

```
tgggccaatg aatccgtgtg atcgcgtctg attggctaga gatatgtttc ttccttgttg      60

gatgtatttt catacataat catatgcata caaatatttc attacacttt atagaaatgg     120

tcagtaataa accctatcac tatgtctggt gtttcatttt atttgctttt aaacgaaaat     180

tgacttcctg attcaatatt taaggatcgt caacggtgtg cagttactaa attctggttt     240

gtaggaacta tagtaaacta ttcaagtctt cacttattgt gcactcacct ctcgccacat     300

caccacagat gttattcacg tcttaaattt gaactacaca tcatattgac acaatatttt     360

ttttaaataa gcgattaaaa cctagcctct atgtcaacaa tggtgtacat aaccagcgaa     420

gtttagggag taaaaaacat cgccttacac aaagttcgct ttaaaaaata aagagtaaat     480

tttactttgg accacccttc aaccaatgtt tcactttaga acgagtaatt ttattattgt     540

cactttggac caccctcaaa tctttttcc atctacatcc aatttatcat gtcaaagaaa      600

tggtctacat acagctaagg agatttatcg acgaatagta gctagcatac tcgaggtcat     660

tcatatgctt gagaagagag tcgggatagt ccaaaataaa acaaaggtaa gattacctgg     720

tcaaaagtga aaacatcagt taaaaggtgg tataaagtaa aatatcggta ataaaaggtg     780

gcccaaagtg aaatttactc ttttctacta ttataaaaat tgaggatgtt tttgtcggta     840

ctttgatacg tcatttttgt atgaattggt ttttaagttt attcgctttt ggaaatgcat     900

atctgtattt gagtcgggtt ttaagttcgt ttgcttttgt aaatacagag ggatttgtat     960

aagaaatatc tttaaaaaaa cccatatgct aatttgacat aatttttgag aaaaatatat    1020

attcaggcga attctcacaa tgaacaataa taagattaaa atagctttcc cccgttgcag    1080

cgcatgggta tttttctag taaaaataaa agataaactt agactcaaaa catttacaaa     1140

aacaacccct aaagttccta aagcccaaag tgctatccac gatccatagc aagcccagcc    1200

caacccaacc caacccaacc caccccagtc cagccaactg gacaatagtc tccacacccc    1260

cccactatca ccgtgagttg tccgcacgca ccgcacgtct cgcagccaaa aaaaaaaaaa    1320

gaaagaaaaa aaagaaaaag aaaaaacagc aggtgggtcc gggtcgtggg ggccggaaac    1380

gcgaggagga tcgcgagcca gcgacgaggc cggccctccc tccgcttcca aagaaacgcc    1440

ccccatcgcc actatataca taccccccc tctcctccca tccccccaac cctaccacca     1500

ccaccaccac cacctccacc tcctcccccc tcgctgccgg acgaccagct cctcccccct    1560

ccccctccgc cgccgccgcg ccggtaacca ccccgcccct ctcctctttc tttctccgtt    1620

tttttttcc gtctcggtct cgatctttgg ccttggtagt ttgggtgggc gagaggcggc     1680

ttcgtgcgcg cccagatcgg tgcgcgggag gggcgggatc tcgcggctgg ggctctcgcc    1740

ggcgtggatc cggcccggat ctcgcgggga atggggctct cggatgtaga tctgcgatcc    1800

gccgttgttg ggggagatga tggggggttt aaaatttccg ccatgctaaa caagatcagg    1860

aagaggggaa aagggcacta tggtttatat ttttatatat ttctgctgct tcgtcaggct    1920

tagatgtgct agatctttct ttcttctttt tgtgggtaga atttgaatcc ctcagcattg    1980

ttcatcggta gtttttcttt tcatgatttg tgacaaatgc agcctcgtgc ggagcttttt    2040

tgtaggtaga a                                                         2051
```

<210> SEQ ID NO 46
<211> LENGTH: 842
<212> TYPE: DNA
<213> ORGANISM: Oryza sativa

<400> SEQUENCE: 46

```
tcgaggtcat tcatatgctt gagaagagag tcgggatagt ccaaaataaa acaaaggtaa      60
```

gattacctgg tcaaaagtga aaacatcagt taaaaggtgg tataaagtaa aatatcggta 120
ataaaaggtg gcccaaagtg aaatttactc ttttctacta ttataaaaat tgaggatgtt 180
tttgtcggta ctttgatacg tcatttttgt atgaattggt ttttaagttt attcgctttt 240
ggaaatgcat atctgtattt gagtcgggtt ttaagttcgt ttgcttttgt aaatacagag 300
ggatttgtat aagaaatatc tttaaaaaaa cccatatgct aatttgacat aatttttgag 360
aaaaatatat attcaggcga attctcacaa tgaacaataa taagattaaa atagctttcc 420
cccgttgcag cgcatgggta ttttttctag taaaaataaa agataaactt agactcaaaa 480
catttacaaa aacaacccct aaagttccta aagcccaaag tgctatccac gatccatagc 540
aagcccagcc caacccaacc caacccaacc caccccagtc cagccaactg gacaatagtc 600
tccacacccc cccactatca ccgtgagttg tccgcacgca ccgcacgtct cgcagccaaa 660
aaaaaaaaaa gaaagaaaaa aaagaaaaag aaaaaacagc aggggtccg ggtcgtgggg 720 gccggaaacg cgaggaggat cgcgagccag cgacgaggcc ggccctccct ccgcttccaa 780
agaaacgccc cccatcgcca ctatatacat acccccccct ctcctcccat ccccccaacc 840
ct 842

<210> SEQ ID NO 47
<211> LENGTH: 1973
<212> TYPE: DNA
<213> ORGANISM: Panicum virgatum

<400> SEQUENCE: 47
cacgtcagtg tttggtttcc actagcacga gtagcgcaat cagaaaattt tcaatgcatg 60
aagtactaaa cgaagtttat ttagaaattt ttttaagaaa tgagtgtaat tttttgcgac 120
gaatttaatg acaataatta atcgatgatt gcctacagta atgctacagt aaccaacctc 180
taatcatgcg tcgaatgcgt cattagattc gtctcgcaaa atagcacaag aattatgaaa 240
ttaattttac aaactatttt tatttaatac taataattaa ctgtcaaagt ttgtgctact 300
cgcaagagta gcgcgaacca aacacggcct ggaggagcac ggtaacggcg tcgacaaact 360
aacggccacc acccgccaac gcaaaggaga cggatgagag ttgacttctt gacggttctc 420
cacccctctg tctctctgtc actgggccct gggtccccct ctcgaaagtt cctctggccg 480
aaattgcgcg gcggagacga ggcgggcgga accgtcacgg cagaggattc cttccccacc 540
ctgcctggcc cggccatata taaacagcca ccgcccctcc ccgttcccca tcgcgtctcg 600
tctcgtgttg ttcccagaac acaaccaaaa tccaaatcct cctcctcctc ccgagcctcg 660
tcgatccctc acccgcttca aggtacggcg atcctcctct cccttctccc ctcgatcgat 720
tatgcgtgtt ccgtttccgt ttccgatcga gcgaatcgat ggttaggacc catgggggac 780
ccatggggtg tcgtgtggtg gtctggtttg atccgcgata tttctccgtt cgtagtgtag 840
atctgatcga atccctggtg aaatcgttga tcgtgctatt cgtgtgaggg ttcttaggtt 900
tggagttgtg gaggtagttc tgatcggttt gtaggtgaga ttttccccat gatttgctt 960 ggctcgtttg tcttggttag attagatctg cccgcatttt gttcgatatt tctgatgcag 1020
atatgatgaa taatttcgtc cttgtatccc gcgtccgtat gtgtattaag tttgcaggtc 1080
ctagttaggt ttttcctact gatttgtctt atccattctg tttagcttgc aaggtttggt 1140
aatggtccgg catgtttgtc tctatagatt agagtagaat aagattatct caacaagctg 1200
ttggcttatc aattttggat ctgcatgtgt ttcgcatcta tatctttgca attaagatgg 1260
tagatggaca tatgctcctg ttgagttgat gttgtacctt ttacctgagg tctgaggaac 1320
atgcatcctc ctgctacttt gtgcttatac agatcatcaa gattatgcag ctaatattcg 1380
atcagtttct agtatctaca tggtaaactt gcatgcactt gctacttatt tttgatatac 1440
ttggatgata acatatgctg ctggttgatt cctacctaca tgatgaacat tttacaggcc 1500
attagtgtct gtctgtatgt gttgttcctg tttgcttcag tctatttctg tttcattcct 1560
agtttattgg ttctctgcta gatacttacc ctgctgggct tagttatcat cttatctcga 1620
atgcattttc atgtttatag atgaatatac actcagatag gtgtagatgt atgctactgt 1680
ttctctacgt tgctgtaggt tttacctgtg gcaactgcat actcctgttg cttcgctaga 1740
tatgtatgtg cttatataga ttaagatatg tgtgatggtt ctttagtata tctgatgatc 1800
atgtatgctc ttttaacttc ttgctacact tggtaacatg ctgtgatgct gtttgttgat 1860
tctgtagcac taccaatgat gaccttatct ctctttgtat atgatgtttc tgtttgtttg 1920
aggcttgtgt tactgctagt tacttaccct gttgcctggc taatcttctg cag 1973

<210> SEQ ID NO 48
<211> LENGTH: 2119
<212> TYPE: DNA
<213> ORGANISM: Oryza sativa

<400> SEQUENCE: 48
ccgtcaacaa aagaaatcaa aagggaaatg caccatctta tatctccagt ttatatgaac 60
agattggata agatcataag atcaagtggt ttatattatt ttgaggaata taacatggat 120
tcatcctaat cactcgtcta ggcagtatgt gtattcatga tggatatggt actatactac 180
ggagtttttt cttcacaaaa taacctgtta ttttgacctc caaccaaaca cgaattatac 240
caaaaattgg gttatttcat ctatagtaca actctattat aaacatgcag taaattatcc 300
tacacatata ccaaaattca agtgtaataa tcctaataca cagacttaaa aaacaaacta 360
tttccttttt aagaaaagga aaaccatttt tttaacggaa ggaaaacaaa ttcgggtcaa 420
ggcggaagcc agcgcgccac cccacgtcag caaatacgga ggcgcggggt tgacggcgtc 480
acccggtcct aacggcgacc aacaaaccag ccagaagaaa ttacagtaaa aaaaaagtaa 540
attgcacttt gatccacctt ttattaccta agtctcaatt tggatcaccc ttaaacctat 600
cttttcaatt tgggccgggt tgtggtttgg actaccatga acaacttttc gtcatgtcta 660
acttcccttt cagcaaacat atgaaccata tatagaggag atcggccgta tactagagct 720
gatgtgttta aggtcgttga ttgcacgaga aaaaaaaatc caaatcgcaa caatagcaaa 780
tttatctggt tcaaagtgaa aagatatgtt taaaggtagt ccaaagtaaa acttatagat 840
aataaaatgt ggtccaaagc gtaattcact caaaaaaaat caacgagacg tgtaccaaac 900
ggagacaaac ggcatcttct cgaaatttcc caaccgctcg ctcgcccgcc tcgtcttccc 960
ggaaaccgcg gtggtttcag cgtggcggat tctccaagca gacggagacg tcacggcacg 1020
ggactcctcc caccacccaa ccgccataaa taccagcccc ctcatctcct ctcctcgcat 1080
cagctccacc cccgaaaaat ttctccccaa tctcgcgagg ctctcgtcgt cgaatcgaat 1140
cctctcgcgt cctcaaggta cgctgcttct cctctcctcg cttcgtttcg attcgatttc 1200
ggacgggtga ggttgttttg ttgctagatc cgattggtgg ttagggttgt cgatgtgatt 1260
atcgtgagat gtttaggggt tgtagatctg atggttgtga tttgggcacg gttggttcga 1320
taggtggaat cgtggttagg ttttgggatt ggatgttggt tctgatgatt ggggggaatt 1380
tttacggtta gatgaattgt tggatgattc gattggggaa atcggtgtag atctgttggg 1440
gaattgtgga actagtcatg cctgagtgat tggtgcgatt tgtagcgtgt tccatcttgt 1500
aggccttgtt gcgagcatgt tcagatctac tgttccgctc ttgattgagt tattggtgcc 1560
atgggttggt gcaaacacag gctttaatat gttatatctg ttttgtgttt gatgtagatc 1620
tgtagggtag ttcttcttag acatggttca attatgtagc ttgtgcgttt cgatttgatt 1680
tcatatgttc acagattaga taatgatgaa ctcttttaat taattgtcaa tggtaaatag 1740
gaagtcttgt cgctatatct gtcataatga tctcatgtta ctatctgcca gtaatttatg 1800
ctaagaacta tattagaata tcatgttaca atctgtagta atatcatgtt acaatctgta 1860
gttcatctat ataatctatt gtggtaattt ctttttacta tctgtgtgaa gattattgcc 1920
actagttcat tctacttatt tctgaagttc aggatacgtg tgctgttact acctatctga 1980
atacatgtgt gatgtgcctg ttactatctt tttgaataca tgtatgttct gttggaatat 2040
gtttgctgtt tgatccgttg ttgtgtcctt aatcttgtgc tagttcttac cctatctgtt 2100
tggtgattat ttcttgcag 2119

<210> SEQ ID NO 49
<211> LENGTH: 1830
<212> TYPE: DNA
<213> ORGANISM: Oryza sativa

<400> SEQUENCE: 49
gttatcacgt cggcacgccg acgtcgctgc gcctgcgcgt gggaggccag ggcagatgct 60
acgtgccatc aggaatgtcg acctgatgat tattttgttg atcatgattt tcttttggct 120
atttgatttt ttgaaagata tttttttccc tgggaagaca cctatgggac gaagatatta 180
tgtttcttat atagcaccaa acaaatttaa tatatatata tatatatata tatatatata 240
tatatatata tatatatata tatatatata tatatatata tatatatata tatcacatca 300
gtctctgcac aaagtgcatc ctgggctgct tcaattataa agccccattc accacatttg 360
ctagatagtc gaaaagcacc atcaatattg agcttcaggt atttttggtt gtgttgtggt 420
tggattgatt ctaatatata ccaaatcaat ataattcact accaaaatat accatagcca 480
tcacaacttt attaatttg gtagcttaag atggtatata taataaccaa ttaacaactg 540
attctaattt tactacggcc cagtatgtac caatacaaaa caacgagtat gttttcttcc 600
atcgtaatcg tacacagtac aaaaaaacct ggccagcctt tcttgggctg gggctctctt 660
tcgaaaggtc acaaaacgta cacggcagta acgccgcttc gctgcgtgtt aacggccacc 720
aaccccgccg tgagcaaacg gcatcagctt tccacctcct cgatatctcc gcggcgccgt 780
ctggacccgc cccctttccg ttcctttctt tccttctcgc gtttgcgtgg tggggacgga 840
ctccccaaac cgcctctccc tctctccttt ctttatttgt ctatattctc actgggcccc 900
acccaccgca cccctgggcc cactcacgag tcccccctc cccacctata aataccccac 960
cccctcctcg cctcttcctc cgtcaatcga accccaaaat cgcagagaaa aaaaaatctc 1020
ccctcgaagc gaagcgtcga atcgccttct caaggtatgc gattttctga tcctctccgt 1080
tcctcgcgtt tgatttgatt tcccggcctg ttcgtgattg tgagatgttg tggttagtct 1140
ccgttttgcg atctgtggta gatttgaaca ggtttagatg gggttcgcgt ggtatgctgg 1200
atctgtgatt atgagcgatg ctgttcgtgg tccaagtatt gattggttcg gatctagaag 1260
tagaactgtg ctagggttgt gatttgttcc gatctgttca attagtagga tttagtctct 1320
gtttttctcg ttgatccaag tagcagcttc aggtatattt tgcttaggtt gtttttgatt 1380
cagtccctct agttgcatag attctactct gttcatgttt aatctaaggg ctgcgtcttg 1440
ttgattagtg attacatagc atagctttca ggatatttta cttgcttatg cctatcttat 1500
caactgttgc acctgtaaat tctagcctat gttaattaac ctgccttatg tgctctcggg 1560
atagtgctag tagttattga atcagtttgc cgatggaatt ctagtagttc atagacctgc 1620
agattatttt tgtgaactcg agcacggtgc gtctctctat tttgttaggt cactgttggt 1680
gttgataggt acactgatgt tattgtggtt taggtcgtgt atctaacata ttggaataat 1740
ttgattgact gatttctgct gtacttgctt ggtattgtta taatttcatg ttcatagttg 1800
ctgaccatgc ttcggtaatt gtgtgtgcag 1830

<210> SEQ ID NO 50
<211> LENGTH: 2212
<212> TYPE: DNA
<213> ORGANISM: Aegilops tauschii

<400> SEQUENCE: 50
tgcagcgtcc cggtgccgtc ggagcttgcc gcgactactg tggagatccg agggagcttc 60
aatggagtgt gtcaagggct gcaatggagc gccgccgggg tcgttggagc ttgtcgtgga 120
ttcaagcttt caccggagct gcaatggagc gccgtcggag cttgaagctt ttttcgcgcc 180
gcagtgcaac accgccgtct atgtgcaact ttccgcctgt ttcaatgaag caccgttgtt 240
cgtgacacct ggtgcaacgc ggcattgccg tcggacgcac gagctgagag gggtgccat 300 ggcgctacca accagggatg ttgcttttct ctcccaacgc aaccacaatc tgctcagctc 360
cccacatgca gcaagctcac atgccgcacc tagcacaccg cgacacgacc acgtgactgc 420
tactatcggg ggccatggcc agcgagctca agggttgggg cagccatatg ccctgcaaag 480
ctcaagggtt gtggcggtca tggcatgtga gctctggggc gagtcgttat aggcggcgct 540
acaaccgcgg aagctgactg ctacaaccgt ggtgaccgtg tgtcgtgacc cccagtgggg 600
ctatgctgcg accgtccggg tgagaagcta cgcccccagc cgaagatgtt ccgactgaca 660
tgggcggggg aggggagcac gggcgggcgg cgcagcaatc gtcggcgaca ggaaggtgca 720
aacctcgaca gccatgctac aaccttccaa tatctggagc tggagacaag aaggttaccg 780
gtgtggtgct cagatcggcc ggccgatgca gagcactgtc caaggcgaat acaaattcga 840
gtcaaaattg tgacaacaca gtaggcgtgg ccgtacgagt tcgagtcacg catgactaac 900
gatgctcacg caccgcacca acggcgtgag cgcggcgtcc aactccaacg gccaccaacc 960
agccaaatcc ccaacagcac caaacgacgt cacctttgga atctcctccc ctattctggc 1020
ttttgcgacc gcctctctct cctccgcctg cctatccgct ccatcctcca cacgtcaggc 1080
gtgccgtgtc tcttcttcct tctctccctc cctcccgtcc gagcctgcta taaaatccct 1140
gccccctccc gtctcctctc cacacatccg atccaatcca atccagtccc cgtccaatcg 1200
aagcgaagcg aagcgaaggc tctctcgtcc tcctcctcaa ggtatgcgat gcgagcctcc 1260
gattttctct ccgccttctc gtcatgtgcg tgcgtgcccc gggatcattg ataagactgc 1320
cctgatcgat tattggtggt tcccctcgat tcctgttagt aggttggagt agatctgcgg 1380
gcgggccgag tctgttatag tcgactgatt gctgctggtt cgctcagtcg aggttgatta 1440
agtctcgatt ttagattaat ctctctcgat tatgcctgga ttttcgagta gatctgccga 1500
ttgggatgcg atttttcttg gtttcgtcca tctatatata tgctgtggtt agctatgtct 1560
gctggttgtt gataaatcgt cgcagtattc ttggatttac gattttgtac ccctcgtatc 1620
acaccagcaa tttgctgttg ctaacctttg cttgctgtac gctgtgcatc gactttttac 1680
cttcatattg ctcccacaag gctaaagatt gcttgtagat ctgctaatat atttctgttg 1740
agttctgcta agatttagca ctgcatgctc tgaaatccgt ttgcttagtc tagcggattc 1800
tttgtactgt ggcctcgttt atctatagat tgacttactg cagatttcat tattcttgtg 1860
gtttcggccc tgtagctact tgtttagtct tttgattcaa ctcttaaata catgtgggtt 1920
tgatgatgtt actgttaata cgtccatgac ttgaccagct tattctgttt aactgactaa 1980
taatatatac tccccatgac catgaggcta gagatttcac tgataataaa tctgctaata 2040
tatttgtggt aggggttctt ccaaaagtta gcatcgtcaa tcatttgatt agcttattct 2100
aagggattcc ttagttacaa ttccatctct gttgtataat ccggttcatg tattgttaca 2160
gatttctctg taccgtttct aactctggtt ctgtgtgctt tgttgtttac ag 2212

<210> SEQ ID NO 51
<211> LENGTH: 2452
<212> TYPE: DNA
<213> ORGANISM: Unknown
<220> FEATURE:
<223> OTHER INFORMATION: Panicum hallii

<400> SEQUENCE: 51
aatcgttggt caactttcct tccattactt tttaatacgt aacaattatc cctaaagcct 60
aattaagtaa ttcaacttcc gaattcaata ggggatcatc tgggcacgac ctaattgaaa 120
ggataacaat agctttcaaa caacatttcc acttgtggta agatttaagg tcttaacatt 180
gtatagttgt ttttctcacg gccctagact tgagaaaggg accttttgat atcgttattg 240
tgctccataa tttttagttg ggacaaatgt aatttcttat atttacgata aactcgattc 300
taatgtattg ataactccaa tgccgtgtcc atttatggtg ttatcatttg tttcctgatt 360
taaagaaaaa atataacaca caaaaaagat gattttggaa gtttacaatc acgttcacca 420
ttactctcta ccatatcttg gcgttgttgc caagcgtatc tagtaatttc attcttgaaa 480
gcctctagct cttaaacgta atttatgata cagtactata ttttttttat taagggcaaa 540
agatcgagag gtaaatggtc tgctccgtaa atttatctta catagaggct ttaaaaagaa 600
atatcatgta aaatcgcttt tgttagaagc aggtcatgca taaccttcca gggacatgcc 660
agttgttagt tgcttttttt tagtttctct ttcttttacc tgattataat cttttaaagt 720
tatagtcttg tatttctaat atagaaacgc atacgtgtgc gccgttgtta aaaacaaaga 780
gatcatgcat gattgaagca tcaccataac gacgttaatc ttccgtccag ccattaacgg 840
ccaccaaccg caggaggcaa acggcgtcac catcctcgat atctccgcgg cggccgctgg 900
cgttttccgg agaaattgcg cggtggggac ggattccacg agagcctctc gctgctgggc 960
cccacatcaa tggcgtaacc tcacgggacg cttcctccct cctgcggccc tcccccgcgt 1020
ataaatagca cccctccctc acctcttcct catccagtcc ccaacccgtc gagaaattct 1080
cccgagcgat tgcaatcgaa gcgaagaggt ctccccccgat cctctcaagg tatgcgagtc 1140
ctcgatcccc ttccgatcta tctcgtttct cgcgtgctct ccctgctcgt gttcgtcgtc 1200
gatctagttt agggtttgat ttggttctga atcgttccct tttcctgctt gcgttcgatt 1260
tgtcgtcgat tctcgggtag atgtgtggat ctgcggggcg tgatgaggta gtttggtgta 1320
gattcgtgtt gggcgttcaa tttgcctcta gggttcggct gctgttggca tgcctgtgat 1380
cgagcggccg gataggatta gttttttta tatatatatg ttggatgcct gatttcctgt 1440
atgttgggtt agattgctgg tacgattcat ctaggcggtg ctttgcagag gaacagcctt 1500

-continued

```
gctgtttagt atttggtagc tctttctaca ttgattactt ttgatcatag cctgataatg   1560

atcaccgatt ggtgtggaat taattatttc attgtcgaaa gcatagctga tgtagatata   1620

gctgcacaat ttcttccttg gctccttact gtctaaattg tagagtatac tgagttactg   1680

cttctttatc agtttctctg gattgttgta tccagttagg ccagtgttgt caaaatttga   1740

catggtagtt catctgaaat ttctccggac tgttggtatg ctcgtggcca gacttaattg   1800

attaggctgt tcttcatgtt ggatcacccc atggtttgtg atacctgttg ggttagattg   1860

ttggttcgat tgctgtttaa tcttggtagc ttcatctaga tttgtacaac ttttggtcac   1920

ctgatgatga tcaccgattg ttgtagaatt agttaattca ttgttgatct aggtgtggaa   1980

ttaattagtt aattgttaat ctatggcatg gctcatgcag atattgatgc aaattttctt   2040

aactggttcc ttgcttcagt gtgtatctgt ttgtctgtgt tttaggccac atcatatgat   2100

tgtcaaaatt ttaaatggta gtttaatgat aaatgtagtt cagcttactt cagtgttgat   2160

ttgcttcaaa tgtagttttc tgtcctattg aacatagaat cttcatgaga tgttaatgta   2220

ttctcttgtt cagaattgat ctgtttcaat atcacaatat tatgtgtcct gtaaagtttt   2280

ttagtatgat ttgttttaaa tttagttagc ctatcctgtt aatataggat gatgagccgt   2340

gagatgttca ttctcttttg ttcagagcta atcattttca atgttgcaat gttctgtgtc   2400

tagctggatg cttacggtgg tttaactctc ttctgttcct taatgtttgc ag           2452
```

```
<210> SEQ ID NO 52
<211> LENGTH: 1783
<212> TYPE: DNA
<213> ORGANISM: Zea mays

<400> SEQUENCE: 52

gtagattacg ttggttaaat atatatgaat gtgaaacaac aactaaaatt tgaactatta     60

attatgtata attttatctt atttttatat aaaacagaga ggagaggagc gatgactgtg    120

gcgtgtggga acgtggaaac tcgctggccc atctcgaata attttgctgc acttctaata    180

ccttcacgag tctgcacaag catagattgg tgctggttga acggccctga ttcttttttt    240

tcatggctct gcgttcgaga gcatgttttt cgttgaaggc ttctttggtt agaagtgacc    300

tgagtgaatt ggagaggatt agaggcatgt ttggttcact acctcagttg ctacattttg    360

cctaactttt ctgcctaagg ttagttattc aatttgaacg actaacctta gacaaagtgg    420

ggcacattta gccacaaacc aaacaggccc taaatctatt tatatttaat tttaaatatg    480

aataaattta attctattaa tctttgtcga gtgttctttg ccgagtgtta cactcggcaa    540

agcctttgcc gagtgtaaaa tagcatttgc cgagtgtgtt agacactcga caaagaacgc    600

gattccggta gtgttaattt cctctagttt ttatacaaca aagcataaga ggatatattt    660

cttttctttt actttgatga aacaatttgg ttcttttgga cgagccaaaa cccggatatg    720

gtccaattaa gaccttattc gtttgtccaa aaatgtaaca ggaatcattt cagatgatca    780

aaacttatat aaattagaga aacaaatcgg ctaggaatta tttcatatct ccattcctga    840

agaaacgaac ggtcctaagg ctccaagcac gggtctatac atcaggttgc gccggtctaa    900

gcccgcacaa cattgggtcg ggtcgtgttc aagcattaat cgtggtatag actggaccat    960

cgtgtcacgg gctatataat acatttgaga atgtagaatt aaatacatac tccccgactc   1020

taaatgacat attcatatac gaggatggta cttctttgga ctatataggg acggaggtcg   1080

ggagggaatt cgcgagagca agaaagcagc tacggtagcc atgcatgacc atatgaaagc   1140

gacgacgcga gaggatgtat ggtttgggct gcttaaatac aatctgcaat agactgtgct   1200
```

gcattgcaca ttattcttat gaaagagtgt gtttcatctc tatttatgtt gttttggata 1260
aaatgttttg tttatttatg aaggacatat ttccttatca ataattccta cgcccaaatt 1320
aaagaagccc tggaatcagg aactaggaag gggcaccgat gtgattttgt gagccaacga 1380
catggggagc atgagcgtga gcaatgcatg tttgccgagt caaacgttgc cccaccaaca 1440
agcaagtgcg tcgtgcgtgg atcctctcct tcctctctct tggttcctgt tatctctctc 1500
ggctgtccac tcccccgtga tgtgagcgcg tttctctccc gtcctctcct ctcctccccc 1560
gcaacaaact cctgcaagct gctctcgatc tctctctccg tcgccatctc tctcgcgcgc 1620
gcattacttg cacgtacgtg ctcagaagga aggcagaggc aaaagcagcc taggtgatat 1680
gatacctcct cctcctcctc ccattagctc ctccgcatgc atcatgcatg ggtacgtgcg 1740
cgtgctacat tttatttgaa atgaaatggc tggttgtctg cag 1783

<210> SEQ ID NO 53
<211> LENGTH: 3710
<212> TYPE: DNA
<213> ORGANISM: Zea mays

<400> SEQUENCE: 53
gcccgacaag aaagctaatg ggctgggctg ccaaccatgt ttactaggct aggctcattc 60
ggatgctagc caatcgttcc tgcactgagg ctctagattt catagatagc taatgggctg 120
ggctgccaac catgtttact aggccataaa atgaactttt ggtttgttta ataatattat 180
gccgggtttt agaaacccat gggtttgcgg gtatgggtac taggatccca tactcgtacc 240
ctcatacccg ctgggtttag cttatcaccc attaagaaac ccgtgggttt ggatattagc 300
ccgtacccgt cccctaatag ggtaaaaacc caccgggttt cgggtttcgg gtacccattg 360
ccatctctac ctgtcaatga cccatttaaa tagagcccat cgaagcccac taaatattta 420
acatttttga gctagttgta ctttttcctt ttttaaccca aatttttaat gtggcaccca 480
caaacaaccc aattttattt tggttatata tgttatgtac ttttatttat gttatttcat 540
gtgatttgtg ctaacctgac acattaattt tgggttaatt aagttggata ggcacactta 600
agtattcatg ggttgtgttt tggatcgacg gcttgacgtc ttggtccacg ggctggcaca 660
ccacgacccg taattgaaat tgtactttag tggactgtgc cttagtggat tgtgctttaa 720
taagcctggg gtgtaccata ttgggctgat ccagatatac atgtacaccg gggagtattt 780
atctttgaca caaggagtat ttacttatta tgaaaccagc tccaaaaagt ggcttctgag 840
cctatccacg tcgtccatta atctttcgac cgtaggatcg gattccaacg gctacacgag 900
tgttctcacg caccaggcgc caggcggcct cctcatgctg gataaatcgt gacgcttcca 960
gatgatacat ctccctcttg gctgccgggc ggcactctcc atggtgaaga gggtgtcgac 1020
cgcgatggct acaacgacga cgatggagca cttgacgccc ccaacagatg cgagccattc 1080
tcctcctccc tacgtccttt ccccctccac gacaccataa ccgtgcctgc tccgccgaat 1140
ctaaaggtgt caggatcccc aatccttccc ctcctctccc cctctccacg acgctgcaac 1200
tgtgctcgca tcgccatccc ctcccctccc ctgtctccaa gccaggaatc ccatccccac 1260
cccaatgtcg cagttctgct cgcgttggcc ggatctgtga atgaagaacc cacggttcca 1320
cgacctcctc ttcgtggaag cctaaaaggc atcaccccca taagcgagag ggaaaagaca 1380
cattcctata tattctctta gtttgtccgc tgttgtctag aaacatcatg taatgaggct 1440
gggaaacgat cccacggagt gctcccgtgt ccgtcgcctc ggttcggcag aggccagcaa 1500

-continued

```
ccgcggcacc tggtccacag cagcagccac cacgactcgc tagggctagg ccgacctaga   1560
tgatatgcag tgagctgatg ggagggatgg gcgagcaaga attggtacag taaccggaag   1620
acgatcttga tttattcctt atgtcatgaa ttccttttta tttacaccca cactttctaa   1680
ctttcgtaca atgattcgta tatttaaaac aaggctaact tatgttctca tgctttacga   1740
accctggcat atgtcgcaaa aaatccttac ctaaagaact aactctgcag cctcttcaag   1800
ctctagattt caattcttat ggcctaagaa gtgttttttt atttcataat ataagctttc   1860
acaacaatct aattcttgga gtcagattct ataaataccc aacatttact aacctacatt   1920
tttttttcaa ttggtgccat gaccatcaca taatgttgat gagctattcc ctccaagttg   1980
ctgattgcat gtggattacc atgcatggct atttgctatt tggttgtctc gacctttctt   2040
aggatctatt ggatgtaata catattatca ttatttagct aatatttgct aactactacc   2100
tagcagagtg gatagtaggt tgtggtgttt atatccataa ctaatgggtt aattaataat   2160
tggagagtaa tgttcctgtt agccccccatt gtttgggtag atagtaagat aatggggatt   2220
tagaaacaat ctaaagttta ttacaatctg ttatctagac ctatttatat ccatagagct   2280
aaagtttagc agattgctac atcctcatta ttagtttgga gccaaacatg tcctgattgt   2340
ataatttaaa tgtttatagg agtaaccaat ttgttttagc tttgctattt tacgagtgtc   2400
aagatgctta actatttcat acttgctttg taggaatgtt cgatgccgac aacatcttgc   2460
tctaccagaa ggtaccagct ccaaatcaag aaccaaaatt taggaaaaat acgaactgca   2520
accttatccg tcatctttag taattcatgt gtttatctta tttgcaccaa gaactatgct   2580
ggaggctata aaactatgaa tgttatttgt gacatgtaaa taatactagc ttgtacatgc   2640
atctaaatgc atataagaaa cacaatgcac cttttgtttg cattccatgt aaattataaa   2700
ttaaatccaa acattgaaaa attacaaaac acacacacac aacactatgc gcgcatgggc   2760
gcgcgcaaga cactagtaca taataataac gatattgttc gcttcggatt aaattaaacc   2820
aagcgagtat gcgtgcatgt gtacgtcgga tgctttgttt gttcatttgt ggcccgtgaa   2880
gtaatatttg ggcccaatag cccattcatc catgtcctaa ccctagggcg cgttccttat   2940
aaaacctatc tccattctgt tctcactctc agacaccaga cgcagtcggc tgccgcagac   3000
tggtagtagc ccgcgcgccg tcaccgtatc ctcagatcag aggcgagcag aaaccacacc   3060
actctactga cgcccgacga ggtacacttc cgcgcgcgcg cttctcttcc ttcttttttc   3120
gctcgacgag gtactctgct tcacgcgcgg gcgcgcttct cttccttctc ttttcgctct   3180
gccttgagcc tgttcgtttg atgcccagat ctactaggtt tgtcgatcgt cgttatgtgt   3240
gatgagctga gccgattcat gcactgtatt tttaattaag tgttttttttc ctccgccgct   3300
acctttattg tctatgtatg aacttgcagc ttacaactgg ttattgagcc ataaattgta   3360
actgagtttc cgagatctat aatattacgt ggctgaggcg cttcatctct gttttgtttg   3420
tatgacagta ggagtactaa tccaagttta gcttccgctt cttcatctac ctttagtatg   3480
tatttcgtat ataaatacga ttgcagtttg caactgattc tcggccatag atgattaccg   3540
ttgcgttgtt catcgggtct agtttcggat ctctgatgtt gtgtgggtgg ggtacttcga   3600
cttgggtttt cctgcccttt gtttgattac tggtttattg acatatattt atctattgac   3660
tttttatctg ctatgtttga tgtaagcagc agtgtaacat tttcctgcag              3710
```

<210> SEQ ID NO 54
<211> LENGTH: 1645
<212> TYPE: DNA
<213> ORGANISM: Zea mays

<400> SEQUENCE: 54
caaagggctt ttggtcatca gccgggagcg cctccatggc cggcttgatg atgttggtag 60
tggagatctt ggtgtgatcc ttaaaaccgg ccatttatgg gccgattttt agcagatcta 120
gacacctatt ccccagcgga gtcgccaaaa gtatgttgac gctttttcgg agcgccaatc 180
actcaagaag aaccggcggc ggtgccctct gcacaggggc ggacggtccg cgcgcagggg 240
ccggacggtc cgcggcctgg tgcgaggcgg cggcgctctc tggttagacg cggacggtcc 300
gcggcacagg gccggacggt ccgcgaccta gtgcaggtgc tcgggttccc tgcctgacgg 360
ccggacggtc cgcgctctag ggccggacgg tccgcgcgtg cgcaggggcg gcggaagatc 420
gccggcggcg cctggatctc gctcccggga gggaccccgt cggggaggag agatcctagg 480
agttgtctag gctcgggccg gccgacctag actcctctaa tcgacgtaga gtcgaggaga 540
ggcagagaat ttggggattg gaatactaaa ctagggctaa actagaacta gactagaact 600
actcctaatt gtgctgaaaa taaatgcgag atagaagttg tattggttcg attgttgggg 660
gtcaatcggc cgtagccctt catctatata aaggggaggt ctggatccgt ttccaactga 720
tttccgagtt aatcccgcgg ttttaggtaa caaatcccgc gagaaactag gaaccctaac 780
tgactctgcg cacgcgcgga ccgtccgcgc caccaccgcg gacggtccgg accgcggacc 840
gtccggcctc cgggccggac cgtccgcacg gtcattttgg gttcgaacag agtcccaacg 900
aggttagtaa atgtagtgat gaaattaagt tttgtacgaa gtttgtaaat ttaaggacct 960
gttttacata actattggag aagagttttc tctgaaaaat tcttaaattt atatttaggg 1020
agttgtttat ataactattg gcatttgaga tgctctaagg aagcgaagga aataacttgg 1080
cggcgatcct agtcgacaac cgttgaattc gtgagaatca atcattctgt aggagtaaaa 1140
aaataaaata aaatatgcat ttcctcgttc ctatacgctt aaattagacg accctggact 1200
ggaaccagga actaggaagg ggcaccgatg tcatttgcga agcaacaaca acatgcgtga 1260
ggacgaccaa gtcaaacgtt gcgtcgcgtt gcctcgccgg cgggccggtc ccaccaagac 1320
gtggcgccat gcaagtgcgt cgtcgaccct cttctctctc tctcttgtag tcttgttcct 1380
gttatctctc tcggctgtcc gctgccccgt gatctgagcg cgtttctctc ccgtcctctc 1440
ttctccctct cccgcaacaa acacctgcta tccgctctcc ctctcccctg ccatctctct 1500
ctatcgcatt gcttgcgcga gcgcagaagg cacacacgta cagcctaggt gatacctcct 1560
cctcctcctc ctcctcctcc tgatctcctc tcctcctccg gcctccgtat acctataact 1620
aaaagatgat catcgtgcga tgcag 1645

<210> SEQ ID NO 55
<211> LENGTH: 899
<212> TYPE: DNA
<213> ORGANISM: Zea mays

<400> SEQUENCE: 55
tgcagtgcag cgtgacccgg tcgtgcccct ctctagagat aatgagcatt gcatgtctaa 60
gttataaaaa attaccacat atttttttg tcacacttgt ttgaagtgca gtttatctat 120
ctttatacat atatttaaac tttactctac gaataatata atctatagta ctacaataat 180
atcagtgttt tagagaatca tataaatgaa cagttagaca tggtctaaag gacaattgag 240
tattttgaca acaggactct acagttttat ctttttagtg tgcatgtgtt ctcctttttt 300
tttgcaaata gcttcaccta tataatactt catccatttt attagtacat ccatttaggg 360

-continued tttagggtta atggttttta tagactaatt tttttagtac atctatttta ttctatttta 420
gcctctaaat taagaaaact aaaactctat tttagttttt ttatttaata atttagatat 480
aaaatagaat aaaataaagt gactaaaaat taaacaaata ccctttaaga aattaaaaaa 540
actaaggaaa catttttctt gtttcgagta gataatgcca gcctgttaaa cgccgtcgac 600
gagtctaacg gacaccaacc agcgaaccag cagcgtcgcg tcgggccaag cgaagcagac 660
ggcacggcat ctctgtcgct gcctctggac ccctctcgag agttccgctc caccgttgga 720
cttgctccgc tgtcggcatc cagaaattgc gtggcggagc ggcagacgtg agccggcacg 780
gcaggcggcc tcctcctcct ctcacggcac cggcagctac gggggattcc tttcccaccg 840
ctccttcgct ttcccttcct cgcccgccgt aataaataga cacccccctcc acaccctct 899

<210> SEQ ID NO 56
<211> LENGTH: 807
<212> TYPE: DNA
<213> ORGANISM: Hordeum vulgare

<400> SEQUENCE: 56
gatctcgatg tgtagtctac gagaagggtt aaccgtctct tcgtgagaat aaccgtggcc 60
taaaaataag ccgatgagga taaataaaat gtggtggtac agtacttcaa gaggtttact 120
catcaagagg atgcttttcc gatgagctct agtagtacat cggacctcac atacctccat 180
tgtggtgaaa tattttgtgc tcatttagtg atgggtaaat tttgtttatg tcactctagg 240
ttttgacatt tcagttttgc cactcttagg ttttgacaaa taatttccat tccgcggcaa 300
aagcaaaaca attttatttt acttttacca ctcttagctt tcacaatgta tcacaaatgc 360
cactctagaa attctgttta tgccacagaa tgtgaaaaaa aacactcact tatttgaagc 420
caaggtgttc atggcatgga aatgtgacat aaagtaacgt tcgtgtataa gaaaaaattg 480
tactcctcgt aacaagagac ggaaacatca tgagacaatc gcgtttggaa ggctttgcat 540
cacctttgga tgatgcgcat gaatggagtc gtctgcttgc tagccttcgc ctaccgccca 600
ctgagtccgg gcggcaacta ccatcggcga acgacccagc tgacctctac cgaccggact 660
tgaatgcgct accttcgtca gcgacgatgg ccgcgtacgc tggcgacgtg cccccgcatg 720
catggcggca catggcgagc tcagaccgtg cgtggctggc tacaaatacg taccccgtga 780
gtgccctagc tagaaactta cacctgc 807

<210> SEQ ID NO 57
<211> LENGTH: 1084
<212> TYPE: DNA
<213> ORGANISM: Hordeum vulgare

<400> SEQUENCE: 57
gggcaagtta aaggccctac tggtggcatg ggtgggcagg ctgaagaccc tactagtggc 60
atgggtgggg agctccctgc caccatgtaa tggaaccttt atgatttact accctttatg 120
ttgtgtgtga gtgtgacaga gaaacctttc tctgccttat taataataaa taaagcacat 180
cacttgtgtg tgttctgaaa aaaagatctc gatgtgtagt ctacgagaag ggttaaccgt 240
ctcttcgtga gaataaccgt ggcctaaaaa taagccgatg aggataaata aaatgtggtg 300
gtacagtact tcaagaggtt tactcatcaa gaggatgctt ttccgatgag ctctagtagt 360
acatcggacc tcacatacct ccattgtggt gaaatatttt gtgctcattt agtgatgggt 420
aaattttgtt tatgtcactc taggttttga catttcagtt ttgccactct taggttttga 480
caaataattt ccattccgcg gcaaaagcaa aacaatttta ttttactttt accactctta 540

```
gctttcacaa tgtatcacaa atgccactct agaaattctg tttatgccac agaatgtgaa    600
aaaaaacact cacttatttg aagccaaggt gttcatggca tggaaatgtg acataaagta    660
acgttcgtgt ataagaaaaa attgtactcc tcgtaacaag agacggaaac atcatgagac    720
aatcgcgttt ggaaggcttt gcatcacctt tggatgatgc gcatgaatgg agtcgtctgc    780
ttgctagcct tcgcctaccg cccactgagt ccgggcggca actaccatcg gcgaaccacc    840
cagatgacct ctaccgatcg accggacatg aatgcgctac cttcgtcggc gacgatggcc    900
gcgtacgctg gcgacgtgcc cccgcatgca tggcggcaca tggcgagcta ggaacctagg    960
accgtgcgtg gccgccggct ataaatatcc catggtcgtg agaccactag aaggaagcag   1020
cacctggcac tgcgagagcg agcgtgcagt gagtagatag actagaccaa cgacgacggc   1080
aggc                                                                1084
```

<210> SEQ ID NO 58
<211> LENGTH: 3064
<212> TYPE: DNA
<213> ORGANISM: Zea mays

<400> SEQUENCE: 58

```
gctcgatcca cctaggcttg ttgcacatct ttacccacaa gtcatgttac ccatctgcca     60
aggggtcatg aatcccatac acctctacca tggaagcgag acagggtaac actacgaggc    120
ctttacaaag ttccactagc tttagaaaac ccgctacaag gatcccccgt ctgaccgcca    180
tcacagcaaa acccgagaac ctccctacac cgaccactcc cctactatcc ttgccccttt    240
cgggtaagat agtcttccac tagctttcct aattagtcag ccaagggcgt cccataccac    300
ccttatggta gcactgtttt tccgggtggt cgctccatgt tccaattaac ataataatct    360
tatcatgaac aataaataac aaaaaatgat aataaaagca tgatcatgaa taatgtgtat    420
ctcaataccc aaaaccacat aaagcaatag caggtactac ccaaaagttc agtggtaaac    480
aaggtataaa gatagtcaaa ctgggttgac ctattgggtc tcatcaaaat taacctatgc    540
agatcataat gattaacagt aacattattg ggtaaataga agtgatcaag ggcacaagtt    600
gccttcaacg agatcctgct cagcagtctc cacctgctga acacctgggt cctcagtggc    660
ttgcttgtct actcgcaaca atacaaacaa acatggtata ggagaaatta acatcacacc    720
aaacagcaga acagaatgca tgataatatt ctacgtgtca taacgagatg gtaggaacaa    780
gaatcactaa attcagagtt acgattttct gaagttatta ggtgcttagt atagaataaa    840
tcaagtggat aattttactc tatgttttat ggctaaacag agttaccaag tgataaacaa    900
tattaataca aaattaatgc aactggaatg gaccaaaaag gagttaaaat ggattttcta    960
tgaattaatc taggttttgg aattgttttt atactaaata ttcattttct cggcttatta   1020
ttaaccctgg tattttattt ggactgcgga cgcaaatgct agaaactaca gggtccaata   1080
tatgaaaatc agggcatgga tgtaattaat ttacaatagc agtggacggc gggttaattc   1140
agtaattccc taggggcact taagcaaata tccatcgcaa aggggtattg ttggatcccg   1200
accgttggat cagatccgaa ggccgagaat agatcgcgcc cacacaactg cgtcgtgcac   1260
tgaccaccct ccggttaaga ttcgacggac caaatttaat gaaatccaaa ccacccacag   1320
ccccacgatc agcaatctac ggtccctctt aacccagatg aatcggtatc cgacttctaa   1380
tctaagcagt tcctcaatcg atcaacgctc cagggccttc ttctatctcc caacgcagat   1440
cgagctacgg tcgcttgcac ccgaggaacg ccgacacagc gagcggcgga ccagcggttc   1500
```

```
tgggtaatga tttggagcac aaacaatatt ggcgcgacat aggaatgatg gcaactatta   1560

ggttgtgacc ttactagtgt cagcggtgtg ggcagggtcg cccacgggaa accagtgcga   1620

cggtgctccc ggcttgttaa tgacggtgtg ctggtcccga cacggtgatg ccccaaacgc   1680

ccccgccgta cgagaacacc gcagacgccc ctgctcgact ccgccctcgg cttcccgcgc   1740

ccacctcgca cttcgacggc cgcaccgacc ctctgacctc tccttttctc tcctttctca   1800

ctcctatcgg tagctacaac agaagcgact cccaacgtgg cgcaaaccct cgaagcatac   1860

ggctggggaa ggtggcagcc aggtttatat cctaggcgcc cgaggaaatc gtgtggacgg   1920

ctgttacgtt tcgcccgcgg ggcgcgattc gcgcgaagaa gactgtatgc gaggtagggc   1980

ccactagcag tgagccatca cccagggaag cgcgcatgca tcgattgaca cgcgacccca   2040

acagtcaggc gacccgagtg tgcagacggt cgcgatggtg aaagtggcta gctcgcgcgg   2100

acgcgtaggg gcattgggcc gaaatgcgtt tcagcggtcc aacttctttt tttcttgtct   2160

tttttctttt cctttccttt tctattttta gatttcaaat ttaagttcaa atttttttgtg   2220

gtgaattttc taaaaatcca catatcagta tgaaaagaat ttatatataa atctatttat   2280

ttatatattt atttttttc tatgttattt ccaatttcta aaatgtaaat taggttaaat   2340

cgccatttgg acactaatat atctttatta gtattactat tattatatgc acaaccaaat   2400

aaactccaac atgatgcatc gattatttgt atgtcattgg ttaattattc actttaaata   2460

tgttccttaa cgattctcat gaaacagaag gccatgcaca taaagatgta tccctttttt   2520

ctatattccc agagttgggt attacaacat tcatctatgc attctaggat ttcaattact   2580

ctcaatcttt tagtatttgt tccttcattg tcaaatcact tctcatctaa ctactatgct   2640

tgtttaacca gcagaacaat actacaacaa tatccattta taaaggcttt aatagcaaac   2700

tttacatatt catatcatgt taaggttgtc acatgtgtaa aggtgaagag atcatgcatg   2760

tcattccaca taaatgaaaa gaattcctat ataaaaatga catgttttgt tgtaggtagt   2820

ggaaattatc tttccagcaa agaccatata atccgataaa gctgataact aaatgtcaaa   2880

atcgagtaag tgccatatca tctatatctt atctgttgtt tggaaaaaga caaaatccaa   2940

aaaaaaatat atgagatctc acatgtataa atagctccca aatcagtagt taatacatct   3000

cccataatat tttcagcatt caaaaacaca ccaagcgaag cgcactagca acgacctaac   3060

acca                                                                3064
```

<210> SEQ ID NO 59
<211> LENGTH: 178
<212> TYPE: DNA
<213> ORGANISM: Zea mays

<400> SEQUENCE: 59

```
cacgtgagct tgcgatgtcc actagggagc tccatccact gatccacccc cacgcggcgt     60

ggcgtcgtca ttaacggctt gtggggaagg gaacgagcaa ctaaccgata attagtacca    120

gaccggccag tgaacgatgc caaaaccggc ttataagctc agctgcgaca accgtttt      178
```

<210> SEQ ID NO 60
<211> LENGTH: 330
<212> TYPE: DNA
<213> ORGANISM: Oryza sativa

<400> SEQUENCE: 60

```
aagaacgaac taagccggac aaaaaaaaaa aggagcacat atacaaaccg gttttattca     60

tgaatggtca cgatggatga tggggctcag acttgagcta cgaggccgca ggcgagagaa    120
```

gcctagtgtg ctctctgctt gtttgggccg taacggagga tacggccgac gagcgtgtac 180
taccgcgcgg gatgccgctg ggcgctgcgg gggccgttgg atggggatcg gtgggtcgcg 240
ggagcgttga ggggagacag gtttagtacc acctcgccta ccgaacaatg aagaacccac 300
cttataaccc cgcgcgctgc cgcttgtgtt 330

<210> SEQ ID NO 61
<211> LENGTH: 246
<212> TYPE: DNA
<213> ORGANISM: Oryza sativa

<400> SEQUENCE: 61
ggatcatgaa ccaacggcct ggctgtattt ggtggttgtg tagggagatg gggagaagaa 60
aagcccgatt ctcttcgctg tgatgggctg gatgcatgcg gggggagcggg aggcccaagt 120 acgtgcacgg tgagcggccc acagggcgag tgtgagcgcg agaggcggga ggaacagttt 180
agtaccacat tgcccagcta actcgaacgc gaccaactta taaacccgcg cgctgtcgct 240
tgtgtt 246

<210> SEQ ID NO 62
<211> LENGTH: 187
<212> TYPE: DNA
<213> ORGANISM: Oryza sativa

<400> SEQUENCE: 62
tgggccgtaa cggaggatac ggccgacgag cgtgtactac cgcgcgggat gccgctgggc 60
gctgcggggg ccgttggatg gggatcggtg ggtcgcggga gcgttgaggg gagacaggtt 120
tagtaccacc tcgcctaccg aacaatgaag aacccacctt ataaccccgc gcgctgccgc 180
ttgtgtt 187

<210> SEQ ID NO 63
<211> LENGTH: 163
<212> TYPE: DNA
<213> ORGANISM: Oryza sativa

<400> SEQUENCE: 63
tgggctggat gcatgcgggg gagcgggagg cccaagtacg tgcacggtga gcggcccaca 60
gggcgagtgt gagcgcgaga ggcgggagga acagtttagt accacattgc ccagctaact 120
cgaacgcgac caacttataa acccgcgcgc tgtcgcttgt gtt 163

<210> SEQ ID NO 64
<211> LENGTH: 287
<212> TYPE: DNA
<213> ORGANISM: Oryza sativa

<400> SEQUENCE: 64
ggtaccgagc tcggatccac tagtaacggc cgccagtgtg ctggaattgc ccttggatca 60
tgaaccaacg gcctggctgt atttggtggt tgtgtaggga gatggggaga agaaaagccc 120
gattctcttc gctgtgatgg gctggatgca tgcgggggag cgggaggccc aagtacgtgc 180
acggtgagcg gcccacaggg cgagtgtgag cgcgagaggc gggaggaaca gtttagtacc 240
acattgccca gctaactcga acgcgaccaa cttataaacc cgcgcgc 287

<210> SEQ ID NO 65
<211> LENGTH: 400
<212> TYPE: DNA

<213> ORGANISM: Triticum aestivum

<400> SEQUENCE: 65
ggcggcaggg agagttttaa cattgactag cgtgctgata atttgtgaga aataataatt 60
gacaagtaga tactgacatt tgagaagagc ttctgaactg ttattagtaa caaaaatgga 120
aagctgatgc acggaaaaag gaaagaaaaa gccatacttt tttttaggta ggaaaagaaa 180
aagccatacg agactgatgt ctctcagatg ggccgggatc tgtctatcta gcaggcagca 240
gccctaccaa cctcacgggc cagcaattac gagtccttct aaaacgtccc gccgagggcg 300
cgtggccgtg ctgtgcagca gcacgtctaa cattagtccc acctcgccag tttacaggga 360
gcagaaccag cttataagcg gaggcgcggc accaagaagc 400

<210> SEQ ID NO 66
<211> LENGTH: 626
<212> TYPE: DNA
<213> ORGANISM: Unknown
<220> FEATURE:
<223> OTHER INFORMATION: Mirabilis mosaic virus

<400> SEQUENCE: 66
ttcgtccaca gacatcaaca tcttatcgtc ctttgaagat aagataataa tgttgaagat 60
aagagtggga gccaccacta aaacattgct ttgtcaaaag ctaaaaaaga tgatgcccga 120
cagccacttg tgtgaagcat gtgaagccgg tccctccact aagaaaatta gtgaagcatc 180
ttccagtggt ccctccactc acagctcaat cagtgagcaa caggacgaag gaaatgacgt 240
aagccatgac gtctaatccc cccaacttcg tccacagaca tcaacatctt atcgtccttt 300
gaagataaga taataatgtt gaagataaga gtgggagcca ccactaaaac attgctttgt 360
caaaagctaa aaaagatgat gcccgacagc cacttgtgtg aagcatgtga agccggtccc 420
tccactaaga aaattagtga agcatcttcc agtggtccct ccactcacag ctcaatcagt 480
gagcaacagg acgaaggaaa tgacgtaagc catgacgtct aatcccacaa gaatttcctt 540
atataaggaa cacaaatcag aaggaagaga tcaatcgaaa tcaaaatcgg aatcgaaatc 600
aaaatcggaa tcgaaatctc tcatct 626

<210> SEQ ID NO 67
<211> LENGTH: 357
<212> TYPE: DNA
<213> ORGANISM: Cauliflower mosaic virus

<400> SEQUENCE: 67
tctggcgcgc ctgagacttt tcaacaaagg gtaatatccg gaaacctcct cggattccat 60
tgcccagcta tctgtcactt catcaaaagg acagtagaaa aggaaggtgg cacctacaaa 120
tgccatcatt gcgataaagg aaaggctatc gttcaagatg cctctgccga cagtggtccc 180
aaagatggac ccccacccac gaggagcatc gtggaaaaag aagacgttcc aaccacgtct 240
tcaaagcaag tggattgatg tgatatctcc actgacgtaa gggatgacgc acaatcccac 300
tatccttcgc aagacccttc ctctatataa ggaagttcat ttcatttgga gagaaca 357

<210> SEQ ID NO 68
<211> LENGTH: 510
<212> TYPE: DNA
<213> ORGANISM: Figwort mosaic virus

<400> SEQUENCE: 68
cagctggctt gtggggacca gacaaaaaag gaatggtgca gaattgttag gcgcacctac 60

-continued

```
caaaagcatc tttgccttta ttgcaaagat aaagcagatt cctctagtac aagtggggaa    120

caaaataacg tggaaaagag ctgtcctgac agcccactca ctaatgcgta tgacgaacgc    180

agtgacgacc acaaaacagc tggcttgtgg ggaccagaca aaaaaggaat ggtgcagaat    240

tgttaggcgc acctaccaaa agcatctttg cctttattgc aaagataaag cagattcctc    300

tagtacaagt ggggaacaaa ataacgtgga aaagagctgt cctgacagcc cactcactaa    360

tgcgtatgac gaacgcagtg acgaccacaa aagaattccc tctatataag aaggcattca    420

ttcccatttg aaggatcatc agatactgaa ccaatatttc tcactctaag aaattaagag    480

ctttgtattc ttcaatgaga ggctaagacc                                     510
```

```
<210> SEQ ID NO 69
<211> LENGTH: 554
<212> TYPE: DNA
<213> ORGANISM: Figwort mosaic virus

<400> SEQUENCE: 69

ctcgagcaag tgtacaaaaa agattaccac ggaagaaatt cacaaggtaa aactttttga     60

gaaaagattg atcaacatca atcaaatcaa ttgtggagac cacacaaaga aattgtggtg    120

taaaattcta cagaaaaagt acgaagagca tctttgccag tactgcagtg gggaccaccc    180

acgtgacaac aaagaagtgg cagacaagtc acctcaaagt ggaacccatc cacgtgataa    240

aagtatcatg gcagacagcc ggtacaataa tggggaggac agcttgcaaa gcagcccatg    300

tggaagccca ctcacaaacg cgtattacga acgcagtgac gacatccact caagaattcc    360

atctatttaa agacggattc attcccattt gaagatcatc aatactcaac caatatttct    420

cactctaaga aataaagagc tttgtattct tcaatgatag gctaagaccc taaagagtct    480

cgaaagagac atgtagtata gtaagagtcc tcccagtccg ggagattgta ataaagagat    540

cttgttaagg atcc                                                      554
```

```
<210> SEQ ID NO 70
<211> LENGTH: 299
<212> TYPE: DNA
<213> ORGANISM: Unknown
<220> FEATURE:
<223> OTHER INFORMATION: Agrobacterium

<400> SEQUENCE: 70

gatcatgagc ggagaattaa gggagtcacg ttatgacccc cgccgatgac gcgggacaag     60

ccgttttacg tttggaactg acagaaccgc aacgttgaag gagccactca gccgcgggtt    120

tctggagttt aatgagctaa gcacatacgt cagaaaccat tattgcgcgt tcaaaagtcg    180

cctaaggtca ctatcagcta gcaaatattt cttgtcaaaa atgctccact gacgttccat    240

aaattcccct cggtatccaa ttagagtctc atattcactc tcaatccaaa taatctgca     299
```

```
<210> SEQ ID NO 71
<211> LENGTH: 711
<212> TYPE: DNA
<213> ORGANISM: Unknown
<220> FEATURE:
<223> OTHER INFORMATION: Agrobacterium

<400> SEQUENCE: 71

cctgctttaa tgagatatgc gagacgccta tgatcgcatg atatttgctt tcaattctgt     60

tgtgcacgtt gtaaaaaacc tgagcatgtg tagctcagat ccttaccgcc ggtttcggtt    120
```

cattctaatg aatatatcac ccgttactat cgtattttta tgaataatat tctccgttca 180
atttactgat tgtaccctac tacttatatg tacaatatta aaatgaaaac aatatattgt 240
gctgaatagg tttatagcga catctatgat agagcgccac aataacaaac aattgcgttt 300
tattattaca aatccaattt taaaaaaagc ggcagaaccg gtcaaaccta aaagactgat 360
tacataaatc ttattcaaat ttcaaaagtg ccccaggggc tagtatctac gacacaccga 420
gcggcgaact aataacgctc actgaaggga actccggttc cccgccggcg cgcatgggtg 480
agattccttg aagttgagta ttggccgtcc gctctaccga aagttacggg caccattcaa 540
cccggtccag cacggcggcc gggtaaccga cttgctgccc cgagaattat gcagcatttt 600
tttggtgtat gtgggcccca aatgaagtgc aggtcaaacc ttgacagtga cgacaaatcg 660
ttgggcgggt ccagggcgaa ttttgcgaca acatgtcgag gctcagcagg a 711

<210> SEQ ID NO 72
<211> LENGTH: 708
<212> TYPE: DNA
<213> ORGANISM: Arabidopsis thaliana

<400> SEQUENCE: 72
atctcgtctc tgttatgctt aagaagttca atgtttcgtt tcatgtaaaa ctttggtggt 60
ttgtgttttg gggccttgta taatccctga tgaataagtg ttctactatg tttccgttcc 120
tgttatctct ttctttctaa tgacaagtcg aacttcttct ttatcatcgc ttcgttttta 180
ttatctgtgc ttcttttgtt taatacgcct gcaaagtgac tcgactctgt ttagtgcagt 240
tctgcgaaac ttgtaaatag tccaattgtt ggcctctagt aatagatgta gcgaaagtgt 300
tgagctgttg ggttctaagg atggcttgaa catgttaatc ttttaggttc tgagtatgat 360
gaacattcgt tgttgctaag aaatgcctgt aatgtcccac aaatgtagaa aatggttcgt 420
acctttgtcc aagcattgat atgtctgatg agaggaaact gcaagatact gagcttggtt 480
taacgaagga gaggcagttt cttccttcca aagcatttca tttgacaatg ccttgatcat 540
cttaagtaga gtttctgttg tggaaagttt gaaactttga agaaacgact ctcaagtaaa 600
ttgatgatca caagtgaaag tgtatgttac ataagtggat atttcaccct ttttccatca 660
atcaaaacat catatagtaa tccattggtt tatacaaaca tcaaaata 708

<210> SEQ ID NO 73
<211> LENGTH: 250
<212> TYPE: DNA
<213> ORGANISM: Arabidopsis thaliana

<400> SEQUENCE: 73
agccattctc tcgcagatga tgttcacttt gtgttttact tcctttatgc attcacagca 60
ataaaagaaa gaaatctcca tcgcttttgg ttttcttctc tgtcttaagt tagtcgtttt 120
cgtgtctaat ctattactta tcattgtaat agactcttct tctattgaga tttgaatata 180
aactaaaaca cattccattt tactgtgttc tcaacattca gaatgcaaac ggactaaccg 240
tagtgactcg 250

<210> SEQ ID NO 74
<211> LENGTH: 480
<212> TYPE: DNA
<213> ORGANISM: Nicotiana tabacum

<400> SEQUENCE: 74
aaagcagaat gctgagctaa aagaaaggct ttttccattt tcgagagaca atgagaaaag 60
aagaagaaga agaagaagaa gaagaagaag aaaagagtaa ataataaagc cccacaggag 120
gcgaagttct tgtagctcca tgttatctaa gttattgata ttgtttgccc tatattttat 180
ttctgtcatt gtgtatgttt tgttcagttt cgatctcctt gcaaaatgca gagattatga 240
gatgaataaa ctaagttata ttattatacg tgttaatatt ctcctcctct ctctagctag 300
ccttttgttt tctctttttc ttatttgatt ttctttaaat caatccattt taggagaggg 360
ccagggagtg atccagcaaa acatgaagat tagaagaaac ttccctcttt tttttcctga 420
aaacaattta acgtcgagat ttatctcttt ttgtaatgga atcatttcta cagttatgac 480

<210> SEQ ID NO 75
<211> LENGTH: 250
<212> TYPE: DNA
<213> ORGANISM: Arabidopsis thaliana

<400> SEQUENCE: 75
atatgaagat gaagatgaaa tatttggtgt gtcaaataaa aagcttgtgt gcttaagttt 60
gtgttttttt cttggcttgt tgtgttatga atttgtggct ttttctaata ttaaatgaat 120
gtaagatcac attataatga ataaacaaat gtttctataa tccattgtga atgttttgtt 180
ggatctcttc tgcagcatat aactactgta tgtgctatgg tatggactat ggaatatgat 240
taaagataag 250

<210> SEQ ID NO 76
<211> LENGTH: 1000
<212> TYPE: DNA
<213> ORGANISM: Glycine max

<400> SEQUENCE: 76
gctggagctg atttctgtgt gatgttcgat gttggatttt cccaaacatt ttaagaagaa 60
atgtgatgtg taatgggtct gtaatgacct ttgaaaataa gtttggtttg tgttgaactc 120
tattgtccca ttaatgttac tactgtttgt tatcaatttg tggagctgat atataattat 180
caactgtatg ctggcatatt gtgtttgaat tttgttctca atccagtgaa ttggcgtata 240
ttagtgggtt ttttattctt catgcttatc acggaggaaa agcagggatg agttgtgtga 300
aggatggtga tcatcccacg aattattaga ttttggtatt ataggttaaa gatatttatt 360
aggtagggag aactcttgga ttagattcta aagtgatatt ttgaaaacac accaaaggat 420
ttttgaacaa acggagatca tgatccctag tttcaattag ctgcccctta ccaagaggta 480
gcaacttaaa aattatgctc gtgaagcata tttggtatcg tatataaatt atgtaagcaa 540
tctgcttcag ttggaacatt aattggcttg cggaatgcac atttagatga tccacacagg 600
tccacataaa aattcctaat caattttagt tatgcaatct ttctgcttca ggtagtcctt 660
gtcttacaga aagcacattg agatgatccc cacacagatc cacataaaaa attcctaatc 720
aataataact tgaaaatcat taaaagatgt aatgccatac taatccctaa tttttgtgca 780
agtttttgta tactggaccc caaaaaatac caaaaagaaa aaacaagtta ttcagtgata 840
tttttctgct ccaatataaa tttgattacc aaataccaaa aaataaaaac actattcagt 900
ggtatttttc tgctccaata ctggacccca aattaatcag aatcggatcc gtttaacaga 960
taaaaacaaa agcgatcggg ttaaaatccc atttttacaa 1000

<210> SEQ ID NO 77
<211> LENGTH: 1000
<212> TYPE: DNA

<213> ORGANISM: Solanum lycopersicum

<400> SEQUENCE: 77
gttgtggttg tctggttgcg tctgttgccc gttgtctgtt gcccattgtg gtggttgtgt 60
ttgtatgatg gtcgttaagg atcatcaatg tgttttcgct ttttgttcca ttctgtttct 120
catttgtgaa taataatggt atctttatga atatgcagtt tgtggtttct tttctgattg 180
cagttctgag cattttgttt ttgcttccgt ttactatacc acttacagtt tgcactaatt 240
tagttgatat gcgagccatc tgatgtttga tgattcaaat ggcgtttatg taactcgtac 300
ccgagtggat ggagaagtgc tccattgccg gtttgtttca tgggtggcgg agggcaactc 360
ctgggaagga acaaaagaaa aaccgtgata cgagttcatg ggtgagtgct ccagcttgat 420
cccttctctg tcgatcaaat ttgaattttt ggatcacggc aggctcacaa gataatccaa 480
agtaaaacat aatgaatagt acttctcaat gatcacttat ttttagcaaa tcagcaattg 540
tgcatgtcaa atgatttcgg tgtaagagaa agagttgatg aatcaaaata tctgtagctg 600
gatcaagaat ctgaggcagt tgtatgtatc aatgatcttt ccgctacaat gatgttagct 660
atccgagtca aattgttgta gaattgcata cttcggcatc acattctgga tgacataata 720
aataggaagt cttcagatcc ctaaaaaatt gagagctaat aacattagtc ctagatgtaa 780
ctgggtgaca accaagaaag agacatgcaa atactacttt tgtttgaagg agcatccctg 840
gtttgacata ttttttctga atatcaaact ttgaaactct acctagtcta atgtctaacg 900
acagatctta ctggtttaac tgcagtgata tctactatct tttggaatgt tttctccttc 960
agttatacat caagttccaa gatgcaggtg tgcttgattg 1000

<210> SEQ ID NO 78
<211> LENGTH: 1000
<212> TYPE: DNA
<213> ORGANISM: Pyrus communis

<400> SEQUENCE: 78
gtgctggatg tggccggtgg ccgtcttcta cccgttttcg ttgaattgtt tatgttttta 60
ctgtttttat gtatttaagt ttgatggtac tgtttctgcc tcctgattga ggcatatgga 120
caagtttggt ttatctttta ctatgttttg ataaataaat tccgttctgg ttaaaaactt 180
cgtgtttgaa atttgttgtg aatctcttgg tttaatttgt ttgtttgcat ggtgttgtgt 240
ttgtgaatgg tttgctttca atcgtctgtt taatgttgat tgtgtggtgc ggttgccatc 300
cttgaactgg acctttggta caagactggc atttcaaggt gtgcctcaat ctgtggtttc 360
gattgtggtt tcagattttc cggtgagctc actctagcgt ccggcattta ccccaatcag 420
ttttccggca cggagaggga aattgatatt taccccaatc agttttccgg caacggagag 480
ggaaattgat atatcggagt gaaggtgtcc gactcaacta tggcaagcgt cactctagca 540
tccaacattt agccgaaaac ctaagacttt gacacccaaa agaagagatg ctgttgagtc 600
tattgaaaac acgagttaca ccagttgtgt ggaaagagga gacgtgccgt gtccaatgta 660
tgctaatttg cccctcatat ctgcagccac tataggctgc cgatgaattt caccgtcccc 720
tgatgtatat tttcagtact tgtccacgtt tgaatattga catccacgtt tgaatttcgc 780
tatcctggtg catccgctcc cgactctctt agtcgagttg gaaaaaccca aataagttaa 840
ctggctttgg accttctgta aacgtctatc catttagggc taaccgcgtg gttttgttac 900
aaaatcgctt tagacctccc gtttatatct cggaaaccat ttttagcgat tgaattttat 960
cttttgtacg aaagtattgg acatactaat ccgaagttag 1000

<210> SEQ ID NO 79
<211> LENGTH: 1000
<212> TYPE: DNA
<213> ORGANISM: Beta vulgaris

<400> SEQUENCE: 79
gcttgtggtg gttcgtcgtt ggttgttggc cttggaacaa tggctttgtt gggtgtttat 60
ccccctataa tctgtgaatt catctatcat ctagtttatg ttgaacaatt ttaatttcag 120
ttggttatca aatgttggtt ttatatcgtc gtatgtctgt tgggttacta tgaactatta 180
aggttcagtt gtgaataata ttctctgttt gtgtctactt tgttctcctt ttgttgcaac 240
tatgttttta atgtttcact ttatcttcct gatttctaag tggcattatc atgcttcatg 300
ccttgccttg tggagttgtg gagtatgttt gattatattc tccagaatga tattgctcag 360
cttattgtta cctaactttt tgtctggctt tttatgcttg ttgattgtag ataaagggaa 420
caaaatttgt gttcacatag tatgcacaca ttttgtgttt gcagattgtg tgccatttat 480
cttgctacac tcttgtttat ggtttttttt ggttgtatac tctgttctca tttgtggttt 540
cacctaaaac aaatgtgatg attttggcaa gggggtgcat ctctgttttt ctggttgttt 600 ttttttttt gatgaccttg agtgatggtg gtgttgatgt atgcgaggag tcgaggactg 660
atgcttttgc acatatgttg tgtctattgt tctggcttgt atgcactgtt acggtatgtc 720
ttgtgagcta ttttgaagta tatttgtaat tgaacattga tctgagagtt cgggctggtg 780
catcttccat tactaccaat gttacagcat tgtaggagtt ccgttagtgt gttgctgatc 840
ccttttgata tctttgaaat gtgattcata acataaatgc cgatggggaa ggaaagatat 900
ttactgttga atctaaatgt gaagagatgc tatgagccta atccattttg ggtaagcctc 960
acctttgctc ataagcttta tgagtcccac tgctgaaaat 1000

<210> SEQ ID NO 80
<211> LENGTH: 1000
<212> TYPE: DNA
<213> ORGANISM: Unknown
<220> FEATURE:
<223> OTHER INFORMATION: Raphanus raphanistrum

<400> SEQUENCE: 80
gtctctcgtc ctttgtctta tcaaaaatca acaatgtctg ctttttagtc tcgttttctt 60
taaaacttat catggtttgt gtgtttgagg cattataagc ctcttttgaa taatcgttga 120
actctgtttc tctcttttcc ttgcaagact tttctatcta tatcctcgtt attcttaaat 180
gctttgtgtt catctttcaa attttgaggt taagttgtcg atgcggtgaa ctttctattt 240
ttgcttagct gttacttctg aaagcacacc tgtaagcttt aacgtgttca cttttcagag 300
ttatgtgaag ttttttagaa cgttcagtct gtacttattg gtcgtctcta caaggaatcg 360
tgtgacaaaa ttgtctgtta ccactagctt gacaagtata gtaatttgga gaattcatcc 420
ttccaaaaga ggttatcagt gatgggttag tctcttggtc ttcatacgca aaattgaatc 480
tggtgaacaa cagaggttag tcgagtttgc aagttaattg gccggatcat aggtcgagtt 540
tgcagatcaa tgggccagat cataggtcgt aattgactgt tttatatcgc tggatcactt 600
cagtaagaaa gaactaccaa agagttcagt gaggtcttaa ttgacagata tgtgaactaa 660
aattaattca gttgctcaaa taatgtttaa ctgcatcaaa cgttttagtg gtgctcgttt 720
tattgatcta aatttaaatt tgtaaagagt tttaaacatg gtgatttatt tggaaacact 780

```
tttgaatgca ttataaagtg taaactaggt gttttgccgg cattttcaga tttaatagtt     840

tctagaaaaa ttataaaaag gtatattata aaattcaaaa atcttaggat aaaatattgg     900

cccatttggg tgaaaaacca agaacgataa gtttattagg catgtatgca acacataatt     960

taattaggta gtcgtgcaga actctagaat cgaatttact                          1000


<210> SEQ ID NO 81
<211> LENGTH: 1000
<212> TYPE: DNA
<213> ORGANISM: Ipomoea nil

<400> SEQUENCE: 81

agagcctcac tgtcctgttt gaattgcttg gtttgtgtgt taagtgccaa agctatagta      60

acttggcact gctggtgaat tgtgtttgtt ttgcttttgg ttgatgaacc catgaaggtt     120

atgtttcctt gaataataat aataataata atagcattac tattattatt attaggtcct     180

actattttgt tagccccatt tgttctgaac tctgtttact tttagtttaa tgttattaat     240

atattttacc aggtaaaatg taatactatt tttatagaata ctttcgttaa aaatgagtgt    300

taccttcata tctatctcaa gtagtaatca atttgagatc cgtctactgg gagcaacata     360

gcattggcct tcacgagaag gaagggacat tattgctcca accgtggcag gagacatttt     420

tataaataat aatctgaact ttataaataa tttgaactta cgtgcagcaa catagctaac     480

aataaagact acatctctag gctctagcca acaataagtg ctttgatgta atttgattat     540

aattgtattg caatttgttt agtcaacaat aagtgccttt ttggttggat gtaatttaaa     600

tgtaattaca ttgcaattca cttttcccat caattacgtt attcaattga atataattca     660

tggaccttat ttaagaatta caattcagtg gtgaaatgga gaaatatatt attgtgaaga     720

catttttacc attatcatta cttatctcat gtcgcccacc gaattacaat ttattctccc     780

taattccttt cttccaacta aaccggtaaa gacttcatct catactatgt gaaactacaa     840

agaaaggttt actttttaca aggcgtttaa gttggaagaa gagaattaag aaaaaacgag     900

tagtaatttt gttggaaagg aatttaaatt atattgtttg ataggaaaaa atataataat     960

tcttaaatta cattgtttga tagggaagaa taaaatgatt                          1000


<210> SEQ ID NO 82
<211> LENGTH: 1000
<212> TYPE: DNA
<213> ORGANISM: Unknown
<220> FEATURE:
<223> OTHER INFORMATION: Cucurbita sp.

<400> SEQUENCE: 82

attgttcttc tgaagatgga taaatcagca tgcggggtgg ggtggccttg ttgcggccat      60

ttgttatttt cttctgttct ctacttctgg tgttatgttt ttaaatgctc cctgagggtt     120

acagtatggg gagaatatta atataagatg tcatatttca aataaaaatt tcgtttcttg     180

tttaagaatc gtgtccagac ttctcttatc cagattctcc tggttgtttg tcattgggga     240

tgatgatgac taaacatggt tgaagctttg tcctttctgg ataattctta attcatgatg     300

ggacgaacac aatcccctgg tcgtccagag aattgaatag ctaaggaact ctttagtgga     360

gtcgaatcag atctgaatca gatatggctg ccctctcctt ttcccccaag aacccgaaat     420

ctagttcatc tcccccaggt ccatccccgt tccctgtgcc tatctccaaa agtcctccag     480

tcttggctac agcttaaatt atcatcagtg ctagccattt tgatcatatc tgcaaaaagt     540

tgatttcggc ggccatgagt gcatctgtta aaacaagaat gtgtattggg gaaactcact     600
```

tcatctccat cttgggaaag tgggaagatt tatggggttt ctaggatacc taacttagaa 660
gacataattg aagacaacat attattagtt taacggtgaa ttggaaaggc tttcatattt 720
cttgtgagag gctttcatat ttcttgtgag atcccatttt agtcaactct ctctaaccaa 780
tacaacttct ccttaaccaa ttcattttaa aatgtgagac cgacgacaat aactgttcaa 840
gcagcagcaa tggtggtatg caggtaggaa ggaactctat tatctttgac tctgagtttc 900
aactattaag tgctttatct gctactcaat cacggaatcg attctgtcta agtggaaaga 960
aaaagaagag gaagttagtg agcccacacc ctccttttat 1000

<210> SEQ ID NO 83
<211> LENGTH: 1006
<212> TYPE: DNA
<213> ORGANISM: Helianthus annuus

<400> SEQUENCE: 83
atgtttgtgg tggttgtgat gtttgaagtt ggtactgttg ttggttttta aatgtctgtg 60
gttgtggtta atgtttgaag ttggaacaat tgttggatac agattctcta tggtttcctt 120
ctatgattgt tgaataaatg aattttatgg tttaatcttg ggtttgatca tggtcattgt 180
tataaattga agtctgggtt gcatattctg aaaatgattt gtcagtagtt tattgtttgg 240
tttaaatgtt gattataacg aaggtagttt atgatatgct tagcaactgt tttgtaagga 300
catagtgatt tgtgccaaga ccaaaagttc aaagtggtag gggtggcgtg aaaaaaaaaa 360
accaatttta aagggctagt gctcttgacc aataaggttt tgtcatgtca tgtgggttgt 420
ctcgctcaac gtctaggctg aaaccccgcc caaggagtca cgctgaaacc caagcccacc 480
ataccacttt gaaattccct tttggtctta gctagcaaat ataccatgtc cttacaaaac 540
agttgctaag tcgttttggc atgtgtttct gtgtctgaag atatgttaat tgcatatttc 600
ataatcattt aagcatagaa acgacggaat ttaataaaca cagatcaaat tatttggtat 660
ttttggataa agtccttttt gagtctttgt ggtgtgtgca ttttaactat ttttgaatct 720
aaaaatcaaa cttgtcttga tttgagtccc tgtagtttgt atttttaaca ctttgattcc 780
ccgtggtttg tatttttaac cttttgaatc aaacactttt agtccatgat ttggatgagg 840
tttgcgtttt ggattcaaag ggttaaaaat acaaacctac aaggactcaa atcaagtcaa 900
gtttagtttt tggattcaaa tagttaaaat gcacaaacca caaggactca aaaaggactt 960
tactcttttg gatataacaa agagtttctt aaattcctct gagctc 1006

<210> SEQ ID NO 84
<211> LENGTH: 306
<212> TYPE: DNA
<213> ORGANISM: Pisum sativum

<400> SEQUENCE: 84
gttcgagtat tatggcattg ggaaaactgt ttttcttgta ccatttgttg tgcttgtaat 60
ttactgtgtt ttttattcgg ttttcgctat cgaactgtga aatggaaatg gatggagaag 120
agttaatgaa tgatatggtc cttttgttca ttctcaaatt aatattattt gttttttctc 180
ttatttgttg tgtgttgaat ttgaaattat aagagatatg caaacatttt gttttgagta 240
aaaatgtgtc aaatcgtggc ctctaatgac cgaagttaat atgaggagta aaacacttgt 300
agttgt 306

<210> SEQ ID NO 85

<211> LENGTH: 469
<212> TYPE: DNA
<213> ORGANISM: Pisum sativum

<400> SEQUENCE: 85
caggcctccc agctttcgtc cgtatcatcg gtttcgacaa cgttcgtcaa gttcaatgca 60
tcagtttcat tgcccacaca ccagaatcct actaagtttg agtattatgg cattggaaaa 120
gctgttttct tctatcattt gttctgcttg taatttactg tgttctttca gtttttgttt 180
tcggacatca aaatgcaaat ggatggataa gagttaataa atgatatggt ccttttgttc 240
attctcaaat tattattatc tgttgttttt actttaatgg gttgaattta agtaagaaag 300
gaactaacag tgtgatatta aggtgcaatg ttagacatat aaaacagtct ttcacctctc 360
tttggttatg tcttgaattg gtttgtttct tcacttatct gtgtaatcaa gtttactatg 420
agtctatgat caagtaatta tgcaatcaag ttaagtacag tataggctt 469

<210> SEQ ID NO 86
<211> LENGTH: 1000
<212> TYPE: DNA
<213> ORGANISM: Helianthus annuus

<400> SEQUENCE: 86
aggatttaag cttgtcttat gtttgaactc ttgtgaaagg tttctgtgac gctacttttt 60
aagtgttggt gcaaatttaa ataaaatcat ggttctataa atacgatgtt tgtatgtaag 120
tttgaacacc caagttcatt caggtttcaa cagatgtgct tatttaagta cacattggcc 180
acgtcatcaa gttctcgtgt ttgtgttgct ttgatcttta gttgttcatt gcacgtactt 240
tggttattga gttgtacaat tacaagtacg gttacaaaaa tctttttaga tacacatcag 300
gatgattatc acaagacaaa tataacaata ctgatgttga ttgagcaaaa tataaaaaaa 360
aaagccatca tactaagggg ctgtttggct aagcttattt tagtgactta tttacttatt 420
tactttttaa aaagttaaaa aaggtgtttg gattagctta ttatgtgaga ggaataagta 480
aataagtcat tccaataagc ttagtcactt tttagataca catcaggatg attatcacaa 540
gacaaatata acaataccga tgttgattga gcaaaataat ataaaaaaag ccaccataca 600
aaagctaagt tttagtcgtg ttactagcca aatttatata aatgtgtaac atactcttta 660
agatccatat aaagttgaac tcaaaccact ttattttccc tcagccacca tatgactaga 720
agacattcca gacgacccct ttgaagacat ttaggctagg atcttcaacc ttactatatt 780
agaggccgca gacaattgcg atttttatac aaacgtcatt attatatgct aaacgtataa 840
acaaccaaaa atttctcaaa atgggcatta tgtcaaatct atagctcaca caatctttcc 900
tcacttaagt gtcagagcac aacacaagag gctctcacgg tatctcctgc ttgtgtagtg 960
tggttaacga gttgtacatc tatctcaacg acactttgaa 1000

<210> SEQ ID NO 87
<211> LENGTH: 999
<212> TYPE: DNA
<213> ORGANISM: Zea mays

<400> SEQUENCE: 87
ccaccggtat ctcgcttcca tttcacaccc cacggcctag ctataaagac taatggttcc 60
aggtgtctga agtactgaag acaggggggc tagctatcta atgtttgtgc cgcacgcatg 120
agctgtaagg aggccatgct taattattct gttgccgttg ctactctatc tatatgcgcc 180
tatgcctccg tgcatgaact atgctttagg tggttgctgc tccacactgt ggtggtgtgc 240
ttttgctttt gtgtggtcgt attgtatgcg taacctgaca gatggatccc tgattgctac 300
atgtttgaat aatttgcatg atctagctag tttctgccta atctaatggt acggctcatg 360
tcttgtcagg tggatttgtt atgtgttttt tttttcaaat tgaggcttgt ttgttttgct 420
ctcaatccat ccatgtgaat tgggtggaat taaatgagtt taaattccaa agtcagtcaa 480
aatctgttat aattcttcca atccataacc gaagatcata ggccctgttt ggaatcccta 540
gaactaatag ttagctagct aatatattat tagtcggtat gagccggctc taataaacta 600
attgttattt gtgagataac taacaattac taatagttag ctagctaata tattattagc 660
tggtttgagc cagctctaat acactaattg ttatttgtga gataactaac aattaattat 720
gatattagct gatgatgttt ggaacctaac aactaatttt taattttatt tctataggtt 780
ctaaacagga ccttagtggc tagtttggat acactaaagt gtcgttcggt tgtttgagat 840
cgatggatcg aaacgattac taatcagatt acttctctaa tttatataaa ctttgattag 900
ctaaaataat ttcgggcgca atctggtaca aacgaacaag ccctaatcag gatggcatgc 960
caatttggat tggtgtgggg tcacgcatgg tgaattatg 999

<210> SEQ ID NO 88
<211> LENGTH: 1007
<212> TYPE: DNA
<213> ORGANISM: Oryza sativa

<400> SEQUENCE: 88
ttcttcggac ccaagaatgc taagccaaga ggagctgtta tcgccgtcct cctgcttgtt 60
tctctctttt tgttgctgtt tcttcattag cgtggacaaa gttttcaacc ggcctatctg 120
ttatcatttt cttctattca aagactgtaa tacctattgc tacctgtggt tctcacttgt 180
gattttggac acatatgttc ggtttattca aatttaatca gatgcctgat gagggtacca 240
gaaaaaatac gtgttctggt tgtttttgag ttgcgattat tctatgaaat gaataacatc 300
gaagttatca tcccagtatt ttcgcatgaa tgttcttttc ttctgtcttg tgcatcagtg 360
atctagtgca tgggagtttg tattgtgatg ttcgacatca cgtaacttcc actttgcctt 420
tgctgttcga tattttaatg acatgtcaca cacacttctg atacttttct ttcttggcta 480
ttgtgccagc atgatgcaag atgcatcaca gcatcagata tattctcatc gtcaggcttt 540
agcagcacac gagcacgctt tgccgcttaa aagttgtacg gcgcagctta gacatcccct 600
gtagaagtga taatcttttc acttttcctt aaacaaattg agaggggaaa tggaaccatg 660
tggatcagag aagcttttgt ttctttacac aagaatattt ggtacagtgg gggtcctatg 720
ttcgtgggtt cgtggcttgg ctgcctgtct tcaaccaagt gttttcagtt caacatgtta 780
gcgtgtagaa agagcacaat tctgtttatc tccaaggtaa aatgtggcat tctgttaaag 840
aacatgatcc tgccaatttt ttaagtttca atggaagagg aatgtaaagc tttctatggt 900
ttgtgtacac aacacagtgg aagaggagtg caagctttct atggtttgtg tgcgcgttgt 960
gtgtcagcac ttcaattttg ttagaaaatg aaagaaaaaa aaggatg 1007

<210> SEQ ID NO 89
<211> LENGTH: 1000
<212> TYPE: DNA
<213> ORGANISM: Oryza sativa

<400> SEQUENCE: 89
tcagccagtt tggtggagct gccgatgtgc ctggtcgtcc cgagcctctg ttcgtcaagt 60
atttgtggtg ctgatgtcta cttgtgtctg gtttaatgga ccatcgagtc cgtatgatat 120
gttagtttta tgaaacagtt tcctgtggga cagcagtatg ctttatgaat aagttggatt 180
tgaacctaaa tatgtgctca atttgctcat ttgcatctca ttcctgttga tgttttatct 240
gagttgcaag tttgaaaatg ctgcatattc ttattaaatc gtcatttact tttatcttaa 300
tgagctttgc aatggcctat gggatataaa agattattct ggagggaagt gatgctggaa 360
ggactatgct gtcctgattt atatttggag ccactatgag catttgggct ttcttttcag 420
aacgctgtag gcgtgtgttg aaatctttgc gacattcaat ttgatatatg attcgaggta 480
attgggcttt aatttgtcat ctcatgtaac atctttttgt ttcttcgctg cttgatttct 540
ctatttcgta gcattggaag ataatagtag aatgatgata tactccaata cttgcaattt 600
caaaaccgtt agaaagaaag gaaaatcacg gctaggggaa aaattctctc tgatgcgtgc 660
atcaccaaaa tctgattgat tgacataagc attggaacac aaatagaaga tggagaggtg 720
gacatgtttc cgagacatag catttgagct cacattgttt ttgatccgtg gctgtgccat 780
acgcgataat ttactaaact ttcccttgcc ccttggtaat ataaagctta taatgtatac 840
accgaaattg aaaaacgtat tagttcactc ttcttccttt ttctcagcaa agcgtgttca 900
tcaattttat tccacatgaa tgtgattgcg aattgtgacc aggaatgcat gatttaacaa 960
tcccgatcaa ccctgttgtc ggtggtggca ctaaaaatta 1000

<210> SEQ ID NO 90
<211> LENGTH: 1000
<212> TYPE: DNA
<213> ORGANISM: Oryza sativa

<400> SEQUENCE: 90
gtcctcagcc atggagctgc tgctgttcta gggttcacaa gtctgcctat ttgtcttccc 60
caatggagct atggttgtct ggtctggtcc ttggtcgtgt cccgtttcat tgtgtactat 120
ttacctgtaa tgtgtatcct taagtctggt ttgatggtgt ctgaaacgtt ttgctgtggt 180
agagcagcat ggaagaacta taatgaataa gtgatcccta atcattgtgt ccaaattttg 240
cttctgctat accctttttgt gctgtttctt atgttttgct taaaaatttg atctgacaaa 300
caaatttgtc taaattatgc tcttgttctg actgtgtact gtacacattt gtattgctac 360
cggtttggca catagttttc tctttgattg cagatcaaac ccttctgatt gcagattgct 420
tggctatggc tgatgtgctc actgttcttc tttagcttgt atattgctga tggtggcttg 480
gctacggctg aaaaagttgc tgctgcgccg acttggcaac tgttgctcca gtaatgcttt 540
gtcctctctt cctagccgcc gacttggcac ttggcagctg ttgctcctgt aatgcgttgt 600
tatctcttat ctcttgagat gtactatgat tttgaggctg tttgacttgt gccagattgc 660
cagtgctgat gctatattat ctcaggtttt tatgctagta tatgttttac tgtgtgctgc 720
ctgtgtcgag ttacgtaatc tattgaaccg ctatgcgtgt tgatgccctg ttgttgcttg 780
ccagattgat gcccctgttg cttgcagctt gcaagctgta gtgaaatcct aaaattcgaa 840
gccaaatcta ttctgaactt ttgaagatct gtgatgtccg gaagaaaaga ttcaaacaga 900
taaacgggac tctccagaat ctataaaata aatgatcgac aaacgctttg ctttggtagg 960
cttctcatta acccaaacat tctggaagac caatgctgga 1000

<210> SEQ ID NO 91
<211> LENGTH: 1000
<212> TYPE: DNA
<213> ORGANISM: Aegilops tauschii

<400> SEQUENCE: 91
gtgcctggca atggagcggc ttctctgcgg gttcacaggt cttgtgtctt cgatatgtcc 60
tccaatggtg catgtgtctg tcgtcctggt cgtttctatg tttctatcgt agtgtgctgc 120
atcgttatgt tcggttgtat ttgagaactg ctgctgttgt gaacagcttt ggtgaacttg 180
ataaataagt gagcccctaa ttgtgtctgc agctgctgag ttatcctgcg ttttcttttg 240
tttgcttcta tctgatgcat ttcatctcta ttcatatgaa tattgtacct tgcatttgtt 300
agttcgacta tatggtactt tgtggcaatt acatcttggt tatcatagag gcttcactct 360
tttgaggagt agggattggg agggaccgga ctatcattag agataaccgt atcctgtttg 420
tcgacaagca gcatggtcgg gcactccggt gggatcatgg ttgaatcgga ctgcattgat 480
gtcgtcgagg tgatgcagca aggggttaaa tctgtgggcg atctttgagg aatgtagttt 540
cttatgccgt aaattttgat catgtcttgt tcaaccatgt cctgtgaatt gaagatgaat 600
ccttagttgt caatcaaaag gataagaaaa acgatgttcc atatgtaata atttgttcat 660
aaccaagtaa aagtatctgt gtaactagta gaaaattcag tagatcagaa caacatatgg 720
taccaaccca ttttgtacat caaggttgat tgaaaaacat tttaaggaaa atctgttgtg 780
attctggtgc gccaactaca aaattatgtg tgtgccttat attataaggt gagaggcatt 840
tcggcaatgc aaattgtgtg gaccttcata tatgtattga cttttttttt gcgatgagta 900
ttgactggtt tattaagtgc atgaatccct aactttcacc atatgcacaa aacttctgag 960
ggttatgtgg gcattatgcc agccagaccg aatcaaatgc 1000

<210> SEQ ID NO 92
<211> LENGTH: 1000
<212> TYPE: DNA
<213> ORGANISM: Unknown
<220> FEATURE:
<223> OTHER INFORMATION: Panicum hallii

<400> SEQUENCE: 92
gtcttgggcc atggagctgc tgttgtccct gggctcacaa gtctggtgcc tgccttgtct 60
ctccaatgga gattgtcttg gtgtcctgtg gtcgtgtcct tgtcgtgcct gtctgatgtg 120
agtcatgtcg tctggttgtg ttttgtgaac acttgctgct gtgcagcagt ttggttgaac 180
tatgcaatga ataagtgagc cctgaagtta ctgtggtaat cttgtcttct ggatgagtcg 240
tcattattat atggtttatt catgtttgtg aagtggaagc attaatttcc tcctggtgcg 300
ttgcttttgc agttctgctt gtgtcgtgat gttactggtt ttgcaagtat gctgcttcct 360
tgatcgcaac ttcattttgg gtcattcttc atttggttat gctggtgctc tggttttaga 420
ttcatcatat atttcagatt aatgtagtgt ttataggaac tatcatttta aattttccca 480
gatgtcattt gtgctgcctg gttgttgcat acggcgtggt tgtcaaggca ggttaagatt 540
gccgatctcc ttttgatcct tgctatctcc agattatttg gaagattttt tttgtttctt 600
gaacaggtag attggttgca gctatgaatt cattgaagct atggtgccca aaatgtcatg 660
tgctccaaat tttgtagcca ttttgcagat gtagcaacac gttttcagat tatatagtac 720
tgcatcaaaa tcaaattgtt ggcgccatag tacattacta tcacactagt aatgaccagg 780
aacaatcgca gccagttaac atgccggagt attccacatg gataaacaat ggtgcatttc 840
ttgaggagtt gatcagaacc actgaactgc caaacatgtc cgcagaacca tgacaacccc 900
ttgcatgaag atgtgctaaa gttgttgaca gaaagtccaa actctatgat atgcacacat 960
tatcagcaag agatggggat tgttatttgc caaaaatttc 1000

<210> SEQ ID NO 93
<211> LENGTH: 1001
<212> TYPE: DNA
<213> ORGANISM: Zea mays

<400> SEQUENCE: 93
ccgtcatcgt ccatcaacga ccaagcaaca acacatccac actatatact caattcacat 60
tgcaatgcat cgttattatt acatcattta tttcagaccc cccgcccact gctaaccgta 120
gtccataaga gattcatcat ccgtggacta tgctcgatct cttccgtacg atacaattct 180
caaatatttc tatttatttc ctaagtgaat tattatatat gtactatttc attccaggtt 240
cattttactt gtgaccattc ttcagttctt ttttctgtaa ggatcggtat atcggagcat 300
atgtgcatgg ctatgccagt tgttgggcgt aagaatgtat ttttttctgt aatatagaaa 360
aaaactattt taagcaacag gttattgtca agttactttg cttgtgaaca aatttcgtac 420
cacgtatata tttgtatgac ctttgtataa aggtgacacg cctagtaaca ttaaccaaac 480
accgaggaaa tattaattct caatccaagg gaactcaagg cggttgagag gatttttagg 540
gctgattcag tgatcagaga tcccgtggat cccctcagga tccctgatca ccaaatcaac 600
ccttaggcta gtttggaaac tcaaatctct tttaggattg aagaagattg gagagaaaat 660
tagttcattt ccacctcaat ctcatttaat cccgaagggg atttgaggtt cccaaagtag 720
cccttactgg gataaaattc cccttaatct ttttcaaggc tactttgatg acaatggaat 780
ttagggagaa aatgaactaa ttcttcacac gatctcctcc aatccttttt aattctctta 840
tatcaccaaa caaggcctca atgtccttgg attggcgagg tcatcccatt ttatctcgtt 900
cacaaaaaca acagcgacat taatagactt aaaaacattt gagatgtcca cggagatatg 960
accaaccgga aacaagtgat attcatggta gctgtcccta c 1001

<210> SEQ ID NO 94
<211> LENGTH: 1000
<212> TYPE: DNA
<213> ORGANISM: Zea mays

<400> SEQUENCE: 94
tctatctgtc tggtgctgtg cttgcttgtt ggttacctcg tggaagctta aaatatctcg 60
tcttgttgac atccttgcag ttgtcgcgtg aacaagtaat ctatgatggc aatgtttgcc 120
tggtcatgaa gtattattac tttcgttgaa accgtgatgc tattaagact taattttttt 180
atggaacatc gaatgtaagg catacatggt tatgagtttt gtactaccct ttgcagtgtg 240
ttcctgttta ccttttgtgc tgatgattcg cttgtctttg tgtcttcaag ttaatcttgc 300
acttaactgt ttttaatatg ccagatcgtt tcaaaagatt tgaaatttgg attcttccga 360
aacgtttttt tgataataat gtagtcctga aaacatgatt ttgattcttc agaaactatt 420
tttgataaat aatgtagtcc tgacaacatg gtcaatttta cgcttttagt tatcaatgca 480
tttttcatga tttccgaaag ttccgctcca accttttcga aatgccagca tttgagttgt 540 tttttttct actttttccg atagcctgaa gtctaattta gttgcaaaaa cataaatgtg 600
gagtaactag agctgtgtct aaggggtaag tgtaaaaatt gccaagagcc ctttttgaag 660
aaggaatgtt tcatgctcta cgatggaggc gaaggaacat ctctacgttg atcagatagc 720
ggtcgtctcc tccagattcg ctgtgcttcg aagatccgcg atcgattcct gctccactca 780
aggtcacctc cactcgagtt ctcaagccta tcctcttcct ctccctgtct ctcacctttc 840

```
ctcttccctg caagatggat ctgccggcgg tggctgccat ggtgaggtca tctccctcat     900
acgaccgtgg ctgctacaac acaagctcgg gtgctccgtc gcctaaggag atcccgctgc     960
caggcgcccg cccgccattc atccatggtg gttcggccgc                          1000
```

<210> SEQ ID NO 95
<211> LENGTH: 1107
<212> TYPE: DNA
<213> ORGANISM: Zea mays

<400> SEQUENCE: 95

```
tcgtcatcgt cctactatca agcaacacga tcgaccacca cctcgattat atatgcatca      60
ttatagtatc gtttattaat ttcagaccca cccactgcta accacatcgt ccacgagaga     120
ttatattcat ccgtggacta cgctctcgat cttacaattt gaaacctttc tattttccta     180
attactatgt attccaggtt cattttgatt gtgaccattc ttcagttctt tctgtaagga     240
tcggagcata ttatatactc tatgtggcta tgccaattat attgttgggt ataagaatgc     300
attttgtttc tgtaatacgg aaaaatatat tttctttaag caacaacaag gtaaaaactt     360
gcctcgttgc atattttctt tatgtcaatc tccttttgtt cgttgtatga tcctctgttt     420
ggaaactgaa tactgatcga acaactgatc aggagttaaa acatattgta aatatatata     480
aaaacttgct gtgtacaact cttctttatt gtataagttt cttgaggtaa ccgaaataga     540
tagtaaatcc caatacaaat agattcctcc gttactaact aatctgaaca taaatgctaa     600
taaaaaaagt ataaatttct atctgcgtat gtaccttgac cttaccttta ttctattaac     660
tcctgatttt ctattcagat tttgaacggt ctgttacttc ctttctattc tgttctggtt     720
tcgtcgtcgt ttgtttccga acggtctgct acttctgatt ttctatttgt tcttacgttt     780
ggttttgccg ttctagtttc ttgcgttttt ccatataaat atagaaacac aaaataaatg     840
taatgttgta gatacttgaa ctatcgatct tttcctttaa aaaatgatat tgctaccact     900
aatgtagttt taattaggaa caaaacttac aaccaatgat caactaatga accggtctag     960
aacagtctat atggacatgg tgagcaagcg tacgtaattc cgggaagcac ttgtcgtccg    1020
gacgcaggct acattactac atagtagcaa aacaaatttt attccgataa tattggttgc    1080
tatacagacc tctgcagaca aaaataa                                        1107
```

<210> SEQ ID NO 96
<211> LENGTH: 1000
<212> TYPE: DNA
<213> ORGANISM: Zea mays

<400> SEQUENCE: 96

```
gtcatgggtc gtttaagctg ccgatgtgcc tgcgtcgtct ggtgccctct ctccatatgg      60
aggttgtcaa agtatctgct gttcgtgtca tgagtcgtgt cagtgttggt ttaataatgg     120
accggttgtg ttgtgtgtgc gtactaccca gaactatgac aaatcatgaa taagtttgat     180
gtttgaaatt aaagcctgtg ctcattatgt tctgtctttc agttgtctcc taatatttgc     240
ctgcaggtac tggctatcta ccgtttctta cttaggaggt gtttgaatgc actaaaacta     300
atagttagtg gctaaaatta gttaaaacat ccaaacacca tagctaatag ttgaactatt     360
agctattttt ggaaaattag ttaatagtga ggtagttatt tgttagctag ctaattcaac     420
taacaatttt tagccaacta acaattagtt tcagtgcatt caaacacccc cttaatgtta     480
acgtggttct atctaccgtc tcctaatata tggttgattg ttcggtttgt tgctatgcta     540
```

ttgggttctg attgctgcta gttcttgctg aatccagaag ttctcgtagt atagctcaga 600
ttcatattat ttatttgagt gataagtgat ccaggttatt actatgttag ctaggttttt 660
tttacaagga taaattatct gtgatcataa ttcttatgaa agctttatgt ttcctggagg 720
cagtggcatg caatgcatga cagcaacttg atcacaccag ctgaggtaga tacggtaaca 780
aggttcttaa atctgttcac caaatcattg gagaacacac atacacattc ttgccagtct 840
tggttagaga aatttcatga caaaatgcca aagctgtctt gactcttcac ttttggccat 900
gagtcgtgac ttagtttggt ttaatggacc ggttctccta gcttgttcta ctcaaaactg 960
ttgttgatgc gaataagttg tgatggttga tctctggatt 1000

<210> SEQ ID NO 97
<211> LENGTH: 1000
<212> TYPE: DNA
<213> ORGANISM: Hordeum vulgare

<400> SEQUENCE: 97
ccgcctagcc gatcgagggc tccaggcacg catgcatgtt cctgttatgt ggatgttgga 60
ataaaatgct ggtgatctat ggcggctagc ttgcttcctg gctagcagct gctgtaatga 120
aatttgtgtt gcaacttttt ttttagtccc atccagagct cttttctttt ctttaatttg 180
ctgtagtaat caaagtaagg taggtcgcca gaaaaattga gttgggccag ttaattatgg 240
gggaatcgat ttgatccgtt ggatgacaca tcttcttcct ctagtcggct tcctccttta 300
aacatatcag tatcacatcg cctgctaccg cctctcacgg ccgcctcacc gcaccgccct 360
tccctgaacc tcccccaccg ccgatcttgg tgccgcccca tacaatccct ctaagtcctt 420
cgaccaccca aaaaaactcc ggcgagaggg ctccaggcat gcatgcatgc atgttcctgt 480
tatgtggttc caccgatgat gtgggaataa aatgatggtg atctagctac aggcggtcag 540
gttgcttctt tcctggctgc tgctagtaat actttttaga gcctcttttc ttttcttttg 600
ctactagtaa tgaaactaag ttaagtcacc aggaaatttg aattgggcca gtcaattccg 660
ggggaatcga tttgagccgg tggatgacaa acgaacggtg atgctcgcgt cttcctctgg 720
tcgatttcct cctggtattc tagacgtggt ctggccgatt caccgattcc aaatatcact 780
ttcacatact gaaagaagca acttcacgaa ttgtaaatca gcttcactca ctggaaatat 840
gagttacact tctttgaaaa aacggtttca catttttgaa ataatcgttt caaatatttg 900
aagaaaatca attttacgta ttaaaatata tgcttcacaa agagaaacaa tccctttcac 960
atatttgaaa agagaactgc gttccacaaa ctgaaaatat 1000

<210> SEQ ID NO 98
<211> LENGTH: 1042
<212> TYPE: DNA
<213> ORGANISM: Zea mays

<400> SEQUENCE: 98
attacatatg agatgtactc gacaatggtg ccctcatacc gacatgtgtt tcctagaaat 60
aatcaatata ttgattgaga tttatctcga tatatttctg aactatgttc atcatataaa 120
taattgaaaa catcaaatca taattttaaa ctcatgcttg gtcaatacat agataataca 180
atattacttc atcatcccaa tgatgtccta gcccaaccta ttgaatgtta atgtttggtt 240
gtgtgagggt gtgtttataa catagatgtg attatttgcg ctttttgttg agtatataca 300
tatatggtat gttgatttga tatagggatg gacacatgct ttggccttgg atattcaaat 360
cacttgtact tgcacgaagc aaaacataat atatagttta gaagtaaact tgtaactatg 420
tccaaacatg ctcacacaaa gtcataccgc attataattt tttggtaaat attcaacaca 480
tgtatttttt acaagaaccc aaattttaca gacaaatgca gcattgtaga catgtagaat 540
tctttgaagc atgtgaactt aacaacacca atgtcattaa atcaactaga ccctatgagt 600
aacaatttcg atattgcaaa caccaaatta tggaacttat ttgctgaaaa aattatgatc 660
aatgtgaagt ttaaattatt ataccataaa tatatcaaag atttttttga ggaaggtaaa 720
aattgcatgg aatgggctgc ccaacgtgat agctcacttt tatgctaggt agcattacca 780
aagatgggaa cgttctgatg aacaccaaac ccactcaaat aatatttata tttgggttgt 840
ttagttgtaa aagtgaagac ccaagtttaa agtaccaatt ggccaatgcc attcgattgt 900
tttgttcaaa gagcacttgg tacgtcattt ggactcgtat cttagtccaa tatattgcat 960
tttgcttcaa tgtgtagaat ccgacaaagt gcatgttcta aaattgtaaa tctaactaaa 1020
ttagaaagct tgttactaat tt 1042

<210> SEQ ID NO 99
<211> LENGTH: 191
<212> TYPE: DNA
<213> ORGANISM: Cauliflower mosaic virus

<400> SEQUENCE: 99
ctcgagtttc tccataataa tgtgtgagta gttcccagat aagggaatta gggttcctat 60
agggtttcgc tcatgtgttg agcatataag aaacccttag tatgtatttg tatttgtaaa 120
atacttctat caataaaatt tctaattcct aaaaccaaaa tccagtacta aaatccagat 180
cccccgaatt a 191

<210> SEQ ID NO 100
<211> LENGTH: 250
<212> TYPE: DNA
<213> ORGANISM: Agrobacterium tumefaciens

<400> SEQUENCE: 100
cgttcaaaca tttggcaata aagtttctta agattgaatc ctgttgccgg tcttgcgatg 60
attatcatat atatttctgt tgattacgtt aagcatgtaa taattaacat gtaatgcatg 120
acgttattta tgagatgggt ttttatgatt agagtcccgc aattatacat ttaatacgcg 180
atagaaaaca aaatatagcg cgcaaactag gataaattat cgcgcgcggt gtcatctatg 240
ttactagatc 250

<210> SEQ ID NO 101
<211> LENGTH: 68
<212> TYPE: DNA
<213> ORGANISM: Tobacco mosaic virus

<400> SEQUENCE: 101
gtatttttac aacaattacc aacaacaaca aacaacaaac aacattacaa ttactattta 60
cataaacc 68

<210> SEQ ID NO 102
<211> LENGTH: 510
<212> TYPE: DNA
<213> ORGANISM: Figwort mosaic virus

<400> SEQUENCE: 102
cagctggctt gtggggacca gacaaaaaag gaatggtgca gaattgttag gcgcacctac 60
caaaagcatc tttgccttta ttgcaaagat aaagcagatt cctctagtac aagtggggaa 120
caaaataacg tggaaaagag ctgtcctgac agcccactca ctaatgcgta tgacgaacgc 180
agtgacgacc acaaaacagc tggcttgtgg ggaccagaca aaaaaggaat ggtgcagaat 240
tgttaggcgc acctaccaaa agcatctttg cctttattgc aaagataaag cagattcctc 300
tagtacaagt ggggaacaaa ataacgtgga aaagagctgt cctgacagcc cactcactaa 360
tgcgtatgac gaacgcagtg acgaccacaa aagaattccc tctatataag aaggcattca 420
ttcccatttg aaggatcatc agatactgaa ccaatatttc tcactctaag aaattaagag 480
ctttgtattc ttcaatgaga ggctaagacc 510

<210> SEQ ID NO 103
<211> LENGTH: 493
<212> TYPE: DNA
<213> ORGANISM: Unknown
<220> FEATURE:
<223> OTHER INFORMATION: figwort and cauliflower mosaic virus/synthetic

<400> SEQUENCE: 103
agctgcttgt ggggaccaga caaaaaagga atggtgcaga attgttaggc gcacctacca 60
aaagcatctt tgcctttatt gcaaagataa agcagattcc tctagtacaa gtggggaaca 120
aaataacgtg gaaaagagct gtcctgacag cccactcact attgcgtttg acgaacgcag 180
tgacgaccac aaaactcgag acttttcaac aaagggtaat atccggaaac ctcctcggat 240
tccattgccc agctatctgt cactttattg tgaagatagt ggaaaaggaa ggtggctcct 300
acaaatgcca tcattgcgat aaaggaaagg ctatcgttga agatgcctct gccgacagtg 360
gtcccaaaga tggaccccca cccacgagga gcatcgtgga aaaagaagac gttccaacca 420
cgtcttcaaa gcaagtggat tgatgtgata tctccactga cgtaagggat gacgaacaat 480
cccactatcc ttc 493

<210> SEQ ID NO 104
<211> LENGTH: 413
<212> TYPE: DNA
<213> ORGANISM: Glycine max

<400> SEQUENCE: 104
gtatgttatg tatctcactc tgctcatctc tttcatatgt gtttctgatc tttctacctc 60
tgggttgtaa ttaatgctaa tagtgtgaga gtgcttaatt ctctatcagt aatgaaaatt 120
ttgtctgctt taattatttt gttcaagtgg ggtctcaatt acaatcaccc cttttcaagt 180
ttgaatatgc ttctagcgtt tttgggactt gagttcatat gggggtctct tcctttctta 240
aattttgtgt ttttccttga ttcaatcatt attgaaaatt aagttcaatt gggggtctca 300
gtctcagagc atttggcttt tgaatcatat gatctttcga taggtgttta aaaagtaatc 360
gactttcagt ttcttgatct gaataatcag tctttcattg tctgcgcatg tag 413

<210> SEQ ID NO 105
<211> LENGTH: 107
<212> TYPE: DNA
<213> ORGANISM: Zea mays

<400> SEQUENCE: 105
gtaactaacc actgccgccg cccatttctt cttcgaccgg ttgccgcctg cgcgcggcac 60
tgctcgtacg tctccccgcc agtgcttact gtaatgcatg catgcag 107

<210> SEQ ID NO 106
<211> LENGTH: 110
<212> TYPE: DNA
<213> ORGANISM: Mus musculus

<400> SEQUENCE: 106
gattcgtcag tagggttgta aaggtttttc ttttcctgag aaaacaacct tttgttttct 60
caggttttgc tttttggcct ttccctagct ttaaaaaaaa aaaagcaaaa 110

<210> SEQ ID NO 107
<211> LENGTH: 1272
<212> TYPE: PRT
<213> ORGANISM: Unknown
<220> FEATURE:
<223> OTHER INFORMATION: Uncultured Clostridium sp. isolate
2789STDY5608795

<400> SEQUENCE: 107

Met Glu Asp Lys Gln Phe Leu Glu Arg Tyr Lys Glu Phe Ile Gly Leu
1 5 10 15

Asn Ser Leu Ser Lys Thr Leu Arg Asn Ser Leu Ile Pro Val Gly Ser
20 25 30

Thr Leu Lys His Ile Gln Glu Tyr Gly Ile Leu Glu Glu Asp Ser Leu
35 40 45

Arg Ala Gln Lys Arg Glu Glu Leu Lys Gly Ile Met Asp Asp Tyr Tyr
50 55 60

Arg Asn Tyr Ile Glu Met His Leu Arg Asp Val His Asp Ile Asp Trp
65 70 75 80

Asn Glu Leu Phe Glu Ala Leu Thr Glu Val Lys Lys Asn Gln Thr Asp
85 90 95

Asp Ala Lys Lys Cys Leu Glu Lys Ile Gln Glu Lys Lys Arg Lys Glu
100 105 110

Ile Tyr Gln Tyr Leu Ser Asp Asp Ala Val Phe Ser Glu Met Phe Lys
115 120 125

Glu Lys Met Ile Ser Gly Ile Leu Pro Asp Phe Ile Arg Cys Asn Glu
130 135 140

Glu Tyr Ser Glu Glu Glu Lys Glu Glu Lys Leu Lys Thr Val Ala Leu
145 150 155 160

Phe His Arg Phe Thr Ser Ser Phe Asn Asp Phe Phe Leu Asn Arg Lys
165 170 175

Asn Val Phe Thr Lys Glu Ala Ile Ala Thr Ala Ile Gly Tyr Arg Val
180 185 190

Val His Glu Asn Ala Glu Ile Phe Leu Glu Asn Met Val Ala Phe Gln
195 200 205

Asn Ile Gln Lys Ser Ala Glu Ser Gln Ile Ser Ile Ile Glu Arg Lys
210 215 220

Asn Glu His Tyr Phe Met Glu Trp Lys Leu Ser His Ile Phe Thr Ala
225 230 235 240

Asp Tyr Tyr Met Met Leu Met Thr Gln Lys Ala Ile Glu His Tyr Asn
245 250 255

Glu Met Cys Gly Val Val Asn Gln His Met Lys Glu Tyr Cys Gln Lys
260 265 270

Glu Lys Lys Asn Trp Asn Leu Tyr Arg Met Lys Arg Leu His Lys Gln
275 280 285

Ile Leu Ser Asn Ala Ser Thr Ser Phe Lys Ile Pro Glu Lys Tyr Glu
290 295 300

-continued

```
Asn Asp Ala Glu Val Tyr Glu Ser Val Asn Ser Phe Leu Gln Asn Val
305                 310                 315                 320

Met Glu Lys Thr Val Met Glu Arg Ile Ala Val Leu Lys Asn Asn Thr
                325                 330                 335

Asp Asn Phe Asp Leu Ser Lys Ile Tyr Ile Thr Ala Pro Tyr Tyr Glu
            340                 345                 350

Lys Ile Ser Asn Tyr Leu Cys Gly Ser Trp Asn Thr Ile Ala Asp Cys
        355                 360                 365

Leu Thr His Tyr Tyr Glu Gln Gln Ile Ala Gly Lys Gly Ala Arg Lys
    370                 375                 380

Asp Gln Lys Val Lys Ala Ala Val Lys Ala Asp Lys Trp Lys Ser Leu
385                 390                 395                 400

Ser Glu Ile Glu Gln Leu Leu Lys Glu Tyr Ala Arg Ala Glu Glu Val
                405                 410                 415

Lys Arg Lys Pro Glu Glu Tyr Ile Ala Glu Ile Glu Asn Ile Val Ser
            420                 425                 430

Leu Lys Glu Val His Leu Leu Glu Tyr His Pro Glu Val Asn Leu Ile
        435                 440                 445

Glu Asn Glu Lys Tyr Ala Thr Glu Ile Lys Asp Val Leu Asp Asn Tyr
    450                 455                 460

Met Glu Leu Phe His Trp Met Lys Trp Phe Tyr Ile Glu Glu Ala Val
465                 470                 475                 480

Glu Lys Glu Val Asn Phe Tyr Gly Glu Leu Asp Asp Leu Tyr Glu Glu
                485                 490                 495

Ile Arg Asp Ile Val Pro Leu Tyr Asn Lys Val Arg Asn Tyr Val Thr
            500                 505                 510

Gln Lys Pro Tyr Ser Asp Thr Lys Ile Lys Leu Asn Phe Gly Thr Pro
        515                 520                 525

Thr Leu Ala Asn Gly Trp Ser Lys Ser Lys Glu Tyr Asp Tyr Asn Ala
    530                 535                 540

Ile Leu Leu Gln Lys Asp Gly Lys Tyr Tyr Met Gly Ile Phe Asn Pro
545                 550                 555                 560

Val Gln Lys Pro Glu Lys Glu Ile Ile Glu Gly His Ser His Pro Leu
                565                 570                 575

Glu Gly Asn Glu Tyr Lys Lys Met Val Tyr Tyr Tyr Leu Pro Ser Ala
            580                 585                 590

Asn Lys Met Leu Pro Lys Val Leu Leu Ser Lys Lys Gly Met Glu Ile
        595                 600                 605

Tyr Gln Pro Ser Glu Tyr Ile Ile Asn Gly Tyr Lys Glu Arg Arg His
    610                 615                 620

Ile Lys Ser Glu Glu Lys Phe Asp Leu Gln Phe Cys His Asp Leu Ile
625                 630                 635                 640

Asp Tyr Phe Lys Ser Gly Ile Glu Arg Asn Pro Asp Trp Lys Val Phe
                645                 650                 655

Gly Phe His Phe Ser Asp Thr Asp Thr Tyr Gln Asp Ile Ser Gly Phe
            660                 665                 670

Tyr Arg Glu Val Glu Asp Gln Gly Tyr Lys Ile Asp Trp Thr Tyr Ile
        675                 680                 685

Lys Glu Ala Asp Ile Asp Arg Leu Asn Glu Glu Gly Lys Leu Tyr Leu
    690                 695                 700

Phe Gln Ile Tyr Asn Lys Asp Phe Ser Glu Lys Ser Thr Gly Arg Glu
705                 710                 715                 720

Asn Leu His Thr Met Tyr Leu Lys Asn Leu Phe Ser Glu Glu Asn Ile
```

```
                725                 730                 735

Arg Glu Gln Val Leu Lys Leu Asn Gly Glu Ala Glu Ile Phe Phe Arg
            740                 745                 750

Lys Ser Ser Val Lys Lys Pro Ile Ile His Lys Lys Gly Thr Met Leu
        755                 760                 765

Val Asn Arg Thr Tyr Met Glu Glu Met His Gly Glu Ser Val Lys Lys
    770                 775                 780

Asn Ile Pro Glu Lys Glu Tyr Gln Glu Ile Tyr Asn Tyr Met Asn His
785                 790                 795                 800

Arg Trp Lys Gly Glu Leu Ser Ala Glu Ala Lys Glu Tyr Leu Lys Lys
                805                 810                 815

Ala Val Cys His Glu Thr Lys Lys Asp Ile Val Lys Asp Tyr Arg Tyr
            820                 825                 830

Ser Val Asp Lys Phe Phe Ile His Leu Pro Ile Thr Ile Asn Tyr Arg
        835                 840                 845

Ala Ser Gly Lys Glu Ala Leu Asn Ser Val Ala Gln Arg Tyr Ile Ala
    850                 855                 860

His Gln Asn Asp Met His Val Ile Gly Ile Asp Arg Gly Glu Arg Asn
865                 870                 875                 880

Leu Ile Tyr Val Ser Val Ile Asn Met Gln Gly Glu Ile Ile Glu Gln
                885                 890                 895

Lys Ser Phe Asn Val Val Asn Lys Tyr Asn Tyr Lys Glu Lys Leu Lys
            900                 905                 910

Glu Arg Glu Gln Asn Arg Asp Glu Ala Arg Lys Asn Trp Lys Glu Ile
        915                 920                 925

Gly Gln Ile Lys Asp Leu Lys Glu Gly Tyr Leu Ser Gly Val Ile His
    930                 935                 940

Glu Ile Ala Lys Met Met Ile Lys Tyr His Ala Ile Val Ala Met Glu
945                 950                 955                 960

Asp Leu Asn Tyr Gly Phe Lys Arg Gly Arg Phe Lys Val Glu Arg Gln
                965                 970                 975

Val Tyr Gln Lys Phe Glu Asn Met Leu Ile Gln Lys Leu Asn Tyr Leu
            980                 985                 990

Val Phe Lys Asp Arg Ser Ala Asp  Glu Asp Gly Gly Val  Leu Arg Gly
        995                 1000                1005

Tyr Gln  Leu Ala Tyr Ile Pro  Asp Ser Val Lys Lys  Leu Gly Arg
    1010                1015                1020

Gln Cys  Gly Met Ile Phe Tyr  Val Pro Ala Ala Phe  Thr Ser Lys
    1025                1030                1035

Ile Asp  Pro Ala Thr Gly Phe  Val Asp Ile Phe Asn  His Lys Ala
    1040                1045                1050

Tyr Thr  Thr Asp Gln Ala Lys  Arg Glu Phe Ile Leu  Ser Phe Asp
    1055                1060                1065

Glu Ile  Cys Tyr Asp Val Glu  Arg Gln Leu Phe Arg  Phe Thr Phe
    1070                1075                1080

Asp Tyr  Ala Asn Phe Ala Thr  His Asn Val Thr Leu  Ala Arg Asn
    1085                1090                1095

Asn Trp  Thr Ile Tyr Thr Asn  Gly Thr Arg Thr Gln  Lys Glu Phe
    1100                1105                1110

Val Asn  Arg Arg Val Arg Asp  Lys Lys Glu Val Phe  Asp Pro Thr
    1115                1120                1125

Glu Lys  Met Leu Lys Leu Leu  Glu Leu Glu Gly Val  Glu Tyr Gln
    1130                1135                1140
```

Ser Gly Ala Asn Leu Leu Pro Lys Leu Glu Lys Ile Ser Asp Pro
1145 1150 1155

His Leu Phe His Glu Leu Gln Arg Ile Val Arg Phe Thr Val Gln
1160 1165 1170

Leu Arg Asn Ser Lys Asn Glu Glu Asn Asp Val Asp Tyr Asp His
1175 1180 1185

Val Ile Ser Pro Val Leu Asn Glu Glu Gly Lys Phe Phe Asp Ser
1190 1195 1200

Ser Lys Tyr Glu Asn Lys Glu Glu Lys Lys Glu Ser Leu Leu Pro
1205 1210 1215

Val Asp Ala Asp Ala Asn Gly Ala Tyr Cys Ile Ala Leu Lys Gly
1220 1225 1230

Leu Tyr Ile Met Gln Ala Ile Gln Lys Asn Trp Ser Glu Glu Lys
1235 1240 1245

Ala Leu Ser Pro Asp Val Leu Arg Leu Asn Asn Asn Asp Trp Phe
1250 1255 1260

Asp Tyr Ile Gln Asn Lys Arg Tyr Arg
1265 1270

<210> SEQ ID NO 108
<211> LENGTH: 1247
<212> TYPE: PRT
<213> ORGANISM: Unknown
<220> FEATURE:
<223> OTHER INFORMATION: Uncultured bacterium (gcode 4) ACD_3C00058, whole genome shotgun sequence

<400> SEQUENCE: 108

Met Phe Lys Gly Asp Ala Phe Thr Gly Leu Tyr Glu Val Gln Lys Thr
1 5 10 15

Leu Arg Phe Glu Leu Val Pro Ile Gly Leu Thr Gln Ser Tyr Leu Glu
20 25 30

Asn Asp Trp Val Ile Gln Lys Asp Lys Glu Val Glu Glu Asn Tyr Gly
35 40 45

Lys Ile Lys Ala Tyr Phe Asp Leu Ile His Lys Glu Phe Val Arg Gln
50 55 60

Ser Leu Glu Asn Ala Trp Leu Cys Gln Leu Asp Asp Phe Tyr Glu Lys
65 70 75 80

Tyr Ile Glu Leu His Asn Ser Leu Glu Thr Arg Lys Asp Lys Asn Leu
85 90 95

Ala Lys Gln Phe Glu Lys Val Met Lys Ser Leu Lys Lys Glu Phe Val
100 105 110

Ser Phe Phe Asp Ala Lys Trp Asn Glu Trp Lys Gln Lys Phe Ser Phe
115 120 125

Leu Lys Lys Trp Trp Ile Asp Val Leu Asn Glu Lys Glu Val Leu Asp
130 135 140

Leu Met Ala Glu Phe Tyr Pro Asp Glu Lys Glu Leu Phe Asp Lys Phe
145 150 155 160

Asp Lys Phe Phe Thr Tyr Phe Ser Asn Phe Lys Glu Ser Arg Lys Asn
165 170 175

Phe Tyr Ala Asp Asp Gly Arg Ala Trp Ala Ile Ala Thr Arg Ala Ile
180 185 190

Asp Glu Asn Leu Ile Thr Phe Ile Lys Asn Ile Glu Asp Phe Lys Lys
195 200 205

Leu Asn Ser Ser Phe Arg Glu Phe Val Asn Asp Asn Phe Ser Glu Glu

-continued

```
    210                 215                 220

Asp Lys Gln Ile Phe Glu Ile Asp Phe Tyr Asn Asn Cys Leu Leu Gln
225                 230                 235                 240

Pro Trp Ile Asp Lys Tyr Asn Lys Ile Val Trp Trp Tyr Ser Leu Glu
                245                 250                 255

Asn Trp Glu Lys Val Gln Trp Leu Asn Glu Lys Ile Asn Asn Phe Lys
            260                 265                 270

Gln Asn Gln Asn Lys Ser Asn Ser Lys Asp Leu Lys Phe Pro Arg Met
        275                 280                 285

Lys Leu Leu Tyr Lys Gln Ile Leu Gly Asp Lys Glu Lys Lys Val Tyr
    290                 295                 300

Ile Asp Glu Ile Arg Asp Asp Lys Asn Leu Ile Asp Leu Ile Asp Asn
305                 310                 315                 320

Ser Lys Arg Arg Asn Gln Ile Lys Ile Asp Asn Ala Asn Asp Ile Ile
                325                 330                 335

Asn Asp Phe Ile Asn Asn Asn Ala Lys Phe Glu Leu Asp Lys Ile Tyr
            340                 345                 350

Leu Thr Arg Gln Ser Ile Asn Thr Ile Ser Ser Lys Tyr Phe Ser Ser
        355                 360                 365

Trp Asp Tyr Ile Arg Trp Tyr Phe Trp Thr Gly Glu Leu Gln Glu Phe
    370                 375                 380

Val Ser Phe Tyr Asp Leu Lys Glu Thr Phe Trp Lys Ile Glu Tyr Glu
385                 390                 395                 400

Thr Leu Glu Asn Ile Phe Lys Asp Cys Tyr Val Lys Gly Ile Asn Thr
                405                 410                 415

Glu Ser Gln Asn Asn Ile Val Phe Glu Thr Gln Gly Ile Tyr Glu Asn
            420                 425                 430

Phe Leu Asn Ile Phe Lys Phe Glu Phe Asn Gln Asn Ile Ser Gln Ile
        435                 440                 445

Ser Leu Leu Glu Trp Glu Leu Asp Lys Ile Gln Asn Glu Asp Ile Lys
    450                 455                 460

Lys Asn Glu Lys Gln Val Glu Val Ile Lys Asn Tyr Phe Asp Ser Val
465                 470                 475                 480

Met Ser Val Tyr Lys Met Thr Lys Tyr Phe Ser Leu Glu Lys Trp Lys
                485                 490                 495

Lys Arg Val Glu Leu Asp Thr Asp Asn Asn Phe Tyr Asn Asp Phe Asn
            500                 505                 510

Glu Tyr Leu Glu Gly Phe Glu Ile Trp Lys Asp Tyr Asn Leu Val Arg
        515                 520                 525

Asn Tyr Ile Thr Lys Lys Gln Val Asn Thr Asp Lys Ile Lys Leu Asn
    530                 535                 540

Phe Asp Asn Ser Gln Phe Leu Thr Trp Trp Asp Lys Asp Lys Glu Asn
545                 550                 555                 560

Glu Arg Leu Gly Ile Ile Leu Arg Arg Glu Trp Lys Tyr Tyr Leu Trp
                565                 570                 575

Ile Leu Lys Lys Trp Asn Thr Leu Asn Phe Gly Asp Tyr Leu Gln Lys
            580                 585                 590

Glu Trp Glu Ile Phe Tyr Glu Lys Met Asn Tyr Lys Gln Leu Asn Asn
        595                 600                 605

Val Tyr Arg Gln Leu Pro Arg Leu Leu Phe Pro Leu Thr Lys Lys Leu
    610                 615                 620

Asn Glu Leu Lys Trp Asp Glu Leu Lys Lys Tyr Leu Ser Lys Tyr Ile
625                 630                 635                 640
```

Gln Asn Phe Trp Tyr Asn Glu Glu Ile Ala Gln Ile Lys Ile Glu Phe
645 650 655

Asp Ile Phe Gln Glu Ser Lys Glu Lys Trp Glu Lys Phe Asp Ile Asp
660 665 670

Lys Leu Arg Lys Leu Ile Glu Tyr Tyr Lys Lys Trp Val Leu Ala Leu
675 680 685

Tyr Ser Asp Leu Tyr Asp Leu Glu Phe Ile Lys Tyr Lys Asn Tyr Asp
690 695 700

Asp Leu Ser Ile Phe Tyr Ser Asp Val Glu Lys Lys Met Tyr Asn Leu
705 710 715 720

Asn Phe Thr Lys Ile Asp Lys Ser Leu Ile Asp Gly Lys Val Lys Ser
725 730 735

Trp Glu Leu Tyr Leu Phe Gln Ile Tyr Asn Lys Asp Phe Ser Glu Ser
740 745 750

Lys Lys Glu Trp Ser Thr Glu Asn Ile His Thr Lys Tyr Phe Lys Leu
755 760 765

Leu Phe Asn Glu Lys Asn Leu Gln Asn Leu Val Val Lys Leu Ser Trp
770 775 780

Trp Ala Asp Ile Phe Phe Arg Asp Lys Thr Glu Asn Leu Lys Phe Lys
785 790 795 800

Lys Asp Lys Asn Gly Gln Glu Ile Leu Asp His Arg Arg Phe Ser Gln
805 810 815

Asp Lys Ile Met Phe His Ile Ser Ile Thr Leu Asn Ala Asn Cys Trp
820 825 830

Asp Lys Tyr Trp Phe Asn Gln Tyr Val Asn Glu Tyr Met Asn Lys Glu
835 840 845

Arg Asp Ile Lys Ile Ile Trp Ile Asp Arg Trp Glu Lys His Leu Ala
850 855 860

Tyr Tyr Cys Val Ile Asp Lys Ser Trp Lys Ile Phe Asn Asn Glu Ile
865 870 875 880

Trp Thr Leu Asn Glu Leu Asn Trp Val Asn Tyr Leu Glu Lys Leu Glu
885 890 895

Lys Ile Glu Ser Ser Arg Lys Asp Ser Arg Ile Ser Trp Trp Glu Ile
900 905 910

Glu Asn Ile Lys Glu Leu Lys Asn Gly Tyr Ile Ser Gln Val Ile Asn
915 920 925

Lys Leu Thr Glu Leu Ile Val Lys Tyr Asn Ala Ile Ile Val Phe Glu
930 935 940

Asp Leu Asn Ile Trp Phe Lys Arg Trp Arg Gln Lys Ile Glu Lys Gln
945 950 955 960

Ile Tyr Gln Lys Leu Glu Leu Ala Leu Ala Lys Lys Leu Asn Tyr Leu
965 970 975

Thr Gln Lys Asp Lys Lys Asp Asp Glu Ile Leu Trp Asn Leu Lys Ala
980 985 990

Leu Gln Leu Val Pro Lys Val Asn Asp Tyr Gln Asp Ile Trp Asn Tyr
995 1000 1005

Lys Gln Ser Trp Ile Met Phe Tyr Val Arg Ala Asn Tyr Thr Ser
1010 1015 1020

Val Thr Cys Pro Asn Cys Trp Leu Arg Lys Asn Leu Tyr Ile Ser
1025 1030 1035

Asn Ser Ala Thr Lys Glu Asn Gln Lys Lys Ser Leu Asn Ser Ile
1040 1045 1050

```
Ala Ile  Lys Tyr Asn Asp Trp  Lys Phe Ser Phe Ser  Tyr Glu Ile
    1055                 1060                 1065

Asp Asp  Lys Ser Trp Lys Gln  Lys Gln Ser Leu Asn  Lys Lys Lys
    1070                 1075                 1080

Phe Ile  Val Tyr Ser Asp Ile  Glu Arg Phe Val Tyr  Ser Pro Leu
    1085                 1090                 1095

Glu Lys  Leu Thr Lys Val Ile  Asp Val Asn Lys Lys  Leu Leu Glu
    1100                 1105                 1110

Leu Phe  Arg Asp Phe Asn Leu  Ser Leu Asp Ile Asn  Lys Gln Ile
    1115                 1120                 1125

Gln Glu  Lys Asp Leu Asp Ser  Val Phe Phe Lys Ser  Leu Thr His
    1130                 1135                 1140

Leu Phe  Asn Leu Ile Leu Gln  Leu Arg Asn Ser Asp  Ser Lys Asp
    1145                 1150                 1155

Asn Lys  Asp Tyr Ile Ser Cys  Pro Ser Cys Tyr Tyr  His Ser Asn
    1160                 1165                 1170

Asn Trp  Leu Gln Trp Phe Glu  Phe Asn Trp Asp Ala  Asn Trp Ala
    1175                 1180                 1185

Tyr Asn  Ile Ala Arg Lys Gly  Ile Ile Leu Leu Asp  Arg Ile Arg
    1190                 1195                 1200

Lys Asn  Gln Glu Lys Pro Asp  Leu Tyr Val Ser Asp  Ile Asp Trp
    1205                 1210                 1215

Asp Asn  Phe Val Gln Ser Asn  Gln Phe Pro Asn Thr  Ile Ile Pro
    1220                 1225                 1230

Ile Gln  Asn Ile Glu Lys Gln  Val Pro Leu Asn Ile  Lys Ile
    1235                 1240                 1245
```

<210> SEQ ID NO 109
<211> LENGTH: 1298
<212> TYPE: PRT
<213> ORGANISM: Unknown
<220> FEATURE:
<223> OTHER INFORMATION: Thiomicrospira sp. XS5 ZB100000

<400> SEQUENCE: 109

```
Met Thr Lys Thr Phe Asp Ser Glu Phe Phe Asn Leu Tyr Ser Leu Gln
1               5                   10                  15

Lys Thr Val Arg Phe Glu Leu Lys Pro Val Gly Glu Thr Ala Ser Phe
            20                  25                  30

Val Glu Asp Phe Lys Asn Glu Gly Leu Lys Arg Val Val Ser Glu Asp
        35                  40                  45

Glu Arg Arg Ala Val Asp Tyr Gln Lys Val Lys Glu Ile Ile Asp Asp
    50                  55                  60

Tyr His Arg Asp Phe Ile Glu Glu Ser Leu Asn Tyr Phe Pro Glu Gln
65                  70                  75                  80

Val Ser Lys Asp Ala Leu Glu Gln Ala Phe His Leu Tyr Gln Lys Leu
                85                  90                  95

Lys Ala Ala Lys Val Glu Glu Arg Glu Lys Ala Leu Lys Glu Trp Glu
            100                 105                 110

Ala Leu Gln Lys Lys Leu Arg Glu Lys Val Val Lys Cys Phe Ser Asp
        115                 120                 125

Ser Asn Lys Ala Arg Phe Ser Arg Ile Asp Lys Lys Glu Leu Ile Lys
    130                 135                 140

Glu Asp Leu Ile Asn Trp Leu Val Ala Gln Asn Arg Glu Asp Asp Ile
145                 150                 155                 160
```

-continued

```
Pro Thr Val Glu Thr Phe Asn Asn Phe Thr Thr Tyr Phe Thr Gly Phe
                165                 170                 175

His Glu Asn Arg Lys Asn Ile Tyr Ser Lys Asp Asp His Ala Thr Ala
            180                 185                 190

Ile Ser Phe Arg Leu Ile His Glu Asn Leu Pro Lys Phe Phe Asp Asn
        195                 200                 205

Val Ile Ser Phe Asn Lys Leu Lys Glu Gly Phe Pro Glu Leu Lys Phe
    210                 215                 220

Asp Lys Val Lys Glu Asp Leu Glu Val Asp Tyr Asp Leu Lys His Ala
225                 230                 235                 240

Phe Glu Ile Glu Tyr Phe Val Asn Phe Val Thr Gln Ala Gly Ile Asp
                245                 250                 255

Gln Tyr Asn Tyr Leu Leu Gly Gly Lys Thr Leu Glu Asp Gly Thr Lys
            260                 265                 270

Lys Gln Gly Met Asn Glu Gln Ile Asn Leu Phe Lys Gln Gln Gln Thr
        275                 280                 285

Arg Asp Lys Ala Arg Gln Ile Pro Lys Leu Ile Pro Leu Phe Lys Gln
    290                 295                 300

Ile Leu Ser Glu Arg Thr Glu Ser Gln Ser Phe Ile Pro Lys Gln Phe
305                 310                 315                 320

Glu Ser Asp Gln Glu Leu Phe Asp Ser Leu Gln Lys Leu His Asn Asn
                325                 330                 335

Cys Gln Asp Lys Phe Thr Val Leu Gln Gln Ala Ile Leu Gly Leu Ala
            340                 345                 350

Glu Ala Asp Leu Lys Lys Val Phe Ile Lys Thr Ser Asp Leu Asn Ala
        355                 360                 365

Leu Ser Asn Thr Ile Phe Gly Asn Tyr Ser Val Phe Ser Asp Ala Leu
    370                 375                 380

Asn Leu Tyr Lys Glu Ser Leu Lys Thr Lys Lys Ala Gln Glu Ala Phe
385                 390                 395                 400

Glu Lys Leu Pro Ala His Ser Ile His Asp Leu Ile Gln Tyr Leu Glu
                405                 410                 415

Gln Phe Asn Ser Ser Leu Asp Ala Glu Lys Gln Gln Ser Thr Asp Thr
            420                 425                 430

Val Leu Asn Tyr Phe Ile Lys Thr Asp Glu Leu Tyr Ser Arg Phe Ile
        435                 440                 445

Lys Ser Thr Ser Glu Ala Phe Thr Gln Val Gln Pro Leu Phe Glu Leu
    450                 455                 460

Glu Ala Leu Ser Ser Lys Arg Arg Pro Pro Glu Ser Glu Asp Glu Gly
465                 470                 475                 480

Ala Lys Gly Gln Glu Gly Phe Glu Gln Ile Lys Arg Ile Lys Ala Tyr
                485                 490                 495

Leu Asp Thr Leu Met Glu Ala Val His Phe Ala Lys Pro Leu Tyr Leu
            500                 505                 510

Val Lys Gly Arg Lys Met Ile Glu Gly Leu Asp Lys Asp Gln Ser Phe
        515                 520                 525

Tyr Glu Ala Phe Glu Met Ala Tyr Gln Glu Leu Glu Ser Leu Ile Ile
    530                 535                 540

Pro Ile Tyr Asn Lys Ala Arg Ser Tyr Leu Ser Arg Lys Pro Phe Lys
545                 550                 555                 560

Ala Asp Lys Phe Lys Ile Asn Phe Asp Asn Asn Thr Leu Leu Ser Gly
                565                 570                 575

Trp Asp Ala Asn Lys Glu Thr Ala Asn Ala Ser Ile Leu Phe Lys Lys
```

```
            580                 585                 590

Asp Gly Leu Tyr Tyr Leu Gly Ile Met Pro Lys Gly Lys Thr Phe Leu
        595                 600                 605

Phe Asp Tyr Phe Val Ser Ser Glu Asp Ser Glu Lys Leu Lys Gln Arg
    610                 615                 620

Arg Gln Lys Thr Ala Glu Glu Ala Leu Ala Gln Asp Gly Glu Ser Tyr
625                 630                 635                 640

Phe Glu Lys Ile Arg Tyr Lys Leu Leu Pro Gly Ala Ser Lys Met Leu
                645                 650                 655

Pro Lys Val Phe Phe Ser Asn Lys Asn Ile Gly Phe Tyr Asn Pro Ser
            660                 665                 670

Asp Asp Ile Leu Arg Ile Arg Asn Thr Ala Ser His Thr Lys Asn Gly
        675                 680                 685

Thr Pro Gln Lys Gly His Ser Lys Val Glu Phe Asn Leu Asn Asp Cys
    690                 695                 700

His Lys Met Ile Asp Phe Phe Lys Ser Ser Ile Gln Lys His Pro Glu
705                 710                 715                 720

Trp Gly Ser Phe Gly Phe Thr Phe Ser Asp Thr Ser Asp Phe Glu Asp
                725                 730                 735

Met Ser Ala Phe Tyr Arg Glu Val Glu Asn Gln Gly Tyr Val Ile Ser
            740                 745                 750

Phe Asp Lys Ile Lys Glu Thr Tyr Ile Gln Ser Gln Val Glu Gln Gly
        755                 760                 765

Asn Leu Tyr Leu Phe Gln Ile Tyr Asn Lys Asp Phe Ser Pro Tyr Ser
    770                 775                 780

Lys Gly Lys Pro Asn Leu His Thr Leu Tyr Trp Lys Ala Leu Phe Glu
785                 790                 795                 800

Glu Ala Asn Leu Asn Asn Val Val Ala Lys Leu Asn Gly Glu Ala Glu
                805                 810                 815

Ile Phe Phe Arg Arg His Ser Ile Lys Ala Ser Asp Lys Val Val His
            820                 825                 830

Pro Ala Asn Gln Ala Ile Asp Asn Lys Asn Pro His Thr Glu Lys Thr
        835                 840                 845

Gln Ser Thr Phe Glu Tyr Asp Leu Val Lys Asp Lys Arg Tyr Thr Gln
    850                 855                 860

Asp Lys Phe Phe Phe His Val Pro Ile Ser Leu Asn Phe Lys Ala Gln
865                 870                 875                 880

Gly Val Ser Lys Phe Asn Asp Lys Val Asn Gly Phe Leu Lys Gly Asn
                885                 890                 895

Pro Asp Val Asn Ile Ile Gly Ile Asp Arg Gly Glu Arg His Leu Leu
            900                 905                 910

Tyr Phe Thr Val Val Asn Gln Lys Gly Glu Ile Leu Val Gln Glu Ser
        915                 920                 925

Leu Asn Thr Leu Met Ser Asp Lys Gly His Val Asn Asp Tyr Gln Gln
    930                 935                 940

Lys Leu Asp Lys Lys Glu Gln Glu Arg Asp Ala Ala Arg Lys Ser Trp
945                 950                 955                 960

Thr Thr Val Glu Asn Ile Lys Glu Leu Lys Glu Gly Tyr Leu Ser His
                965                 970                 975

Val Val His Lys Leu Ala His Leu Ile Ile Lys Tyr Asn Ala Ile Val
            980                 985                 990

Cys Leu Glu Asp Leu Asn Phe Gly  Phe Lys Arg Gly Arg  Phe Lys Val
        995                 1000                1005
```

```
Glu Lys Gln Val Tyr Gln Lys Phe Glu Lys Ala Leu Ile Asp Lys
    1010                1015                1020

Leu Asn Tyr Leu Val Phe Lys Glu Lys Glu Leu Gly Glu Val Gly
    1025                1030                1035

His Tyr Leu Thr Ala Tyr Gln Leu Thr Ala Pro Phe Glu Ser Phe
    1040                1045                1050

Lys Lys Leu Gly Lys Gln Ser Gly Ile Leu Phe Tyr Val Pro Ala
    1055                1060                1065

Asp Tyr Thr Ser Lys Ile Asp Pro Thr Thr Gly Phe Val Asn Phe
    1070                1075                1080

Leu Asp Leu Arg Tyr Gln Ser Val Glu Lys Ala Lys Gln Leu Leu
    1085                1090                1095

Ser Asp Phe Asn Ala Ile Arg Phe Asn Ser Val Gln Asn Tyr Phe
    1100                1105                1110

Glu Phe Glu Ile Asp Tyr Lys Lys Leu Thr Pro Lys Arg Lys Val
    1115                1120                1125

Gly Thr Gln Ser Lys Trp Val Ile Cys Thr Tyr Gly Asp Val Arg
    1130                1135                1140

Tyr Gln Asn Arg Arg Asn Gln Lys Gly His Trp Glu Thr Glu Glu
    1145                1150                1155

Val Asn Val Thr Glu Lys Leu Lys Ala Leu Phe Ala Ser Asp Ser
    1160                1165                1170

Lys Thr Thr Thr Val Ile Asp Tyr Ala Asn Asp Asp Asn Leu Ile
    1175                1180                1185

Asp Val Ile Leu Glu Gln Asp Lys Ala Ser Phe Phe Lys Glu Leu
    1190                1195                1200

Leu Trp Leu Leu Lys Leu Thr Met Thr Leu Arg His Ser Lys Ile
    1205                1210                1215

Lys Ser Glu Asp Asp Phe Ile Leu Ser Pro Val Lys Asn Glu Gln
    1220                1225                1230

Gly Glu Phe Tyr Asp Ser Arg Lys Ala Gly Glu Val Trp Pro Lys
    1235                1240                1245

Asp Ala Asp Ala Asn Gly Ala Tyr His Ile Ala Leu Lys Gly Leu
    1250                1255                1260

Trp Asn Leu Gln Gln Ile Asn Gln Trp Glu Lys Gly Lys Thr Leu
    1265                1270                1275

Asn Leu Ala Ile Lys Asn Gln Asp Trp Phe Ser Phe Ile Gln Glu
    1280                1285                1290

Lys Pro Tyr Gln Glu
    1295
```

<210> SEQ ID NO 110
<211> LENGTH: 1318
<212> TYPE: PRT
<213> ORGANISM: Unknown
<220> FEATURE:
<223> OTHER INFORMATION: Flavobacterium branchiophilum FL-15

<400> SEQUENCE: 110

```
Met Thr Asn Lys Phe Thr Asn Gln Tyr Ser Leu Ser Lys Thr Leu Arg
1               5                   10                  15

Phe Glu Leu Ile Pro Gln Gly Lys Thr Leu Glu Phe Ile Gln Glu Lys
            20                  25                  30

Gly Leu Leu Ser Gln Asp Lys Gln Arg Ala Glu Ser Tyr Gln Glu Met
        35                  40                  45
```

-continued

```
Lys Lys Thr Ile Asp Lys Phe His Lys Tyr Phe Ile Asp Leu Ala Leu
    50                  55                  60

Ser Asn Ala Lys Leu Thr His Leu Glu Thr Tyr Leu Glu Leu Tyr Asn
65                  70                  75                  80

Lys Ser Ala Glu Thr Lys Lys Glu Gln Lys Phe Lys Asp Asp Leu Lys
                85                  90                  95

Lys Val Gln Asp Asn Leu Arg Lys Glu Ile Val Lys Ser Phe Ser Asp
            100                 105                 110

Gly Asp Ala Lys Ser Ile Phe Ala Ile Leu Asp Lys Lys Glu Leu Ile
        115                 120                 125

Thr Val Glu Leu Glu Lys Trp Phe Glu Asn Asn Glu Gln Lys Asp Ile
    130                 135                 140

Tyr Phe Asp Glu Lys Phe Lys Thr Phe Thr Thr Tyr Phe Thr Gly Phe
145                 150                 155                 160

His Gln Asn Arg Lys Asn Met Tyr Ser Val Glu Pro Asn Ser Thr Ala
                165                 170                 175

Ile Ala Tyr Arg Leu Ile His Glu Asn Leu Pro Lys Phe Leu Glu Asn
            180                 185                 190

Ala Lys Ala Phe Glu Lys Ile Lys Gln Val Glu Ser Leu Gln Val Asn
        195                 200                 205

Phe Arg Glu Leu Met Gly Glu Phe Gly Asp Glu Gly Leu Ile Phe Val
    210                 215                 220

Asn Glu Leu Glu Glu Met Phe Gln Ile Asn Tyr Tyr Asn Asp Val Leu
225                 230                 235                 240

Ser Gln Asn Gly Ile Thr Ile Tyr Asn Ser Ile Ile Ser Gly Phe Thr
                245                 250                 255

Lys Asn Asp Ile Lys Tyr Lys Gly Leu Asn Glu Tyr Ile Asn Asn Tyr
            260                 265                 270

Asn Gln Thr Lys Asp Lys Lys Asp Arg Leu Pro Lys Leu Lys Gln Leu
        275                 280                 285

Tyr Lys Gln Ile Leu Ser Asp Arg Ile Ser Leu Ser Phe Leu Pro Asp
    290                 295                 300

Ala Phe Thr Asp Gly Lys Gln Val Leu Lys Ala Ile Phe Asp Phe Tyr
305                 310                 315                 320

Lys Ile Asn Leu Leu Ser Tyr Thr Ile Glu Gly Gln Glu Glu Ser Gln
                325                 330                 335

Asn Leu Leu Leu Leu Ile Arg Gln Thr Ile Glu Asn Leu Ser Ser Phe
            340                 345                 350

Asp Thr Gln Lys Ile Tyr Leu Lys Asn Asp Thr His Leu Thr Thr Ile
        355                 360                 365

Ser Gln Gln Val Phe Gly Asp Phe Ser Val Phe Ser Thr Ala Leu Asn
    370                 375                 380

Tyr Trp Tyr Glu Thr Lys Val Asn Pro Lys Phe Glu Thr Glu Tyr Ser
385                 390                 395                 400

Lys Ala Asn Glu Lys Lys Arg Glu Ile Leu Asp Lys Ala Lys Ala Val
                405                 410                 415

Phe Thr Lys Gln Asp Tyr Phe Ser Ile Ala Phe Leu Gln Glu Val Leu
            420                 425                 430

Ser Glu Tyr Ile Leu Thr Leu Asp His Thr Ser Asp Ile Val Lys Lys
        435                 440                 445

His Ser Ser Asn Cys Ile Ala Asp Tyr Phe Lys Asn His Phe Val Ala
    450                 455                 460
```

-continued

```
Lys Lys Glu Asn Glu Thr Asp Lys Thr Phe Asp Phe Ile Ala Asn Ile
465                 470                 475                 480

Thr Ala Lys Tyr Gln Cys Ile Gln Gly Ile Leu Glu Asn Ala Asp Gln
                485                 490                 495

Tyr Glu Asp Glu Leu Lys Gln Asp Gln Lys Leu Ile Asp Asn Leu Lys
            500                 505                 510

Phe Phe Leu Asp Ala Ile Leu Glu Leu Leu His Phe Ile Lys Pro Leu
        515                 520                 525

His Leu Lys Ser Glu Ser Ile Thr Glu Lys Asp Thr Ala Phe Tyr Asp
    530                 535                 540

Val Phe Glu Asn Tyr Tyr Glu Ala Leu Ser Leu Leu Thr Pro Leu Tyr
545                 550                 555                 560

Asn Met Val Arg Asn Tyr Val Thr Gln Lys Pro Tyr Ser Thr Glu Lys
                565                 570                 575

Ile Lys Leu Asn Phe Glu Asn Ala Gln Leu Leu Asn Gly Trp Asp Ala
            580                 585                 590

Asn Lys Glu Gly Asp Tyr Leu Thr Thr Ile Leu Lys Lys Asp Gly Asn
        595                 600                 605

Tyr Phe Leu Ala Ile Met Asp Lys Lys His Asn Lys Ala Phe Gln Lys
    610                 615                 620

Phe Pro Glu Gly Lys Glu Asn Tyr Glu Lys Met Val Tyr Lys Leu Leu
625                 630                 635                 640

Pro Gly Val Asn Lys Met Leu Pro Lys Val Phe Phe Ser Asn Lys Asn
                645                 650                 655

Ile Ala Tyr Phe Asn Pro Ser Lys Glu Leu Leu Glu Asn Tyr Lys Lys
            660                 665                 670

Glu Thr His Lys Lys Gly Asp Thr Phe Asn Leu Glu His Cys His Thr
        675                 680                 685

Leu Ile Asp Phe Phe Lys Asp Ser Leu Asn Lys His Glu Asp Trp Lys
    690                 695                 700

Tyr Phe Asp Phe Gln Phe Ser Glu Thr Lys Ser Tyr Gln Asp Leu Ser
705                 710                 715                 720

Gly Phe Tyr Arg Glu Val Glu His Gln Gly Tyr Lys Ile Asn Phe Lys
                725                 730                 735

Asn Ile Asp Ser Glu Tyr Ile Asp Gly Leu Val Asn Glu Gly Lys Leu
            740                 745                 750

Phe Leu Phe Gln Ile Tyr Ser Lys Asp Phe Ser Pro Phe Ser Lys Gly
        755                 760                 765

Lys Pro Asn Met His Thr Leu Tyr Trp Lys Ala Leu Phe Glu Glu Gln
    770                 775                 780

Asn Leu Gln Asn Val Ile Tyr Lys Leu Asn Gly Gln Ala Glu Ile Phe
785                 790                 795                 800

Phe Arg Lys Ala Ser Ile Lys Pro Lys Asn Ile Ile Leu His Lys Lys
                805                 810                 815

Lys Ile Lys Ile Ala Lys Lys His Phe Ile Asp Lys Lys Thr Lys Thr
            820                 825                 830

Ser Glu Ile Val Pro Val Gln Thr Ile Lys Asn Leu Asn Met Tyr Tyr
        835                 840                 845

Gln Gly Lys Ile Ser Glu Lys Glu Leu Thr Gln Asp Asp Leu Arg Tyr
    850                 855                 860

Ile Asp Asn Phe Ser Ile Phe Asn Glu Lys Asn Lys Thr Ile Asp Ile
865                 870                 875                 880

Ile Lys Asp Lys Arg Phe Thr Val Asp Lys Phe Gln Phe His Val Pro
```

```
            885                 890                 895

Ile Thr Met Asn Phe Lys Ala Thr Gly Gly Ser Tyr Ile Asn Gln Thr
        900                 905                 910

Val Leu Glu Tyr Leu Gln Asn Asn Pro Glu Val Lys Ile Ile Gly Leu
    915                 920                 925

Asp Arg Gly Glu Arg His Leu Val Tyr Leu Thr Leu Ile Asp Gln Gln
930                 935                 940

Gly Asn Ile Leu Lys Gln Glu Ser Leu Asn Thr Ile Thr Asp Ser Lys
945                 950                 955                 960

Ile Ser Thr Pro Tyr His Lys Leu Leu Asp Asn Lys Glu Asn Glu Arg
            965                 970                 975

Asp Leu Ala Arg Lys Asn Trp Gly Thr Val Glu Asn Ile Lys Glu Leu
        980                 985                 990

Lys Glu Gly Tyr Ile Ser Gln Val  Val His Lys Ile Ala  Thr Leu Met
    995                 1000                1005

Leu Glu  Glu Asn Ala Ile Val  Val Met Glu Asp Leu  Asn Phe Gly
    1010                1015                1020

Phe Lys  Arg Gly Arg Phe Lys  Val Glu Lys Gln Ile  Tyr Gln Lys
    1025                1030                1035

Leu Glu  Lys Met Leu Ile Asp  Lys Leu Asn Tyr Leu  Val Leu Lys
    1040                1045                1050

Asp Lys  Gln Pro Gln Glu Leu  Gly Gly Leu Tyr Asn  Ala Leu Gln
    1055                1060                1065

Leu Thr  Asn Lys Phe Glu Ser  Phe Gln Lys Met Gly  Lys Gln Ser
    1070                1075                1080

Gly Phe  Leu Phe Tyr Val Pro  Ala Trp Asn Thr Ser  Lys Ile Asp
    1085                1090                1095

Pro Thr  Thr Gly Phe Val Asn  Tyr Phe Tyr Thr Lys  Tyr Glu Asn
    1100                1105                1110

Val Asp  Lys Ala Lys Ala Phe  Phe Glu Lys Phe Glu  Ala Ile Arg
    1115                1120                1125

Phe Asn  Ala Glu Lys Lys Tyr  Phe Glu Phe Glu Val  Lys Lys Tyr
    1130                1135                1140

Ser Asp  Phe Asn Pro Lys Ala  Glu Gly Thr Gln Gln  Ala Trp Thr
    1145                1150                1155

Ile Cys  Thr Tyr Gly Glu Arg  Ile Glu Thr Lys Arg  Gln Lys Asp
    1160                1165                1170

Gln Asn  Asn Lys Phe Val Ser  Thr Pro Ile Asn Leu  Thr Glu Lys
    1175                1180                1185

Ile Glu  Asp Phe Leu Gly Lys  Asn Gln Ile Val Tyr  Gly Asp Gly
    1190                1195                1200

Asn Cys  Ile Lys Ser Gln Ile  Ala Ser Lys Asp Asp  Lys Ala Phe
    1205                1210                1215

Phe Glu  Thr Leu Leu Tyr Trp  Phe Lys Met Thr Leu  Gln Met Arg
    1220                1225                1230

Asn Ser  Glu Thr Arg Thr Asp  Ile Asp Tyr Leu Ile  Ser Pro Val
    1235                1240                1245

Met Asn  Asp Asn Gly Thr Phe  Tyr Asn Ser Arg Asp  Tyr Glu Lys
    1250                1255                1260

Leu Glu  Asn Pro Thr Leu Pro  Lys Asp Ala Asp Ala  Asn Gly Ala
    1265                1270                1275

Tyr His  Ile Ala Lys Lys Gly  Leu Met Leu Leu Asn  Lys Ile Asp
    1280                1285                1290
```

Gln Ala Asp Leu Thr Lys Lys Val Asp Leu Ser Ile Ser Asn Arg
    1295                1300                1305

Asp Trp Leu Gln Phe Val Gln Lys Asn Lys
    1310                1315

<210> SEQ ID NO 111
<211> LENGTH: 1251
<212> TYPE: PRT
<213> ORGANISM: Unknown
<220> FEATURE:
<223> OTHER INFORMATION: Moraxella bovoculi strain 57922

<400> SEQUENCE: 111

Met Leu Phe Gln Asp Phe Thr His Leu Tyr Pro Leu Ser Lys Thr Val
1               5                   10                  15

Arg Phe Glu Leu Lys Pro Ile Gly Arg Thr Leu Glu His Ile His Ala
            20                  25                  30

Lys Asn Phe Leu Ser Gln Asp Glu Thr Met Ala Asp Met Tyr Gln Lys
        35                  40                  45

Val Lys Val Ile Leu Asp Asp Tyr His Arg Asp Phe Ile Ala Asp Met
    50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Gly Leu Gln Lys Gln Leu
                85                  90                  95

Lys Asp Leu Gln Ala Val Leu Arg Lys Glu Ser Val Lys Pro Ile Gly
            100                 105                 110

Ser Gly Gly Lys Tyr Lys Thr Gly Tyr Asp Arg Leu Phe Gly Ala Lys
        115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
        195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Arg Ile Ile
                245                 250                 255

Gly Glu Val Asn Gly Tyr Thr Asn Lys His Asn Gln Ile Cys His Lys
            260                 265                 270

Ser Glu Arg Ile Ala Lys Leu Arg Pro Leu His Lys Gln Ile Leu Ser
        275                 280                 285

Asp Gly Met Gly Val Ser Phe Leu Pro Ser Lys Phe Ala Asp Asp Ser
    290                 295                 300

Glu Met Cys Gln Ala Val Asn Glu Phe Tyr Arg His Tyr Thr Asp Val
305                 310                 315                 320

Phe Ala Lys Val Gln Ser Leu Phe Asp Gly Phe Asp Asp His Gln Lys
                325                 330                 335

```
Asp Gly Ile Tyr Val Glu His Lys Asn Leu Asn Glu Leu Ser Lys Gln
            340                 345                 350

Ala Phe Gly Asp Phe Ala Leu Leu Gly Arg Val Leu Asp Gly Tyr Tyr
        355                 360                 365

Val Asp Val Val Asn Pro Glu Phe Asn Glu Arg Phe Ala Lys Ala Lys
    370                 375                 380

Thr Asp Asn Ala Lys Ala Lys Leu Thr Lys Glu Lys Asp Lys Phe Ile
385                 390                 395                 400

Lys Gly Val His Ser Leu Ala Ser Leu Glu Gln Ala Ile Glu His His
                405                 410                 415

Thr Ala Arg His Asp Asp Glu Ser Val Gln Ala Gly Lys Leu Gly Gln
            420                 425                 430

Tyr Phe Lys His Gly Leu Ala Gly Val Asp Asn Pro Ile Gln Lys Ile
        435                 440                 445

His Asn Asn His Ser Thr Ile Lys Gly Phe Leu Glu Arg Glu Arg Pro
    450                 455                 460

Ala Gly Glu Arg Ala Leu Pro Lys Ile Lys Ser Gly Lys Asn Pro Glu
465                 470                 475                 480

Met Thr Gln Leu Arg Gln Leu Lys Glu Leu Leu Asp Asn Ala Leu Asn
                485                 490                 495

Val Ala His Phe Ala Lys Leu Leu Thr Thr Lys Thr Thr Leu Asp Asn
            500                 505                 510

Gln Asp Gly Asn Phe Tyr Gly Glu Phe Gly Val Leu Tyr Asp Glu Leu
        515                 520                 525

Ala Lys Ile Pro Thr Leu Tyr Asn Lys Val Arg Asp Tyr Leu Ser Gln
    530                 535                 540

Lys Pro Phe Ser Thr Glu Lys Tyr Lys Leu Asn Phe Gly Asn Pro Thr
545                 550                 555                 560

Leu Leu Asn Gly Trp Asp Leu Asn Lys Glu Lys Asp Asn Phe Gly Val
                565                 570                 575

Ile Leu Gln Lys Asp Gly Cys Tyr Tyr Leu Ala Leu Leu Asp Lys Ala
            580                 585                 590

His Lys Lys Val Phe Asp Asn Ala Pro Asn Thr Gly Lys Asn Val Tyr
        595                 600                 605

Gln Lys Met Val Tyr Lys Leu Leu Pro Gly Pro Asn Lys Met Leu Pro
    610                 615                 620

Lys Val Phe Phe Ala Lys Ser Asn Leu Asp Tyr Tyr Asn Pro Ser Ala
625                 630                 635                 640

Glu Leu Leu Asp Lys Tyr Ala Lys Gly Thr His Lys Lys Gly Asp Asn
                645                 650                 655

Phe Asn Leu Lys Asp Cys His Ala Leu Ile Asp Phe Phe Lys Ala Gly
            660                 665                 670

Ile Asn Lys His Pro Glu Trp Gln His Phe Gly Phe Lys Phe Ser Pro
        675                 680                 685

Thr Ser Ser Tyr Arg Asp Leu Ser Asp Phe Tyr Arg Glu Val Glu Pro
    690                 695                 700

Gln Gly Tyr Gln Val Lys Phe Val Asp Ile Asn Ala Asp Tyr Ile Asp
705                 710                 715                 720

Glu Leu Val Glu Gln Gly Lys Leu Tyr Leu Phe Gln Ile Tyr Asn Lys
                725                 730                 735

Asp Phe Ser Pro Lys Ala His Gly Lys Pro Asn Leu His Thr Leu Tyr
            740                 745                 750
```

-continued

```
Phe Lys Ala Leu Phe Ser Glu Asp Asn Leu Ala Asp Pro Ile Tyr Lys
        755                 760                 765

Leu Asn Gly Glu Ala Gln Ile Phe Tyr Arg Lys Ala Ser Leu Asp Met
    770                 775                 780

Asn Glu Thr Thr Ile His Arg Ala Gly Glu Val Leu Glu Asn Lys Asn
785                 790                 795                 800

Pro Asp Asn Pro Lys Lys Arg Gln Phe Val Tyr Asp Ile Ile Lys Asp
                805                 810                 815

Lys Arg Tyr Thr Gln Asp Lys Phe Met Leu His Val Pro Ile Thr Met
            820                 825                 830

Asn Phe Gly Val Gln Gly Met Thr Ile Lys Glu Phe Asn Lys Lys Val
        835                 840                 845

Asn Gln Ser Ile Gln Gln Tyr Asp Glu Val Asn Val Ile Gly Ile Asp
    850                 855                 860

Arg Gly Glu Arg His Leu Leu Tyr Leu Thr Val Ile Asn Ser Lys Gly
865                 870                 875                 880

Glu Ile Leu Glu Gln Arg Ser Leu Asn Asp Ile Thr Thr Ala Ser Ala
                885                 890                 895

Asn Gly Thr Gln Val Thr Thr Pro Tyr His Lys Ile Leu Asp Lys Arg
            900                 905                 910

Glu Ile Glu Arg Leu Asn Ala Arg Val Gly Trp Gly Glu Ile Glu Thr
        915                 920                 925

Ile Lys Glu Leu Lys Ser Gly Tyr Leu Ser His Val Val His Gln Ile
    930                 935                 940

Asn Gln Leu Met Leu Lys Tyr Asn Ala Ile Val Val Leu Glu Asp Leu
945                 950                 955                 960

Asn Phe Gly Phe Lys Arg Gly Arg Phe Lys Val Glu Lys Gln Ile Tyr
                965                 970                 975

Gln Asn Phe Glu Asn Ala Leu Ile Lys Lys Leu Asn His Leu Val Leu
            980                 985                 990

Lys Asp Lys Ala Asp Asp Glu Ile  Gly Ser Tyr Lys Asn  Ala Leu Gln
        995                 1000                1005

Leu Thr  Asn Asn Phe Thr Asp  Leu Lys Ser Ile Gly  Lys Gln Thr
    1010                 1015                 1020

Gly Phe  Leu Phe Tyr Val Pro  Ala Trp Asn Thr Ser  Lys Ile Asp
    1025                 1030                 1035

Pro Glu  Thr Gly Phe Val Asp  Leu Leu Lys Pro Arg  Tyr Glu Asn
    1040                 1045                 1050

Ile Ala  Gln Ser Gln Ala Phe  Phe Gly Lys Phe Asp  Lys Ile Cys
    1055                 1060                 1065

Tyr Asn  Thr Asp Lys Gly Tyr  Phe Glu Phe His Ile  Asp Tyr Ala
    1070                 1075                 1080

Lys Phe  Thr Asp Lys Ala Lys  Asn Ser Arg Gln Lys  Trp Ala Ile
    1085                 1090                 1095

Cys Ser  His Gly Asp Lys Arg  Tyr Val Tyr Asp Lys  Thr Ala Asn
    1100                 1105                 1110

Gln Asn  Lys Gly Ala Ala Lys  Gly Ile Asn Val Asn  Asp Glu Leu
    1115                 1120                 1125

Lys Ser  Leu Phe Ala Arg Tyr  His Ile Asn Asp Lys  Gln Pro Asn
    1130                 1135                 1140

Leu Val  Met Asp Ile Cys Gln  Asn Asn Asp Lys Glu  Phe His Lys
    1145                 1150                 1155

Ser Leu  Met Cys Leu Leu Lys  Thr Leu Leu Ala Leu  Arg Tyr Ser
```

```
    1160                1165                1170

Asn Ala  Ser Ser Asp Glu Asp  Phe Ile Leu Ser Pro  Val Ala Asn
    1175                1180                1185

Asp Glu  Gly Val Phe Phe Asn  Ser Ala Leu Ala Asp  Asp Thr Gln
    1190                1195                1200

Pro Gln  Asn Ala Asp Ala Asn  Gly Ala Tyr His Ile  Ala Leu Lys
    1205                1210                1215

Gly Leu  Trp Leu Leu Asn Glu  Leu Lys Asn Ser Asp  Asp Leu Asn
    1220                1225                1230

Lys Val  Lys Leu Ala Ile Asp  Asn Gln Thr Trp Leu  Asn Phe Ala
    1235                1240                1245

Gln Asn  Arg
    1250


<210> SEQ ID NO 112
<211> LENGTH: 1285
<212> TYPE: PRT
<213> ORGANISM: Unknown
<220> FEATURE:
<223> OTHER INFORMATION: Candidatus Roizmanbacteria bacterium
      GW2011_GWA2_37_7 US54_C0016

<400> SEQUENCE: 112

Met Lys Ser Phe Asp Ser Phe Thr Asn Leu Tyr Ser Leu Ser Lys Thr
1               5                   10                  15

Leu Lys Phe Glu Met Arg Pro Val Gly Asn Thr Gln Lys Met Leu Asp
            20                  25                  30

Asn Ala Gly Val Phe Glu Lys Asp Lys Leu Ile Gln Lys Lys Tyr Gly
        35                  40                  45

Lys Thr Lys Pro Tyr Phe Asp Arg Leu His Arg Glu Phe Ile Glu Glu
    50                  55                  60

Ala Leu Thr Gly Val Glu Leu Ile Gly Leu Asp Glu Asn Phe Arg Thr
65                  70                  75                  80

Leu Val Asp Trp Gln Lys Asp Lys Lys Asn Asn Val Ala Met Lys Ala
                85                  90                  95

Tyr Glu Asn Ser Leu Gln Arg Leu Arg Thr Glu Ile Gly Lys Ile Phe
            100                 105                 110

Asn Leu Lys Ala Glu Asp Trp Val Lys Asn Lys Tyr Pro Ile Leu Gly
        115                 120                 125

Leu Lys Asn Lys Asn Thr Asp Ile Leu Phe Glu Glu Ala Val Phe Gly
    130                 135                 140

Ile Leu Lys Ala Arg Tyr Gly Glu Glu Lys Asp Thr Phe Ile Glu Val
145                 150                 155                 160

Glu Glu Ile Asp Lys Thr Gly Lys Ser Lys Ile Asn Gln Ile Ser Ile
                165                 170                 175

Phe Asp Ser Trp Lys Gly Phe Thr Gly Tyr Phe Lys Lys Phe Phe Glu
            180                 185                 190

Thr Arg Lys Asn Phe Tyr Lys Asn Asp Gly Thr Ser Thr Ala Ile Ala
        195                 200                 205

Thr Arg Ile Ile Asp Gln Asn Leu Lys Arg Phe Ile Asp Asn Leu Ser
    210                 215                 220

Ile Val Glu Ser Val Arg Gln Lys Val Asp Leu Ala Glu Thr Glu Lys
225                 230                 235                 240

Ser Phe Ser Ile Ser Leu Ser Gln Phe Phe Ser Ile Asp Phe Tyr Asn
                245                 250                 255
```

-continued

Lys Cys Leu Leu Gln Asp Gly Ile Asp Tyr Tyr Asn Lys Ile Ile Gly
260 265 270

Gly Glu Thr Leu Lys Asn Gly Glu Lys Leu Ile Gly Leu Asn Glu Leu
275 280 285

Ile Asn Gln Tyr Arg Gln Asn Asn Lys Asp Gln Lys Ile Pro Phe Phe
290 295 300

Lys Leu Leu Asp Lys Gln Ile Leu Ser Glu Lys Ile Leu Phe Leu Asp
305 310 315 320

Glu Ile Lys Asn Asp Thr Glu Leu Ile Glu Ala Leu Ser Gln Phe Ala
325 330 335

Lys Thr Ala Glu Glu Lys Thr Lys Ile Val Lys Lys Leu Phe Ala Asp
340 345 350

Phe Val Glu Asn Asn Ser Lys Tyr Asp Leu Ala Gln Ile Tyr Ile Ser
355 360 365

Gln Glu Ala Phe Asn Thr Ile Ser Asn Lys Trp Thr Ser Glu Thr Glu
370 375 380

Thr Phe Ala Lys Tyr Leu Phe Glu Ala Met Lys Ser Gly Lys Leu Ala
385 390 395 400

Lys Tyr Glu Lys Lys Asp Asn Ser Tyr Lys Phe Pro Asp Phe Ile Ala
405 410 415

Leu Ser Gln Met Lys Ser Ala Leu Leu Ser Ile Ser Leu Glu Gly His
420 425 430

Phe Trp Lys Glu Lys Tyr Tyr Lys Ile Ser Lys Phe Gln Glu Lys Thr
435 440 445

Asn Trp Glu Gln Phe Leu Ala Ile Phe Leu Tyr Glu Phe Asn Ser Leu
450 455 460

Phe Ser Asp Lys Ile Asn Thr Lys Asp Gly Glu Thr Lys Gln Val Gly
465 470 475 480

Tyr Tyr Leu Phe Ala Lys Asp Leu His Asn Leu Ile Leu Ser Glu Gln
485 490 495

Ile Asp Ile Pro Lys Asp Ser Lys Val Thr Ile Lys Asp Phe Ala Asp
500 505 510

Ser Val Leu Thr Ile Tyr Gln Met Ala Lys Tyr Phe Ala Val Glu Lys
515 520 525

Lys Arg Ala Trp Leu Ala Glu Tyr Glu Leu Asp Ser Phe Tyr Thr Gln
530 535 540

Pro Asp Thr Gly Tyr Leu Gln Phe Tyr Asp Asn Ala Tyr Glu Asp Ile
545 550 555 560

Val Gln Val Tyr Asn Lys Leu Arg Asn Tyr Leu Thr Lys Lys Pro Tyr
565 570 575

Ser Glu Glu Lys Trp Lys Leu Asn Phe Glu Asn Ser Thr Leu Ala Asn
580 585 590

Gly Trp Asp Lys Asn Lys Glu Ser Asp Asn Ser Ala Val Ile Leu Gln
595 600 605

Lys Gly Gly Lys Tyr Tyr Leu Gly Leu Ile Thr Lys Gly His Asn Lys
610 615 620

Ile Phe Asp Asp Arg Phe Gln Glu Lys Phe Ile Val Gly Ile Glu Gly
625 630 635 640

Gly Lys Tyr Glu Lys Ile Val Tyr Lys Phe Phe Pro Asp Gln Ala Lys
645 650 655

Met Phe Pro Lys Val Cys Phe Ser Ala Lys Gly Leu Glu Phe Phe Arg
660 665 670

Pro Ser Glu Glu Ile Leu Arg Ile Tyr Asn Asn Ala Glu Phe Lys Lys

-continued

```
        675                 680                 685

Gly Glu Thr Tyr Ser Ile Asp Ser Met Gln Lys Leu Ile Asp Phe Tyr
    690                 695                 700

Lys Asp Cys Leu Thr Lys Tyr Glu Gly Trp Ala Cys Tyr Thr Phe Arg
705                 710                 715                 720

His Leu Lys Pro Thr Glu Glu Tyr Gln Asn Asn Ile Gly Glu Phe Phe
                725                 730                 735

Arg Asp Val Ala Glu Asp Gly Tyr Arg Ile Asp Phe Gln Gly Ile Ser
            740                 745                 750

Asp Gln Tyr Ile His Glu Lys Asn Glu Lys Gly Glu Leu His Leu Phe
        755                 760                 765

Glu Ile His Asn Lys Asp Trp Asn Leu Asp Lys Ala Arg Asp Gly Lys
    770                 775                 780

Ser Lys Thr Thr Gln Lys Asn Leu His Thr Leu Tyr Phe Glu Ser Leu
785                 790                 795                 800

Phe Ser Asn Asp Asn Val Val Gln Asn Phe Pro Ile Lys Leu Asn Gly
                805                 810                 815

Gln Ala Glu Ile Phe Tyr Arg Pro Lys Thr Glu Lys Asp Lys Leu Glu
            820                 825                 830

Ser Lys Lys Asp Lys Lys Gly Asn Lys Val Ile Asp His Lys Arg Tyr
        835                 840                 845

Ser Glu Asn Lys Ile Phe Phe His Val Pro Leu Thr Leu Asn Arg Thr
    850                 855                 860

Lys Asn Asp Ser Tyr Arg Phe Asn Ala Gln Ile Asn Asn Phe Leu Ala
865                 870                 875                 880

Asn Asn Lys Asp Ile Asn Ile Ile Gly Val Asp Arg Gly Glu Lys His
                885                 890                 895

Leu Val Tyr Tyr Ser Val Ile Thr Gln Ala Ser Asp Ile Leu Glu Ser
            900                 905                 910

Gly Ser Leu Asn Glu Leu Asn Gly Val Asn Tyr Ala Glu Lys Leu Gly
        915                 920                 925

Lys Lys Ala Glu Asn Arg Glu Gln Ala Arg Arg Asp Trp Gln Asp Val
    930                 935                 940

Gln Gly Ile Lys Asp Leu Lys Lys Gly Tyr Ile Ser Gln Val Val Arg
945                 950                 955                 960

Lys Leu Ala Asp Leu Ala Ile Lys His Asn Ala Ile Ile Ile Leu Glu
                965                 970                 975

Asp Leu Asn Met Arg Phe Lys Gln Val Arg Gly Gly Ile Glu Lys Ser
            980                 985                 990

Ile Tyr Gln Gln Leu Glu Lys Ala  Leu Ile Asp Lys Leu  Ser Phe Leu
        995                 1000                1005

Val Asp  Lys Gly Glu Lys Asn  Pro Glu Gln Ala Gly  His Leu Leu
    1010                1015                1020

Lys Ala  Tyr Gln Leu Ser Ala  Pro Phe Glu Thr Phe  Gln Lys Met
    1025                1030                1035

Gly Lys  Gln Thr Gly Ile Ile  Phe Tyr Thr Gln Ala  Ser Tyr Thr
    1040                1045                1050

Ser Lys  Ser Asp Pro Val Thr  Gly Trp Arg Pro His  Leu Tyr Leu
    1055                1060                1065

Lys Tyr  Phe Ser Ala Lys Lys  Ala Lys Asp Asp Ile  Ala Lys Phe
    1070                1075                1080

Thr Lys  Ile Glu Phe Val Asn  Asp Arg Phe Glu Leu  Thr Tyr Asp
    1085                1090                1095
```

Ile Lys Asp Phe Gln Gln Ala Lys Glu Tyr Pro Asn Lys Thr Val
1100 1105 1110

Trp Lys Val Cys Ser Asn Val Glu Arg Phe Arg Trp Asp Lys Asn
1115 1120 1125

Leu Asn Gln Asn Lys Gly Gly Tyr Thr His Tyr Thr Asn Ile Thr
1130 1135 1140

Glu Asn Ile Gln Glu Leu Phe Thr Lys Tyr Gly Ile Asp Ile Thr
1145 1150 1155

Lys Asp Leu Leu Thr Gln Ile Ser Thr Ile Asp Glu Lys Gln Asn
1160 1165 1170

Thr Ser Phe Phe Arg Asp Phe Ile Phe Tyr Phe Asn Leu Ile Cys
1175 1180 1185

Gln Ile Arg Asn Thr Asp Asp Ser Glu Ile Ala Lys Lys Asn Gly
1190 1195 1200

Lys Asp Asp Phe Ile Leu Ser Pro Val Glu Pro Phe Phe Asp Ser
1205 1210 1215

Arg Lys Asp Asn Gly Asn Lys Leu Pro Glu Asn Gly Asp Asp Asn
1220 1225 1230

Gly Ala Tyr Asn Ile Ala Arg Lys Gly Ile Val Ile Leu Asn Lys
1235 1240 1245

Ile Ser Gln Tyr Ser Glu Lys Asn Glu Asn Cys Glu Lys Met Lys
1250 1255 1260

Trp Gly Asp Leu Tyr Val Ser Asn Ile Asp Trp Asp Asn Phe Val
1265 1270 1275

Thr Gln Ala Asn Ala Arg His
1280 1285

<210> SEQ ID NO 113
<211> LENGTH: 1207
<212> TYPE: PRT
<213> ORGANISM: Unknown
<220> FEATURE:
<223> OTHER INFORMATION: Pseudobutyrivibrio xylanivorans

<400> SEQUENCE: 113

Met Tyr Tyr Gln Asn Leu Thr Lys Met Tyr Pro Ile Ser Lys Thr Leu
1 5 10 15

Arg Asn Glu Leu Ile Pro Val Gly Lys Thr Leu Glu Asn Ile Arg Lys
20 25 30

Asn Gly Ile Leu Glu Ala Asp Ile Gln Arg Lys Ala Asp Tyr Glu His
35 40 45

Val Lys Lys Leu Met Asp Asn Tyr His Lys Gln Leu Ile Asn Glu Ala
50 55 60

Leu Gln Gly Val His Leu Ser Asp Leu Ser Asp Ala Tyr Asp Leu Tyr
65 70 75 80

Phe Asn Leu Ser Lys Glu Lys Asn Ser Val Asp Ala Phe Ser Lys Cys
85 90 95

Gln Asp Lys Leu Arg Lys Glu Ile Val Ser Phe Leu Lys Asn His Glu
100 105 110

Asn Phe Pro Lys Ile Gly Asn Lys Glu Ile Ile Lys Leu Ile Gln Ser
115 120 125

Leu Asn Asp Asn Asp Ala Asp Asn Asn Ala Leu Asp Ser Phe Ser Asn
130 135 140

Phe Tyr Thr Tyr Phe Ser Ser Tyr Asn Glu Val Arg Lys Asn Leu Tyr
145 150 155 160

```
Ser Asp Glu Glu Lys Ser Ser Thr Val Ala Tyr Arg Leu Ile Asn Glu
                165                 170                 175

Asn Leu Pro Lys Ser Leu Asp Asn Ile Lys Ala Tyr Ala Ile Ala Lys
            180                 185                 190

Lys Ala Gly Val Arg Ala Glu Gly Leu Ser Glu Glu Glu Gln Asp Cys
        195                 200                 205

Leu Phe Ile Ile Glu Thr Phe Glu Arg Thr Leu Thr Gln Asp Gly Ile
    210                 215                 220

Asp Asn Tyr Asn Ala Asp Ile Gly Lys Leu Asn Thr Ala Ile Asn Leu
225                 230                 235                 240

Tyr Asn Gln Gln Asn Lys Lys Gln Glu Gly Phe Arg Lys Val Pro Gln
                245                 250                 255

Met Lys Cys Leu Tyr Lys Gln Ile Leu Ser Asp Arg Glu Glu Ala Phe
            260                 265                 270

Ile Asp Glu Phe Ser Asp Asp Glu Asp Leu Ile Thr Asn Ile Glu Ser
        275                 280                 285

Phe Ala Glu Asn Met Asn Val Phe Leu Asn Ser Glu Ile Ile Thr Asp
    290                 295                 300

Phe Lys Asn Ala Leu Val Glu Ser Asp Gly Ser Leu Val Tyr Ile Lys
305                 310                 315                 320

Asn Asp Val Ser Lys Thr Leu Phe Ser Asn Ile Val Phe Gly Ser Trp
                325                 330                 335

Asn Ala Ile Asp Glu Lys Leu Ser Asp Glu Tyr Asp Leu Ala Asn Ser
            340                 345                 350

Lys Lys Lys Lys Asp Glu Lys Tyr Tyr Glu Lys Arg Gln Lys Glu Leu
        355                 360                 365

Lys Lys Asn Lys Ser Tyr Asp Leu Glu Thr Ile Ile Gly Leu Phe Asp
    370                 375                 380

Asp Ser Ile Asp Val Ile Gly Lys Tyr Ile Glu Lys Leu Glu Ser Asp
385                 390                 395                 400

Ile Thr Ala Ile Ala Glu Ala Lys Asn Asp Phe Asp Glu Ile Val Leu
                405                 410                 415

Arg Lys His Asp Lys Asn Lys Ser Leu Arg Lys Asn Thr Asn Ala Val
            420                 425                 430

Glu Ala Ile Lys Ser Tyr Leu Asp Thr Val Lys Asp Phe Glu Arg Asp
        435                 440                 445

Ile Lys Leu Ile Asn Gly Ser Gly Gln Glu Val Glu Lys Asn Leu Val
    450                 455                 460

Val Tyr Ala Glu Gln Glu Asn Ile Leu Ala Glu Ile Lys Asn Val Asp
465                 470                 475                 480

Ser Leu Tyr Asn Met Ser Arg Asn Tyr Leu Thr Gln Lys Pro Phe Ser
                485                 490                 495

Thr Glu Lys Phe Lys Leu Asn Phe Glu Asn Pro Thr Leu Leu Asn Gly
            500                 505                 510

Trp Asp Arg Asn Lys Glu Lys Asp Tyr Leu Gly Ile Leu Phe Glu Lys
        515                 520                 525

Glu Gly Met Tyr Tyr Leu Gly Ile Ile Asn Asn Asn His Arg Lys Ile
    530                 535                 540

Phe Glu Asn Glu Lys Leu Cys Thr Gly Lys Glu Ser Cys Phe Asn Lys
545                 550                 555                 560

Ile Val Tyr Lys Gln Ile Ser Asn Ala Ala Lys Tyr Leu Ser Ser Lys
                565                 570                 575
```

```
Gln Ile Asn Pro Gln Asn Pro Pro Lys Glu Ile Ala Glu Ile Leu Leu
            580                 585                 590

Lys Arg Lys Ala Asp Ser Ser Ser Leu Ser Arg Lys Glu Thr Glu Leu
        595                 600                 605

Phe Ile Asp Tyr Leu Lys Asp Asp Phe Leu Val Asn Tyr Pro Met Ile
    610                 615                 620

Ile Asn Ser Asp Gly Glu Asn Phe Phe Asn Phe His Phe Lys Gln Ala
625                 630                 635                 640

Lys Asp Tyr Gly Ser Leu Gln Glu Phe Phe Lys Glu Val Glu His Gln
                645                 650                 655

Ala Tyr Ser Leu Lys Thr Arg Pro Ile Asp Asp Ser Tyr Ile Tyr Arg
            660                 665                 670

Met Ile Asp Glu Gly Lys Leu Tyr Leu Phe Gln Ile His Asn Lys Asp
        675                 680                 685

Phe Ser Pro Tyr Ser Lys Gly Asn Leu Asn Leu His Thr Ile Tyr Leu
    690                 695                 700

Gln Met Leu Phe Asp Gln Arg Asn Leu Asn Asn Val Val Tyr Lys Leu
705                 710                 715                 720

Asn Gly Glu Ala Glu Val Phe Tyr Arg Pro Ala Ser Ile Asn Asp Glu
                725                 730                 735

Glu Val Ile Ile His Lys Ala Gly Glu Glu Ile Lys Asn Lys Asn Ser
            740                 745                 750

Lys Arg Ala Val Asp Lys Pro Thr Ser Lys Phe Gly Tyr Asp Ile Ile
        755                 760                 765

Lys Asp Arg Arg Tyr Ser Lys Asp Lys Phe Met Leu His Ile Pro Val
    770                 775                 780

Thr Met Asn Phe Gly Val Asp Glu Thr Arg Arg Phe Asn Asp Val Val
785                 790                 795                 800

Asn Asp Ala Leu Arg Asn Asp Glu Lys Val Arg Val Ile Gly Ile Asp
                805                 810                 815

Arg Gly Glu Arg Asn Leu Leu Tyr Val Val Val Val Asp Thr Asp Gly
            820                 825                 830

Thr Ile Leu Glu Gln Ile Ser Leu Asn Ser Ile Ile Asn Asn Glu Tyr
        835                 840                 845

Ser Ile Glu Thr Asp Tyr His Lys Leu Leu Asp Glu Lys Glu Gly Asp
    850                 855                 860

Arg Asp Arg Ala Arg Lys Asn Trp Thr Thr Ile Glu Asn Ile Lys Glu
865                 870                 875                 880

Leu Lys Glu Gly Tyr Leu Ser Gln Val Val Asn Val Ile Ala Lys Leu
                885                 890                 895

Val Leu Lys Tyr Asn Ala Ile Ile Cys Leu Glu Asp Leu Asn Phe Gly
            900                 905                 910

Phe Lys Arg Gly Arg Gln Lys Val Glu Lys Gln Val Tyr Gln Lys Phe
        915                 920                 925

Glu Lys Met Leu Ile Asp Lys Leu Asn Tyr Leu Val Ile Asp Lys Ser
    930                 935                 940

Arg Lys Gln Glu Lys Pro Glu Glu Phe Gly Gly Ala Leu Asn Ala Leu
945                 950                 955                 960

Gln Leu Thr Ser Lys Phe Thr Ser Phe Lys Asp Met Gly Lys Gln Thr
                965                 970                 975

Gly Ile Ile Tyr Tyr Val Pro Ala Tyr Leu Thr Ser Lys Ile Asp Pro
            980                 985                 990

Thr Thr Gly Phe Ala Asn Leu Phe  Tyr Val Lys Tyr Glu  Asn Val Glu
```

```
        995                 1000                1005

Lys Ala  Lys Glu Phe Phe Ser  Arg Phe Asp Ser Ile  Ser Tyr Asn
    1010                 1015                 1020

Asn Glu  Ser Gly Tyr Phe Glu  Phe Ala Phe Asp Tyr  Lys Lys Phe
    1025                 1030                 1035

Thr Asp  Arg Ala Cys Gly Ala  Arg Ser Gln Trp Thr  Val Cys Thr
    1040                 1045                 1050

Tyr Gly  Glu Arg Ile Ile Lys  Tyr Arg Asn Ala Asp  Lys Asn Asn
    1055                 1060                 1065

Ser Phe  Asp Asp Lys Thr Ile  Val Leu Ser Glu Glu  Phe Lys Glu
    1070                 1075                 1080

Leu Phe  Ser Ile Tyr Gly Ile  Ser Tyr Glu Asp Gly  Ala Glu Leu
    1085                 1090                 1095

Lys Asn  Lys Ile Met Ser Val  Asp Glu Ala Asp Phe  Phe Arg Cys
    1100                 1105                 1110

Leu Thr  Gly Leu Leu Gln Lys  Thr Leu Gln Met Arg  Asn Ser Ser
    1115                 1120                 1125

Asn Asp  Gly Thr Arg Asp Tyr  Ile Ile Ser Pro Ile  Met Asn Asp
    1130                 1135                 1140

Arg Gly  Glu Phe Phe Asn Ser  Glu Ala Cys Asp Ala  Ser Lys Pro
    1145                 1150                 1155

Lys Asp  Ala Asp Ala Asn Gly  Ala Phe Asn Ile Ala  Arg Lys Gly
    1160                 1165                 1170

Leu Trp  Val Leu Glu Gln Ile  Arg Asn Thr Pro Ser  Gly Asp Lys
    1175                 1180                 1185

Leu Asn  Leu Ala Met Ser Asn  Ala Glu Trp Leu Glu  Tyr Ala Gln
    1190                 1195                 1200

Arg Asn  Gln Ile
    1205
```

<210> SEQ ID NO 114
<211> LENGTH: 1247
<212> TYPE: PRT
<213> ORGANISM: Unknown
<220> FEATURE:
<223> OTHER INFORMATION: Prevotella bryantii B14

<400> SEQUENCE: 114

```
Met Lys Phe Thr Asp Phe Thr Gly Leu Tyr Ser Leu Ser Lys Thr Leu
1               5                   10                  15

Arg Phe Glu Leu Lys Pro Ile Gly Lys Thr Leu Glu Asn Ile Lys Lys
            20                  25                  30

Ala Gly Leu Leu Glu Gln Asp Gln His Arg Ala Asp Ser Tyr Lys Lys
        35                  40                  45

Val Lys Lys Ile Ile Asp Glu Tyr His Lys Ala Phe Ile Glu Lys Ser
    50                  55                  60

Leu Ser Asn Phe Glu Leu Lys Tyr Gln Ser Glu Asp Lys Leu Asp Ser
65                  70                  75                  80

Leu Glu Glu Tyr Leu Met Tyr Tyr Ser Met Lys Arg Ile Glu Lys Thr
                85                  90                  95

Glu Lys Asp Lys Phe Ala Lys Ile Gln Asp Asn Leu Arg Lys Gln Ile
            100                 105                 110

Ala Asp His Leu Lys Gly Asp Glu Ser Tyr Lys Thr Ile Phe Ser Lys
        115                 120                 125

Asp Leu Ile Arg Lys Asn Leu Pro Asp Phe Val Lys Ser Asp Glu Glu
```

```
    130                 135                 140

Arg Thr Leu Ile Lys Glu Phe Lys Asp Phe Thr Thr Tyr Phe Lys Gly
145                 150                 155                 160

Phe Tyr Glu Asn Arg Glu Asn Met Tyr Ser Ala Glu Asp Lys Ser Thr
                165                 170                 175

Ala Ile Ser His Arg Ile Ile His Glu Asn Leu Pro Lys Phe Val Asp
            180                 185                 190

Asn Ile Asn Ala Phe Ser Lys Ile Ile Leu Ile Pro Glu Leu Arg Glu
        195                 200                 205

Lys Leu Asn Gln Ile Tyr Gln Asp Phe Glu Glu Tyr Leu Asn Val Glu
    210                 215                 220

Ser Ile Asp Glu Ile Phe His Leu Asp Tyr Phe Ser Met Val Met Thr
225                 230                 235                 240

Gln Lys Gln Ile Glu Val Tyr Asn Ala Ile Ile Gly Gly Lys Ser Thr
                245                 250                 255

Asn Asp Lys Lys Ile Gln Gly Leu Asn Glu Tyr Ile Asn Leu Tyr Asn
            260                 265                 270

Gln Lys His Lys Asp Cys Lys Leu Pro Lys Leu Lys Leu Leu Phe Lys
        275                 280                 285

Gln Ile Leu Ser Asp Arg Ile Ala Ile Ser Trp Leu Pro Asp Asn Phe
    290                 295                 300

Lys Asp Asp Gln Glu Ala Leu Asp Ser Ile Asp Thr Cys Tyr Lys Asn
305                 310                 315                 320

Leu Leu Asn Asp Gly Asn Val Leu Gly Glu Gly Asn Leu Lys Leu Leu
                325                 330                 335

Leu Glu Asn Ile Asp Thr Tyr Asn Leu Lys Gly Ile Phe Ile Arg Asn
            340                 345                 350

Asp Leu Gln Leu Thr Asp Ile Ser Gln Lys Met Tyr Ala Ser Trp Asn
        355                 360                 365

Val Ile Gln Asp Ala Val Ile Leu Asp Leu Lys Lys Gln Val Ser Arg
    370                 375                 380

Lys Lys Lys Glu Ser Ala Glu Asp Tyr Asn Asp Arg Leu Lys Lys Leu
385                 390                 395                 400

Tyr Thr Ser Gln Glu Ser Phe Ser Ile Gln Tyr Leu Asn Asp Cys Leu
                405                 410                 415

Arg Ala Tyr Gly Lys Thr Glu Asn Ile Gln Asp Tyr Phe Ala Lys Leu
            420                 425                 430

Gly Ala Val Asn Asn Glu His Glu Gln Thr Ile Asn Leu Phe Ala Gln
        435                 440                 445

Val Arg Asn Ala Tyr Thr Ser Val Gln Ala Ile Leu Thr Thr Pro Tyr
    450                 455                 460

Pro Glu Asn Ala Asn Leu Ala Gln Asp Lys Glu Thr Val Ala Leu Ile
465                 470                 475                 480

Lys Asn Leu Leu Asp Ser Leu Lys Arg Leu Gln Arg Phe Ile Lys Pro
                485                 490                 495

Leu Leu Gly Lys Gly Asp Glu Ser Asp Lys Asp Glu Arg Phe Tyr Gly
            500                 505                 510

Asp Phe Thr Pro Leu Trp Glu Thr Leu Asn Gln Ile Thr Pro Leu Tyr
        515                 520                 525

Asn Met Val Arg Asn Tyr Met Thr Arg Lys Pro Tyr Ser Gln Glu Lys
    530                 535                 540

Ile Lys Leu Asn Phe Glu Asn Ser Thr Leu Leu Gly Gly Trp Asp Leu
545                 550                 555                 560
```

```
Asn Lys Glu His Asp Asn Thr Ala Ile Ile Leu Arg Lys Asn Gly Leu
                565                 570                 575

Tyr Tyr Leu Ala Ile Met Lys Lys Ser Ala Asn Lys Ile Phe Asp Lys
            580                 585                 590

Asp Lys Leu Asp Asn Ser Gly Asp Cys Tyr Glu Lys Met Val Tyr Lys
        595                 600                 605

Leu Leu Pro Gly Ala Asn Lys Met Leu Pro Lys Val Phe Phe Ser Lys
    610                 615                 620

Ser Arg Ile Asp Glu Phe Lys Pro Ser Glu Asn Ile Ile Glu Asn Tyr
625                 630                 635                 640

Lys Lys Gly Thr His Lys Lys Gly Ala Asn Phe Asn Leu Ala Asp Cys
                645                 650                 655

His Asn Leu Ile Asp Phe Phe Lys Ser Ser Ile Ser Lys His Glu Asp
            660                 665                 670

Trp Ser Lys Phe Asn Phe His Phe Ser Asp Thr Ser Ser Tyr Glu Asp
        675                 680                 685

Leu Ser Asp Phe Tyr Arg Glu Val Glu Gln Gln Gly Tyr Ser Ile Ser
    690                 695                 700

Phe Cys Asp Val Ser Val Glu Tyr Ile Asn Lys Met Val Glu Lys Gly
705                 710                 715                 720

Asp Leu Tyr Leu Phe Gln Ile Tyr Asn Lys Asp Phe Ser Glu Phe Ser
                725                 730                 735

Lys Gly Thr Pro Asn Met His Thr Leu Tyr Trp Asn Ser Leu Phe Ser
            740                 745                 750

Lys Glu Asn Leu Asn Asn Ile Ile Tyr Lys Leu Asn Gly Gln Ala Glu
        755                 760                 765

Ile Phe Phe Arg Lys Lys Ser Leu Asn Tyr Lys Arg Pro Thr His Pro
    770                 775                 780

Ala His Gln Ala Ile Lys Asn Lys Asn Lys Cys Asn Glu Lys Lys Glu
785                 790                 795                 800

Ser Ile Phe Asp Tyr Asp Leu Val Lys Asp Lys Arg Tyr Thr Val Asp
                805                 810                 815

Lys Phe Gln Phe His Val Pro Ile Thr Met Asn Phe Lys Ser Thr Gly
            820                 825                 830

Asn Thr Asn Ile Asn Gln Gln Val Ile Asp Tyr Leu Arg Thr Glu Asp
        835                 840                 845

Asp Thr His Ile Ile Gly Ile Asp Arg Gly Glu Arg His Leu Leu Tyr
    850                 855                 860

Leu Val Val Ile Asp Ser His Gly Lys Ile Val Glu Gln Phe Thr Leu
865                 870                 875                 880

Asn Glu Ile Val Asn Glu Tyr Gly Gly Asn Ile Tyr Arg Thr Asn Tyr
                885                 890                 895

His Asp Leu Leu Asp Thr Arg Glu Gln Asn Arg Glu Lys Ala Arg Glu
            900                 905                 910

Ser Trp Gln Thr Ile Glu Asn Ile Lys Glu Leu Lys Glu Gly Tyr Ile
        915                 920                 925

Ser Gln Val Ile His Lys Ile Thr Asp Leu Met Gln Lys Tyr His Ala
    930                 935                 940

Val Val Val Leu Glu Asp Leu Asn Met Gly Phe Met Arg Gly Arg Gln
945                 950                 955                 960

Lys Val Glu Lys Gln Val Tyr Gln Lys Phe Glu Glu Met Leu Ile Asn
                965                 970                 975
```

-continued

```
Lys Leu Asn Tyr Leu Val Asn Lys Lys Ala Asp Gln Asn Ser Ala Gly
            980                 985                 990

Gly Leu Leu His Ala Tyr Gln Leu  Thr Ser Lys Phe Glu  Ser Phe Gln
        995                 1000                1005

Lys Leu  Gly Lys Gln Ser Gly  Phe Leu Phe Tyr Ile  Pro Ala Trp
    1010                 1015                1020

Asn Thr  Ser Lys Ile Asp Pro  Val Thr Gly Phe Val  Asn Leu Phe
    1025                 1030                1035

Asp Thr  Arg Tyr Glu Ser Ile  Asp Lys Ala Lys Ala  Phe Phe Gly
    1040                 1045                1050

Lys Phe  Asp Ser Ile Arg Tyr  Asn Ala Asp Lys Asp  Trp Phe Glu
    1055                 1060                1065

Phe Ala  Phe Asp Tyr Asn Asn  Phe Thr Thr Lys Ala  Glu Gly Thr
    1070                 1075                1080

Arg Thr  Asn Trp Thr Ile Cys  Thr Tyr Gly Ser Arg  Ile Arg Thr
    1085                 1090                1095

Phe Arg  Asn Gln Ala Lys Asn  Ser Gln Trp Asp Asn  Glu Glu Ile
    1100                 1105                1110

Asp Leu  Thr Lys Ala Tyr Lys  Ala Phe Phe Ala Lys  His Gly Ile
    1115                 1120                1125

Asn Ile  Tyr Asp Asn Ile Lys  Glu Ala Ile Ala Met  Glu Thr Glu
    1130                 1135                1140

Lys Ser  Phe Phe Glu Asp Leu  Leu His Leu Leu Lys  Leu Thr Leu
    1145                 1150                1155

Gln Met  Arg Asn Ser Ile Thr  Gly Thr Thr Thr Asp  Tyr Leu Ile
    1160                 1165                1170

Ser Pro  Val His Asp Ser Lys  Gly Asn Phe Tyr Asp  Ser Arg Ile
    1175                 1180                1185

Cys Asp  Asn Ser Leu Pro Ala  Asn Ala Asp Ala Asn  Gly Ala Tyr
    1190                 1195                1200

Asn Ile  Ala Arg Lys Gly Leu  Met Leu Ile Gln Gln  Ile Lys Asp
    1205                 1210                1215

Ser Thr  Ser Ser Asn Arg Phe  Lys Phe Ser Pro Ile  Thr Asn Lys
    1220                 1225                1230

Asp Trp  Leu Ile Phe Ala Gln  Glu Lys Pro Tyr Leu  Asn Asp
    1235                 1240                1245


<210> SEQ ID NO 115
<211> LENGTH: 1064
<212> TYPE: PRT
<213> ORGANISM: Unknown
<220> FEATURE:
<223> OTHER INFORMATION: Smithella sp. SCADC

<400> SEQUENCE: 115

Met Glu Lys Tyr Lys Ile Thr Lys Thr Ile Arg Phe Lys Leu Leu Pro
1               5                   10                  15

Asp Lys Ile Gln Asp Ile Ser Arg Gln Val Ala Val Leu Gln Asn Ser
            20                  25                  30

Thr Asn Ala Glu Lys Lys Asn Asn Leu Leu Arg Leu Val Gln Arg Gly
        35                  40                  45

Gln Glu Leu Pro Lys Leu Leu Asn Glu Tyr Ile Arg Tyr Ser Asp Asn
    50                  55                  60

His Lys Leu Lys Ser Asn Val Thr Val His Phe Arg Trp Leu Arg Leu
65                  70                  75                  80
```

```
Phe Thr Lys Asp Leu Phe Tyr Asn Trp Lys Lys Asp Asn Thr Glu Lys
                85                  90                  95

Lys Ile Lys Ile Ser Asp Val Val Tyr Leu Ser His Val Phe Glu Ala
            100                 105                 110

Phe Leu Lys Glu Trp Glu Ser Thr Ile Glu Arg Val Asn Ala Asp Cys
        115                 120                 125

Asn Lys Pro Glu Glu Ser Lys Thr Arg Asp Ala Glu Ile Ala Leu Ser
    130                 135                 140

Ile Arg Lys Leu Gly Ile Lys His Gln Leu Pro Phe Ile Lys Gly Phe
145                 150                 155                 160

Val Asp Asn Ser Asn Asp Lys Asn Ser Glu Asp Thr Lys Ser Lys Leu
                165                 170                 175

Thr Ala Leu Leu Ser Glu Phe Glu Ala Val Leu Lys Ile Cys Glu Gln
            180                 185                 190

Asn Tyr Leu Pro Ser Gln Ser Ser Gly Ile Ala Ile Ala Lys Ala Ser
        195                 200                 205

Phe Asn Tyr Tyr Thr Ile Asn Lys Lys Gln Lys Asp Phe Glu Ala Glu
    210                 215                 220

Ile Val Ala Leu Lys Lys Gln Leu His Ala Arg Tyr Gly Asn Lys Lys
225                 230                 235                 240

Tyr Asp Gln Leu Leu Arg Glu Leu Asn Leu Ile Pro Leu Lys Glu Leu
                245                 250                 255

Pro Leu Lys Glu Leu Pro Leu Ile Glu Phe Tyr Ser Glu Ile Lys Lys
            260                 265                 270

Arg Lys Ser Thr Lys Lys Ser Glu Phe Leu Glu Ala Val Ser Asn Gly
        275                 280                 285

Leu Val Phe Asp Asp Leu Lys Ser Lys Phe Pro Leu Phe Gln Thr Glu
    290                 295                 300

Ser Asn Lys Tyr Asp Glu Tyr Leu Lys Leu Ser Asn Lys Ile Thr Gln
305                 310                 315                 320

Lys Ser Thr Ala Lys Ser Leu Leu Ser Lys Asp Ser Pro Glu Ala Gln
                325                 330                 335

Lys Leu Gln Thr Glu Ile Thr Lys Leu Lys Lys Asn Arg Gly Glu Tyr
            340                 345                 350

Phe Lys Lys Ala Phe Gly Lys Tyr Val Gln Leu Cys Glu Leu Tyr Lys
        355                 360                 365

Glu Ile Ala Gly Lys Arg Gly Lys Leu Lys Gly Gln Ile Lys Gly Ile
    370                 375                 380

Glu Asn Glu Arg Ile Asp Ser Gln Arg Leu Gln Tyr Trp Ala Leu Val
385                 390                 395                 400

Leu Glu Asp Asn Leu Lys His Ser Leu Ile Leu Ile Pro Lys Glu Lys
                405                 410                 415

Thr Asn Glu Leu Tyr Arg Lys Val Trp Gly Ala Lys Asp Asp Gly Ala
            420                 425                 430

Ser Ser Ser Ser Ser Ser Thr Leu Tyr Tyr Phe Glu Ser Met Thr Tyr
        435                 440                 445

Arg Ala Leu Arg Lys Leu Cys Phe Gly Ile Asn Gly Asn Thr Phe Leu
    450                 455                 460

Pro Glu Ile Gln Lys Glu Leu Pro Gln Tyr Asn Gln Lys Glu Phe Gly
465                 470                 475                 480

Glu Phe Cys Phe His Lys Ser Asn Asp Asp Lys Glu Ile Asp Glu Pro
                485                 490                 495

Lys Leu Ile Ser Phe Tyr Gln Ser Val Leu Lys Thr Asp Phe Val Lys
```

```
            500                 505                 510

Asn Thr Leu Ala Leu Pro Gln Ser Val Phe Asn Glu Val Ala Ile Gln
        515                 520                 525

Ser Phe Glu Thr Arg Gln Asp Phe Gln Ile Ala Leu Glu Lys Cys Cys
    530                 535                 540

Tyr Ala Lys Lys Gln Ile Ile Ser Glu Ser Leu Lys Lys Glu Ile Leu
545                 550                 555                 560

Glu Asn Tyr Asn Thr Gln Ile Phe Lys Ile Thr Ser Leu Asp Leu Gln
                565                 570                 575

Arg Ser Glu Gln Lys Asn Leu Lys Gly His Thr Arg Ile Trp Asn Arg
            580                 585                 590

Phe Trp Thr Lys Gln Asn Glu Glu Ile Asn Tyr Asn Leu Arg Leu Asn
        595                 600                 605

Pro Glu Ile Ala Ile Val Trp Arg Lys Ala Lys Lys Thr Arg Ile Glu
    610                 615                 620

Lys Tyr Gly Glu Arg Ser Val Leu Tyr Glu Pro Glu Lys Arg Asn Arg
625                 630                 635                 640

Tyr Leu His Glu Gln Tyr Thr Leu Cys Thr Thr Val Thr Asp Asn Ala
                645                 650                 655

Leu Asn Asn Glu Ile Thr Phe Ala Phe Glu Asp Thr Lys Lys Lys Gly
            660                 665                 670

Thr Glu Ile Val Lys Tyr Asn Glu Lys Ile Asn Gln Thr Leu Lys Lys
        675                 680                 685

Glu Phe Asn Lys Asn Gln Leu Trp Phe Tyr Gly Ile Asp Ala Gly Glu
    690                 695                 700

Ile Glu Leu Ala Thr Leu Ala Leu Met Asn Lys Asp Lys Glu Pro Gln
705                 710                 715                 720

Leu Phe Thr Val Tyr Glu Leu Lys Lys Leu Asp Phe Phe Lys His Gly
                725                 730                 735

Tyr Ile Tyr Asn Lys Glu Arg Glu Leu Val Ile Arg Glu Lys Pro Tyr
            740                 745                 750

Lys Ala Ile Gln Asn Leu Ser Tyr Phe Leu Asn Glu Glu Leu Tyr Glu
        755                 760                 765

Lys Thr Phe Arg Asp Gly Lys Phe Asn Glu Thr Tyr Asn Glu Leu Phe
    770                 775                 780

Lys Glu Lys His Val Ser Ala Ile Asp Leu Thr Thr Ala Lys Val Ile
785                 790                 795                 800

Asn Gly Lys Ile Ile Leu Asn Gly Asp Met Ile Thr Phe Leu Asn Leu
                805                 810                 815

Arg Ile Leu His Ala Gln Arg Lys Ile Tyr Glu Glu Leu Ile Glu Asn
            820                 825                 830

Pro His Ala Glu Leu Lys Glu Lys Asp Tyr Lys Leu Tyr Phe Glu Ile
        835                 840                 845

Glu Gly Lys Asp Lys Asp Ile Tyr Ile Ser Arg Leu Asp Phe Glu Tyr
    850                 855                 860

Ile Lys Pro Tyr Gln Glu Ile Ser Asn Tyr Leu Phe Ala Tyr Phe Ala
865                 870                 875                 880

Ser Gln Gln Ile Asn Glu Ala Arg Glu Glu Glu Gln Ile Asn Gln Thr
                885                 890                 895

Lys Arg Ala Leu Ala Gly Asn Met Ile Gly Val Ile Tyr Tyr Leu Tyr
            900                 905                 910

Gln Lys Tyr Arg Gly Ile Ile Ser Ile Glu Asp Leu Lys Gln Thr Lys
        915                 920                 925
```

Val Glu Ser Asp Arg Asn Lys Phe Glu Gly Asn Ile Glu Arg Pro Leu
930 935 940

Glu Trp Ala Leu Tyr Arg Lys Phe Gln Gln Glu Gly Tyr Val Pro Pro
945 950 955 960

Ile Ser Glu Leu Ile Lys Leu Arg Glu Leu Glu Lys Phe Pro Leu Lys
965 970 975

Asp Val Lys Gln Pro Lys Tyr Glu Asn Ile Gln Gln Phe Gly Ile Ile
980 985 990

Lys Phe Val Ser Pro Glu Glu Thr Ser Thr Thr Cys Pro Lys Cys Leu
995 1000 1005

Arg Arg Phe Lys Asp Tyr Asp Lys Asn Lys Gln Glu Gly Phe Cys
1010 1015 1020

Lys Cys Gln Cys Gly Phe Asp Thr Arg Asn Asp Leu Lys Gly Phe
1025 1030 1035

Glu Gly Leu Asn Asp Pro Asp Lys Val Ala Ala Phe Asn Ile Ala
1040 1045 1050

Lys Arg Gly Phe Glu Asp Leu Gln Lys Tyr Lys
1055 1060

<210> SEQ ID NO 116
<211> LENGTH: 1251
<212> TYPE: PRT
<213> ORGANISM: Unknown
<220> FEATURE:
<223> OTHER INFORMATION: Bacteroidetes bacterium GWF2_33_38

<400> SEQUENCE: 116

Met Asn His Met Lys Gln Phe Thr Asn Gln Phe Ser Leu Ser Lys Thr
1 5 10 15

Leu Arg Phe Glu Leu Ile Pro Gln Gly Lys Thr Lys Glu Phe Ile Glu
20 25 30

Ile Asn Gly Leu Ile Glu Lys Asp Asn Glu Arg Ala Val Ser Tyr Lys
35 40 45

Lys Val Lys Lys Ile Ile Asp Glu Tyr His Lys Tyr Phe Ile Glu Met
50 55 60

Val Leu Cys Asp Phe Lys Leu His Gly Leu Glu Thr Tyr Glu Thr Ile
65 70 75 80

Phe Asn Lys Lys Glu Lys Asp Asp Thr Asp Lys Lys Glu Phe Asp Asn
85 90 95

Ile Arg Asn Ser Leu Arg Lys Gln Ile Ala Asp Ala Phe Ala Lys Asn
100 105 110

Pro Asn Asp Glu Ile Lys Glu Arg Phe Lys Asn Leu Phe Ala Lys Glu
115 120 125

Leu Ile Lys Gln Asp Leu Leu Asn Phe Val Asp Asp Glu Gln Lys Glu
130 135 140

Leu Val Asn Glu Phe Lys Asp Phe Thr Thr Tyr Phe Thr Gly Phe His
145 150 155 160

Gln Asn Arg Arg Asn Met Tyr Val Ala Asp Glu Lys Ala Thr Ala Ile
165 170 175

Ala Tyr Arg Leu Val Asn Glu Asn Leu Pro Lys Phe Ile Asp Asn Leu
180 185 190

Lys Ile Tyr Glu Lys Ile Lys Lys Asp Ala Pro Glu Leu Ile Ser Asp
195 200 205

Leu Asn Lys Thr Leu Val Glu Met Glu Glu Ile Val Gln Gly Lys Thr
210 215 220

```
Leu Asp Glu Ile Phe Ser Leu Ser Phe Phe Asn Gln Thr Leu Thr Gln
225                 230                 235                 240

Thr Gly Ile Glu Leu Tyr Asn Ile Val Ile Gly Gly Arg Thr Ala Asp
                245                 250                 255

Glu Gly Lys Thr Lys Ile Lys Gly Leu Asn Glu Tyr Ile Asn Thr Asp
            260                 265                 270

Tyr Asn Gln Lys Gln Thr Asp Lys Lys Lys Lys Gln Ala Lys Phe Lys
        275                 280                 285

Gln Leu Tyr Lys Gln Ile Leu Ser Asp Arg His Ser Val Ser Phe Val
    290                 295                 300

Ala Glu Thr Phe Glu Thr Asp Ala Gln Leu Leu Glu Asn Ile Glu Gln
305                 310                 315                 320

Phe Tyr Ser Ser Val Leu Cys Asn Tyr Glu Asp Asp Gly His Thr Thr
                325                 330                 335

Asn Ile Phe Glu Ala Ile Lys Asn Leu Ile Ile Gly Leu Lys Thr Phe
            340                 345                 350

Asp Leu Ser Lys Ile Tyr Leu Arg Asn Asp Thr Ser Leu Thr Asp Ile
        355                 360                 365

Ser Gln Lys Leu Phe Gly Asp Trp Ser Ile Ile Ser Ser Ala Leu Asn
    370                 375                 380

Asp Tyr Tyr Glu Lys Gln Asn Pro Ile Ser Ser Lys Glu Lys Gln Glu
385                 390                 395                 400

Lys Tyr Asp Glu Arg Lys Ala Lys Trp Leu Lys Gln Asp Phe Asn Ile
                405                 410                 415

Glu Thr Ile Gln Thr Ala Leu Asn Glu Cys Asp Ser Glu Ile Ile Lys
            420                 425                 430

Glu Lys Asn Asn Lys Asn Ile Val Ser Glu Tyr Phe Ala Lys Leu Gly
        435                 440                 445

Leu Asp Lys Asp Asn Lys Ile Asp Leu Leu Gln Lys Ile His His Asn
    450                 455                 460

Tyr Val Val Ile Lys Asp Leu Leu Asn Glu Pro Tyr Pro Glu Asn Ile
465                 470                 475                 480

Lys Leu Gly Asn Gln Lys Glu Gln Val Ser Gln Ile Lys Asp Phe Leu
                485                 490                 495

Asp Ser Ile Leu Asn Leu Ile His Phe Leu Lys Pro Leu Ser Leu Lys
            500                 505                 510

Asp Lys Asp Lys Glu Lys Asp Glu Leu Phe Tyr Ser Leu Phe Thr Ala
        515                 520                 525

Leu Phe Glu His Leu Ser Gln Thr Ile Ser Ile Tyr Asn Lys Val Arg
    530                 535                 540

Asn Tyr Leu Thr Gln Lys Ala Tyr Ser Thr Glu Lys Ile Lys Leu Asn
545                 550                 555                 560

Phe Glu Asn Ser Thr Leu Leu Asn Gly Trp Asp Val Asn Lys Glu Pro
                565                 570                 575

Val Asn Thr Ser Val Ile Phe Arg Lys Asn Gly Leu Phe Tyr Leu Gly
            580                 585                 590

Ile Met Ser Lys Ser Asn Asn Arg Ile Phe Glu Arg Asn Val Pro Val
        595                 600                 605

Cys Lys Asn Glu Glu Thr Ala Phe Glu Lys Met Asn Tyr Lys Leu Leu
    610                 615                 620

Pro Gly Ala Asn Lys Met Leu Pro Lys Val Phe Leu Ser Ala Lys Gly
625                 630                 635                 640
```

```
Ile Glu Ser Phe Gln Pro Ser Ala Glu Ile Gln Ser Lys Tyr Gln Lys
                645                 650                 655

Glu Thr His Lys Lys Gly Asp Ala Phe Val Arg Lys Asp Met Glu Asn
            660                 665                 670

Leu Ile Asp Phe Phe Lys Gln Ser Ile Ala Lys His Thr Asp Trp Lys
        675                 680                 685

His Phe Asn His Gln Phe Ser Lys Thr Glu Thr Tyr Asn Asp Leu Ser
    690                 695                 700

Glu Phe Tyr Lys Glu Val Glu Lys Gln Gly Tyr Lys Leu Thr Phe Thr
705                 710                 715                 720

Lys Leu Asp Glu Thr Tyr Ile Asn Gln Leu Val Asp Glu Gly Lys Leu
                725                 730                 735

Tyr Leu Phe Gln Ile Tyr Asn Lys Asp Phe Ser Pro Phe Ser Lys Gly
            740                 745                 750

Lys Pro Asn Met His Thr Leu Tyr Trp Lys Met Leu Phe Asp Glu Gln
        755                 760                 765

Asn Leu Gln Asn Val Val Tyr Lys Leu Asn Gly Glu Ala Glu Val Phe
    770                 775                 780

Phe Arg Gln Ser Ser Ile Lys Gln Thr Asp Arg Ile Ile His Lys Ala
785                 790                 795                 800

Asn Gln Ala Ile Asp Asn Lys Asn Pro Leu Asn Asn Lys Lys Gln Ser
                805                 810                 815

Ser Phe Asn Tyr Asp Leu Ile Lys Asp Lys Arg Phe Thr Leu Asp Lys
            820                 825                 830

Phe Gln Phe His Val Pro Ile Thr Leu Asn Phe Lys Ala Glu Gly Asn
        835                 840                 845

Glu Tyr Leu Asn Thr Lys Val Asn Glu Tyr Leu Lys Ser Asn Ser Asp
    850                 855                 860

Val Lys Ile Ile Gly Leu Asp Arg Gly Glu Arg His Leu Ile Tyr Leu
865                 870                 875                 880

Thr Leu Ile Asn Gln Lys Gly Glu Leu Leu Lys Gln Gln Ser Leu Asn
                885                 890                 895

Val Ile Ala Thr Ser Gln Glu His Glu Thr Asp Tyr Lys Asn Leu Leu
            900                 905                 910

Val Asn Lys Glu Asn Glu Arg Ala Asn Ala Arg Gln Asp Trp Lys Thr
        915                 920                 925

Ile Glu Thr Ile Lys Glu Leu Lys Glu Gly Tyr Leu Ser Gln Val Val
    930                 935                 940

His Gln Ile Ala Thr Met Met Val Asp Glu Asn Ala Ile Val Val Met
945                 950                 955                 960

Glu Asp Leu Asn Ala Gly Phe Met Arg Gly Arg Gln Lys Val Glu Arg
                965                 970                 975

Gln Val Tyr Gln Lys Leu Glu Lys Met Leu Ile Glu Lys Leu Asn Tyr
            980                 985                 990

Leu Val Phe Lys Asn Asn Asp Val  Asn Glu Thr Ala Gly  Val Leu Asn
        995                 1000                1005

Ala Leu  Gln Leu Thr Asn Lys  Phe Glu Ser Phe Glu  Lys Met Gly
    1010                1015                1020

Lys Gln  Ser Gly Phe Leu Phe  Tyr Val Pro Ala Trp  Asn Thr Ser
    1025                1030                1035

Lys Ile  Asp Pro Ala Thr Gly  Phe Val Asp Phe Leu  Lys Pro Lys
    1040                1045                1050

Tyr Glu  Ser Val Glu Lys Ala  Lys Leu Phe Phe Glu  Lys Phe Glu
```

```
    1055                1060                1065

Ser Ile  Lys Phe Asn Ala Asp  Lys Asn Tyr Phe Glu  Phe Glu Phe
    1070                1075                1080

Asp Tyr  Lys Lys Phe Thr Glu  Lys Ala Glu Gly Ser  Gln Thr Lys
    1085                1090                1095

Trp Thr  Val Cys Thr His Ser  Asp Val Arg Tyr Arg  Tyr Asn Pro
    1100                1105                1110

Gln Thr  Lys Ala Ser Asp Glu  Val Asn Val Thr Asn  Glu Leu Lys
    1115                1120                1125

Leu Ile  Phe Asp Lys Phe Lys  Ile Glu Tyr Lys Asn  Gly Lys Asn
    1130                1135                1140

Leu Lys  Thr Glu Leu Leu Leu  Gln Asp Asp Lys Gln  Leu Phe Ser
    1145                1150                1155

Lys Leu  Leu His Tyr Leu Ala  Leu Thr Leu Met Leu  Arg Gln Ser
    1160                1165                1170

Lys Ser  Gly Thr Asp Ile Asp  Phe Ile Leu Ser Pro  Val Ala Lys
    1175                1180                1185

Asn Gly  Val Phe Tyr Asp Ser  Arg Asn Ala Met Pro  Asn Leu Pro
    1190                1195                1200

Lys Asp  Ala Asp Ala Asn Gly  Ala Phe His Ile Ala  Leu Lys Gly
    1205                1210                1215

Leu Trp  Cys Val Gln Gln Ile  Lys Lys Ala Asp Asp  Leu Lys Lys
    1220                1225                1230

Ile Lys  Leu Ala Ile Ser Asn  Lys Glu Trp Leu Ser  Phe Val Gln
    1235                1240                1245

Asn Leu  Lys
    1250


<210> SEQ ID NO 117
<211> LENGTH: 1353
<212> TYPE: PRT
<213> ORGANISM: Unknown
<220> FEATURE:
<223> OTHER INFORMATION: Candidatus Peribacteria bacterium RIFCSPLOWO2

<400> SEQUENCE: 117

Met Ala Asn Asp Ile Tyr Ala Gln Phe Thr Arg Lys Tyr Ala Leu Ser
1               5                   10                  15

Lys Thr Leu Arg Phe Glu Leu Lys Pro Val Gly Lys Thr Leu Asp Asn
            20                  25                  30

Met Arg Lys His Leu Glu Tyr Asp Pro Glu Leu Arg Thr Phe Leu Lys
        35                  40                  45

Asp Gln Cys Ile Glu Asp Ala Tyr Gln Ala Leu Lys Pro Lys Val Asp
    50                  55                  60

Glu Leu His Gln Arg Phe Ile Asn Leu Ala Leu Gly Ser Ala Arg Ala
65                  70                  75                  80

Lys Ser Met Glu Phe Ser Pro Phe Phe Glu Ile Arg Arg Gln Leu Leu
                85                  90                  95

Glu Leu Lys Met Lys Ala Lys Glu Lys Gly Val Gly Asp Lys Asp Ile
            100                 105                 110

Gln Asn Leu Glu Gly Glu Leu Asp Gly Ala Gly Glu Thr Leu Arg Lys
        115                 120                 125

Ala Phe Gly Asp Ile Phe Lys Asp Ala Gly Ala Arg Trp Lys Glu Leu
    130                 135                 140

Tyr Gly Ala Tyr Gly Trp Lys Lys Gly Gly Lys Glu Thr Lys Gly Ser
```

-continued

```
145                 150                 155                 160

Ala Val Leu Ser Cys Pro Asp Val Leu Lys Val Ile Asp Glu Glu Asn
                165                 170                 175

Glu Lys Lys Glu Leu Pro Glu Gln Cys Val Arg Asp Ala Ile Lys Ala
            180                 185                 190

Leu Glu Gly Phe Phe Thr Tyr Leu Gly Gly Phe Asn Gln Asn Arg Glu
        195                 200                 205

Asn Tyr Tyr Glu Thr Ala Lys Glu Ala Ala Thr Ala Ile Ala Thr Arg
    210                 215                 220

Ile Val His Glu Asn Leu Pro Arg Phe Thr Asp Asn Ala Leu Thr Phe
225                 230                 235                 240

Glu Ser Gly Asn Lys Glu Tyr Leu Asp Ala Tyr Arg Phe Leu Lys Asp
                245                 250                 255

Ala Gly Lys Val Ile Gln Arg Lys Asp Glu Lys Pro Val Thr Pro Ile
            260                 265                 270

Ser Glu Ala Ile Phe Cys Gln Asn Tyr Phe Gly Asn Cys Leu Thr Gln
        275                 280                 285

Glu Glu Ile Glu Arg Tyr Asn Glu Glu Ile Gly Asn Cys Asn Leu Val
    290                 295                 300

Ile Asn Leu Tyr Asn Gln Thr Glu Asp Glu Glu Gly Phe Arg Arg Leu
305                 310                 315                 320

Pro Ile Phe Lys Val Leu Tyr Lys Gln Ile Gly Cys Gly Lys Lys Asp
                325                 330                 335

Ala Leu Phe Phe Arg Leu Thr His Glu Lys Lys Glu Asp Ala Asp Ala
            340                 345                 350

Ala Arg Arg Glu Asn Pro Asn Lys Gln Phe Asp Ser Val Glu Glu Ile
        355                 360                 365

Leu Glu Arg Ala Arg Thr Ala Gly Glu Lys Tyr Phe Gln Pro Asn Lys
    370                 375                 380

Thr Ala Asp Met Asp Thr Leu Ser Glu Phe Ile Arg Tyr Leu Lys Glu
385                 390                 395                 400

Arg Lys Asp Tyr Ser Gly Phe Tyr Trp Ser Lys Asn Ala Leu Asn Thr
                405                 410                 415

Ile Ser Asn Lys Tyr Phe Ala Asn Trp His Ala Leu Lys Asp Arg Leu
            420                 425                 430

Lys Glu Thr Gly Val Phe Lys Lys Gly Gly Lys Asp Asp Glu Glu Tyr
        435                 440                 445

Val Lys Ile Pro Asp Ala Ile Glu Leu Gln Pro Phe Phe Glu Leu Leu
    450                 455                 460

Asp Val Thr Lys Asp Trp Arg Lys Thr Leu Phe Lys Leu Ser Gln Arg
465                 470                 475                 480

Asn Gly Ser Glu Glu Ile Glu Lys Met Arg Ile Ile Asp Asn Ala Lys
                485                 490                 495

Thr Pro His Glu Ala Leu Leu Gly Met Leu Thr Leu Asp Val Ala Asp
            500                 505                 510

Arg Ala Glu Lys Phe Val Asn Gly Ala Ala Gly Val Met Arg Val Thr
        515                 520                 525

Arg Glu Tyr Phe Ala Asn Ala Asp Lys Met Lys Glu Glu Arg Arg Arg
    530                 535                 540

Val Trp Lys Glu Glu Ile Lys Gln Trp Met Asp His Ala Leu Ala Val
545                 550                 555                 560

Asn Arg Met Leu Lys Tyr Phe Lys Val Arg Glu Ser Lys Val Lys Gly
                565                 570                 575
```

-continued

Ala Pro Ile Asp Ala Thr Leu Thr Lys Ala Leu Gly Ile Leu Leu Tyr
580 585 590

Gly Lys Asp Gly Asp Ala Glu Trp Phe Lys Trp Tyr Asp Thr Leu Arg
595 600 605

Asn Phe Leu Thr Lys Lys Pro Gln Asp Asp Ala Lys Glu Asn Lys Leu
610 615 620

Lys Leu Asn Phe Glu Asn Gly Ser Leu Leu Gly Gly Trp Ser Asp Gly
625 630 635 640

Gln Glu Lys Asn Lys Ala Ala Val Leu Leu Arg Lys Asp Gly Leu Tyr
645 650 655

Tyr Leu Gly Ile Leu Lys Lys Lys Ser Leu Phe Asp Thr Lys Gln Glu
660 665 670

Asn Asn Pro Met Tyr Glu His Phe Thr Gln Gly Cys Glu Arg Leu Ile
675 680 685

Leu Thr Asn Leu Lys Phe Gln Thr Leu Ala Gly Lys Gly Phe Ser Arg
690 695 700

Lys Phe Arg Ile Ala Tyr Gly Ala Met Gly Lys Gln Asp Pro Gln Lys
705 710 715 720

Ala Ile Ile Ser Leu Gln Asp Ile Met Lys Glu Arg Tyr Leu Asn Lys
725 730 735

Tyr Pro Leu Leu Ser Pro Ile Ala Ser Ala Ser Tyr Thr Asp Lys Lys
740 745 750

Lys Phe Asp Lys Glu Val Gln Glu Ala Leu Lys Glu Ser Tyr Asp Cys
755 760 765

Lys Phe Arg Lys Ile Asn Trp Asn Glu Ile Glu Gln Tyr Thr Lys Ser
770 775 780

Gly Asp Met Tyr Leu Phe Gln Ile His Ser Lys Asp Phe Ala Pro Gly
785 790 795 800

Ala Ser Gly Lys Lys Asp Leu Gln Thr Ile Tyr Trp Gln Ser Leu Phe
805 810 815

Asp Ser Asn Gly Ser His Gln Leu Asn Gly Gly Gly Glu Ile Phe Tyr
820 825 830

Arg Lys Gln Ala Leu Arg Asp Lys His Val Lys Lys Gly Tyr Glu Gln
835 840 845

Lys Pro Trp Ile Ile Glu Ser Arg Arg Phe Thr Leu Glu Ser Gly Lys
850 855 860

Phe Met Phe His Cys Pro Ile Lys Leu Asn Tyr Lys Ser Ser Ala Gln
865 870 875 880

Ser Asp Pro Lys Tyr Ala Phe Pro Phe Val Asn Lys Tyr Ile Asn Glu
885 890 895

His Phe Ala Gly Asn Ala Asp Ile Cys Phe Leu Gly Ile Asp Arg Gly
900 905 910

Glu Lys His Leu Ala Tyr Tyr Ser Leu Val Asp Ser Arg Gly Thr Ile
915 920 925

Val Asp Gln Gly Thr Leu Asn Ile Pro Phe Thr Asp Ser Lys Gly Asn
930 935 940

Pro Arg Thr Val Arg Ala Ile Lys Arg Thr Leu Asp Lys Asn Gly His
945 950 955 960

Glu Trp Val Glu Glu Val Glu Cys Ser Asn Tyr Asn Asp Leu Leu Ala
965 970 975

Ala Arg Ala Gly Asp Arg Asp Tyr Ala Arg Lys Asn Trp Gln Thr Ile
980 985 990

```
Gly Thr Ile Lys Glu Leu Lys Glu  Gly Tyr Ile Ser Gln  Val Ile His
        995                 1000                 1005

Lys Ile  Val Arg Leu Ala Ala  Leu Asp Ser Asp Lys  Pro Met Phe
    1010                 1015                 1020

Ile Val  Leu Glu Asp Leu Ser  Ile Gly Phe Met Arg  Gly Arg Gln
    1025                 1030                 1035

Lys Ile  Glu Lys Ser Val Tyr  Lys Gln Phe Glu Val  Ala Leu Ala
    1040                 1045                 1050

Lys Lys  Leu Ser Phe Leu Val  Asp Lys Ser Lys Asp  Gly Lys Tyr
    1055                 1060                 1065

Gly Glu  Val Gly Ser Val Thr  Ala Ala Leu Gln Leu  Thr Pro Pro
    1070                 1075                 1080

Ile Lys  Asn Phe Asp Glu Leu  Lys Glu Arg Gly Lys  Gln Ala Gly
    1085                 1090                 1095

Val Met  Leu Phe Val Arg Pro  Asp Tyr Thr Ser Gln  Thr Asp Pro
    1100                 1105                 1110

Val Thr  Gly Trp Arg Lys Arg  Ile Tyr Ile Asp Ser  Gly Ser Glu
    1115                 1120                 1125

Leu Thr  Ile Arg Lys Lys Val  Thr Glu Ser Phe Glu  Asp Ile Ala
    1130                 1135                 1140

Phe Asp  Gly Lys Asp Tyr Val  Phe Val Tyr Lys Asp  Val Val Thr
    1145                 1150                 1155

Gly Lys  Cys Trp Ser Met Tyr  Ser Gly Lys Asp Gly  Glu Ser Leu
    1160                 1165                 1170

Lys Arg  Phe His Arg Val Arg  Ser Val Asp Lys Asp  Glu Trp Lys
    1175                 1180                 1185

Ser Glu  Pro Gln Asn Leu Ala  Glu Met Leu Asp Cys  Leu Phe Lys
    1190                 1195                 1200

Asp Phe  Asp Lys Asp Arg Ser  Leu Leu Ser Gln Ile  Val Asp Glu
    1205                 1210                 1215

Gly Met  Gln Pro Lys Lys Val  Asn Glu His Ser Ala  Trp Glu Ser
    1220                 1225                 1230

Phe Arg  Phe Val Ile Lys Leu  Ile Gln Gln Ile Arg  Asn Thr Asp
    1235                 1240                 1245

Gly Gly  Asp Gly Gly Arg Glu  Ser Asp Phe Leu Leu  Ser Pro Val
    1250                 1255                 1260

Arg Glu  His Gly Asn His Phe  Asp Ser Arg Pro Tyr  Trp Asp Glu
    1265                 1270                 1275

Glu Gln  Arg Thr Gly His Pro  Ala Leu Leu Pro Ser  Cys Gly Asp
    1280                 1285                 1290

Ala Asn  Gly Ala Tyr Asn Ile  Ala Arg Lys Gly Ile  Ile Leu His
    1295                 1300                 1305

Glu His  Met Lys Arg Asp Phe  Lys Leu Tyr Val Arg  Asp Glu Glu
    1310                 1315                 1320

Trp Asp  Ser Trp Leu Ala Gly  Lys Glu Thr Trp Asp  Asn Trp Leu
    1325                 1330                 1335

Arg Asn  His Glu Lys Asp Leu  Arg Lys Thr Pro Arg  Lys Gly Gly
    1340                 1345                 1350
```

<210> SEQ ID NO 118
<211> LENGTH: 1289
<212> TYPE: PRT
<213> ORGANISM: Unknown
<220> FEATURE:
<223> OTHER INFORMATION: Nitrospinae bacterium RIFCSPLOWO2

<400> SEQUENCE: 118

Met Glu Asn Lys Glu Leu Phe Asn Ser Phe Thr Lys Lys Cys Gln Leu
1 5 10 15

Ser Lys Thr Leu Arg Phe Glu Leu Val Pro Gln Gly Glu Thr Glu Lys
20 25 30

Phe Ile Lys Lys Lys Gly Leu Leu Lys Gln Asp Lys Asp Arg Ala Asp
35 40 45

Asp Tyr Arg Lys Ala Lys Lys Leu Ile Asp Glu Tyr His Lys Asp Phe
50 55 60

Ile Glu His Ala Leu Ser Gly Lys Gln Leu Lys Lys Leu Gln Ala Tyr
65 70 75 80

Tyr Asp Glu Phe Thr Ala Leu Leu Gly Lys Pro Ala Lys Glu Arg Asp
85 90 95

Thr Arg Val Leu Ser Asn Ile Ser Glu Ala Leu Arg Lys Glu Ile Ala
100 105 110

Gly Trp Leu Lys Asp Asn Pro Ile Lys Asp Glu Lys Lys Leu Ile Lys
115 120 125

Glu Ile Val Pro Asn Phe Leu Lys Ser Lys Asp Arg Asn Asp Asp Ala
130 135 140

Ala Leu Val Leu Lys Phe Lys Gly Phe Thr Thr Tyr Phe Gly Gly Phe
145 150 155 160

Asn Glu Asn Arg Arg Asn Met Tyr Ser Ala Glu Glu Lys Ser Thr Ala
165 170 175

Ile Ala Tyr Arg Ile Val His Glu Asn Leu Pro Lys Phe Ile Ser Asn
180 185 190

Met Lys Thr Phe Gln Arg Leu Thr Glu Asn His Lys Ile Asp Phe Leu
195 200 205

Glu Val Glu Thr Gln Met Asn Asp Glu Leu Asp Gly Asn Lys Leu Lys
210 215 220

Asp Val Phe Ser Ile Asp Tyr Phe Asn Gln Cys Leu Thr Gln Ser Gly
225 230 235 240

Ile Asp Arg Tyr Asn Thr Ile Leu Gly Gly Lys Thr Asp Ser Arg Gly
245 250 255

Ala Gln Ile Gln Gly Val Asn Ile Lys Ile Asn Leu Phe Gly Gln Lys
260 265 270

Asn Asn Leu Lys Ser Lys Asp Ala Pro Val Leu Ala Arg Leu Tyr Lys
275 280 285

Gln Ile Leu Ser Asp Arg Thr Ser Ala Ser Phe Leu Pro Glu Lys Phe
290 295 300

Glu Thr Ala Lys Glu Leu Ile Ala Ser Ile Arg Glu Phe Tyr Glu Lys
305 310 315 320

Ala Ile Asn Gly Phe Ile Lys Asn Asn Glu Arg Lys Asn Val Ile Asp
325 330 335

Glu Ile Glu Ser Leu Phe Asn Lys Lys Leu Asn Pro Thr Asp Cys Asp
340 345 350

Leu Ser Gln Ile Tyr Ile Arg Asn Ile Phe Ile Ser Ala Val Ser Gln
355 360 365

Gln Ile Phe Gly Ser Tyr Ser Val Ile Thr Ser Ala Leu Asn Ala Phe
370 375 380

Ile Asp Lys Thr Tyr Lys Thr Lys Lys Glu Lys Glu Lys Gln Gln Lys
385 390 395 400

Lys Ser Tyr Phe Gly Ile Ala Glu Ile Glu Ala Ala Leu Lys Ala Tyr

-continued

```
                405                 410                 415

Leu Gln Glu Thr Glu Ile Glu Asn Lys Glu Lys Arg Glu Glu Val Leu
            420                 425                 430

Lys His Ala Asn Pro Val Leu Gln Tyr Leu Asn Ser Leu Thr Thr Asn
        435                 440                 445

Ile Glu Ile Asn Asn Lys Lys Glu Lys Ala Asn Val Ile Val Arg Phe
    450                 455                 460

Arg Gln Gln His Glu Ala Val Gln Ser Val Leu Asn Lys Glu Tyr Gly
465                 470                 475                 480

Asn Asn Ser Glu Leu Ile Gln Asp Lys Asn Ala Val Ala Ala Ile Lys
                485                 490                 495

Asp Tyr Leu Asp Ser Cys Gln His Ile Leu His Phe Val Lys Pro Leu
            500                 505                 510

Phe Val Val Pro Pro Lys Lys Glu Asn Ala Glu Leu Pro Asp Lys Asp
        515                 520                 525

Ala Phe Tyr Ser Glu Phe Asp Glu Leu Phe Glu Gln Leu Lys Ser Val
    530                 535                 540

Thr Pro Leu Tyr Asn Met Val Arg Asn Phe Leu Thr Gln Lys Pro Tyr
545                 550                 555                 560

Ser Thr Glu Lys Ile Lys Leu Asn Phe Glu Asn Val Ser Leu Leu Ser
                565                 570                 575

Gly Trp Asp Val Asn Lys Glu Thr Asp Asn Thr Ser Val Ile Phe Arg
            580                 585                 590

Lys Asp Ser Leu Tyr Tyr Leu Gly Ile Met Asp Lys Lys His Asn Lys
        595                 600                 605

Val Phe His Asp Ile Pro Ala Ser Ser Asp Asn Asp Phe Tyr Glu Lys
    610                 615                 620

Met Asn Tyr Lys Leu Leu Pro Gly Ala Asn Lys Met Leu Pro Lys Val
625                 630                 635                 640

Ile Phe Ser Asp Arg Trp Ile Glu Tyr Phe Asn Pro Ser Lys Glu Leu
                645                 650                 655

Ile Glu Lys Tyr Lys Lys Gly Thr His Lys Lys Gly Glu Ile Phe Ser
            660                 665                 670

Leu Ser Asp Cys His Ala Leu Ile Asp Phe Phe Lys Thr Ser Ile Ala
        675                 680                 685

Lys His Glu Asp Trp Lys Gln Phe Asn Phe Gln Phe Ser Pro Thr Lys
    690                 695                 700

Thr Tyr Gln Asp Ile Asn Glu Phe Tyr Arg Glu Val Glu His Gln Gly
705                 710                 715                 720

Tyr Lys Ile Ser Phe Gln Asn Val Ser Ala Lys Tyr Ile His Gln Leu
                725                 730                 735

Val Ser Glu Gly Lys Leu Phe Leu Phe Lys Ile Tyr Asn Lys Asp Phe
            740                 745                 750

Ser Pro Tyr Ser Lys Gly Lys Pro Asn Leu His Thr Leu Tyr Trp Lys
        755                 760                 765

Ala Val Phe Asp Lys Glu Asn Leu Lys Asp Val Val Val Lys Leu Asn
    770                 775                 780

Gly Glu Ala Glu Val Phe Tyr Arg Pro Gln Ser Ile Pro Lys Lys Ser
785                 790                 795                 800

Lys Ile Val His Lys Lys Asn Lys Pro Ile Val Asn Lys Asn Pro Asn
                805                 810                 815

Asn Pro Lys Lys Gln Ser Leu Phe Lys Glu Tyr Asp Ile Val Lys Asp
            820                 825                 830
```

-continued

```
Lys Arg Tyr Thr Glu Asp Lys Tyr His Phe His Val Pro Ile Thr Leu
        835                 840                 845

Asn Phe Lys Glu Ala Lys Val Pro Ser Glu Asn Asp Arg Lys Lys Ala
    850                 855                 860

Phe Ala Tyr Thr Phe Asn Lys Gly Ala Asn Glu Thr Leu Lys Glu Asn
865                 870                 875                 880

Phe Pro Asn Ile Ile Gly Ile Asp Arg Gly Glu Arg His Leu Ala Tyr
                885                 890                 895

Tyr Ser Leu Ile Asn Ser Lys Gly Glu Ile Leu Glu Gln Gly Ser Phe
            900                 905                 910

Asn Val Ile Lys Asn Glu Phe Asn Gly Thr Lys His Glu Thr Asp Tyr
        915                 920                 925

Tyr Ala Ser Leu Val Glu Lys Glu Lys Ala Arg Asp Ala Ala Arg Lys
    930                 935                 940

Ser Trp Asp Thr Ile Gly Lys Ile Lys Glu Leu Lys Glu Gly Tyr Leu
945                 950                 955                 960

Ser Gln Val Val His Lys Ile Ala Arg Met Met Ile Glu His Asn Ala
                965                 970                 975

Ile Ile Val Leu Glu Asp Leu Thr Met Lys Phe Lys Asp Ile Arg Lys
            980                 985                 990

Lys Val Glu Arg Gln Val Tyr Gln  Lys Leu Glu Lys Met  Leu Ile Asp
        995                 1000                 1005

Lys Leu  Asn Tyr Leu Val Phe  Lys Asp Arg Glu Ala  Tyr Glu Pro
    1010                 1015                 1020

Gly Gly  Val Leu Asn Ala Tyr  Gln Leu Ala Ala Pro  Phe Thr Ser
    1025                 1030                 1035

Phe Lys  Asp Met Gly Lys Gln  Thr Gly Phe Ile Phe  Tyr Val Pro
    1040                 1045                 1050

Ala Ala  Asn Thr Ser Lys Ile  Asp Tyr Ala Thr Gly  Phe Met Asn
    1055                 1060                 1065

Phe Ile  Tyr Pro Lys Ile Glu  Asp Ala Val Glu Phe  Phe Gln Lys
    1070                 1075                 1080

Phe Glu  Tyr Ile Arg Phe Asn  Pro Asp Lys Asn Tyr  Phe Glu Phe
    1085                 1090                 1095

Ala Ala  Arg Tyr Asn Asn Phe  Val Lys Asp Asp Glu  Ala Lys Leu
    1100                 1105                 1110

Pro Asp  Glu Tyr Asn Glu Pro  Trp Ile Ile Cys Thr  His Gly Glu
    1115                 1120                 1125

Gln Arg  Phe Gln Tyr Gln Pro  Ser Tyr Lys Ser Phe  Lys Glu Val
    1130                 1135                 1140

Asn Val  Thr Gln Glu Leu Gln  Asp Leu Phe Ser Lys  His Ala Ile
    1145                 1150                 1155

Met Pro  Tyr Ala His Gly Asn  Asp Leu Ser Pro Gln  Ile Lys Asp
    1160                 1165                 1170

Lys Gly  Asn Thr Ser Phe Tyr  Lys Gly Leu Ile Ala  Leu Leu Arg
    1175                 1180                 1185

Leu Val  Leu Gln Met Arg Tyr  Thr Asp Gly Lys Gly  Arg Asp Phe
    1190                 1195                 1200

Ile Leu  Ser Pro Val Ala Asn  Asp Glu Gly Val Phe  Phe Asn Ser
    1205                 1210                 1215

Glu Lys  Ala Lys Glu Thr Glu  Pro Asn Asp Ala Asp  Ala Asn Gly
    1220                 1225                 1230
```

Ala Tyr His Ile Ala Leu Lys Gly Leu Leu Leu Leu Lys Arg Ile
    1235                1240                1245

Lys Gly Glu Phe Lys Lys Glu Glu Lys Thr Gly Lys Lys Lys Thr
    1250                1255                1260

Gln Lys Glu Asn Trp Ile Asp Leu Ser Ile Ser Asn Lys Glu Trp
    1265                1270                1275

Tyr Glu Phe Ala Gln Lys Lys Glu Tyr Arg Lys
    1280                1285

<210> SEQ ID NO 119
<211> LENGTH: 1342
<212> TYPE: PRT
<213> ORGANISM: Unknown
<220> FEATURE:
<223> OTHER INFORMATION: Candidatus Ryanbacteria bacterium RIFCSPHIGHO2

<400> SEQUENCE: 119

Met Ala Asn Glu Lys Lys Glu Lys Ser Ile Phe Asp Glu Phe Thr Gly
1               5                   10                  15

Lys Tyr Ser Leu Ser Lys Thr Leu Lys Phe Glu Leu Arg Pro Val Gly
            20                  25                  30

Lys Thr Leu Glu Asn Met Arg Gln His Leu Gly Tyr Asp Lys Asn Leu
        35                  40                  45

Gln Thr Phe Leu Ala Asp Gln Lys Ile Glu Asp Ala Tyr Gln Ser Leu
    50                  55                  60

Lys Pro Ile Phe Asp Phe Leu His Glu Lys Phe Ile Thr Glu Ser Leu
65                  70                  75                  80

Glu Ser Asp Val Ala Arg Lys Ile Asp Phe Thr Glu Tyr Phe Glu Lys
                85                  90                  95

Tyr Lys Arg Arg Lys Asp Leu Ser Glu Lys Asp Phe Val Gly Val Glu
            100                 105                 110

Lys Ser Leu Arg Asp Glu Phe Leu Lys Ala Tyr Asp Glu Thr Ala Glu
        115                 120                 125

Ser Leu Arg Ile Lys Ala Gly Lys Asn Glu Lys Gly Lys Phe Ile Leu
    130                 135                 140

Ser Glu Asn Gly His Lys Ile Leu Thr Glu His Gly Ile Leu Glu Tyr
145                 150                 155                 160

Ile Lys Lys Asn Ile Asp Glu Phe Val Glu Ile Thr Pro Glu Arg Glu
                165                 170                 175

Ile Glu Lys Ser Leu Ala Ala Phe Glu Gly Phe Phe Thr Tyr Phe Gly
            180                 185                 190

Gly Phe Asn Gln Asn Arg Glu Asn Tyr Tyr Glu Thr Lys Lys Glu Thr
        195                 200                 205

Ala Thr Ser Val Ala Thr Arg Val Ile His Glu Asn Leu Pro Lys Phe
    210                 215                 220

Cys Asp Asn Ile Leu Ala Phe Asp Gly Arg Ser Arg Asp Tyr Lys Asn
225                 230                 235                 240

Ala Tyr Ser Ile Leu Gln Lys Leu Gly Arg Thr Leu Val Asp Lys Glu
                245                 250                 255

Gly Lys Glu Leu Ile Pro Ile Glu Glu Asn Ile Phe Lys Ile Glu Tyr
            260                 265                 270

Phe Asn Ser Cys Met Ser Gln Arg Gly Val Glu Lys Tyr Asn Asp Gln
        275                 280                 285

Ile Gly Asn Ala Asn Phe Leu Ile Asn Leu Tyr Asn Gln Ala Lys Lys
    290                 295                 300

-continued

```
Glu Glu Asn Gly Phe Lys Lys Leu Pro Leu Leu Lys Thr Leu Tyr Lys
305                 310                 315                 320

Gln Ile Gly Cys Gly Glu Lys Arg Ser Leu Phe Phe Ala Ile Asn Tyr
                325                 330                 335

Asp Gln Ala Asp Glu Cys Lys Lys Gln Glu Asn Asn Thr Glu Ile Arg
            340                 345                 350

Ser Leu Glu Glu Val Leu Asn Leu Ala Asn Lys Ala Gly Lys Lys Tyr
        355                 360                 365

Phe Lys Gly Lys Ser Asp Asp Gly Met Ile Asn Thr Leu Pro Glu Phe
    370                 375                 380

Leu Glu Tyr Leu Lys Asn Arg Glu Asn Tyr Leu Gly Val Tyr Trp Ser
385                 390                 395                 400

Lys Thr Ala Leu Asn Thr Ile Ser Ser Lys Tyr Phe Thr Asn Trp His
                405                 410                 415

Thr Leu Lys Glu Arg Leu Lys Glu Ala Lys Val Phe Lys Lys Ala Gly
            420                 425                 430

Lys Asp Ser Glu Glu Glu Ile Met Ile Pro Glu Ala Val Glu Leu Glu
        435                 440                 445

Gly Phe Phe Ser Val Leu Asp Val Val Glu Asn Trp Lys Asp Glu Gly
    450                 455                 460

Val Leu Phe Lys Gln Asn Leu Thr Glu Ala Gln Lys Gly Ala Gln Gly
465                 470                 475                 480

Glu Asp Lys Asn Lys Ala Arg Lys Asp Ile Ile Leu Asn Ala Ser Ile
                485                 490                 495

Pro Ser Glu Ala Leu Leu Asn Leu Ile Phe Leu Gly Ile Glu Gln His
            500                 505                 510

Ala Lys Ala Phe Leu Asp Arg Ala Pro Glu Val Leu Ala Leu Lys Glu
        515                 520                 525

Tyr Lys Asn Ala Thr Ser Lys Glu Val Ile Lys Ser Trp Met Asp His
    530                 535                 540

Ala Leu Ser Ile Thr Gln Met Leu Lys Tyr Phe Leu Val Lys Glu Ser
545                 550                 555                 560

Lys Val Lys Gly Thr Ala Leu Asp Ser Thr Ile Ser Gln Ala Leu Glu
                565                 570                 575

Val Phe Leu Gln Ser Asp Asp Ala Asp Trp Phe Gly Trp Tyr Asp Ala
            580                 585                 590

Leu Arg Asn Tyr Leu Thr Lys Lys Pro Gln Asp Asp Leu Lys Glu Asn
        595                 600                 605

Lys Leu Lys Leu Asn Phe Glu Asn Ser Thr Leu Ala Ser Gly Trp Asp
    610                 615                 620

Val Ser Lys Glu Pro Asp Asn Tyr Cys Val Ile Phe Gln Asn Pro Glu
625                 630                 635                 640

Gly Glu Lys Phe Leu Ala Ile Ile Ala Arg Lys Lys Asp Arg Lys Gly
                645                 650                 655

Phe Asn Lys Ile Phe Glu Lys Asn Asn His Asn Arg Leu Tyr Thr Val
            660                 665                 670

Ser Gly Asn Lys Asn Trp Lys Lys Ile Glu Tyr Lys Leu Leu Pro Gly
        675                 680                 685

Pro Asn Lys Met Leu Pro Lys Cys Leu Met Pro Lys Ser Asp Arg Phe
    690                 695                 700

Lys Tyr Gly Ala Thr Gln Glu Ile Leu Asp Ile Tyr Asp Glu Gly Ser
705                 710                 715                 720

Phe Lys Lys Asn Glu Val Ser Phe Ser Ile Gln Lys Leu Tyr Lys Met
```

-continued

```
                725                 730                 735

Ile Asp Phe Tyr Lys Met Ala Leu Glu Arg Tyr Lys Asp Trp Gly Cys
            740                 745                 750

Phe Asn Phe Ser Phe Gln Glu Thr Ser Lys Tyr Gln Asp Ile Ser Gln
        755                 760                 765

Phe Tyr Asn Asp Val Glu Lys Gln Gly Tyr Lys Leu Asp Val Val Asp
    770                 775                 780

Ile Asn Lys Ser Ile Val Asp Ser Leu Val Glu Asp Gly Ser Ile Tyr
785                 790                 795                 800

Leu Phe Glu Ile Lys Asn Gln Asp Ser Asn Gln Gly Lys Lys Glu Asn
                805                 810                 815

His Arg Asp Asn Leu His Thr Ile Tyr Trp Arg Ala Val Phe Glu Ser
            820                 825                 830

Val Glu Asn Arg Pro Lys Leu Asn Gly Gly Ala Glu Ile Phe Tyr Arg
        835                 840                 845

Lys Ala Leu Leu Pro Glu Lys Leu Glu Arg Asn Glu Asp Arg Lys Gly
    850                 855                 860

Lys Lys Ile Ile Lys Asn Pro Arg Phe Ser Lys Glu Lys Phe Leu Phe
865                 870                 875                 880

His Val Pro Ile Thr Leu Asn Phe Ser Ser Lys Asn Thr Arg Ile Asn
                885                 890                 895

Asp Leu Val Asn Asp Ile Leu Ser Arg Tyr Gly Asp Val His Phe Leu
            900                 905                 910

Gly Ile Asp Arg Gly Glu Lys His Leu Ala Tyr Tyr Ser Leu Val Asp
        915                 920                 925

Gln Asn Gly Arg Ile Lys Asp His Gly Thr Leu Asn Ile Pro Phe Leu
    930                 935                 940

Asp Lys Asp Gly Asn Ser Arg Met Val Arg Ala Lys Lys Arg Thr Leu
945                 950                 955                 960

Gly Lys Asp Gly Lys Glu Gln Ile Glu Met Val Glu Cys Lys Asp Tyr
                965                 970                 975

Asn Glu Leu Leu Asp Ala Arg Ala Gly Asp Arg Asp Tyr Ala Arg Lys
            980                 985                 990

Asn Trp Gln Thr Ile Gly Thr Ile  Lys Asp Leu Lys Asp  Gly Tyr Ile
        995                 1000                1005

Ser Gln  Val Val Arg Thr Ile  Ala Asp Leu Ala Leu  Ala Asn Asn
    1010                1015                1020

Ala Phe  Ile Val Leu Glu Ser  Leu Asp Thr Gly Phe  Lys Arg Gly
    1025                1030                1035

Arg Gln  Lys Ile Glu Lys Ser  Val Tyr Gln Lys Leu  Glu Leu Ala
    1040                1045                1050

Leu Ala  Lys Lys Leu Asn Phe  Leu Val Asp Lys Lys  Ala Lys Phe
    1055                1060                1065

Gly Glu  Ile Gly Ser Val Thr  Asn Ala Leu Gln Leu  Thr Pro Pro
    1070                1075                1080

Val Ala  Asn Tyr Gly Asp Ile  Glu Asn Arg Lys Gln  Leu Gly Val
    1085                1090                1095

Met Leu  Tyr Val Lys Ala Asp  Tyr Thr Ser Gln Thr  Asp Pro Ile
    1100                1105                1110

Thr Gly  Trp Arg Lys Ser Ile  Tyr Leu Lys Lys Gly  Ser Glu Glu
    1115                1120                1125

Tyr Ile  Arg Ser Gln Ile Arg  Asp Gly Phe Ser Asp  Ile Ser Phe
    1130                1135                1140
```

Asp Gly Lys Asp Tyr Val Phe Thr Tyr Glu Asp Lys Asn Thr His
1145 1150 1155

Lys Gln Trp Lys Leu Tyr Ser Gly Lys Asn Gly Lys Ser Leu Asp
1160 1165 1170

Arg Tyr His Arg Glu Lys Gly Glu Thr Arg Asn Ser Trp Asp Pro
1175 1180 1185

Ile Arg Lys Asp Val Thr Glu Met Leu Asn Gly Ile Phe Glu Asn
1190 1195 1200

Phe Asn Arg Ser Asn Ser Ile His Ser Gln Ile Val Asp Glu Gly
1205 1210 1215

Val Glu Leu Lys Lys Ile Asp Ser Ala His Thr Ala Trp Glu Ser
1220 1225 1230

Leu Arg Phe Thr Ile Asp Leu Ile Gln Gln Ile Arg Asn Thr Gly
1235 1240 1245

Thr Ala Lys Glu Asp Asp Asp Phe Ile Leu Ser Pro Val Arg Asp
1250 1255 1260

Glu Asn Gly Asn His Phe Asp Ser Arg Lys Thr Ile Lys Tyr Gln
1265 1270 1275

Pro Asn Ser Gly Asp Ala Asn Gly Ala Tyr Asn Ile Ala Arg Lys
1280 1285 1290

Gly Ile Val Leu Asn Glu His Ile Lys Arg Gly Tyr Arg Leu Phe
1295 1300 1305

Ile Ser Asp Glu Glu Trp Asp Ala Trp Leu Ala Gly Lys Glu Arg
1310 1315 1320

Trp Glu Lys Trp Ile Ser Asp His Lys Lys Asp Leu Ala Lys Lys
1325 1330 1335

Gln Thr Ala Gln
1340

<210> SEQ ID NO 120
<211> LENGTH: 1390
<212> TYPE: PRT
<213> ORGANISM: Unknown
<220> FEATURE:
<223> OTHER INFORMATION: Candidatus Wildermuthbacteria bacterium RIFCSPHIGHO2

<400> SEQUENCE: 120

Met Ile Asp Asn Thr Lys Glu Lys Lys Glu Gly Ser Val Phe Asp Gly
1 5 10 15

Phe Thr Arg Lys Tyr Gln Leu Ser Lys Thr Leu Arg Phe Glu Leu Arg
20 25 30

Pro Ile Leu Asn Thr Pro Lys Met Leu Asp Asp Glu Gln Val Ile Lys
35 40 45

Asn Asp Glu Thr Arg Arg Lys Lys Tyr Glu Ala Val Lys Pro Trp Phe
50 55 60

Asp Gln Leu His Arg Glu Phe Ile Glu Asp Ala Leu Lys Ser Phe Lys
65 70 75 80

Phe Lys Asn Leu Ala Ile Tyr Gln Asp Thr Phe Gln Thr Trp Gln Lys
85 90 95

Asp Arg Lys Ser Lys Gln Lys Lys Asp Thr Leu Val Lys Ile Glu Val
100 105 110

Gly Leu Arg Glu Glu Ile Val Arg Arg Phe Glu Glu Val Ala Asn Ile
115 120 125

Trp Val Arg Ser Glu Gln Tyr Lys Leu Leu Gly Ile Lys Lys Glu Gly

-continued

```
    130                 135                 140

Leu Gly Met Leu Phe Glu Ala Gly Val Phe Arg Leu Leu Lys Glu Arg
145                 150                 155                 160

Phe Lys Asn Glu Lys Asp Thr Thr Val Asp Gly Asn Asn Ile Phe Asp
                165                 170                 175

Glu Trp Thr Arg Trp Thr Gly Tyr Phe Lys Lys Phe Phe Glu Thr Arg
            180                 185                 190

Lys Asn Phe Tyr Lys Ser Asp Asp Thr Ser Thr Ala Ile Ala Tyr Arg
        195                 200                 205

Val Ile Asn Gln Asn Leu Arg Arg Phe Cys Glu Asn Ile Gln Ile Phe
    210                 215                 220

Glu Lys Ile Ser Glu Lys Ile Glu Phe Ser Glu Val Glu Lys Ser Phe
225                 230                 235                 240

Asp Ile Ser Cys Ala Gly Ile Phe Ser Leu Ala Tyr Tyr Asn Ala Cys
                245                 250                 255

Leu Leu Gln Gly Gly Ile Asp Thr Tyr Asn Lys Ile Ile Gly Gly Glu
            260                 265                 270

Val Asp Glu Lys Asp Lys Lys Ile Pro Gly Ile Asn Glu Leu Ile Asn
        275                 280                 285

Lys Tyr Arg Gln Asp Asn Ser Gly Glu Lys Ile Pro Phe Leu Lys Gln
    290                 295                 300

Leu Asp Lys Gln Ile His Ser Ala Lys Glu Ala Phe Ile Glu Ser Ile
305                 310                 315                 320

Glu Thr Asn Lys Glu Leu Val Gly Lys Leu Lys Thr Phe Tyr Glu Asn
                325                 330                 335

Ala Glu Val Lys Ile Gln Ser Phe Arg Asn Leu Ile Ala Asp Ile Val
            340                 345                 350

Thr Asp Tyr Ser Gly Tyr Asp Ile Asp Lys Ile Tyr Leu Thr Lys Glu
        355                 360                 365

Ala Val Ser His Asn Ala Ser Arg Trp Phe Ala Ser Phe Glu Ser Phe
    370                 375                 380

Glu Arg Asp Leu Phe Ala Val Val Ala Glu Lys Gln Asn Lys Leu Val
385                 390                 395                 400

Tyr Glu Leu Leu Arg Thr His Lys Asn Asp Ser Lys Ile Ser Asp Lys
                405                 410                 415

Asp Gly Lys Phe Ser Phe Pro Asp Phe Ile Lys Cys Ser His Ile Lys
            420                 425                 430

Arg Ala Leu Glu Lys Gln Glu Gly Arg Ile Trp Lys Gly Glu Tyr Tyr
        435                 440                 445

Glu Asp Ile Val Asp Phe Glu Lys Ile Lys Asp Val Phe Thr Gln Phe
    450                 455                 460

Leu Cys Val Phe Lys Phe Glu Leu Glu Gln Gln Phe Phe Arg Lys Thr
465                 470                 475                 480

Thr Ser Ala Gln Thr Gly Glu Gln Thr Lys Ile Gly Tyr Glu Ile Phe
                485                 490                 495

Val Thr Lys Ile Asn Glu Leu Ile Thr Arg Glu Asn Pro Val Ile Asp
            500                 505                 510

Leu Glu Glu Lys Ile Ala Ile Lys Asn Phe Ala Asp Ala Thr Leu Leu
        515                 520                 525

Ile Tyr Gln Ile Ala Lys Tyr Phe Ala Val Glu Lys Arg Arg Gly Trp
    530                 535                 540

Leu Asp Asn Tyr Asp Leu Asp Asp Arg Phe Tyr Lys Ser Ser Asp Ile
545                 550                 555                 560
```

```
Gly Tyr Leu Asn Phe Tyr Arg Asp Ala Phe Glu Gln Ile Val Arg Pro
                565                 570                 575

Tyr Asn Leu Phe Arg Asn Tyr Leu Thr Lys Lys Pro Tyr Asn Thr Asn
            580                 585                 590

Lys Trp Val Leu Ser Phe Glu Asn Pro Thr Leu Ala Asp Gly Trp Asp
        595                 600                 605

Lys Asn Lys Glu Lys Thr Asn Ala Ala Val Ile Leu Arg Lys Asp Gly
    610                 615                 620

Arg Tyr Tyr Leu Gly Ile Ile Lys Glu Asp Cys Lys Ser Leu Phe Ala
625                 630                 635                 640

Asp Arg Tyr Ser Lys Glu Met Ser Glu Gly Ile Glu Ser Gly Ser Phe
                645                 650                 655

Gln Lys Met Ala Tyr Lys Phe Phe Pro Glu Ala Ser Lys Met Ile Pro
            660                 665                 670

Lys Cys Ser Thr Gln Thr Lys Asn Val Lys Glu His Phe Arg Lys Ser
        675                 680                 685

Ser Ser Asp Tyr Asn Leu Phe His Glu Lys Asp Tyr Lys Ile Ser Val
    690                 695                 700

Ala Ile Thr Lys Asn Ile Tyr Glu Leu Asn Asn Val Phe Tyr Arg Lys
705                 710                 715                 720

Asp Asn Ile Glu Glu Ser Phe Val Pro Lys Asn Asp Phe Glu Lys Lys
                725                 730                 735

Leu Gly Val Lys Lys Phe Gln Arg Gln Tyr Leu Glu Ile Ser Arg Asp
            740                 745                 750

Asn Asn Gly Tyr Lys Gln Ala Leu Ala Gln Trp Ile Glu Phe Cys Ile
        755                 760                 765

Arg Phe Leu Lys Ala Tyr Lys Ser Thr Thr Ile Phe Asp Tyr Ser Arg
    770                 775                 780

Leu Arg Glu Ala Lys Glu Tyr Glu Ser Leu Asp Ala Phe Tyr Gln Asp
785                 790                 795                 800

Ile Asn Ala Leu Thr Tyr Asn Ile Ser Phe Val Pro Ile Ser Glu Gln
                805                 810                 815

Tyr Ile Lys Glu Lys Asn Asp Asn Gly Glu Leu Phe Leu Phe Glu Ile
            820                 825                 830

Tyr Asn Lys Asp Trp Ser Leu Gly Pro Met Asp Lys Asn Arg Lys Arg
        835                 840                 845

Thr Lys Asn Leu His Thr Leu Tyr Phe Glu Gln Leu Phe Ser Lys Glu
    850                 855                 860

Asn Glu Gln Glu Asn Phe Leu Phe Gln Leu Asn Gly Glu Ala Glu Leu
865                 870                 875                 880

Phe Phe Arg Pro Lys Thr Glu Glu Lys Arg Leu Gly Tyr Lys Val Trp
                885                 890                 895

Asp Ala Gly Glu Lys Lys Trp Val Lys Ala Lys Glu Lys Glu Asp Gly
            900                 905                 910

Ala Val Ile Asp Arg Lys Arg Tyr Ala Lys Asp Ile Ile Leu Phe His
        915                 920                 925

Cys Pro Ile Thr Leu Asn Arg Val Ser Glu Ser Lys Thr Lys Arg Glu
    930                 935                 940

Met Asp Val Glu Ile Arg Glu Val Leu Ser Ser Thr Pro Gly Val His
945                 950                 955                 960

Ile Ile Gly Val Asp Arg Gly Glu Lys His Leu Ala Tyr Tyr Ser Val
                965                 970                 975
```

```
Ile Asp Gln Asn Gly Lys Ile Ile Glu Thr Asp Thr Leu Asn Ser Ile
            980                 985                 990

Gly Lys Asp Gly Arg Gly Lys Pro  Val Glu Tyr Ala Ser  Lys Leu Glu
        995                 1000                1005

Lys Arg  Ala Gln Glu Arg Glu  Ala Ser Arg Arg Asp  Trp Glu Glu
    1010                 1015                 1020

Val Glu  Ala Ile Lys Asp Leu  Lys Lys Gly Tyr Ile  Ser Gln Val
    1025                 1030                 1035

Ile Arg  Asn Leu Ala Asp Leu  Ile Ile Lys His Asn  Ala Ile Ile
    1040                 1045                 1050

Val Phe  Glu Asp Leu Asn Met  Arg Phe Lys Gln Ile  Arg Gly Gly
    1055                 1060                 1065

Ile Glu  Lys Ser Ala Tyr Gln  Gln Leu Glu Arg Ala  Leu Ile Asp
    1070                 1075                 1080

Lys Leu  Ser Phe Leu Val Lys  Lys Gly Glu Glu Asp  Pro Lys Gln
    1085                 1090                 1095

Thr Gly  His Ile Leu Arg Ala  Tyr Gln Leu Ala Ala  Pro Val Ile
    1100                 1105                 1110

Ala Phe  Lys Asp Met Gly Lys  Gln Thr Gly Leu Ile  Phe Tyr Thr
    1115                 1120                 1125

Gln Ala  Gly Tyr Thr Ser Lys  Thr Cys Pro Glu Cys  Gly Tyr Arg
    1130                 1135                 1140

Arg Asn  Ile Lys Cys Leu Phe  Glu Asn Ile Glu Gln  Ala Lys Thr
    1145                 1150                 1155

Leu Ile  Glu Asn Leu Glu Ser  Ile Asn Tyr Asn Lys  Lys Glu Asp
    1160                 1165                 1170

Val Phe  Gln Ile Ser Tyr Ser  Leu Glu Lys Leu Ser  Ser Lys Asp
    1175                 1180                 1185

Gln Lys  Lys Glu Lys Lys Val  Ser Asn Glu Leu Tyr  Ala Lys Thr
    1190                 1195                 1200

Leu Lys  Lys Asp Ile Phe Ile  Leu Thr Thr Lys Asn  Ala Leu Arg
    1205                 1210                 1215

Tyr Lys  Trp Tyr Asp Arg Tyr  Ser Glu Lys Ala Lys  Val Ala Lys
    1220                 1225                 1230

Arg Gly  Ile Asp Glu Tyr Lys  Gly Glu Val Asn Glu  Ser Glu Thr
    1235                 1240                 1245

Lys Lys  Gly Val Val Lys Glu  Phe Asn Leu Thr Glu  Tyr Leu Lys
    1250                 1255                 1260

Gly Leu  Leu Lys Thr Tyr Glu  Ile Asp Tyr Glu His  Gly Gly Ile
    1265                 1270                 1275

Arg Glu  Gln Ile Leu Ser Val  Ala Arg Gly Arg Glu  Phe Tyr Lys
    1280                 1285                 1290

Asp Phe  Leu Tyr Ala Leu Phe  Leu Leu Thr Glu Thr  Arg His Ser
    1295                 1300                 1305

Ile Ser  Gly Arg Asn Thr Asp  Tyr Ile Gln Cys Pro  Glu Cys Glu
    1310                 1315                 1320

Phe Asp  Ser Arg Lys Gly Phe  Lys Asp Ile Lys Glu  Phe Asn Gly
    1325                 1330                 1335

Asp Ala  Asn Gly Ala Tyr Asn  Ile Ala Arg Lys Gly  Ile Met Ile
    1340                 1345                 1350

Leu Glu  Lys Ile Lys Gln Phe  Lys Lys Asp Asn Asp  Gly Asn Leu
    1355                 1360                 1365

Glu Lys  Met Gly Trp Gly Asp  Leu Ser Ile Ser Ile  Glu Glu Trp
```

1370 1375 1380

Asp Lys Phe Thr Gln Lys Glu
1385 1390

<210> SEQ ID NO 121
<211> LENGTH: 1265
<212> TYPE: PRT
<213> ORGANISM: Unknown
<220> FEATURE:
<223> OTHER INFORMATION: Firmicutes bacterium CAG_194_44_15

<400> SEQUENCE: 121

Met Glu Arg Lys Asp Phe Ile Asn Tyr Asp Gln Val Ser Lys Thr Ile
1 5 10 15

Arg Asn Gly Leu Ile Pro Thr Glu Tyr Thr Leu Lys Asn Ile Glu Glu
20 25 30

Thr Gly Val Leu Val Ser Asp Glu Tyr Arg Ala Glu Val Arg Asn Val
35 40 45

Leu Lys Lys Ile Met Asp Asp Tyr Tyr Lys Glu Tyr Ile Asn Met Cys
50 55 60

Leu Asn Arg Glu Ile Lys Met Asp Trp Arg Pro Leu Phe Asp Ala Tyr
65 70 75 80

Glu Leu Val Lys Lys Gly Lys Met Lys Pro Lys Glu Ile Glu Asn Ile
85 90 95

Gln Asp Glu Lys Arg Lys Glu Ile Tyr Asp Ile Leu Ser Ala His Asp
100 105 110

Glu Phe Lys Lys Met Phe Ser Ala Lys Met Ile Thr Glu Leu Leu Pro
115 120 125

Gln Phe Ile Ser Gln Ser Thr Gly Tyr Asn Glu Asp Glu Lys Lys Gln
130 135 140

Tyr Glu Glu Val Ile His Ile Tyr Ser Arg Phe Thr Ser Asp Phe Thr
145 150 155 160

Asp Phe Phe Gln Asn Arg Lys Asn Val Phe Ser Ser Ala Gly Ile Ala
165 170 175

Thr Ser Ile Cys Asn Arg Ile Val Asn Glu Asn Ala Glu Ile Phe Ser
180 185 190

Asp Asn Lys Ser Thr Phe Asp Arg Ile Lys Lys Asp Ile Ser Tyr Ile
195 200 205

Asp Glu Ile Ile Asp Ser Asp Leu Lys Thr Tyr Leu Asp Gly Trp Glu
210 215 220

Leu Glu Gln Ile Tyr Ser Val Asp Phe Tyr Ser Arg Leu Met Ser Gln
225 230 235 240

Ser Gly Ile Asp Phe Tyr Asn Met Ile Ser Gly Ala Val Asn Lys Ala
245 250 255

Val Asn Glu Tyr Cys Gln Lys Asn Gly Leu Asn Lys Asn Lys Tyr Leu
260 265 270

Leu Arg Lys Leu Arg Lys Gln Ile Leu Ser Asn Ser Glu Ser Thr Phe
275 280 285

Gln Ile Pro Glu Lys Phe Leu Ala Asp Glu Glu Val Tyr Lys Ala Val
290 295 300

Gly Gln Phe Ile Asp Asn Ile Lys Ser Lys Asn Val Ile Glu Ile Leu
305 310 315 320

Lys Asp Ile Gly Ser Asn Cys Glu Asn Tyr Asp Leu Arg Arg Ile Tyr
325 330 335

Ile Ala Glu Ser Ala Tyr Glu Asp Val Ser Ile Phe Met Gly Tyr Gly

-continued

```
            340                 345                 350

Trp Asn Gly Ile Lys Gly Cys Leu Glu Lys Lys Tyr Glu Lys Glu Ile
        355                 360                 365

Ala Pro Gly Lys Ala Lys Asp Ile Lys Ile Lys Lys Leu Ile Ser Gln
    370                 375                 380

Glu Lys Glu Arg Ser Ile Gly Glu Ile Asp Glu Leu Phe His Ile Tyr
385                 390                 395                 400

Gly Glu Glu Lys Asp Gly Lys Ala Ala Ile Gln Tyr Ile Glu Glu Val
                405                 410                 415

Val Glu Leu Cys Asn Glu Val Pro Thr Arg Leu Val Tyr Asp Ser Ser
            420                 425                 430

Glu Lys Leu Thr Glu Asn Asp Asn Lys Ala Ala Glu Ile Lys Asn Val
        435                 440                 445

Leu Asp Tyr Tyr Phe Lys Ile Phe His Trp Ile Lys Thr Phe Ile Thr
    450                 455                 460

Asp Asp Ile Leu Asp Lys Asp Ile Val Phe Tyr Ser Gly Ile Glu Phe
465                 470                 475                 480

Ala Tyr Glu Glu Ile Lys Asp Ile Val Pro Leu Tyr Asn Lys Val Arg
                485                 490                 495

Asn Tyr Val Thr Gln Lys Pro Tyr Ser Ser Glu Lys Ile Lys Leu Lys
            500                 505                 510

Phe Gly Thr Pro Thr Leu Ala Asn Gly Trp Ser Lys Ser Lys Glu Phe
        515                 520                 525

Asp Asn Asn Ala Ile Leu Leu Val Arg Asp Asn Lys Tyr Tyr Leu Gly
    530                 535                 540

Ile Phe Asn Val Leu Asn Lys Pro Asp Lys Lys Ile Met Ala Gly Tyr
545                 550                 555                 560

Ala Asn Lys Lys Asn Ser Ser Asp Tyr Ala Lys Met Val Tyr Asn Leu
                565                 570                 575

Leu Pro Gly Pro Ser Lys Met Leu Pro Lys Val Cys Leu Ser Gln Lys
            580                 585                 590

Gly Lys Asp Thr Tyr His Pro Ser Ala Tyr Ile Val Asp Asn Tyr Glu
        595                 600                 605

Arg Lys Ala His Val Lys Ser Ser Glu His Phe Ser Ile Gln Tyr Cys
    610                 615                 620

His Asp Leu Ile Asp Tyr Phe Lys Glu Cys Ile Lys Arg Asn Asp Asp
625                 630                 635                 640

Trp Lys Cys Phe Asp Phe Lys Phe Ser Asp Thr Glu Gln Tyr Asn Asp
                645                 650                 655

Ile Ser Glu Phe Tyr Lys Glu Val Glu Leu Gln Gly Tyr Ser Ile Gly
            660                 665                 670

Trp Thr Tyr Ile Ser Gly Glu Asp Ile Glu Ala Leu Asp Lys Glu Gly
        675                 680                 685

Lys Leu Tyr Leu Phe Gln Ile Tyr Asn Lys Asp Phe Ser Glu Gln Ser
    690                 695                 700

His Gly Thr Asp Asn Leu His Thr Met Tyr Leu Lys Asn Leu Phe Ser
705                 710                 715                 720

Pro Glu Asn Leu Asn Asn Ile Val Leu Lys Leu Asn Gly Glu Ala Glu
                725                 730                 735

Leu Phe Tyr Arg Lys Ser Ser Ile Lys Lys Pro Val Val His Lys Lys
            740                 745                 750

Gly Ser Ile Leu Val Asn Lys Thr Tyr Thr Glu Lys Thr Gly Asn Gly
        755                 760                 765
```

```
Glu Glu Val Arg Arg Pro Val Pro Asp Asp Val Tyr Leu Glu Leu Val
    770                 775                 780

Asn Tyr Tyr Asn Gly Glu Gln Lys Ala Ile Leu Ser Asp Glu Ala Lys
785                 790                 795                 800

Lys Tyr Met Lys Val Val Glu His His Glu Ala Val Lys Asp Ile Thr
                805                 810                 815

Lys Asp Tyr Arg Tyr Thr Val Asn Lys Phe Phe Ile His Leu Pro Ile
            820                 825                 830

Thr Ile Asn Phe Lys Ala Glu His Thr Gly Asn Leu Asn Glu Met Val
        835                 840                 845

Ile Gln Tyr Ile Ala Lys Gln Glu Asn Met His Val Ile Gly Ile Asp
    850                 855                 860

Arg Gly Glu Arg Asn Leu Ile Tyr Val Ser Val Ile Asp Met Asn Gly
865                 870                 875                 880

Lys Ile Lys Glu Gln Lys Ser Phe Asn Ile Val Asn Ser Tyr Asn Tyr
                885                 890                 895

Gln Glu Lys Leu Arg Gly Arg Glu Lys Asp Arg Leu Asn Ala Arg Lys
            900                 905                 910

Asn Trp Lys Gln Ile Ala Asn Ile Lys Glu Met Lys Glu Gly Tyr Leu
        915                 920                 925

Ser Leu Val Ile His Glu Ile Thr Glu Met Met Met Lys Tyr Asn Ala
    930                 935                 940

Ile Ile Ala Met Glu Asp Leu Asn Tyr Gly Phe Lys Arg Gly Arg Phe
945                 950                 955                 960

Lys Val Glu Arg Gln Val Tyr Gln Lys Phe Glu Thr Met Leu Ile Ser
                965                 970                 975

Lys Leu Asn Tyr Leu Val Asp Lys His Lys Lys Val Asp Glu Pro Gly
            980                 985                 990

Gly Leu Leu Arg Gly Tyr Gln Phe  Ala Tyr Val Pro Ala  Ser Leu Asp
        995                 1000                 1005

Arg Leu  Gly Arg Gln Cys Gly  Phe Ile Phe Tyr Val  Pro Ala Ala
    1010                 1015                 1020

Tyr Thr  Ser Lys Ile Asp Pro  Thr Thr Gly Phe Val  Asp Leu Phe
    1025                 1030                 1035

Asn His  Ser Glu Leu Ile Lys  Ala Gly Lys Arg Arg  Asp Asn Leu
    1040                 1045                 1050

Ser Lys  Phe Asp Gly Ile Tyr  Tyr Asp Glu Gln Lys  Asp Met Phe
    1055                 1060                 1065

Cys Tyr  Ala Phe Asp Tyr Lys  Asn Phe Val Thr His  Asn Thr Asp
    1070                 1075                 1080

Ile Tyr  Gln Asn Ser Trp Glu  Ile Tyr Thr Asn Lys  Glu Arg Leu
    1085                 1090                 1095

Arg Lys  Ile Phe Gly Asn Gly  Arg Pro Thr Gly Lys  Thr Glu Lys
    1100                 1105                 1110

Ile Glu  Leu Thr Gln Met Met  Lys Glu Val Leu Thr  Gly Ala Gly
    1115                 1120                 1125

Val Glu  Tyr Lys Asp Gly His  Asn Leu Ile Asp Asp  Ile Leu Asn
    1130                 1135                 1140

Ser Asn  Asp Asn Cys Ile Lys  Gln Val Leu Asp Ile  Phe Leu Tyr
    1145                 1150                 1155

Ser Ile  Gln Leu Arg Asn Ser  Lys Gly Glu Asn Glu  Asp Ser Lys
    1160                 1165                 1170
```

-continued

```
Glu Ser  Asp Tyr Asp Arg Ile  Ile Ser Pro Val Leu  Asn Gln Glu
    1175                 1180                 1185

Asn Glu  Phe Phe Asp Ser Val  Val Tyr Ala Asp Lys  Tyr Lys Lys
    1190                 1195                 1200

Asp Glu  Lys Leu Ala Asp Lys  Pro Ile Asp Ala Asp  Ala Asn Gly
    1205                 1210                 1215

Ala Tyr  Cys Ile Ala Leu Lys  Gly Leu Tyr Glu Ile  Leu Gln Ile
    1220                 1225                 1230

Lys Asn  Asn Trp Lys Glu Gly  Glu Val Phe Ser Arg  Asp Thr Leu
    1235                 1240                 1245

Lys Ile  Thr Asn Ala Asp Trp  Leu Arg Phe Met Gln  Ser Arg Gly
    1250                 1255                 1260

Phe Glu
    1265


<210> SEQ ID NO 122
<211> LENGTH: 1322
<212> TYPE: PRT
<213> ORGANISM: Unknown
<220> FEATURE:
<223> OTHER INFORMATION: Candidatus Gottesmanbacteria bacterium
      CG1_02_37_22

<400> SEQUENCE: 122

Met Thr Gly Ile Phe Lys Asp Phe Thr His Leu Tyr Glu Leu Gln Lys
1               5                   10                  15

Thr Leu Arg Phe Glu Leu Ile Pro Val Gly Arg Thr Lys Glu Leu Leu
            20                  25                  30

Glu Lys Asn His Val Phe Glu Lys Asp Glu Lys Ile Ala Glu Asn Tyr
        35                  40                  45

Lys Asp Val Lys Lys Tyr Phe Asp Arg Leu His Lys Glu Phe Ile Lys
    50                  55                  60

Asp Ala Phe Ser His Thr Asn Leu Pro Glu Asn Leu Leu Glu Gly Tyr
65                  70                  75                  80

Glu Gln Lys Tyr Phe Ser His Lys Leu Asn Pro Ser Arg Ala Ser Arg
                85                  90                  95

Ile Asp Leu Glu Lys Ile Ala Lys Arg Leu Arg Thr Ile Leu Leu Lys
            100                 105                 110

Ser Phe Asn Thr Glu Ala Asp Gln Trp Lys Asn Arg Tyr Leu Lys Asn
        115                 120                 125

Ile Glu Gln Thr Leu Lys Asn Lys Asn Glu Lys Gln Gln Lys Lys Glu
    130                 135                 140

Leu Glu Lys Lys Leu Lys Lys Ile Lys Glu Gly Thr Lys Gly Ile Glu
145                 150                 155                 160

Leu Phe Phe Lys Val Glu Val Phe Asp Phe Leu Lys Tyr Lys Tyr Pro
                165                 170                 175

Glu Ala Gln Ile Asn Gly Lys Ser Ile Phe Asp Pro Phe Asn Lys Phe
            180                 185                 190

Gly Cys Tyr Phe Lys Lys Phe His Glu Thr Arg Ile Asn Phe Tyr Lys
        195                 200                 205

Asp Asp Gly Thr Ser Thr Ala Ile Pro Thr Arg Ile Ile Asn Asp Asn
    210                 215                 220

Leu Ser Ile Phe Leu Glu Asn Lys Lys Ile Phe Glu Ser Lys Tyr Ser
225                 230                 235                 240

Lys Lys His Lys Ser Val Phe Ala Lys Asn Glu Leu Arg Ile Phe Val
                245                 250                 255
```

```
Leu Phe Tyr Phe Asn Asn Cys Phe Ser Gln Lys Gln Ile Asp Gly Tyr
            260                 265                 270

Asn Asn Thr Ile Ala Leu Ile Asn Ser Asn Val Asn Gln Leu Arg Gln
        275                 280                 285

Asn Asn Pro Glu Val Ser Lys Lys Asp Leu Pro Phe Phe Lys Arg Leu
    290                 295                 300

Phe Lys Gln Ile Leu Ser Gln Pro Ser Lys Gln Glu Ile Glu Gln Asp
305                 310                 315                 320

Ser Phe Ile Glu Ile Phe Gln Asp Glu Asp Val Phe Pro Thr Met Gln
                325                 330                 335

Lys Phe Ile Asn Glu Asn Lys Ile Cys Ile Pro Lys Ala Lys Ser Ile
            340                 345                 350

Phe Lys Lys Phe Ile Ser Ser Gln Lys Val Lys Ser Asp Glu Tyr Asn
        355                 360                 365

Ile Ser Gln Ile Tyr Val Ala Lys Arg Phe Ile Asn Thr Ile Ser Asn
    370                 375                 380

Lys Trp Phe Ser Asn Trp Asn Thr Ile Arg Asn Leu Leu Ile Pro Lys
385                 390                 395                 400

Asp Lys Lys Asn Ile Pro Asp Phe Ile Ser Val Thr Ser Leu Lys Ala
                405                 410                 415

Ala Leu Gln Lys Thr Gln Asn Ile Val Glu Val Asn Asp Leu Phe Arg
            420                 425                 430

Lys Glu Tyr Arg Asp Ile Leu Glu Glu Gly Ser Asp Phe Tyr Gln Ile
        435                 440                 445

Phe Leu Lys Ile Trp Glu Lys Glu Phe Glu Lys Ala Thr Asp Ile Tyr
    450                 455                 460

Leu Asn Glu Thr Lys Glu Ile Glu Lys Met Ile Thr Glu Asp Lys Lys
465                 470                 475                 480

Tyr Leu Pro Asn Lys Lys Gly Arg Leu Lys Ser Gly Lys Lys Gly Ser
                485                 490                 495

Ile Gln Lys Glu Lys Phe Leu Asp Tyr Thr Gln Ser Val Phe Asp Ile
            500                 505                 510

Tyr Leu Met Met Lys Tyr Phe Ser Leu Glu Lys Gly Lys Glu Arg Val
        515                 520                 525

Trp Asn Pro Glu Ala Leu Asp Glu Asp Ala Ile Gly Gly Phe Tyr Glu
    530                 535                 540

Lys Phe Lys Glu Tyr Tyr Glu Asn Ile Asn Thr Trp Lys Tyr Phe Asn
545                 550                 555                 560

Val Phe Arg Asn Tyr Leu Thr Lys Lys Pro Tyr Asn Ser Glu Lys Ile
                565                 570                 575

Lys Leu Asn Phe Glu Cys Ser Ser Leu Leu Ser Gly Trp Ser Lys Asn
            580                 585                 590

Tyr Asp Ser Tyr Gly Ala Leu Ile Phe Glu Lys Asn Glu Lys Tyr Tyr
        595                 600                 605

Leu Gly Ile Ile Asn Gly Thr Lys Phe Thr Lys Asp Glu Ile Glu Gln
    610                 615                 620

Leu Tyr Leu Asp Ile Arg Asn Asn Asn Ile Ser Leu Arg Leu Val Tyr
625                 630                 635                 640

Asn Tyr Gln Lys Pro Asp Phe Lys Asn Phe Pro Lys Leu Phe Ile Arg
                645                 650                 655

Ser Ser Gly Ser Asn Phe Ala Pro Ala Val Lys Lys Tyr Asn Leu Pro
            660                 665                 670
```

-continued

```
Ile Asp Ser Val Leu Asn Ile Tyr Asp Lys Gly Leu Phe Lys Thr Ser
        675                 680                 685

Asn Lys Ser Ser Gln Asn Tyr His Glu Ser Leu Lys Lys Ile Ile Asp
    690                 695                 700

Tyr Phe Lys Leu Gly Ile Ser Gln His Glu Ser Tyr Lys Gly Phe Ser
705                 710                 715                 720

Phe Lys Trp Gln Glu Thr Ser Glu Tyr Asp Asn Ile Ser Asp Phe Tyr
                725                 730                 735

Lys Asp Ala Thr Arg Ser Cys Tyr Lys Val Thr Trp Glu Asn Ile Asn
            740                 745                 750

Phe Ser Lys Leu Tyr Glu Leu Ile Glu Ser Gly Arg Leu Tyr Leu Phe
        755                 760                 765

Gln Ile Tyr Asn Lys Asp Phe Glu Leu Asp Glu Asn Ile Ala Pro Lys
    770                 775                 780

Gly Tyr Asn Phe Lys Asp Lys Asn Gly Arg Arg Asn Leu His Ser Ile
785                 790                 795                 800

Tyr Trp Lys Ala Leu Phe Ser Asn Thr Asn Phe Lys Lys Thr Ile Leu
                805                 810                 815

Lys Leu Asn Gly Gly Ala Glu Leu Phe Tyr Arg Lys Leu Thr Lys Asn
            820                 825                 830

Leu Thr Lys Asp Pro Ile Ile Thr Val Lys Asn Gln Ile Lys Ile Ile
        835                 840                 845

Lys Lys Asn Asn Asn Ile Phe His Lys Lys Arg Phe Thr Gln Asn Lys
    850                 855                 860

Ile Tyr Phe His Cys Pro Val Ser Ile Asn Phe Thr Glu Asn Asp Trp
865                 870                 875                 880

Lys Ile Asn Thr Lys Ile Cys Asn Thr Ile Arg Asn Asn Ser Lys Val
                885                 890                 895

Lys Ile Ile Gly Ile Asp Arg Gly Glu Lys Asn Leu Ala Tyr Tyr Ser
            900                 905                 910

Val Ile Asp His Gln Gly Asn Ile Leu Glu Thr Asp Ser Phe Asn Glu
        915                 920                 925

Val Gln Glu Arg Glu Asp Arg Glu Pro Thr Asp Tyr Gln Lys Lys Leu
    930                 935                 940

Asp Gln Ile Gln Lys Glu Arg Asp Trp Gln Arg Lys Ser Trp Gln Glu
945                 950                 955                 960

Ile Ser Ser Ile Lys Glu Met Lys Lys Gly Tyr Ile Ser Gln Val Val
                965                 970                 975

His Gln Ile Cys Lys Leu Ile Arg Lys Tyr Glu Ala Ile Val Val Phe
            980                 985                 990

Glu Asp Leu Asn Ile Gly Phe Lys  Arg Gly Arg Phe Ala  Ile Glu Lys
        995                 1000                1005

Gln Ile  Tyr Gln Asn Leu Glu  Leu Ala Leu Ala Lys  Lys Leu Asn
    1010                 1015                1020

Tyr Met  Val Phe Lys Asp Ala  Lys Glu Glu Glu Thr  Gly His Phe
    1025                 1030                1035

Leu Gln  Ala Tyr Gln Leu Thr  Pro Pro Val Ile Asn  Phe Gln Asp
    1040                 1045                1050

Ile Gly  Lys Gln Cys Gly Ile  Ile Phe Tyr Val Pro  Ala Ser Tyr
    1055                 1060                1065

Thr Ser  Ala Ile Cys Pro Ala  Cys Gly Phe Arg Lys  Asn Ile Ser
    1070                 1075                1080

Thr Ser  Val Glu Lys Ile Glu  Lys Asn Ile Asp Leu  Ile Asn Lys
```

```
    1085                1090                1095

Phe Asn  Ile Val Tyr Asp Pro  Asp Lys Asp Arg Phe  Cys Phe Arg
    1100                1105                1110

Tyr Lys  Arg Ser Asp Phe Ile  Lys Ser Glu Lys Glu  Lys Glu Asp
    1115                1120                1125

Asp Ser  Lys Val Lys Leu Tyr  Ser Asn Thr Lys Leu  Pro Asp Asp
    1130                1135                1140

Phe Thr  Phe Tyr Ser Asn Val  Glu Arg Phe Lys Tyr  Ile Arg Asp
    1145                1150                1155

Gln Asn  Asn Arg Gly Gly Lys  Val Glu Leu Lys Tyr  Pro Asn Asp
    1160                1165                1170

Ser Leu  Lys Lys Leu Phe His  Glu Asn Gly Ile Asn  Phe Gln Asn
    1175                1180                1185

Phe Ser  Asn Ile Ser Gln Leu  Ile Lys Thr Arg Asn  Phe Glu Asn
    1190                1195                1200

Glu Asn  Phe Tyr Lys Pro Phe  Ile Tyr Ile Ile Ser  Leu Ile Leu
    1205                1210                1215

Gln Leu  Arg Asn Thr Thr Ile  Glu Ile Asn Gln Asn  Glu Asn Asn
    1220                1225                1230

Glu Lys  Tyr Arg Asp Phe Ile  Ser Cys Pro His Cys  Tyr Phe His
    1235                1240                1245

Ser Glu  Asn Asn Leu Ile Thr  Leu Thr Lys Arg Tyr  Lys Gly Lys
    1250                1255                1260

Lys Pro  Phe Glu Phe Asn Gly  Asp Ala Asn Gly Ala  Tyr Asn Ile
    1265                1270                1275

Ala Arg  Lys Gly Ile Leu Ile  Leu Gln Lys Ile Asn  Lys Ala Lys
    1280                1285                1290

Arg Leu  Glu Glu Ile Glu Tyr  Gly Gly Leu Thr Val  Thr Gln Gln
    1295                1300                1305

Glu Tyr  Asp Lys Tyr Leu Ala  Leu Val Ser Ser Lys  Lys Ala
    1310                1315                1320


<210> SEQ ID NO 123
<211> LENGTH: 1329
<212> TYPE: PRT
<213> ORGANISM: Unknown
<220> FEATURE:
<223> OTHER INFORMATION: Candidatus Gracilibacteria bacterium
      CG1_02_38_174

<400> SEQUENCE: 123

Met Ser Asn Asn Phe Gln Glu Phe Thr Gln Lys Tyr Ala Leu Ser Lys
1               5                   10                  15

Thr Leu Arg Phe Glu Leu Lys Pro Val Gly Lys Thr Lys Glu Ile Leu
            20                  25                  30

Glu Lys Glu Met Pro Met Tyr Gln Ile Ile Asn Ala Asp Lys Asn Ile
        35                  40                  45

Lys Ala Lys Tyr Ile Gln Thr Lys Pro Phe Phe Asp Gln Leu His Arg
    50                  55                  60

Asp Phe Ile Lys Glu Ala Phe Glu Asn Val Glu Leu Ser Gly Leu Ser
65                  70                  75                  80

Asp Phe Phe Glu Asn Trp Lys Ile Tyr Lys Gln Asp Lys Lys Ala Asn
                85                  90                  95

Glu Lys Ile Tyr Lys Lys Ser Ala Glu Asn Leu Arg Lys Glu Val Val
            100                 105                 110
```

-continued

```
Ser Phe Leu Asn Ala Lys Gly Lys Asp Trp Ala Glu Lys Tyr His Ser
        115                 120                 125

Ser Gly Leu Lys Lys Ala Asp Ile Glu Ile Leu Phe Glu Glu Gly Ile
    130                 135                 140

Phe Lys Val Leu Glu Ile Arg Tyr Gly Thr Asp Thr Asn Ser Phe Ile
145                 150                 155                 160

Thr Asn Ala Thr Thr Gly Glu Ile Thr Ser Ile Phe Gln Gly Trp Lys
                165                 170                 175

Gly Phe Thr Gly Tyr Phe Leu Lys Phe Trp Asn Thr Arg Glu Asn Tyr
            180                 185                 190

Tyr Lys Thr Asp Gly Thr Ser Thr Ala Ile Ala Thr Arg Ile Val Asp
        195                 200                 205

Gln Asn Leu Pro Arg Tyr Leu Glu Asn Leu Glu Ile Phe Glu Lys Met
    210                 215                 220

Lys Gly Lys Ile Asp Phe Glu Ser Val Arg Gly Asp Phe Ser Asp Phe
225                 230                 235                 240

Glu Lys Ile Gly Thr Val Glu Tyr Tyr Ser Thr Cys Leu Leu Gln Glu
                245                 250                 255

Gly Ile Asp Gly Tyr Asn Arg Ile Ile Gly Gly Tyr Thr Tyr Glu Asn
            260                 265                 270

Gly Glu Lys Ile Lys Gly Ile Asn Glu Ile Ile Asn Leu Tyr Arg Gln
        275                 280                 285

Thr His Lys Asp Glu Lys Val Pro Phe Leu Lys Thr Leu Asp Lys Gln
    290                 295                 300

Ile Gly Ser Glu Lys Ile Ala Phe Met Glu Thr Ile Asp Thr Pro Glu
305                 310                 315                 320

Glu Phe Arg Lys Ile Phe Glu Glu Phe Val Leu Lys Ser Ser Glu Lys
                325                 330                 335

Val Val Leu Leu Lys Gln Cys Leu Asn His Leu Phe Glu Asn Glu Leu
            340                 345                 350

Thr Asp Gly Val Phe Leu Ser Lys Glu Ser Leu Asn Thr Ile Ser His
        355                 360                 365

Lys Trp Ile Asp Ile Gly Asn Met Lys Leu Phe His Glu Ser Leu Phe
    370                 375                 380

Thr Ile Leu Lys Lys Glu Gly Ala Lys Tyr Asp Ser Lys Glu Asp Glu
385                 390                 395                 400

Tyr Lys Phe Pro Asp Phe Ile Arg Ile Ser Asp Ile Lys Thr Ala Leu
                405                 410                 415

Val Lys Ile Thr Thr Glu Ser Phe Phe Trp Lys Asn Arg Tyr Leu Tyr
            420                 425                 430

Glu Lys Asp Glu Asn Pro Thr Gly Phe Leu Thr Ser Asp Asn Ser Leu
        435                 440                 445

Trp Glu Gly Phe Ile Gln Ile Phe Ser His Glu Phe Ser Ser Leu Phe
    450                 455                 460

Glu Arg Thr Glu Lys Asp Glu Glu Gly Lys Asp Ile Gln Trp Gly Tyr
465                 470                 475                 480

Asp Ile Ser Leu Leu Asn Ile Gln Lys Leu Leu Glu Asn Asn Glu Tyr
                485                 490                 495

Asn Pro Asn Asp Glu Lys Asn Lys Ile Ile Ile Lys Ser Phe Ala Asp
            500                 505                 510

Asp Ile Leu Arg Ile Tyr Gln Met Gly Lys Tyr Phe Ala Leu Glu Lys
        515                 520                 525

Lys Arg Gln Trp Asn Pro Asp Asn Leu Glu Ile Gly Glu Phe Tyr Ser
```

-continued

```
    530                 535                 540

His Pro Glu Ile Gly Tyr Asp Lys Phe Tyr Phe Asp Ser Tyr Lys Ile
545                 550                 555                 560

Ile Val Gln Gly Tyr Asn Asp Ile Arg Asn Tyr Leu Thr Lys Asn Pro
                565                 570                 575

Trp Ser Glu Glu Lys Trp Lys Leu Asn Phe Glu Asn Pro Thr Leu Ala
            580                 585                 590

Asn Gly Trp Asp Lys Asn Lys Glu Thr Asp Asn Ser Cys Ile Phe Leu
        595                 600                 605

Lys Arg Asp Asn Lys Phe Phe Leu Ala Leu Met Ser Arg Gly Asn Asn
    610                 615                 620

Gln Val Phe Asp Glu Arg Asn Ile Gln Lys Phe Ala Gln Asn Ile Glu
625                 630                 635                 640

Gln Gly Lys Tyr Glu Lys Met Val Tyr Lys Tyr Met Lys Asp Val Ala
                645                 650                 655

Leu Gly Ile Pro Lys Ala Thr Thr Gln Leu Asn Ala Val Gln Glu His
            660                 665                 670

Phe Phe Gln Ser Asp Lys Asp Tyr Ile Ile Thr Lys Gly Gly Ser Ser
        675                 680                 685

Ile Gly Glu Phe Ile Lys Pro Leu Arg Val Thr Lys Arg Ile Phe Glu
    690                 695                 700

Leu Asn Asn Arg Ile Tyr Pro Lys Asp Asn Leu Gly Ile Ser Phe Leu
705                 710                 715                 720

Arg Asn Gln Val Asn Glu Lys Glu Gln Lys Asn Tyr Ile Lys Ile Phe
                725                 730                 735

Gln Lys Glu Phe Ile Thr Leu Gly Gly Asp Glu Val Val Tyr Lys Lys
            740                 745                 750

Ala Val His Asp Trp Ile Asp Phe Cys Lys Glu Tyr Thr Lys Ser Tyr
        755                 760                 765

Pro Ser Cys Ala Tyr Phe Asp Tyr Ser Gly Leu Lys Asp Thr Lys Glu
    770                 775                 780

Tyr Ser Ser Ile Asp Glu Phe Tyr Asn Asp Leu Asp Ser Phe Gly Tyr
785                 790                 795                 800

Gln Ile Ser Trp Gln Asp Ile Ser Ser Ser Tyr Ile Asp Glu Leu Val
                805                 810                 815

Glu Ser Gly Lys Leu Tyr Leu Phe Glu Ile Tyr Asn Gln Asp Phe Ser
            820                 825                 830

Asn Gly Lys Thr Gly Ala Lys Asn Leu His Thr Leu Tyr Phe Glu His
        835                 840                 845

Ile Phe Ser Lys Glu Asn Gln Glu Val Asn Phe Pro Leu Lys Leu Asn
    850                 855                 860

Gly Gln Ala Glu Leu Phe Phe Arg Pro Lys Ser Ile Glu Ala Lys Gly
865                 870                 875                 880

Glu Asn Arg Lys Phe Asn Arg Glu Ile Ile Ala Lys Lys Arg Tyr Thr
                885                 890                 895

Glu Asp Lys Ile Phe Phe His Val Pro Leu Thr Leu Asn Arg Thr Glu
            900                 905                 910

Gly Asp Ile Tyr Gly Phe Asn Thr Glu Ile Asn Asn Phe Leu Ala His
        915                 920                 925

Asn Pro Asp Ile Asn Ile Ile Gly Ile Asp Arg Gly Glu Lys His Leu
    930                 935                 940

Ala Tyr Tyr Ser Val Ile Asp Gln Lys Gly Asn Ile Ile Glu Ser Asp
945                 950                 955                 960
```

```
Ser Leu Asn Thr Val Asn Glu Ile Asn Tyr Gly Glu Lys Leu Thr Asp
                965                 970                 975

Thr Ala Glu Lys Arg Lys Gln Ala Arg Gln Asp Trp Gln Ala Val Glu
            980                 985                 990

Gly Ile Lys Asn Leu Lys Lys Gly  Tyr Ile Ser Ala Val  Val His Lys
        995                 1000                 1005

Leu Thr  Asp Leu Ile Ile Lys  Tyr Asn Ala Ile Val  Ile Phe Glu
    1010                 1015                 1020

Asp Leu  Asn Met Arg Phe Lys  Gln Ile Arg Gly Gly  Ile Glu Lys
    1025                 1030                 1035

Ser Val  Tyr Gln Gln Leu Glu  Lys Ala Leu Ile Glu  Lys Leu Asn
    1040                 1045                 1050

Tyr Leu  Val Glu Lys Gly Glu  Ile Asn Pro Glu Lys  Ala Gly His
    1055                 1060                 1065

Leu Leu  Asn Ala Tyr Gln Leu  Thr Ala Pro Phe Glu  Thr Phe Lys
    1070                 1075                 1080

Asp Met  Gly Lys Gln Thr Gly  Ile Val Phe Tyr Thr  Gln Ala Ala
    1085                 1090                 1095

Tyr Thr  Ser Lys Ile Asp Pro  Val Thr Gly Trp Arg  Pro His Leu
    1100                 1105                 1110

Tyr Leu  Lys Tyr Ser Ser Ala  Glu Gln Val Lys Lys  Glu Ile Ala
    1115                 1120                 1125

Lys Phe  Ser Asn Ile Ile Trp  Asn Asn Thr Glu Lys  Arg Phe Asp
    1130                 1135                 1140

Phe Met  Tyr Asp Ile Arg Asn  Phe Ser Thr Gln Lys  Glu Tyr Pro
    1145                 1150                 1155

Lys Asn  Asn Ile Trp Thr Val  Cys Ser Ser Val Glu  Arg Tyr Arg
    1160                 1165                 1170

Trp Asp  Lys Thr Leu Asn Gln  Asn Lys Gly Asp Tyr  Val His Tyr
    1175                 1180                 1185

Lys Ser  Ile Thr Pro Glu Phe  Glu Lys Leu Phe Ser  Asp Phe Gln
    1190                 1195                 1200

Ile Asp  Gly Thr Lys Asn Ile  Leu Glu Gln Ile Asn  Arg Met Glu
    1205                 1210                 1215

Thr Lys  Gly Asn Glu Lys Phe  Phe Lys Ser Phe Ile  Phe Phe Phe
    1220                 1225                 1230

Gly Leu  Ile Cys Gln Ile Arg  Asn Thr Asn Lys Ala  Asp Ser Asp
    1235                 1240                 1245

Glu Asn  Lys Gln Asp Phe Ile  Leu Ser Pro Val Val  Pro Phe Phe
    1250                 1255                 1260

Asp Ser  Arg Asp Ser Glu Asn  Thr Lys Asn Gly Leu  Pro Arg Asn
    1265                 1270                 1275

Gly Asp  Glu Asn Gly Ala Tyr  Asn Ile Ala Arg Lys  Gly Leu Ile
    1280                 1285                 1290

Ile Leu  Gln Lys Ile Asn Glu  Phe Ser Asp Glu Asn  Gly Asn Cys
    1295                 1300                 1305

Asp Lys  Leu Gly Trp Lys Glu  Leu Ser Ile Ser Gln  Val Asp Trp
    1310                 1315                 1320

Asp Asn  Tyr Ile Lys Thr
    1325
```

<210> SEQ ID NO 124
<211> LENGTH: 1231

```
<212> TYPE: PRT
<213> ORGANISM: Unknown
<220> FEATURE:
<223> OTHER INFORMATION: Butyrivibrio fibrisolvens MD2001

<400> SEQUENCE: 124

Met Tyr Tyr Glu Ser Leu Thr Lys Leu Tyr Pro Ile Lys Lys Thr Ile
1               5                   10                  15

Arg Asn Glu Leu Val Pro Ile Gly Lys Thr Leu Glu Asn Ile Lys Lys
            20                  25                  30

Asn Asn Ile Leu Glu Ala Asp Glu Asp Arg Lys Ile Ala Tyr Ile Arg
        35                  40                  45

Val Lys Ala Ile Met Asp Asp Tyr His Lys Arg Leu Ile Asn Glu Ala
    50                  55                  60

Leu Ser Gly Phe Ala Leu Ile Asp Leu Asp Lys Ala Ala Asn Leu Tyr
65                  70                  75                  80

Leu Ser Arg Ser Lys Ser Ala Asp Asp Ile Glu Ser Phe Ser Arg Phe
                85                  90                  95

Gln Asp Lys Leu Arg Lys Ala Ile Ala Lys Arg Leu Arg Glu His Glu
            100                 105                 110

Asn Phe Gly Lys Ile Gly Asn Lys Asp Ile Ile Pro Leu Leu Gln Lys
        115                 120                 125

Leu Ser Glu Asn Glu Asp Asp Tyr Asn Ala Leu Glu Ser Phe Lys Asn
    130                 135                 140

Phe Tyr Thr Tyr Phe Glu Ser Tyr Asn Asp Val Arg Leu Asn Leu Tyr
145                 150                 155                 160

Ser Asp Lys Glu Lys Ser Ser Thr Val Ala Tyr Arg Leu Ile Asn Glu
                165                 170                 175

Asn Leu Pro Arg Phe Leu Asp Asn Ile Arg Ala Tyr Asp Ala Val Gln
            180                 185                 190

Lys Ala Gly Ile Thr Ser Glu Glu Leu Ser Ser Glu Ala Gln Asp Gly
        195                 200                 205

Leu Phe Leu Val Asn Thr Phe Asn Asn Val Leu Ile Gln Asp Gly Ile
    210                 215                 220

Asn Thr Tyr Asn Glu Asp Ile Gly Lys Leu Asn Val Ala Ile Asn Leu
225                 230                 235                 240

Tyr Asn Gln Lys Asn Ala Ser Val Gln Gly Phe Arg Lys Val Pro Lys
                245                 250                 255

Met Lys Val Leu Tyr Lys Gln Ile Leu Ser Asp Arg Glu Glu Ser Phe
            260                 265                 270

Ile Asp Glu Phe Glu Ser Asp Thr Glu Leu Leu Asp Ser Leu Glu Ser
        275                 280                 285

His Tyr Ala Asn Leu Ala Lys Tyr Phe Gly Ser Asn Lys Val Gln Leu
    290                 295                 300

Leu Phe Thr Ala Leu Arg Glu Ser Lys Gly Val Asn Val Tyr Val Lys
305                 310                 315                 320

Asn Asp Ile Ala Lys Thr Ser Phe Ser Asn Val Val Phe Gly Ser Trp
                325                 330                 335

Ser Arg Ile Asp Glu Leu Ile Asn Gly Glu Tyr Asp Asp Asn Asn Asn
            340                 345                 350

Arg Lys Lys Asp Glu Lys Tyr Tyr Asp Lys Arg Gln Lys Glu Leu Lys
        355                 360                 365

Lys Asn Lys Ser Tyr Thr Ile Glu Lys Ile Ile Thr Leu Ser Thr Glu
    370                 375                 380
```

-continued

```
Asp Val Asp Val Ile Gly Lys Tyr Ile Glu Lys Leu Glu Ser Asp Ile
385                 390                 395                 400

Asp Asp Ile Arg Phe Lys Gly Lys Asn Phe Tyr Glu Ala Val Leu Cys
                405                 410                 415

Gly His Asp Arg Ser Lys Lys Leu Ser Lys Asn Lys Gly Ala Val Glu
            420                 425                 430

Ala Ile Lys Gly Tyr Leu Asp Ser Val Lys Asp Phe Glu Arg Asp Leu
        435                 440                 445

Lys Leu Ile Asn Gly Ser Gly Gln Glu Leu Glu Lys Asn Leu Val Val
    450                 455                 460

Tyr Gly Glu Gln Glu Ala Val Leu Ser Glu Leu Ser Gly Ile Asp Ser
465                 470                 475                 480

Leu Tyr Asn Met Thr Arg Asn Tyr Leu Thr Lys Lys Pro Phe Ser Thr
                485                 490                 495

Glu Lys Ile Lys Leu Asn Phe Asn Lys Pro Thr Phe Leu Asp Gly Trp
            500                 505                 510

Asp Tyr Gly Asn Glu Glu Ala Tyr Leu Gly Phe Phe Met Ile Lys Glu
        515                 520                 525

Gly Asn Tyr Phe Leu Ala Val Met Asp Ala Asn Trp Asn Lys Glu Phe
    530                 535                 540

Arg Asn Ile Pro Ser Val Asp Lys Ser Asp Cys Tyr Lys Lys Val Ile
545                 550                 555                 560

Tyr Lys Gln Ile Ser Ser Pro Glu Lys Ser Ile Gln Asn Leu Met Val
                565                 570                 575

Ile Asp Gly Lys Thr Val Lys Lys Asn Gly Arg Lys Glu Lys Glu Gly
            580                 585                 590

Ile His Ser Gly Glu Asn Leu Ile Leu Glu Glu Leu Lys Asn Thr Tyr
        595                 600                 605

Leu Pro Lys Lys Ile Asn Asp Ile Arg Lys Arg Arg Ser Tyr Leu Asn
    610                 615                 620

Gly Asp Thr Phe Ser Lys Lys Asp Leu Thr Glu Phe Ile Gly Tyr Tyr
625                 630                 635                 640

Lys Gln Arg Val Ile Glu Tyr Tyr Asn Gly Tyr Ser Phe Tyr Phe Lys
                645                 650                 655

Ser Asp Asp Asp Tyr Ala Ser Phe Lys Glu Phe Gln Glu Asp Val Gly
            660                 665                 670

Arg Gln Ala Tyr Gln Ile Ser Tyr Val Asp Val Pro Val Ser Phe Val
        675                 680                 685

Asp Asp Leu Ile Asn Ser Gly Lys Leu Tyr Leu Phe Arg Val Tyr Asn
    690                 695                 700

Lys Asp Phe Ser Glu Tyr Ser Lys Gly Arg Leu Asn Leu His Thr Leu
705                 710                 715                 720

Tyr Phe Lys Met Leu Phe Asp Glu Arg Asn Leu Lys Asn Val Val Tyr
                725                 730                 735

Lys Leu Asn Gly Gln Ala Glu Val Phe Tyr Arg Pro Ser Ser Ile Lys
            740                 745                 750

Lys Glu Glu Leu Ile Val His Arg Ala Gly Glu Glu Ile Lys Asn Lys
        755                 760                 765

Asn Pro Lys Arg Ala Ala Gln Lys Pro Thr Arg Arg Leu Asp Tyr Asp
    770                 775                 780

Ile Val Lys Asp Arg Arg Tyr Ser Gln Asp Lys Phe Met Leu His Thr
785                 790                 795                 800

Ser Ile Ile Met Asn Phe Gly Ala Glu Glu Asn Val Ser Phe Asn Asp
```

-continued

```
                805                 810                 815

Ile Val Asn Gly Val Leu Arg Asn Glu Asp Lys Val Asn Val Ile Gly
            820                 825                 830

Ile Asp Arg Gly Glu Arg Asn Leu Leu Tyr Val Val Val Ile Asp Pro
        835                 840                 845

Glu Gly Lys Ile Leu Glu Gln Arg Ser Leu Asn Cys Ile Thr Asp Ser
    850                 855                 860

Asn Leu Asp Ile Glu Thr Asp Tyr His Arg Leu Leu Asp Glu Lys Glu
865                 870                 875                 880

Ser Asp Arg Lys Ile Ala Arg Arg Asp Trp Thr Thr Ile Glu Asn Ile
                885                 890                 895

Lys Glu Leu Lys Ala Gly Tyr Leu Ser Gln Val Val His Ile Val Ala
            900                 905                 910

Glu Leu Val Leu Lys Tyr Asn Ala Ile Ile Cys Leu Glu Asp Leu Asn
        915                 920                 925

Phe Gly Phe Lys Arg Gly Arg Gln Lys Val Glu Lys Gln Val Tyr Gln
    930                 935                 940

Lys Phe Glu Lys Met Leu Ile Asp Lys Leu Asn Tyr Leu Val Met Asp
945                 950                 955                 960

Lys Ser Arg Glu Gln Leu Ser Pro Glu Lys Ile Ser Gly Ala Leu Asn
                965                 970                 975

Ala Leu Gln Leu Thr Pro Asp Phe Lys Ser Phe Lys Val Leu Gly Lys
            980                 985                 990

Gln Thr Gly Ile Ile Tyr Tyr Val  Pro Ala Tyr Leu Thr  Ser Lys Ile
        995                 1000                1005

Asp Pro  Met Thr Gly Phe Ala  Asn Leu Phe Tyr Val  Lys Tyr Glu
    1010                1015                1020

Asn Val  Asp Lys Ala Lys Glu  Phe Phe Ser Lys Phe  Asp Ser Ile
    1025                1030                1035

Lys Tyr  Asn Lys Asp Gly Lys  Asn Trp Asn Thr Lys  Gly Tyr Phe
    1040                1045                1050

Glu Phe  Ala Phe Asp Tyr Lys  Lys Phe Thr Asp Arg  Ala Tyr Gly
    1055                1060                1065

Arg Val  Ser Glu Trp Thr Val  Cys Thr Val Gly Glu  Arg Ile Ile
    1070                1075                1080

Lys Phe  Lys Asn Lys Glu Lys  Asn Asn Ser Tyr Asp  Asp Lys Val
    1085                1090                1095

Ile Asp  Leu Thr Asn Ser Leu  Lys Glu Leu Phe Asp  Ser Tyr Lys
    1100                1105                1110

Val Thr  Tyr Glu Ser Glu Val  Asp Leu Lys Asp Ala  Ile Leu Ala
    1115                1120                1125

Ile Asp  Asp Pro Ala Phe Tyr  Arg Asp Leu Thr Arg  Arg Leu Gln
    1130                1135                1140

Gln Thr  Leu Gln Met Arg Asn  Ser Ser Cys Asp Gly  Ser Arg Asp
    1145                1150                1155

Tyr Ile  Ile Ser Pro Val Lys  Asn Ser Lys Gly Glu  Phe Phe Cys
    1160                1165                1170

Ser Asp  Asn Asn Asp Asp Thr  Thr Pro Asn Asp Ala  Asp Ala Asn
    1175                1180                1185

Gly Ala  Phe Asn Ile Ala Arg  Lys Gly Leu Trp Val  Leu Asn Glu
    1190                1195                1200

Ile Arg  Asn Ser Glu Glu Gly  Ser Lys Ile Asn Leu  Ala Met Ser
    1205                1210                1215
```

Asn Ala Gln Trp Leu Glu Tyr Ala Gln Asp Asn Thr Ile
1220 1225 1230

<210> SEQ ID NO 125
<211> LENGTH: 999
<212> TYPE: PRT
<213> ORGANISM: Unknown
<220> FEATURE:
<223> OTHER INFORMATION: Sneathia amnii strain SN35

<400> SEQUENCE: 125

Met Asn Leu Leu Ile Asn Glu Val Asn Gln Lys Tyr Lys Ser Lys Leu
1 5 10 15

Asn Val Phe Asn Ser Leu Tyr Lys Gln Ile Leu Thr Glu Glu Asp Thr
20 25 30

Lys Ser Phe Val Asp Glu Ile Leu Leu Thr Pro Glu Ser Val Ile Lys
35 40 45

Thr Ile Asp Asn Phe Ile Asp Ser Ile Ile Met Asn Asp Ile Glu Gly
50 55 60

Leu Lys Glu Glu Phe Leu Lys Ile Ser Leu Glu Asn Phe Glu Gly Ile
65 70 75 80

Tyr Ile Ser Asn Lys Lys Leu Asn Glu Ile Ser Asn Arg Lys Phe Gly
85 90 95

Asp Tyr Asn Ser Ile Asn Met Met Ile Lys Gln Ser Met Asn Glu Lys
100 105 110

Gly Ile Leu Ser Lys Lys Glu Ile Asn Glu Leu Ile Pro Asp Leu Glu
115 120 125

Asn Ile Asn Lys Pro Lys Val Lys Ser Phe Asn Leu Ser Phe Ile Phe
130 135 140

Glu Asn Leu Thr Lys Glu His Lys Glu Leu Ile Ile Asp Tyr Ile Arg
145 150 155 160

Glu Asn Ile Cys Asn Val Ile Glu Asn Val Lys Ile Thr Ile Glu Lys
165 170 175

Tyr Arg Asn Ile Asp Asn Lys Ile Glu Phe Lys Asn Asn Ala Glu Lys
180 185 190

Val Ser Lys Ile Lys Glu Met Leu Glu Ser Ile Asn Glu Leu Cys Lys
195 200 205

Leu Ile Lys Glu Phe Asn Thr Asp Glu Ile Glu Lys Asn Asn Glu Phe
210 215 220

Tyr Asn Ile Leu Asn Lys Asn Phe Glu Ile Phe Glu Ser Ser Tyr Lys
225 230 235 240

Val Leu Asn Lys Val Arg Asn Phe Val Thr Lys Lys Glu Val Ile Glu
245 250 255

Asn Lys Met Lys Leu Asn Phe Ser Asn Tyr Gln Leu Gly Asn Gly Trp
260 265 270

His Lys Asn Lys Glu Lys Asp Cys Ser Ile Ile Leu Phe Arg Lys Arg
275 280 285

Asn Asn Glu Arg Trp Ile Tyr Tyr Leu Gly Ile Leu Lys His Gly Thr
290 295 300

Lys Ile Lys Glu Asn Asp Tyr Leu Ser Ser Val Asp Thr Gly Phe Tyr
305 310 315 320

Lys Met Asp Tyr Tyr Ala Gln Asn Ser Leu Ser Lys Met Ile Pro Lys
325 330 335

Cys Ser Ile Thr Val Lys Asn Val Lys Asn Ala Pro Glu Asp Glu Ser
340 345 350

-continued

```
Val Ile Leu Asn Asp Ser Lys Lys Phe Asn Glu Pro Leu Glu Ile Thr
        355                 360                 365

Pro Glu Ile Arg Lys Leu Tyr Gly Asn Asn Glu His Ile Lys Gly Asp
    370                 375                 380

Lys Phe Lys Lys Glu Ser Leu Val Lys Trp Ile Asp Phe Cys Lys Glu
385                 390                 395                 400

Phe Leu Leu Lys Tyr Lys Ser Phe Glu Lys Ala Lys Lys Glu Ile Leu
                405                 410                 415

Lys Leu Lys Glu Ser Asn Leu Tyr Glu Asn Leu Glu Glu Phe Tyr Ser
            420                 425                 430

Asp Ala Glu Glu Lys Ala Tyr Phe Leu Glu Phe Ile Asn Ile Asp Glu
        435                 440                 445

Asp Lys Ile Lys Lys Leu Val Lys Glu Lys Asn Leu Tyr Leu Phe Gln
    450                 455                 460

Ile Tyr Asn Lys Asp Phe Ser Ala Tyr Ser Thr Gly Asn Lys Asn Leu
465                 470                 475                 480

His Thr Met Tyr Phe Glu Glu Leu Phe Thr Asp Glu Asn Leu Lys Lys
                485                 490                 495

Pro Val Phe Lys Leu Asn Gly Asn Thr Glu Val Phe Tyr Arg Ile Ala
            500                 505                 510

Ser Ser Lys Pro Lys Ile Val His Asn Lys Gly Glu Lys Leu Val Asn
        515                 520                 525

Lys Thr Tyr Leu Asp Asp Gly Ile Ile Lys Thr Ile Pro Asp Ser Val
    530                 535                 540

Tyr Glu Glu Ile Ser Glu Lys Val Lys Asn Asn Glu Asp Tyr Ser Lys
545                 550                 555                 560

Leu Leu Glu Glu Asn Asn Ile Lys Asn Leu Glu Ile Lys Val Ala Thr
                565                 570                 575

His Glu Ile Val Lys Asp Lys Arg Tyr Phe Glu Asn Lys Phe Leu Phe
            580                 585                 590

Tyr Leu Pro Ile Thr Leu Asn Lys Lys Val Ser Asn Lys Asn Thr Asn
        595                 600                 605

Lys Asn Ile Asn Lys Asn Val Ile Asp Glu Ile Lys Asp Cys Asn Glu
    610                 615                 620

Tyr Asn Val Ile Gly Ile Asp Arg Gly Glu Arg Asn Leu Ile Ser Leu
625                 630                 635                 640

Cys Ile Ile Asn Gln Asn Gly Glu Ile Ile Leu Gln Lys Glu Met Asn
                645                 650                 655

Ile Ile Gln Ser Ser Asp Lys Tyr Asn Val Asp Tyr Asn Glu Lys Leu
            660                 665                 670

Glu Ile Lys Ser Lys Glu Arg Asp Asn Ala Lys Lys Asn Trp Ser Glu
        675                 680                 685

Ile Gly Lys Ile Lys Asp Leu Lys Ser Gly Tyr Leu Ser Ala Val Val
    690                 695                 700

His Glu Ile Val Lys Leu Ala Ile Glu Tyr Asn Ala Val Ile Ile Leu
705                 710                 715                 720

Glu Asp Leu Asn Asn Gly Phe Lys Asn Ser Arg Lys Lys Val Asp Lys
                725                 730                 735

Gln Ile Tyr Gln Lys Phe Glu Arg Ala Leu Ile Glu Lys Leu Gln Phe
            740                 745                 750

Leu Ile Phe Lys Asn Tyr Asp Lys Asn Glu Lys Gly Gly Leu Arg Asn
        755                 760                 765
```

-continued

Ala Phe Gln Leu Thr Pro Glu Leu Lys Asn Ile Thr Lys Val Ala Ser
770 775 780

Gln Gln Gly Ile Ile Ile Tyr Thr Asn Pro Ala Tyr Thr Ser Lys Ile
785 790 795 800

Asp Pro Thr Thr Gly Tyr Ala Asn Ile Ile Lys Lys Ser Asn Asn Asn
805 810 815

Glu Glu Ser Ile Val Lys Ala Ile Asp Lys Ile Ser Tyr Asp Lys Glu
820 825 830

Lys Asp Met Phe Tyr Phe Asp Ile Asn Leu Ser Asn Ser Ser Phe Asn
835 840 845

Leu Thr Val Lys Asn Val Leu Lys Lys Glu Trp Arg Ile Tyr Thr Asn
850 855 860

Gly Glu Arg Ile Ile Tyr Lys Asp Arg Lys Tyr Ile Thr Leu Asn Ile
865 870 875 880

Thr Gln Glu Met Lys Asp Ile Leu Ser Lys Cys Gly Ile Asp Tyr Leu
885 890 895

Asn Ile Asp Asn Leu Lys Gln Asp Ile Leu Lys Asn Lys Leu His Lys
900 905 910

Lys Val Tyr Tyr Ile Phe Glu Leu Ala Asn Lys Met Arg Asn Glu Asn
915 920 925

Lys Asp Val Asp Tyr Ile Ile Ser Pro Val Leu Asn Lys Asp Gly Lys
930 935 940

Phe Phe Met Thr Gln Glu Ile Asn Glu Leu Thr Pro Lys Asp Ala Asp
945 950 955 960

Leu Asn Gly Ala Tyr Asn Ile Ala Leu Lys Gly Lys Leu Met Ile Asp
965 970 975

Asn Leu Asn Lys Lys Glu Lys Phe Val Phe Leu Ser Asn Glu Asp Trp
980 985 990

Leu Asn Phe Ile Gln Gly Arg
995

<210> SEQ ID NO 126
<211> LENGTH: 1287
<212> TYPE: PRT
<213> ORGANISM: Unknown
<220> FEATURE:
<223> OTHER INFORMATION: Coprococcus eutactus strain 2789STDY5608843

<400> SEQUENCE: 126

Met Asn Asn Asn Thr Asn Asn Ser Phe Glu Pro Phe Ile Gly Gly Asn
1 5 10 15

Ser Val Ser Lys Thr Leu Arg Asn Glu Leu Arg Val Gly Ser Glu Tyr
20 25 30

Thr Gly Lys His Ile Lys Glu Cys Ala Ile Ile Ala Glu Asp Ala Val
35 40 45

Lys Ala Glu Asn Gln Tyr Ile Val Lys Glu Met Met Asp Asp Phe Tyr
50 55 60

Arg Asp Phe Ile Asn Arg Lys Leu Asp Ala Leu Gln Gly Ile Asn Trp
65 70 75 80

Glu Gln Leu Phe Asp Ile Met Lys Lys Ala Lys Leu Asp Lys Ser Asn
85 90 95

Lys Val Ser Lys Glu Leu Asp Lys Ile Gln Glu Ser Thr Arg Lys Glu
100 105 110

Ile Val Lys Ile Phe Ser Ser Asp Pro Ile Tyr Lys Asp Met Leu Lys
115 120 125

-continued

```
Ala Asp Met Ile Ser Lys Ile Leu Pro Glu Tyr Ile Val Asp Lys Tyr
    130                 135                 140

Gly Asp Ala Ala Ser Arg Ile Glu Ala Val Lys Val Phe Tyr Gly Phe
145                 150                 155                 160

Ser Gly Tyr Phe Ile Asp Phe Trp Ala Ser Arg Lys Asn Val Phe Ser
                165                 170                 175

Asp Lys Asn Ile Ala Ser Ala Ile Pro His Arg Ile Val Asn Val Asn
            180                 185                 190

Ala Arg Ile His Leu Asp Asn Ile Thr Ala Phe Asn Arg Ile Ala Glu
        195                 200                 205

Ile Ala Gly Asp Glu Val Ala Gly Ile Ala Glu Asp Ala Cys Ala Tyr
    210                 215                 220

Leu Gln Asn Met Ser Leu Glu Asp Val Phe Thr Gly Ala Cys Tyr Gly
225                 230                 235                 240

Glu Phe Ile Cys Gln Lys Asp Ile Asp Arg Tyr Asn Asn Ile Cys Gly
                245                 250                 255

Val Ile Asn Gln His Met Asn Gln Tyr Cys Gln Asn Lys Lys Ile Ser
            260                 265                 270

Arg Ser Lys Phe Lys Met Glu Arg Leu His Lys Gln Ile Leu Cys Arg
        275                 280                 285

Ser Glu Ser Gly Phe Glu Ile Pro Ile Gly Phe Gln Thr Asp Gly Glu
    290                 295                 300

Val Ile Asp Ala Ile Asn Ser Phe Ser Thr Ile Leu Glu Glu Lys Asp
305                 310                 315                 320

Ile Leu Asp Arg Leu Arg Thr Leu Ser Gln Glu Val Thr Gly Tyr Asp
                325                 330                 335

Met Glu Arg Ile Tyr Val Ser Ser Lys Ala Phe Glu Ser Val Ser Lys
            340                 345                 350

Tyr Ile Asp His Lys Trp Asp Val Ile Ala Ser Ser Met Tyr Asn Tyr
        355                 360                 365

Phe Ser Gly Ala Val Arg Gly Lys Asp Asp Lys Lys Asp Ala Lys Ile
    370                 375                 380

Gln Thr Glu Ile Lys Lys Ile Lys Ser Cys Ser Leu Leu Asp Leu Lys
385                 390                 395                 400

Lys Leu Val Asp Met Tyr Tyr Lys Met Asp Gly Met Cys Leu Glu His
                405                 410                 415

Glu Ala Thr Glu Tyr Val Ala Gly Ile Thr Glu Ile Leu Val Asp Phe
            420                 425                 430

Asn Tyr Lys Thr Phe Asp Met Asp Asp Ser Val Lys Met Ile Gln Asn
        435                 440                 445

Glu His Met Ile Asn Glu Ile Lys Glu Tyr Leu Asp Thr Tyr Met Ser
    450                 455                 460

Ile Tyr His Trp Ala Lys Asp Phe Met Ile Asp Glu Leu Val Asp Arg
465                 470                 475                 480

Asp Met Glu Phe Tyr Ser Glu Leu Asp Glu Ile Tyr Tyr Asp Leu Ser
                485                 490                 495

Asp Ile Val Pro Leu Tyr Asn Lys Val Arg Asn Tyr Val Thr Gln Lys
            500                 505                 510

Pro Tyr Ser Gln Asp Lys Ile Lys Leu Asn Phe Gly Ser Pro Thr Leu
        515                 520                 525

Ala Asn Gly Trp Ser Lys Ser Lys Glu Phe Asp Asn Asn Val Val Val
    530                 535                 540

Leu Leu Arg Asp Glu Lys Ile Tyr Leu Ala Ile Leu Asn Val Gly Asn
```

545 550 555 560

Lys Pro Ser Lys Asp Ile Met Ala Gly Glu Asp Arg Arg Arg Ser Asp
565 570 575

Thr Asp Tyr Lys Lys Met Asn Tyr Tyr Leu Leu Pro Gly Ala Ser Lys
580 585 590

Thr Leu Pro His Val Phe Ile Ser Ser Asn Ala Trp Lys Lys Ser His
595 600 605

Gly Ile Pro Asp Glu Ile Met Tyr Gly Tyr Asn Gln Asn Lys His Leu
610 615 620

Lys Ser Ser Pro Asn Phe Asp Leu Glu Phe Cys Arg Lys Leu Ile Asp
625 630 635 640

Tyr Tyr Lys Glu Cys Ile Asp Ser Tyr Pro Asn Tyr Gln Ile Phe Asn
645 650 655

Phe Lys Phe Ala Ala Thr Glu Thr Tyr Asn Asp Ile Ser Glu Phe Tyr
660 665 670

Lys Asp Val Glu Arg Gln Gly Tyr Lys Ile Glu Trp Ser Tyr Ile Ser
675 680 685

Glu Asp Asp Ile Asn Gln Met Asp Arg Asp Gly Gln Ile Tyr Leu Phe
690 695 700

Gln Ile Tyr Asn Lys Asp Phe Ala Pro Asn Ser Lys Gly Met Gln Asn
705 710 715 720

Leu His Thr Leu Tyr Leu Lys Asn Ile Phe Ser Glu Glu Asn Leu Ser
725 730 735

Asp Val Val Ile Lys Leu Asn Gly Glu Ala Glu Leu Phe Phe Arg Lys
740 745 750

Ser Ser Ile Gln His Lys Arg Gly His Lys Lys Gly Ser Val Leu Val
755 760 765

Asn Lys Thr Tyr Lys Thr Thr Glu Lys Thr Glu Asn Gly Gln Gly Glu
770 775 780

Ile Glu Val Ile Glu Ser Val Pro Asp Gln Cys Tyr Leu Glu Leu Val
785 790 795 800

Lys Tyr Trp Ser Glu Gly Gly Val Gly Gln Leu Ser Glu Glu Ala Ser
805 810 815

Lys Tyr Lys Asp Lys Val Ser His Tyr Ala Ala Thr Met Asp Ile Val
820 825 830

Lys Asp Arg Arg Tyr Thr Glu Asp Lys Phe Phe Ile His Met Pro Ile
835 840 845

Thr Ile Asn Phe Lys Ala Asp Asn Arg Asn Asn Val Asn Glu Lys Val
850 855 860

Leu Lys Phe Ile Ala Glu Asn Asp Asp Leu His Val Ile Gly Ile Asp
865 870 875 880

Arg Gly Glu Arg Asn Leu Leu Tyr Val Ser Val Ile Asp Ser Arg Gly
885 890 895

Arg Ile Val Glu Gln Lys Ser Phe Asn Ile Val Glu Asn Tyr Glu Ser
900 905 910

Ser Lys Asn Val Ile Arg Arg His Asp Tyr Lys Gly Lys Leu Val Asn
915 920 925

Lys Glu His Tyr Arg Asn Glu Ala Arg Lys Ser Trp Lys Glu Ile Gly
930 935 940

Lys Ile Lys Glu Ile Lys Glu Gly Tyr Leu Ser Gln Val Ile His Glu
945 950 955 960

Ile Ser Lys Leu Val Leu Lys Tyr Asn Ala Ile Ile Val Met Glu Asp
965 970 975

Leu Asn Tyr Gly Phe Lys Arg Gly Arg Phe Lys Val Glu Arg Gln Val
980 985 990

Tyr Gln Lys Phe Glu Thr Met Leu Ile Asn Lys Leu Ala Tyr Leu Val
995 1000 1005

Asp Lys Ser Arg Ala Val Asp Glu Pro Gly Gly Leu Leu Lys Gly
1010 1015 1020

Tyr Gln Leu Thr Tyr Val Pro Asp Asn Leu Gly Glu Leu Gly Ser
1025 1030 1035

Gln Cys Gly Ile Ile Phe Tyr Val Pro Ala Ala Tyr Thr Ser Lys
1040 1045 1050

Ile Asp Pro Val Thr Gly Phe Val Asp Val Phe Asp Phe Lys Ala
1055 1060 1065

Tyr Ser Asn Ala Glu Ala Arg Leu Asp Phe Ile Asn Lys Leu Asp
1070 1075 1080

Cys Ile Arg Tyr Asp Ala Ser Arg Asn Lys Phe Glu Ile Ala Phe
1085 1090 1095

Asp Tyr Gly Asn Phe Arg Thr His His Thr Thr Leu Ala Lys Thr
1100 1105 1110

Ser Trp Thr Ile Phe Ile His Gly Asp Arg Ile Lys Lys Glu Arg
1115 1120 1125

Gly Ser Tyr Gly Trp Lys Asp Glu Ile Ile Asp Ile Glu Ala Arg
1130 1135 1140

Ile Arg Lys Leu Phe Glu Asp Thr Asp Ile Glu Tyr Ala Asp Gly
1145 1150 1155

His Asn Leu Ile Gly Asp Ile Asn Glu Leu Glu Ser Pro Ile Gln
1160 1165 1170

Lys Lys Phe Val Gly Glu Leu Phe Asp Ile Ile Arg Phe Thr Val
1175 1180 1185

Gln Leu Arg Asn Ser Lys Ser Glu Lys Tyr Asp Gly Thr Glu Lys
1190 1195 1200

Glu Tyr Asp Lys Ile Ile Ser Pro Val Met Asp Glu Glu Gly Val
1205 1210 1215

Phe Phe Thr Thr Asp Ser Tyr Ile Arg Ala Asp Gly Thr Glu Leu
1220 1225 1230

Pro Lys Asp Ala Asp Ala Asn Gly Ala Tyr Cys Ile Ala Leu Lys
1235 1240 1245

Gly Leu Tyr Asp Val Leu Ala Val Lys Lys Tyr Trp Lys Glu Gly
1250 1255 1260

Glu Lys Phe Asp Arg Lys Leu Leu Ala Ile Thr Asn Tyr Asn Trp
1265 1270 1275

Phe Asp Phe Ile Gln Asn Arg Arg Phe
1280 1285

<210> SEQ ID NO 127
<211> LENGTH: 1305
<212> TYPE: PRT
<213> ORGANISM: Unknown
<220> FEATURE:
<223> OTHER INFORMATION: Lachnospira pectinoschiza strain
2789STDY5834886

<400> SEQUENCE: 127

Met Asn Lys Ala Ala Asp Asn Tyr Thr Gly Gly Asn Tyr Asp Glu Phe
1 5 10 15

Ile Ala Leu Ser Lys Val Gln Lys Thr Leu Arg Asn Glu Leu Lys Pro

-continued

```
            20                  25                  30

Thr Pro Phe Thr Ala Glu His Ile Lys Gln Arg Gly Ile Ile Ser Glu
        35                  40                  45

Asp Glu Tyr Arg Ala Gln Gln Ser Leu Glu Leu Lys Lys Ile Ala Asp
    50                  55                  60

Glu Tyr Tyr Arg Asn Tyr Ile Thr His Lys Leu Asn Asp Ile Asn Asn
65                  70                  75                  80

Leu Asp Phe Tyr Asn Leu Phe Asp Ala Ile Glu Glu Lys Tyr Lys Lys
                85                  90                  95

Asn Asp Lys Asp Asn Arg Asp Lys Leu Asp Leu Val Glu Lys Ser Lys
            100                 105                 110

Arg Gly Glu Ile Ala Lys Met Leu Ser Ala Asp Asp Asn Phe Lys Ser
        115                 120                 125

Met Phe Glu Ala Lys Leu Ile Thr Lys Leu Leu Pro Asp Tyr Val Glu
    130                 135                 140

Arg Asn Tyr Thr Gly Glu Asp Lys Glu Lys Ala Leu Glu Thr Leu Ala
145                 150                 155                 160

Leu Phe Lys Gly Phe Thr Thr Tyr Phe Lys Gly Tyr Phe Lys Thr Arg
                165                 170                 175

Lys Asn Met Phe Ser Gly Glu Gly Gly Ala Ser Ser Ile Cys His Arg
            180                 185                 190

Ile Val Asn Val Asn Ala Ser Ile Phe Tyr Asp Asn Leu Lys Thr Phe
        195                 200                 205

Met Arg Ile Gln Glu Lys Ala Gly Asp Glu Ile Ala Leu Ile Glu Glu
    210                 215                 220

Glu Leu Thr Glu Lys Leu Asp Gly Trp Arg Leu Glu His Ile Phe Ser
225                 230                 235                 240

Arg Asp Tyr Tyr Asn Glu Val Leu Ala Gln Lys Gly Ile Asp Tyr Tyr
                245                 250                 255

Asn Gln Ile Cys Gly Asp Ile Asn Lys His Met Asn Leu Tyr Cys Gln
            260                 265                 270

Gln Asn Lys Phe Lys Ala Asn Ile Phe Lys Met Met Lys Leu Gln Lys
        275                 280                 285

Gln Ile Met Gly Ile Ser Glu Lys Val Phe Glu Ile Pro Pro Met Tyr
    290                 295                 300

Gln Asn Asp Glu Glu Val Tyr Ala Ser Phe Asn Glu Phe Ile Ser Arg
305                 310                 315                 320

Leu Glu Glu Val Lys Leu Thr Asp Arg Leu Arg Asn Ile Leu Gln Asn
                325                 330                 335

Ile Asn Ile Tyr Asn Thr Ala Lys Ile Tyr Ile Asn Ala Arg Tyr Tyr
            340                 345                 350

Thr Asn Val Ser Thr Tyr Val Tyr Gly Gly Trp Gly Val Ile Glu Ser
        355                 360                 365

Ala Ile Glu Arg Tyr Leu Cys Asn Thr Ile Ala Gly Lys Gly Gln Ser
    370                 375                 380

Lys Val Lys Lys Ile Glu Asn Ala Lys Lys Asp Asn Lys Phe Met Ser
385                 390                 395                 400

Val Lys Glu Leu Asp Ser Ile Val Ala Glu Tyr Glu Pro Asp Tyr Phe
                405                 410                 415

Asn Ala Pro Tyr Ile Asp Asp Asp Asn Ala Val Lys Val Phe Gly
            420                 425                 430

Gly Gln Gly Val Leu Gly Tyr Phe Asn Lys Met Ser Glu Leu Leu Ala
        435                 440                 445
```

Asp Val Ser Leu Tyr Thr Ile Asp Tyr Asn Ser Asp Asp Ser Leu Ile
    450                 455                 460

Glu Asn Lys Glu Ser Ala Leu Arg Ile Lys Lys Gln Leu Asp Asp Ile
465                 470                 475                 480

Met Ser Leu Tyr His Trp Leu Gln Thr Phe Ile Ile Asp Glu Val Val
                485                 490                 495

Glu Lys Asp Asn Ala Phe Tyr Ala Glu Leu Glu Asp Ile Cys Cys Glu
            500                 505                 510

Leu Glu Asn Val Val Thr Leu Tyr Asp Arg Ile Arg Asn Tyr Val Thr
        515                 520                 525

Arg Lys Pro Tyr Ser Thr Gln Lys Phe Lys Leu Asn Phe Ala Ser Pro
    530                 535                 540

Thr Leu Ala Ser Gly Trp Ser Arg Ser Lys Glu Phe Asp Asn Asn Ala
545                 550                 555                 560

Ile Ile Leu Leu Arg Asn Asn Lys Tyr Tyr Ile Ala Ile Phe Asn Val
                565                 570                 575

Asn Asn Lys Pro Asp Lys Gln Ile Ile Lys Gly Ser Glu Glu Gln Arg
            580                 585                 590

Leu Ser Thr Asp Tyr Lys Lys Met Val Tyr Asn Leu Leu Pro Gly Pro
        595                 600                 605

Asn Lys Met Leu Pro Lys Val Phe Ile Lys Ser Asp Thr Gly Lys Arg
    610                 615                 620

Asp Tyr Asn Pro Ser Ser Tyr Ile Leu Glu Gly Tyr Glu Lys Asn Arg
625                 630                 635                 640

His Ile Lys Ser Ser Gly Asn Phe Asp Ile Asn Tyr Cys His Asp Leu
                645                 650                 655

Ile Asp Tyr Tyr Lys Ala Cys Ile Asn Lys His Pro Glu Trp Lys Asn
            660                 665                 670

Tyr Gly Phe Lys Phe Lys Glu Thr Asn Gln Tyr Asn Asp Ile Gly Gln
        675                 680                 685

Phe Tyr Lys Asp Val Glu Lys Gln Gly Tyr Ser Ile Ser Trp Ala Tyr
    690                 695                 700

Ile Ser Glu Glu Asp Ile Asn Lys Leu Asp Glu Glu Gly Lys Ile Tyr
705                 710                 715                 720

Leu Phe Glu Ile Tyr Asn Lys Asp Leu Ser Ala His Ser Thr Gly Arg
                725                 730                 735

Asp Asn Leu His Thr Met Tyr Leu Lys Asn Ile Phe Ser Glu Asp Asn
            740                 745                 750

Leu Lys Asn Ile Cys Ile Glu Leu Asn Gly Glu Ala Glu Leu Phe Tyr
        755                 760                 765

Arg Lys Ser Ser Met Lys Ser Asn Ile Thr His Lys Lys Asp Thr Ile
    770                 775                 780

Leu Val Asn Lys Thr Tyr Ile Asn Glu Thr Gly Val Arg Val Ser Leu
785                 790                 795                 800

Ser Asp Glu Asp Tyr Met Lys Val Tyr Asn Tyr Tyr Asn Asn Asn Tyr
                805                 810                 815

Val Ile Asp Thr Glu Asn Asp Lys Asn Leu Ile Asp Ile Ile Glu Lys
            820                 825                 830

Ile Gly His Arg Lys Ser Lys Ile Asp Ile Val Lys Asp Lys Arg Tyr
        835                 840                 845

Thr Glu Asp Lys Tyr Phe Leu Tyr Leu Pro Ile Thr Ile Asn Tyr Gly
    850                 855                 860

```
Ile Glu Asp Glu Asn Val Asn Ser Lys Ile Ile Glu Tyr Ile Ala Lys
865                 870                 875                 880

Gln Asp Asn Met Asn Val Ile Gly Ile Asp Arg Gly Glu Arg Asn Leu
                885                 890                 895

Ile Tyr Ile Ser Val Ile Asp Asn Lys Gly Asn Ile Ile Glu Gln Lys
            900                 905                 910

Ser Phe Asn Leu Val Asn Asn Tyr Asp Tyr Lys Asn Lys Leu Lys Asn
        915                 920                 925

Met Glu Lys Thr Arg Asp Asn Ala Arg Lys Asn Trp Gln Glu Ile Gly
    930                 935                 940

Lys Ile Lys Asp Val Lys Ser Gly Tyr Leu Ser Gly Val Ile Ser Lys
945                 950                 955                 960

Ile Ala Arg Met Val Ile Asp Tyr Asn Ala Ile Ile Val Met Glu Asp
                965                 970                 975

Leu Asn Lys Gly Phe Lys Arg Gly Arg Phe Lys Val Glu Arg Gln Val
            980                 985                 990

Tyr Gln Lys Phe Glu Asn Met Leu  Ile Ser Lys Leu Asn  Tyr Leu Val
        995                 1000                1005

Phe Lys  Glu Arg Lys Ala Asp  Glu Asn Gly Gly Ile  Leu Arg Gly
    1010                1015                1020

Tyr Gln  Leu Thr Tyr Ile Pro  Lys Ser Ile Lys Asn  Val Gly Lys
    1025                1030                1035

Gln Cys  Gly Cys Ile Phe Tyr  Val Pro Ala Ala Tyr  Thr Ser Lys
    1040                1045                1050

Ile Asp  Pro Ala Thr Gly Phe  Ile Asn Ile Phe Asp  Phe Lys Lys
    1055                1060                1065

Tyr Ser  Gly Ser Gly Ile Asn  Ala Lys Val Lys Asp  Lys Lys Glu
    1070                1075                1080

Phe Leu  Met Ser Met Asn Ser  Ile Arg Tyr Ile Asn  Glu Gly Ser
    1085                1090                1095

Glu Glu  Tyr Glu Lys Ile Gly  His Arg Glu Leu Phe  Ala Phe Ser
    1100                1105                1110

Phe Asp  Tyr Asn Asn Phe Lys  Thr Tyr Asn Val Ser  Ser Pro Val
    1115                1120                1125

Asn Glu  Trp Thr Ala Tyr Thr  Tyr Gly Glu Arg Ile  Lys Lys Leu
    1130                1135                1140

Tyr Lys  Asp Gly Arg Trp Leu  Arg Ser Glu Val Leu  Asn Leu Thr
    1145                1150                1155

Glu Asn  Leu Ile Lys Leu Met  Glu Gln Tyr Asn Ile  Glu Tyr Lys
    1160                1165                1170

Asp Gly  His Asp Ile Arg Glu  Asp Ile Ser His Met  Asp Glu Thr
    1175                1180                1185

Arg Asn  Ala Asp Phe Ile Cys  Ser Leu Phe Glu Glu  Leu Lys Tyr
    1190                1195                1200

Thr Val  Gln Leu Arg Asn Ser  Lys Ser Glu Ala Glu  Asp Glu Asn
    1205                1210                1215

Tyr Asp  Arg Leu Val Ser Pro  Ile Leu Asn Ser Ser  Asn Gly Phe
    1220                1225                1230

Tyr Asp  Ser Ser Asp Tyr Met  Glu Asn Glu Asn Asn  Thr Thr His
    1235                1240                1245

Thr Met  Pro Lys Asp Ala Asp  Ala Asn Gly Ala Tyr  Cys Ile Ala
    1250                1255                1260

Leu Lys  Gly Leu Tyr Glu Ile  Asn Lys Ile Lys Gln  Asn Trp Ser
```

1265 1270 1275

Asp Asp Lys Lys Phe Lys Glu Asn Glu Leu Tyr Ile Asn Val Thr
1280 1285 1290

Glu Trp Leu Asp Tyr Ile Gln Asn Arg Arg Phe Glu
1295 1300 1305

<210> SEQ ID NO 128
<211> LENGTH: 1262
<212> TYPE: PRT
<213> ORGANISM: Unknown
<220> FEATURE:
<223> OTHER INFORMATION: Bacteroidetes oral taxon 274 str. F0058

<400> SEQUENCE: 128

Met Arg Lys Phe Asn Glu Phe Val Gly Leu Tyr Pro Ile Ser Lys Thr
1 5 10 15

Leu Arg Phe Glu Leu Lys Pro Ile Gly Lys Thr Leu Glu His Ile Gln
20 25 30

Arg Asn Lys Leu Leu Glu His Asp Ala Val Arg Ala Asp Asp Tyr Val
35 40 45

Lys Val Lys Lys Ile Ile Asp Lys Tyr His Lys Cys Leu Ile Asp Glu
50 55 60

Ala Leu Ser Gly Phe Thr Phe Asp Thr Glu Ala Asp Gly Arg Ser Asn
65 70 75 80

Asn Ser Leu Ser Glu Tyr Tyr Leu Tyr Tyr Asn Leu Lys Lys Arg Asn
85 90 95

Glu Gln Glu Gln Lys Thr Phe Lys Thr Ile Gln Asn Asn Leu Arg Lys
100 105 110

Gln Ile Val Asn Lys Leu Thr Gln Ser Glu Lys Tyr Lys Arg Ile Asp
115 120 125

Lys Lys Glu Leu Ile Thr Thr Asp Leu Pro Asp Phe Leu Thr Asn Glu
130 135 140

Ser Glu Lys Glu Leu Val Glu Lys Phe Lys Asn Phe Thr Thr Tyr Phe
145 150 155 160

Thr Glu Phe His Lys Asn Arg Lys Asn Met Tyr Ser Lys Glu Glu Lys
165 170 175

Ser Thr Ala Ile Ala Phe Arg Leu Ile Asn Glu Asn Leu Pro Lys Phe
180 185 190

Val Asp Asn Ile Ala Ala Phe Glu Lys Val Val Ser Ser Pro Leu Ala
195 200 205

Glu Lys Ile Asn Ala Leu Tyr Glu Asp Phe Lys Glu Tyr Leu Asn Val
210 215 220

Glu Glu Ile Ser Arg Val Phe Arg Leu Asp Tyr Tyr Asp Glu Leu Leu
225 230 235 240

Thr Gln Lys Gln Ile Asp Leu Tyr Asn Ala Ile Val Gly Gly Arg Thr
245 250 255

Glu Glu Asp Asn Lys Ile Gln Ile Lys Gly Leu Asn Gln Tyr Ile Asn
260 265 270

Glu Tyr Asn Gln Gln Gln Thr Asp Arg Ser Asn Arg Leu Pro Lys Leu
275 280 285

Lys Pro Leu Tyr Lys Gln Ile Leu Ser Asp Arg Glu Ser Val Ser Trp
290 295 300

Leu Pro Pro Lys Phe Asp Ser Asp Lys Asn Leu Leu Ile Lys Ile Lys
305 310 315 320

Glu Cys Tyr Asp Ala Leu Ser Glu Lys Glu Lys Val Phe Asp Lys Leu

-continued

```
                325                 330                 335

Glu Ser Ile Leu Lys Ser Leu Ser Thr Tyr Asp Leu Ser Lys Ile Tyr
            340                 345                 350

Ile Ser Asn Asp Ser Gln Leu Ser Tyr Ile Ser Gln Lys Met Phe Gly
        355                 360                 365

Arg Trp Asp Ile Ile Ser Lys Ala Ile Arg Glu Asp Cys Ala Lys Arg
    370                 375                 380

Asn Pro Gln Lys Ser Arg Glu Ser Leu Glu Lys Phe Ala Glu Arg Ile
385                 390                 395                 400

Asp Lys Lys Leu Lys Thr Ile Asp Ser Ile Ser Ile Gly Asp Val Asp
            405                 410                 415

Glu Cys Leu Ala Gln Leu Gly Glu Thr Tyr Val Lys Arg Val Glu Asp
            420                 425                 430

Tyr Phe Val Ala Met Gly Glu Ser Glu Ile Asp Asp Glu Gln Thr Asp
        435                 440                 445

Thr Thr Ser Phe Lys Lys Asn Ile Glu Gly Ala Tyr Glu Ser Val Lys
    450                 455                 460

Glu Leu Leu Asn Asn Ala Asp Asn Ile Thr Asp Asn Asn Leu Met Gln
465                 470                 475                 480

Asp Lys Gly Asn Val Glu Lys Ile Lys Thr Leu Leu Asp Ala Ile Lys
            485                 490                 495

Asp Leu Gln Arg Phe Ile Lys Pro Leu Leu Gly Lys Gly Asp Glu Ala
            500                 505                 510

Asp Lys Asp Gly Val Phe Tyr Gly Glu Phe Thr Ser Leu Trp Thr Lys
        515                 520                 525

Leu Asp Gln Val Thr Pro Leu Tyr Asn Met Val Arg Asn Tyr Leu Thr
    530                 535                 540

Ser Lys Pro Tyr Ser Thr Lys Lys Ile Lys Leu Asn Phe Glu Asn Ser
545                 550                 555                 560

Thr Leu Met Asp Gly Trp Asp Leu Asn Lys Glu Pro Asp Asn Thr Thr
            565                 570                 575

Val Ile Phe Cys Lys Asp Gly Leu Tyr Tyr Leu Gly Ile Met Gly Lys
            580                 585                 590

Lys Tyr Asn Arg Val Phe Val Asp Arg Glu Asp Leu Pro His Asp Gly
        595                 600                 605

Glu Cys Tyr Asp Lys Met Glu Tyr Lys Leu Leu Pro Gly Ala Asn Lys
    610                 615                 620

Met Leu Pro Lys Val Phe Phe Ser Glu Thr Gly Ile Gln Arg Phe Leu
625                 630                 635                 640

Pro Ser Glu Glu Leu Leu Gly Lys Tyr Glu Arg Gly Thr His Lys Lys
            645                 650                 655

Gly Ala Gly Phe Asp Leu Gly Asp Cys Arg Ala Leu Ile Asp Phe Phe
            660                 665                 670

Lys Lys Ser Ile Glu Arg His Asp Asp Trp Lys Lys Phe Asp Phe Lys
        675                 680                 685

Phe Ser Asp Thr Ser Thr Tyr Gln Asp Ile Ser Glu Phe Tyr Arg Glu
    690                 695                 700

Val Glu Gln Gln Gly Tyr Lys Met Ser Phe Arg Lys Val Ser Val Asp
705                 710                 715                 720

Tyr Ile Lys Ser Leu Val Glu Glu Gly Lys Leu Tyr Leu Phe Gln Ile
            725                 730                 735

Tyr Asn Lys Asp Phe Ser Ala His Ser Lys Gly Thr Pro Asn Met His
            740                 745                 750
```

```
Thr Leu Tyr Trp Lys Met Leu Phe Asp Glu Glu Asn Leu Lys Asp Val
        755                 760                 765

Val Tyr Lys Leu Asn Gly Glu Ala Glu Val Phe Phe Arg Lys Ser Ser
    770                 775                 780

Ile Thr Val Gln Ser Pro Thr His Pro Ala Asn Ser Pro Ile Lys Asn
785                 790                 795                 800

Lys Asn Lys Asp Asn Gln Lys Lys Glu Ser Lys Phe Glu Tyr Asp Leu
                805                 810                 815

Ile Lys Asp Arg Arg Tyr Thr Val Asp Lys Phe Leu Phe His Val Pro
            820                 825                 830

Ile Thr Met Asn Phe Lys Ser Val Gly Gly Ser Asn Ile Asn Gln Leu
        835                 840                 845

Val Lys Arg His Ile Arg Ser Ala Thr Asp Leu His Ile Ile Gly Ile
    850                 855                 860

Asp Arg Gly Glu Arg His Leu Leu Tyr Leu Thr Val Ile Asp Ser Arg
865                 870                 875                 880

Gly Asn Ile Lys Glu Gln Phe Ser Leu Asn Glu Ile Val Asn Glu Tyr
                885                 890                 895

Asn Gly Asn Thr Tyr Arg Thr Asp Tyr His Glu Leu Leu Asp Thr Arg
            900                 905                 910

Glu Gly Glu Arg Thr Glu Ala Arg Arg Asn Trp Gln Thr Ile Gln Asn
        915                 920                 925

Ile Arg Glu Leu Lys Glu Gly Tyr Leu Ser Gln Val Ile His Lys Ile
    930                 935                 940

Ser Glu Leu Ala Ile Lys Tyr Asn Ala Val Ile Val Leu Glu Asp Leu
945                 950                 955                 960

Asn Phe Gly Phe Met Arg Ser Arg Gln Lys Val Glu Lys Gln Val Tyr
                965                 970                 975

Gln Lys Phe Glu Lys Met Leu Ile Asp Lys Leu Asn Tyr Leu Val Asp
            980                 985                 990

Lys Lys Lys Pro Val Ala Glu Thr  Gly Gly Leu Leu Arg  Ala Tyr Gln
        995                 1000                 1005

Leu Thr  Gly Glu Phe Glu Ser  Phe Lys Thr Leu Gly  Lys Gln Ser
    1010                 1015                 1020

Gly Ile  Leu Phe Tyr Val Pro  Ala Trp Asn Thr Ser  Lys Ile Asp
    1025                 1030                 1035

Pro Val  Thr Gly Phe Val Asn  Leu Phe Asp Thr His  Tyr Glu Asn
    1040                 1045                 1050

Ile Glu  Lys Ala Lys Val Phe  Phe Asp Lys Phe Lys  Ser Ile Arg
    1055                 1060                 1065

Tyr Asn  Ser Asp Lys Asp Trp  Phe Glu Phe Val Val  Asp Asp Tyr
    1070                 1075                 1080

Thr Arg  Phe Ser Pro Lys Ala  Glu Gly Thr Arg Arg  Asp Trp Thr
    1085                 1090                 1095

Ile Cys  Thr Gln Gly Lys Arg  Ile Gln Ile Cys Arg  Asn His Gln
    1100                 1105                 1110

Arg Asn  Asn Glu Trp Glu Gly  Gln Glu Ile Asp Leu  Thr Lys Ala
    1115                 1120                 1125

Phe Lys  Glu His Phe Glu Ala  Tyr Gly Val Asp Ile  Ser Lys Asp
    1130                 1135                 1140

Leu Arg  Glu Gln Ile Asn Thr  Gln Asn Lys Lys Glu  Phe Phe Glu
    1145                 1150                 1155
```

```
Glu Leu  Leu Arg Leu Leu Arg  Leu Thr Leu Gln Met  Arg Asn Ser
    1160                 1165                 1170

Met Pro  Ser Ser Asp Ile Asp  Tyr Leu Ile Ser Pro  Val Ala Asn
    1175                 1180                 1185

Asp Thr  Gly Cys Phe Phe Asp  Ser Arg Lys Gln Ala  Glu Leu Lys
    1190                 1195                 1200

Glu Asn  Ala Val Leu Pro Met  Asn Ala Asp Ala Asn  Gly Ala Tyr
    1205                 1210                 1215

Asn Ile  Ala Arg Lys Gly Leu  Leu Ala Ile Arg Lys  Met Lys Gln
    1220                 1225                 1230

Glu Glu  Asn Asp Ser Ala Lys  Ile Ser Leu Ala Ile  Ser Asn Lys
    1235                 1240                 1245

Glu Trp  Leu Lys Phe Ala Gln  Thr Lys Pro Tyr Leu  Glu Asp
    1250                 1255                 1260


<210> SEQ ID NO 129
<211> LENGTH: 998
<212> TYPE: PRT
<213> ORGANISM: Unknown
<220> FEATURE:
<223> OTHER INFORMATION: Arcobacter butzleri L348 isolate CHRB125

<400> SEQUENCE: 129

Met Gly Leu Leu Glu His Leu Glu Gly Ala Ile Val Glu Asp Met Phe
1               5                   10                  15

Ser Leu Asp Tyr Phe Ser Leu Thr Leu Ser Gln Arg Tyr Ile Asp Ile
            20                  25                  30

Tyr Asn Thr Met Ile Gly Gly Asn Thr Leu Ala Asp Gly Thr Lys Val
        35                  40                  45

Gln Gly Ile Asn Glu Asn Ile Asn Ile Tyr Arg Gln Lys Asn Asn Ile
    50                  55                  60

Asp Arg Lys Asn Leu Pro Thr Leu Lys Pro Leu His Lys Gln Leu Leu
65                  70                  75                  80

Ser Asp Arg Glu Thr Leu Ser Trp Ile Pro Glu Ala Phe Lys Thr Lys
                85                  90                  95

Glu Glu Val Val Gly Ala Ile Glu Asp Phe Tyr Lys Asn Asn Ile Ile
            100                 105                 110

Ser Phe Lys Cys Cys Asp Asn Ile Val Asp Ile Thr Lys Gln Phe Ile
        115                 120                 125

Asp Ile Phe Ser Leu Asn Glu Asp Tyr Glu Leu Asn Lys Ile Phe Ile
    130                 135                 140

Lys Asn Asp Ile Ser Ile Thr Ser Ile Ser Gln Asp Ile Phe Lys Asp
145                 150                 155                 160

Tyr Arg Ile Ile Lys Glu Ala Leu Trp Gln Lys His Ile Asn Glu Asn
                165                 170                 175

Pro Lys Ala Ala Lys Ser Lys Asp Leu Thr Gly Asp Lys Glu Lys Tyr
            180                 185                 190

Phe Ser Arg Lys Asn Ser Phe Phe Ser Phe Glu Glu Ile Ile Ser Ser
        195                 200                 205

Leu Lys Leu Met Gly Arg Lys Ile Asp Leu Phe Ser Tyr Phe Lys Asp
    210                 215                 220

Asn Val Glu Tyr Arg Ala His Ser Ile Glu Thr Thr Phe Ile Lys Trp
225                 230                 235                 240

Gln Lys Asn Lys Asn Asp Lys Lys Thr Thr Lys Glu Leu Leu Asp Asn
                245                 250                 255
```

-continued

Ile Leu Asn Leu Gln Arg Val Leu Lys Pro Leu Tyr Leu Lys Ala Glu
260 265 270

Val Glu Lys Asp Ile Leu Phe Tyr Ser Ile Phe Asp Ile Tyr Phe Glu
275 280 285

Ser Leu Asn Glu Ile Val Lys Leu Tyr Asn Lys Val Arg Asp Phe Glu
290 295 300

Ser Lys Lys Pro Tyr Ser Leu Glu Lys Phe Lys Leu Asn Phe Gln Asn
305 310 315 320

Ser Thr Leu Leu Ser Gly Trp Asp Val Asn Lys Glu Pro Asp Asn Thr
325 330 335

Ser Ile Leu Leu Lys Lys Asp Gly Leu Tyr Tyr Leu Gly Ile Met Asp
340 345 350

Lys Lys His Asn Arg Val Phe Lys Asn Leu Glu Ser Ser Lys Gly Gly
355 360 365

Tyr Glu Lys Ile Glu Tyr Lys Leu Leu Ser Gly Pro Asn Lys Met Leu
370 375 380

Pro Lys Val Phe Phe Ser Asn Lys Ser Ile Gly Tyr Tyr Asn Pro Ser
385 390 395 400

Pro Ala Leu Leu Glu Lys Tyr Lys Ser Gly Val His Lys Lys Gly Glu
405 410 415

Ser Phe Asp Leu Asn Phe Cys His Glu Leu Ile Asp Phe Phe Lys Ala
420 425 430

Ser Ile Asp Lys His Glu Asp Trp Lys Asn Phe Asn Phe Lys Phe Ser
435 440 445

Asp Thr Ser Glu Tyr Ala Asp Ile Ser Gly Phe Tyr Arg Glu Val Glu
450 455 460

Gln Gln Gly Tyr Lys Ile Thr Phe Lys Asn Ile Asp Glu Glu Phe Ile
465 470 475 480

Asn Thr Leu Ile Asn Glu Gly Lys Leu Tyr Leu Phe Gln Ile Tyr Asn
485 490 495

Lys Asp Phe Ser Thr Phe Ser Lys Gly Thr Lys Asn Leu His Thr Leu
500 505 510

Tyr Trp Glu Met Ile Phe Asn Glu Glu Asn Leu Lys Asn Val Val Tyr
515 520 525

Lys Leu Asn Gly Glu Ala Glu Ile Phe Tyr Arg Lys Lys Ser Ile Glu
530 535 540

Tyr Ser Glu Asp Lys Met Lys Tyr Gly His His Tyr Glu Glu Leu Lys
545 550 555 560

Asp Lys Phe Asn Tyr Pro Ile Ile Lys Asp Lys Arg Phe Thr Met Asp
565 570 575

Lys Phe Gln Phe His Val Pro Ile Thr Met Asn Phe Lys Ala Thr Gly
580 585 590

Arg Ser Tyr Ile Asn Glu Glu Val Asn Asp Phe Leu Arg Gln Asn Ser
595 600 605

Lys Asp Val Lys Ile Ile Gly Ile Asn Arg Gly Glu Arg His Leu Ile
610 615 620

Tyr Leu Thr Met Ile Asn Ala Lys Gly Glu Ile Ile Gln Gln Tyr Ser
625 630 635 640

Leu Asn Glu Ile Val Asn Ser Tyr Asn Asn Lys Asn Phe Thr Val Asn
645 650 655

Tyr Asn Glu Lys Leu Ser Lys Lys Glu Gly Glu Arg Ala Ile Ala Arg
660 665 670

Glu Asn Trp Gly Val Val Glu Asn Ile Lys Glu Leu Lys Glu Gly Tyr

-continued

```
        675                 680                 685

Leu Ser His Ala Ile His Thr Ile Ser Asn Leu Ile Val Glu Asn Asn
    690                 695                 700

Ala Ile Val Val Leu Glu Asp Leu Asn Phe Glu Phe Lys Arg Glu Arg
705                 710                 715                 720

Leu Lys Val Glu Lys Ser Ile Tyr Gln Lys Phe Glu Lys Met Leu Ile
                725                 730                 735

Asp Lys Leu Asn Tyr Leu Val Asp Lys Lys Lys Asp Ile Asn Glu Asn
            740                 745                 750

Gly Gly Leu Leu Lys Ala Leu Gln Leu Thr Asn Lys Phe Glu Ser Phe
        755                 760                 765

Glu Lys Ile Gly Lys Gln Asn Gly Phe Leu Phe Phe Val Asn Ala Trp
    770                 775                 780

Asn Ile Thr Lys Ile Cys Pro Val Thr Gly Phe Val Ser Leu Phe Asp
785                 790                 795                 800

Thr Arg Tyr Gln Ser Val Asp Lys Ala Arg Glu Phe Phe Ser Lys Phe
                805                 810                 815

Asp Ser Ile Lys Tyr Asn Glu Glu Lys Glu His Tyr Glu Phe Val Phe
            820                 825                 830

Asp Tyr Ser Asn Phe Thr Asp Lys Ala Lys Asp Thr Lys Thr Lys Trp
        835                 840                 845

Thr Val Cys Ser Tyr Gly Thr Arg Ile Lys Thr Phe Arg Asn Ser Glu
    850                 855                 860

Lys Asn Asn Asn Trp Asp Asn Lys Thr Val Ser Pro Thr Glu Asp Leu
865                 870                 875                 880

Ser Lys Leu Leu Lys Ser Cys Asp Arg Asp Ile Lys Glu Phe Ile Ile
                885                 890                 895

Ser Gln Asp Lys Lys Glu Phe Phe Val Glu Leu Leu Glu Ile Phe Ser
            900                 905                 910

Leu Ile Val Gln Met Lys Asn Ser Ile Ile Asn Ser Glu Ile Asp Tyr
        915                 920                 925

Ile Ile Ser Pro Val Ala Asn Glu Asn Gly Glu Phe Phe Asp Ser Arg
    930                 935                 940

Phe Ala Asn Ser Ser Leu Pro Lys Asn Ala Asp Ala Asn Ala Ala Tyr
945                 950                 955                 960

Asn Thr Ala Arg Lys Gly Leu Met Leu Leu Glu Lys Ile Arg Asp Ser
                965                 970                 975

Glu Ile Gly Lys Lys Ile Asp Met Lys Ile Thr Asn Thr Glu Trp Leu
            980                 985                 990

Asn Phe Val Gln Glu Arg
        995


<210> SEQ ID NO 130
<211> LENGTH: 1242
<212> TYPE: PRT
<213> ORGANISM: Unknown
<220> FEATURE:
<223> OTHER INFORMATION: Bacteroidales bacterium KA00251

<400> SEQUENCE: 130

Met Lys Lys Phe Thr Asn Leu Tyr Pro Val Gln Lys Thr Leu Arg Phe
1               5                   10                  15

Glu Leu Ile Pro Gln Gly Asn Thr Ser Lys His Leu Cys Lys Ile Ile
            20                  25                  30

Gln Glu Asp Glu Gln Ile Ala Glu Asp Ser Gln Glu Val Lys Lys Leu
```

-continued

```
        35                  40                  45

Leu Asp Arg Tyr His Lys Glu Phe Ile Ala Ile Ala Leu Ser Ser Phe
    50                  55                  60

Pro Thr Ser Pro Leu Ala Lys Glu Ile Ile Pro Lys Leu Lys Glu Phe
65                  70                  75                  80

Ala Gln Ile Arg Ala Thr Gly Asp Ala Lys Gln Ile Ser Thr Ile Gln
                85                  90                  95

Asp Glu Leu Arg Glu Leu Val Val Lys Gly Phe Lys Gly Glu Gly Glu
            100                 105                 110

Gln Glu Arg Arg Tyr Lys Ile Leu Ile Gly Ala Lys Gly Asn Pro Asn
        115                 120                 125

Ala Asp Glu Leu Phe Asn Thr Glu Leu Ile Asn Phe Leu Lys Asp Pro
    130                 135                 140

Ala Glu Gln Ala Leu Val Lys Lys Phe Gln Lys His Thr Gly Tyr Phe
145                 150                 155                 160

Leu Gly Phe Asn Glu Asn Arg Lys Asn Met Tyr Ser Ala Lys Ala Gln
                165                 170                 175

Ser Thr Ala Ile Ala Tyr Arg Leu Ile His Glu Asn Leu Pro Arg Phe
            180                 185                 190

Leu Asp Asn Ile Thr Thr Tyr Glu Lys Val Lys Thr Tyr Leu Lys Glu
        195                 200                 205

Glu Ile Pro Gln Leu Glu Lys Glu Leu Val Arg Ala Gly Ala Ser Leu
    210                 215                 220

Val Ser His Val Asp Ser Val Phe Thr Ile Asp Phe Phe Leu Glu Val
225                 230                 235                 240

Phe Thr Gln Ser Gly Ile Asp Gln Tyr Asn Ala Leu Ile Gly Lys Ile
                245                 250                 255

Val Asn Gln Glu Gln Gly Glu Val Lys Gly Leu Asn Glu Arg Ile Asn
            260                 265                 270

Leu Tyr Asn Gln Gln His Lys Gln Glu Ala Lys Leu Pro Leu Phe Lys
        275                 280                 285

Pro Leu Tyr Lys Gln Ile Leu Ser Asp Arg Glu Gln Leu Ser Trp Leu
    290                 295                 300

Ala Glu Ala Tyr Asn Ser Asp Lys Asp Leu Leu Asp Ser Ile Gln Lys
305                 310                 315                 320

Tyr Tyr Gln Leu Leu Ile Asp Asn Gln Ile Phe Glu Arg Ile Pro Arg
                325                 330                 335

Leu Met His Thr Leu Glu Lys Ala Pro Leu Asp Lys Ile Trp Ile Thr
            340                 345                 350

Tyr Asp Thr Gln Leu Thr Ser Ile Ser Asn Thr Leu Tyr Gly Ser Trp
        355                 360                 365

Arg Val Ile Gly Glu Ala Leu Gly Arg Asn Ala Lys Ser Glu Lys Glu
    370                 375                 380

Arg Lys Ser Ser Gln Lys Lys Ala Leu Asn Tyr Ser Leu Glu Ser Ile
385                 390                 395                 400

Asn Gln Ala Ile Ala Lys Met Pro Ser Asp Glu Glu Leu Pro Pro Ile
                405                 410                 415

Gln Lys Tyr Phe Ile Ala Leu Gly Ser Asn Pro Ser Lys Lys Asp Ala
            420                 425                 430

Ser Ser Gly Thr Leu Val Asp Lys Val Arg Ser Ser Tyr Lys Ala Cys
        435                 440                 445

Gln Asp Ile Leu Thr Asn Pro Asp His Thr Gly Lys Lys Leu Ile Gln
    450                 455                 460
```

```
Asp Lys Lys Gln Val Asp Leu Leu Lys Gln Leu Leu Asp Asp Leu Leu
465                 470                 475                 480

Ile Leu Gln Arg Phe Ile Lys Pro Leu Leu Tyr Ser Asn Asn Glu Asn
                485                 490                 495

Glu Thr His Lys Asp Glu Val Phe Tyr Thr Glu Leu Thr Asp Ile Met
            500                 505                 510

Asp Leu Leu Asn Pro Ile Val Gly Leu Tyr Asn Lys Val Arg Asn Tyr
        515                 520                 525

Leu Thr Gln Lys Pro Tyr Ser Thr Glu Lys Phe Lys Ile Asn Phe Lys
    530                 535                 540

Ser Ser Ser Leu Leu Ala Gly Trp Asp Arg Asn Lys Glu Lys Asp Asn
545                 550                 555                 560

Leu Gly Val Ile Leu Lys Arg Glu Asp Lys Tyr Tyr Leu Ala Ile Met
                565                 570                 575

Asp Lys Ala His Asn Ala Thr Phe Lys Asn Lys Ser Leu Pro Thr Gln
            580                 585                 590

Gly Glu Cys Tyr Glu Lys Met Glu Tyr Lys Leu Leu Pro Gly Ala Asn
        595                 600                 605

Lys Met Leu Pro Lys Val Tyr Ile Thr Ser Lys Lys Gly Ile Glu Ser
    610                 615                 620

Phe His Pro Ser Glu Glu Leu Gln Lys Lys Tyr Lys Leu Gly Thr His
625                 630                 635                 640

Lys Lys Gly Ala Ser Phe Asn Leu Ser Asp Met Arg Ala Leu Ile Asp
                645                 650                 655

Tyr Phe Lys Glu Ser Leu Glu Lys His Glu Glu His Ser Gln Phe Gly
            660                 665                 670

Phe His Phe Ser Asp Thr Ser Thr Tyr Glu Asp Ile Ser Gly Phe Tyr
        675                 680                 685

Arg Glu Val Glu Gln Gln Ala Tyr Lys Ile Thr Phe Arg Lys Val Ser
    690                 695                 700

Val Glu Tyr Ile Asp Gln Leu Val Asn Glu Gly Lys Leu Tyr Leu Phe
705                 710                 715                 720

Gln Ile Tyr Asn Lys Asp Phe Ser Pro Tyr Ser Lys Gly Thr Pro Asn
                725                 730                 735

Leu His Thr Leu Tyr Trp Lys Met Leu Phe Asp Pro Ala Asn Leu Gln
            740                 745                 750

Asp Ile Val Tyr Lys Leu Asn Gly Glu Ala Glu Val Phe Phe Arg Lys
        755                 760                 765

Lys Ser Leu Gln Tyr Asp Arg Pro Thr His Pro Lys Gly Gln Pro Ile
    770                 775                 780

Asn Lys Lys Ser Leu Leu Asn Glu Gly Glu Thr Ser Leu Phe Asp Tyr
785                 790                 795                 800

Asp Leu Ile Lys Asp Arg Arg Phe Thr Val Asp Lys Phe Gln Phe His
                805                 810                 815

Val Pro Ile Thr Met Asn Phe Lys Ala Thr Gln Gly Thr Lys Val Asn
            820                 825                 830

Gln Met Val Gln Glu Glu Val Lys Lys Ser Lys Gly Phe His Leu Ile
        835                 840                 845

Gly Ile Asp Arg Gly Glu Arg Asn Leu Leu Tyr Ile Val Val Ile Asn
    850                 855                 860

Glu Arg Gly Glu Ile Ile Glu Gln Cys Ser Leu Asn Lys Ile Val Asn
865                 870                 875                 880
```

```
Thr Tyr Gln Glu Lys Glu His Thr Val Asp Tyr Lys Ala Leu Leu Glu
                885                 890                 895

Lys Arg Ser Gln Ser Arg Leu Glu Glu Arg Lys Ser Trp Gln Thr Ile
            900                 905                 910

Glu Asn Ile Lys Glu Leu Lys Gly Gly Tyr Leu Ser Gln Val Val His
        915                 920                 925

Lys Ile Ala Gln Leu Met Ile Lys Tyr Asn Ala Ile Ala Val Leu Glu
    930                 935                 940

Asp Leu Asn Phe Gly Phe Ile Arg Thr Arg Lys Lys Phe Glu Phe Ser
945                 950                 955                 960

Val Tyr Gln Glu Phe Glu Lys Lys Leu Ile Asp Lys Leu Gly Tyr Val
                965                 970                 975

Val Asp Lys Lys Ala Pro Ile Gln Gln Glu Gly Gly Leu Leu Gln Ala
            980                 985                 990

Tyr Gln Leu Thr Ala Pro Phe Lys  Ser Phe Arg Glu Met  Gly Lys Gln
        995                 1000                1005

Asn Gly  Phe Leu Phe Tyr Val  Pro Ala Trp Asn Thr  Ser Ala Ile
    1010                 1015                1020

Asp Pro  Arg Thr Gly Phe Val  Asn Leu Leu Asp Thr  Arg Tyr Glu
    1025                 1030                1035

Ser Ile  Ala Lys Thr Lys Glu  Leu Ile Lys Lys Leu  Lys Asp Ile
    1040                 1045                1050

Arg Tyr  Asn Ser Gln Lys Asp  Trp Phe Glu Ile Asp  Leu Asp Tyr
    1055                 1060                1065

Asn Ala  Phe Gly Asn Arg Ala  Lys Gly Ser Arg Ser  Lys Trp Arg
    1070                 1075                1080

Leu Cys  Ser Tyr Gly Glu Arg  Ile Glu His Thr Arg  Lys Gln Asp
    1085                 1090                1095

Ser Asn  Gly Gln Glu Glu Ser  Asp Ser Met Val Val  Leu Thr Glu
    1100                 1105                1110

Ala Phe  Lys Asp Val Phe Thr  Lys Tyr Gln Ile Asp  Tyr Arg Glu
    1115                 1120                1125

Asn Leu  Lys Glu Gln Leu Leu  Leu Gln Ser Asp Lys  Ala Phe Phe
    1130                 1135                1140

Val Asp  Phe Leu Ser Leu Leu  Arg Leu Thr Leu Gln  Leu Arg Asn
    1145                 1150                1155

Ser Leu  Ser Asn Ser Leu Ile  Asp Tyr Ile Leu Ser  Pro Val Ala
    1160                 1165                1170

Asp Glu  Asn Gly Glu Phe Phe  Asp Ser Arg Lys Ala  Leu Ser Asn
    1175                 1180                1185

Glu Pro  Gln Asp Ala Asp Ala  Asn Gly Ala Tyr His  Ile Ala Leu
    1190                 1195                1200

Lys Gly  Leu Trp Val Leu Asp  Lys Ile Arg Lys Thr  Glu Lys Val
    1205                 1210                1215

Thr Pro  Ala Lys Leu Ala Leu  Ser Asn Gln Glu Trp  Leu Ser Phe
    1220                 1225                1230

Ala Gln  Glu Lys Pro Phe Phe  Asn Glu
    1235                 1240
```

<210> SEQ ID NO 131
<211> LENGTH: 1302
<212> TYPE: PRT
<213> ORGANISM: Unknown
<220> FEATURE:
<223> OTHER INFORMATION: Acidaminococcus massiliensis strain Marseille-P2828

<400> SEQUENCE: 131

Met Ala Ala Phe Asp Lys Phe Ile His Gln Tyr Gln Val Ser Lys Thr
1               5                   10                  15

Leu Arg Phe Ala Leu Ile Pro Gln Gly Lys Thr Leu Glu Asn Thr Lys
            20                  25                  30

Asn Asn Val Leu Gln Glu Asp Asp Glu Arg Gln Lys Asn Tyr Glu Lys
        35                  40                  45

Val Lys Pro Ile Leu Asp Arg Ile Tyr Lys Val Phe Ala Glu Glu Ser
    50                  55                  60

Leu Lys Asp Cys Ser Val Asp Trp Asn Asp Leu Asn Ala Cys Leu Asp
65                  70                  75                  80

Ala Tyr Gln Lys Asn Pro Ser Ala Asp Lys Arg Gln Lys Val Lys Ala
                85                  90                  95

Ala Gln Asp Ala Leu Arg Asp Glu Ile Ala Gly Tyr Phe Thr Gly Lys
            100                 105                 110

Gln Tyr Ala Asn Gly Lys Asn Lys Asn Ala Val Lys Glu Lys Glu Gln
        115                 120                 125

Ala Glu Leu Tyr Lys Asp Ile Phe Ser Lys Lys Ile Phe Asp Gly Thr
    130                 135                 140

Val Thr Asn Asn Lys Leu Pro Gln Val Asn Leu Ser Ala Glu Glu Thr
145                 150                 155                 160

Glu Leu Leu Gly Cys Phe Asp Lys Phe Thr Thr Tyr Phe Val Gly Phe
                165                 170                 175

Tyr Gln Asn Arg Glu Asn Val Phe Ser Gly Glu Asp Ile Ala Thr Ala
            180                 185                 190

Ile Pro His Arg Ile Val Gln Asp Asn Phe Pro Lys Phe Arg Glu Asn
        195                 200                 205

Cys Arg Ile Tyr Gln Asp Leu Ile Lys Asn Glu Pro Ala Leu Lys Pro
    210                 215                 220

Leu Leu Gln Gln Ala Ala Ala Ala Val Met Ala Gln Asn Pro Lys Gly
225                 230                 235                 240

Ile Tyr Gln Pro Arg Lys Ser Leu Asp Asp Ile Phe Val Ile Pro Phe
                245                 250                 255

Tyr Asn His Leu Leu Leu Gln Asp Asp Ile Asp Tyr Phe Asn Gln Ile
            260                 265                 270

Leu Gly Gly Ile Ser Gly Ala Ala Gly Gln Lys Lys Ile Gln Gly Leu
        275                 280                 285

Asn Glu Thr Ile Asn Leu Phe Met Gln Gln His Pro Gln Glu Ala Asp
    290                 295                 300

Lys Leu Lys Lys Lys Lys Ile Arg His Arg Phe Ile Pro Leu Tyr Lys
305                 310                 315                 320

Gln Ile Leu Ser Asp Arg Thr Ser Phe Ser Phe Ile Pro Glu Ala Phe
                325                 330                 335

Ser Asn Ser Gln Glu Ala Leu Asp Gly Ile Glu Thr Phe Lys Lys Ser
            340                 345                 350

Leu Lys Lys Asn Asp Thr Phe Gly Ala Leu Glu Arg Leu Ile Gln Asn
        355                 360                 365

Leu Ala Ser Leu Asp Leu Lys Tyr Val Tyr Leu Ser Asn Lys Lys Val
    370                 375                 380

Asn Glu Ile Ser Gln Ala Leu Tyr Gly Glu Trp His Cys Ile Gln Asp
385                 390                 395                 400

-continued

```
Val Leu Lys Gln Asp Phe Ser Leu Glu Ser Leu Ile Gln Ile Asn Pro
                405                 410                 415

Gln Asn Ser Ser Asn Gly Phe Leu Ala Thr Leu Thr Asp Glu Gly Lys
            420                 425                 430

Lys Arg Ile Ser Gln Cys Arg Asn Val Leu Gly Asn Pro Leu Pro Val
        435                 440                 445

Lys Leu Ala Asp Asp Gln Asp Lys Ala Gln Val Lys Asn Gln Leu Asp
    450                 455                 460

Thr Leu Leu Ala Ala Val His Tyr Leu Glu Trp Phe Lys Ala Asp Pro
465                 470                 475                 480

Asp Leu Glu Thr Asp Pro Asn Phe Thr Val Pro Phe Glu Lys Ile Trp
                485                 490                 495

Glu Glu Leu Val Pro Leu Leu Ser Leu Tyr Ser Lys Val Arg Asn Phe
            500                 505                 510

Val Thr Lys Lys Pro Tyr Ser Thr Ala Lys Phe Lys Leu Asn Phe Ala
        515                 520                 525

Asn Pro Thr Leu Ala Asp Gly Trp Asp Ile His Lys Glu Ser Asp Asn
    530                 535                 540

Gly Ala Leu Leu Phe Glu Lys Gly Gly Leu Tyr Tyr Leu Gly Ile Met
545                 550                 555                 560

Asn Pro Lys Asp Lys Pro Asn Phe Lys Ser Tyr Gln Gly Ala Glu Pro
                565                 570                 575

Tyr Tyr Gln Lys Met Val Tyr Arg Phe Phe Pro Asp Cys Ser Lys Thr
            580                 585                 590

Ile Pro Lys Cys Ser Thr Gln Arg Lys Asp Val Lys Lys Tyr Phe Glu
        595                 600                 605

Asp His Pro Gln Ala Thr Ser Tyr Gln Ile His Asp Ser Lys Lys Glu
    610                 615                 620

Lys Phe Arg Gln Asp Phe Phe Glu Ile Pro Arg Glu Ile Tyr Glu Leu
625                 630                 635                 640

Asn Asn Thr Thr Tyr Gly Thr Gly Lys Ser Lys Tyr Lys Lys Phe Gln
                645                 650                 655

Thr Gln Tyr Tyr Gln Lys Thr Gln Asp Lys Ser Gly Tyr Gln Lys Ala
            660                 665                 670

Leu Arg Lys Trp Ile Asp Phe Ser Lys Lys Phe Leu Gln Thr Tyr Val
        675                 680                 685

Ser Thr Ser Ile Phe Asp Phe Lys Gly Leu Arg Pro Ser Lys Asp Tyr
    690                 695                 700

Gln Asp Leu Gly Glu Phe Tyr Lys Asp Val Asn Ser Arg Cys Tyr Arg
705                 710                 715                 720

Val Thr Phe Glu Lys Ile Arg Val Gln Asp Ile His Glu Ala Val Lys
                725                 730                 735

Asn Gly Gln Leu Tyr Leu Phe Gln Leu Tyr Asn Lys Asp Phe Ser Pro
            740                 745                 750

Lys Ser His Gly Leu Pro Asn Leu His Thr Leu Tyr Trp Lys Ala Val
        755                 760                 765

Phe Asp Pro Glu Asn Leu Lys Asp Pro Ile Val Lys Leu Asn Gly Gln
    770                 775                 780

Ala Glu Leu Phe Tyr Arg Pro Lys Ser Asn Met Gln Ile Ile Gln His
785                 790                 795                 800

Lys Thr Gly Glu Glu Ile Val Asn Lys Lys Leu Lys Asp Gly Thr Pro
                805                 810                 815

Val Pro Asp Asp Ile Tyr Arg Glu Ile Ser Ala Tyr Val Gln Gly Lys
```

-continued

```
            820                 825                 830

Cys Gln Gly Asn Leu Ser Pro Glu Ala Glu Lys Trp Leu Pro Ser Val
        835                 840                 845

Thr Ile Lys Lys Ala Ala His Asp Ile Thr Lys Asp Arg Arg Phe Thr
    850                 855                 860

Glu Asp Lys Phe Phe Phe His Val Pro Ile Thr Leu Asn Tyr Gln Ser
865                 870                 875                 880

Ser Gly Lys Pro Thr Ala Phe Asn Ser Gln Val Asn Asp Phe Leu Thr
                885                 890                 895

Glu His Pro Glu Thr Asn Ile Ile Gly Ile Asp Arg Gly Glu Arg Asn
            900                 905                 910

Leu Ile Tyr Ala Val Val Ile Thr Pro Asp Gly Lys Ile Leu Glu Gln
        915                 920                 925

Lys Ser Phe Asn Val Ile His Asp Phe Asp Tyr His Glu Ser Leu Ser
    930                 935                 940

Gln Arg Glu Lys Gln Arg Val Ala Ala Arg Gln Ala Trp Thr Ala Ile
945                 950                 955                 960

Gly Arg Ile Lys Asp Leu Lys Glu Gly Tyr Leu Ser Leu Val Val His
                965                 970                 975

Glu Ile Ala Gln Met Met Ile Lys Tyr Gln Ala Val Val Val Leu Glu
            980                 985                 990

Asn Leu Asn Thr Gly Phe Lys Arg  Val Arg Gly Gly Ile  Ser Glu Lys
        995                 1000                1005

Ala Val  Tyr Gln Gln Phe Glu  Lys Met Leu Ile Glu  Lys Leu Asn
    1010                1015                1020

Phe Leu  Val Phe Lys Asp Arg  Ala Ile Asn Gln Glu  Gly Gly Val
    1025                1030                1035

Leu Lys  Ala Tyr Gln Leu Thr  Asp Ser Phe Thr Ser  Phe Ala Lys
    1040                1045                1050

Leu Gly  Asn Gln Ser Gly Phe  Leu Phe Tyr Ile Pro  Ser Ala Tyr
    1055                1060                1065

Thr Ser  Lys Ile Asp Pro Gly  Thr Gly Phe Val Asp  Pro Phe Ile
    1070                1075                1080

Trp Ser  His Val Thr Ala Ser  Glu Glu Asn Arg Asn  Glu Phe Leu
    1085                1090                1095

Lys Gly  Phe Asp Ser Leu Lys  Tyr Asp Ala Gln Ser  Ser Ala Phe
    1100                1105                1110

Val Leu  His Phe Lys Met Lys  Ser Asn Lys Gln Phe  Gln Lys Asn
    1115                1120                1125

Asn Val  Glu Gly Phe Met Pro  Glu Trp Asp Ile Cys  Phe Glu Lys
    1130                1135                1140

Asn Glu  Glu Lys Ile Ser Leu  Gln Gly Ser Lys Tyr  Thr Ala Gly
    1145                1150                1155

Lys Arg  Ile Ile Phe Asp Ser  Lys Lys Lys Gln Tyr  Met Glu Cys
    1160                1165                1170

Phe Pro  Gln Asn Glu Leu Met  Lys Ala Leu Gln Asp  Val Gly Ile
    1175                1180                1185

Thr Trp  Asn Thr Gly Asn Asp  Ile Trp Gln Asp Val  Leu Lys Gln
    1190                1195                1200

Ala Ser  Thr Asp Thr Gly Phe  Arg His Arg Met Ile  Asn Leu Ile
    1205                1210                1215

Arg Ser  Val Leu Gln Met Arg  Ser Ser Asn Gly Ala  Thr Gly Glu
    1220                1225                1230
```

Asp Tyr Ile Asn Ser Pro Val Met Asp Leu Asp Gly Arg Phe Phe
1235 1240 1245

Asp Thr Arg Ala Gly Ile Arg Asp Leu Pro Leu Asp Ala Asp Ala
1250 1255 1260

Asn Gly Ala Tyr His Ile Ala Leu Lys Gly Arg Met Val Leu Glu
1265 1270 1275

Arg Ile Arg Ser Gln Lys Asn Thr Ala Ile Lys Asn Thr Asp Trp
1280 1285 1290

Leu Tyr Ala Ile Gln Glu Glu Arg Asn
1295 1300

<210> SEQ ID NO 132
<211> LENGTH: 1310
<212> TYPE: PRT
<213> ORGANISM: Helcococcus kunzii

<400> SEQUENCE: 132

Met Phe Glu Lys Leu Ser Asn Ile Val Ser Ile Ser Lys Thr Ile Arg
1 5 10 15

Phe Lys Leu Ile Pro Val Gly Lys Thr Leu Glu Asn Ile Glu Lys Leu
20 25 30

Gly Lys Leu Glu Lys Asp Phe Glu Arg Ser Asp Phe Tyr Pro Ile Leu
35 40 45

Lys Asn Ile Ser Asp Asp Tyr Tyr Arg Gln Tyr Ile Lys Glu Lys Leu
50 55 60

Ser Asp Leu Asn Leu Asp Trp Gln Lys Leu Tyr Asp Ala His Glu Leu
65 70 75 80

Leu Asp Ser Ser Lys Lys Glu Ser Gln Lys Asn Leu Glu Met Ile Gln
85 90 95

Ala Gln Tyr Arg Lys Val Leu Phe Asn Ile Leu Ser Gly Glu Leu Asp
100 105 110

Lys Ser Gly Glu Lys Asn Ser Lys Asp Leu Ile Lys Asn Asn Lys Ala
115 120 125

Leu Tyr Gly Lys Leu Phe Lys Lys Gln Phe Ile Leu Glu Val Leu Pro
130 135 140

Asp Phe Val Asn Asn Asn Asp Ser Tyr Ser Glu Glu Asp Leu Glu Gly
145 150 155 160

Leu Asn Leu Tyr Ser Lys Phe Thr Thr Arg Leu Lys Asn Phe Trp Glu
165 170 175

Thr Arg Lys Asn Val Phe Thr Asp Lys Asp Ile Val Thr Ala Ile Pro
180 185 190

Phe Arg Ala Val Asn Glu Asn Phe Gly Phe Tyr Tyr Asp Asn Ile Lys
195 200 205

Ile Phe Asn Lys Asn Ile Glu Tyr Leu Glu Asn Lys Ile Pro Asn Leu
210 215 220

Glu Asn Glu Leu Lys Glu Ala Asp Ile Leu Asp Asp Asn Arg Ser Val
225 230 235 240

Lys Asp Tyr Phe Thr Pro Asn Gly Phe Asn Tyr Val Ile Thr Gln Asp
245 250 255

Gly Ile Asp Val Tyr Gln Ala Ile Arg Gly Gly Phe Thr Lys Glu Asn
260 265 270

Gly Glu Lys Val Gln Gly Ile Asn Glu Ile Leu Asn Leu Thr Gln Gln
275 280 285

Gln Leu Arg Arg Lys Pro Glu Thr Lys Asn Val Lys Leu Gly Val Leu

-continued

```
    290                 295                 300

Thr Lys Leu Arg Lys Gln Ile Leu Glu Tyr Ser Glu Ser Thr Ser Phe
305                 310                 315                 320

Leu Ile Asp Gln Ile Glu Asp Asp Asn Asp Leu Val Asp Arg Ile Asn
                325                 330                 335

Lys Phe Asn Val Ser Phe Phe Glu Ser Thr Glu Val Ser Pro Ser Leu
            340                 345                 350

Phe Glu Gln Ile Glu Arg Leu Tyr Asn Ala Leu Lys Ser Ile Lys Lys
        355                 360                 365

Glu Glu Val Tyr Ile Asp Ala Arg Asn Thr Gln Lys Phe Ser Gln Met
    370                 375                 380

Leu Phe Gly Gln Trp Asp Val Ile Arg Arg Gly Tyr Thr Val Lys Ile
385                 390                 395                 400

Thr Glu Gly Ser Lys Glu Glu Lys Lys Lys Tyr Lys Glu Tyr Leu Glu
                405                 410                 415

Leu Asp Glu Thr Ser Lys Ala Lys Arg Tyr Leu Asn Ile Arg Glu Ile
            420                 425                 430

Glu Glu Leu Val Asn Leu Val Glu Gly Phe Glu Glu Val Asp Val Phe
        435                 440                 445

Ser Val Leu Leu Glu Lys Phe Lys Met Asn Asn Ile Glu Arg Ser Glu
    450                 455                 460

Phe Glu Ala Pro Ile Tyr Gly Ser Pro Ile Lys Leu Glu Ala Ile Lys
465                 470                 475                 480

Glu Tyr Leu Glu Lys His Leu Glu Glu Tyr His Lys Trp Lys Leu Leu
                485                 490                 495

Leu Ile Gly Asn Asp Asp Leu Asp Thr Asp Glu Thr Phe Tyr Pro Leu
            500                 505                 510

Leu Asn Glu Val Ile Ser Asp Tyr Tyr Ile Ile Pro Leu Tyr Asn Leu
        515                 520                 525

Thr Arg Asn Tyr Leu Thr Arg Lys His Ser Asp Lys Asp Lys Ile Lys
    530                 535                 540

Val Asn Phe Asp Phe Pro Thr Leu Ala Asp Gly Trp Ser Glu Ser Lys
545                 550                 555                 560

Ile Ser Asp Asn Arg Ser Ile Ile Leu Arg Lys Gly Gly Tyr Tyr Tyr
                565                 570                 575

Leu Gly Ile Leu Ile Asp Asn Lys Leu Leu Ile Asn Lys Lys Asn Lys
            580                 585                 590

Ser Lys Lys Ile Tyr Glu Ile Leu Ile Tyr Asn Gln Ile Pro Glu Phe
        595                 600                 605

Ser Lys Ser Ile Pro Asn Tyr Pro Phe Thr Lys Lys Val Lys Glu His
    610                 615                 620

Phe Lys Asn Asn Val Ser Asp Phe Gln Leu Ile Asp Gly Tyr Val Ser
625                 630                 635                 640

Pro Leu Ile Ile Thr Lys Glu Ile Tyr Asp Ile Lys Lys Glu Lys Lys
                645                 650                 655

Tyr Lys Lys Asp Phe Tyr Lys Asp Asn Asn Thr Asn Lys Asn Tyr Leu
            660                 665                 670

Tyr Thr Ile Tyr Lys Trp Ile Glu Phe Cys Lys Gln Phe Leu Tyr Lys
        675                 680                 685

Tyr Lys Gly Pro Asn Lys Glu Ser Tyr Lys Glu Met Tyr Asp Phe Ser
    690                 695                 700

Thr Leu Lys Asp Thr Ser Leu Tyr Val Asn Leu Asn Asp Phe Tyr Ala
705                 710                 715                 720
```

```
Asp Val Asn Ser Cys Ala Tyr Arg Val Leu Phe Asn Lys Ile Asp Glu
                725                 730                 735

Asn Thr Ile Asp Asn Ala Val Glu Asp Gly Lys Leu Leu Leu Phe Gln
            740                 745                 750

Ile Tyr Asn Lys Asp Phe Ser Pro Glu Ser Lys Gly Lys Lys Asn Leu
        755                 760                 765

His Thr Leu Tyr Trp Leu Ser Met Phe Ser Glu Glu Asn Leu Arg Thr
    770                 775                 780

Arg Lys Leu Lys Leu Asn Gly Gln Ala Glu Ile Phe Tyr Arg Lys Lys
785                 790                 795                 800

Leu Glu Lys Lys Pro Ile Ile His Lys Glu Gly Ser Ile Leu Leu Asn
                805                 810                 815

Lys Ile Asp Lys Glu Gly Asn Thr Ile Pro Glu Asn Ile Tyr His Glu
            820                 825                 830

Cys Tyr Arg Tyr Leu Asn Lys Lys Ile Gly Arg Glu Asp Leu Ser Asp
        835                 840                 845

Glu Ala Ile Ala Leu Phe Asn Lys Asp Val Leu Lys Tyr Lys Glu Ala
    850                 855                 860

Arg Phe Asp Ile Ile Lys Asp Arg Arg Tyr Ser Glu Ser Gln Phe Phe
865                 870                 875                 880

Phe His Val Pro Ile Thr Phe Asn Trp Asp Ile Lys Thr Asn Lys Asn
                885                 890                 895

Val Asn Gln Ile Val Gln Gly Met Ile Lys Asp Gly Glu Ile Lys His
            900                 905                 910

Ile Ile Gly Ile Asp Arg Gly Glu Arg His Leu Leu Tyr Tyr Ser Val
        915                 920                 925

Ile Asp Leu Glu Gly Asn Ile Val Glu Gln Gly Ser Leu Asn Thr Leu
    930                 935                 940

Glu Gln Asn Arg Phe Asp Asn Ser Thr Val Lys Val Asp Tyr Gln Asn
945                 950                 955                 960

Lys Leu Arg Thr Arg Glu Glu Asp Arg Asp Arg Ala Arg Lys Asn Trp
                965                 970                 975

Thr Asn Ile Asn Lys Ile Lys Glu Leu Lys Asp Gly Tyr Leu Ser His
            980                 985                 990

Val Val His Lys Leu Ser Arg Leu  Ile Ile Lys Tyr Glu  Ala Ile Val
        995                 1000                 1005

Ile Met  Glu Asn Leu Asn Gln  Gly Phe Lys Arg Gly  Arg Phe Lys
    1010                 1015                 1020

Val Glu  Arg Gln Val Tyr Gln  Lys Phe Glu Leu Ala  Leu Met Asn
    1025                 1030                 1035

Lys Leu  Ser Ala Leu Ser Phe  Lys Glu Lys Tyr Asp  Glu Arg Lys
    1040                 1045                 1050

Asn Leu  Glu Pro Ser Gly Ile  Leu Asn Pro Ile Gln  Ala Cys Tyr
    1055                 1060                 1065

Pro Val  Asp Ala Tyr Gln Glu  Leu Gln Gly Gln Asn  Gly Ile Val
    1070                 1075                 1080

Phe Tyr  Leu Pro Ala Ala Tyr  Thr Ser Val Ile Asp  Pro Val Thr
    1085                 1090                 1095

Gly Phe  Thr Asn Leu Phe Arg  Leu Lys Ser Ile Asn  Ser Ser Lys
    1100                 1105                 1110

Tyr Glu  Glu Phe Ile Lys Lys  Phe Lys Asn Ile Tyr  Phe Asp Asn
    1115                 1120                 1125
```

```
Glu Glu  Glu Asp Phe Lys Phe  Ile Phe Asn Tyr Lys  Asp Phe Ala
    1130                 1135                 1140

Lys Ala  Asn Leu Val Ile Leu  Asn Asn Ile Lys Ser  Lys Asp Trp
    1145                 1150                 1155

Lys Ile  Ser Thr Arg Gly Glu  Arg Ile Ser Tyr Asn  Ser Lys Lys
    1160                 1165                 1170

Lys Glu  Tyr Phe Tyr Val Gln  Pro Thr Glu Phe Leu  Ile Asn Lys
    1175                 1180                 1185

Leu Lys  Glu Leu Asn Ile Asp  Tyr Glu Asn Ile Asp  Ile Ile Pro
    1190                 1195                 1200

Leu Ile  Asp Asn Leu Glu Glu  Lys Ala Lys Arg Lys  Ile Leu Lys
    1205                 1210                 1215

Ala Leu  Phe Asp Thr Phe Lys  Tyr Ser Val Gln Leu  Arg Asn Tyr
    1220                 1225                 1230

Asp Phe  Glu Asn Asp Tyr Ile  Ile Ser Pro Thr Ala  Asp Asp Asn
    1235                 1240                 1245

Gly Asn  Tyr Tyr Asn Ser Asn  Glu Ile Asp Ile Asp  Lys Thr Asn
    1250                 1255                 1260

Leu Pro  Asn Asn Gly Asp Ala  Asn Gly Ala Phe Asn  Ile Ala Arg
    1265                 1270                 1275

Lys Gly  Leu Leu Leu Lys Asp  Arg Ile Val Asn Ser  Asn Glu Ser
    1280                 1285                 1290

Lys Val  Asp Leu Lys Ile Lys  Asn Glu Asp Trp Ile  Asn Phe Ile
    1295                 1300                 1305

Ile Ser
    1310
```

<210> SEQ ID NO 133
<211> LENGTH: 1263
<212> TYPE: PRT
<213> ORGANISM: Unknown
<220> FEATURE:
<223> OTHER INFORMATION: Agathobacter rectalis strain 2789STDY5834884

<400> SEQUENCE: 133

```
Met Asn Asn Gly Thr Asn Asn Phe Gln Asn Phe Ile Gly Ile Ser Ser
1               5                   10                  15

Leu Gln Lys Thr Leu Arg Asn Ala Leu Thr Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Ala Glu Lys Arg Lys Ala Ile Tyr Lys Lys
            100                 105                 110

Phe Ala Asp Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
    130                 135                 140

Ser Glu Lys Glu Glu Lys Thr Gln Val Ile Lys Leu Phe Ser Arg Phe
145                 150                 155                 160
```

-continued

Ala Thr Ser Phe Lys Asp Tyr Phe Lys Asn Arg Ala Asn Cys Phe Ser
165 170 175

Ala Asp Asp Ile Ser Ser Ser Ser Cys His Arg Ile Val Asn Asp Asn
180 185 190

Ala Glu Ile Phe Phe Ser Asn Ala Leu Val Tyr Arg Arg Ile Val Lys
195 200 205

Asn Leu Ser Asn Asp Asp Ile Asn Lys Ile Ser Gly Asp Met Lys Asp
210 215 220

Ser Leu Lys Lys Met Ser Leu Glu Lys Ile Tyr Ser Tyr Glu Lys Tyr
225 230 235 240

Gly Glu Phe Ile Thr Gln Glu Gly Ile Ser Phe Tyr Asn Asp Ile Cys
245 250 255

Gly Lys Val Asn Ser Phe Met Asn Leu Tyr Cys Gln Lys Asn Lys Glu
260 265 270

Asn Lys Asn Leu Tyr Lys Leu Arg Lys Leu His Lys Gln Ile Leu Cys
275 280 285

Ile Ala Asp Thr Ser Tyr Glu Val Pro Tyr Lys Phe Glu Ser Asp Glu
290 295 300

Glu Val Tyr Gln Ser Val Asn Gly Phe Leu Asp Asn Ile Ser Ser Lys
305 310 315 320

His Ile Val Glu Arg Leu Arg Lys Ile Gly Asp Asn Tyr Asn Gly Tyr
325 330 335

Asn Leu Asp Lys Ile Tyr Ile Val Ser Lys Phe Tyr Glu Ser Val Ser
340 345 350

Gln Lys Thr Tyr Arg Asp Trp Glu Thr Ile Asn Thr Ala Leu Glu Ile
355 360 365

His Tyr Asn Asn Ile Leu Pro Gly Asn Gly Lys Ser Lys Ala Asp Lys
370 375 380

Val Lys Lys Ala Val Lys Asn Asp Leu Gln Lys Ser Ile Thr Glu Ile
385 390 395 400

Asn Glu Leu Val Ser Asn Tyr Lys Leu Cys Pro Asp Asp Asn Ile Lys
405 410 415

Ala Glu Thr Tyr Ile His Glu Ile Ser His Ile Leu Asn Asn Phe Glu
420 425 430

Ala Gln Glu Leu Lys Tyr Asn Pro Glu Ile His Leu Val Glu Ser Glu
435 440 445

Leu Lys Ala Ser Glu Leu Lys Asn Val Leu Asp Val Ile Met Asn Ala
450 455 460

Phe His Trp Cys Ser Val Phe Met Thr Glu Glu Leu Val Asp Lys Asp
465 470 475 480

Asn Asn Phe Tyr Ala Glu Leu Glu Glu Ile Tyr Asp Glu Ile Tyr Pro
485 490 495

Val Ile Ser Leu Tyr Asn Leu Val Arg Asn Tyr Val Thr Gln Lys Pro
500 505 510

Tyr Ser Thr Lys Lys Ile Lys Leu Asn Phe Gly Ile Pro Thr Leu Ala
515 520 525

Asp Gly Trp Ser Lys Ser Lys Glu Tyr Ser Asn Asn Ala Ile Ile Leu
530 535 540

Met Arg Asp Asn Leu Tyr Tyr Leu Gly Ile Phe Asn Ala Lys Asn Lys
545 550 555 560

Pro Glu Lys Lys Ile Ile Glu Gly Asn Thr Ser Glu Asn Lys Gly Asp
565 570 575

Tyr Lys Lys Met Ile Tyr Asn Leu Leu Pro Gly Pro Asn Lys Met Ile

```
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Leu Lys Ser
    610                 615                 620

Ser Lys Asp Phe Asp Ile Thr Phe Cys Arg Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Val
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Ile Gln Ile Val
    770                 775                 780

Arg Lys Thr Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Ala Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Lys Thr Ser Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser  Ile Thr Glu Asn Gly  Gly Leu Leu
        995                 1000                1005
```

Lys Gly Tyr Gln Leu Thr Tyr Ile Pro Glu Lys Leu Lys Asn Val
1010 1015 1020

Gly His Gln Cys Gly Cys Ile Phe Tyr Val Pro Ala Ala Tyr Thr
1025 1030 1035

Ser Lys Ile Asp Pro Thr Thr Gly Phe Val Asn Ile Phe Lys Phe
1040 1045 1050

Lys Asp Leu Thr Val Asp Ala Lys Arg Glu Phe Ile Lys Lys Phe
1055 1060 1065

Asp Ser Ile Arg Tyr Asp Ser Asp Lys Asn Leu Phe Cys Phe Thr
1070 1075 1080

Phe Asp Tyr Asn Asn Phe Ile Thr Gln Asn Thr Val Met Ser Lys
1085 1090 1095

Ser Ser Trp Ser Val Tyr Thr Tyr Gly Val Arg Ile Lys Arg Arg
1100 1105 1110

Phe Val Asn Gly Arg Phe Ser Asn Glu Ser Asp Thr Ile Asp Ile
1115 1120 1125

Thr Lys Asp Met Glu Lys Thr Leu Glu Met Thr Asp Ile Asn Trp
1130 1135 1140

Arg Asp Gly His Asp Leu Arg Gln Asp Ile Ile Asp Tyr Glu Ile
1145 1150 1155

Val Gln His Ile Phe Glu Ile Phe Lys Leu Thr Val Gln Met Arg
1160 1165 1170

Asn Ser Leu Ser Glu Leu Glu Asp Arg Asn Tyr Asp Arg Leu Ile
1175 1180 1185

Ser Pro Val Leu Asn Glu Asn Asn Ile Phe Tyr Asp Ser Ala Lys
1190 1195 1200

Ala Gly Asp Ala Leu Pro Lys Asp Ala Asp Ala Asn Gly Ala Tyr
1205 1210 1215

Cys Ile Ala Leu Lys Gly Leu Tyr Glu Ile Lys Gln Ile Thr Glu
1220 1225 1230

Asn Trp Lys Glu Asp Gly Lys Phe Ser Arg Asp Lys Leu Lys Ile
1235 1240 1245

Ser Asn Lys Asp Trp Phe Asp Phe Ile Gln Asn Lys Arg Tyr Leu
1250 1255 1260

<210> SEQ ID NO 134
<211> LENGTH: 1307
<212> TYPE: PRT
<213> ORGANISM: Unknown
<220> FEATURE:
<223> OTHER INFORMATION: Acidaminococcus sp. BV3L6

<400> SEQUENCE: 134

Met Thr Gln Phe Glu Gly Phe Thr Asn Leu Tyr Gln Val Ser Lys Thr
1 5 10 15

Leu Arg Phe Glu Leu Ile Pro Gln Gly Lys Thr Leu Lys His Ile Gln
20 25 30

Glu Gln Gly Phe Ile Glu Glu Asp Lys Ala Arg Asn Asp His Tyr Lys
35 40 45

Glu Leu Lys Pro Ile Ile Asp Arg Ile Tyr Lys Thr Tyr Ala Asp Gln
50 55 60

Cys Leu Gln Leu Val Gln Leu Asp Trp Glu Asn Leu Ser Ala Ala Ile
65 70 75 80

Asp Ser Tyr Arg Lys Glu Lys Thr Glu Glu Thr Arg Asn Ala Leu Ile
85 90 95

```
Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510
```

-continued

```
Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
```

-continued

```
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110

Ile Leu  His Phe Lys Met Asn  Arg Asn Leu Ser Phe  Gln Arg Gly
    1115                1120                1125

Leu Pro  Gly Phe Met Pro Ala  Trp Asp Ile Val Phe  Glu Lys Asn
    1130                1135                1140

Glu Thr  Gln Phe Asp Ala Lys  Gly Thr Pro Phe Ile  Ala Gly Lys
    1145                1150                1155

Arg Ile  Val Pro Val Ile Glu  Asn His Arg Phe Thr  Gly Arg Tyr
    1160                1165                1170

Arg Asp  Leu Tyr Pro Ala Asn  Glu Leu Ile Ala Leu  Leu Glu Glu
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245

Phe Asp  Ser Arg Phe Gln Asn  Pro Glu Trp Pro Met  Asp Ala Asp
    1250                1255                1260

Ala Asn  Gly Ala Tyr His Ile  Ala Leu Lys Gly Gln  Leu Leu Leu
    1265                1270                1275

Asn His  Leu Lys Glu Ser Lys  Asp Leu Lys Leu Gln  Asn Gly Ile
    1280                1285                1290

Ser Asn  Gln Asp Trp Leu Ala  Tyr Ile Gln Glu Leu  Arg Asn
    1295                1300                1305
```

<210> SEQ ID NO 135
<211> LENGTH: 1246
<212> TYPE: PRT
<213> ORGANISM: Unknown

<220> FEATURE:
<223> OTHER INFORMATION: Lachnospiraceae bacterium ND2006

<400> SEQUENCE: 135

```
Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
        115                 120                 125

Gly Asn Glu Gly Tyr Lys Ser Leu Phe Lys Lys Asp Ile Ile Glu Thr
    130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
        195                 200                 205

Glu Lys Val Asp Ala Ile Phe Asp Lys His Glu Val Gln Glu Ile Lys
    210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
                245                 250                 255

Ala Ile Ile Gly Gly Phe Val Thr Glu Ser Gly Glu Lys Ile Lys Gly
            260                 265                 270

Leu Asn Glu Tyr Ile Asn Leu Tyr Asn Gln Lys Thr Lys Gln Lys Leu
        275                 280                 285

Pro Lys Phe Lys Pro Leu Tyr Lys Gln Val Leu Ser Asp Arg Glu Ser
    290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
            340                 345                 350

Gly Ile Phe Val Lys Asn Gly Pro Ala Ile Ser Thr Ile Ser Lys Asp
        355                 360                 365

Ile Phe Gly Glu Trp Asn Val Ile Arg Asp Lys Trp Asn Ala Glu Tyr
    370                 375                 380

Asp Asp Ile His Leu Lys Lys Lys Ala Val Val Thr Glu Lys Tyr Glu
385                 390                 395                 400
```

```
Asp Asp Arg Arg Lys Ser Phe Lys Lys Ile Gly Ser Phe Ser Leu Glu
                405                 410                 415

Gln Leu Gln Glu Tyr Ala Asp Ala Asp Leu Ser Val Val Glu Lys Leu
            420                 425                 430

Lys Glu Ile Ile Ile Gln Lys Val Asp Glu Ile Tyr Lys Val Tyr Gly
        435                 440                 445

Ser Ser Glu Lys Leu Phe Asp Ala Asp Phe Val Leu Glu Lys Ser Leu
    450                 455                 460

Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Glu Gly Lys
                485                 490                 495

Glu Thr Asn Arg Asp Glu Ser Phe Tyr Gly Asp Phe Val Leu Ala Tyr
            500                 505                 510

Asp Ile Leu Leu Lys Val Asp His Ile Tyr Asp Ala Ile Arg Asn Tyr
        515                 520                 525

Val Thr Gln Lys Pro Tyr Ser Lys Asp Lys Phe Lys Leu Tyr Phe Gln
    530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
            580                 585                 590

Asn Gly Asn Tyr Glu Lys Ile Asn Tyr Lys Leu Leu Pro Gly Pro Asn
        595                 600                 605

Lys Met Leu Pro Lys Val Phe Phe Ser Lys Lys Trp Met Ala Tyr Tyr
    610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
            660                 665                 670

Phe Asn Phe Ser Glu Thr Glu Lys Tyr Lys Asp Ile Ala Gly Phe Tyr
        675                 680                 685

Arg Glu Val Glu Glu Gln Gly Tyr Lys Val Ser Phe Glu Ser Ala Ser
    690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
            740                 745                 750

Gln Ile Arg Leu Ser Gly Gly Ala Glu Leu Phe Met Arg Arg Ala Ser
        755                 760                 765

Leu Lys Lys Glu Glu Leu Val Val His Pro Ala Asn Ser Pro Ile Ala
    770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815
```

-continued

```
Pro Ile Ala Ile Asn Lys Cys Pro Lys Asn Ile Phe Lys Ile Asn Thr
            820                 825                 830

Glu Val Arg Val Leu Leu Lys His Asp Asp Asn Pro Tyr Val Ile Gly
        835                 840                 845

Ile Asp Arg Gly Glu Arg Asn Leu Leu Tyr Ile Val Val Val Asp Gly
    850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
            900                 905                 910

Asn Ile Lys Glu Leu Lys Ala Gly Tyr Ile Ser Gln Val Val His Lys
        915                 920                 925

Ile Cys Glu Leu Val Glu Lys Tyr Asp Ala Val Ile Ala Leu Glu Asp
    930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
            980                 985                 990

Gln Ile Thr Asn Lys Phe Glu Ser  Phe Lys Ser Met Ser  Thr Gln Asn
        995                 1000                1005

Gly Phe  Ile Phe Tyr Ile Pro  Ala Trp Leu Thr Ser  Lys Ile Asp
    1010                1015                1020

Pro Ser  Thr Gly Phe Val Asn  Leu Leu Lys Thr Lys  Tyr Thr Ser
    1025                1030                1035

Ile Ala  Asp Ser Lys Lys Phe  Ile Ser Ser Phe Asp  Arg Ile Met
    1040                1045                1050

Tyr Val  Pro Glu Glu Asp Leu  Phe Glu Phe Ala Leu  Asp Tyr Lys
    1055                1060                1065

Asn Phe  Ser Arg Thr Asp Ala  Asp Tyr Ile Lys Lys  Trp Lys Leu
    1070                1075                1080

Tyr Ser  Tyr Gly Asn Arg Ile  Arg Ile Phe Arg Asn  Pro Lys Lys
    1085                1090                1095

Asn Asn  Val Phe Asp Trp Glu  Glu Val Cys Leu Thr  Ser Ala Tyr
    1100                1105                1110

Lys Glu  Leu Phe Asn Lys Tyr  Gly Ile Asn Tyr Gln  Gln Gly Asp
    1115                1120                1125

Ile Arg  Ala Leu Leu Cys Glu  Gln Ser Asp Lys Ala  Phe Tyr Ser
    1130                1135                1140

Ser Phe  Met Ala Leu Met Ser  Leu Met Leu Gln Met  Arg Asn Ser
    1145                1150                1155

Ile Thr  Gly Arg Thr Asp Val  Asp Phe Leu Ile Ser  Pro Val Lys
    1160                1165                1170

Asn Ser  Asp Gly Ile Phe Tyr  Asp Ser Arg Asn Tyr  Glu Ala Gln
    1175                1180                1185

Glu Asn  Ala Ile Leu Pro Lys  Asn Ala Asp Ala Asn  Gly Ala Tyr
    1190                1195                1200

Asn Ile  Ala Arg Lys Val Leu  Trp Ala Ile Gly Gln  Phe Lys Lys
    1205                1210                1215

Ala Glu  Asp Glu Lys Leu Asp  Lys Val Lys Ile Ala  Ile Ser Asn
```

1220 1225 1230

Lys Glu Trp Leu Glu Tyr Ala Gln Thr Ser Val Lys His
1235 1240 1245

<210> SEQ ID NO 136
<211> LENGTH: 1300
<212> TYPE: PRT
<213> ORGANISM: Unknown
<220> FEATURE:
<223> OTHER INFORMATION: Francisella tularensis subsp. novicida U112

<400> SEQUENCE: 136

Met Ser Ile Tyr Gln Glu Phe Val Asn Lys Tyr Ser Leu Ser Lys Thr
1 5 10 15

Leu Arg Phe Glu Leu Ile Pro Gln Gly Lys Thr Leu Glu Asn Ile Lys
20 25 30

Ala Arg Gly Leu Ile Leu Asp Asp Glu Lys Arg Ala Lys Asp Tyr Lys
35 40 45

Lys Ala Lys Gln Ile Ile Asp Lys Tyr His Gln Phe Phe Ile Glu Glu
50 55 60

Ile Leu Ser Ser Val Cys Ile Ser Glu Asp Leu Leu Gln Asn Tyr Ser
65 70 75 80

Asp Val Tyr Phe Lys Leu Lys Lys Ser Asp Asp Asp Asn Leu Gln Lys
85 90 95

Asp Phe Lys Ser Ala Lys Asp Thr Ile Lys Lys Gln Ile Ser Glu Tyr
100 105 110

Ile Lys Asp Ser Glu Lys Phe Lys Asn Leu Phe Asn Gln Asn Leu Ile
115 120 125

Asp Ala Lys Lys Gly Gln Glu Ser Asp Leu Ile Leu Trp Leu Lys Gln
130 135 140

Ser Lys Asp Asn Gly Ile Glu Leu Phe Lys Ala Asn Ser Asp Ile Thr
145 150 155 160

Asp Ile Asp Glu Ala Leu Glu Ile Ile Lys Ser Phe Lys Gly Trp Thr
165 170 175

Thr Tyr Phe Lys Gly Phe His Glu Asn Arg Lys Asn Val Tyr Ser Ser
180 185 190

Asn Asp Ile Pro Thr Ser Ile Ile Tyr Arg Ile Val Asp Asp Asn Leu
195 200 205

Pro Lys Phe Leu Glu Asn Lys Ala Lys Tyr Glu Ser Leu Lys Asp Lys
210 215 220

Ala Pro Glu Ala Ile Asn Tyr Glu Gln Ile Lys Lys Asp Leu Ala Glu
225 230 235 240

Glu Leu Thr Phe Asp Ile Asp Tyr Lys Thr Ser Glu Val Asn Gln Arg
245 250 255

Val Phe Ser Leu Asp Glu Val Phe Glu Ile Ala Asn Phe Asn Asn Tyr
260 265 270

Leu Asn Gln Ser Gly Ile Thr Lys Phe Asn Thr Ile Ile Gly Gly Lys
275 280 285

Phe Val Asn Gly Glu Asn Thr Lys Arg Lys Gly Ile Asn Glu Tyr Ile
290 295 300

Asn Leu Tyr Ser Gln Gln Ile Asn Asp Lys Thr Leu Lys Lys Tyr Lys
305 310 315 320

Met Ser Val Leu Phe Lys Gln Ile Leu Ser Asp Thr Glu Ser Lys Ser
325 330 335

Phe Val Ile Asp Lys Leu Glu Asp Asp Ser Asp Val Val Thr Thr Met

```
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765
```

-continued

```
Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
    1055                1060                1065

Lys Gln  Thr Gly Ile Ile Tyr  Tyr Val Pro Ala Gly  Phe Thr Ser
    1070                1075                1080

Lys Ile  Cys Pro Val Thr Gly  Phe Val Asn Gln Leu  Tyr Pro Lys
    1085                1090                1095

Tyr Glu  Ser Val Ser Lys Ser  Gln Glu Phe Phe Ser  Lys Phe Asp
    1100                1105                1110

Lys Ile  Cys Tyr Asn Leu Asp  Lys Gly Tyr Phe Glu  Phe Ser Phe
    1115                1120                1125

Asp Tyr  Lys Asn Phe Gly Asp  Lys Ala Ala Lys Gly  Lys Trp Thr
    1130                1135                1140

Ile Ala  Ser Phe Gly Ser Arg  Leu Ile Asn Phe Arg  Asn Ser Asp
    1145                1150                1155

Lys Asn  His Asn Trp Asp Thr  Arg Glu Val Tyr Pro  Thr Lys Glu
    1160                1165                1170
```

Leu Glu Lys Leu Leu Lys Asp Tyr Ser Ile Glu Tyr Gly His Gly
1175 1180 1185

Glu Cys Ile Lys Ala Ala Ile Cys Gly Glu Ser Asp Lys Lys Phe
1190 1195 1200

Phe Ala Lys Leu Thr Ser Val Leu Asn Thr Ile Leu Gln Met Arg
1205 1210 1215

Asn Ser Lys Thr Gly Thr Glu Leu Asp Tyr Leu Ile Ser Pro Val
1220 1225 1230

Ala Asp Val Asn Gly Asn Phe Phe Asp Ser Arg Gln Ala Pro Lys
1235 1240 1245

Asn Met Pro Gln Asp Ala Asp Ala Asn Gly Ala Tyr His Ile Gly
1250 1255 1260

Leu Lys Gly Leu Met Leu Leu Gly Arg Ile Lys Asn Asn Gln Glu
1265 1270 1275

Gly Lys Lys Leu Asn Leu Val Ile Lys Asn Glu Glu Tyr Phe Glu
1280 1285 1290

Phe Val Gln Asn Arg Asn Asn
1295 1300

<210> SEQ ID NO 137
<211> LENGTH: 1067
<212> TYPE: PRT
<213> ORGANISM: Unknown
<220> FEATURE:
<223> OTHER INFORMATION: Omnitrophica WOR_2 bacterium GWF2_38_59

<400> SEQUENCE: 137

Met Lys Asn Gly Ile Asn Leu Phe Lys Thr Lys Thr Thr Lys Thr Lys
1 5 10 15

Gly Val Asp Met Glu Lys Tyr Gln Ile Thr Lys Thr Ile Arg Phe Lys
20 25 30

Leu Leu Pro Asp Asn Ala His Glu Ile Val Glu Lys Val Lys Ser Leu
35 40 45

Lys Thr Ser Asn Val Asp Glu Leu Met Asp Glu Val Lys Asn Val His
50 55 60

Leu Lys Gly Leu Glu Leu Leu Phe Ala Leu Lys Lys Tyr Phe Tyr Phe
65 70 75 80

Asp Gly Asn Gln Cys Lys Ser Phe Lys Ser Thr Leu Glu Ile Lys Ala
85 90 95

Arg Trp Leu Arg Leu Tyr Thr Pro Asp Gln Tyr Tyr Leu Lys Lys Ser
100 105 110

Ser Lys Asn Ser Tyr Gln Leu Lys Ser Leu Ser Tyr Phe Lys Asp Val
115 120 125

Phe Asn Asp Trp Leu Phe Asn Trp Glu Glu Ser Val Ser Glu Leu Ala
130 135 140

Ile Ile Tyr Glu Lys Tyr Lys Ile Cys Gln His Gln Arg Asp Ser Arg
145 150 155 160

Ala Asp Ile Ala Leu Leu Ile Lys Lys Leu Ser Met Lys Glu Tyr Phe
165 170 175

Pro Phe Ile Ser Asp Leu Ile Asp Cys Val Asn Asp Lys Asn Ser Asn
180 185 190

Lys Thr Phe Leu Met Lys Leu Ser Glu Glu Leu Ser Val Leu Leu Glu
195 200 205

Lys Cys Asn Ser Arg Ala Leu Pro Tyr Gln Ser Asn Gly Ile Val Val
210 215 220

-continued

```
Gly Lys Ala Ser Leu Asn Tyr Tyr Thr Val Ser Lys Ser Glu Lys Met
225                 230                 235                 240

Leu Gln Asn Glu Tyr Glu Asp Val Cys Gln Ser Leu Asp Lys Asn Tyr
                245                 250                 255

Asp Ile Thr Glu Met Lys Val Ile Leu Tyr Lys Glu Lys Leu Asp Asn
            260                 265                 270

Leu Asn Phe Lys Asp Val Thr Ile Ala Asn Ala Tyr Asn Leu Leu Lys
        275                 280                 285

Glu Asn Lys Ala Leu Gln Lys Arg Leu Phe Ser Glu Tyr Val Ser Gln
    290                 295                 300

Gly Lys Val Leu Ser Leu Ile Lys Thr Glu Leu Pro Leu Phe Ser Asn
305                 310                 315                 320

Ile Asn Asp Asn Asp Phe Glu Lys Tyr Lys Glu Trp Ser Asn Glu Ile
                325                 330                 335

Lys Lys Leu Ala Asp Lys Lys Asn Thr Phe Cys Lys Lys Thr Gln Gln
            340                 345                 350

Asp Lys Ile Lys Asp Ile Gln Asn Lys Ile Ser Glu Leu Lys Lys Lys
        355                 360                 365

Arg Gly Ala Leu Phe Gln Tyr Lys Phe Thr Ser Phe Gln Lys His Cys
    370                 375                 380

Asp Asn Tyr Lys Lys Val Ala Val Gln Tyr Gly Lys Leu Lys Ala Arg
385                 390                 395                 400

Lys Lys Ala Ile Glu Lys Asp Glu Ile Glu Ala Asn Leu Leu Arg Tyr
                405                 410                 415

Trp Ser Val Ile Leu Glu Gln Glu Asp Lys His Ser Leu Val Leu Ile
            420                 425                 430

Pro Lys Asn Asn Ala Lys Asp Ala Lys Gln Tyr Ile Glu Thr Ile Asn
        435                 440                 445

Thr Lys Gly Gly Lys Tyr Ile Ile His His Leu Asp Ser Leu Thr Leu
    450                 455                 460

Arg Ala Leu Asn Lys Leu Cys Phe Asn Ala Val Asp Ile Glu Lys Gly
465                 470                 475                 480

Gln Met Val Arg Glu Asn Thr Phe Tyr Gln Gly Ile Lys Glu Glu Phe
                485                 490                 495

Glu Arg Asn Lys Ile Asn Cys Asp Asn Gln Gly Val Leu Lys Ile Gln
            500                 505                 510

Gly Leu Tyr Ser Phe Lys Thr Glu Gly Gly Gln Ile Asn Glu Lys Glu
        515                 520                 525

Ala Val Glu Phe Phe Lys Glu Val Leu Lys Ser Asn Tyr Ala Arg Glu
    530                 535                 540

Val Leu Asn Leu Pro Tyr Asp Leu Glu Ser Asn Ile Phe Gln Lys Glu
545                 550                 555                 560

Tyr Thr Asn Leu Asp Gln Phe Arg Gln Asp Leu Glu Lys Cys Cys Tyr
                565                 570                 575

Ala Leu His Ser Lys Ile Gly Lys Asp Asp Leu Asp Glu Phe Thr Arg
            580                 585                 590

Arg Phe Glu Ala Gln Val Phe Asp Ile Thr Ser Ile Asp Leu Lys Ser
        595                 600                 605

Lys Lys Glu Lys Thr Lys Thr Thr Gly Glu Met Lys Lys His Thr Gln
    610                 615                 620

Leu Trp Leu Glu Phe Trp Lys Gly Ala Ile Glu Gln Asn Phe Ala Thr
625                 630                 635                 640

Arg Val Asn Pro Glu Leu Ser Ile Phe Trp Arg Ala Pro Lys Ser Ser
```

-continued

```
                645                 650                 655

Arg Glu Lys Lys Tyr Gly Lys Gly Ser Asp Leu Tyr Asp Pro Asn Lys
            660                 665                 670

Asn Asn Arg Tyr Leu Tyr Glu Gln Tyr Thr Leu Ala Leu Thr Ile Thr
        675                 680                 685

Glu Asn Ala Gly Ser His Phe Lys Asp Ile Ala Phe Lys Asp Thr Ser
    690                 695                 700

Lys Ile Lys Glu Ala Ile Lys Glu Phe Asn Met Ser Leu Ser Gln Ser
705                 710                 715                 720

Lys Tyr Cys Phe Gly Ile Asp Arg Gly Asn Ala Glu Leu Val Ser Leu
                725                 730                 735

Cys Leu Ile Lys Asn Glu Lys Asp Phe Pro Phe Glu Lys Phe Pro Val
            740                 745                 750

Tyr Arg Leu Arg Asp Leu Thr Tyr Gln Gly Asp Phe Lys Asp Lys His
        755                 760                 765

Asp Gln Met Arg Tyr Gly Val Ala Ile Lys Asn Ile Ser Tyr Phe Ile
    770                 775                 780

Asp Gln Glu Asp Leu Phe Glu Lys Asn Asn Leu Ser Ala Ile Asp Met
785                 790                 795                 800

Thr Thr Ala Lys Leu Ile Lys Asn Lys Ile Val Leu Asn Gly Asp Val
                805                 810                 815

Leu Thr Tyr Leu Lys Leu Lys Glu Glu Thr Ala Lys His Lys Leu Thr
            820                 825                 830

Gln Phe Phe Gln Gly Ser Ser Ile Asn Lys Asn Ser Arg Val Tyr Phe
        835                 840                 845

Asp Glu Asp Glu Asn Val Phe Lys Ile Thr Thr Asn Arg Asn His Asn
    850                 855                 860

Pro Glu Glu Ile Ile Tyr Phe Tyr Arg Gly Glu Tyr Gly Ala Ile Lys
865                 870                 875                 880

Asn Lys Asn Asp Leu Glu Asp Ile Leu Asn Glu Tyr Leu Cys Lys Met
                885                 890                 895

Glu Thr Gly Glu Ser Glu Ile Val Leu Leu Asn Arg Val Asn His Leu
            900                 905                 910

Arg Asp Ala Ile Ser Ala Asn Ile Val Gly Ile Leu Ser Tyr Leu Ile
        915                 920                 925

Asp Leu Phe Pro Glu Thr Ile Val Ala Leu Glu Asn Leu Ala Lys Gly
    930                 935                 940

Thr Ile Asp Arg His Val Ser Gln Ser Tyr Glu Asn Ile Thr Arg Arg
945                 950                 955                 960

Phe Glu Trp Ala Leu Tyr Arg Lys Leu Leu Asn Lys Gln Leu Ala Pro
                965                 970                 975

Pro Glu Leu Lys Glu Asn Ile Leu Leu Arg Glu Gly Asp Asp Lys Ile
            980                 985                 990

Asp Gln Phe Gly Ile Ile His Phe  Val Glu Glu Lys Asn  Thr Ser Lys
        995                 1000                1005

Asp Cys  Pro Asn Cys Arg Lys  Thr Thr Gln Gln Thr  Asn Asp Asn
    1010                 1015                1020

Lys Phe  Lys Glu Lys Lys Phe  Val Cys Lys Ser Cys  Gly Phe Asp
    1025                 1030                1035

Thr Ser  Lys Asp Arg Lys Gly  Met Asp Ser Leu Asn  Ser Pro Asp
    1040                 1045                1050

Thr Val  Ala Ala Tyr Asn Val  Ala Arg Lys Lys Phe  Glu Ser
    1055                 1060                1065
```

<210> SEQ ID NO 138
<211> LENGTH: 1057
<212> TYPE: PRT
<213> ORGANISM: Unknown
<220> FEATURE:
<223> OTHER INFORMATION: Candidatus Roizmanbacteria bacterium
      GW2011_GWA2_37_7 US54_C0016

<400> SEQUENCE: 138

```
Met Glu Ile Gln Glu Leu Lys Asn Leu Tyr Glu Val Lys Lys Thr Val
1               5                   10                  15

Arg Phe Glu Leu Lys Pro Ser Lys Lys Lys Ile Phe Glu Gly Gly Asp
            20                  25                  30

Val Ile Lys Leu Gln Lys Asp Phe Glu Lys Val Gln Lys Phe Phe Leu
        35                  40                  45

Asp Ile Phe Val Tyr Lys Asn Glu His Thr Lys Leu Glu Phe Lys Lys
    50                  55                  60

Lys Arg Glu Ile Lys Tyr Thr Trp Leu Arg Thr Asn Thr Lys Asn Glu
65                  70                  75                  80

Phe Tyr Asn Trp Arg Gly Lys Ser Asp Thr Gly Lys Asn Tyr Ala Leu
                85                  90                  95

Asn Lys Ile Gly Phe Leu Ala Glu Glu Ile Leu Arg Trp Leu Asn Glu
            100                 105                 110

Trp Gln Glu Leu Thr Lys Ser Leu Lys Asp Leu Thr Gln Arg Glu Glu
        115                 120                 125

His Lys Gln Glu Arg Lys Ser Asp Ile Ala Phe Val Leu Arg Asn Phe
    130                 135                 140

Leu Lys Arg Gln Asn Leu Pro Phe Ile Lys Asp Phe Phe Asn Ala Val
145                 150                 155                 160

Ile Asp Ile Gln Gly Lys Gln Gly Lys Glu Ser Asp Asp Lys Ile Arg
                165                 170                 175

Lys Phe Arg Glu Glu Ile Lys Glu Ile Glu Lys Asn Leu Asn Ala Cys
            180                 185                 190

Ser Arg Glu Tyr Leu Pro Thr Gln Ser Asn Gly Val Leu Leu Tyr Lys
        195                 200                 205

Ala Ser Phe Ser Tyr Tyr Thr Leu Asn Lys Thr Pro Lys Glu Tyr Glu
    210                 215                 220

Asp Leu Lys Lys Glu Lys Glu Ser Glu Leu Ser Ser Val Leu Leu Lys
225                 230                 235                 240

Glu Ile Tyr Arg Arg Lys Arg Phe Asn Arg Thr Thr Asn Gln Lys Asp
                245                 250                 255

Thr Leu Phe Glu Cys Thr Ser Asp Trp Leu Val Lys Ile Lys Leu Gly
            260                 265                 270

Lys Asp Ile Tyr Glu Trp Thr Leu Asp Glu Ala Tyr Gln Lys Met Lys
        275                 280                 285

Ile Trp Lys Ala Asn Gln Lys Ser Asn Phe Ile Glu Ala Val Ala Gly
    290                 295                 300

Asp Lys Leu Thr His Gln Asn Phe Arg Lys Gln Phe Pro Leu Phe Asp
305                 310                 315                 320

Ala Ser Asp Glu Asp Phe Glu Thr Phe Tyr Arg Leu Thr Lys Ala Leu
                325                 330                 335

Asp Lys Asn Pro Glu Asn Ala Lys Lys Ile Ala Gln Lys Arg Gly Lys
            340                 345                 350

Phe Phe Asn Ala Pro Asn Glu Thr Val Gln Thr Lys Asn Tyr His Glu
```

-continued

```
        355                 360                 365

Leu Cys Glu Leu Tyr Lys Arg Ile Ala Val Lys Arg Gly Lys Ile Ile
    370                 375                 380

Ala Glu Ile Lys Gly Ile Glu Asn Glu Glu Val Gln Ser Gln Leu Leu
385                 390                 395                 400

Thr His Trp Ala Val Ile Ala Glu Glu Arg Asp Lys Lys Phe Ile Val
                405                 410                 415

Leu Ile Pro Arg Lys Asn Gly Gly Lys Leu Glu Asn His Lys Asn Ala
            420                 425                 430

His Ala Phe Leu Gln Glu Lys Asp Arg Lys Glu Pro Asn Asp Ile Lys
        435                 440                 445

Val Tyr His Phe Lys Ser Leu Thr Leu Arg Ser Leu Glu Lys Leu Cys
    450                 455                 460

Phe Lys Glu Ala Lys Asn Thr Phe Ala Pro Glu Ile Lys Lys Glu Thr
465                 470                 475                 480

Asn Pro Lys Ile Trp Phe Pro Thr Tyr Lys Gln Glu Trp Asn Ser Thr
                485                 490                 495

Pro Glu Arg Leu Ile Lys Phe Tyr Lys Gln Val Leu Gln Ser Asn Tyr
            500                 505                 510

Ala Gln Thr Tyr Leu Asp Leu Val Asp Phe Gly Asn Leu Asn Thr Phe
        515                 520                 525

Leu Glu Thr His Phe Thr Thr Leu Glu Glu Phe Glu Ser Asp Leu Glu
    530                 535                 540

Lys Thr Cys Tyr Thr Lys Val Pro Val Tyr Phe Ala Lys Lys Glu Leu
545                 550                 555                 560

Glu Thr Phe Ala Asp Glu Phe Glu Ala Glu Val Phe Glu Ile Thr Thr
                565                 570                 575

Arg Ser Ile Ser Thr Glu Ser Lys Arg Lys Glu Asn Ala His Ala Glu
            580                 585                 590

Ile Trp Arg Asp Phe Trp Ser Arg Glu Asn Glu Glu Glu Asn His Ile
        595                 600                 605

Thr Arg Leu Asn Pro Glu Val Ser Val Leu Tyr Arg Asp Glu Ile Lys
    610                 615                 620

Glu Lys Ser Asn Thr Ser Arg Lys Asn Arg Lys Ser Asn Ala Asn Asn
625                 630                 635                 640

Arg Phe Ser Asp Pro Arg Phe Thr Leu Ala Thr Thr Ile Thr Leu Asn
                645                 650                 655

Ala Asp Lys Lys Lys Ser Asn Leu Ala Phe Lys Thr Val Glu Asp Ile
            660                 665                 670

Asn Ile His Ile Asp Asn Phe Asn Lys Lys Phe Ser Lys Asn Phe Ser
        675                 680                 685

Gly Glu Trp Val Tyr Gly Ile Asp Arg Gly Leu Lys Glu Leu Ala Thr
    690                 695                 700

Leu Asn Val Val Lys Phe Ser Asp Val Lys Asn Val Phe Gly Val Ser
705                 710                 715                 720

Gln Pro Lys Glu Phe Ala Lys Ile Pro Ile Tyr Lys Leu Arg Asp Glu
                725                 730                 735

Lys Ala Ile Leu Lys Asp Glu Asn Gly Leu Ser Leu Lys Asn Ala Lys
            740                 745                 750

Gly Glu Ala Arg Lys Val Ile Asp Asn Ile Ser Asp Val Leu Glu Glu
        755                 760                 765

Gly Lys Glu Pro Asp Ser Thr Leu Phe Glu Lys Arg Glu Val Ser Ser
    770                 775                 780
```

Ile Asp Leu Thr Arg Ala Lys Leu Ile Lys Gly His Ile Ile Ser Asn
785 790 795 800

Gly Asp Gln Lys Thr Tyr Leu Lys Leu Lys Glu Thr Ser Ala Lys Arg
805 810 815

Arg Ile Phe Glu Leu Phe Ser Thr Ala Lys Ile Asp Lys Ser Ser Gln
820 825 830

Phe His Val Arg Lys Thr Ile Glu Leu Ser Gly Thr Lys Ile Tyr Trp
835 840 845

Leu Cys Glu Trp Gln Arg Gln Asp Ser Trp Arg Thr Glu Lys Val Ser
850 855 860

Leu Arg Asn Thr Leu Lys Gly Tyr Leu Gln Asn Leu Asp Leu Lys Asn
865 870 875 880

Arg Phe Glu Asn Ile Glu Thr Ile Glu Lys Ile Asn His Leu Arg Asp
885 890 895

Ala Ile Thr Ala Asn Met Val Gly Ile Leu Ser His Leu Gln Asn Lys
900 905 910

Leu Glu Met Gln Gly Val Ile Ala Leu Glu Asn Leu Asp Thr Val Arg
915 920 925

Glu Gln Ser Asn Lys Lys Met Ile Asp Glu His Phe Glu Gln Ser Asn
930 935 940

Glu His Val Ser Arg Arg Leu Glu Trp Ala Leu Tyr Cys Lys Phe Ala
945 950 955 960

Asn Thr Gly Glu Val Pro Pro Gln Ile Lys Glu Ser Ile Phe Leu Arg
965 970 975

Asp Glu Phe Lys Val Cys Gln Ile Gly Ile Leu Asn Phe Ile Asp Val
980 985 990

Lys Gly Thr Ser Ser Asn Cys Pro Asn Cys Asp Gln Glu Ser Arg Lys
995 1000 1005

Thr Gly Ser His Phe Ile Cys Asn Phe Gln Asn Asn Cys Ile Phe
1010 1015 1020

Ser Ser Lys Glu Asn Arg Asn Leu Leu Glu Gln Asn Leu His Asn
1025 1030 1035

Ser Asp Asp Val Ala Ala Phe Asn Ile Ala Lys Arg Gly Leu Glu
1040 1045 1050

Ile Val Lys Val
1055

<210> SEQ ID NO 139
<211> LENGTH: 78
<212> TYPE: RNA
<213> ORGANISM: Unknown
<220> FEATURE:
<223> OTHER INFORMATION: Uncultured Clostridium sp. isolate 2789STDY5608795

<400> SEQUENCE: 139
cagucuuaau aaacgaaaaa gaauauauua cuuaaccaga ugugugcaaa ugugauaaaa 60
agaauaaguu uaaauaag 78

<210> SEQ ID NO 140
<211> LENGTH: 67
<212> TYPE: RNA
<213> ORGANISM: Unknown
<220> FEATURE:
<223> OTHER INFORMATION: Uncultured bacterium (gcode 4) ACD_3C00058, whole genome shotgun sequence

<400> SEQUENCE: 140
agagaaaaau gcaaaccuaa gucuuaauuu uuucaccuuc cuacagauaa gccaaaaguc 60
guaauuu 67

<210> SEQ ID NO 141
<211> LENGTH: 81
<212> TYPE: RNA
<213> ORGANISM: Unknown
<220> FEATURE:
<223> OTHER INFORMATION: Thiomicrospira sp. XS5 ZB100000

<400> SEQUENCE: 141
uucucugaua aaauaauuaa cucaggucuu uucgagaaaa aacugcaaac cuuggucuua 60
augagaaaaa ucaugaaaaa a 81

<210> SEQ ID NO 142
<211> LENGTH: 82
<212> TYPE: RNA
<213> ORGANISM: Unknown
<220> FEATURE:
<223> OTHER INFORMATION: Flavobacterium branchiophilum FL-15

<400> SEQUENCE: 142
caugaaaaca agcuuucgaa ugcuguuuuu uuauuuaaaa gcaaccaaaa acgguaaaaa 60
aggguuguuu uugugucauu uu 82

<210> SEQ ID NO 143
<211> LENGTH: 63
<212> TYPE: RNA
<213> ORGANISM: Unknown
<220> FEATURE:
<223> OTHER INFORMATION: Moraxella bovoculi strain 57922

<400> SEQUENCE: 143
gucuaacgac cuuuuaaauu ucuacuguuu guagauauuc gugcguauuu gauuucuuug 60
ugu 63

<210> SEQ ID NO 144
<211> LENGTH: 85
<212> TYPE: RNA
<213> ORGANISM: Unknown
<220> FEATURE:
<223> OTHER INFORMATION: Candidatus Roizmanbacteria bacterium
GW2011_GWA2_37_7 US54_C0016

<400> SEQUENCE: 144
aauggaaaaa guggaaauug uauuaucagu acaaaaccua agucuuuauu uuuuugaaga 60
cgauguagag uuguagucua augag 85

<210> SEQ ID NO 145
<211> LENGTH: 84
<212> TYPE: RNA
<213> ORGANISM: Unknown
<220> FEATURE:
<223> OTHER INFORMATION: Pseudobutyrivibrio xylanivorans

<400> SEQUENCE: 145
accuauaacu uaauuugugg auacuaaguc uugagugaug aaaauggcag uuuuguuagu 60
aaauaaacau aauaauauga ugaa 84

<210> SEQ ID NO 146

<211> LENGTH: 83
<212> TYPE: RNA
<213> ORGANISM: Unknown
<220> FEATURE:
<223> OTHER INFORMATION: Prevotella bryantii B14

<400> SEQUENCE: 146
auauacgaua uuauguuuua gccuacauuu ucauaaaguu cugauaucaa acacauuaua 60
aacuuuuaua uaacaaucaa gaa 83

<210> SEQ ID NO 147
<211> LENGTH: 63
<212> TYPE: RNA
<213> ORGANISM: Unknown
<220> FEATURE:
<223> OTHER INFORMATION: Smithella sp. SCADC

<400> SEQUENCE: 147 uuauggugu ucagcaauuu aaucuugcgc gugaaagaaa aaugugcuua uuaaacaacu 60
aua 63

<210> SEQ ID NO 148
<211> LENGTH: 57
<212> TYPE: RNA
<213> ORGANISM: Unknown
<220> FEATURE:
<223> OTHER INFORMATION: Smithella sp. SCADC

<400> SEQUENCE: 148
aaaaauuggc ugauuuuaug guguuucagc aauuuaaucu ugcgcgugaa agaaaaa 57

<210> SEQ ID NO 149
<211> LENGTH: 82
<212> TYPE: RNA
<213> ORGANISM: Unknown
<220> FEATURE:
<223> OTHER INFORMATION: Bacteroidetes bacterium GWF2_33_38

<400> SEQUENCE: 149
gcacaaagaa gcaaagcuuu uuuaaaaagc uuugcuucua aaacaauuag uuauuugaaa 60
uaguuguauu uuuuuuuuac ga 82

<210> SEQ ID NO 150
<211> LENGTH: 74
<212> TYPE: RNA
<213> ORGANISM: Unknown
<220> FEATURE:
<223> OTHER INFORMATION: Candidatus Peribacteria bacterium RIFCSPLOWO2

<400> SEQUENCE: 150
aaauccauau guggauaucu caucuugcag accaucgucc uuauuuucuu aagaagaccu 60
cuucaaacca aaaa 74

<210> SEQ ID NO 151
<211> LENGTH: 74
<212> TYPE: RNA
<213> ORGANISM: Unknown
<220> FEATURE:
<223> OTHER INFORMATION: Nitrospinae bacterium RIFCSPLOWO2

<400> SEQUENCE: 151
uucuacuauu guagaucaaa ccucggucuu aauguaaaaa auggcgcuug gacuggcggu 60
caaaaccaca aaaa 74

<210> SEQ ID NO 152
<211> LENGTH: 67
<212> TYPE: RNA
<213> ORGANISM: Unknown
<220> FEATURE:
<223> OTHER INFORMATION: Candidatus Ryanbacteria bacterium RIFCSPHIGHO2

<400> SEQUENCE: 152
cucgugaaag guggaaaucc agugaaggua uuugguuuaa uauguauauu acgagauaug 60
cgggaaa 67

<210> SEQ ID NO 153
<211> LENGTH: 85
<212> TYPE: RNA
<213> ORGANISM: Unknown
<220> FEATURE:
<223> OTHER INFORMATION: Candidatus Wildermuthbacteria bacterium
RIFCSPHIGHO2

<400> SEQUENCE: 153
uuauacugaa gcauaaagua uaaauugcgu guggauauua auuuagacuc aauauauaac 60
gguggaaaac cuuugccuuu auaaa 85

<210> SEQ ID NO 154
<211> LENGTH: 59
<212> TYPE: RNA
<213> ORGANISM: Unknown
<220> FEATURE:
<223> OTHER INFORMATION: Firmicutes bacterium CAG_194_44_15

<400> SEQUENCE: 154
gucuuucuau uuaguuuuaa uuuuagguua cuugacaaua ugguaauaau aaacaaaau 59

<210> SEQ ID NO 155
<211> LENGTH: 83
<212> TYPE: RNA
<213> ORGANISM: Unknown
<220> FEATURE:
<223> OTHER INFORMATION: Candidatus Gottesmanbacteria bacterium
CG1_02_37_22

<400> SEQUENCE: 155
auuauaaaag cagaagugaa acuguuaaua uuugagaaaa cuuaagucuu uaugagccug 60
uuucuugcua uuuuacgccu aaa 83

<210> SEQ ID NO 156
<211> LENGTH: 87
<212> TYPE: RNA
<213> ORGANISM: Unknown
<220> FEATURE:
<223> OTHER INFORMATION: Candidatus Gracilibacteria bacterium
CG1_02_38_174

<400> SEQUENCE: 156
aacaagggug gaaaucuuua uguuggguuu uacgaaaacu gcaaaccuca gucuucauuu 60
uuugcgagua ccguuuuaag ccaagaa 87

<210> SEQ ID NO 157
<211> LENGTH: 76
<212> TYPE: RNA
<213> ORGANISM: Unknown
<220> FEATURE:
<223> OTHER INFORMATION: Butyrivibrio fibrisolvens MD2001

<400> SEQUENCE: 157
aaccuccgau uugauuuuua uuuaugggau cuuggaaaua auauaugggc aaauuauugg 60
ugauaaguua uaaaaa 76

<210> SEQ ID NO 158
<211> LENGTH: 60
<212> TYPE: RNA
<213> ORGANISM: Unknown
<220> FEATURE:
<223> OTHER INFORMATION: Sneathia amnii strain SN35

<400> SEQUENCE: 158
aaucaaggug uuaauauuuu uaaaaugcga aaaaaucaaa ucucucaaau guaaaaaaaa 60

<210> SEQ ID NO 159
<211> LENGTH: 73
<212> TYPE: RNA
<213> ORGANISM: Unknown
<220> FEATURE:
<223> OTHER INFORMATION: Coprococcus eutactus strain 2789STDY5608843

<400> SEQUENCE: 159
cagucuuucu gaggaaaaau uaaggguua cucaacagau augaacauaa caaacaaaaa 60
aagaauguau aua 73

<210> SEQ ID NO 160
<211> LENGTH: 65
<212> TYPE: RNA
<213> ORGANISM: Unknown
<220> FEATURE:
<223> OTHER INFORMATION: Lachnospira pectinoschiza strain 2789STDY5834886

<400> SEQUENCE: 160
ugaccuuaau auuuaaaauu agaugggua cuuaauauaa uauguguaua uugcauaaaa 60
aauaa 65

<210> SEQ ID NO 161
<211> LENGTH: 80
<212> TYPE: RNA
<213> ORGANISM: Unknown
<220> FEATURE:
<223> OTHER INFORMATION: Bacteroidetes oral taxon 274 str. F0058

<400> SEQUENCE: 161
auggagaaua caaaguuuga uuauugucuu gauaauaaau aaacuaugaa aauuuguuuu 60
uugcaggggg ggauaaaaua 80

<210> SEQ ID NO 162
<211> LENGTH: 63
<212> TYPE: RNA
<213> ORGANISM: Unknown
<220> FEATURE:
<223> OTHER INFORMATION: Arcobacter butzleri L348 isolate CHRB125

<400> SEQUENCE: 162
uauggaaaua uuguuaaaaa auauaaauuu uaagagggua aauaagcuuu uuuaauauga 60
uuu 63

<210> SEQ ID NO 163
<211> LENGTH: 65

<212> TYPE: RNA
<213> ORGANISM: Unknown
<220> FEATURE:
<223> OTHER INFORMATION: Bacteroidales bacterium KA00251

<400> SEQUENCE: 163
acucccuauu auucaacuaa aaaaggccau uuuccccgau cauuuagaag agagaggggg 60
ggaaa 65

<210> SEQ ID NO 164
<211> LENGTH: 67
<212> TYPE: RNA
<213> ORGANISM: Unknown
<220> FEATURE:
<223> OTHER INFORMATION: Acidaminococcus massiliensis strain
Marseille-P2828

<400> SEQUENCE: 164
agugaaaauc guggaaaauc acuugguaca auggacggga acacuauaua uuguggcaga 60
cuccaag 67

<210> SEQ ID NO 165
<211> LENGTH: 71
<212> TYPE: RNA
<213> ORGANISM: Helcococcus kunzii

<400> SEQUENCE: 165
uucuuaaagg auaucuaaaa auguauucau uaaaugagag uuuaugcauu gcaauacuaa 60
cuauagugac a 71

<210> SEQ ID NO 166
<211> LENGTH: 57
<212> TYPE: RNA
<213> ORGANISM: Unknown
<220> FEATURE:
<223> OTHER INFORMATION: Agathobacter rectalis strain 2789STDY5834884

<400> SEQUENCE: 166
uggaccuuaa uuuuauaaua aucuauauua cuuaacauau uuugugcaaa uguuaua 57

<210> SEQ ID NO 167
<211> LENGTH: 72
<212> TYPE: RNA
<213> ORGANISM: Unknown
<220> FEATURE:
<223> OTHER INFORMATION: Acidaminococcus sp. BV3L6

<400> SEQUENCE: 167
cauugucuaa ccugcaaacc uccaacuuac uauugcuaag gaguauauau uuuguauaaa 60
aggucuuuuu uc 72

<210> SEQ ID NO 168
<211> LENGTH: 65
<212> TYPE: RNA
<213> ORGANISM: Unknown
<220> FEATURE:
<223> OTHER INFORMATION: Lachnospiraceae bacterium ND2006

<400> SEQUENCE: 168
aauugcaaau cuuugaaaua augcagacuu aaauuuauaa auucauggaa uaaggugauu 60
uuauu 65

-continued

<210> SEQ ID NO 169
<211> LENGTH: 81
<212> TYPE: RNA
<213> ORGANISM: Unknown
<220> FEATURE:
<223> OTHER INFORMATION: Francisella tularensis subsp. novicida U112

<400> SEQUENCE: 169
aaguucuuag agauauuuaa aaauaugacu guuguuauau aucaaaaugc uaaaaaaauc 60
auagauuuua ggucuuuuuu u 81

<210> SEQ ID NO 170
<211> LENGTH: 72
<212> TYPE: RNA
<213> ORGANISM: Unknown
<220> FEATURE:
<223> OTHER INFORMATION: Omnitrophica WOR_2 bacterium GWF2_38_59

<400> SEQUENCE: 170
gccuuuauuu auuggacuua cgaaaauacu cuuaaaaacu augaugcugu aaauuguugg 60
gguaucguuu gu 72

<210> SEQ ID NO 171
<211> LENGTH: 69
<212> TYPE: RNA
<213> ORGANISM: Unknown
<220> FEATURE:
<223> OTHER INFORMATION: Candidatus Roizmanbacteria bacterium
GW2011_GWA2_37_7 US54_C0016

<400> SEQUENCE: 171
auggaaaaag uggaaauugu auuaucagua caaaaccuaa gucuuuauuu uuuugaagac 60
gauguagag 69

<210> SEQ ID NO 172
<211> LENGTH: 1300
<212> TYPE: PRT
<213> ORGANISM: Francisella tularensis

<400> SEQUENCE: 172

Met Ser Ile Tyr Gln Glu Phe Val Asn Lys Tyr Ser Leu Ser Lys Thr
1 5 10 15

Leu Arg Phe Glu Leu Ile Pro Gln Gly Lys Thr Leu Glu Asn Ile Lys
20 25 30

Ala Arg Gly Leu Ile Leu Asp Asp Glu Lys Arg Ala Lys Asp Tyr Lys
35 40 45

Lys Ala Lys Gln Ile Ile Asp Lys Tyr His Gln Phe Phe Ile Glu Glu
50 55 60

Ile Leu Ser Ser Val Cys Ile Ser Glu Asp Leu Leu Gln Asn Tyr Ser
65 70 75 80

Asp Val Tyr Phe Lys Leu Lys Lys Ser Asp Asp Asp Asn Leu Gln Lys
85 90 95

Asp Phe Lys Ser Ala Lys Asp Thr Ile Lys Lys Gln Ile Ser Glu Tyr
100 105 110

Ile Lys Asp Ser Glu Lys Phe Lys Asn Leu Phe Asn Gln Asn Leu Ile
115 120 125

Asp Ala Lys Lys Gly Gln Glu Ser Asp Leu Ile Leu Trp Leu Lys Gln
130 135 140

Ser Lys Asp Asn Gly Ile Glu Leu Phe Lys Ala Asn Ser Asp Ile Thr
145 150 155 160

```
Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asp Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Val Ala Pro Lys Asn Leu Asp Asn
            420                 425                 430

Pro Ser Lys Lys Glu Gln Asp Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Leu Lys Tyr Gln Asn Gln Gly Lys Lys
            500                 505                 510

Asp Leu Leu Gln Ala Ser Ala Glu Glu Asp Val Lys Ala Ile Lys Asp
        515                 520                 525

Leu Leu Asp Gln Thr Asn Asn Leu Leu His Arg Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575
```

```
Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Asn Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Glu Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu His Asn  Ala Ile Val Val Phe  Glu Asp Leu
```

```
        995                 1000                1005

Asn Phe  Gly Phe Lys Arg Gly  Arg Phe Lys Val Glu  Lys Gln Val
    1010                 1015                 1020

Tyr Gln  Lys Leu Glu Lys Met  Leu Ile Glu Lys Leu  Asn Tyr Leu
    1025                 1030                 1035

Val Phe  Lys Asp Asn Glu Phe  Asp Lys Thr Gly Gly  Val Leu Arg
    1040                 1045                 1050

Ala Tyr  Gln Leu Thr Ala Pro  Phe Glu Thr Phe Lys  Lys Met Gly
    1055                 1060                 1065

Lys Gln  Thr Gly Ile Ile Tyr  Tyr Val Pro Ala Gly  Phe Thr Ser
    1070                 1075                 1080

Lys Ile  Cys Pro Val Thr Gly  Phe Val Asn Gln Leu  Tyr Pro Lys
    1085                 1090                 1095

Tyr Glu  Ser Val Ser Lys Ser  Gln Glu Phe Phe Ser  Lys Phe Asp
    1100                 1105                 1110

Lys Ile  Cys Tyr Asn Leu Asp  Lys Gly Tyr Phe Glu  Phe Ser Phe
    1115                 1120                 1125

Asp Tyr  Lys Asn Phe Gly Asp  Lys Ala Ala Lys Gly  Lys Trp Thr
    1130                 1135                 1140

Ile Ala  Ser Phe Gly Ser Arg  Leu Ile Asn Phe Arg  Asn Ser Asp
    1145                 1150                 1155

Lys Asn  His Asn Trp Asp Thr  Arg Glu Val Tyr Pro  Thr Lys Glu
    1160                 1165                 1170

Leu Glu  Lys Leu Leu Lys Asp  Tyr Ser Ile Glu Tyr  Gly His Gly
    1175                 1180                 1185

Glu Cys  Ile Lys Ala Ala Ile  Cys Gly Glu Ser Asp  Lys Lys Phe
    1190                 1195                 1200

Phe Ala  Lys Leu Thr Ser Val  Leu Asn Thr Ile Leu  Gln Met Arg
    1205                 1210                 1215

Asn Ser  Lys Thr Gly Thr Glu  Leu Asp Tyr Leu Ile  Ser Pro Val
    1220                 1225                 1230

Ala Asp  Val Asn Gly Asn Phe  Phe Asp Ser Arg Gln  Ala Pro Lys
    1235                 1240                 1245

Asn Met  Pro Gln Asp Ala Asp  Ala Asn Gly Ala Tyr  His Ile Gly
    1250                 1255                 1260

Leu Lys  Gly Leu Met Leu Leu  Asp Arg Ile Lys Asn  Asn Gln Glu
    1265                 1270                 1275

Gly Lys  Lys Leu Asn Leu Val  Ile Lys Asn Glu Glu  Tyr Phe Glu
    1280                 1285                 1290

Phe Val  Gln Asn Arg Asn Asn
    1295                 1300
```

<210> SEQ ID NO 173
<211> LENGTH: 36
<212> TYPE: DNA
<213> ORGANISM: Unknown
<220> FEATURE:
<223> OTHER INFORMATION: Lachnospiraceae bacterium ND2006

<400> SEQUENCE: 173
gtttcaaaga ttaaataatt tctactaagt gtagat 36

<210> SEQ ID NO 174
<211> LENGTH: 28
<212> TYPE: DNA
<213> ORGANISM: Unknown

<220> FEATURE:
<223> OTHER INFORMATION: Lachnospiraceae bacterium ND2006

<400> SEQUENCE: 174
cggtctcgca aagaatggat atactcat 28

<210> SEQ ID NO 175
<211> LENGTH: 49
<212> TYPE: DNA
<213> ORGANISM: Unknown
<220> FEATURE:
<223> OTHER INFORMATION: Lachnospiraceae bacterium ND2006

<400> SEQUENCE: 175
taatttctac taagtgtaga tcggtctcgc aaagaatgga tatactcat 49

<210> SEQ ID NO 176
<211> LENGTH: 35
<212> TYPE: DNA
<213> ORGANISM: Unknown
<220> FEATURE:
<223> OTHER INFORMATION: Acidaminococcus sp. BV3L6

<400> SEQUENCE: 176
gtcaaaagac ctttttaatt tctactcttg tagat 35

<210> SEQ ID NO 177
<211> LENGTH: 26
<212> TYPE: DNA
<213> ORGANISM: Unknown
<220> FEATURE:
<223> OTHER INFORMATION: Acidaminococcus sp. BV3L6

<400> SEQUENCE: 177
gtctaaactg gtcgaaatcg accagt 26

<210> SEQ ID NO 178
<211> LENGTH: 46
<212> TYPE: DNA
<213> ORGANISM: Unknown
<220> FEATURE:
<223> OTHER INFORMATION: Acidaminococcus sp. BV3L6

<400> SEQUENCE: 178
taatttctac tcttgtagat gtctaaactg gtcgaaatcg accagt 46

<210> SEQ ID NO 179
<211> LENGTH: 41
<212> TYPE: RNA
<213> ORGANISM: Artificial sequence
<220> FEATURE:
<223> OTHER INFORMATION: Synthetic construct

<400> SEQUENCE: 179
uaauuucuac ucuuguagau uggacagagc uccaagugac c 41

<210> SEQ ID NO 180
<211> LENGTH: 19
<212> TYPE: RNA
<213> ORGANISM: Artificial sequence
<220> FEATURE:
<223> OTHER INFORMATION: Synthetic construct

<400> SEQUENCE: 180
uaauuucuac ucuuguaga 19

<210> SEQ ID NO 181
<211> LENGTH: 21
<212> TYPE: RNA
<213> ORGANISM: Artificial sequence
<220> FEATURE:
<223> OTHER INFORMATION: Synthetic construct

<400> SEQUENCE: 181
uggacagagc uccaagugac c 21

<210> SEQ ID NO 182
<211> LENGTH: 1259
<212> TYPE: PRT
<213> ORGANISM: Artificial sequence
<220> FEATURE:
<223> OTHER INFORMATION: Synthetic construct

<400> SEQUENCE: 182

Gly Pro Ala Gly Ser Gly Gly Pro Lys Lys Lys Arg Lys Val Gly Gly
1 5 10 15

Ser Gly Met Ser Lys Leu Glu Lys Phe Thr Asn Cys Tyr Ser Leu Ser
20 25 30

Lys Thr Leu Arg Phe Lys Ala Ile Pro Val Gly Lys Thr Gln Glu Asn
35 40 45

Ile Asp Asn Lys Arg Leu Leu Val Glu Asp Glu Lys Arg Ala Glu Asp
50 55 60

Tyr Lys Gly Val Lys Lys Leu Leu Asp Arg Tyr Tyr Leu Ser Phe Ile
65 70 75 80

Asn Asp Val Leu His Ser Ile Lys Leu Lys Asn Leu Asn Asn Tyr Ile
85 90 95

Ser Leu Phe Arg Lys Lys Thr Arg Thr Glu Lys Glu Asn Lys Glu Leu
100 105 110

Glu Asn Leu Glu Ile Asn Leu Arg Lys Glu Ile Ala Lys Ala Phe Lys
115 120 125

Gly Asn Glu Gly Tyr Lys Ser Leu Phe Lys Lys Asp Ile Ile Glu Thr
130 135 140

Ile Leu Pro Glu Phe Leu Asp Asp Lys Asp Glu Ile Ala Leu Val Asn
145 150 155 160

Ser Phe Asn Gly Phe Thr Thr Ala Phe Thr Gly Phe Phe Asp Asn Arg
165 170 175

Glu Asn Met Phe Ser Glu Glu Ala Lys Ser Thr Ser Ile Ala Phe Arg
180 185 190

Cys Ile Asn Glu Asn Leu Thr Arg Tyr Ile Ser Asn Met Asp Ile Phe
195 200 205

Glu Lys Val Asp Ala Ile Phe Asp Lys His Glu Val Gln Glu Ile Lys
210 215 220

Glu Lys Ile Leu Asn Ser Asp Tyr Asp Val Glu Asp Phe Phe Glu Gly
225 230 235 240

Glu Phe Phe Asn Phe Val Leu Thr Gln Glu Gly Ile Asp Val Tyr Asn
245 250 255

Ala Ile Ile Gly Gly Phe Val Thr Glu Ser Gly Glu Lys Ile Lys Gly
260 265 270

Leu Asn Glu Tyr Ile Asn Leu Tyr Asn Gln Lys Thr Lys Gln Lys Leu
275 280 285

Pro Lys Phe Lys Pro Leu Tyr Lys Gln Val Leu Ser Asp Arg Glu Ser
290 295 300

-continued

Leu Ser Phe Tyr Gly Glu Gly Tyr Thr Ser Asp Glu Glu Val Leu Glu
305 310 315 320

Val Phe Arg Asn Thr Leu Asn Lys Asn Ser Glu Ile Phe Ser Ser Ile
325 330 335

Lys Lys Leu Glu Lys Leu Phe Lys Asn Phe Asp Glu Tyr Ser Ser Ala
340 345 350

Gly Ile Phe Val Lys Asn Gly Pro Ala Ile Ser Thr Ile Ser Lys Asp
355 360 365

Ile Phe Gly Glu Trp Asn Val Ile Arg Asp Lys Trp Asn Ala Glu Tyr
370 375 380

Asp Asp Ile His Leu Lys Lys Lys Ala Val Val Thr Glu Lys Tyr Glu
385 390 395 400

Asp Asp Arg Arg Lys Ser Phe Lys Lys Ile Gly Ser Phe Ser Leu Glu
405 410 415

Gln Leu Gln Glu Tyr Ala Asp Ala Asp Leu Ser Val Val Glu Lys Leu
420 425 430

Lys Glu Ile Ile Ile Gln Lys Val Asp Glu Ile Tyr Lys Val Tyr Gly
435 440 445

Ser Ser Glu Lys Leu Phe Asp Ala Asp Phe Val Leu Glu Lys Ser Leu
450 455 460

Lys Lys Asn Asp Ala Val Val Ala Ile Met Lys Asp Leu Leu Asp Ser
465 470 475 480

Val Lys Ser Phe Glu Asn Tyr Ile Lys Ala Phe Phe Gly Glu Gly Lys
485 490 495

Glu Thr Asn Arg Asp Glu Ser Phe Tyr Gly Asp Phe Val Leu Ala Tyr
500 505 510

Asp Ile Leu Leu Lys Val Asp His Ile Tyr Asp Ala Ile Arg Asn Tyr
515 520 525

Val Thr Gln Lys Pro Tyr Ser Lys Asp Lys Phe Lys Leu Tyr Phe Gln
530 535 540

Asn Pro Gln Phe Met Gly Gly Trp Asp Lys Asp Lys Glu Thr Asp Tyr
545 550 555 560

Arg Ala Thr Ile Leu Arg Tyr Gly Ser Lys Tyr Tyr Leu Ala Ile Met
565 570 575

Asp Lys Lys Tyr Ala Lys Cys Leu Gln Lys Ile Asp Lys Asp Asp Val
580 585 590

Asn Gly Asn Tyr Glu Lys Ile Asn Tyr Lys Leu Leu Pro Gly Pro Asn
595 600 605

Lys Met Leu Pro Lys Val Phe Phe Ser Lys Lys Trp Met Ala Tyr Tyr
610 615 620

Asn Pro Ser Glu Asp Ile Gln Lys Ile Tyr Lys Asn Gly Thr Phe Lys
625 630 635 640

Lys Gly Asp Met Phe Asn Leu Asn Asp Cys His Lys Leu Ile Asp Phe
645 650 655

Phe Lys Asp Ser Ile Ser Arg Tyr Pro Lys Trp Ser Asn Ala Tyr Asp
660 665 670

Phe Asn Phe Ser Glu Thr Glu Lys Tyr Lys Asp Ile Ala Gly Phe Tyr
675 680 685

Arg Glu Val Glu Glu Gln Gly Tyr Lys Val Ser Phe Glu Ser Ala Ser
690 695 700

Lys Lys Glu Val Asp Lys Leu Val Glu Glu Gly Lys Leu Tyr Met Phe
705 710 715 720

Gln Ile Tyr Asn Lys Asp Phe Ser Asp Lys Ser His Gly Thr Pro Asn

-continued

```
                725                 730                 735

Leu His Thr Met Tyr Phe Lys Leu Leu Phe Asp Glu Asn Asn His Gly
            740                 745                 750

Gln Ile Arg Leu Ser Gly Gly Ala Glu Leu Phe Met Arg Arg Ala Ser
        755                 760                 765

Leu Lys Lys Glu Glu Leu Val Val His Pro Ala Asn Ser Pro Ile Ala
    770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
            820                 825                 830

Glu Val Arg Val Leu Leu Lys His Asp Asp Asn Pro Tyr Val Ile Gly
        835                 840                 845

Ile Asp Arg Gly Glu Arg Asn Leu Leu Tyr Ile Val Val Val Asp Gly
    850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
            900                 905                 910

Asn Ile Lys Glu Leu Lys Ala Gly Tyr Ile Ser Gln Val Val His Lys
        915                 920                 925

Ile Cys Glu Leu Val Glu Lys Tyr Asp Ala Val Ile Ala Leu Glu Asp
    930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
            980                 985                 990

Gln Ile Thr Asn Lys Phe Glu Ser  Phe Lys Ser Met Ser  Thr Gln Asn
        995                 1000                1005

Gly Phe  Ile Phe Tyr Ile Pro  Ala Trp Leu Thr Ser  Lys Ile Asp
    1010                1015                1020

Pro Ser  Thr Gly Phe Val Asn  Leu Leu Lys Thr Lys  Tyr Thr Ser
    1025                1030                1035

Ile Ala  Asp Ser Lys Lys Phe  Ile Ser Ser Phe Asp  Arg Ile Met
    1040                1045                1050

Tyr Val  Pro Glu Glu Asp Leu  Phe Glu Phe Ala Leu  Asp Tyr Lys
    1055                1060                1065

Asn Phe  Ser Arg Thr Asp Ala  Asp Tyr Ile Lys Lys  Trp Lys Leu
    1070                1075                1080

Tyr Ser  Tyr Gly Asn Arg Ile  Arg Ile Phe Arg Asn  Pro Lys Lys
    1085                1090                1095

Asn Asn  Val Phe Asp Trp Glu  Glu Val Cys Leu Thr  Ser Ala Tyr
    1100                1105                1110

Lys Glu  Leu Phe Asn Lys Tyr  Gly Ile Asn Tyr Gln  Gln Gly Asp
    1115                1120                1125

Ile Arg  Ala Leu Leu Cys Glu  Gln Ser Asp Lys Ala  Phe Tyr Ser
    1130                1135                1140
```

```
Ser Phe  Met Ala Leu Met Ser  Leu Met Leu Gln Met  Arg Asn Ser
    1145                 1150                 1155

Ile Thr  Gly Arg Thr Asp Val  Asp Phe Leu Ile Ser  Pro Val Lys
    1160                 1165                 1170

Asn Ser  Asp Gly Ile Phe Tyr  Asp Ser Arg Asn Tyr  Glu Ala Gln
    1175                 1180                 1185

Glu Asn  Ala Ile Leu Pro Lys  Asn Ala Asp Ala Asn  Gly Ala Tyr
    1190                 1195                 1200

Asn Ile  Ala Arg Lys Val Leu  Trp Ala Ile Gly Gln  Phe Lys Lys
    1205                 1210                 1215

Ala Glu  Asp Glu Lys Leu Asp  Lys Val Lys Ile Ala  Ile Ser Asn
    1220                 1225                 1230

Lys Glu  Trp Leu Glu Tyr Ala  Gln Thr Ser Val Lys  His Gly Gly
    1235                 1240                 1245

Ser Gly  Pro Lys Lys Lys Arg  Lys Val Gly Gly
    1250                 1255
```

<210> SEQ ID NO 183
<211> LENGTH: 5
<212> TYPE: DNA
<213> ORGANISM: Artificial sequence
<220> FEATURE:
<223> OTHER INFORMATION: Synthetic construct

<400> SEQUENCE: 183 ggtga 5

<210> SEQ ID NO 184
<211> LENGTH: 5
<212> TYPE: DNA
<213> ORGANISM: Artificial sequence
<220> FEATURE:
<223> OTHER INFORMATION: Synthetic construct

<400> SEQUENCE: 184 ggtga 5

<210> SEQ ID NO 185
<211> LENGTH: 6
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: R is A or G

<400> SEQUENCE: 185 tccrac 6

<210> SEQ ID NO 186
<211> LENGTH: 5
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: S is G or C

<400> SEQUENCE: 186 ttsaa 5

<210> SEQ ID NO 187
<211> LENGTH: 11
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(9)
<223> OTHER INFORMATION: N is A, C, G, or T

<400> SEQUENCE: 187
gcnnnnnnng c 11

<210> SEQ ID NO 188
<211> LENGTH: 4
<212> TYPE: DNA
<213> ORGANISM: Artificial sequence
<220> FEATURE:
<223> OTHER INFORMATION: Synthetic construct

<400> SEQUENCE: 188 gcgc 4

<210> SEQ ID NO 189
<211> LENGTH: 4
<212> TYPE: DNA
<213> ORGANISM: Artificial sequence
<220> FEATURE:
<223> OTHER INFORMATION: Synthetic construct

<400> SEQUENCE: 189 gcgc 4

<210> SEQ ID NO 190
<211> LENGTH: 4
<212> TYPE: DNA
<213> ORGANISM: Artificial sequence
<220> FEATURE:
<223> OTHER INFORMATION: Synthetic construct

<400> SEQUENCE: 190 gcgc 4

<210> SEQ ID NO 191
<211> LENGTH: 6
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: R is A or G
<220> FEATURE:
<221> NAME/KEY: misc_feature
<222> LOCATION: (5)..(5)
<223> OTHER INFORMATION: Y is C or T

<400> SEQUENCE: 191 grcgyc 6

<210> SEQ ID NO 192
<211> LENGTH: 6
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: R is A or G
<220> FEATURE:
<221> NAME/KEY: misc_feature
<222> LOCATION: (6)..(6)
<223> OTHER INFORMATION: Y is C or T

<400> SEQUENCE: 192 rgcgcy 6

<210> SEQ ID NO 193
<211> LENGTH: 6
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: N is A, C, G, or T

<400> SEQUENCE: 193 ggnncc 6

<210> SEQ ID NO 194
<211> LENGTH: 6
<212> TYPE: DNA
<213> ORGANISM: Artificial sequence
<220> FEATURE:
<223> OTHER INFORMATION: Synthetic construct

<400> SEQUENCE: 194 ggcgcc 6

<210> SEQ ID NO 195
<211> LENGTH: 6
<212> TYPE: DNA
<213> ORGANISM: Artificial sequence
<220> FEATURE:
<223> OTHER INFORMATION: Synthetic construct

<400> SEQUENCE: 195 ggcgcc 6

<210> SEQ ID NO 196
<211> LENGTH: 6
<212> TYPE: DNA
<213> ORGANISM: Artificial sequence
<220> FEATURE:
<223> OTHER INFORMATION: Synthetic construct

<400> SEQUENCE: 196 ggcgcc 6

<210> SEQ ID NO 197
<211> LENGTH: 6
<212> TYPE: DNA
<213> ORGANISM: Artificial sequence
<220> FEATURE:
<223> OTHER INFORMATION: Synthetic construct

<400> SEQUENCE: 197 ggcgcc 6

<210> SEQ ID NO 198
<211> LENGTH: 6
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Y is C or T
<220> FEATURE:
<221> NAME/KEY: misc_feature
<222> LOCATION: (4)..(4)
<223> OTHER INFORMATION: R is A or G

<400> SEQUENCE: 198 ggyrcc 6

<210> SEQ ID NO 199
<211> LENGTH: 6
<212> TYPE: DNA
<213> ORGANISM: Artificial sequence
<220> FEATURE:
<223> OTHER INFORMATION: Synthetic construct

<400> SEQUENCE: 199 atgcat 6

<210> SEQ ID NO 200
<211> LENGTH: 6
<212> TYPE: DNA
<213> ORGANISM: Artificial sequence
<220> FEATURE:
<223> OTHER INFORMATION: Synthetic construct

<400> SEQUENCE: 200 gaatgc 6

<210> SEQ ID NO 201
<211> LENGTH: 10
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Y is C or T
<220> FEATURE:
<221> NAME/KEY: misc_feature
<222> LOCATION: (4)..(7)
<223> OTHER INFORMATION: N is A, C, G, or T
<220> FEATURE:
<221> NAME/KEY: misc_feature
<222> LOCATION: (8)..(8)
<223> OTHER INFORMATION: R is A or G

<400> SEQUENCE: 201 caynnnnrtg 10

<210> SEQ ID NO 202
<211> LENGTH: 5
<212> TYPE: DNA
<213> ORGANISM: Artificial sequence
<220> FEATURE:
<223> OTHER INFORMATION: Synthetic construct

<400> SEQUENCE: 202 atgaa 5

-continued

```
<210> SEQ ID NO 203
<211> LENGTH: 6
<212> TYPE: DNA
<213> ORGANISM: Artificial sequence
<220> FEATURE:
<223> OTHER INFORMATION: Synthetic construct

<400> SEQUENCE: 203

catatg                                                              6
```